US009222142B2

(12) United States Patent
Chiu et al.

(10) Patent No.: US 9,222,142 B2
(45) Date of Patent: Dec. 29, 2015

(54) ADENOVIRUSES AND THEIR USE

(71) Applicants: THE REGENTS OF THE UNIVERSITY OF CALIFORNIA, Oakland, CA (US); TEXAS BIOMEDICAL RESEARCH INSTITUTE, San Antonio, TX (US); THE GOVERNMENT OF THE UNITED STATES OF AMERICA AS REPRESENTED BY THE, Atlanta, GA (US)

(72) Inventors: Charles Chiu, San Francisco, CA (US); Jean Patterson, San Antonio, TX (US); Mary Michelle Leland, San Antonio, TX (US); Kenneth Dee Carey, San Antonio, TX (US); Dean Ehrdman, Decatur, GA (US)

(73) Assignees: The Regents of the University of California, Oakland, CA (US); The United States of America as represented by the Secretary of the Department of Health and Human Services, Washington, DC (US); Texas Biomedical Research Institute, San Antonio, TX (US)

( * ) Notice: Subject to any disclaimer, the term of this patent is extended or adjusted under 35 U.S.C. 154(b) by 0 days.

(21) Appl. No.: 14/233,710

(22) PCT Filed: Jan. 15, 2014

(86) PCT No.: PCT/US2014/011624
§ 371 (c)(1),
(2) Date: Jan. 17, 2014

(87) PCT Pub. No.: WO2014/113436
PCT Pub. Date: Jul. 24, 2014

(65) Prior Publication Data

US 2015/0037364 A1 Feb. 5, 2015

Related U.S. Application Data

(60) Provisional application No. 61/752,876, filed on Jan. 15, 2013.

(51) Int. Cl.

| | |
|---|---|
| ***C12Q 1/70*** | (2006.01) |
| ***C07K 14/075*** | (2006.01) |
| ***C12N 15/861*** | (2006.01) |
| ***G01N 33/569*** | (2006.01) |
| ***C12N 7/00*** | (2006.01) |
| ***C12N 15/86*** | (2006.01) |
| ***C07K 14/005*** | (2006.01) |
| ***C07K 16/08*** | (2006.01) |
| ***C12Q 1/68*** | (2006.01) |
| *A61K 39/00* | (2006.01) |

(52) U.S. Cl.
CPC .............. *C12Q 1/701* (2013.01); *C07K 14/005* (2013.01); *C07K 14/075* (2013.01); *C07K 16/081* (2013.01); *C12N 7/00* (2013.01); *C12N 15/86* (2013.01); *C12N 15/861* (2013.01); *C12Q 1/68* (2013.01); *C12Q 1/702* (2013.01); *G01N 33/56983* (2013.01); *A61K 2039/55566* (2013.01); *C07K 2317/76* (2013.01); *C12N 2710/10321* (2013.01); *C12N 2710/10343* (2013.01); *C12Q 2563/131* (2013.01); *C12Q 2600/156* (2013.01)

(58) Field of Classification Search
CPC ............. C07K 14/075; C07K 2317/76; C07K 16/081; C07K 14/005; C12N 15/861; C12N 2710/10343; C12N 2710/10321; C12N 15/86; C12N 7/00; C12Q 2600/156; C12Q 1/701; C12Q 1/702; C12Q 2563/131; G01N 33/56983
See application file for complete search history.

(56) References Cited

U.S. PATENT DOCUMENTS

| | | | | |
|---|---|---|---|---|
| 2005/0069866 | A1* | 3/2005 | Wilson et al. | 435/5 |
| 2012/0093778 | A1 | 4/2012 | Wilson et al. | |
| 2012/0189582 | A1 | 7/2012 | Roy et al. | |
| 2013/0034576 | A1* | 2/2013 | Chiu et al. | 424/186.1 |

FOREIGN PATENT DOCUMENTS

WO WO 2011/057254 A2 5/2011

OTHER PUBLICATIONS

Kovács GM, Harrach B, Zakhartchouk AN, Davison AJ. Complete genome sequence of simian adenovirus 1: an Old World monkey adenovirus with two fiber genes. J Gen Virol. Jun. 2005;86(Pt 6):1681-6.*

Chiu et.al. E1A [Simian adenovirus C]. NCBI Reference Sequence: YP_007905994.1. Sub. May 1, 2013.*

Chiu CY, Yagi S, Lu X, Yu G, Chen EC, Liu M, Dick EJ Jr, Carey KD, Erdman DD, Leland MM, Patterson JL. A novel adenovirus species associated with an acute respiratory outbreak in a baboon colony and evidence of coincident human infection. MBio. Apr. 16, 2013;4(2):e00084.*

Kovacs GM, Davison AJ. III [Simian adenovirus 1]. NCBI Reference Sequence: YP_213970.1. Dep. Mar. 17, 2005.*

Kovacs GM, Harrach B, Zakhartchouk AN, Davison AJ. Complete genome sequence of simian adenovirus 1: an Old World monkey adenovirus with two fiber genes. J Gen Virol. Jun. 2005;86(Pt 6):1681-6.*

(Continued)

*Primary Examiner* — Benjamin P Blumel
*Assistant Examiner* — Rachel Gill
(74) *Attorney, Agent, or Firm* — Klarquist Sparkman, LLP

(57) ABSTRACT

Baboon Adenovirus (BaAdV)-2/4 and BaAdV-3 are described herein. BaAdV-2/4 and BaAdV-3 polynucleotide, polypeptides and antibodies that specifically bind BaAdV-2/4 and/or BaAdV-3 are described. Methods are described for detecting BaAdV-2/4 and BaAdV-3. Methods are also described for treating, preventing, and inducing an immune response to BaAdV-2/4 and/or BaAdV-3. Kits are also provided.

19 Claims, 13 Drawing Sheets

(56) References Cited

OTHER PUBLICATIONS

Eugster et al., "Isolation of advenoviruses from baboons (*Papio* sp.) with respiratory and enteric infections," *Archives of Virology* 26(3):260-270 (1969) (Abstract).

Chen et al., "Cross-Species Transmission of a Novel Adenovirus Associated with a Fulminant Pneumonia Outbreak in a New World Monkey Colony," *PLos Pathogens* 7(7):1-16 (Jul. 2011).

Database GenBank Accession No. AY771780.1 (May 25, 2005).

Database UniProtKB/TrEMBL Accession No. Q5C8Q7 (Apr. 12, 2005).

International Search Report from parent PCT Application No. PCT/US2014/011624 3 pages (mailed on May 15, 2014).

Written Opinion from parent PCT Application No. PCT/US2014/011624 5 pages (mailed on May 15, 2014).

* cited by examiner

FIG. 5A

Amino Acid Pairwise Identity against $BaAdV_1$ (species SAdV-B)

| | E1B-55K | DNApol | pTP | penton base (III) | hexon (II) | DBP | fiber (long) | fiber (short) |
|---|---|---|---|---|---|---|---|---|
| $BaAdV_{2,4}$ (baboon, species H) | 56% | 74% | 80% | 83% | 86% | 53% | 34% | 32% |
| $BaAdV_3$ (baboon, species H) | 57% | 74% | 80% | 82% | 85% | 53% | 36% | 33% |
| SAdV-A1335 (rhesus, SAdV-B) | 100% | 99% | 100% | 100% | 100% | 99% | 95% | 93% |
| SAdV-3 (rhesus, SAdV-A) | 43% | 69% | 78% | 79% | 80% | 59% | 33% | |
| SAdV-18 (vervet) | 58% | 76% | 79% | 85% | 83% | 56% | 36% | |
| TMAdV (titi) | 36% | 63% | 68% | 68% | 78% | 36% | 27% | |
| HAdV-12 (human, species A) | 53% | 71% | 77% | 83% | 84% | 53% | 41% | |
| HAdV-14 (human, species B) | 41% | 73% | 76% | 74% | 79% | 47% | 28% | |
| HAdV-1 (human, species C) | 45% | 75% | 78% | 70% | 78% | 49% | 37% | |
| HAdV-8 (human, species D) | 43% | 75% | 75% | 77% | 80% | 48% | 28% | |
| HAdV-4 (human, species E) | 49% | 77% | 73% | 75% | 80% | 43% | 27% | |
| HAdV-40 (human, species F) | 56% | 74% | 76% | 83% | 84% | 55% | 36% | 39% |
| HAdV-52 (human, species G) | 59% | 76% | 80% | 83% | 93% | 55% | 35% | 36% |
| MAdV-2 (mouse) | 25% | 47% | 37% | 56% | 67% | 31% | 24% | |

FIG. 5B

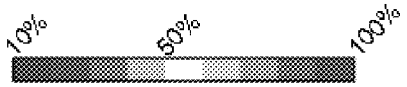

Amino Acid Pairwise Identity against $BaAdV_{2,4}$ (species H)

| | E1B-55K | DNApol | pTP | penton base (III) | hexon (II) | DBP | fiber (long) | fiber (short) |
|---|---|---|---|---|---|---|---|---|
| $BaAdV_1$ (baboon, SAdV-B) | 56% | 74% | 80% | 82% | 86% | 53% | 34% | 32% |
| $BaAdV_3$ (baboon, species H) | 98% | 98% | 99% | 91% | 92% | 95% | 93% | 58% |
| SAdV-A1335 (rhesus, SAdV-B) | 56% | 75% | 80% | 83% | 86% | 53% | 35% | 32% |
| SAdV-3 (rhesus, SAdV-A) | 43% | 69% | 77% | 79% | 81% | 50% | 32% | |
| SAdV-18 (vervet) | 67% | 79% | 89% | 88% | 86% | 62% | 57% | |
| TMAdV (titi) | 36% | 63% | 69% | 67% | 77% | 37% | 26% | |
| HAdV-12 (human, species A) | 56% | 72% | 80% | 79% | 84% | 62% | 36% | |
| HAdV-14 (human, species B) | 47% | 74% | 77% | 74% | 78% | 52% | 22% | |
| HAdV-1 (human, species C) | 49% | 73% | 79% | 69% | 76% | 52% | 34% | |
| HAdV-8 (human, species D) | 47% | 76% | 77% | 75% | 86% | 52% | 27% | |
| HAdV-4 (human, species E) | 54% | 77% | 74% | 76% | 80% | 48% | 31% | |
| HAdV-40 (human, species F) | 67% | 77% | 83% | 86% | 89% | 62% | 54% | 46% |
| HAdV-52 (human, species G) | 72% | 85% | 93% | 91% | 95% | 72% | 62% | 33% |
| MAdV-2 (mouse) | 25% | 46% | 38% | 58% | 65% | 31% | 21% | |

ADENOVIRUSES AND THEIR USE

CROSS REFERENCE TO RELATED APPLICATIONS

This is the U.S. national stage of PCT Application No. PCT/US2014/011624, Jan. 15, 2014, which claims the benefit of U.S. provisional application 61/752,876, filed on Jan. 15, 2013, which is incorporated by reference herein.

STATEMENT OF GOVERNMENT SUPPORT

This invention was made with government support under Grant Nos. U54-AI057156, U54-AI57168, R56-AI089532, and R01-HL105704 awarded by the National Institutes of Health. The government has certain rights in the invention.

FIELD

This disclosure relates to the field of adenoviruses, including the viruses themselves, viral vectors, methods of detection, and methods of treatment.

BACKGROUND

Many emerging infectious diseases in humans, including those caused by Ebola virus and H5N1 avian influenza, are zoonotic (Morens et al., 2004, Nature 430: 242-249). Given the close phylogenetic relationship between humans and non-human primates (NHPs), humans are especially vulnerable to cross-species infections from pathogens harbored in apes and monkeys (Pedersen and Davies, Ecohealth 6: 496-508). The risk of disease transfer between NHPs and humans may be greatest in hotspots such as the forests of central and West Africa and the Amazon basin, where humans come into frequent contact with a diverse range of closely related species of NHPs (Pedersen and Davies, supra). Zoos and research facilities housing captive NHPs also represent settings in which cross-species transmission of emerging pathogens can occur (Chen et al., 2011, PLoS Pathog 7: e1002155; Miller and Fowler, 2012, Fowler's zoo and wild animal medicine: current therapy. St. Louis, Mo.: Elsevier/Saunders. xviii, 669 p.; Murphy et al., 2006, J Zoo Wildl Med 37: 219-233).

Adenoviruses (AdVs) are double-stranded DNA viruses that naturally infect a broad range of vertebrate hosts, including humans and NHPs (Wold and Horwitz, 2007, Adenoviruses. In: Fields B N, Knipe D M, Howley P M, editors. Fields Virology. 5th ed. Philadelphia: Wolters Kluwer Health/Lippincott Williams & Wilkins. pp. 2395-2436). In humans, infections caused by AdVs include conjunctivitis, gastroenteritis, hepatitis, myocarditis, and pneumonia (Wold and Horwitz, 2007, supra; Lewis et al., 2009 J Infect Dis 199: 1427-1434; Louie et al., 2008, Clin Infect Dis 46: 421-425. Members of the genus *Mastadenovirus*, which encompass the AdVs infecting primates, have been classified by the International Committee on Taxonomy of Viruses (ICTV) to include the 7 human AdV species A-G (HAdV-A to HAdV-G) and 1 simian AdV species A (SAdV-A) (Harrach et al., 2011, Family Adenoviridae. In: King A, Adams M, Carstens E, Lefkowitz E, editors. Virus Taxonomy: Classification and Nomenclature of Viruses Ninth Report of the International Committee on Taxonomy of Viruses. San Diego: Elsevier. pp. 95-111. Recently, members of a phylogenetically distinct AdV species group, SAdV-B, were also discovered in fecal samples from asymptomatic captive rhesus monkeys (Roy et al., 2012, Emerg Infect Dis 18: 1081-1088). Although AdVs are conventionally thought to exhibit a very narrow host range due to co-evolution with their respective hosts (Wold and Horwitz, 2007, supra; Roy et al., 2009, PLoS Pathog 5: e1000503), there is mounting evidence supporting the potential for cross-species transmission of AdVs between monkeys and humans. AdVs identified in fecal samples from NHPs were found to share a remarkable similarity to human strains, and could be classified phylogenetically into the conventional "human" species groups HAdV-A through HAdV-E (Roy et al., 2011, supra; Wevers et al., 2011, J Virol 85: 10774-10784). Large-scale serological surveys have detected antibodies to monkey AdVs in humans living in endemic regions (Ersching et al., 2010, Virology 407: 1-6; Xiang et al., 2006, Emerg Infect Dis 12: 1596-1599) Furthermore, a novel AdV, titi monkey adenovirus (TMAdV) was previously described as the cause of a fatal outbreak of pneumonia and hepatitis in a colony of New World titi monkeys, which was also associated with a cross-species respiratory infection in a scientist investigating the outbreak and household family member (Chen et al., 2011, supra). A need remains to identify NHP adenoviruses and determine which of these viruses can infect humans.

SUMMARY

Isolated baboon Adenovirus (BaAdV)-2/4 and BaAdV-3 are disclosed herein. In some embodiments, BaAdV-2/4 and BaAdV-3 polynucleotides, polypeptides and antibodies that specifically bind BaAdV-2/4 and/or BaAdV-3 are disclosed. In additional embodiments, methods are disclosed for detecting BaAdV-2/4 and BaAdV-3. In further embodiments, methods are disclosed for treating, preventing, and inducing an immune response to a BaAdV-2/4 and/or BaAdV-3 infection.

In some embodiments, an isolated nucleic acid is provided that includes a nucleotide sequence at least 100 nucleotides in length that has at least 90% sequence identity over its length to SEQ ID NO:1, SEQ ID NO: 2, SEQ ID NO: 3, or their complement. In other embodiments, an isolated nucleic acid comprising: (a) a nucleic acid sequence at least 90% identical to nucleotides 1-29686 and 29812-34402 of the nucleic acid sequence set forth as SEQ ID NO: 1; (b) a nucleic acid sequence at least 90% identical to nucleotides 1-11334 and 13060-34391 of the nucleic acid sequence set forth as SEQ ID NO: 2; or (c) a nucleotide sequence at least 90% identical to the nucleotide sequence set forth as nucleotides 1-11334 and 13060-34391 of SEQ ID NO: 3. In some specific non-limiting examples, these nucleic acids can be recombinant nucleic acids. In additional non-limiting examples, these nucleic acids are cDNAs. Viruses including these polynucleotides, including replication defective viruses are also provided. In additional embodiments, expression vectors encoding polypeptides encoded by these nucleic acids and host cells transformed with these nucleic acids are provided.

Additional embodiments include polypeptides encoded by these polynucleotides, and antibodies that bind these polypeptides.

These nucleic acids, polypeptides, viruses, expression vectors, host cells and antibodies are of use in methods for detecting, treating, preventing, and producing an immune response to a BaAdV-2/4 and/or BaAdV-3 infection.

The foregoing and other features and advantages will become more apparent from the following detailed description of several embodiments, which proceeds with reference to the accompanying figures.

BRIEF DESCRIPTION OF THE FIGURES

FIG. 5A-5B. Amino acid pairwise identities of $BaAdV_1$ and $BaAdV_{2,4}$ relative to other adenoviruses. Comparisons are made against representative human, simian, and murine AdVs. The amino acid pairwise identity table is displayed as a heat map; grey scale corresponds to pairwise identities of 10-100% (bar).

SEQUENCE LISTING

Figure 1A:
FIGS. 1A-1B. Epidemiological features of the baboon adenovirus outbreak. (A) Image of an adult female baboon and her infant. The outbreak was associated with cases of fatal pneumonia in previously healthy newborn baboons. (B) Map of the baboon nursery during the outbreak with cages situated in two separate rooms, showing the locations of baboons who died from pneumonia (skeleton), baboons who became clinically ill with respiratory symptoms but survived (black), and asymptomatic baboons (grey). The novel AdVs genetically characterized in this study ($BaAdV_{1,2,3,4}$) were isolated from nasal swabs from both sick (B5) and asymptomatic (B4, B8, and B9) baboons.

A Sequence Listing is submitted herewith as an ASCII compliant text file named "Sequence_Listing.txt", created on Jan. 17, 2014, and having a size of ~564 kilobytes, as permitted under 37 CFR 1.821(c). The material in the aforementioned file is hereby incorporated by reference in its entirety. The nucleic and amino acid are shown using standard letter abbreviations for nucleotide bases, and three or one letter code for amino acids, as defined in 37 C.F.R. 1.822. Only one strand of each nucleic acid sequence is shown, but the complementary strand is understood as included by any reference to the displayed strand.

SEQ ID NO: 1 is the nucleic acid sequence of BaAdV-2.

SEQ ID NO: 2 is the nucleic acid sequence of BaAdV-4.

SEQ ID NO: 3 is the nucleic acid sequence of BaAdV-3.

SEQ ID NO: 4 is the nucleic acid sequence of BaAdV-1.

SEQ ID NOs: 5-39 are the amino acid sequences of polypeptides encoded by BaAdV-2.

SEQ ID NOs: 40-74 are the amino acid sequences of polypeptides encoded by BaAdV-4.

SEQ ID NOs: 75-109 are the amino acid sequences of polypeptides encoded by BaAdV-3.

SEQ ID NOs: 110-143 are the amino acid sequences of polypeptides encoded by BaAdV-1.

The location of the open reading frames for SEQ ID NO: 1-4 are provided in the Examples section.

DETAILED DESCRIPTION

Baboon adenoviruses are disclosed herein that cause flu-like symptoms in human and non-human primates. These adenoviruses are related to baboon adenovirus (BaAdV)-1, but are in a new adenovirus group that is intermediate between baboon adenovirus groups F and G. These adenoviruses include BaAdV-2 and BaAdv-2/4.

BaAdV-2/4 and BaAdV-3 polynucleotides, polypeptides and antibodies that specifically bind BaAdV-2/4 and/or BaAdV-3 are disclosed. In additional embodiments, methods are disclosed for detecting BaAdV-2/4 and BaAdV-3. Disclosed herein are diagnostic assays to detect BaAdV-3, BaAdV-2/4, BaAdV nucleic acids (genome and genes of both BaAdV-3 and BaAdV-2/4), BaAdV-2/4 and BaAdV-3 antibodies, and BaAdV-2/4 and BaAdV-3 polypeptides. The methods can be used to diagnose an earlier BaAdV-2/4 and/or BaAdV-3 infection in as subject.

In further embodiments, methods are disclosed for treating, preventing, and inducing an immune response to a BaAdV-2/4 and/or BaAdV-3 infection in a subject.

II. TERMS

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). In order to facilitate review of the various embodiments of this disclosure, the following explanations of specific terms are provided:

Adenovirus: An family of icosahedral (20-sided) viruses that contain DNA. Two genuses, *Mastadenovirus* and *Aviadenovirus* are included in the adenovirus family. While there are over 40 serotype strains of adenovirus, most of which cause benign respiratory tract infections in humans, subgroup C serotypes 2 or 5 are predominantly used as vectors. The life cycle does not normally involve integration into the host genome, rather an adenovirus replicates as episomal elements in the nucleus of the host cell and does not insert into the genome. An "adenoviral vector" is a vector derived from publicly available adenoviral DNA. At a minimum, an adenoviral vector includes the inverted terminal repetitions of an adenovirus.

Administering or administration: Therapeutically or prophylactically administering an effective amount of a composition or medicament during the course of therapy. Prophylactic administration can occur prior to manifestation of symptoms characteristic of an adenovirus infection.

Animal: Living multicellular vertebrate organisms, a category which includes, for example, mammals and birds.

Antibody: A polypeptide substantially encoded by an immunoglobulin gene or immunoglobulin genes, or antigen binding fragments thereof, which specifically binds and recognizes an analyte (antigen) such as adenovirus polypeptide or an antigenic fragment of thereof. Immunoglobulin genes include the kappa, lambda, alpha, gamma, delta, epsilon and mu constant region genes, as well as the myriad immunoglobulin variable region genes.

Antibodies exist, for example as intact immunoglobulins and as a number of well characterized fragments produced by digestion with various peptidases. For instance, Fabs, Fvs, and single-chain Fvs (scFvs) that specifically bind to an adenovirus would be adenvirus-specific binding agents. A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (such as humanized murine antibodies), heteroconjugate antibodies such as bispecific antibodies). See also, *Pierce Catalog and Handbook,* 1994-1995 (Pierce Chemical Co., Rockford, Ill.); Kuby, J., *Immunology,* $3^{rd}$ Ed., W.H. Freeman & Co., New York, 1997.

Antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) $(Fab')_2$, the fragment of the antibody obtained by treating whole antibody with the enzyme pepsin without subsequent reduction; (4) $F(ab')_2$, a dimer of two Fab' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. The term "antibody," as used herein, also includes antibody fragments either produced by the modification of whole antibodies or those synthesized de novo using recombinant DNA methodologies.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs have been defined (see, Kabat et al., *Sequences of Proteins of Immunological Interest*, U.S. Department of Health and Human Services, 1991, which is hereby incorporated by reference in its entirety). The Kabat database is now maintained online. Other databases include the IMGT database. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. Light chain CDRs are sometimes referred to as CDR L1, CDR L2, and CDR L3. Heavy chain CDRs are sometimes referred to as CDR H1, CDR H2, and CDR H3.

References to "$V_H$" or "VH" refer to the variable region of an immunoglobulin heavy chain, including that of an antibody fragment, such as Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas." Monoclonal antibodies include humanized monoclonal antibodies. In some examples monoclonal antibodies are isolated from a subject. The amino acid sequences of such isolated monoclonal antibodies can be determined.

"Polyclonal" antibodies are antibodies that are obtained from different B-lymphocytes that specifically bind the same antigen; the antibodies can bind several epitopes of the same antigen. In some embodiments, these antibodies are produced by inoculation of a suitable mammal, such as, but not limited to, a mouse, rabbit or goat, with the antigen. Many methodologies are known in the art for the production of polyclonal antibodies that are designed to produce high titer, high affinity antisera.

A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, such as at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (for example, see U.S. Pat. No. 5,585,089).

Antibody affinity is a measurement of specific binding of an antibody to its antigen. In one embodiment, affinity is calculated by a modification of the Scatchard method described by Frankel et al., *Mol. Immunol.,* 16:101-106, 1979. In another embodiment, binding affinity is measured by an antigen/antibody dissociation rate. In yet another embodiment, a high binding affinity is measured by a competition radioimmunoassay. In several examples, a high binding affinity is at least about $1\times10^{-8}$ M. In other embodiments, a high binding affinity is at least about $1.5\times10^{-8}$, at least about $2.0\times10^{-8}$, at least about $2.5\times10^{-8}$, at least about $3.0\times10^{-8}$, at least about $3.5\times10^{-8}$, at least about $4.0\times10^{-8}$, at least about $4.5\times10^{-8}$, or at least about $5.0\times10^{-8}$ M.

The phrase "specifically (or selectively) binds" or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, antibodies that specifically bind BaAdV-3, polymorphic variants, alleles, orthologs, and conservatively modified variants, or splice variants, or portions thereof, can be selected to obtain only those antibodies that are specifically immunoreactive with BaAdV-3 and not with other proteins, such as those of BaAdV-1 and/or BaAdV-2/4. Similarly, antibodies that specifically bind BaAdV-2/4, polymorphic variants, alleles, orthologs, and conservatively modified variants, or splice variants, or portions thereof, can be selected to obtain only those antibodies that are specifically immunoreactive with BaAdV-2/4 and not with other proteins, such as those of BaAdV-1 and/or BaAdV-3. This selection can be achieved by subtracting out antibodies that cross-react with other molecules. A variety of immunoassay formats can be used to select antibodies specifically immunoreactive with a particular protein, as described herein.

Antisense, Sense, and Antigene: Double-stranded DNA (dsDNA) has two strands, a 5'->3' strand, referred to as the plus strand, and a 3'->5' strand, referred to as the minus strand. Because RNA polymerase adds nucleic acids in a 5'->3' direction, the minus strand of the DNA serves as the template for the RNA during transcription. Thus, the RNA formed will have a sequence complementary to the minus strand, and identical to the plus strand (except that the base uracil is substituted for thymine).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a DNA target.

Aptamer: A non-naturally occurring nucleic acid having a desirable action on a target. A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. Aptamer action can be specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule.

An "siRNA" molecule or an "RNAi" molecule refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 or about 24-29 nucleotides in length, e.g., 20, 21, 22, 23, 24, 25, 26, 27, 28, 29, or 30 nucleotides in length. See also PCT/US03/07237, herein incorporated by reference in its entirety.

The term "antisense" refers to an oligomeric compound or molecule that is at least partially complementary to a target nucleic acid molecule to which it hybridizes. Antisense compounds or molecules can include, but are not limited to, oligonucleotides, oligonucleosides, oligonucleotide analogs, oligonucleotide mimetics, and chimeric combination.

An siRNA or antisense molecule or RNAi molecule is "specific" for a target nucleic acid if it reduces expression of the nucleic acid by at least about 10% when the siRNA or RNAi is expressed in a cell that expresses the target nucleic acid.

Baboon Adenovirus (BaAdV): A term used to refer to the genetic components of the virus, e.g., the genome and RNA transcripts thereof, proteins encoded by the genome (including structural and nonstructural proteins), and viral particles of a baboon adenovirus, such as B. A nucleic acid sequence as it refers to a BaAdV, such as BaAdV-3 and BaAdV-2/4 can refers to nucleic acids and polypeptide polymorphic variants, alleles, mutants, and interspecies homologs that: (1) have a nucleotide sequence that has greater than about 90%, preferably 91%, 92%, 93%, 94%, 95%, 96%, 97%, 98% or 99% or greater nucleotide sequence identity, preferably over a region of over a region of at least about 25, 50, 100, 200, 500, 1000, or more nucleic acids, up to the full length sequence, to the nucleotide sequence of SEQ ID NO:1, SEQ ID NO: 2 and SEQ ID NO: 3; (2) bind to antibodies, e.g., polyclonal or monoclonal antibodies, raised against an immunogen comprising an amino acid sequence of a protein encoded by an open reading frame (ORF) of SEQ ID NO: 1-3; and conservatively modified variants thereof; (3) specifically hybridize under stringent hybridization conditions to an anti-sense strand corresponding to a nucleic acid sequence of SEQ ID NO:1, SEQ ID NO: 2 and SEQ ID NO: 3 and variants thereof; (4) encoding a protein having an amino acid sequence that has greater than about 60% nucleotide sequence identity, 65%, 70%, 75%, 80%, 85%, 90%, preferably 91%, 92%, 93%, 94%, 95%, 96%, 97%, 98% or 99% or greater nucleotide sequence identity, preferably over a region of over a region of at least about 25, 50, 100, 200, 500, 1000, or more amino acids, to a polypeptide (such as a short fiber, E1, E3, E4, etc. protein) encoded by an open reading frame of SEQ ID NO: 1, 2 and 3. The locations of the open reading frames are shown in the attached appendices, and amino acid sequences of the encoded polypeptides are provided.

A "polypeptide encoded by BaAdV" or "polypeptide encoded by the nucleotide sequence" comprising identity to a BaAdV open reading frame (ORF) refers to structural and non-structural adenovirus proteins: (1) encoded by nucleic acids that have a nucleotide sequence that has greater than about 60% nucleotide sequence identity, 65%, 70%, 75%, 80%, 85%, 90%, preferably 91%, 92%, 93%, 94%, 95%, 96%, 97%, 98% or 99% or greater nucleotide sequence identity, preferably over a region of over a region of at least about 25, 50, 100, 200, 500, 1000, or more nucleic acids, up to the full length sequence, to the nucleotide sequence of SEQ ID NO:1, SEQ ID NO: 2 and SEQ ID NO: 3; (2) specifically bind to antibodies, e.g., polyclonal or monoclonal antibodies, raised against an immunogen comprising an amino acid sequence of a protein encoded by an open reading frame of SEQ ID NO: 1, SEQ ID NO: 2 and SEQ ID NO: 3; and conservatively modified variants thereof; (3) encode a protein having an amino acid sequence that has greater than about 60% nucleotide sequence identity, 65%, 70%, 75%, 80%, 85%, 90%, preferably 91%, 92%, 93%, 94%, 95%, 96%, 97%, 98% or 99% or greater, preferably over a region of at least about 25, 50, 100, 200, 500, 1000 or more amino acids, to a protein encoded by an open reading frame of SEQ ID NO: 1, SEQ ID NO: 2 and SEQ ID NO: 3, such as to one of SEQ ID NOs: 5-109. The amino acid sequence of the structural and non-structural viral proteins can be easily identified by one of skill in the art, using the algorithms disclosed herein, by aligning the presently disclosed sequence with other adenovirus sequences.

A "BaAdV infection" refers to the invasion by, multiplication and/or presence of BaAdV in a cell or a subject.

Binding or stable binding: An oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target:oligonucleotide complex. Binding between a target and an oligonucleotide can be detected by any procedure known to one skilled in the art, including both functional or physical binding assays. Binding may be detected functionally by determining whether binding has an observable effect upon a biosynthetic process such as expression of a gene, DNA replication, transcription, translation and the like.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, a method which is widely used, because it is so simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target dissociate or melt.

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

Biological sample: A sample from a living organism, including sections of tissues such as biopsy and autopsy samples, and frozen sections taken for histologic purposes. Such samples include blood and blood fractions or products (e.g., serum, plasma, platelets, red blood cells, and the like), sputum, cloacal swabs, mucosa, tissue, cultured cells, e.g., primary cultures, explants, and transformed cells, biological fluids, stool, urine, etc. A biological sample is typically obtained from a eukaryotic organism. The tissue sampled can be, for instance, skin, brain (e.g., cerebrum, cerebellum, optic lobe), spinal cord, adrenals, pectoral muscle, lung, heart, liver, crop, proventriculus, ventriculus, duodenum, small intestine, large intestine, cloaca, kidney, bursa of fabricus, spleen, pancreas, adrenal gland, bone marrow, lumbosacral spinal cord, or blood. Contacting a sample refers to exposing the sample under conditions suitable for a reaction to occur.

Capsid: The protein covering, or outer coat, of a virus particle. The capsid is a protein coat that covers the nucleoprotein core or nucleic acid of a virion. The capsid generally shows icosahedral symmetry and in some viruses (not adenoviruses) is enclosed in an envelope. The capsid is built up of subunits (some integer multiple of 60, the number required to give strict icosahedral symmetry) that self assemble in a pattern typical of a particular virus. The subunits are often packed, in smaller capsids, into 5 or 6 membered rings (pentamers or hexamers) that constitute the morphological unit (capsomere). A capsid is required for viral infection of a cell.

Detecting: Determining the presence, using any method, of the virus or viral particles including viral peptides, inside cells, on cells, and/or in medium with which cells or the virus have come into contact. The methods are exemplified by, but not limited to, the observation of cytopathic effect, detection of viral protein, such as by immunofluorescence, ELISA, or Western blot hybridization, detection of viral nucleic acid sequence, such as by PCR, RT-PCR, Southern blots, and Northern blots, nucleic acid hybridization, nucleic acid arrays, and the like.

Expression Vector: A plasmid, a virus or another medium, known in the art, into which a nucleic acid sequence for encoding a desired protein can be inserted or introduced.

Essential Gene: A gene required for viral replication, packaging or infection. Deletion of an essential gene renders a virus replication defective. For example, in an adenovirus, E1 and E2 are essential genes.

Functional Deletion: A mutation in a sequence that has an effect equivalent to deletion of the sequence, for example eliminating the function of a packaging signal or an essential gene product by a deletion, insertion, or substitution.

Functional effect: In the context of assays for testing agents that modulate activity of BaAdV, or for treating or preventing BaAdV infection, includes the determination of a parameter that is indirectly or directly under the influence of BaAdV, e.g., a phenotypic or chemical effect, such as the ability to increase or decrease viral genome replication, viral RNA and protein production, virus packaging, viral particle production (particularly replication competent viral particle production), cell receptor binding, viral transduction, cellular infection, antibody binding, inducing a cellular or humoral immune response, viral protein enzymatic activity, etc. "Functional effects" include in vitro, in vivo, and ex vivo activities. Such functional effects can be measured by any means known to those skilled in the art, e.g., changes in spectroscopic characteristics (e.g., fluorescence, absorbance, refractive index); hydrodynamic (e.g., shape); chromatographic; or solubility properties for a protein; measuring inducible markers or transcriptional activation of a protein; measuring binding activity or binding assays, e.g. binding to antibodies; measuring changes in ligand or substrate binding activity; measuring viral replication; measuring cell surface marker expression; measurement of changes in protein levels; measurement of RNA stability; identification of downstream or reporter gene expression (CAT, luciferase, 0-gal, GFP and the like), e.g., via chemiluminescence, fluorescence, colorimetric reactions, antibody binding, and inducible markers.

Functionally Equivalent: Sequence alterations, in either the transfer or packaging vector sequences, that yield the same results as described herein. Such sequence alterations can include, but are not limited to, conservative substitutions, deletions, mutations, frameshifts, and insertions. In an adenoviral vector deleted for E1 of the invention, deletions in an another gene, such as E4, are functionally equivalent to a similar vector including an E3 deletion. In addition, alterations of the adenoviral vector sequence which yield enhanced encapsidation of the transfer vector genome, are functionally equivalent to the transfer vector of the invention.

Heterologous: A heterologous sequence is a sequence that is not normally (i.e. in the wild-type sequence) found adjacent to a second sequence. In one embodiment, the sequence is from a different genetic source, such as a virus or organism, than the second sequence.

Host cell: A cell that is susceptible to transformation, transfection, transduction, conjugation, and the like with an exogenous nucleic acid construct or expression vector. Host cells can be from mammals, plants, bacteria, yeast, fungi, insects, animals, etc. A host cell can be from a human or a non-human primate.

Infective: A virus or vector is "infective" when it transduces a cell, replicates, and (without the benefit of any complementary virus or vector) spreads progeny vectors or viruses of the same type as the original transducing virus or vector to other cells in an organism or cell culture, where the progeny vectors or viruses have the same ability to reproduce and spread throughout the organism or cell culture. Thus, for example, a nucleic acid encoding an adenoviral particle is not infective if the nucleic acid cannot be packaged (e.g. if the adenoviral particle lacks a packaging site), even though the nucleic acid can be used to transfect a cell. Similarly, an adenoviral nucleic acid packaged by an adenovrial particle is not infective if it does not encode the adenoviral capsid proteins that it is packaged in.

Immune response: A reaction of the immune system to an antigen in the body of a host, which includes generation of an antigen-specific antibody and/or cellular cytotoxic response. The term further refers to an immune system response that leads to a condition of induce sensitivity to an immunogenic product.

Inverted Terminal Repetition (ITR): A sequence found in adenovirus located the end of each strand, these sequences are inverted repeats. When the virus is denatured the repeats enable the formation of "panhandle" structures of 100-140 bp from the single nucleic acid strands.

Isolated: An "isolated" nucleic acid has been substantially separated or purified away from other nucleic acid sequences and in the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids. The term "isolated" as used herein with respect to nucleic acids, such as DNA or RNA, refers to molecules separated from other DNAs, or RNAs, respectively that are present in the natural source of the macromolecule. Isolated is meant to include nucleic acid fragments which are not naturally occurring as fragments and would not be found in the natural state. The term isolated as used herein also refers to a nucleic acid or peptide that is substantially free of cellular material, viral material, or culture medium when produced by recombinant DNA techniques, or chemical precursors, or other chemicals when chemically synthesized.

Label: A detectable moiety or any atom, molecule or a portion thereof, the presence, absence or level of which is directly or indirectly monitorable. A variety of detectable moieties are well known to those skilled in the art, and can be any material detectable by spectroscopic, photochemical, biochemical, immunochemical, electrical, optical or chemical means. Such detectable labels can include, but are not limited to, magnetic beads, fluorescent dyes, radiolabels, enzymes, and colorimetric labels such as colloidal gold or colored glass or plastic beads.

Mammal: This term includes both human and non-human mammals. Similarly, the term "subject" includes both human and veterinary subjects.

Nucleic acid: Deoxyribonucleotides or ribonucleotides and polymers thereof in either single-or double-stranded form, and complements thereof. Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions can be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide. A particular nucleotide sequence also implicitly encompasses "splice variants," which as the name suggests, are products of alternative splicing of a gene. After transcription, an initial nucleic acid transcript can be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. A polynucleotide is generally a linear nucleotide sequence, including sequences of greater than 100 nucleotide bases in length.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

ORF (open reading frame): A series of nucleotide triplets (codons) coding for amino acids without any termination codons. These sequences are usually translatable into a peptide. Generally, these are a length of DNA or RNA sequence capable of being translated into a peptide normally located between a start or initiation signal and a termination signal. Exemplary non-limiting open reading frames encode a polypeptide set forth as one of SEQ ID NOs: 5-109.

Packaging cell: A cell that provides packaging functions in trans for a gene introduced into a cell with a transfer vector, but which does not encapsidate its own genome.

Packaging Vector: Packaging vector nucleic acids lack the nucleic acids necessary for packaging of a DNA corresponding to the packaging vector nucleic acid into an adenoviral capsid. That is, packaging vector nucleic acids are not themselves encapsidated in the viral particles which they encode, i.e. they are not infective. The packaging vector optionally includes all of the components necessary for production of viral particles, or optionally includes a subset of the components necessary for viral packaging. For instance, a packaging cell may be transformed with more than one packaging vector, each of which has a complementary role in the production of an adenoviral particle.

Two (or more) adenoviral-based packaging vectors are "complementary" when they together encode all of the functions necessary for adenovirus packaging, and when each individually does not encode all of the functions necessary for packaging. For example, when two vectors transduce a single cell and together they encode the information for production of adenovirus packaging particles, the two vectors are "complementary." The use of complementary vectors increases the safety of any packaging cell made by transformation with a packaging vector by reducing the possibility that a recombination event will produce an infective virus.

Adenoviral packaging cell lines are cells including nucleic acid molecules that encode adenoviral capsid proteins which can be used to form adenoviral particles. The adenoviral particles are competent to package target adenovirus which has a packaging site.

Polypeptide or peptide or protein: A polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Macromolecular structures such as polypeptide structures can be described in terms of various levels of organization. For a general discussion of this organization (see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980)). "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity. Typical domains are made up of sections of lesser organization such as stretches of 3-sheet and a-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes. Amino acid substitutions, deletions or additions to individual or a small percentage of amino acids in the encoded sequence is a conservatively modified variant, where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Recombinant: A non-naturally occurring molecule, such as a nucleic acid molecule or protein. In some embodiments, non-naturally occurring nucleic acid molecule is a DNA encoding a protein that is operably linked to a heterologous regulatory element, such as a promoter or an enhancer, a cDNA molecule, or a viral genome that has been engineered to be deficient for a specific nucleic acid sequence, such as a viral particles that include this nucleic acid will be replication deficient, attenuated, and/or deficient from the production of a protein normally encoded by the virus.

Sequence identity: In the context of two or more nucleic acids or polypeptide sequences that correspond to each other refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using, for example, a BLAST or BLAST 2.0 sequence comparison algorithms with default parameters described below, or by manual alignment and visual inspection (see, e.g., NCBI web site ncbi_nlm_nih_gov/BLAST or the like). Such sequences are then said to be "substantially identical" and are embraced by the term "substantially identical." This definition also refers to, or can be applied to, the compliment of a test sequence. The definition also includes sequences that have deletions and/or additions, as well as those that have substitutions. As described below, the preferred algorithms can account for gaps and the like. Preferably, identity exists for a specified entire sequence or a specified portion thereof or over a region of the sequence that is at least about 25 amino acids or nucleotides in length, or more preferably over a region that is 50-100 amino acids or nucleotides in length. A corresponding region is any region within the reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters. A comparison window includes reference to a segment of any one of the number of contiguous positions selected from the group consisting of from 20 to 600, usually about 50 to about 200, more usually about 100 to about 150 in which a sequence can be compared to a reference sequence of the same number of contiguous positions after the two sequences are optimally aligned. Methods of alignment of sequences for comparison are well-known in the art. Optimal alignment of sequences for comparison can be conducted (e.g., by the local homology algorithm of Smith & Waterman, *Adv. AppL Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection, e.g., *Current Protocols in Molecular Biology* (Ausubel et al., eds. 1995 supplement)).

One example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J MoL. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (ncbi_nlm-_nih_gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Stringent conditions: Conditions under which a probe will hybridize to its target subsequence, typically in a complex mixture of nucleic acids, but to no other sequences. The term "hybridize" refers to the process by which single strands of nucleic acid sequences form double-helical segments through hydrogen bonding between complementary nucleotides. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The T. is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions can also be achieved with the addition of destabilizing agents such as formamide. For selective or specific hybridization, a positive signal is at least two times background, preferably 10 times background hybridization. Exemplary stringent hybridization conditions can be as following: 50% fonnamide, 5×SSC, and 1% SDS, incubating at 42° C., or, 5×SSC, 1% SDS, incubating at 65° C., with wash in 0.2×SSC, and 0.1% SDS at 65° C. Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference (e.g., and *Current Protocols in Molecular Biology*, ed. Ausubel, et al.).

Subject: Any animal, including, but not limited to, humans, baboons, and other non-human primates, that presents one or more symptoms indicative of BaAdV infection.

Test agent or agent: Any molecule or compound, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, oligonucleotide, etc., to be tested for the capacity to directly or indirectly modulation tumor cell proliferation. The test agent can be in the form of a library of test compounds, such as a combinatorial or randomized library that provides a sufficient range of diversity. Test agents are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test agent (called a “lead agent”) with some desirable property or activity, e g, inhibiting activity, creating variants of the lead compound, and evaluating the property and activity of those variant compounds. Often, high throughput screening (HTS) methods are employed for such an analysis. Agents can be inhibitors, activators, or modulators of BaAdV nucleic acid and polypeptide sequences, and are used to refer to activating, inhibitory, or modulating molecules identified using in vitro and in vivo assays of the BaAdV nucleic acid and polypeptide sequences. Inhibitors are agents that, e.g., bind to, partially or totally block activity, decrease, prevent, delay activation, inactivate, desensitize, or down regulate the activity or expression of BaAdV, e.g., antagonists. Activators are agents that increase, open, activate, facilitate, enhance activation, sensitize, agonize, or up regulate BaAdV activity, e.g., agonists Inhibitors, activators, or modulators also include genetically modified versions of BaAdV, e.g., versions with altered activity, as well as naturally occurring and synthetic ligands, substrates, antagonists, agonists, antibodies, peptides, cyclic peptides, nucleic acids, antisense molecules, ribozymes, or small chemical molecules for example.

The phrase “small organic molecule” refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

Therapeutically effective amount: A dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); and Pickar, *Dosage Calculations* (1999)).

Treating or treatment: Includes the application or administration of a composition to a subject, or application or administration of a composition to a cell or tissue from a subject who has been infected with BaAdV, or has symptoms of BaAdV infection, with the purpose of curing, healing, alleviating, relieving, altering, remedying, ameliorating, improving, or affecting the disease or condition, the symptom of the disease or condition, or the risk of the disease or condition. The term “preventing” or “prevention” includes stopping or hindering a disease, disorder, or symptoms associated with BaAdV infection before it develops in full.

Vaccine: A pharmaceutical composition comprising at least one immunologically active component that induces an immunological response in an animal and possibly but not necessarily one or more additional components that enhance the immunological activity of the active component. A vaccine can additionally comprise further components typical to pharmaceutical compositions. The immunologically active component of a vaccine can comprise complete virus particles in either their original form or as attenuated particles in a so called modified live vaccine (MLV) or particles inactivated by appropriate methods in a so called killed vaccine (KV). A vaccine comprising antigenic substances can be administered for the purpose of inducing a specific and active immunity against a disease provoked by a BaAdV infection. A vaccine can also provide passive immunity in the form of antibodies previously generated against BaAdV antigens.

Vector: A nucleic acid molecule as introduced into a host cell, thereby producing a transformed host cell. A vector may include nucleic acid sequences that permit it to replicate in the host cell, such as an origin of replication. A vector may also include sequences encoding one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like. A vector may be a viral vector, derived from a virus, such as an adenoviral vector.

Unless otherwise explained, all technical and scientific terms used herein have the same meaning as commonly understood by one of ordinary skill in the art to which this disclosure belongs. The singular terms “a,” “an,” and “the” include plural referents unless context clearly indicates otherwise. Similarly, the word “or” is intended to include “and” unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term “comprises” means “includes.” All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Baboon Adenovirus (BaAdV) Nucleic Acids

The baboon adenovirus (BaAdV) nucleic acid sequence disclosed herein include nucleic acid sequences at least about 91%, about 92%, about 93%, about 94%, about 95%, about 96%, about 97%, about 98%, about 99% identical, or about 100% identical to nucleotides 1-34402 of BaAdV-3 (SEQ ID NO: 3) and/or nucleotides 1-34391 of BaAdV-2/4 (SEQ ID NO: 1 and SEQ ID NO: 2), or nucleotides of at least 100, at least 200, at least 300, at least 400 or at least 500 nucleotides in length. Nucleic acids sequences and adenoviruses including a nucleic acid sequence at least about 91%, about 92%, about 93%, about 94%, about 95%, about 96%, about 97%, about 98%, about 99%, or about 100% identical to an open reading frame from SEQ ID NOs: 1, 2 and 3 are also provided. The nucleic acid sequences are also provided that are the strand which is complementary to the sequences of SEQ ID NO: 1, 2 and 3, as well as the RNA and cDNA sequences corresponding to the open reading frames and their complementary strands. Further included are nucleic acid sequences which are greater than 95 to 98%, such as about 99 to 99.9% homologous or identical to SEQ ID NO: 1, SEQ ID NO: 2, SEQ ID NO: 3. Nucleic acids that include, or consist of the nucleic acid sequence sent forth as one of SEQ ID NOs: 1, 2, and 3, and degenerate variants thereof, are also provided herein. I Nucleic acids are also provided that include or consist of (a) a nucleic acid sequence at least about 90%, 91%, 92%, 93%, 95%, 95%, 96%, 97%, 98%, 99% or 100% identical to nucleotides 1-29685 and 29867-34391 of the nucleic acid sequence set forth as SEQ ID NO: 1; (b) a nucleic acid sequence at least about 990%, 91%, 92%, 93%, 95%, 95%, 96%, 97%, 98%, 99% or 100% identical to nucleotides 1-29865 and 29867-34391 of the nucleic acid sequence set forth as SEQ ID NO: 2; (c) a nucleotide sequence at least about 90%, 91%, 92%, 93%, 95%, 95%, 96%, 97%, 98%, 99% or 100% identical to the nucleotide sequence set forth as nucleotides 1-28677 and 29812-34402 of SEQ ID NO: 3. Nucleic acids are also provided that include or consist of a nucleic acid sequence at least about 90%, 91%, 92%, 93%, 95%, 95%, 96%, 97%, 98%, 99% or 100% identical to an open reading frame of SEQ ID NO 1, SEQ ID NO: 2 or SEQ ID NO: 3. Nucleic acids are also provided that include or consist of an open reading frame of SEQ ID NO: 1, SEQ ID NO: 2 or SEQ ID NO: 3.

Nucleic acids are also provided that encode a polypeptide at least about 90%, 01%, 92%, 93%, 94%, 95%, 96%, 97%, 98%, 99% or 100% identical to the amino acid sequence set forth as one of SEQ ID NOs: 5-109. In some embodiments, nucleic acids are provided that encode a polypeptide comprising or consisting of the amino acid sequence set forth as one of SEQ ID NOs: 5-10. In some embodiments, cDNAs are provided that encode a polypeptide at least about 90%, 91%, 92%, 93%, 94%, 95%, 96%, 97%, 98%, 99% or 100% identical to the amino acid sequence set forth as one of SEQ ID NOs: 5-109. In some embodiments, nucleic acids, or degenerate variants thereof, are provided that encode a polypeptide with an amino acid sequence set forth as one of SEQ ID NOs: 5-109. These nucleic acids can be cDNAs.

In some embodiments, a nucleic acid molecule is provided containing Ad ITR sequences of BaAdV-1 and/or BaAdV-2/4. In other embodiments, a nucleic acid is provided including a BaAdV-1 and BaAdV-2/4 nucleic acid sequence encoding a desired gene product, including but not limited to an early or a late gene product, a long fiber or a short fiber, or polymerase. These nucleic acids can be cDNAs. Still other nucleic acid molecules constructed using the sequences disclosed herein will be readily apparent to one of skill in the art, in view of the information provided herein. For example, nucleic acids are provided that include a nucleotide sequence at least 50, at least 100 nucleotides, at least 250, at least 500, at least 1000, at least 1500, at least 2000, or at least 3,000 nucleotides in length that has at least about 91%, 92%, 93%, 94%, 95%, 96%, 97% 98%, 99% or 100% sequence identity over its length to SEQ ID NO:1 and/or SEQ ID NO: 2 and/or SEQ ID NO: 3, and/or their complements. In specific non-limiting examples, these nucleic acids are non-naturally occurring.

The BaAdV-1 and BaAdV-2/4 adenoviral nucleic acid sequences can be used as therapeutic agents (such as by including a nucleic acid encoding a therapeutic moiety) and in construction of a variety of vector systems and host cells. As used herein, a vector includes any suitable nucleic acid molecule including, naked DNA, a plasmid, a virus, a cosmid, or an episome. These sequences and products may be used alone or in combination with other adenoviral sequences or fragments, or in combination with elements from other adenoviral or non-adenoviral sequences. The adenoviral sequences can be used as antisense delivery vectors, gene therapy vectors, or vaccine vectors.

In one embodiment, the baboon Ad gene regions identified herein may be used in a variety of vectors for delivery of a heterologous molecule to a cell. For example, vectors are generated for expression of an adenoviral capsid protein (or fragment thereof) for purposes of generating a viral vector in a packaging host cell. Such vectors may be designed for expression in trans. Alternatively, such vectors are designed to provide cells which stably contain sequences which express desired adenoviral functions, e.g., one or more of E1a, E1b, the terminal repeat sequences, E2a, E2b, E4, E4ORF6 region.

In addition, the adenoviral gene sequences and fragments thereof can be used to provide helper functions necessary for production of helper-dependent viruses (e.g., adenoviral vectors deleted of essential functions or adeno-associated viruses (AAV)). Methods of producing rAAV using adenoviral helper functions have been described at length in the literature with human adenoviral serotypes (see U.S. Pat. No. 6,258,595; U.S. Pat. No. 5,871,982; PCT Publication No. WO 99/14354; PCT Publication No. WO 99/15685; and PCT Publication No. WO 99/47691. The baboon adenoviral gene sequences that provide the necessary helper functions (such as E1a, E1b, E2a and/or E4 ORF6) can be useful in providing the necessary adenoviral function while minimizing or eliminating the possibility of recombination with any other adenoviruses present in the rAAV-packaging cell which are typically of human origin.

Alternatively, recombinant adenoviral baboon vectors can be utilized in these methods. Such recombinant adenoviral baboon vectors may include, e.g., a hybrid baboon Ad/AAV in which baboon Ad sequences flank a rAAV expression cassette composed of, e.g., AAV 3' and/or 5' ITRs and a transgene under the control of regulatory sequences which control its expression. One of skill in the art will recognize that still other baboon adenoviral vectors and/or gene sequences are useful for production of rAAV and other viruses dependent upon adenoviral helper functions.

In still another embodiment, nucleic acid molecules are designed for delivery and expression of one or more selected adenoviral gene product in a host cell to achieve a desired physiologic effect. For example, a nucleic acid molecule containing sequences encoding an adenovirus E1a protein can be delivered to a subject for use as a cancer therapeutic. Optionally, such a molecule is formulated in a lipid-based carrier and preferentially targets cancer cells. Such a formulation may be combined with other cancer therapeutics (e.g., cisplatin, taxol, or the like). Still other uses for the adenoviral sequences provided herein will be readily apparent to one of skill in the art.

In addition, one of skill in the art will readily understand that the adenoviral sequences disclosed herein can be readily adapted for use for a variety of viral and non-viral vector systems for in vitro, ex vivo or in vivo delivery of therapeutic and immunogenic molecules. For example, the genomes disclosed herein can be utilized in a variety of recombinant adenoviral (rAd) and non-rAd vector systems. Such vectors systems may include, but are not limited to, plasmids, lentiviruses, retroviruses, poxviruses, vaccinia viruses, and adeno-associated viral systems, among others. Molecules which include polynucleotides including the baboon Ad DNA sequences disclosed herein can be in the form of naked DNA, a plasmid, a virus or any other genetic element.

In one embodiment, the baboon adenoviral gene regions identified herein can be used as or in a variety of vectors for delivery of a heterologous molecule to a cell. For example, vectors are generated for expression of an adenoviral capsid protein (or fragment thereof) for purposes of generating a viral vector in a packaging host cell. Such vectors may be designed for expression in trans. Alternatively, such vectors are designed to provide cells which stably contain sequences which express desired adenoviral functions, e.g., one or more of E1a, E1b, the terminal repeat sequences, E2a, E2b, E4, E4 ORF region.

Methods of producing recombinant (r)AAV using adenoviral helper functions have been described with human adenoviral serotypes (see, for example, U.S. Pat. Nos. 6,258,595; 5,871,982; PCT Publication No. WO 99/14354; PCT Publication No. WO 99/15685; and PCT Publication No. WO 99/47691. These methods may also be used in production of non-human serotype AAV, including non-human primate AAV serotypes. The baboon adenoviral genes that provide the necessary helper functions (e.g., E1a, E1b, E2a and/or E4 ORF6) can be particularly useful in providing the necessary adenoviral function. Without being bound by theory, they can minimize or eliminate the possibility of recombination with any other adenoviruses present in the rAAV-packaging cell which are typically of human origin. Thus, selected genes or open reading frames of the adenoviral sequences of the invention may be utilized in these rAAV production methods. Recombinant adenoviral simian vectors include, e.g., a hybrid baboon adenovirus (Ad)/AAV in which baboon adenovirus Ad sequences flank a rAAV expression cassette composed of, e.g., AAV 3' and/or 5' ITRs and a transgene under the control of regulatory sequences which control its expression. One of skill in the art will recognize that still other simian adenoviral vectors and/or gene sequences of the invention will be useful for production of rAAV and other viruses dependent upon adenoviral helper.

Molecules useful for production of the polypeptides are also disclosed herein. Such molecules which include polynucleotides including the baboon adenoviral nucleic acid sequences of the invention can be in the form of naked DNA, a plasmid, a virus or any other genetic element. Any protein can be encoded by these vectors, including markers and therapeutic proteins. Thus, the vectors can be used for the delivery of a heterologous polypeptide in a target cell. In some embodiment, the nucleic acid encoding a heterologous polypeptide is operably linked to one or more expression control sequences, such as a promoter and/or an enhancer. One of skill in the art can readily engineer the adenoviruses nucleic acids disclosed herein to include a heterologous nucleic acid sequence encoding a polypeptide of interest, and express the polypeptide in a host cell. Similarly, heterologous promoters and enhancers can be operably linked to a nucleic acid encoding an adenovirus polypeptide.

Expression

To obtain high level expression of a cloned gene or genome, such as a polypeptide encoded by an open reading frame disclosed herein, such as, but not limited to, a polypeptide at least about 90%, 91%, 92%, 93%, 94%, 95%, 96%, 97%, 98%, 99% or 100% identical to one of SEQ ID NOs: 5-109, one typically subclones the nucleic acid into an expression vector that contains a strong promoter to direct transcription, a transcription/translation terminator, and if for a nucleic acid encoding a protein, a ribosome binding site for translational initiation. The open reading frames include any of those listed in the accompanying sequence information. Suitable bacterial promoters are well known in the art and described (e.g., in Sambrook et al., and Ausubel et al, supra. Bacterial expression systems for expressing the protein are available in, e.g., *E. coli, Bacillus* sp., and *Salmonella* (Palva et al., *Gene* 22:229-235 (1983); Mosbach et al., *Nature* 302: 543-545 (1983)). Kits for such expression systems are commercially available. Eukaryotic expression systems for mammalian cells, yeast, and insect cells are well known in the art and are also commercially available. Retroviral expression systems can be used.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function. Heterologous refers to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

In addition to the promoter, the expression vector typically contains a transcription unit or expression cassette that contains all the additional elements required for the expression of the nucleic acid in host cells. A typical expression cassette thus contains a promoter operably linked to the nucleic acid sequence encoding the nucleic acid of choice and signals required for efficient polyadenylation of the transcript, ribosome binding sites, and translation termination. Additional elements of the cassette can include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region can be obtained from the same gene as the promoter sequence or can be obtained from different genes.

The particular expression vector used to transport the genetic information into the cell is not particularly critical. Any of the conventional vectors used for expression in eukaryotic or prokaryotic cells can be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. A heterologous adenoviral vector can be used. Sequence tags can be included in an expression cassette for nucleic acid rescue. Markers such as fluorescent proteins, green or red fluorescent protein, 13-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/$A^+$, pMT010/$A^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can also be regulated using inducible promoters. With inducible promoters, expression levels are tied to the concentration of inducing agents, such as tetracycline, by the incorporation of response elements for these agents into the promoter. Generally, high level expression is obtained from inducible promoters only in the presence of the inducing agent; basal expression levels are minimal.

Vectors can have a regulatable promoter, e.g., tet-regulated systems and the RU-486 system (see, e.g., Gossen & Bujard, *PNAS* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a sequence of choice under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, as any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of protein, which are then purified using standard techniques (see, e.g., Colley et al., *J. Biol. Chem.* 264:17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J Bact.* 132:349-351 (1977); Clark-Curtiss & Curtiss, *Methods in Enzymology* 101:347-362 (Wu et al., eds, 1983)).

Any of the well-known procedures for introducing foreign nucleotide sequences into host cells can be used. These include the use of calcium phosphate transfection, polybrene, protoplast fusion, electroporation, biolistics, liposomes, microinjection, plasma vectors, viral vectors and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing BaAdV proteins and nucleic acids. The host cells can be human cells, or non-human primate cells.

After the expression vector is introduced into the cells, the transfected cells are cultured under conditions favoring expression of the protein of choice, which is recovered from the culture using standard techniques identified below.

Either naturally occurring or recombinant BaAdV proteins can be purified for use in diagnostic assays, for making antibodies (for diagnosis and therapy) and vaccines, and for assaying for anti-viral compounds. Naturally occurring protein can be purified, e.g., from primate tissue samples. Recombinant protein can be purified from any suitable expression system.

BaAdV Polypeptides

BaAdV polypeptides, such as those encoded by the open reading frames specified herein, and functional fragments thereof, can be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et aL, supra; and Sambrook et al., supra). Exemplary BaAdV polypeptides are provided herein, such as polypeptides at least about 90%, 91%, 92%, 93%, 94%, 95%, 96%, 97%, 98%, 99% or 100% identical to one of SEQ ID NOs: 5-109. In specific non-limiting examples, the polypeptide comprises, or consists of, the amino acid sequence set forth as one of SEQ ID NOs: 5-109.

A number of procedures can be employed when recombinant protein is being purified. For example, proteins having established molecular adhesion properties can be reversible fused to the protein. With the appropriate ligand or substrate, a specific protein can be selectively adsorbed to a purification column and then freed from the column in a relatively pure form. The fused protein is then removed by enzymatic activity. Finally, protein could be purified using immunoaffinity columns. Recombinant protein can be purified from any suitable source, include yeast, insect, bacterial, and mammalian cells.

Recombinant proteins can be expressed and purified by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria can form insoluble aggregates ("inclusion bodies"). Several protocols are suitable for purification of protein inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM MgCl2, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies can be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation can occur upon removal (by dialysis, for example) or dilution of the denaturant, allowing re-formation of immunologically and/or biologically active protein. Other suitable buffers are known to those skilled in the art. Human proteins are separated from other bacterial proteins by standard separation techniques, e.g., with Ni-NTA agarose resin.

Alternatively, it is possible to purify recombinant protein from bacteria periplasm. After lysis of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM MgSO4 and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

Solubility fractionation can be used as a standard protein separation technique for purifying proteins. As an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

The molecular weight of the protein can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

The protein can also be separated from other proteins on the basis of its size, net surface charge, hydrophobicity, and affinity for ligands or substrates using column chromatography. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

The polypeptides disclosed herein can be used to detect the presence of antibodies that specifically bind BaAdV-2/4 or BaAdV-3 antibodies in a biological sample from a subject. The biological sample can be any sample, including, but not limited to, a blood or serum sample. The method includes contacting the biological sample with one or more of the polypeptides disclosed herein for a sufficient time to for any antibodies to form an immune complex with the one or more polypeptides, and detecting the presence of the immune complex. Methods for detecting the presence of an immune complex are known in the art, and are disclosed below. In several embodiments, the methods include the use of secondary antibodies that specifically bind human antibodies. In some example, the secondary antibodies are labeled.

Probes, Primers, and Detecting BaAdV Nucleic Acids

A BaAdV infection, such as a BaAdV-2/4 and a BaAdV-3 infection, can be detected based on the level of the particular BaAdV RNA or DNA in a biological sample. Primers and probes that are specific to a BaAdV can be used for detection of BaAdV, diagnosis of a BaAdV infection, confirm an earlier infection, and determine BaAdV viral load. In some embodiments, probes and/or primers that specifically bind BaAdV-2/4 can be used for detection of BaAdV-2/4, diagnosis, and determination of BaAdV-2/4 viral load. In other embodiments, probes and/or primers that specifically bind BaAdV-3 can be used for detection of BaAdV-3, diagnosis, and determination of BaAdV-3 viral load. In further embodiments, these methods distinguish a BaAdV-3 infection, such as from a BaAdV-2/4 infection and/or a BaAdV-1 infection. In further embodiments, primers from BaAdV-2/4 can be used for detection of BaAdV-2/4, diagnosis, and determination of BaAdV-2/4 viral load. In further embodiments, these methods distinguish a BaAdV-2/4 infection, such as from a BaAdV-3 infection and/or a BaAdV-1 infection. In some embodiments, the method distinguishes BaAdV-2/4 and/or BaAdV-3 from BaAdV-1. In additional embodiments, the assay is a multiplex assay.

Any suitable primer can be used to detect the genome, nucleic acid sub sequence, ORF, or protein of choice, for example using methods described in US Published Patent Application No. 2003/0104009. In some examples, the subject nucleic acid compositions can be used as single-or double-stranded probes or primers for the detection of BaAdV-2/4 mRNA or cDNA generated from such mRNA, as obtained can be present in a biological sample (e.g., extracts of human cells). In other examples, the subject nucleic acid compositions can be used as single-or double-stranded probes or primers for the detection of BaAdV-3 mRNA or cDNA generated from such mRNA, as obtained can be present in a biological sample (e.g., extracts of human cells). In some embodiments, the probe or primer is specific to the short fiber gene of BaAdV-2/4 or BaAdV-3.

The BaAdV-2/4 and BaAdV-3 polynucleotides can also be used to generate additional copies of the polynucleotides, to generate antisense oligonucleotides, and as triple-strand forming oligonucleotides. For example, two oligonucleotide primers can be employed in a polymerase chain reaction (PCR) based assay to amplify a portion of BaAdV cDNA derived from a biological sample, wherein at least one of the oligonucleotide primers is specific for (i.e., hybridizes to) the BaAdV polynucleotide. In some examples, the primers specifically bind BaAdV-3 nucleic acid, and thus can be used to delineate BaAdV-3 from BaAdV-2/4 and/or BaAdV-1. In other examples, the primers specifically bind BaAdV-2/4 nucleic acid, and thus can be used to delineate BaAdV-2/4 from BaAdV-3 and/or BaAdV-1. In specific, non-limiting examples, the probes and/or primers specifically bind a nucleic acid encoding the short fiber polypeptide.

The primers can be at least or about 12, 15, 16, 18, 20, 22, 24, 25, 30, 35, 40, 45, or 50 nucleotides (nt) or are, for instance, from about 12 to 50 nt in length, 15 to 30 nt in length, 15 to 25 nt in length, or 20 to 30 nt in length) fragments of a contiguous sequence of SEQ ID NO: 1, SEQ ID NO: 2, SEQ ID NO: 3, or other polynucleotide sequence encoding a BaAdV-2/4 or BaAdV-3 polypeptide. The amplified cDNA is then separated and detected using techniques well known in the art, such as gel electrophoresis. Similarly, oligonucleotide probes that specifically hybridize to a BaAdV-2/4 or BaAdV-3 polynucleotide can be used in a hybridization assay to detect the presence of the BaAdV-2/4 or BaAdV-3 polynucleotide in a biological sample, respectively.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided (e.g., in Innis et al. (1990) *PCR Protocols, A Guide to Methods and Applications,* Academic Press, Inc. N.Y.).

In some embodiments, methods are provided for detecting a Baboon adenovirus (BaAdV)-3 or BaAdV-2/4 nucleic acid. The method includes the steps of: (a) contacting a sample suspected of comprising an adenoviral nucleic acid with at least one primer that hybridizes under stringent conditions to the nucleotide sequence set forth as SEQ ID NO:1, SEQ ID NO: 2, and/or SEQ ID NO: 3; (b) performing a PCR reaction; and (c) detecting presence or absence of a reaction product from the PCR reaction, wherein the presence of the reaction product detects the BaAdV-3 or a BaAdV-2/4 adenovirus.

The probes for BaAdV-2/4 and BaAdV-3 polynucleotides (natural or derived) are of a length or have a sequence which allows the detection of unique viral sequences by hybridization. While about 6-8 nucleotides may be useful, longer sequences may be more effective, e.g., sequences of about 10-12 nucleotides, or about 15, 16, 17, 18, 19, 20 nucleotides or more. In some embodiments, these sequences will derive from regions which lack heterogeneity among viral isolates.

Nucleic acid probes or primers specific to BaAdV-2/4 and/or BaAdV-3 can be generated using the polynucleotide sequences disclosed herein. In some embodiments, the probes are at least about 12, 15, 16, 18, 20, 22, 24, or 25 nucleotide (nt) fragments of a contiguous sequence of SEQ ID NO: 1, SEQ ID NO: 2, SEQ ID NO: 3, or other polynucleotide sequence encoding a BaAdV polypeptide, such as degenerate variants of BaAdV-2/4 and/or BaAdV-3. Nucleic acid probes can be less than about 200 bp, 150 bp, 100 bp, 75 bp, 50 bp, 60 bp, 40 bp, 30 bp, 25 by 2 kb, 1.5 kb, 1 kb, 0.5 kb, 0.25 kb, 0.1 kb, or 0.05 kb in length. The probes can be produced by, for example, chemical synthesis, PCR amplification, generation from longer polynucleotides using restriction enzymes, or other methods well known in the art. Generally, primers and probes are identical to a BaAdV nucleic acid sequence and different from a non-BaAdV sequence. As noted above, primers and probes can be used to distinguish BaAdV-2/4 and BaAdV-3 from each other, and from BaAdV-1.

The polynucleotides described herein, particularly where used as a probe in a diagnostic assay, can be detectably labeled. Exemplary detectable labels include, but are not limited to, radiolabels, fluorochromes, (e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein, 6-carboxy-X-rhodamine (ROX), 6-carboxy-2',4',T,4,7-hexachlorofluorescein (HEX), 5-carboxyfluorescein (5-FAM) or N,N,N',N'-tetramethyl-6-carboxyrho-damine (TAMRA)), radioactive labels, (e.g. .sup.32p, .sup.35S, and sup.3H), and the like. The detectable label can involve two stage systems (e.g., biotin-avidin, hapten-anti-hapten antibody, and the like).

Non-PCR-based, sequence specific DNA amplification techniques can also be used with the invention to detect BaAdV sequences. An example of such techniques includes, but is not limited to, the Invader assay (see, e.g., Kwiatkowski et al. *Mol Diagn.* December 1999, 4:353-64 and U.S. Pat. No. 5,846,717).

In other embodiments, solid substrates, such as arrays, are provided that include any of the polynucleotides described herein. The polynucleotides are immobilized on the arrays using methods known in the art. An array can have one or more different polynucleotides.

Any suitable qualitative or quantitative methods known in the art for detecting specific BaAdV nucleic acid (e.g., RNA or DNA) can be used. BaAdV nucleic acid can be detected by, for example, in situ hybridization in tissue sections, using methods that detect single base pair differences between hybridizing nucleic acid (e.g., using the INVADER® technology described in, for example, U.S. Pat. No. 5,846,717), by reverse transcriptase-PCR, or in Northern blots containing poly A mRNA, and other methods well known in the art. For detection of BaAdV-2/4 and BaAdV-3 polynucleotides in blood or blood-derived samples, the use of methods that allow for detection of single base pair mismatches is preferred.

Using the BaAdV-2/4 and BaAdV-3 nucleic acid as a basis, nucleic acid probes (e.g., including oligomers of at least about 8 nucleotides or more, see above) can be prepared, either by excision from recombinant polynucleotides or synthetically, which probes hybridize with the desired BaAdV nucleic acid, and thus are useful in detection of a specific BaAdV virus in a sample, and identification of infected individuals, as well as further characterization of the viral genome(s). In some examples, the probes and primers can be designed to detect both BaAdV-2/4 and BaAdV-3. In some examples, the probes and primers distinguish BaAdV-2/4 and BaAdV-3 from BaAdV-1. In other embodiments, the probes and primers can be designed to detect BaAdV-2/4 only. In some examples, the probes and primers distinguish BaAdV-2/4 from BaAdV-3 and BaAdV-1. In further embodiments, the probes and primers can be designed to detect BaAdV-3 only. In some examples, the probes and primers distinguish BaAdV-3 from BaAdV-2/4 and BaAdV-1.

Nucleic acid probes can be prepared using routine methods, including automated oligonucleotide synthetic methods. A complement to any unique portion of the BaAdV-2/4 and/or BaAdV-3 genome will be satisfactory, for example a portion of the genome that allows for distinguishing the BaAdV of interest from other viruses that may be present in the sample, e.g., other BaAdV such as BaAdV-1 or other adenoviruses. For use as probes, complete complementarity is desirable, though it can be unnecessary as the length of the fragment is increased.

For use of such probes as diagnostics, the biological sample to be analyzed, such as blood or serum, can be treated, if desired, to extract the nucleic acids contained therein. The resulting nucleic acid from the sample can be subjected to gel electrophoresis or other size separation techniques; alternatively, the nucleic acid sample can be dot blotted without size separation. The probes are usually labeled with a detectable label. Suitable labels, and methods for labeling probes are known in the art, can include, for example, radioactive labels incorporated by nick translation or kinasing, biotin, fluorescent probes, and chemiluminescent probes. The nucleic acids extracted from the sample are then treated with the labeled probe under hybridization conditions of suitable stringencies.

The probes can be made completely complementary to the BaAdV-2/4 and/or BaAdV-3 genome or portion thereof (e.g., to all or a portion of a sequence encoding a BaAdV polypeptide). Therefore, usually high stringency conditions are desirable in order to prevent or at least minimize false positives. However, conditions of high stringency should only be used if the probes are complementary to regions of the viral genome which lack heterogeneity among BaAdV viral isolates. The stringency of hybridization is determined by a number of factors during hybridization and during the washing procedure, including temperature, ionic strength, length of time, and concentration of formamide (Sambrook et al. (1989), “Molecular Cloning; A Laboratory Manual,” Second Edition (Cold Spring Harbor Press, Cold Spring Harbor, N.Y.)).

Generally, it is expected that the BaAdV-2/4 or BaAdV-3 sequences will be present in a biological sample (e.g., blood, cells, and the liked) obtained from an infected individual at relatively low levels, such as at approximately $10^2$-$10^4$ BaAdV-2/4 or BaAdV-3 sequences per $10^6$ cells. This level can require that amplification techniques be used in hybridization assays. Such techniques are known in the art.

For example, the Enzo Biochemical Corporation “Bio-Bridge” system uses terminal deoxynucleotide transferase to add unmodified 3'-poly-dT-tails to a DNA probe. The poly dT-tailed probe is hybridized to the target nucleotide sequence, and then to a biotin-modified poly-A. PCT Publication No. WO84/03520 and European Application No. EPA124221 describe a DNA hybridization assay in which: (1) analyte is annealed to a single-stranded DNA probe that is complementary to an enzyme-labeled oligonucleotide; and (2) the resulting tailed duplex is hybridized to an enzyme-labeled oligonucleotide. European Published Patent Application No. 204510 describes a DNA hybridization assay in which analyte DNA is contacted with a probe that has a tail, such as a poly-dT tail, an amplifier strand that has a sequence that hybridizes to the tail of the probe, such as a poly-A sequence, and which is capable of binding a plurality of labeled strands.

One technique can first involve amplification of the target BaAdV-2/4 and/or BaAdV-3 sequences in sera approximately 10,000 fold, e.g., to approximately 10 sequences/mL. This can be accomplished, for example, by the polymerase chain reactions (PCR) technique (Saiki et al. (1986), by Mullis, U.S. Pat. No. 4,683,195, and by Mullis et al. U.S. Pat. No. 4,683,202). Other amplification methods are well known in the art.

The probes, or alternatively nucleic acid from the samples, can be provided in solution for such assays, or can be affixed to a support (e.g., solid or semi-solid support). Examples of supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride, diazotized paper, nylon membranes, activated beads, and Protein A beads.

Probes (or sample nucleic acid) can be provided on an array for detection. Arrays can be created by, for example, spotting polynucleotide probes onto a substrate (e.g., glass, nitrocellulose, and the like) in a two-dimensional matrix or array. The probes can be bound to the substrate by either covalent bonds or by non-specific interactions, such as hydrophobic interactions. Samples of polynucleotides can be detectably labeled (e.g., using radioactive or fluorescent labels) and then hybridized to the probes. Double stranded polynucleotides, comprising the labeled sample polynucleotides bound to probe polynucleotides, can be detected once the unbound portion of the sample is washed away. Techniques for constructing arrays and methods of using these arrays are described in EP 799 897; WO 97/29212; WO 97/27317; EP 785 280; WO 97/02357; U.S. Pat. Nos. 5,593,839; 5,578,832; EP 728 520; U.S. Pat. No. 5,599,695; EP 721 016; U.S. Pat. No. 5,556,752; WO 95/22058; and U.S. Pat. No. 5,631,734. Arrays are particularly useful where, for example a single sample is to be analyzed for the presence of two or more nucleic acid target regions, as the probes for each of the target regions, as well as controls (both positive and negative) can be provided on a single array. Arrays thus facilitate rapid and convenience analysis.

BaAdV Antibodies

Antibodies raised against BaAdV-2/4 and/or BaAdV-3 can serve a wide variety of purposes, as described herein, which include, but are not limited to, diagnostic assays for the detection of BaAdV-2/4 and/or BaAdV-3. These antibodies can also be used for treatment. The antibody specifically binds a BaAdV-2/4 polypeptide, or as a BaAdV-3 polypeptide. Specific, non-limiting examples include an antibody that specifically binds a polypeptide at least about 90%, 91%, 92%, 93%, 94%, 95%, 96%, 97%, 98%, 99%, or 100% identical to one of SEQ ID NOs: 5-109. The antibodies include polyclonal or monoclonal antibodies. In some embodiments, the antibody specifically binds to a polypeptide encoded by one of SEQ ID NOs: 1-3, wherein the antibody does not specifically bind to a polypeptide encoded by SEQ ID NO: 4.

A number of immunogens comprising portions of a BaAdV-2/4 and/or BaAdV-3 protein, virus or nucleic acid can be used to produce antibodies specifically reactive with the BaAdV-2/4 and/or BaAdV-3. In some embodiments, the antibody specifically binds BaAdV-2/4 and not BaAd-3 or BaAdV-1. In other embodiments, the antibody specifically binds BaAdV-3 and not BaAd-2/4 or BaAdV-1. In further embodiments, the antibody specifically binds BaAdV-3 and BaAd-2/4 but not BaAdV-1. In several non-limiting examples, the antibody specifically binds one of SEQ ID NO: 5-109. The antibody can be a monoclonal antibody, or a fragment thereof that specifically binds one of SEQ ID NOs: 5-109.

In some embodiments, a recombinant BaAdV-2/4 or BaAdV-3 protein or an antigenic fragment thereof, can be isolated as described herein. Recombinant protein can be expressed in eukaryotic or prokaryotic cells as described above, and purified as generally described above. Recombinant protein can then be used as an immunogen for the production of monoclonal or polyclonal antibodies. Alternatively, a synthetic peptide derived from the sequences disclosed herein and conjugated to a carrier protein can be used an immunogen. Naturally occurring protein can also be used either in pure or impure form. The product is then injected into an animal capable of producing antibodies. Either monoclonal or polyclonal antibodies can be generated, for subsequent use in immunoassays to measure the polypeptide.

Methods of producing an antibody that specifically binds a BaAdV-2/4 or BaAdV-3 are disclosed herein. For preparation of antibodies, e.g., recombinant, monoclonal, or polyclonal antibodies, many technique can be used (see, e.g., Kohler & Milstein, *Nature* 256:495-497 (1975); Kozbor et al., *Immunology Today* 4: 72 (1983); Cole et al., pp. 77-96 in *Mono-*

*clonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)).

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies can be obtained by various techniques familiar to those skilled in the art. Briefly, spleen cells from an animal immunized with a desired antigen, such as a BaAdV-2/4 or BaAdV-3 polypeptide, are immortalized, commonly by fusion with a myeloma cell (see, Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells can be enhanced by various techniques, including injection into the peritoneal cavity of a vertebrate host. Alternatively, one can isolate DNA sequences which encode a monoclonal antibody or a binding fragment thereof by screening a DNA library from human B cells according to the general protocol outlined by Huse, et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-BaAdV proteins and nucleic acids, using a competitive binding immunoassay. Specific polyclonal antisera and monoclonal antibodies will usually bind with a Kd of at least about 0.1 mM, more usually at least about 1 uM, preferably at least about 0.1 uM or better, and most preferably, 0.01 uM or better. Antibodies specific only for a particular BaAdV protein can also be made by subtracting out other cross-reacting proteins. In this manner, antibodies that bind only to the protein of choice can be obtained.

Phage display technology can be used to identify antibodies and heteromeric Fab fragments that specifically bind to selected antigens, such as a BaAdV-2/4 or BaAdV-3 polypeptide (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Chimeric antibodies can be used, which is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

Humanized or primatized antibodies can be used. Generally, a humanized antibody has one or more amino acid residues introduced into it from a source which is non-human. These non-human amino acid residues are often referred to as import residues, which are typically taken from an import variable domain. Methods for humanizing or primatizing non-human antibodies are well known in the art. Humanization can be essentially performed following the method of Winter and co-workers (see, e.g., Jones et al., *Nature* 321: 522-525 (1986); Riechmann et al., *Nature* 332:323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816, 567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Antibody fragments are encompassed by the present disclosure, such as Fab, $F(ab')_2$, and Fv which include a heavy chain and light chain variable region. These antibody fragments retain the ability to selectively bind with the antigen. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab)_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule.

(6) A dimer of a single chain antibody ($scFV_2$), defined as a dimer of a scFV. This has also been termed a "minianti-body."

Methods of making these fragments are known in the art (see for example, Harlow and Lane, *Antibodies: A Laboratory Manual*, Cold Spring Harbor Laboratory, New York, 1988).

In some embodiments, the antibodies and antigen binding fragments thereof can be conjugated to an effector molecule, such as a label or a toxin. Useful detection agents include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein, Yellow fluorescent protein. An antibody or antigen binding fragment thereof can also be labeled with enzymes that are useful for detection, such as horseradish peroxidase, β-galactosidase, luciferase, alkaline phosphatase, glucose oxidase and the like. When an antibody or antigen binding fragment thereof is labeled with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody or antigen binding fragment thereof may also be labeled with biotin, and detected through indirect measurement of avidin or streptavidin binding. It should be noted that the avidin itself can be labeled with an enzyme or a fluorescent label.

An antibody or antigen binding fragment thereof may be labeled with a magnetic agent, such as gadolinium. Antibodies and antigen binding fragments can also be labeled with lanthanides (such as europium and dysprosium), and manganese. Paramagnetic particles such as superparamagnetic iron oxide are also of use as labels. An antibody or antigen binding fragment may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

An antibody or antigen binding fragment can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

Detecting BaAdV Polypeptides

A BaAdV infection, such as a BaAdV-2/4 and a BaAdV-3 infection, can be detected based on the level of the particular BaAdV polypeptide sample. Antibodies that are specific to a BaAdV can be used for detection of BaAdV, diagnosis of a BaAdV infection, confirm an earlier infection, and determine BaAdV viral load. In some embodiments, antibodies that specifically bind BaAdV-2/4 can be used for detection of BaAdV-2/4, diagnosis, and determination of BaAdV-2/4 viral load. In other embodiments, antibodies that specifically bind BaAdV-3 can be used for detection of BaAdV-3, diagnosis, and determination of BaAdV-3 viral load. In further embodiments, these methods distinguish a BaAdV-3 infection, such as from a BaAdV-2/4 infection and/or a BaAdV-1 infection. In further embodiments, antibodies that specifically bind BaAdV-2/4 can be used for detection of BaAdV-2/4, diagnosis, and determination of BaAdV-2/4 viral load. In further embodiments, these methods distinguish a BaAdV-2/4 infection, such as from a BaAdV-3 infection and/or a BaAdV-1 infection. In some embodiments, the method distinguishes BaAdV-2/4 and/or BaAdV-3 from BaAdV-1.

Thus, in certain embodiments, methods are provided that utilize an antibody specifically binds BaAdV-2/4 and not BaAd-3 or BaAdV-1 polypeptide(s), and thus can be used for the specific detection of BaAdV-2/4. Thus, the antibody can be used to distinguish (delineate) a BaAdV-2/4 infection from a BaAd3-and BaAdV-1 infection. In other embodiments, methods are provided that utilize an antibody specifically binds BaAdV-3 and not BaAd-2/4 or BaAdV-1 polypeptide(s), and thus can be utilized for specific detection of BaAdV-3. Thus, the antibody can be used to distinguish (delineate) a BaAdV-infection from a BaAdV-1 and BaAd-2/4 infection. In further embodiments, methods are provided that utilize an antibody that specifically binds both BaAdv-3 and BaAdv-2/4 polypeptides, and thus can be utilized to specifically detect both BaAdV-3 and BaAd-2/4, but not BaAdV-1. Thus, the antibody can be used to distinguish (delineate) a BaAdV-3/BaAdV-2/4 infection from a BaAdV-1 infection. In some embodiments, the antibody is a monoclonal antibody. In other embodiments, the antibody is directly labeled. In some non-limiting examples, the antibody specifically binds a BaAdV-2/4 polypeptide, and/or a BaAdV-3 polypeptide, such as polypeptide at least about 90%, 91%, 92%, 93%, 94%, 95%, 96%, 97%, 98%, 99%, or 100% identical to one of SEQ ID NOs: 5-109.

Once the specific antibodies against a BaAdV protein, virus or nucleic acid in are available, the antigen can be detected and/or quantified using any of a number of well recognized immunological binding assays (see, e.g., U.S. Pat. Nos. 4,366,241; 4,376,110; 4,517,288; and 4,837,168). BaAdV viral particles can be detected based on an epitope defined by the viral proteins as presented in a viral particle and/or an epitope defined by a viral protein that is separate from a viral particle. As used in this context, then, "antigen" is meant to refer to a BaAdV polypeptide as well as BaAdV viral particles. For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice. The antibody can be produced by any of a number of means well known to those of skill in the art and as described above. Immunoassays for detecting BaAdV protein, virus and nucleic acid in samples can be either competitive or noncompetitive, and can be either quantitative or non-quantitative.

Noncompetitive immunoassays are assays in which antigen is directly detected and, in some instances the amount of antigen directly measured. Enzyme mediated immunoassays such as immunofluorescence assays (IFA), enzyme linked immunosorbent assays (ELISA), immunoblotting (western), and capture assays can be readily adapted to accomplish the noncompetitive detection of the BaAdV proteins.

An ELISA method effective for the detection of the BaAdV can, for example, be as follows: (1) bind an antibody or antigen to a substrate; (2) contact the bound receptor with a fluid or tissue sample containing the virus, a viral antigen, or antibodies to the virus; (3) contact the above with an antibody bound to a detectable moiety (e.g., horseradish peroxidase enzyme or alkaline phosphatase enzyme); (4) contact the above with the substrate for the enzyme; (5) contact the above with a color reagent; (6) observe color change. The above method can be readily modified to detect presence of an anti-BaAdV antibody in the sample or a specific BaAdV polypeptide as well as the virus.

Western blot (immunoblot) analysis can be used to detect and quantify the presence of BaAdV antigen in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the BaAdV antigen. The anti-BaAdV antigen antibodies specifically bind to the BaAdV antigen on the solid support. These antibodies can be directly labeled or alternatively can be subsequently detected using labeled antibodies (e.g., labeled sheep anti-mouse antibodies) that specifically bind to the anti-BaAdV antigen antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. CIM. Prod. Rev.* 5:34-41 (1986)).

A BaAdV antigen and/or a patient's antibodies to the virus can be detected utilizing a capture assay. Briefly, to detect antibodies to BaAdV in a patient sample, antibodies to the patient's immunoglobulin, e.g., anti-IgG (or IgM) are bound to a solid phase substrate and used to capture the patient's immunoglobulin from serum. BaAdV, or reactive fragments of BaAdV, are then contacted with the solid phase followed by addition of a labeled antibody. The amount of patient BaAdV specific antibody can then be quantitated by the amount of labeled antibody binding. In some embodiments, a method is provided for detecting a baboon adenovirus (BaAdV)-3 or a BaAdV-2/4 infection in a subject. The method includes the steps of: (a) contacting a sample from the subject suspected of having an infection caused by the BaAdV-3 or the BaAdV-2/4 with a BaAdv-3 or BaAdv-2/4 polypeptide, wherein the sample comprises antibodies from the subject, and (b) detecting the binding of the antibodies to the polypeptide, thereby detecting the BaAdV-3 or a BaAdV-2/4 infection.

In competitive assays, BaAdV antigen present in a sample can be detected indirectly by detecting a decrease in a detectable signal associated with a known, added (exogenous) BaAdV antigen displaced (competed away) from an anti-BaAdV antigen antibody by the unknown BaAdV antigen present in a sample.

Competitive assays can also be adapted to provide for an indirect measurement of the amount of BaAdV antigen present in the sample. Briefly, serum or other body fluids from the subject is reacted with an antibody bound to a substrate (e.g. an ELISA 96-well plate). Excess serum is thoroughly washed away. A labeled (enzyme-linked, fluorescent, radioactive, etc.) monoclonal antibody is then reacted with the previously reacted BaAdV virus-antibody complex. The amount of inhibition of monoclonal antibody binding is measured relative to a control. MABs can also be used for detection directly in samples by IFA for MABs specifically reactive for the antibody-virus complex.

A hapten inhibition assay is another competitive assay. In this assay the known BaAdV antigen can be immobilized on a solid substrate. A known amount of anti-BaAdV antibody is added to the sample, and the sample is then contacted with the immobilized BaAdV antigen. The amount of anti-BaAdV antibody bound to the known immobilized BaAdV antigen is inversely proportional to the amount of BaAdV antigen present in the sample. The amount of immobilized antibody can be detected by detecting either the immobilized fraction of antibody or the fraction of the antibody that remains in solution. Detection can be direct where the antibody is labeled or indirect by the subsequent addition of a labeled moiety that specifically binds to the antibody as described above.

Immunoassays in the competitive binding format can also be used for crossreactivity determinations. For example, a BaAdV antigen can be immobilized to a solid support. Proteins can be added to the assay that compete for binding of the antisera to the immobilized antigen. The ability of the added proteins to compete for binding of the antisera to the immobilized protein is compared to the ability of the BaAdV antigen to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera can then be used in a competitive binding immunoassay as described above to compare a second protein, thought to be perhaps an allele or polymorphic variant of a BaAdV antigen, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the BaAdV antigen that is required to inhibit 50% of binding, then the second protein is said to specifically bind to the polyclonal antibodies generated to BaAdV antigen.

Immunoassays (both competitive and non-competitive) also often use a labeling agent to specifically bind to and label the complex formed by the antibody and antigen. The labeling agent can itself be one of the moieties comprising the antibody/antigen complex. Thus, the labeling agent can be a labeled BaAdV protein nucleic acid or a labeled anti-BaAdV antibody. Alternatively, the labeling agent can be a third moiety, such a secondary antibody that specifically binds to the antibody/antigen complex (a secondary antibody is typically specific to antibodies of the species from which the first antibody is derived). Other proteins capable of specifically binding immunoglobulin constant regions, such as protein A or protein G can also be used as a label agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art, and can be any material detectable by spectroscopic, photochemical, biochemical, immunochemical, electrical, optical or chemical means. Such detectable labels have been well-developed in the field of immunoassays and can include, but are not limited to, magnetic beads (e.g., DYNABEADS™), fluorescent dyes (e.g., fluorescein isothiocyanate, Texas red, rhodamine, and the like), radiolabels (e.g., 3H, 125j 35s, 14, e, or —$^{12}$P) enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label can be coupled directly or indirectly to the desired component of the assay according to methods well known in the art. As indicated above, a wide variety of labels can be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize BaAdV antigen, or secondary antibodies that recognize anti-BaAdV antigen.

The molecules can also be conjugated directly to signal generating compounds, e.g., by conjugation with an enzyme or fluorophore, see above. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that can be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it can be detected by exciting the fluorochrome with the appropriate wavelength of light and detecting the resulting fluorescence. The fluorescence can be detected visually, by the use of electronic detectors such as charge coupled devices (CCDs) or photomultipliers and the like. Similarly, enzymatic labels can be detected by providing the appropriate substrates for the enzyme and detecting the resulting reaction product. Colorimetric or chemiluminescent labels can be detected simply by observing the color associated with the label. Thus, in various dipstick assays, conjugated gold often appears pink, while various conjugated beads appear the color of the bead.

Some assay formats do not require the use of labeled components. For instance, a micro-agglutination test can also be used to detect the presence of BaAdV in test samples. Briefly, latex beads are coated with an antibody and mixed with a test sample, such that BaAdV in the tissue or body fluids that is specifically reactive with the antibody crosslink with the receptor, causing agglutination. The agglutinated antibody-virus complexes within a precipitate, visible with the naked eye or by spectrophotometer. Other assays include serologic assays, in which the relative concentrations of IgG and IgM are measured.

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

In the diagnostic methods described above, the sample can be taken directly from a subject or in a partially purified form. The sample can be any sample of interest, including blood, serum or plasma. The antibody specific for a particular BaAdV (the primary reaction) reacts by binding to the virus. Thereafter, a secondary reaction with an antibody bound to, or labeled with, a detectable moiety can be added to enhance the detection of the primary reaction. Generally, in the secondary reaction, an antibody or other ligand which is reactive, either specifically or nonspecifically with a different binding site (epitope) of the virus will be selected for its ability to react with multiple sites on the complex of antibody and virus. Thus, for example, several molecules of the antibody in the secondary reaction can react with each complex formed by the primary reaction, making the primary reaction more detectable.

Assays for Modulators of BaAdV

Modulation of a BaAdV, such as BaAdV-2/4 or BaAdV-3, can be assessed using a variety of in vitro and in vivo assays, including cell-based models. Such assays can be used to test for inhibitors and activators of BaAdV-2/4 and/or BaAdV-3. Modulators of BaAdV-2/4 and/or BaAdV-3 are tested using either recombinant or naturally occurring protein of choice. Modulation can include, but is not limited to, modulation of infection, replication, receptor binding, cell entry, particle formation, and the like.

Measurement of modulation of a BaAdV-2/4 and/or BaAdV-3 polypeptide, or a cell expressing BaAdV-2/4 and/or BaAdV-3, either recombinant or naturally occurring, can be performed using a variety of assays, in vitro, in vivo, and ex vivo, as described herein. A suitable physical, chemical or phenotypic change that affects activity, e.g., enzymatic activity, cell surface marker expression, viral replication and proliferation can be used to assess the influence of a test compound on the polypeptide of this invention. When the functional effects are determined using intact cells or animals, one can also measure a variety of effects.

Assays to identify compounds with BaAdV-2/4 and/or BaAdV-3 modulating activity can be performed in vitro. Such assays can use full length BaAdV-2/4 or BaAdV-3 polypeptide or a variant thereof, or a mutant thereof, or a fragment thereof. Purified recombinant or naturally occurring protein can be used in the in vitro methods of the invention. The recombinant or naturally occurring protein can be part of a cellular lysate or a cell membrane. As disclosed below, the binding assay can be either solid state or soluble. Preferably, the protein or membrane is bound to a solid support, either covalently or non-covalently. Often, the in vitro assays of the invention are substrate or ligand binding or affinity assays, either non-competitive or competitive. Other in vitro assays include measuring changes in spectroscopic (e.g., fluorescence, absorbance, refractive index), hydrodynamic (e.g., shape), chromatographic, or solubility properties for the protein.

A high throughput binding assay can be performed in which the protein or a fragment thereof is contacted with a potential modulator and incubated for a suitable amount of time. In one embodiment, the potential modulator is bound to a solid support, and the protein is added. In another embodiment, the protein is bound to a solid support. A wide variety of modulators can be used, as described below, including small organic molecules, peptides, antibodies, etc. A wide variety of assays can be used to identify BaAdV-2/4 and/or BaAdV-3-modulator binding, including labeled protein-protein binding assays, electrophoretic mobility shifts, immunoassays, enzymatic assays, and the like. In some cases, the binding of the candidate modulator is determined through the use of competitive binding assays, where interference with binding of a known ligand or substrate is measured in the presence of a potential modulator. Either the modulator, the known ligand, or substrate is bound first; then the competitor is added. After the protein is washed, interference with binding, either of the potential modulator or of the known ligand or substrate, is determined. Often, either the potential modulator or the known ligand or substrate is labeled.

A cell-based assay can be used in which the BaAdV-2/4 or BaAdV-3 is expressed in a cell, and functional, physical, chemical and phenotypic changes are assayed to identify viral modulators. Any suitable functional effect can be measured as described herein, in addition to viral inhibition assays as are well known in the art. The BaAdV-2/4 or BaAdV-3 can be naturally occurring or recombinant. Also, fragments of the BaAdV-2/4 or BaAdV-3 or chimeric proteins can be used in cell based assays. In addition, point mutants in essential residues required by the catalytic site can be used in these assays.

In one embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks. The assay can also be used to screen libraries of molecular agents, such as antibodies or inhibitory RNAs, or to screen libraries of small molecules.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. *J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *I Amer. Chem. Soc.* 116:2661 (1994)), oligocarbamates (Cho et al., *Science* 261:1303 (1993)), and/or peptidyl phosphonates (Campbell et al., *I Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996)), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

A solid state or soluble high throughput assaying using a BaAdV-2/4 or BaAdV-3, or a cell or tissue expressing a BaAdV-2/4 or BaAdV-3 protein can be used. A solid phase based in vitro assay can be used in a high throughput format can be used where BaAdV-2/4 and/or BaAdV-3 is attached to a solid phase. Any one of the assays described herein can be adapted for high throughput screening.

In high throughput assays, either soluble or solid state, it is possible to screen up to several thousand different modulators or ligands in a single day. This methodology can be used for BaAdV-2/4 or BaAdV-3 in vitro, or for cell-based or membrane-based assays comprising a BaAdV. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non-covalent linkage. A tag for covalent or non-covalent binding can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like (see, e.g., Pigott & Power, *The Adhesion Molecule Facts Book I* (1993)). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, polyethylene glycol linkers are available from Shearwater Polymers, Inc. Huntsville, Ala. These linkers optionally have amide linkages, sulfhydryl linkages, or hetero functional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature (e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., Science, 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates)). Non-chemical approaches for fixing tag binders to substrates include other common methods, such as heat, cross-linking by UV radiation, and the like.

The compounds tested as modulators of BaAdV-2/4 or BaAdV-3 can be any small organic molecule, or a biological entity, such as a protein, e.g., an antibody or peptide, a sugar, a nucleic acid, e.g., an antisense oligonucleotide or a ribozyme or siRNA, or a lipid.

Alternatively, modulators can be genetically altered versions of a BaAdV. Typically, test compounds will be small organic molecules, peptides, circular peptides, siRNA, antisense molecules, ribozymes, and lipids.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

Treating/Preventing BaAdV and Pharmaceutical Compositions

Embodiments described herein further relate to the therapeutic, prophylactic and research uses of various techniques to block or modulate the expression of BaAdV-2/4 and/or BaAdV-3 viral proteins or propagation of the virus. Methods are also provided for inducing an immune response to BaAdV-2/4 and/or BaAdV-3. Modulators of BaAdV-2/4 and/or BaAdV-3 useful for treating or preventing BaAdV-2/4 and/or BaAdV-3 can include, but is not limited to, genetically modified versions of BaAdV-2/4 and/or BaAdV-3, e.g., versions with altered activity, heat killed and attenuated viruses, as well as naturally occurring and synthetic ligands, substrates, antagonists, agonists, antibodies, peptides, cyclic peptides, aptamers, nucleic acids, antisense molecules, ribozymes, siRNA molecules, miRNA molecules, and small chemical molecules, as is well known in the art.

Methods of treating or preventing a Baboon adenovirus (BaAdV)-2/4 or BaAdV-3 infection in a subject are provided herein. These methods include administering to the subject a therapeutically effective dose of one or more of an agents identified using the assays disclosed herein, the nucleic acid molecules discloses herein, the polypeptides disclosed herein or an immunogenic fragment thereof, a replication defective adenovirus disclosed herein, or an antibody disclosed herein.

Methods of inducing an immune response to a Baboon adenovirus (BaAdV)-2/4 or BaAdV-3 are disclosed herein. These methods include administering to the subject a therapeutically effective dose of one or more of an agents identified using the assays disclosed herein, the nucleic acid molecules discloses herein, the polypeptides disclosed herein or an immunogenic fragment thereof, a replication defective adenovirus disclosed herein, or an antibody disclosed herein. The subject can be any subject of interest, including a human or a non-human primate.

In some embodiments, an aptamer is administered to the subject. The aptamer is an siRNA or antisense molecule comprising a double-stranded region of about 15 to about 60 nucleotides in length and has at least 90% identity over its length to a corresponding segment of SEQ ID NO:1, SEQ ID NO: 2 or SEQ ID NO: 3.

Further disclosed herein are BaAdV-2/4 and BaAdV-3 vaccines for therapeutic or prophylactic purposes. Within certain aspects, BaAdV-2/4 and/or BaAdV-3 virus, proteins or peptides and immunogenic fragments thereof, and/or polynucleotides, as well as anti-BaAdV-2/4 and anti-BaAdV-3 antibodies and/or T cells, can be incorporated into pharmaceutical compositions or immunogenic compositions. Whole virus vaccines (live and attenuated, or replication incompetent, or killed) or subunit vaccines, such as structural or non-structural BaAdV-2/4 and/or BaAdV-3 proteins or immunogenic fragments thereof, can be used to treat or prevent BaAdV-2/4 and/or BaAdV-3 infections, respectively by eliciting an immune response in a subject. Alternatively, a pharmaceutical composition can comprise an antigen-presenting cell (e.g., a dendritic cell) transfected with a BaAdV-2/4 or BaAdV-3 polynucleotide such that the antigen-presenting cell expresses a BaAdV-2/4 or BaAdV-3 peptide, respectively.

Nucleic acid vaccines encoding a genome, structural protein or non-structural protein or a fragment thereof of BaAdV-2/4 and/or BaAdV-3 can also be used to elicit an immune response to treat or prevent BaAdV-2/4 and/or BaAdV-3 infection, respectively. Numerous gene delivery techniques are well known in the art, such as those described by Rolland (1998) *Crit. Rev. Therap. Drug Carrier Systems* 15:143-198, and references cited therein. Appropriate nucleic acid expression systems contain the necessary DNA sequences for expression in the patient (such as a suitable promoter and terminating signal). In a preferred embodiment, the DNA can be introduced using a viral expression system (e.g., vaccinia, pox virus, retrovirus, or adenovirus), which can involve the use of a non-pathogenic (defective), replication competent virus. Suitable systems are disclosed, for example, in Fisher-Hoch et al. (1989) *Proc. Natl. Acad. Sci. USA* 86:317-321; Flexner et al. (1989) *Ann. N.Y. Acad. Sci.* 569:86-103; Flexner et al. (1990) *Vaccine* 8:17-21; U.S. Pat. Nos. 4,603,112, 4,769,330, 4,777,127 and 5,017,487; PCT Publication No. WO 89/01973; Great Britain Publication No. 2,200,651; European Publication No. 0,345,242; PCT Publication No. WO 91/02805; Berkner (1988) *Biotechniques* 6:616-627; Rosenfeld et al. (1991) *Science* 252:431-434; Kolls et al. (1994) *Proc. Natl. Acad. Sci. USA* 91:215-219; Kass-Eisler et al. (1993) *Proc. Natl. Acad. Sci. USA* 90:11498-11502; Guzman et al. (1993) *Circulation* 88:2838-2848; and Guzman et al. (1993) *Cir. Res.* 73:1202-1207. Techniques for incorporating DNA into such expression systems are well known to those of ordinary skill in the art. The DNA can also be "naked," as described, for example, in Ulmer et al. (1993) *Science* 259:1745-1749 and reviewed by Cohen (1993) *Science* 259:1691-1692. The uptake of naked DNA can be increased by coating the DNA onto biodegradable beads, which are efficiently transported into the cells. It will be apparent that a vaccine can comprise both a polynucleotide and a polypeptide component. Such vaccines can provide for an enhanced immune response.

Vaccine preparation is generally described in, for example, Powell and Newman, eds., *Vaccine Design* (the subunit and adjuvant approach), Plenum Press (NY, 1995). Vaccines can be designed to generate antibody immunity and/or cellular immunity such as that arising from CTL or CD4+ T cells.

A non-specific immune response enhancer can be any substance that enhances an immune response to an exogenous antigen. Examples of non-specific immune response enhancers include adjuvants, biodegradable microspheres (e.g., polylactic galactide) and liposomes (into which the compound is incorporated; see, e.g., U.S. Pat. No. 4,235,877). Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, can also be used as adjuvants. These are of use in inducing an immune response.

Pharmaceutical compositions and vaccines can also contain other compounds, which can be biologically active or inactive. For example, one or more immunogenic portions of other antigens can be present, either incorporated into a fusion polypeptide or as a separate compound, within the composition or vaccine. Polypeptides can, but need not be, conjugated to other macromolecules as described, for example, within U.S. Pat. Nos. 4,372,945 and 4,474,757. Pharmaceutical compositions and vaccines can generally be used for prophylactic and therapeutic purposes.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and *acacia* emulsions, gels, and the like containing, in addition to the active ingredient, carriers known in the art.

Aerosol formulations (i.e., they can be "nebulized") are administered via inhalation. Aerosol formulations can be placed into pressurized acceptable propellants, such as dichlorodifluoromethane, propane, nitrogen, and the like.

Formulations suitable for parenteral administration, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Compositions can be administered, for example, by intravenous infusion, inhalation, parenterally, orally, topically, intradermally, intraperitoneally, intravenously, intravesically, rectally or intrathecally. The formulations can be presented in unit-dose or multi-dose sealed containers, such as ampules and vials. Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences,* 17$^{th}$ ed., 1989).

Such compositions can also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention can be formulated as a lyophilizate. Compounds can also be encapsulated within liposomes using well known technology.

Injection solutions and suspensions can be prepared from sterile powders, granules, and tablets of the kind previously described. Cells transduced by nucleic acids for ex vivo therapy can also be administered intravenously or parenterally.

The dose administered to a subject should be sufficient to affect a beneficial therapeutic response in the subject over time, and/or to induce an immune response. The dose will be determined by the efficacy of the particular agent employed and the condition of the subject, as well as the body weight or surface area of the subject to be treated. The size of the dose also will be determined by the existence, nature, and extent of any adverse side-effects that accompany the administration of a particular vector, or transduced cell type in a particular subject. In some embodiments, the agent is the agent is administered orally, topically, intraarticularly, intravenously, intramuscularly, intradermally, intraperitoneally or subcutaneously.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

Pharmaceutical and vaccine compositions can be presented in unit-dose or multi-dose containers, such as sealed ampoules or vials. Such containers are preferably hermetically sealed to preserve sterility of the formulation until use. In general, formulations can be stored as suspensions, solutions or emulsions in oily or aqueous vehicles. Alternatively, a vaccine or pharmaceutical composition can be stored in a freeze-dried condition requiring only the addition of a sterile liquid carrier immediately prior to use.

Additional Diagnostic and Therapeutic Methods

Methods are also provided for identifying subjects and managing the therapeutic treatment of subjects, such as those subjects who are at an increased risk of a BaAdV-2/4 or a BaAdV-3 infection. In some embodiments the methods include using the BaAdV-2/4 or a BaAdV-3 nucleic acids, polypeptides or antibodies disclosed herein to detect a BaAdV-2/4 or a BaAdV-3 infection in a subject. The subject can be at increased risk for infection, such as a worker in a primate colony, such as one that houses baboons. The subject can also be an individual who has contact with a worker in a primate colony, such as, but not limited to, a household member. In some embodiments, the subject can be asymptomatic.

The provided methods of identifying BaAdV-2/4 or a BaAdV-3 can be used to assist a clinician in selection of a therapy for an infected subject. These therapies include, but are not limited to, therapeutically effective amounts of antiviral agents and/or BaAdV-2/4 or a BaAdV-3 polypeptides, polynucleotides and/or antibodies sufficient to induce an immune response to BaAdV-2/4 or a BaAdV-3.

In some embodiments, the disclosed methods of identifying BaAdV-2/4 or a BaAdV-3 can be used to identify subjects that are at risk of developing a symptomatic infection. If the subject is identified as having a BaAdV-2/4 or a BaAdV-3 infection (e.g., by detection of a BaAdV-2/4 or a BaAdV-3 nucleic acid, polypeptide, or antibodies), but is not symptomatic, then the subject is treated.

In several embodiments, the disclosed methods of identifying BaAdV-2/4 or BaAdV-3 can be used to assist a clinician in selection and/or monitoring of a therapy for a subject. In additional embodiments, a subject receiving therapy (e.g., subject with BaAdV-2/4 or a BaAdV-3 infection) can be monitored for the presence of BaAdV-2/4 and/or a BaAdV-3 polynucleotide, polypeptide and/or antibodies in a biological sample from the subject. In some embodiments, the subject is initially identified as having a BaAdV-2/4 or a BaAdV-3 infection (e.g., by detection of a BaAdV-2/4 or a BaAdV-3 polypeptide, polynucleotide or antibody in a biological sample from the subject as described herein). The subject is administered a therapeutic agent of interest. In some examples, if a level of a BaAdV-2/4 or a BaAdV-3 polypeptide, polynucleotide or antibody decreases following administration of the therapeutic agent, as compared to a control, then the therapy is effective. In other examples, if the level of a BaAdV-2/4 or a BaAdV-3 polypeptide, polynucleotide or antibody increases or does not change after administration of the therapeutic agent, as compared to a control, then the therapy is ineffective. In some examples, if more severe symptoms of BaAdV-2/4 or a BaAdV-3 infection appear in the subject, the treatment can be stopped, or the dosage of the therapeutic agent can be increased.

The control can be a standard value. The control can be the level of the BaAdV-2/4 or a BaAdV-3 polypeptide, polynucleotide or antibody in a control sample, such as, but not limited to, a sample from the subject at a prior time-point, such as prior to initiation of therapy, or can be the level of the BaAdV-2/4 or a BaAdV-3 polypeptide, polynucleotide or antibody in a sample from a subject with a known infection.

Methods for determining the prognosis of a BaAdV-2/4 or a BaAdV-3 infection are also provided. In some examples, if a level of a BaAdV-2/4 or a BaAdV-3 polypeptide, polynucleotide or antibody is decreased as compared to a control, then the subject will not develop an active infection with BaAdV-2/4 or a BaAdV-3. In other examples, if the level of a BaAdV-2/4 or a BaAdV-3 polypeptide, polynucleotide or antibody is increased (or does not change), as compared to a control, then the subject will develop an active infection with BaAdV-2/4 or a BaAdV-3. The control can be a standard value. The control can be the level of the BaAdV-2/4 or a BaAdV-3 polypeptide, polynucleotide or antibody in a control sample, such as, but not limited to, a sample from the subject prior to infection, or can be the level of the BaAdV-2/4 or a BaAdV-3 polypeptide, polynucleotide or antibody in a sample from a subject known not to be infected.

In some embodiments, the subject can be monitored daily, weekly, biweekly, monthly, bi-monthly, quarterly, or annually.

Kits

The invention further provides diagnostic reagents and kits comprising one or more such reagents for use in a variety of diagnostic assays, including for example, immunoassays such as ELISA and "sandwich" type immunoassays, as well as nucleic acid assay, e.g., PCR assays. In a related embodiment, the assay is performed in a flow-through or strip test format, wherein the binding agent is immobilized on a membrane, such as nitrocellulose.

In some embodiments, the kit includes a container comprising a nucleic acid molecule as disclosed herein, a polypeptide encoded by the nucleic acid or an immunogenic fragment thereof, a vector comprising the nucleic acid, a host cell comprising the vector, an adenovirus comprising the nucleic acid, or an antibody that specifically binds the polypeptide, or a primer that hybridizes to the nucleotide sequence set forth SEQ ID NO:1, SEQ ID NO: 2 or SEQ ID NO: 3 under highly stringent conditions, and instructions for using the kit.

In additional embodiments, the kit can include the polypeptide as disclosed herein, and instructions for the detection of the presence of antibodies that specifically bind Baboon adenovirus (BaAdV)-3 or BaAdV-4 in a sample from a subject. In further embodiments, the kit includes an antibody as disclosed herein and instructions for the detection of the presence of a Baboon adenovirus (BaAdV)-3 or BaAdV-4 polypeptide in a sample from a subject.

The kit can include one or more probes or primers specific for a BaAd-3 or a BaAdv-2/4 nucleic acid sequence. The kit can include one or more antibodies, such as a monoclonal or polyclonal antibody that specifically binds a BaAdV-3 or BaAdv-2/4 polypeptide. The kit can also include one or more BaAdV-2/4 or BaAdv-3 polypeptides.

In several embodiments, such kits can include at least a first peptide, or a first antibody or antigen binding fragment of the invention, a functional fragment thereof, or a cocktail thereof, or a first nucleic acid molecule, and means for signal generation. The kit's components can be pre-attached to a solid support, or can be applied to the surface of a solid support when the kit is used. The signal generating means can come pre-associated with an antibody or nucleic acid of the invention or can require combination with one or more components, e.g., buffers, nucleic acids, antibody-enzyme conjugates, enzyme substrates, or the like, prior to use.

Kits can also include additional reagents, e.g., blocking reagents for reducing nonspecific binding to the solid phase surface, washing reagents, enzyme substrates, enzymes, and the like. The solid phase surface can be in the form of microtiter plates, microspheres, or other materials suitable for immobilizing nucleic acids, proteins, peptides, or polypeptides. An enzyme that catalyzes the formation of a chemiluminescent or chromogenic product or the reduction of a chemiluminescent or chromogenic substrate is one such component of the signal generating means. Such enzymes are well known in the art. Where a radiolabel, chromogenic, fluorigenic, or other type of detectable label or detecting means is included within the kit, the labeling agent can be provided either in the same container as the diagnostic or therapeutic composition itself, or can alternatively be placed in a second distinct container means into which this second composition can be placed and suitably aliquoted. Alternatively, the detection reagent and the label can be prepared in a single container means, and in most cases, the kit will also typically include a means for containing the vial(s) in close confinement for commercial sale and/or convenient packaging and delivery.

The kit can include one or more containers for storing a disclosed antibody, nucleic acid or polypeptide, as well as and a label or package insert on or associated with the container. Suitable containers include, for example, bottles, vials, syringes, etc. The containers may be formed from a variety of materials such as glass or plastic. The container holds a composition which is effective for diagnosis and/or treatment. In some embodiments, the container can have a sterile access port (for example the container may be an intravenous solution bag or a vial having a stopper pierceable by a hypodermic injection needle). The label or package insert indicates that the contents are used for treating the particular condition, or for detection/diagnosis.

In some embodiments, the kit includes instructional materials, such as the package insert, which discloses means of use of a BaAdv-3 or BaAd-2/4 polypeptide, nucleic acid, or antibody. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method.

The disclosure is illustrated by the following non-limiting Examples.

EXAMPLES

Adenoviruses (AdVs) are DNA viruses that infect and cause a broad range of clinical illnesses in vertebrate hosts, including humans and nonhuman primates. As disclosed below, a novel AdV species was identified, provisionally named "species H", linked to an outbreak of acute respiratory illness in captive baboons (4 of 9) at a primate research facility, with a case fatality rate of 50%. AdVs isolated from baboons (BaAdVs) during the outbreak, including the two baboons that died from pneumonia, were untypeable by neutralization assays using sera reactive to HAdV species A-F and SAdV-A. Among the 4 BAdVs characterized by whole-genome sequencing, one ($BaAdV_1$) was a member of the recently described monkey SAdV-B species, while the remaining 3 AdVs $BaAdV_2$, $BaAdV_3$, and $BaAdV_4$ (genetically identical to $BaAdV_2$) were members of species H. $BaAdV_3$, a closely related species H AdV to $BaAdV_{2,4}$, was the only AdV among the 4 isolated from a clinically ill baboon, and thus thought to be the cause of the pneumonia outbreak. Although $BaAdV_3$ shared >90% genomic sequence identity overall with $BaAdV_{2,4}$, the significant divergence in the short fiber protein (~58% amino acid identity) and bootscan analysis suggested that $BaAdV_3$ is a rare species H recombinant of unknown origin. In support of this possibility, specific neutralizing antibodies to $BaAdV_1$ and $BaAdV_{2,4}$, but not $BaAdV_3$, were detected in both present-day healthy baboons and staff personnel at the primate research facility. These results implicate a novel species H AdV in a fatal pneumonia outbreak in a baboon colony, and further establish the potential for cross-species transmission of AdVs between humans and nonhuman primates.

Example 1

Materials and Methods

Animals: All studies were performed in accordance with established guidelines. No animal research protocol was used, as only excess clinical samples were analyzed.

Biosafety: Analysis of post-necropsy tissues and cultivation of the novel baboon adenoviruses described in this study were performed under Biosafety Level 2 (BSL-2) or BSL-3 conditions.

Outbreak Management and Investigation: The original outbreak lasted approximately 3 weeks. Affected baboons were quarantined immediately after development of respiratory symptoms. The two fatal cases died or were humanely euthanized 5 and 13 days after onset of clinical signs. Daily reports on clinical and epidemiological parameters were tracked and recorded by veterinary and management staff.

In response to the outbreak, all incubator rooms were decontaminated with paraformaldehyde gas. Cages, walls, floors, and all exposed work area surfaces were cleaned with 2.6% buffered glutaraldehyde (METRICIDE™) or bleach. Disposable protective suits and gloves were worn at all times when feeding or otherwise in contact with infant baboons for a period of at least 2 weeks. Hematological testing and cultures for bacterial, *mycoplasma*, and fungi were performed. Samples were also tested for RSV, influenza, parainfluenza, human adenovirus, and herpesviruses including CMV. In addition, respiratory samples were also sent out to an outside laboratory and tested for *Bordetella pertussis, Chlamydia* spp., *Mycoplasma* spp. *Ureaplasma* spp. *Legionella* spp., and hantavirus. AdV typing by virus neutralization testing using sera reactive against HAdV species A-F and SAdV-A viruses was also performed.

Pathology: Gross and histopathological analyses of necropsy tissues were performed by a board-certified veterinary pathologist. Necropsy tissues were fixed in 10% formalin and embedded in paraffin. Five μm sections were then cut using a microtome, stained with hematoxylin and eosin (H&E) and visualized under light microscopy.

Nucleic Acid Extraction: Total nucleic acid was extracted from cultured AdV supernatant using commercially available kits (Qiagen, Valencia, Calif.). 200 μL of sample were passed through a 0.4 μm filter to remove bacteria and cellular debris and then treated with RNase (Invitrogen, Carlsbad, Calif.).

Virus Cultivation: All inoculations of monkey cells (PMK, or primary monkey kidney; CyMK, or cynomolgus monkey kidney; and Vero, African green monkey kidney) were made using primary nasal swab specimens. Inoculations of human cells and cell lines were made with P1 virus after a single passage in monkey cells. Cell or cell lines were grown in media consisting of Hank's medium (for A549 cells) or Dulbecco's modified Eagle's medium (DMEM) (for other cells) supplemented with 1× nonessential amino acids (Invitrogen, Carlsbad, Calif.), 10% fetal bovine serum, 100 U of penicillin/mL and 100 μg of streptomycin/mL. After achieving 80-90% confluency, cell culture media were changed to maintenance media with 2% FBS and inoculated with 200 μL of clinical sample or 100 μL of passaged viral supernatant. Prior to inoculation, nasal samples were clarified by centrifugation for 10 min×4000 g; lung tissue was homogenized using a tissue homogenizer in 5 volumes of buffer. Prior to passaging, cell culture supernatant was subjected to 3 freeze-thaw cycles and clarified as above. Viral replication was monitored over 2 weeks by visual inspection under light microscopy for cytopathic effect (CPE). Viral supernatants were quantified by an end-point dilution assay.

Deep Sequencing Library Preparation: Deep sequencing libraries were prepared for whole-genome AdV sequencing using a variation of the TruSeq protocol (Illumina, San Diego, Calif.) (Chen et al., 2011, PLoS Pathog 7: e1002155). Briefly, nucleic acid extracts were randomly amplified to cDNA using a Round A/B procedure as previously described (Chen et al., 2011, J. Vis. Exp.; Greninger et al., 2010, PLoS One 5: e13381) and then digested using the restriction enzyme BpmI (New Engladn Biolabs, Ipswich, Mass.) for 2 hr at 37° C., followed by end-repair and A-tailing with Klenow and Taq polymerase, respectively (Invitrogen, Carlsbad, Calif.). Size selection targeting 200-300 bp fragments was then performed using AMPURE® beads, followed by attachment of adapters containing 6-nucleotide barcode tags using DNA ligase. Final libraries were quantified using the Bioanalyzer DNA 12000 chip (Agilent) and SYBR FAST® qPCR system (KAPA Biosystems), pooled into a single lane, and sequenced on an Illumina HiSeq2000 instrument (100-bp paired-end sequencing).

De novo viral genome assembly: Raw deep sequencing reads were initially trimmed by removal of adapters, primers, and low-complexity/low-quality sequences. De novo assembly of partial AdV genomes was performed using the PRICE assembler (Grard et al., 2012, PloS Pathogens 8: e1002924). Gaps were filled by BLASTn or BLASTx alignments of the deep sequencing reads to reference simian and human AdVs in GENBANK® (Altschul et al., 1990, J Mol Biol 215: 403-410), followed by manual assembly using GENEIOUS® software (Drummond et al., 2010, Geneious v5.6.3. Available on the internet from geneious website as downloaded November, 2012). Regions with little or no sequence coverage were confirmed by PCR and Sanger sequencing. After assembly of the full viral genomes corresponding to the 4 AdV isolates $BaAdV_{1,2,3,4}$, trimmed deep sequencing reads were then mapped to the AdV genome using GENEIOUS® software with the following parameters (no gaps allowed, maximum mismatches allowed per read of 5%, and maximum ambiguity of 1).

Structural features and phylogenetic analysis: Predicted coding regions in the $BaAdV_{1,2,3,4}$ genomes were identified using the fully annotated genome sequences of species F and G AdVs in GENBANK® as a reference. First, each BaAdV genome was aligned to the most similar reference genome in GENBANK®, followed by identification of all open reading frames (ORFs) using GENEIOUS®. The candidate ORF that best matched the corresponding ORF in the annotated reference genome was selected. The GT-AG intron start-stop signal was used to pinpoint the correct ORF for spliced genes. To confirm the accuracy of the predicted coding regions, each identified ORF was then aligned using BLASTx to a reference database consisting of all adenoviral proteins in GenBank. Whole-genome nucleotide pairwise identity plots (window size of 100) and amino acid pairwise identity calculations were performed in Geneious. Similarity and bootscanning plots were generated using SIMPLOT® (Lole et al., 1999, J Virol 73: 152-160), with a window size of 1000 bp and step size of 50 bp.

To construct the amino acid phylogeny trees corresponding to the hexon, penton base, DNA polymerase, and short/long fiber proteins, the translated protein sequences corresponding to representative human and simian AdVs in species groups A-G, SAdV-A, and SAdV-B, as well as non-primate AdVs, were first downloaded from GENBANK®. Multiple sequence alignments were then performed using the FFT-NS-Ix1000 algorithm of MAFFT at default parameters (Katoh et al., 2002, Nucleic Acids Res 30: 3059-3066). A phylogenetic tree was constructed in Geneious using the Jukes-Cantor neighbor joining method and 100,000 bootstrap replicates, using mouse adenovirus A (MADV-A) as an outgroup.

Baboon adenovirus neutralization assay (human and baboon sera): Viral stocks of $BaAdV_1$, $BaAdV_2$, and $BaAdV_3$ were generated by passaging in Vero E6 cells, aliquotted, and quantitated by end-point dilution. To perform the virus neutralization assay, 100 μL of viral supernatant or control serum was mixed to the correct dilution and incubated for 1 hour at 37° C. After incubation, the mixture was inoculated into wells containing 4,000 Vero E6 cells per well and incubated at 37° C., 5% $CO_2$. Cells in the plate wells were observed every other day for evidence of CPE. For wells that showed inhibition of viral CPE at the screening dilution of 1:10, the corresponding serum samples were diluted in six 2-fold steps and then retested. The reciprocal of the highest dilution where replicate well monolayers showed <3+CPE was taken as the neutralizing antibody titer.

Human adenovirus types A-F cross-neutralization assay (rabbit typing sera): Seven pools of rabbit hyperimmune reference sera at the California DPH, collectively containing antibodies to human AdV serotypes 1 through 41 (species A-F), were available for testing. For each pool, 100 μL of rabbit sera and 100 μL of viral supernatant at a $TCID_{50}$ of $10^3$/mL were mixed to the screening dilution of 1:10 and used to inoculate Vero E6 cells. Cells in plate wells were observed every other day for 2 weeks for evidence of CPE. For wells that showed inhibition of viral CPE at the screening dilution of 1:10, the corresponding serum samples were diluted in six 2-fold steps and then retested. An individual rabbit serum reactive to HAdV-40 and HAdV-41 (the species F AdVs) was used for confirmatory testing.

Human adenovirus type G indirect cross-neutralization assay (baboon sera): Since neutralizing reference sera to human HAdV-52 (species G) was not available, the serum sample from baboon B107, shown previously to be positive for neutralizing antibody to species SAdV-B and H AdVs (Table 2), was tested for cross-neutralization of HAdV-52 in an indirect neutralization assay. To perform the assay, 100 μL HAdV-52 supernatant at a $TCID_{50}$ of $10^3$/mL was mixed with serum from baboon B107 to the screening dilution of 1:10 and used to inoculate Vero E6 cells. Cells in plate wells were observed every other day for 2 weeks for evidence of CPE.

Nucleotide sequence accession numbers: GENBANK® accession numbers for the adenoviral sequences used in FIGS. 3, 4, and 5 are as follows: CAdV-1 (canine adenovirus 1), AC_000003; NC_002501; HAdV-1, AC_000017; HAdV-3, DQ086466; HAdV-4, AY458656; HAdV-7, AC_000018; HAdV-8, AF532578; HAdV-12, NC_001460; HAdV-14, FJ822614; HAdV-18, GU191019; HAdV-21, AY601633; HADV-36, GQ384080; HAdV-40, NC_001454; HAdV-41, DQ315364; HAdV-48, EF153473; HAdV-49, DQ393829; HAdV-50, AY737798; HAdV-52, DQ923122; MAdV-2 (murine adenovirus 2), $NC_{13}$ 014899; PAdV-A (porcine adenovirus A), AC_000009; SAdV-1, AY771780; SAdV-3, NC_006144; SAdV-6, JQ776547; SAdV-7, DQ792570; SAdV-18, FJ025931; SAdV-20, HQ605912; SAdV-21, AC_000010; SAdV-22, AY530876; SAdV-48, HQ241818; SAdV-49, NC_015225; SAdV-50, HQ241820; SAdV-A1139, JN880448; SAdV-A1163, JN880449; SAdV-A1173, JN880450; SAdV-A1258, JN880451; SAdV-A1312, JN880454; SAdV-A1335, JN880456; TMAdV (titi monkey adenovirus), HQ913600; TSAdV (tree shrew adenovirus), NC_004453. These sequences are incorporated by reference herein in their entirety as available on Jan. 2, 2013.

Example 2

Outbreak of Fatal Pneumonia in a Baboon Colony

In one outbreak, 4 of 9 infant baboons at the TBRI developed an acute respiratory infection shortly after being isolated from birth in preparation for a research study on respiratory syncytial virus (FIGS. 1A and B). The index case (FIG. 1B, B1) was a female infant baboon. After birth, she was admitted to the nursery, maintained in an incubator for 1 week, and then moved to an individual cage in a dedicated nursery bay. At 12 days of age, she was noted to be sneezing with clear mucous discharge. No fever was present. Laboratories revealed a normal complete blood count (CBC) with a white blood cell (WBC) count of $5.6\times10^6$/mL (57% neutrophils). Her condition deteriorated rapidly over the next 4 days with the development of progressive malaise, anorexia, >20% loss of body weight, and shortness of breath (dyspnea). Body temperature dropped below 95° F. Chest radiographs revealed a bilateral interstitial pneumonia. Despite aggressive treatment with antibiotics (ampicillin and gentamicin), oxygen, and intravenous fluids, she died 13 days after onset of symptoms and at 25 days of age.

On necropsy, the lung tissue was hemorrhagic with patchy regions of consolidation. Neutrophils were evident in the airways with extension into the minor airways, interstitium, and alveolar spaces. Notably, intranuclear inclusions were evident throughout the respiratory epithelium, and were most evident in the major airways. The tonsils contained multifocal areas of necrosis with increased numbers of neutrophils, and mediastinal lymph nodes contained excess inflammatory cells. Mild cellular necrosis was noted in the liver. Histologic lesions were not observed in the heart, kidney, adrenal glands, or spleen. The final pathologic diagnosis was bronchointerstitial pneumonia, probably viral in etiology, with accompanying tonsillitis, lymphadenitis, and mild liver necrosis. Although a Gram stain of the lung tissue was negative for organisms, bacterial cultures grew methicillin-sensitive *Staphylococcus aureus* (MSSA) and rare *Kluyvera ascorbata* (Sarria et al., 2001, Clin Infect Dis 33: E69-74). Tests from lung tissue were negative for *Bordetella pertussis, Chlamydophila* spp., *Mycoplasma* spp., *Ureaplasma* spp. *Legionella* spp., and hantavirus. A respiratory viral culture of lung tissue was positive for AdV. The isolate was untypeable by virus neutralization testing at an outside laboratory using sera reactive to HAdV species A-F and SAdV-A.

The second case (FIG. 1B, B2) was a male infant baboon. He was also admitted to the nursery upon birth, maintained in an incubator during the first week of life, and then moved to an individual cage in the nursery bay. At 16 days of age, he began sneezing and coughing up milk through his nose. The WBC count was normal at $5.8\times10^6$/mL (46% neutrophils), but a few atypical lymphocytes were present. The animal clinically worsened, with lethargy, >20% weight loss, abnormally low body temperature, and dyspnea. A nasal swab collected at the time was positive for MSSA, but cultures of bronchoalveolar lavage fluid and blood were negative for MSSA. Although also treated aggressively with intravenous fluids, oxygen, and antibiotics, he was humanely euthanized three days later after developing muscle spasticity (opisthotonus), 5 days after onset of symptoms and at 21 days of age.

On necropsy, the lungs revealed a bronchointerstitial pneumonia with prominent areas of congestion (edema) and consolidation. Inflammatory neutrophilic infiltrates were evident in the major airways with extension into the interstitium and alveolar spaces. Intranuclear inclusions were evident in epithelial cells and subtracheal gland epithelium, and excess inflammatory cells were visualized in mediastinal lymph nodes. Other tissues were negative for histologic lesions, with the exception of medullary necrosis of the thymus consistent with stress. Gram stain and cultures of lung tissue were negative for bacteria or fungi, although rare WBCs were seen. A respiratory viral culture of the lung tissue was positive for AdV, and the isolate was also untypeable by neutralization testing.

Figure 1B:
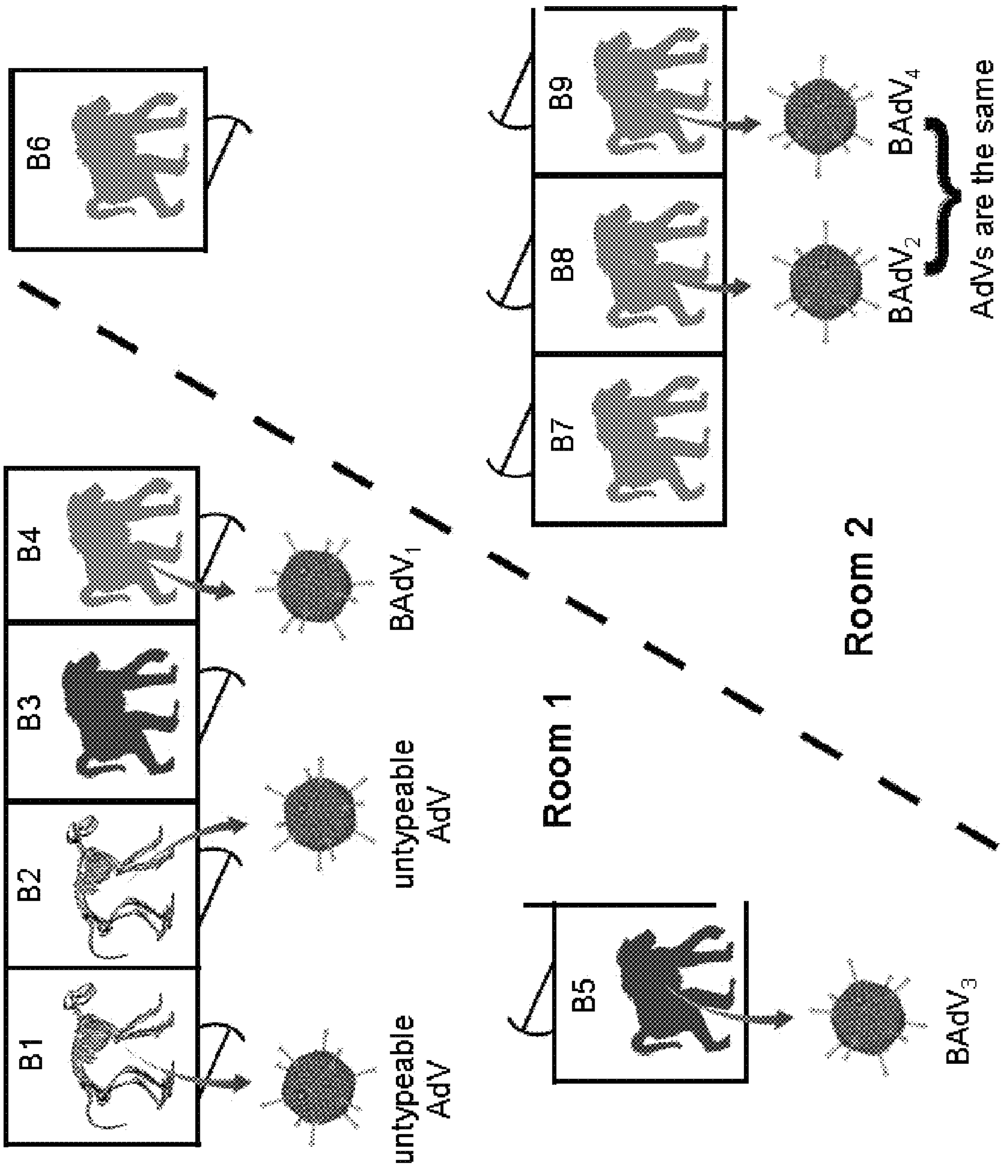

Two other animals in the room were noted to be sneezing and coughing around the same time cases B1 and B2 presented with fatal pneumonia (FIG. 1B, B3 and B5). A nasal swab collected from one of these two symptomatic individuals was culture-positive for an adenovirus (FIG. 1B, $BaAdV_3$). Nasal swabs were also collected from the sole remaining asymptomatic baboon in the same room as the symptomatic cases (FIG. 1B, Room 1, B4) and from asymptomatic baboons in a nearby but separate room (FIG. 1B, Room 2). From these nasal swabs, 3 additional AdV isolates were obtained (FIG. 1B, $BaAdV_1$, $BaAdV_2$, and $BaAdV_4$). The two symptomatic baboons in Room 1, cases B3 and B5, were quarantined and recovered completely within 1 week with supportive care including intravenous fluids, oxygen administration, and empiric antibiotics. None of the 4 baboon AdV isolates ($BaAdV_{1,2,3,4}$) was typeable as HAdV species A-F or SAdV-A by neutralization testing done at this time.

Example 3

Cell Culture Tropism of Novel Baboon Adenoviruses (BaAdV-1 through BaAdV-4)

The 4 adenoviruses isolated from sick and asymptomatic baboons during the first outbreak were cultured in a variety of human and monkey cell lines. The majority of cells and cell lines tested resulted in productive infection as determined by magnitude of cytopathic effect (CPE) (Table 1).

TABLE 1

Tropism of 4 novel baboon adenoviruses in human and monkey cells.

| Virus | Source | Name of | Cell Type | Growth |
|---|---|---|---|---|
| $BaAdV_1$ | Human | A549 | human epithelial lung adenocarcinoma | +++ |
| | | HFDL | human fetal diploid lung | – |
| | | HFDK | human fetal diploid kidney | – |
| | Monkey | PMK | primary rhesus monkey kidney (Old World | +++ |
| | | B95a | marmoset monkey lymphoblastoid (New World | – |
| | | Vero | African green monkey kidney (Old World | +++ |
| | | CyMK | Cynomolgus monkey kidney (Old World monkey) | +++ |
| $BaAdV_{2,4}$ | Human | A549 | human epithelial lung adenocarcinoma | +++ |
| | | HFDL | human fetal diploid lung | – |
| | | HFDK | human fetal diploid kidney | – |
| | Monkey | PMK | primary rhesus monkey kidney (Old World | +++ |
| | | B95a | marmoset monkey lymphoblastoid (New World | – |
| | | Vero | African green monkey kidney (Old World | +++ |
| | | CyMK | Cynomolgus monkey kidney (Old World monkey) | +++ |
| $BaAdV_3$ | Human | A549 | human epithelial lung adenocarcinoma | +++ |
| | | HFDL | human fetal diploid lung | ++ |
| | | HFDK | human fetal diploid kidney | ++ |
| | Monkey | PMK | primary rhesus monkey kidney (Old World | +++ |
| | | B95a | marmoset monkey lymphoblastoid (New World | – |
| | | Vero | African green monkey kidney (Old World | +++ |
| | | CyMK | Cynomolgus monkey kidney (Old World monkey) | +++ |

+++, strong cytopathic effect (CPE);
++, moderate CPE;
–, no CPE

All 4 baboon adenoviruses were successfully propagated in cells from other Old World monkey species (rhesus, cynomolgus, African green monkeys). The BaAdVs were tested for growth in human cell lines; all 4 grew efficiently in the human lung adenocarcinoma A549 cell line, which is commonly employed in isolation of human AdVs (Lipson et al., 1993, FEMS Microbiol Lett 113: 175-18) Notably, unlike the other 3 AdV strains, $BaAdV_3$ was also successfully cultured from two additional human cell lines. No growth was observed in lymphoblastoid B95a cells from marmosets, which are New World monkeys.

Example 4

De Novo Assembly and Whole-Genome Phylogenetic Analysis of Novel Baboon Adenoviruses (BaAdV-1 Through BaAdV-4)

Figure 2:
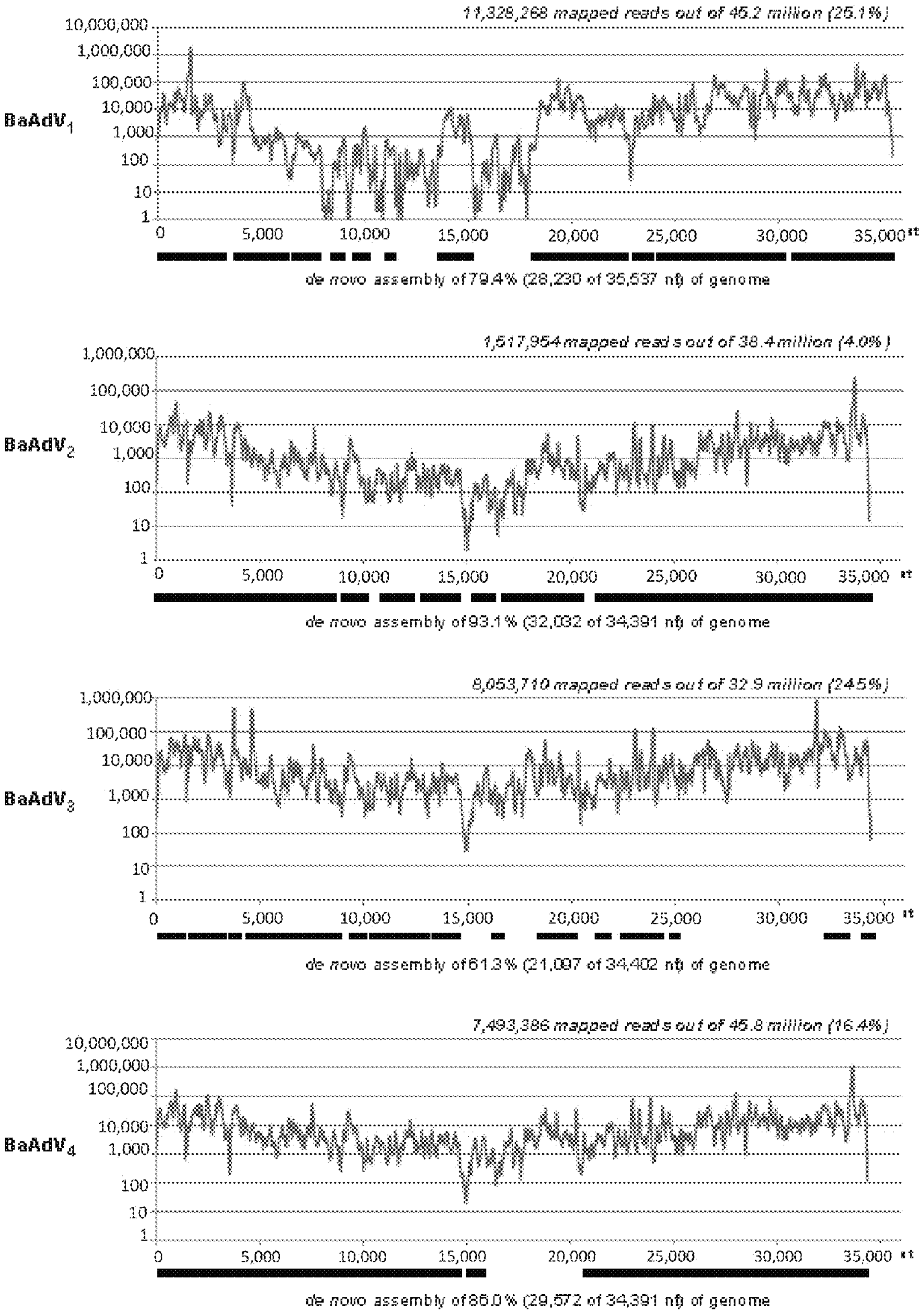
FIG. 2. Genomic coverage of novel baboon adenoviruses ($BaAdV_{1,2,3,4}$) by deep sequencing. Part of the viral genome was recovered directly from deep sequencing reads using a de novo assembly approach (black bars). After completion of the genome and confirmation by Sanger sequencing, deep sequencing reads are mapped to the corresponding AdV genome. The coverage (y-axis) achieved at each position along the genome (x-axis) is plotted on a logarithmic scale. Abbreviations: nt, nucleotide.

The 4 adenoviruses isolated from baboons were further characterized by whole-genome sequencing and phylogenetic analysis. The sequences of the adenovirus hexon, polymerase, and fiber were initially recovered by Sanger sequencing. To sequence the entire genome, early passaged cultures corresponding to isolates BaAdV-1 through BaAdV-4 were subjected to unbiased deep sequencing on an Illumina HiSeq2000 (FIG. 2). Out of 32.9-45.2 million raw reads, from 61.3%-93.1% of the genome was assembled de novo for each of the 4 adenovirus strains; the remainder of the genome was then assembled manually from the deep sequencing reads with Sanger sequencing used to fill in the gaps.

Figure 3A:
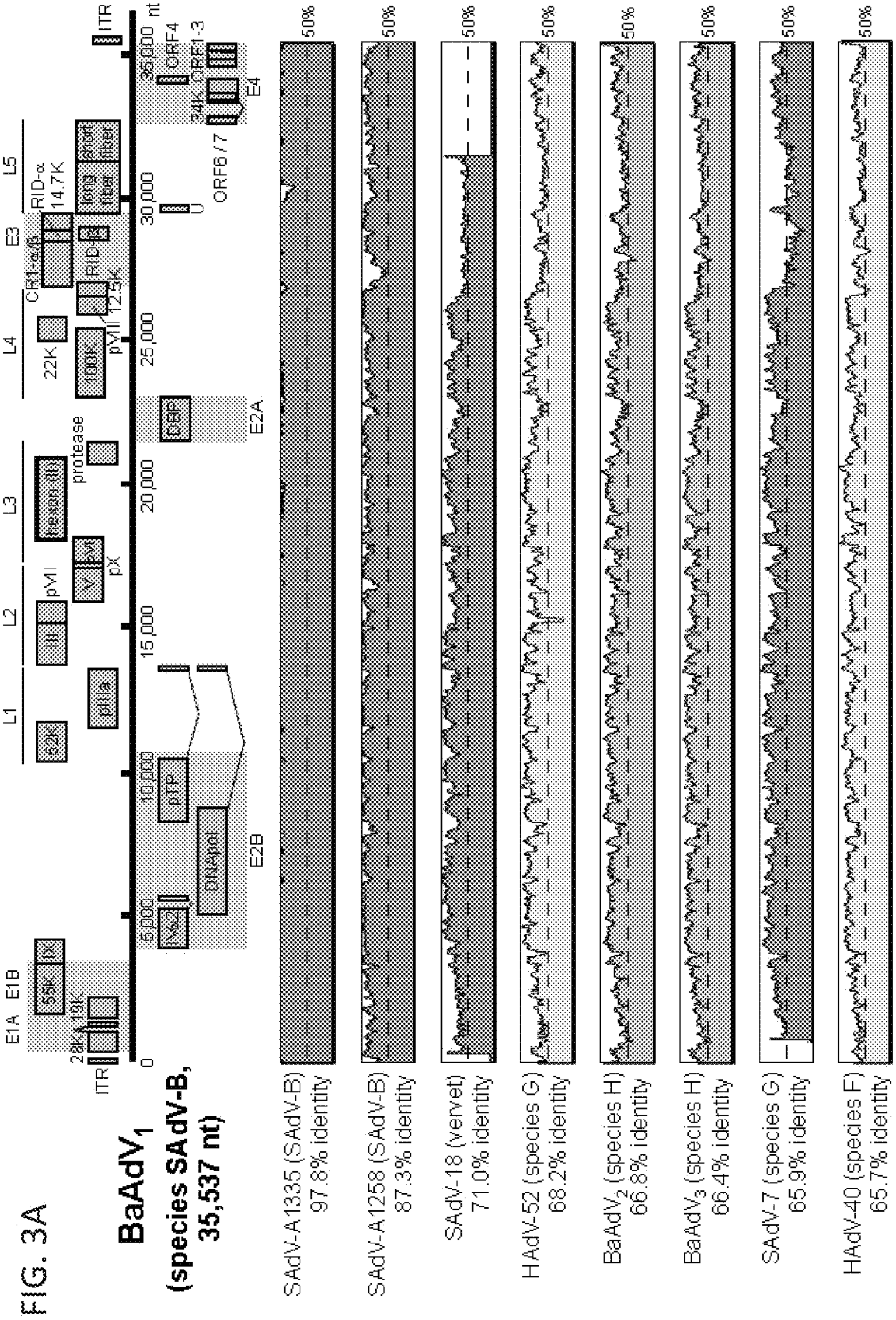
FIGS. 3A-3B. Genome organization of $BaAdV_1$ and $BaAdV_{2,4}$ and pairwise alignment with related adenoviruses. Maps of the genome organization corresponding to two baboon AdVs, $BaAdV_1$ (A), a species SAdV-B AdV, and $BaAdV_{2,4}$ (B), a species H AdV, are shown. Boxes above the central black line represent open reading frames (ORFs) encoded on the forward strand, while boxes below the black line represent reverse-strand encoded ORFs. Early region ORFs are shaded in gray. The scanning nucleotide pairwise identities of $BaAdV_1$ (A) and $BaAdV_{2,4}$ (B) relative to selected related human (light grey), simian (dark grey) or novel baboon (medium grey) AdVs are shown ranked in order of decreasing overall percent identity. The x-axis refers to the nucleotide position along the genome.
Figure 3B:
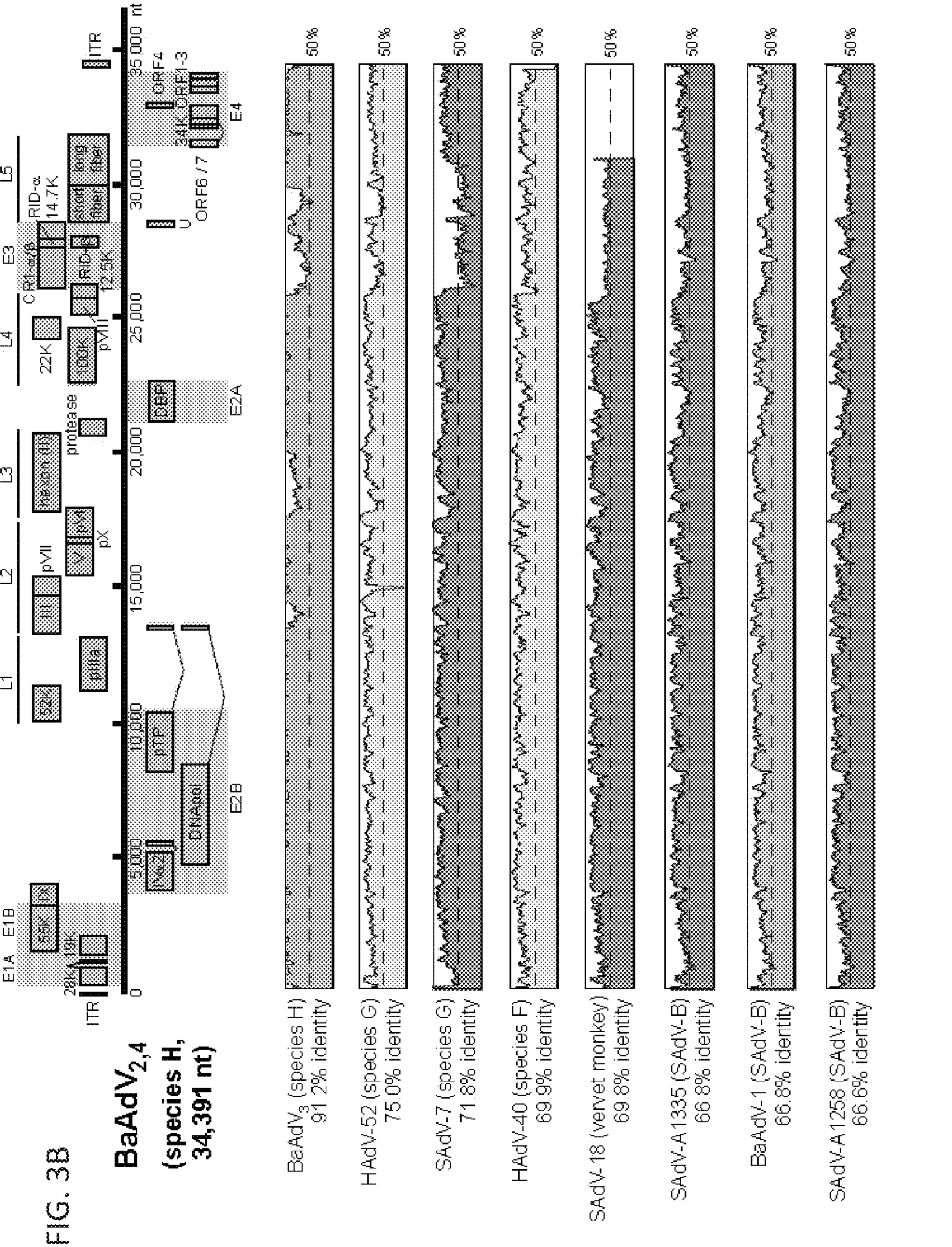
Figure 4A:
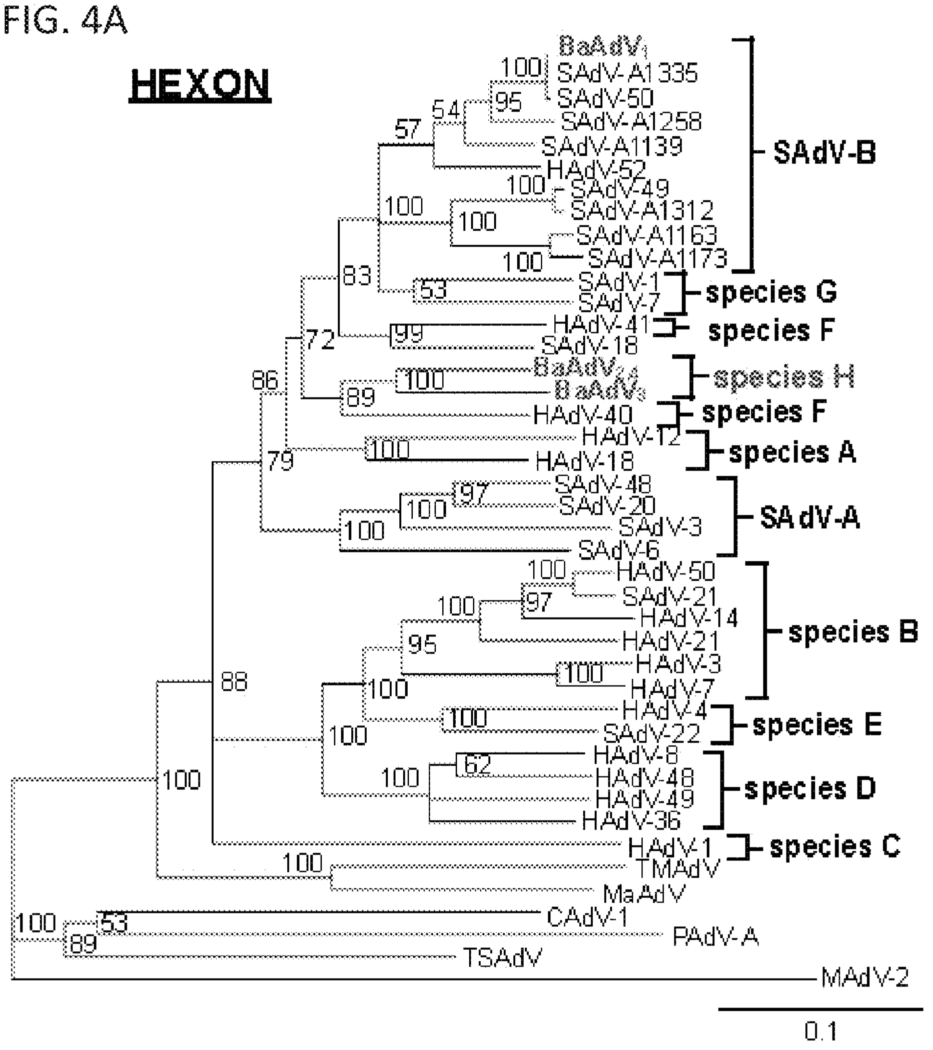
FIG. 4A-4D. Amino acid phylogenetic analysis of $BaAdV_1$, $BaAdV_{2,4}$, and $BaAdV_3$ relative to other adenoviruses. (A) hexon, (B) penton base, (C) DNA polymerase, (D) fiber. Representative primate AdVs in species A-G, SAdV-A, and SAdV-B, as well as non-primate AdVs, were included in the phylogenetic analysis. Bayesian support levels are displayed at each branching point. The 4 novel BaAdVs identified in this study and the proposed "species H" designation are in bold. Abbreviations and GENBANK® accession numbers are described in the text.
Figure 4B:
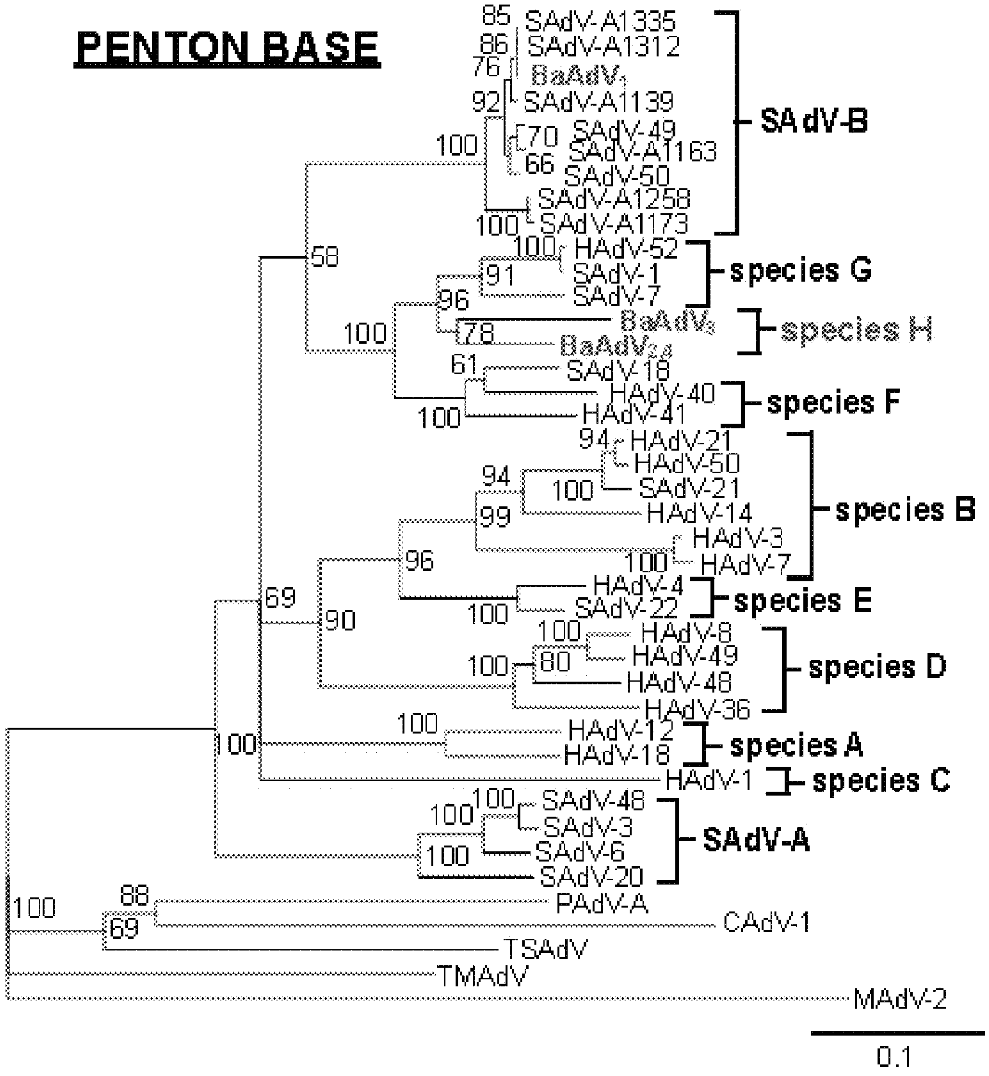
Figure 4C:
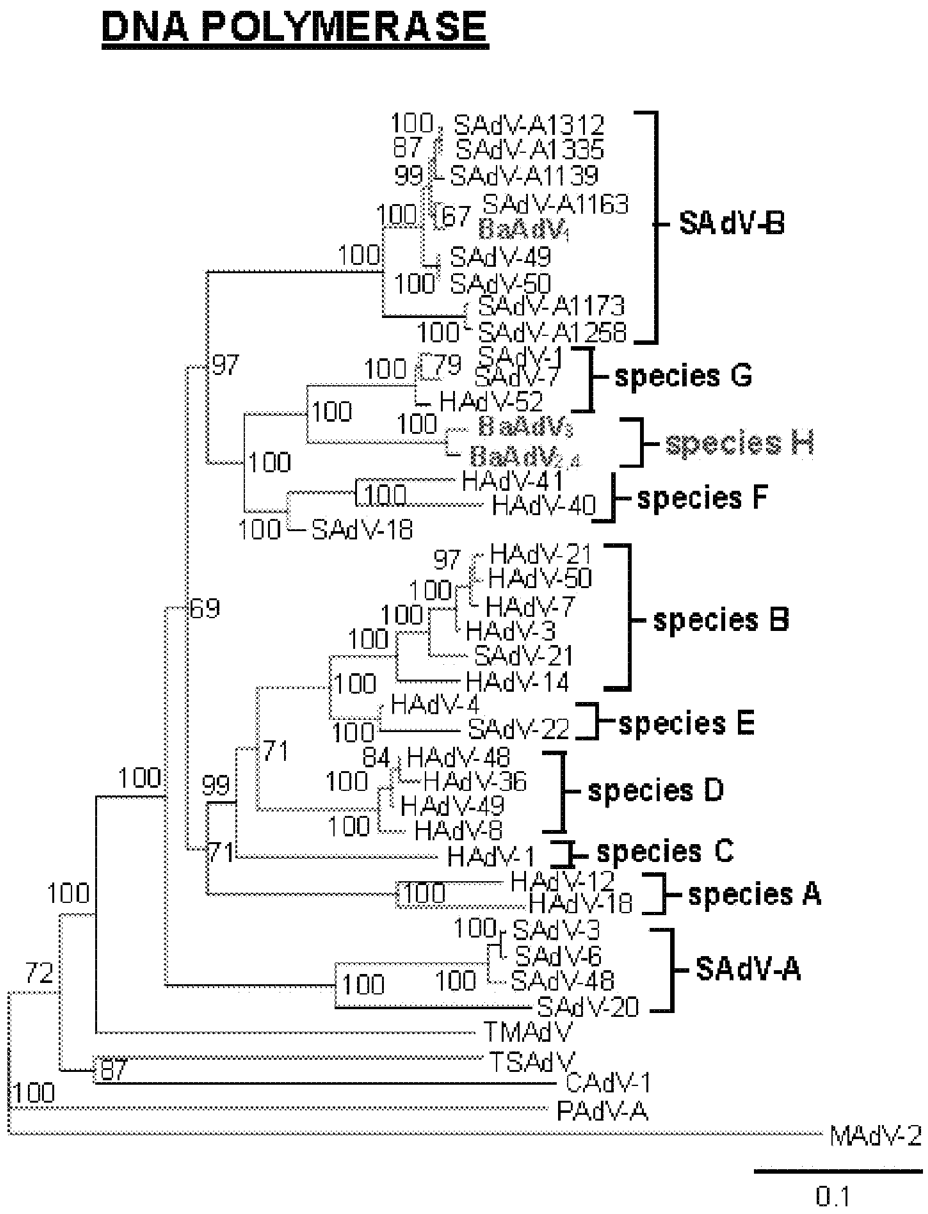
Figure 4D:
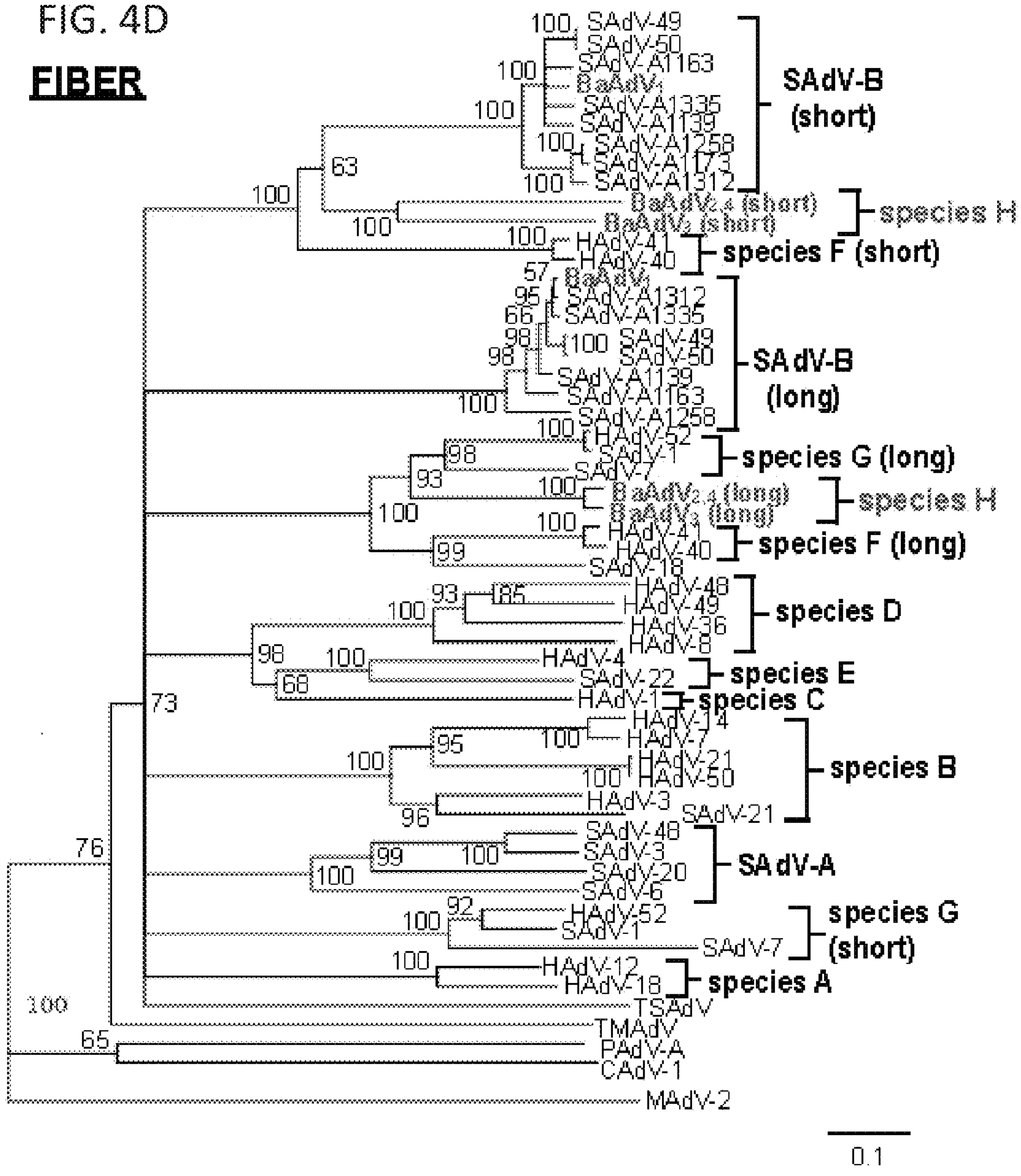

Scanning nucleotide pairwise identity plots across the assembled genomes revealed that all 4 baboon adenoviral strains retained the major core adenoviral proteins and, similar to AdVs in species SAdV-B, F, and G, all 4 strains contained two fiber proteins, a long fiber and a short fiber (FIG. 3). $BaAdV_1$, the strain isolated from an asymptomatic baboon in the outbreak room (FIG. 1B, B4), was found to be closely related to a previously described SAdV-B species AdV isolated from stool from a captive rhesus monkey (SAdV-A1335, GENBANK® accession number JN880456, 97.8% identity) (FIG. 3A)) (Roy et al., 2009, PLoS Pathog 5: e1000503). Strains $BaAdV_2$ and $BaAdV_4$, both isolated from asymptomatic baboons housed away from the outbreak location in a separate room (FIG. 1B, B8 and B9), were 100% identical to each other, while strain $BaAdV_3$, isolated from a symptomatic baboon positioned near the two baboons who died from adenoviral pneumonia (FIG. 1B, B5), was 91.2% identical to strains $BaAdV_{2,4}$ (FIG. 3B). The closest relatives to $BaAdV_{2,4}$ and $BaAdV_3$ were members of adenoviral species F and G (FIGS. 3B and 4A-D). Phylogenetic analysis of the individual hexon, penton base, DNA polymerase, and fiber proteins and amino acid pairwise identity comparisons revealed that $BaAdV_1$ is a member of the SAdV-B species group (FIGS. 4A-D and 5A), while $BaAdV_{2,4}$ and $BaAdV_3$ appear to be members of a new species intermediate between F and G, provisionally named "species H" (FIGS. 4A-D and 5B). Repeat serological testing in 2012 using sera containing neutralizing antibodies against human AdVs in species A-G (Table 2) revealed only a low level of cross-neutralizing activity to species F AdVs with $BaAdV_1$ (SAdV-B) and $BaAdV_{2,4}$ (species H). No cross-neutralization with human AdVs in species A-G was observed with $BaAdV_3$.

Figure 6A:
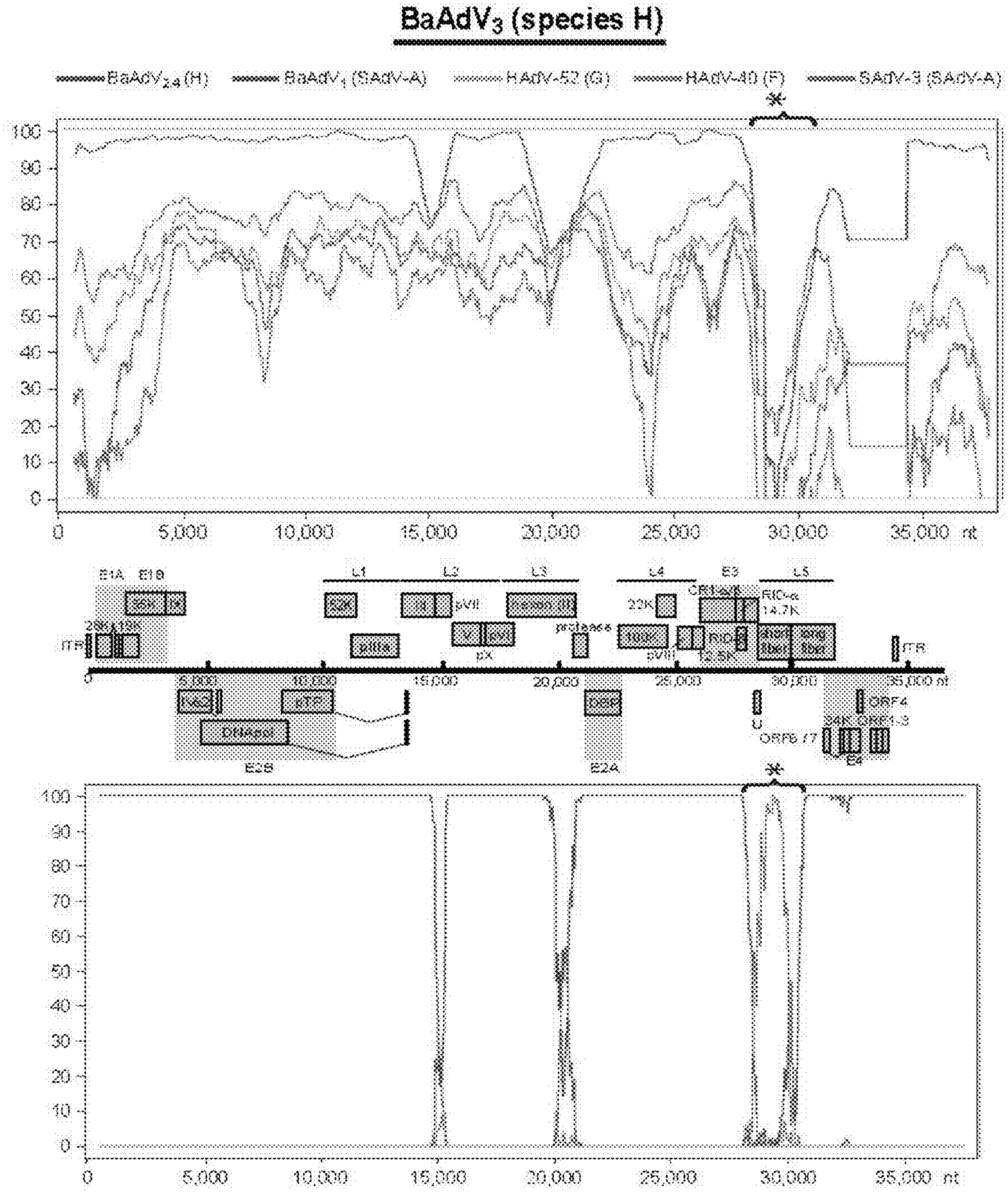
FIG. 6A-6B. Evidence for recombination in species H adenovirus $BaAdV_3$. (A) Similarity (upper) and bootscanning (lower) plots of AdVs in species SAdV-B, F, G, and H relative to BaAdV3 are shown. Bootscanning analysis reveals a likely recombination breakpoint in the region corresponding to the divergent short fiber gene (asterisk). The x-axis refers to the nucleotide position. The genome organization map is annotated in the same fashion as in FIG. 3. (B) Shown is a hypothetical model in which $BaAdV_3$ is generated by a recombination event involving $BaAdV_{2,4}$ and the short fiber gene from an as-yet unidentified AdV. Abbreviations: nt, nucleotide.

Notably, despite sharing 91.2% overall nucleotide identity across the genome (FIG. 3B), the sequence of $BaAdV_3$, the only AdV among the 4 that had been isolated from a symptomatic baboon, diverged significantly from that of $BaAdV_{2,4}$ in the short fiber region. While the other major adenoviral proteins were >90% identical, the short fiber of $BaAdV_3$ shared only 58% amino acid identity relative to that of $BaAdV_{2,4}$ (FIG. 5B). This strongly suggested the possibility of a recombination event involving $BaAdV_{2,4}$ and the short fiber of $BaAdV_3$. Similarity and bootscanning plots of $BaAdV_3$ relative to $BaAdV_{2,4}$ (species H) and related AdVs in species SAdV-A, F, and G confirmed the likelihood of a recombination event (FIG. 6A). However, since the short fiber of $BaAdV_3$ was found to lack any closely related phylogenetic neighbors (~58% to $BaAdV_{2,4}$ and ≤50% amino acid identity to other sequenced fiber proteins in GENBANK®), the presumptive AdV donor strain for the short fiber has yet to be identified.

Example 5

Seroprevalence of $BaAdV_1$, $BaAdV_3$, and $BaAdV_{2,4}$ in Baboons and Humans Of note, many staff members had anecdotally reported experiencing "flu-like" symptoms around the time of onset of this baboon outbreak. To investigate the possibility that a cross-species transmission event, either zoonotic (from baboon to human) or anthroponotic (from human to baboon), may have occurred, pre-outbreak and post-outbreak sera from potentially exposed human staff personnel at the TBRI (Table 2, H1-H6) were tested for antibodies to $BaAdV_1$, $BaAdV_3$, and $BaAdV_{2,4}$ by virus neutralization in a blinded fashion. As additional controls for baseline seroprevalence, sera from a random selection of 5 human children less than 5 years of age and available sera from 10 baboons born approximately the same time as affected baboons with pneumonia, but not part of the outbreak, were tested. Significantly, 5 of 6 (83%) and 6 of 6 (100%) personnel, while seronegative prior to the outbreak, had evidence of neutralizing antibody titers to $BaAdV_1$ and $BaAdV_{2,4}$, respectively, after the outbreak. The greatest magnitude of neutralizing antibody response, ≥1:80, corresponded to the researcher in closest contact with sick baboons during the outbreak (Table 2, H1). Interestingly, no neutralization to $BaAdV_3$ was observed in any of the staff personnel. The specificity of the neutralization assays was further confirmed by the screening of 5 epidemiologically unassociated children under 5 years of age, all of whom were negative for neutralizing antibodies to $BaAdV_1$, $BaAdV_{2,4}$, and $BaAdV_3$ (Table 2, H8-H12). Among 10 healthy baboons in the colony who were not part of this outbreak, 4 of 10 (40%) and 3 of 10 (30%) harbored antibodies to $BaAdV_1$ and $BaAdV_{2,4}$, respectively (Table 2, B100-B110). Very little to no neutralization was observed to $BaAdV_3$; neutralizing antibody at 1:10 titer was detected in only one baboon, B107, with high existing titers of 1:80 to closely related strain $BaAdV_{2,4}$.

TABLE 2

Neutralizing antibody titers to $BaAdV_1$, $BaAdV_{2,4}$, and $BaAdV_3$ in rabbit neutralizing sera to HAdV species A-F, laboratory staff (H1-H6), young children (H8-H12), and baboons currently housed (B100-B110). No cross-reactivity with HAdV species A-F is observed except for a low level of cross-neutralization of $BaAdV_1$ $BaAdV_{2/4}$, but not $BaAdV_3$, with rabbit neutralizing sera against HAdV species F. There was also no evidence of cross-reactivity to a species G adenovirus HAdV-52 in an indirect neutralization assay with a baboon serum sample reactive to $BaAdV_1$, $BaAdV_3$, and $BaAdV_{2,4}$ (B107).

| Serum Sample | Identification | $BaAdV_1$ | BaAdV2,4 | BaAdV3 |
|---|---|---|---|---|
| Rabbit neutralizing sera to HAdVs (A-F), 7 pools | N/A | Only HAdV-F pool, 1:20 | Only HAdV-F pool, 1:20 | — |
| Rabbit neutralizing sera to HAdV-F (HAdV-40 and HAddV-41) | N/A | 1:20 | 1:20 | — |
| | primate | | | |
| H1 (pre-outbreak) | primate | — | — | — |
| H1 (post-outbreak) | primate | ≥1:80 | ≥1:80 | — |
| H2 (pre-outbreak) | primate | — | — | — |
| H2 (post-outbreak) | primate | 1:80 | 1:80 | — |
| H3 (pre-outbreak) | primate | — | — | — |
| H3 (post-outbreak) | primate | 1:80 | 1:80 | — |
| H4 (pre-outbreak) | primate | — | — | — |
| H4 (post-outbreak) | primate | 1:40 | 1:40 | — |
| H5 (pre-outbreak) | primate | — | — | — |
| H5 (post-outbreak) | primate | — | 1:80 | — |
| H6 (pre-outbreak) | primate | — | — | — |
| H6 (post-outbreak) | primate | 1:80 | 1:80 | — |
| H8 | child <5 years of age | — | — | — |
| H9 | child <5 years of age | — | — | — |
| H10 | child <5 years of age | — | — | — |
| H11 | child <5 years of age | — | — | — |
| H12 | child <5 years of age | — | — | — |
| B100 | primate | — | — | — |

TABLE 2-continued

Neutralizing antibody titers to $BaAdV_1$, $BaAdV_{2,4}$, and $BaAdV_3$ in rabbit neutralizing sera to HAdV species A-F, laboratory staff (H1-H6), young children (H8-H12), and baboons currently housed (B100-B110). No cross-reactivity with HAdV species A-F is observed except for a low level of cross-neutralization of $BaAdV_1$ $BaAdV_{2/4}$, but not $BaAdV_3$, with rabbit neutralizing sera against HAdV species F. There was also no evidence of cross-reactivity to a species G adenovirus HAdV-52 in an indirect neutralization assay with a baboon serum sample reactive to $BaAdV_1$, $BaAdV_3$, and $BaAdV_{2,4}$ (B107).

| Serum Sample | Identification | $BaAdV_1$ | BaAdV2,4 | BaAdV3 |
|---|---|---|---|---|
| Rabbit neutralizing sera to HAdVs (A-F), 7 pools | N/A | Only HAdV-F pool, 1:20 | Only HAdV-F pool, 1:20 | — |
| B101 (earlier) | primate | — | — | — |
| B101 (later) | primate | 1:10 | — | — |
| B102 | primate | — | 1:10 | — |
| B103 | primate | — | — | — |
| B104 | primate | — | — | — |
| B105 | primate | — | — | — |
| B106 | primate | — | — | — |
| B107 | primate | 1:10 | 1:80 | 1:10 |
| B108 | primate | 1:10 | 1:10 | — |
| B109 | primate | — | — | — |
| B110 | primate | 1:10 | — | — |

Abbreviations:
N/A, not applicable.

Thus, an outbreak of rapidly fatal adenovirus pneumonia in infant baboons occurred. The diagnosis of primary AdV infection was supported by the presence of atypical lymphocytes in the peripheral circulation, hemorrhagic and necrotic lesions in the lung and liver, and intranuclear inclusions in bronchial epithelium, with subsequent confirmation by direct isolation of AdV from lung tissue. Two of four baboons presenting with acute respiratory infection (50%) died in the outbreak. Although numbers are low, the case fatality rate of 50% is high for AdV infections, which typically cause much lower mortality rates in susceptible human children of <15% (Hong et al., 2001, Clin Infect Dis 32: 1423-1429; Siminovich et al., 2011, Pediatr Dev Pathol 14: 214-217; Murtagh et al., 2009, Pediatr Pulmonol 44: 450-456). One explanation for the high death rate may be the concurrent identification of bacteria such as MSSA in at least one of the 2 baboons, which may have predisposed AdV-infected baboons with severe and potentially fatal bacterial superinfections of the lung (Bakaletz, 1995, Trends Microbiol 3: 110-114). It is also possible that newborn baboons are highly susceptible in general to severe infection from AdVs, which can cause more severe disease in immunocompromised, elderly, or very young individuals (Wold W, Horwitz M (2007) Adenoviruses. In: Fields B N, Knipe D M, Howley P M, editors. Fields Virology. 5th ed. Philadelphia: Wolters Kluwer Health/Lippincott Williams & Wilkins pp. 2395-24361 Echavarria, 2008, Clin Microbiol Rev 21: 704-715).

The AdV strains isolated from lung tissue from the two baboons who died from pneumonia were untypeable by virus neutralization testing for AdVs in HAdV species A-F and SAdV-A, including HAdVs in species B, C, and E that are typically associated with human respiratory disease and pneumonia (Echavarria et al., 2006, J Clin Microbiol 44: 625-627). This finding raised the possibility that the causative agent of the outbreak may be a novel AdV strain of unknown pathogenicity. Since tissue and primary cultures from the two fatal cases had been sent out to outside laboratories and were unavailable for further analysis, AdVs isolated from other symptomatic and/or asymptomatic baboons (BaAdVs) involved in the outbreak were characterized. Four AdV isolates ($BaAdV_{1,2,3,4}$) had been successfully cultured from nasal swabs, of which only one, $BaAdV_3$, was derived from a surviving baboon with acute respiratory symptoms. Similar to the two AdV strains from dead baboons, the 4 isolates were untypeable at the time of the outbreak for HAdV species A-F and SAdV-A by virus neutralization testing (although subsequent repeat neutralization testing against HAdV species A-G found a low level of serological cross-reactivity between $BaAdV_1$ or $BaAdV_{2,4}$ and the species F HAdVs) (Table 2).

To further characterize these untypeable AdVs, the genomes corresponding to all 4 isolates were recovered by a combined deep sequencing, traditional Sanger sequencing, and de novo assembly approach (FIG. 2). $BaAdV_1$ was found to be a member of the recently described SAdV-B species (Roy et al., 2012, Emerg Infect Dis 18: 1081-1088), but $BaAdV_2$, $BaAdV_3$, and $BaAdV_4$ (identical to $BaAdV_2$) were found to represent members of a potentially novel species (FIGS. 3B and 4). Both $BaAdV_{2,4}$ and $BaAdV_3$ meet one of the two ICTV criteria for a new AdV species by exhibiting >10% phylogenetic distance from their nearest AdV neighbors, members of species F and G (FIG. 3B). The other criterion, lack of cross-neutralization with other AdVs, appears to be satisfied by at least $BaAdV_3$ (Table 2). Since it is currently unclear whether these new AdVs are human or simian in origin, the designation "species H" has been proposed for members of this new species.

Figure 6B:
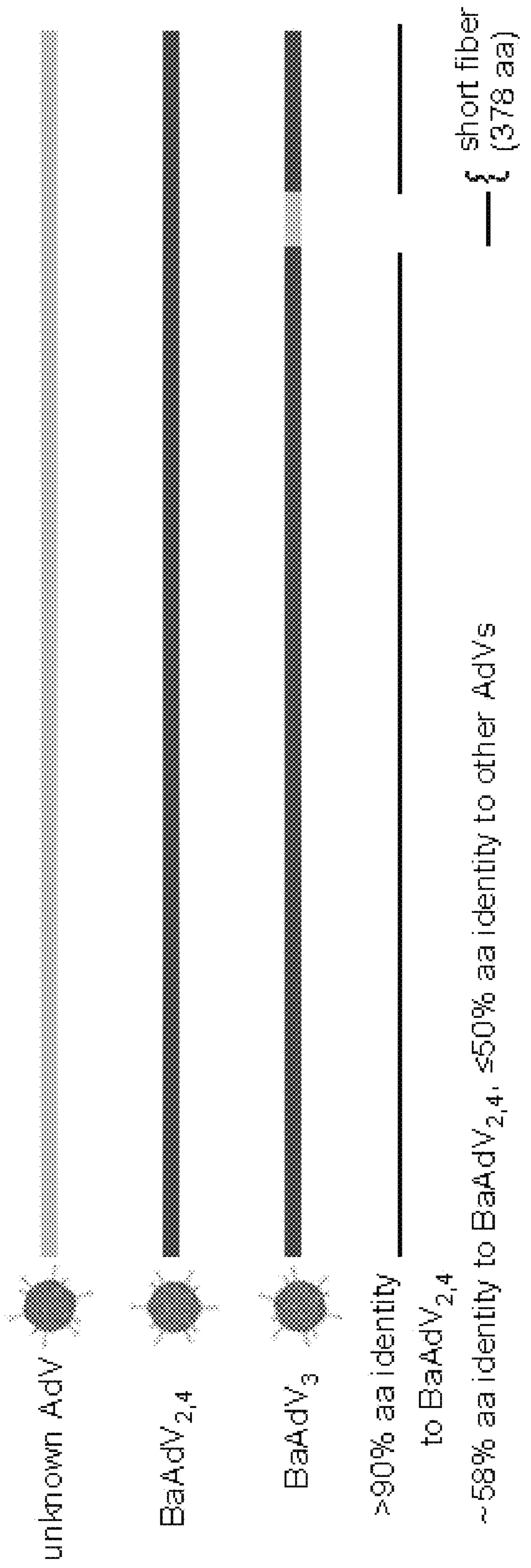

Interestingly, $BaAdV_3$, despite being a species H AdV with 91.2% overall nucleotide identity to $BaAdV_{2,4}$ (FIG. 3B), exhibits little to no cross-reactivity with $BaAdV_{2,4}$ in testing of both human and baboon sera (Table 2). The basis for this serological specificity may be the sequence of the short fiber, which diverges significantly in $BaAdV_3$ relative to both $BaAdV_{2,4}$ and all other sequenced AdVs (≤58% identity at the amino acid level) (FIG. 5B). Bootscan analysis suggests that $BaAdV_3$ may have arisen from a recombination event involving a species H AdV such as $BaAdV_{2,4}$ and an as-yet unidentified donor strain harboring the divergent $BaAdV_3$ short fiber (FIG. 6). Since productive infection by $BaAdV_3$, but not $BaAdV_{2,4}$, was observed in two human fetal cell lines (Table 1), this donor strain may potentially be a human adenovirus, or at least human-tropic.

Anecdotal reports of "flu-like" symptoms in staff members around the time of the baboon outbreak precipitated an investigation of serological responses to $BaAdV_1$, $BaAdV_{2,4}$, and $BaAdV_3$ in baboons currently in the colony and potentially exposed staff personnel. Neutralizing antibody titers to $BaAdV_1$ (species SAdV-B) and $BaAdV_{2,4}$ (species H), were detected in both baboons and humans (Table 2). Although it is possible that these titers may reflect borderline cross-reactivity with human species F AdVs (Table 1), it is far more likely that $BaAdV_1$ (species SAdV-B) and $BaAdV_{2,4}$ (species H) are serologically distinct from HAdV-F, given the low protein homology with the species F AdVs (FIG. 5), and the high rates of seroconversion and magnitude of antibody titer rise in exposed staff personnel over a relatively brief period (Table 2). Thus, the serological results likely provide the first glimpse of zoonotic transmission of a presumptive simian AdV in the species SAdV-B lineage, $BaAdV_1$, to exposed humans. The observed seroconversion in exposed staff personnel to $BaAdV_{2,4}$ also raises concerns regarding the pathogenicity of novel species H AdV infection in humans. As the origin and host reservoir of the species H AdVs remain unknown, it is unclear whether the direction of transmission for $BaAdV_{2,4}$ was zoonotic or anthroponotic. These findings continue to underscore the threat from potentially pathogenic AdVs with capacity for cross-species transmission between monkeys and humans.

In a previous outbreak of respiratory and enteric illness in baboons (Eugster et al., 1969, Arch Gesamte Virusforsch 26: 260-270), the cause was found to be SAdV-20, a species SAdV-A AdV which had been originally isolated as strain V340 in association with an outbreak of pneumoenteritis in vervet monkeys (Kim et al., J Infect Dis 117: 292-300, 1967). The data presented herein indicate that $BaAdV_3$, a novel species H AdV, is the most likely cause of this pneumonia outbreak. $BaAdV_3$ was the only sequenced AdV among recovered species H and SAdV-B AdVs that was isolated from the sick baboon, and the two baboons who died from pneumonia had previously tested negative at the time of the outbreak for HAdV species A-F and SAdV-A. Collectively with the serological testing showing little to no seroreactivity to $BaAdV_3$ in currently captive baboons and human staff, these data suggest that $BaAdV_3$ may be a rare pathogenic species H recombinant whose emergence precipitated the outbreak.

Example 6

Annotated Sequence Information

The locations of the open reading frames (coding sequence, CDS) in SEQ ID NOs: 1-4 are provided below, along with information on the identities of the encoded proteins. The location of the terminal repeats (ITRs) is also provided.

BaAdV-2 (SEQ ID NO: 1)
LOCUS BaAdV-2_final_an 34391 bp DNA linear
DEFINITION .

| | |
|---|---|
| ACCESSION | urn.local . . . 1357154693134.16 |
| VERSION | urn.local . . . 1357154693134.16 |
| KEYWORDS | . |
| SOURCE | |
| ORGANISM | . |

| FEATURES | Location/Qualifiers |
|---|---|
| misc_feature | 1 . . . 87<br>/label = "ITR repeat" |
| CDS | order(982 . . . 1199, 444 . . . 903)<br>/label = "E1A CDS" |
| CDS | 1320 . . . 1820<br>/label = "E1B 19K CDS" |

| | |
|---|---|
| CDS | 1625 . . . 3049<br>/label = "E1B 55K CDS" |
| CDS | 3056 . . . 3535<br>/label = "IX CDS" |
| CDS | order(complement(5190 . . . 5202), complement(3581 . . . 4911))<br>/label = "IVa2 CDS" |
| CDS | order(complement(13081 . . . 13089), complement(4684 . . . 8232))<br>/label = "pol CDS" |
| CDS | order(complement(13081 . . . 13089), complement(8031 . . . 9968))<br>/label = "pTP CDS" |
| CDS | 10187 . . . 11314<br>/label = "52K CDS" |
| CDS | 11335 . . . 13059<br>/label = "pIIIa CDS" |
| CDS | 13135 . . . 14646<br>/label = "III (penton) CDS" |
| CDS | 14649 . . . 15194<br>/label = "pVII CDS" |
| CDS | 15251 . . . 16303<br>/label = "pV CDS" |
| CDS | 16323 . . . 16532<br>/label = "pX CDS" |
| CDS | 16564 . . . 17403<br>/label = "pVI CDS" |
| CDS | 17490 . . . 20273<br>/label = "II (hexon) CDS" |
| CDS | 20146 . . . 20898<br>/label = "protease CDS" |
| CDS | complement(20948 . . . 22333)<br>/label = "DBP CDS" |
| CDS | 22357 . . . 24642<br>/label = "100K protein CDS" |
| CDS | order(24344 . . . 24664, 24944 . . . 25144)<br>/label = "33K protein CDS" |
| CDS | 24344 . . . 24886<br>/label = "22K protein CDS" |
| CDS | 25203 . . . 25904<br>/label = "pVIII CDS" |
| CDS | 25904 . . . 26218<br>/label = "E3 12.5K CDS" |
| CDS | 26175 . . . 26648<br>/label = "E3 CR1-alpha CDS" |
| CDS | 26645 . . . 27517<br>/label = "E3 CR1-beta CDS" |
| CDS | 27531 . . . 27803<br>/label = "E3 RID-alpha CDS" |
| CDS | 27791 . . . 28132<br>/label = "E3 RID-beta CDS" |
| CDS | 28125 . . . 28490<br>/label = "E3 14.7 CDS" |
| CDS | complement(28504 . . . 28665)<br>/label = "U exon CDS" |
| CDS | 28676 . . . 29866<br>/label = "IV (fiber 1) CDS" |
| CDS | 29697 . . . 31535<br>/label = "IV (fiber 2) CDS" |
| CDS | order(complement(32509 . . . 32652), complement(31559 . . . 31777))<br>/label = "E4 ORF 6/7 CDS" |
| CDS | complement(31795 . . . 32652)<br>/label = "E4 34K CDS" |
| CDS | complement(32585 . . . 32947)<br>/label = "E4 ORF4 CDS" |
| CDS | complement(32949 . . . 33299)<br>/label = "E4 ORF3 CDS" |
| CDS | complement(33296 . . . 33688)<br>/label = "E4 ORF2 CDS" |
| CDS | complement(33703 . . . 34083)<br>/label = "E4 ORF1 CDS" |
| misc_feature | 34305 . . . 34391<br>/label = "ITR repeat" |

BaAdV-4 (SEQ ID NO: 2)
LOCUS BaAdV-4_final_an 34391 bp DNA linear
DEFINITION .

| | |
|---|---|
| ACCESSION | urn.local . . . 1357154692931.12 |
| VERSION | urn.local . . . 1357154692931.12 |
| KEYWORDS | . |
| SOURCE | |

-continued

| ORGANISM | . |
|---|---|
| FEATURES | Location/Qualifiers |
| misc_feature | 1 . . . 87<br>/label = "ITR repeat" |
| CDS | order(444 . . . 903, 982 . . . 1199)<br>/label = "E1A CDS" |
| CDS | 1320 . . . 1820<br>/label = "E1B 19K" |
| CDS | 1625 . . . 3049<br>/label = "E1B 55K CDS" |
| CDS | 3056 . . . 3535<br>/label = "IX CDS" |
| CDS | order(complement(3581 . . . 4911), complement(5190 . . . 5202))<br>/label = "IVa2 CDS" |
| CDS | order(complement(13081 . . . 13089), complement(4684 . . . 8232))<br>/label = "pol CDS" |
| CDS | order(complement(13081 . . . 13089), complement(8031 . . . 9968))<br>/label = "pTP CDS" |
| CDS | 10187 . . . 11314<br>/label = "52K CDS" |
| CDS | 11335 . . . 13059<br>/label = "pIIIa CDS" |
| CDS | 13135 . . . 14646<br>/label = "III (penton) CDS" |
| CDS | 14649 . . . 15194<br>/label = "pVII CDS" |
| CDS | 15251 . . . 16303<br>/label = "pV CDS" |
| CDS | 16323 . . . 16532<br>/label = "pX CDS" |
| CDS | 16564 . . . 17403<br>/label = "pVI CDS" |
| CDS | 17490 . . . 20273<br>/label = "II (hexon) CDS" |
| CDS | 20281 . . . 20898<br>/label = "protease CDS" |
| CDS | complement(20948 . . . 22333)<br>/label = "DBP CDS" |
| CDS | 22357 . . . 24642<br>/label = "100K protein CDS" |
| CDS | order(24876 . . . 25151, 24344 . . . 24664)<br>/label = "33K protein CDS" |
| CDS | 24344 . . . 24886<br>/label = "22K protein CDS" |
| CDS | 25203 . . . 25904<br>/label = "pVIII CDS" |
| CDS | 25904 . . . 26178<br>/label = "E3 12.5K CDS" |
| CDS | 26175 . . . 26648<br>/label = "E3-CR-1-alpha CDS" |
| CDS | 26645 . . . 27517<br>/label = "E3 CR1-beta CDS" |
| CDS | 27531 . . . 27803<br>/label = "E3 RID-alpha CDS" |
| CDS | 27791 . . . 28132<br>/label = "E3 RID-beta CDS" |
| CDS | 28125 . . . 28490<br>/label = "E3 14.7 protein CDS" |
| CDS | complement(28504 . . . 28665)<br>/label = "U exon CDS" |
| CDS | 28676 . . . 29866<br>/label = "IV (fiber1)" |
| CDS | 29697 . . . 31535<br>/label = "IV (fiber 2) CDS" |
| CDS | order(complement(31559 . . . 31735), complement(32509 . . . 32652))<br>/label = "E4 ORF 6/7" |
| CDS | complement(31795 . . . 32652)<br>/label = "E4 34K CDS" |
| CDS | complement(32585 . . . 32947)<br>/label = "E4 ORF4 CDS" |
| CDS | complement(32949 . . . 33299)<br>/label = "E4 ORF3 CDS" |
| CDS | complement(33296 . . . 33688)<br>/label = "E4 ORF2 CDS" |
| CDS | complement(33703 . . . 34083)<br>/label = "E4 ORF1 CDS" |
| misc_feature | 34305 . . . 34391 |

-continued

| | |
|---|---|
| | /label = "ITR repeat" |

BaAdV-3 (SEQ ID NO: 3)

LOCUS BaAdV-3_final_an 34402 bp DNA linear
DEFINITION .

| | |
|---|---|
| ACCESSION | urn.local . . . 1350955631692.388 |
| VERSION | urn.local . . . 1350955631692.388 |
| KEYWORDS | . |
| SOURCE | |
| ORGANISM | . |

| FEATURES | Location/Qualifiers |
|---|---|
| misc_feature | 1 . . . 124<br>/label = "ITR repeat" |
| CDS | order(1024 . . . 1241, 487 . . . 949)<br>/label = "E1A CDS" |
| CDS | 1364 . . . 1858<br>/label = "E1B 19K" |
| CDS | 1669 . . . 3087<br>/label = "E1B 55K CDS" |
| CDS | 3092 . . . 3571<br>/label = "pIX CDS" |
| CDS | order(complement(3608 . . . 4938), complement(5217 . . . 5229))<br>/label = "IVa2 CDS" |
| CDS | order(complement(13105 . . . 13113), complement(4711 . . . 8259))<br>/label = "pol CDS" |
| CDS | order(complement(13105 . . . 13113), complement(8058 . . . 9989))<br>/label = "pTP CDS" |
| CDS | 10208 . . . 11335<br>/label = "52K CDS" |
| CDS | 11356 . . . 13080<br>/label = "pIIIa CDS" |
| CDS | 13159 . . . 14676<br>/label = "III (penton)" |
| CDS | 14679 . . . 15230<br>/label = "pVII CDS" |
| CDS | 15288 . . . 16328<br>/label = "pV CDS" |
| CDS | 16342 . . . 16557<br>/label = "pX CDS" |
| CDS | 16496 . . . 17422<br>/label = "pVI CDS" |
| CDS | 17509 . . . 20301<br>/label = "II (hexon)" |
| CDS | 20156 . . . 20926<br>/label = "protease CDS" |
| CDS | complement(20976 . . . 22361)<br>/label = "DBP CDS" |
| CDS | 22385 . . . 24661<br>/label = "100K protein CDS" |
| CDS | order(24366 . . . 24683, 24895 . . . 25163)<br>/label = "33K protein CDS" |
| CDS | 24366 . . . 24905<br>/label = "22K protein CDS" |
| CDS | 25222 . . . 25923<br>/label = "pVIII CDS" |
| CDS | 25920 . . . 26231<br>/label = "E3 12.5K CDS" |
| CDS | 26179 . . . 26724<br>/label = "E3-CR-1-alpha CDS" |
| CDS | 26721 . . . 27533<br>/label = "E3 CR1-beta CDS" |
| CDS | 27547 . . . 27819<br>/label = "E3 RID-alpha CDS" |
| CDS | 27816 . . . 28145<br>/label = "E3 RID-beta CDS" |
| CDS | 28138 . . . 28503<br>/label = "E7 14.7 protein CDS" |
| CDS | complement(28506 . . . 28667)<br>/label = "U exon CDS" |
| CDS | 28678 . . . 29811<br>/label = "IV (fiber)" |
| CDS | 29687 . . . 31480<br>/label = "IV (fiber 2) CDS" |
| CDS | order(complement(32482 . . . 32625), complement(31504 . . . 31680))<br>/label = "E4 ORF 6/7 CDS" |

-continued

| | |
|---|---|
| CDS | complement(31774 . . . 32625)<br>/label = "E4 34K CDS" |
| CDS | complement(32558 . . . 32920)<br>/label = "E4 ORF4 CDS" |
| CDS | complement(32922 . . . 33272)<br>/label = "E4 ORF3 CDS" |
| CDS | complement(33269 . . . 33661)<br>/label = "E4 ORF2 CDS" |
| CDS | complement(33675 . . . 34055)<br>/label = "E4 ORF1 CDS" |
| misc__feature | 34279 . . . 34402<br>/label = "ITR repeat" |

BaAdV-1 (SEQ ID NO: 4)
LOCUS BaAdV-1__final__an 35537 bp DNA linear UNA
DEFINITION .

| | |
|---|---|
| ACCESSION | urn.local . . . 1357154805381.28 |
| VERSION | urn.local . . . 1357154805381.28 |
| KEYWORDS | . |
| SOURCE | |
| ORGANISM | . |

| FEATURES | Location/Qualifiers |
|---|---|
| misc__feature | 1 . . . 215<br>/label = "ITR repeat region" |
| CDS | order(1171 . . . 1451, 528 . . . 1101)<br>/label = "E1A CDS" |
| CDS | 1579 . . . 2124<br>/label = "E1B 19K" |
| CDS | 1884 . . . 3362<br>/label = "E1B55K CDS" |
| CDS | 3429 . . . 3878<br>/label = "IX CDS" |
| CDS | order(complement(3916 . . . 5255), complement(5534 . . . 5546))<br>/label = "IVa2 CDS" |
| CDS | order(complement(13577 . . . 13585), complement(5025 . . . 8621))<br>/label = "pol CDS" |
| CDS | order(complement(13577 . . . 13585), complement(8420 . . . 10405))<br>/label = "pTP CDS" |
| CDS | 10522 . . . 11736<br>/label = "52K CDS" |
| CDS | 11755 . . . 13551<br>/label = "pIIIa CDS" |
| CDS | 13636 . . . 15171<br>/label = "III (penton) CDS" |
| CDS | 15200 . . . 15754<br>/label = "pVII CDS" |
| CDS | 15803 . . . 16903<br>/label = "pV CDS" |
| CDS | 16925 . . . 17149<br>/label = "pX CDS" |
| CDS | 17204 . . . 17998<br>/label = "pVI CDS" |
| CDS | 18071 . . . 20833<br>/label = "II (hexon) CDS" |
| CDS | 20834 . . . 21451<br>/label = "protease CDS" |
| CDS | complement(21499 . . . 22980)<br>/label = "DBP CDS" |
| CDS | 23018 . . . 25381<br>/label = "100K CDS" |
| CDS | order(25071 . . . 25627, 25806 . . . 25902)<br>/label = "33K CDS" |
| CDS | 25071 . . . 25775<br>/label = "22K CDS" |
| CDS | 25948 . . . 26649<br>/label = "pVIII CDS" |
| CDS | 26649 . . . 26975<br>/label = "E3 12.5K CDS" |
| CDS | 26920 . . . 28341<br>/label = "E3 CR1 alpha-beta CDS" |
| CDS | 28357 . . . 28629<br>/label = "E3 RID-alpha CDS" |
| CDS | 28536 . . . 28997<br>/label = "E3 RID-beta CDS" |
| CDS | 29000 . . . 29392<br>/label = "E3 14.7K protein CDS" |

-continued

| | |
|---|---|
| CDS | complement(29409 . . . 29567)<br>/label = "U exon CDS" |
| CDS | 29586 . . . 31196<br>/label = "IV (fiber 1) CDS" |
| CDS | 31218 . . . 32474<br>/label = "IV (fiber 2) CDS" |
| CDS | order(complement(32507 . . . 32716), complement(33481 . . . 33630))<br>/label = "E4 ORF 6/7 CDS" |
| CDS | complement(32755 . . . 33630)<br>/label = "E4 34K CDS" |
| CDS | complement(33563 . . . 33928)<br>/label = "E4 ORF4 CDS" |
| CDS | complement(33933 . . . 34283)<br>/label = "E4 ORF3 CDS" |
| CDS | complement(34294 . . . 34680)<br>/label = "E4 ORF2 CDS" |
| CDS | complement(34705 . . . 35088)<br>/label = "E4 ORF1 CDS" |
| misc_feature | 35323 . . . 35537<br>/label = "ITR repeat" |

Example 7

Annotated Sequence Information

The table below provides identity of the molecules listed in the sequence listing.

| SEQ ID NO: | Baboon Adenovirus | Molecule |
|---|---|---|
| 1 | BaAdV-2 | Viral genome |
| 2 | BaAdV-4 | Viral genome |
| 3 | BaAdv-3 | Viral genome |
| 4 | BaAdv-1 | Viral genome |
| 5 | BaAdv-2 | 100K_protein_CDS_translation |
| 6 | BaAdv-2 | 22K_protein_CDS_translation |
| 7 | BaAdv-2 | 33K_protein_CDS_translation |
| 8 | BaAdv-2 | 52K_CDS_translation |
| 9 | BaAdv-2 | DBP_CDS_translation |
| 10 | BaAdv-2 | E1A_CDS_translation |
| 11 | BaAdv-2 | E1B_55K_CDS_translation |
| 12 | BaAdv-2 | E3_12.5K_CDS_translation |
| 13 | BaAdv-2 | E3_14.7_CDS_translation |
| 14 | BaAdv-2 | E3_CR1-alpha_CDS_translation |
| 15 | BaAdv-2 | E3_CR1-beta_CDS_translation |
| 16 | BaAdv-2 | E3_RID-alpha_CDS_translation |
| 17 | BaAdv-2 | E3_RID-beta_CDS_translation |
| 18 | BaAdv-2 | E4_34K_CDS_translation |
| 19 | BaAdv-2 | E4_ORF_6/7_CDS_translation |
| 20 | BaAdv-2 | E4_ORF1_CDS_translation |
| 21 | BaAdv-2 | E4_ORF2_CDS_translation |
| 22 | BaAdv-2 | E4_ORF3_CDS_translation |
| 23 | BaAdv-2 | E4_ORF4_CDS_translation |
| 24 | BaAdv-2 | II_(hexon)_CDS_translation |
| 25 | BaAdv-2 | III_(penton)_CDS_translation |
| 26 | BaAdv-2 | IV_(fiber_1)_CDS_translation |
| 27 | BaAdv-2 | IV_(fiber_2)_CDS_translation |
| 28 | BaAdv-2 | IVa2_CDS_translation |
| 29 | BaAdv-2 | IX_CDS_translation |
| 30 | BaAdv-2 | pIIIa_CDS_translation |
| 31 | BaAdv-2 | pol_CDS_translation |
| 32 | BaAdv-2 | protease_CDS_translation |
| 33 | BaAdv-2 | pTP_CDS_translation |
| 34 | BaAdv-2 | pV_CDS_translation |
| 35 | BaAdv-2 | pVI_CDS_translation |
| 36 | BaAdv-2 | pVII_CDS_translation |
| 37 | BaAdv-2 | pVIII_CDS_translation |
| 38 | BaAdv-2 | pX_CDS_translation |
| 39 | BaAdv-2 | U_exon_CDS_translation |
| 40 | BaAdV-4 | U_exon_CDS_translation |
| 41 | BaAdV-4 | pX_CDS_translation |
| 42 | BaAdV-4 | pVIII_CDS_translation |
| 43 | BaAdV-4 | pVII_CDS_translation |
| 44 | BaAdV-4 | pVI_CDS_translation |

-continued

| SEQ ID NO: | Baboon Adenovirus | Molecule |
|---|---|---|
| 45 | BaAdV-4 | pV_CDS_translation |
| 46 | BaAdV-4 | pTP_CDS_translation |
| 47 | BaAdV-4 | protease_CDS_translation |
| 48 | BaAdV-4 | pol_CDS_translation |
| 49 | BaAdV-4 | pIIIa_CDS_translation |
| 50 | BaAdV-4 | IX_CDS_translation |
| 51 | BaAdV-4 | IVa2_CDS_translation |
| 52 | BaAdV-4 | IV_(fiber1)_CDS_translation |
| 53 | BaAdV-4 | IV_(fiber_2)_CDS_translation |
| 54 | BaAdV-4 | III_(penton)_CDS_translation |
| 55 | BaAdV-4 | II_(hexon)_CDS_translation |
| 56 | BaAdV-4 | E4_ORF4_CDS_translation |
| 57 | BaAdV-4 | E4_ORF3_CDS_translation |
| 58 | BaAdV-4 | E4_ORF2_CDS_translation |
| 59 | BaAdV-4 | E4_ORF1_CDS_translation |
| 60 | BaAdV-4 | E4_ORF_6/7_translation |
| 61 | BaAdV-4 | E4_34K_CDS_translation |
| 62 | BaAdV-4 | E3_RID-beta_CDS_translation |
| 63 | BaAdV-4 | E3_RID-alpha_CDS_translation |
| 64 | BaAdV-4 | E3_CR1-beta_CDS_translation |
| 65 | BaAdV-4 | E3_CR1-alpha_CDS_translation |
| 66 | BaAdV-4 | E3_14.7_protein_CDS_translation |
| 67 | BaAdV-4 | E3_12.5K_CDS_translation |
| 68 | BaAdV-4 | E1B_55K_CDS_translation |
| 69 | BaAdV-4 | E1A_CDS_translation |
| 70 | BaAdV-4 | DBP_CDS_translation |
| 71 | BaAdV-4 | 52K_CDS_translation |
| 72 | BaAdV-4 | 33K_protein_CDS_translation |
| 73 | BaAdV-4 | 22K_protein_CDS_translation |
| 74 | BaAdV-4 | 100K_protein_CDS_translation |
| 75 | BaAdv-3 | 100K_protein_CDS_translation |
| 76 | BaAdv-3 | 22K_protein_CDS_translation |
| 77 | BaAdv-3 | 33K_protein_CDS_translation |
| 78 | BaAdv-3 | 52K_CDS_translation |
| 79 | BaAdv-3 | DBP_CDS_translation |
| 80 | BaAdv-3 | E1A_CDS_translation |
| 81 | BaAdv-3 | E1B_55K_CDS_translation |
| 82 | BaAdv-3 | E3_12.5K_CDS_translation |
| 83 | BaAdv-3 | E3_14.7_protein_CDS_translation |
| 84 | BaAdv-3 | E3_CR1-beta_CDS_translation |
| 85 | BaAdv-3 | E3_RID-alpha_CDS_translation |
| 86 | BaAdv-3 | E3_RID-beta_CDS_translation |
| 87 | BaAdv-3 | E3-CR1-alpha_CDS_translation |
| 88 | BaAdv-3 | E4_34K_CDS_translation |
| 89 | BaAdv-3 | E4_ORF_6/7_CDS_translation |
| 90 | BaAdv-3 | E4_ORF1_CDS_translation |
| 91 | BaAdv-3 | E4_ORF2_CDS_translation |
| 92 | BaAdv-3 | E4_ORF3_CDS_translation |
| 93 | BaAdv-3 | E4_ORF4_CDS_translation |
| 94 | BaAdv-3 | pII_(hexon)_translation |
| 95 | BaAdv-3 | pIII_(penton)_translation |

-continued

| SEQ ID NO: | Baboon Adenovirus | Molecule |
|---|---|---|
| 96 | BaAdv-3 | pIV__(fiber__2)__CDS__translation |
| 97 | BaAdv-3 | pIV__(fiber)__translation |
| 98 | BaAdv-3 | pIVa2__CDS__translation |
| 99 | BaAdv-3 | pIIIa__CDS__translation |
| 100 | BaAdv-3 | pIX__CDS__translation |
| 101 | BaAdv-3 | pol__CDS__translation |
| 102 | BaAdv-3 | protease__CDS__translation |
| 103 | BaAdv-3 | pTP__CDS__translation |
| 104 | BaAdv-3 | pV__CDS__translation |
| 105 | BaAdv-3 | pVI__CDS__translation |
| 106 | BaAdv-3 | pVII__CDS__translation |
| 107 | BaAdv-3 | pVIII__CDS__translation |
| 108 | BaAdv-3 | pX__CDS__translation |
| 109 | BaAdv-3 | U__exon__CDS__translation |
| 110 | BaAdv-1 | 100K__CDS__translation |
| 111 | BaAdv-1 | 22K__CDS__translation |
| 112 | BaAdv-1 | 33K__CDS__translation |
| 113 | BaAdv-1 | 52K__CDS__translation |
| 114 | BaAdv-1 | DBP__CDS__translation |
| 115 | BaAdv-1 | E1A__CDS__translation |
| 116 | BaAdv-1 | E1B__55K__CDS__translation |
| 117 | BaAdv-1 | E3__12.5K__CDS |
| 118 | BaAdv-1 | E3__14.7K__protein__CDS__translation |
| 116 | BaAdv-1 | E3__CR1__alpha-beta__CDS__translation |
| 1120 | BaAdv-1 | E3__RID-alpha__CDS__translation |
| 121 | BaAdv-1 | E3__RID-beta__CDS__translation |
| 122 | BaAdv-1 | E4__34K__CDS__translation |
| 123 | BaAdv-1 | E4__ORF__6/7__CDS__translation |

-continued

| SEQ ID NO: | Baboon Adenovirus | Molecule |
|---|---|---|
| 124 | BaAdv-1 | E4__ORF1__CDS__translation |
| 125 | BaAdv-1 | E4__ORF2__CDS__translation |
| 126 | BaAdv-1 | E4__ORF3__CDS__translation |
| 127 | BaAdv-1 | E4__ORF4__CDS__translation |
| 128 | BaAdv-1 | II__(hexon)__CDS__translation |
| 129 | BaAdv-1 | III__(penton)__CDS__translation |
| 130 | BaAdv-1 | IV__(fiber__1)__CDS__translation |
| 131 | BaAdv-1 | IV__(fiber__2)__CDS__translation |
| 132 | BaAdv-1 | IVa2__CDS__translation |
| 133 | BaAdv-1 | pIIIa__CDS__translation |
| 134 | BaAdv-1 | pIX__CDS__translation |
| 135 | BaAdv-1 | pol__CDS__translation |
| 136 | BaAdv-1 | protease__CDS__translation |
| 137 | BaAdv-1 | pTP__CDS__translation |
| 138 | BaAdv-1 | pV__CDS__translation |
| 139 | BaAdv-1 | pVI__CDS__translation |
| 140 | BaAdv-1 | pVII__CDS__translation |
| 141 | BaAdv-1 | pVIII__CDS__translation |
| 142 | BaAdv-1 | pX__CDS__translation |
| 143 | BaAdv-1 | U__exon__CDS__translation |

It will be apparent that the precise details of the methods or compositions described may be varied or modified without departing from the spirit of the described invention. We claim all such modifications and variations that fall within the scope and spirit of the claims below.

The invention claimed is:

1. A method of detecting a baboon adenovirus type 3 (BaAdV-3) or a baboon adenovirus type 2/4 (BaAdV-2/4) infection in a subject, the method comprising the steps of:

(a) obtaining a sample from a subject suspected of having an infection caused by BaAdV-3or BaAdV-2/4, wherein the sample comprises antibodies from the subject;

(b) contacting the sample of step (a) with a full-length BaAdV-3 or BaAdV-2/4 polypeptide(s) encoded by SEQ ID NO 1 , SEQ ID NO: 2 or SEQ ID NO: 3, (c) screening for antibodies bound to a full length polypeptide;

wherein antibody binding confirms the BaAdV-3 or the BaAdV-2/4 infection.

2. The method of claim 1, wherein the full-length polypeptide comprises the amino acid sequence set forth as one of SEQ ID NOs: 5-109.

3. The method of claim 1, wherein the full-length polypeptide is conjugated to a label.

4. The method of claim 1, wherein the full-length polypeptide is immobilized on a solid substrate.

5. The method of claim 1, further comprising contacting the sample with a labeled antibody that specifically binds an immunoglobulin constant region; and detecting the labeled antibody.

6. The method of claim 3, wherein the label is detected by spectroscopic, photochemical, biochemical, immunochemical, electrical, optical or chemical means.

7. The method of claim 3, wherein the label is a magnetic bead, fluorescent dye, an enzyme, a radiolabel, a colorimetric label, or a plastic bead.

8. The method of claim 1, wherein the sample is a blood, serum or plasma sample.

9. The method of claim 1, wherein the full-length polypeptide comprises the amino acid sequence set forth as one of SEQ ID NO: 24, SEQ ID NO: 55, or SEQ ID NO: 94.

10. The method of claim 9, wherein the full-length polypeptide comprises the amino acid sequence set forth as SEQ ID NO: 94, and wherein the method detects BaAdV-3.

11. The method of claim 1, wherein the full-length BaAdV-2/4 polypeptide(s) of step (b) is encoded by SEQ ID NO: 1 or SEQ ID NO: 2.

12. The method of claim 1, wherein the full-length BaAdV-3 polypeptide(s) of step (b) is encoded by SEQ ID NO: 3.

13. The method of claim 2, wherein the full-length polypeptide comprises the amino acid sequence set forth as one of SEQ ID NOs: 75-80.

14. The method of claim 2, wherein the full-length polypeptide comprises the amino acid sequence set forth as one of SEQ ID NOs: 81-85.

15. The method of claim 2, wherein the full-length polypeptide comprises the amino acid sequence set forth as one of SEQ ID NOs: 86-90.

16. The method of claim 2, wherein the full-length polypeptide comprises the amino acid sequence set forth as one of SEQ ID NOs: 91-95.

17. The method of claim 2, wherein the full-length polypeptide comprises the amino acid sequence set forth as one of SEQ ID NOs: 96-100.

18. The method of claim 2, wherein the full-length polypeptide comprises the amino acid sequence set forth as one of SEQ ID NOs: 101-105.

19. The method of claim 2, wherein the full-length polypeptide comprises the amino acid sequence set forth as one of SEQ ID NOs: 106-109.

* * * * *

UNITED STATES PATENT AND TRADEMARK OFFICE

CERTIFICATE OF CORRECTION

PATENT NO. : 9,222,142 B2
APPLICATION NO. : 14/233710
DATED : December 29, 2015
INVENTOR(S) : Chiu et al.

It is certified that error appears in the above-identified patent and that said Letters Patent is hereby corrected as shown below:

On the Title Page

Item (72) Inventors, line 5, “Dean Ehrdman,” should read -Dean Erdman-.

Signed and Sealed this
Twenty-sixth Day of April, 2016

Michelle K. Lee
*Director of the United States Patent and Trademark Office*

SEQUENCE LISTING

<160> NUMBER OF SEQ ID NOS: 143

<210> SEQ ID NO 1
<211> LENGTH: 34391
<212> TYPE: DNA
<213> ORGANISM: Adenovirus

<400> SEQUENCE: 1

```
tgataatgag agaggaggag tgggggtggc agggggtggg aagaagtgac gtgcggggtg      60

acggggtggg cggcgcggga gcggaagttg gtttgtgcta atgaggcgca tcggaactga     120

cgtgtaaaag gcgactttgg accggaaatg aggcgtgttt tggcatttct gcaagttttc     180

tgcggatttt ggcgcgaaaa ctgggcaatg aggaagttgt ggttaatgtg tactttttat     240

gactgggagg gaaaactgct gatgtgcagt gaactttggg cgctgacggg taggtttcgc     300

tacgtggcag tgccacgaga aggctcaaag gtcccattta ttgtactgct cagcgttttc     360

cgtgcctatt taaacgcctt cagatcgtca agaggccact cttgagtgct ggcgagtaga     420

gttttctcct ccgcgctgtg aagatgaggc tggttcctga gatgtacgga gtgtcctggg     480

atgagacggc cgaagagctg ctgaatgctg aaatttacga cgtgccgaat ttgcctccag     540

gaacaccctc gcttcacgat ttgtttgatg tggaaaatga tggcggacag gacgagaacg     600

aagacgcggt aaatagtatg tttcctgact caatgctgtc ggcgggcgag ggttacgctg     660

gggatgtaga tccgagtggg agcgacatgg acttaaagtg ctacgaagat ggtttgccga     720

gcagcagttc agaaggatca gatgaggatg agcaaaagcc tttgaaacat gaactggtct     780

tagactgtcc taagaaccct ggccatgatt gtcgcgcctg tgctttccat agagctacca     840

gcggaaatac tgaagcaata tgctgtttgt gttatatgcg ccttaccagc gattttgtat     900

acagtaagta taggcgatta tgagggacgg gtggtatgtc tgtgtgtatg ccagtgtgct     960

taatgttgtg tgtgatttca ggcgatgtgt ccgacgtgga aggagacgga gacaagtcaa    1020
```

-continued aagtatctga gtctcctggc tctttgggga ctgtggttcc agatggtgtt cttaagccca 1080
ccgcggtgag agtatcggca aggcgacgcc aagcggtaga gaagttggaa gatttgctcc 1140
aggaaccaga gcaaactgaa cctttggact tgtccttaaa gcaacccagg atgacctaat 1200
cgtttatggt attttatgac gcgcaataaa gagtgttaaa ccttaacttg tgtttattta 1260
ttgggcggtc tgcgggtata taagcaggtg gctgacactg aggcgttact tttttccgaa 1320
tggatctcct aaggttgctc agtgattacg aggtgctgcg caagttgctg gagacagcct 1380
gtgagaaaac ttccagctgt tggaggtttt tctttggctc tactcttagc aacgtggtgc 1440
acagagtcaa gcgagagcac agtgaggaat tttctagact agtggcagat gttcccgggc 1500
tttttgtttc tttagactta ggacatcact cttactttca ggagaaaatt gtaaagggtc 1560
tagtgtttga gtcaactggc cgcacggttg tgtccgtggc ttttatctgt tttcttttgg 1620
ataaatggag cagcgacagc cacctgtcgt gggattacat gctggattac atgaccatgg 1680
cgctgtggcg ggcgctcctg aggaggagga gggcttgcat ttacttgccg gtgcagcctc 1740
agcgaggtct ggagcgagtg gaggaagagg aggaggagaa cgagaacccg agggccggcg 1800
tggaccctcc tctggaatag aagctgtggg cgagccagaa gagggtacta gtgatggggt 1860
tagaaagagg cggaggacag aaatggaaga ggtgaacgct cgagattacc ttactgattt 1920
gactgtgcgg ttgatgagtc gtaggcgacc tgaaacggtt gcatggagtg aactggagac 1980
tgaatttaaa aatggcaata tgaatttgct gtacaagtat agctttgaac agatacaaac 2040
tcattggttg gaaccgtggg aggattggga gacggccttt gccaattttg caaaaatcgc 2100
cctgcggcca gataaaatct acaccataag gcgcatggtt aacattagga agtgtgtgta 2160
tgtcctgggg aatggggcta tggttcagat tcagacgtgt gaccgcgtgg cttttaattg 2220
ctgcatgcag agcatgggcc ccggggtaat aggcatgagc ggcgtgactt ttgccaacgt 2280
gcgattcacc ggggaaaact tctttggcgc tgtgattatg aacaacacta gccttactct 2340
tcacggggtc tattttctaa atctcagtaa cacctgtgta gagtgctggg gtcgcgcgtg 2400
tctgaggggc tgtacgttct atggctgttg gaaagcagtg gtgggcagaa caaaaagtca 2460
tgtgtctgta aagaagtgta tgtttgaacg ctgtgtgatt gctataatgg tggaggggca 2520
ggggcgtata agaaacaatg ttggggcaga gaacgggtgt ttctcttttgt tgaagggctc 2580 ggccagtgtt aagcacaaca tgatctgtgg tactggcact tgtaacatat cacacttgtt 2640
aacgtgttca gatggaaatt gccaggcttt acgcaccttg catattgtgt ctcatcgacg 2700
cctcccctgg ccggttcttg aacacaatat gctgacgcgc tgttctgttc acgtaggcgc 2760
tagacgaggt atgctggtgc cttaccaatg taacttcagc tatactaaag ttttactgga 2820
aacagatgcg tttcctaggg tgtgttttaa tggagtgttt gacatgactg tggaggtttt 2880
taaagttgta aggtatgacg agtcaaagtc tcgttgtcgc ccatgtgagt gcggagccaa 2940
tcacctgaga ttgtatcctg tgaccctgaa tgtgacggag gagttaagag cggaccactt 3000
gacactatcg tgtttgcgaa cggactacga gtctagtgac gaggagtaag gtaatatggg 3060
cggagttaca aaaggtataa aacggacgtg gtggtggggt ggtttcattg ccaaaatgag 3120
cgggtctacg gatagcaact ctgtgaactt cgagggaggg gtgtttagcc catatttgac 3180
aactcgtctt ccttcttggg caggggtgcg tcagaatgtg gtgggctcta gcatggacgg 3240
tcgcccggtt gcccccgcga actctgctac tctcacctac gctacggtgg gatcgtcgtt 3300
ggacgctgct gccgctgctg ctgcttctgc tgccgcttct acagctcgtg ttatggcggt 3360

-continued

```
tgattttgga ctgtacaacc aactggctac cgcggctgct gcatctcgct ctgtggttca   3420
gcaagatgcc ctgaacgtca tactggctcg cctggaaatg ttgtctcaac gtttggatca   3480
gctcgctgcc cagattgccc tttccccagc cccgattcc acttcagatt cttaaataaa    3540
gtaaataaag taaaaaaaca tttgatttaa aataaacgtt ttatttgttt tttttggcgc   3600
ggtaggctct agaccatctg tcgcggtcgt taaggacttt gtgtatggtt tccaaaacac   3660
ggtacaagtg ggactgaatg tttaagtaca taggcatgag gccgtctttg gggtgcaggt   3720
aagaccactg aagggcgtcg tgctctgggg tagtgttata aatcacccag tcgtagcaag   3780
gtttttgggc atggaattgg aagatgtctt ttagaagcaa gctaatagct aagggaaggc   3840
ctttggtgta ggtgttgaca aagcgattaa gctgtgaggg atgcatgcga ggggagatga   3900
tgtgcatttt agcctggatc ttaaggttag caatattgcc ccccaggtct ctgcgaggat   3960
tcatgttatg caacaccacc aacacggtgt acccggtgca tttggggaac ttgtcatgta   4020
gctttgaagg aaaggcgtga aagaatttgg aaacccctttt gtgccctcct aggttttcca  4080
tgcattcgtc cataataatg gcaatgggtc ccctggcggc cgctttggca aacacgttgt   4140
ctgggttgga cacgtcatag ttttgttcca gagtaaggtc gtcgtaggcc atctttacaa   4200
agcgcgggag tagggtgcca gattggggga tgatagtgcc ctcgggacct ggagcgtagt   4260
ttccctcgca gatttgcatc tcccaagcct taatttctga gggggggtatc atgtccactt  4320
gaggggcgat aaaaaacaca gtttccggag ggggattaat gagctgggtg gagagcaagt   4380
tgcgtaaaag ctgggactta ccacagcctg tggggccgta gatgacccca atgacaggct   4440
gcagctggta gttaagagac ttgcagctgc cgtcattgcg caacaatggg gccacttcat   4500
tcatcatact tcttacatgg cggttttccc tcaccaagtt ttggagaagt cgctccccgc   4560
ctagggagag tagctcttcc aagctgttaa agtgtttcag cggtttgaga ccatctgcca   4620
tgggcatttt ttcaagcgat tggcgcagta gatacaagcg atcccacagt tcggtaacgt   4680
gttctatggc atctcgatcc agcagacttc ttggttgcga gggttgggac gactttcgct   4740
gtagggcacc agccggtggg cgtccagggc tgcgagagtc atgtccttcc agggtctgag   4800
ggtccgcgtc agggtggtct cggtgacggt aaaagggtgg gcccctggtt gggcgcttgc   4860
cagtgtgcgt ttgaggctca tcctgctggt gctgaagtgg acgttttcgc cctgggaatc   4920
ggccaagtag cacttaagca tgaggtcgta gctgagagat tcagccgcgt gtcctttggc   4980
gcgcagcttc cccttagaaa catgcagaca cttgctacag tgcagagact tgagcgcata   5040
gagcttaggg gctaaaaaaa ctgattcagg ggaaaaggca tctgcgccac actgagcgca   5100
tacagtctca cactctacca gccaggtgag ctcgggttgg tttgggtcaa aaaccaactt   5160
gcctccattt tttttaatcc gcttcttacc tcgggtttcc atgagtctgt gtcctgcttc   5220
ggtcacaaaa agactgtcgg tgtccccgta gaccgatttg agctgtctct gttccagagg   5280
ggtgccgcgg tcctcgtcgt acaaaaactg agaccactct gagacgaaag ctctggtcca   5340
cgctaataca aatgaagcta tctgcgaggg gtatctgtca ttttcaatga gagggtcaac   5400
cttttgtaag gtgtggagac agaggtcgtc ctcttccgcg tccataaaag tgattggctt   5460
ataggtgtaa gtcacgtgac catcggggtg gcgtggtggg ctataaaagg gggcgttacc   5520
cgcttcgtcg tcactttctt ccgcatcgct gtggatcaga gccagttgtt ctggtaagta   5580
agccctttcg aaggcgggca tgacctcggc gctcaaggtg tcagtttcta caaacgaggt   5640
ggatttgata ttcacgcggc cggaggcaat gtccttgacg gtggaggttt ccatttggtc   5700
agaaaagaca atctttttat tgtcaagttt ggtggcaaac gacccgtaga gggcgttaga   5760
```

-continued

```
tagcaatttg gcaatggaac gtaaagtttg attttttca cggtcggccc gctccttggc   5820
cgcgatgtta agttgtacgt actcccgggc cacgcagcgc cactccggga aaacagtagt   5880
gcgctcgtcg ggcactatac ggacgctcca gcccctgttg tgcagggtaa taaggtccac   5940
actggtagct acctcacccc tgagcggttc gttggtccag cacaacctac cgccttttcg   6000
ggagcaaaac gggggaagta cgtctagcaa gttggaagcc ggtgggtcgg cgtcgatggt   6060
gaagatgccg gggaggagag acttgttaaa ataattaatt tctacgcggt gttgcaaggc   6120
caagtcccac tttttgacgg ccagagccct ctcgtacgga ttaaggggag gaccccaagg   6180
catggggtgg gtaagggcgg aagcgtacat gccacaaatg tcataaacat aaagaggctg   6240
gcgtaaaacg ccaatgtatg taggatagca acgtccgccg cgaatgctgg ccctgacgta   6300
atcgtacatt tcatgggagg gtgccaaaag gccgctcccc aggtgggttt tttggggttt   6360
tacggcgcgg taggcgatct gtcgaaagat ggcgtgggag ttggaagaga tggtaggcct   6420
ctgaaacaca ttgaagctgg cctgcgaaag gcccacggcg tcctgtagga actgcgcgta   6480
cgactccctg agtttgtcca ccagcgcagc ggtgacgagg acgtccaagg cgcagtagtc   6540
cagggtttcg cgtacgaggt cgtaggtttt ttcttgcttt ttttcccaga gttcgcggtt   6600
gaggaggtac tcttcgcggt ctttccagta gtctgcggca ggaaatcctc ggtcgtctgc   6660
tcggtaagcg cccaacatgt aaaactcgtt aaccgctttg taaggacaac agccttttc    6720
tatgggcagg gcgtaggcct gagccgcctt gcgaagagag gtgtgggtga gctggaaggt   6780
gtctcttacc atgaccttta agtactgatg tttgaagtcg gtgtcgtcgc aacagccctg   6840
ctcccacaag gtgaaatccg tgcgcttttt ctgccgagga tttggcaggg caaaggtgac   6900
atcgttaaac aggattttac cggcgcgagg cataaaattt ctggagatgc ggaaaggccc   6960
gggaacgtcc gagcgattgt tgataacctg cgcggccaga acaatctcgt caaatccgtt   7020
gatgttatgc ccgacgatgt aaagttcgag aaagcgcgga acgcctttga gggcgggagc   7080
tttctttagt tcttcaaacg ttaggcattc tggagaaaag agccctagct ccgctcggga   7140
ccattcttct aagtgggaat tggctgcaag aaacgagcgc cacagttcgc gggctagcag   7200
agtttggagg cgatctctaa agtctctgaa ctttctgcct accgccattt tttccggcgt   7260
gacaacgtaa aaggtagcag ggcggttgtt ccaggtgtcc catttcaact caacggctag   7320
ggcacaggct ttaagaacga gagcgtcgtc gccggagatg tgcataacca gcatgaaggg   7380
caccaactgt tttccgaagg aacccatcca cgtataggtt tctacgtcgt aggtaacaaa   7440
cagcctctcg gtgcgaggat gggaaccgat cggaaagaag ctgatctcct gccaccagct   7500
ggaggagtgc gcgttaatgt gatggaagta gaagtttcgc cggcgcacag agcattcgtg   7560
ctgatgtttg taaaagcgac cgcagtagtc gcagcgctgc acgctctgta tctcttcaat   7620
gagatgtacc ttgcgaccgc ggaccaaaaa tcgcaagggg aaagtcagtg gggaggaggc   7680
ctgtggttcg ttttcccctt cgcggtgttc gtcggggtat gcgccggcgc cctgatcttg   7740
ggggtggatg acaacagggg tcacgacgcc ccttgtgccg caagaccaga tttccgccac   7800
cgtagggcgc aggcggcgca caagggcttc cagttgactg cagtccagag aatccaaaga   7860
gccgttcgcc aagtcggagg gaagagactg caggttgact tgcaagagag cggtaagggc   7920
gcgggtgaga tgcaaatggt acttgatctc tagcgggcag ttagaagaag agtctacggc   7980
atacaggaga gcgtgaccgc gtggggcgac gacggttccc ctggggagtt ttatctcatc   8040
cggcggggtc gcgcacccgg aggtagtgga ggctcgacgc ctggagggag cggaggaaga   8100
```

```
ggcacgtttt cgtgaagatt tggcagcggc aggtgacgcg ctcggagatc gctggcatgg   8160
gcgacgacgc ggcggttgag atcttgaatg tgctgcctct gcgtaaagac taccggtccc   8220
ctggttctga acctgaaaga gagttccaca gaatcaatat cggtgtcgtt aacggccgcc   8280
tgccgcagaa tctcctgtac gtcgccagag ttgtcctggt aggcgatctc ggccataaac   8340
tgctcgatct cctcttcttg gaggtcgccg tggccggccc tctccacggt ggcggccagg   8400
tcgttagaga tgcgacgcat gagttgagaa aaggcgttta ggccgttttc gttccacacg   8460
cggctgtaca ccaccccccc ggcggagtca cgggcccgca tgacgacctg agcgacgttc   8520
aattctacgt gacgggcgaa gacagcgtag tttctaagac gctgaaagag gtagttgagg   8580
gtggtggcga tgtgctcgca cacgaaaaag tacatgatcc agcggcgcag tgtggactcg   8640
ttgatgtctc cgatggcctc gaggcgctcc atggcctcgt agaaatccac ggcaaaattg   8700
aaaaactggg aatttcgggc cgacaccgtg agttcctctt gcagcagacg gattaggtcc   8760
gctatggtgt cgcggacttc tcgctcgaaa gccccggggg gcgcctcttc ttcttccagt   8820
tcctcctcct cccccctcttc cagcagcata ggctcttctg gaacttccgc tgcgggagcc   8880
ggacggcggc ggcgtcgtct caccggcagt cggtccacga agcgttcgat catttcaccg   8940
cgacggcggc gcatggtttc cgtgacggcg cggccgtgtt cgcgaggacg cagttcgaaa   9000
acgccgcctc gtagtccgcc gccctgtagg gagggtaagt gatgggggcc gtcgggtaga   9060
gagaccgcac taacgatgca ttttattaat tgctgcgtag gcactccgtg caaggatctg   9120
agagcatcca agtcaacggg atctgagaac ttctctaaga aggcgtttaa ccaatcgcaa   9180
tcgcaaggta agctaagaac gctgggccgc tgggtgcttt cggggggcag gcgggaggtg   9240
atgctgctga tgatgtaatt aaagtaggcg gttttcaaac ggcggatggt ggcgaggaga   9300
accacgtctt ttggtccagc ctgttggatg cgaaggcggt cggccattcc ccacgcttcg   9360
ttttgacagc gacgcaggtc cttgtagtag tcttgcatca gtctctccac cgggatttct   9420
gcttctcctc tgtctgccat tctggtcgat ccgtagcctc gtagtggttg cagcaaggcc   9480
aagtccgcta ccactctttc ggccaaaact gcctgctgaa cctgcgtgag ggtggtttga   9540
aaatcatcta gatctacgaa gcggtggtat gcgccggtgt tgatggtgta cgtacagtta   9600
gccatcacgg accaatttac cacttgcatt cctggttggg tgatttctgt gtactttaga   9660
cgagagtaag cgcgggattc aaagacgtag tcgttgcaag tgcgcacgag gtactggtat   9720
cctactagga agtgaggcgg aggctcgcgg tagaggggcc aacccacggt ggccggcgcc   9780
ccaggggcga gatcgtccag catgagccgg tgataatgat agacgtatcg ggagagccac   9840
gtgatgccgg cggaggtggt ggccgctctg gtgaactctc gtacgcggtt ccagatgttg   9900
cgcagtgggc ggaaacgttc catggtgggc acgctctgtc ccgtgaggcg ggcgcagtcc   9960
tgtacgctct agacagaaaa aacagagagc catcatcgac tcctctccgt agtctggagg  10020
ttaggtcgca agggtgcggc ggcggggaac cctggttcga gaccagctgg atccgccgtc  10080
ccgatgcgct tggctccgca tccacgacgg ccgcgggcgt cgagacccag ccgcgatgcg  10140
cacaccccaa atacggaggg gagtcttttt gttgtttgtt ttgtagatgc atcccgtgct  10200
gcggcagatg cgacctcaga ccgccgcatt tcagcctacc accaccgcca cggcggccgt  10260
gtgtggcgcc ggccgcgggg aggaggaact ggccttagac ttggaggagg gggaaggctt  10320
agctcgcttg ggagcgccct ctcccgaacg ccatccccgg gtgcagctgg ccagggacgc  10380
ccggcaggcc tacgttccgc ggcagaacct ctttagagac ggcagcggac aggaggccga  10440
ggagatgcgc gactgtcggt ttcgggcagg gaaggagctg cgagcggggt ttgaccgaga  10500
```

-continued

```
aaagctgttg cgcgccgagg actttgaacc ggacgagggt tcgggcatca gtccggcccg  10560
cgcccacgtg acggctgcca atctagttac cgcgtacgag cagacggtga acgaggagcg  10620
aaacttccaa aaaagcttta acaatcacgt taggaccctg attgcgcgag aggaggtggc  10680
cacgggactg atgcatctgt gggatttcat agaggcgtac gtacagaatc ctactagcaa  10740
gccgttgacg gcgcagctgt tcttgatagt tcagcacagt cgcgacaacg aaacgtttcg  10800
cgaggccatg ttaaacatcg cggagcccga gggtcggtgg ttgctggatc tggtgaacat  10860
cttgcaaagc atagtagttc aggagaggag cctgagcttg gccgataagg tagcggctat  10920
taactactca atgcagagtc tgggtaaatt ttacgcccgc aaaatctaca agagtccata  10980
cgttcccatc gacaaagagg taaagatcga cagcttttac atgcgcatgg ctctaaaggt  11040
gctgaccctc agcgacgacc tcggggtgta ccgcaacgat cggatacaca aagctgtgag  11100
cgccagccgg cggagggaac tgagcgacag ggagctgatg cacagcttgc gaagggctct  11160
ggcgggcgcg ggcgacccgg accgcgaaac gtactttgac atgggggccg acctgcagtg  11220
gaggcccagc gcccgggcgt tagaggcggc cggttatcgc ggcgagcgag aggagataga  11280
tgatgaagac gaagagtacg aggacgaccc ctgaccgggc agctgttttt ttagatgcag  11340
cagcagtcgt cggcggacgg gaccagcgtg aatcccgcac ttttggcgtc catgcaaagt  11400
caaccatcgg gcgtgaacgc ctccgatgac tggtcggcgg ccatggatcg cataatggcg  11460
ctgacgaccc gtaatcccga agcttttaga cagcagcctc aggctaaccg tttttcggcc  11520
attctggagg ccgtggttcc ttcccgcact aaccctacgc atgaaaaggt tctgacgatc  11580
gtaaacgccc tggtggacag caaagccatc cgccgcgacg aggcgggctt gatttacaac  11640
gctctactgg aacgcgtggc gcgctacaac agcactaacg tgcaggctaa cctcgaccgt  11700
ctgaatacag acgttagaga ggcgctggcg caaaaggagc gctttctgcg agacagcaat  11760
ctggggtcct tggtggcgtt gaacgctttt ttgagcactc agcctgctaa cgtccctcgc  11820
ggtcaggagg attacgtgag cttcatcagc gccctgcgtc tcctggtgtc cgaggtcccc  11880
cagagcgagg tgtaccagtc aggcccggat tacttctttc aaacctcccg ccagggcttg  11940
cagacggtaa atctcagcca ggcctttaag aacttgcagg gcatgtgggg tgttaaagct  12000
ccgctggggg atcgcgccac catctccagc cttctgaccc ctaacacgcg cctgttgttg  12060
ctgctcatcg ccccgtttac taacagcagc agcatcagcc gtgactctta cctagggcat  12120
ttaatcactc tttatcggga ggccatagga caggcgcagg tggacgaaca cacctaccag  12180
gagattacta acgttagtcg ggcgctgggg caggaggaca ccggcagcct ggaggccacg  12240
ctgaacttcc tgctcaccaa ccgcagacag aaaatcccct cacagtttac gctgagcgcc  12300
gaggaggaaa gaatcctccg ctacgtgcag cagtcggtta gcctgtactt gatgcgagag  12360
ggcgccaccg cttctacggc gctggacatg acggctcgta acatggagcc ctctttttac  12420
gcgtccaacc gtcccttcat aaaccgcttg atggactact tgcatcgtgc cgccgccatg  12480
aacggggaat actttacgaa cgccattcta aatccgcact ggatgccccc gtctggcttt  12540
tatacgggcg agtttgacct gcccgaggcg gatgacggct ttctctggga tgacgtgtcc  12600
gacagcattt tttctccgtc gagtcagcgg atgcaaaaaa aagagggagg agatgagctg  12660
cctttgtcta gcattgaagc ggctagtcgc ggcgagagtc ctttccctag tctgtcttcc  12720
gtgagtagcg gacgggtgtc gcgtccgagg ctccccgccg agagcgaata cctaagcgat  12780
ccgattctgc agcccagtcg caagaaaaac tttcccaata acggggtgga gagcttggta  12840
```

-continued

```
gataagatga aacgttggaa aacctacgcc caggaacaaa aggagtggga agaaacgcag  12900
gtgcggccgg ttcccccgcc gacgcaacgg cgctggcgtc gcccgcgcga agaccctgac  12960
gactccgccg acgacagtag cgtgttggat ctgggaggga gcggagctaa ccccttttgcc  13020
cacttgcgac cccaagggcg cctgggacgc ttgtactaat aataaaaaac ccaaccttac  13080
cagagccatg gccacagcgt ccttcctttt tgtttcttcc tcgctagcgg tacaatgaga  13140
agagccgtga gagtgccgcc ggtgtatccc gagggtccgc ctccgtctta cgaaagcgta  13200
atggaagctc tcaatacgcc ggccacgctg gaggcccctt acgttcctcc cagatacctg  13260
ggacctacag aggggagaaa cagcattcgt tactccgagc tggcacccct gtacgacacc  13320
accaaggtgt acctggtgga caacaagtcg gccgacatag cttccctgaa ttaccagaac  13380
gatcacagta actttttaac caccgtagtt caaaataacg acttcacccc ggtagaggct  13440
ggcacgcaaa ctattaattt tgacgagcgc tctcgctggg gcggtcagct aaagactatt  13500
ctgcacacca acatgcccaa cattaacgag tttatgtata cgaacaagtt tagggctaga  13560
ctgatggtgg agaaaccgca gacgggctct cctcggtacg agtggtttga atttaccatt  13620
cccgagggca actactcgga aacgatgacc attgatctca tgaacaatgc cattgtggac  13680
aattacctgc aagtaggacg acagaacggc gtccttgaga gcgatatagg cgtgaaattc  13740
gatacccgaa acttccgact ggggtgggat ccggtgacca ggctggtgat gcccggggtg  13800
tacaccaacg aagcttttca cccggacatc gtgctgctgc cgggctgcgg ggtggacttt  13860
acgcagagcc ggctgagtaa cctgctagga attagaaagc gccgtccctt tcaagaaggc  13920
tttcaaatca tgtatgaaga tttggaggga ggaaacatcc ccgccctgct ggacgtgccc  13980
gcctacgagg ccagcctgtc tctggccgaa gcggaagggc gcgtaactcg cggagacacc  14040
ttcgctaccg ctcctcagga gctgaccatc cagcctctta ccaaagacag taaaaatcgc  14100
agttacaacc tactgcccaa caacaccgac acggcgtacc gcagctggtt tttggcttac  14160
aactacggag atcccgagaa gggagtgcgc tcgtggacgt tgctgacgac tacggacgtg  14220
acgtgcggct cgcagcaagt ctattggtct ctgcccgata tgatgcagga ccctgtgacg  14280
tttcggtcct ccacccaagt gaacaatttt ccggtggtgg gcaccgagct gcttcccgtc  14340
tacgcgaaaa gcttttacaa cgagcaggcc gtctactcgc aactcattcg ccagtccacc  14400
gccctcaccc acgtgtttaa ccgatttccc gagaaccaga ttttggtgcg tcctcccgct  14460
cctaccatta ccaccgtgag tgaaaacgtt cccgccctca cagatcacgg aaccctgccg  14520
ctgcgcagca gtatcagtgg agttcagcgc gtgaccatca ccgacgccag acgtcgaacg  14580
tgtccctacg tttacaaagc tttgggcgta gtggcaccta aagtcctttc tagtcgcact  14640
ttctaaacat gtccatcttg atctctcccg ataacaacac cggctggggt ctcggctcca  14700
ccaagatgta cggcggcgcc aagaggcgtt ctagtcagca tccggtgcgc gtccgaggtc  14760
actaccgcgc tccctggggg gcctataagc gcggactgtc cgcccgcacg gccgtggatg  14820
acactatcga cgccgtcatc gccgacgccc gacagtacaa acctgccgtg tccacagtgg  14880
attccgtaat agacagcgtg gtggccggag cccgagccta tgctcgtcgc aagaggaggc  14940
tgcacaggcg aaggcgtccc acggcggcga tgctggcagc cagggccgtg ctgcgtcgtg  15000
cgcgcagggt aggcagaagg gcgatgcgcc gggcagccgc cgccaacgcc gggagagtga  15060
gacggcaagc agctcgtcag gccgccgccg ccatcgccaa catggccaga ccccgaagag  15120
ggaacgtgta ctgggttcga gattctgtca cgggagtccg ggttccggtg cggactcgcc  15180
ctcctcgaag ttagaagacg catgtgcgaa gacggcggtt ctcagtttcc catgttgtta  15240
```

-continued

```
ccagccagcc atgagcaagc gcaagtttaa agaagagctg ctgcagaccc tggcgccaga  15300
aatctatggg ccaccggaag tgaagcgtga cattaagcct cgcgacatta agcgagttaa  15360
aaagcgggaa aaaaaggagg aggagctggc gatggcggcg gctgcagagg acgcggtgga  15420
gtttgttagg tctttcgcac cgcggcgcag ggtgcggtgg aaagggcggc gtgtccagcg  15480
cgtgctgaga cccggcacca cggtggtgtt taccccggga cagcgttcgg ctgtgcgggg  15540
tttcaagcgg cagtacgatg aggtgtacgg cgacgaagac attttggagc aagccgcgca  15600
gcaaattgga gagtttgcgt acggaaagcg ctctcgtggc gaaaacgtcg ccgtggctct  15660
ggacgagggc aatcccacgc ctagcttgaa acccgtgacg ctacaacagg tgttgcccgt  15720
tagcgccagc actgaaagca agaggggaat caagagagag ttggacctac agcccactct  15780
gcagcttatg gttccaaagc gccaaaaatt agaggaggtg ctggaaaaca tgaaagtgga  15840
tccaaccgtc gagccggatg ttaaagtcag gcccatcaag gaggtggctc ccggtctggg  15900
ggtacagacg gtggacattc aaatccccgt tagttcctct gcggccgctg tggaggccat  15960
ggaaacccaa accgaaacgc cgacggccgc cgccaccaga gaagtggcgc tgcagaccga  16020
gccgtggtat gaatatgcaa cgtccgcgcg tccaaggcga tccaggcgct acgccgtaac  16080
tagcgccctt atgccggagt acgctttgca cccctctatc acgcccacgc cgggctaccg  16140
cggagttacc ttccgcccct cgggcactcg ccgacgatct cgccgcagaa catcgcgtcg  16200
tcgctctcgt cgcgttttag ctcccgtgtc cgtgcgtcgc gtgacccgcc ggggaagaac  16260
ggtgacaatt cctaacccgc gctaccatcc tagcattctt taataactct gccgttttgc  16320
agatggctct gacatgtcgc gtgcgcatcc cagttccgca ctatcgagga agaactcgcc  16380
gtaggagagg catggcgggc agcggccgcc ggcgcgctct tcgccggcgc atgaaagggg  16440
gcattttgcc cgcgctgatc cccattatcg ccgccgctat tggggcgatt cccggcatcg  16500
cctctgtggc cgtgcaagca tctcgcaaat aataaataaa aaccatcgct tttcacttat  16560
gtcatggtcc tgactatttt atgcagaaag atcatggaag acatcaattt ttcgtcgctg  16620
gctccgcggc acggctcgcg gccgttcatg ggcacctgga acgacatcgg caccagccag  16680
ctcaacgggg gcgctttcag ttggagcagc ctttggagcg gccttaaaaa ctttggctcc  16740
acgattaaaa cctatggcaa caaagcctgg aacagtagta ctggtcagat gctccgagat  16800
aaactgaaag accagaactt ccagcagaaa gtagtggacg ggctggcctc gggcatcaac  16860
ggggtggtgg acctagctaa ccaagcggtg cagaatcaga ttaaccagcg tttggagaac  16920
tctcgagtac cgccgcaaaa aggggcggag gttgaggaag tagaagtgga ggaaaagctg  16980
cctcctttgg aagttgttcc cggagcccct cctaagggag aaaagcgacc taggccagac  17040
ttagaagaaa ccttagtcac cggcaccttg gaacctcctt cctacgagca ggctttgaag  17100
gaaggcgctt ccccttaccc catgaccaag cctatcgctc ccatggcccg ccccgtgtac  17160
gggaaggacc acaaacccgt gacgctagag ttacctccgc cgccgaccgt ccctccgctg  17220
cccgctcctt cggtgggaac cgtggccagc gctcccgccg tggttccggc gccgcagccg  17280
gccgttcgtc ccgtggccgt ggcaaccgcc agaaacccca gaggagccaa ctggcaaagc  17340
acgctgaaca gcattgtggg cctgggagtg aaaaccctga aacgccgccg ttgttattat  17400
taaagtgcag ctaaaaattt cccgttgtat gcgcctccta tgttaccgcc agagacgcgt  17460
gactggtcgc cgctaccgcc gctttcaaga tggccacccc atcgatgatg ccgcagtggt  17520
cttacatgca catcgccggg caggacgcct cggagtacct gagccccggc ctcgtgcagt  17580
```

-continued

```
ttgcccgcgc caccgacacc tacttcagct tgggaaacaa gtttagaaac cccaccgtgg  17640
cccccacgca cgatgtgacc acggaccgct cgcagagact gaccctgcgc tttgtgcccg  17700
tagaccgcga ggacaccgcg tactcgtaca aagtgcgcta cacgctagcc gtaggggaca  17760
acagggtgct ggacatggcc agcacgtact tcgatatccg gggcgtttta gatcggggtc  17820
ccagctttaa accctactcc gggaccgcgt acaactcgtt ggcgcccaaa ggggctccca  17880
atccaagtca atggacaaca acaaatggag gaaacaaaac taattctttc ggtcaagcgc  17940
cttttattgg agaaagcctc acaaaggacg gaattcaagt aggggtagat accggaaatc  18000
caggcactgc cgtatacgct gacaaattat accagccaga gccccaagta gggctctcaa  18060
aatggaatca gaatccatcg gaaaacgctg cgggcagaat cctaaaacca tcaactccca  18120
tgcagccgtg ctacggttct tatgcgtatc ctaccaacac aaacggtggg caggtgaaaa  18180
ccagcgcgac cgatgctact ggggcaaata acgttaccct aaattttttt aacaacgcgg  18240
cagataacgg taacaataat cccaaagtgg tgctgtacag tgaagatgtg aatcttgaag  18300
cgcccgatac gcatctcgtt tttaaacctg atgctaacaa cgcaacaagt gcagaaacgc  18360
tactaggtca gcaagcggct cccaatcggc ctaactacat tggcttcaga gacaacttta  18420
ttggcttaat gtactacaat tctactggaa acatgggcgt tttggccggt caggcgtctc  18480
aactgaatgc tgtggtggat ctccaagaca ggaacaccga actgtcgtat cagcttatgc  18540
ttgatgcctt gggggatcgc agccgctatt tttctatgtg gaaccaggcc gtagatagtt  18600
atgatccgga cgtaaggatt attgagaacc acggtgtaga agacgagcta ccaaactact  18660
gctttccgct aaacgggcaa ggaatatcga atacatacaa aggagtaaaa accaacaacg  18720
gtggagcggc ttggactcaa gatacagacg ttgtcactac taacgaaatc tccataggaa  18780
atgttttcgc tatggaaatc aacctggctg caaatctgtg gcgcagcttt ctatactcaa  18840
atgtagcgct ctatctgcca gattcttaca aatacactcc agataacatt gagctcccac  18900
aaaacaaaaa cagttacggt tacataaacg gtagggtcac tgctccaaat gccatagaca  18960
cctacgttaa catcggcgct cgctggtcgc cagatcccat ggacaacgtc aacccgttta  19020
atcaccaccg aaacgccggg ctccgttacc gctctatgct tttgggtaac ggacggtacg  19080
tgcccttcca cattcaagtg ccccagaaat tcttcgccat taaaaacctt ttgctgctac  19140
caggttcgta cacgtatgaa tggaacttca ggaaggacgt gaacatgatt ttgcagagca  19200
cgcttggtaa cgacttacgg gtggacggtg ccagcatacg atttgacagc attaacttat  19260
acgccaattt ctttccgatg gcgcataaca ctgcttctac tctggaggcc atgctgcgca  19320
acgatactaa cgaccagtcg ttcaacgact acctgtgcgc tgctaacatg ctgtacccca  19380
ttcccagcaa tgccaccagc gtgcctattt ctatcccatc aagaaactgg gccgccttta  19440
gaggatggag ctttacccga ctaaaaacga aggaaacgcc ttccctgggc tcaggctttg  19500
atccctactt tgtgtactct ggctccattc cttacctgga tggtacattt tacctaaatc  19560
acaccttcaa aaaagtgtct attatgtttg actcgtccgt gagctggcca ggtaatgacc  19620
gccttctcac ccctaacgag tttgaaatta agcgctcagt ggacggagaa ggctacaacg  19680
tagctcaaag caatatgact aaggactggt ttttaattca aatgttaagt cactacaaca  19740
tcggctacca aggcttctac gtgccggagt catacaaaga cagaatgtac tccttcttca  19800
gaaacttcca gccgatgagt cgtcaagtgg tagacaccgt taactatgct aactacaaag  19860
aggtcaaaat gccattccag cacaacaact ctggcttcgt gggttacatg ggtcccacca  19920
tgagggaggg acaggcgtac cccgccaatt atccctatcc acttattgga gaaacggcag  19980
```

```
tgcctagtgt cacccagaaa aagtttctgt gcgacagggt gatgtggaga attccctttt  20040
ctagcaactt tatgtctatg gggctttaa ccgatctggg gcagaacatg ctgtatgcca  20100
actccgctca tgccttggac atgacttttg aggtggatcc catggatgag cccacgcttc  20160
tttatgtttt gtttgaagtc ttcgacgtgg tgcgcatcca tcagccgcac cgcggcgtca  20220
tcgaggctgt ctacctgcgc acgcctttct ctgccggcaa cgccaccacc taagaagcca  20280
atgggctcca gcgaacagga gctgcggagc attgtgcgcg atctgggctg cggaccttat  20340
tttttaggca ctttcgacaa acgctttccg ggctttatgt ccccccaaaa gccggcctgt  20400
gccattgtca acacggcagg acgggaaacc ggcggagtgc actggttagc ttttgcctgg  20460
aatccgcaaa accgaacgtg ctacctgttt gacccttttg gtttttcaga tgaaagactg  20520
aaacagatct accagtttca gtacgaaggc ctgctgaaac gcagcgccct ggcttccacg  20580
ccggaccact gcgtcaccct ggaaaagtct acccagtctg ttcagggacc actttcggcg  20640
gcctgcgggc ttttttgttg tatgtttctg cacgcctttg ttcactggcc tcactcccct  20700
atggacaaaa atcccaccat ggacctcctg accggggttc ctaacagtat gcttcaaagc  20760
ccccaggttg ttcccaccct gcgtcgcaac caagaacagt tgtatcattt tcttagtaaa  20820
aattcagcct attttcgccg tcatcggcaa cgtatagaga aagccactga ttttgaaagc  20880
atgaaacaca cagtgtaact tgcaataaaa ggttgatttt atttatacaa gtgcgcatct  20940
ttcgttatta aaactcaaag ggctcggggc agtcgtcgcc gtggctgctg ggagggcca  21000
cgtttcggta ctgaaaacgg ggatgccagc gaaattcggg aatgatcatc tttgggagcg  21060
gtttgtcttc catgttctcc ttccaaaact gccgaacgag ctgcagggct ccgatgatgt  21120
cgggtcccga aattttgaaa tcgcaattgg gcgccgcgcc gccgcgggaa ttgcggtaca  21180
ccgggttggc acactggaac accagaacgc tgggatactt gatactggct agggccgtag  21240
cgtcgttcac ttctgccaca tccaagtcgt ctgcgttgct cagaccgtaa ggggtgacct  21300
tgcacatttg tcgacccatg cgagggatga catcgggctt atggagacaa tcgcagcgca  21360
ggggaatgag tatgcgcccc tgaccacgct gcatctcggg gtagctggcg cgcagaaacg  21420
cttccaactg cctgaaggcc atttgggctt tcaaaccttc cgtataaaac aggccacagg  21480
atttaccaga aaacacatta gggccacagc tcacgtcttc cgggcagcag cgcgcgtcat  21540
cgtttctaat ttgcaccacg ttgcgtcccc agcgattctg gactacctta gctttgccgg  21600
ggttctcctt caaggccttc tgaccgtttt cgctggtcac gtccatctcc gtgacgtgct  21660
ccttgcgaat catctcggtt ccatggaagc agcacaggac tccgtcttcc ttggcgctgc  21720
gatgctgcca caccgcacag ccggtagctt cccaattttt ctgaacaacc cccgcatagg  21780
attgcatgta ggccatcaag aatcttccca tcatctcggt aaaggttttg ttgctagtga  21840
aggtgagcgc caagccccga tgttcctcgt ttagccatgt ttgacagatt tttctataca  21900
ccgggccctg ctccggcaga aacttgaacg tggctctgtc ttcgtgggga acgtggaact  21960
tttccatcag tatcatcata gcttccatgc cctttttccca cgccgttacc aacggagagc  22020
tgtgcggatt taccactagc acagacgaac gctcctctct ctcagggttt gcttcttcta  22080
ctgttactct ttgaaacaca cggccgccgt cggcttgctt cacaatgcgc accggagggt  22140
agctgaaacc caccccgatt accgtgcctt cgccttcgct gtcggagatg atttccggcg  22200
agggcgggcg agcctgcgag cttttgcgtg cctttttctt gggaggtagg ggaacagcta  22260
cgtccctctc cgggcttctt tcccgcagat acggggtgat agaacgctcg cccgggttct  22320
```

-continued

```
gattgccggc catgatttac tcctaggcga aaaaacatgg atcttatgcg caaagaatcc  22380
ttaaccaccc cgcccctcag cgacgaagac gtgccaatcg agcaggaccc gggttttgtt  22440
acgccgcccg aagagccaga gttgcccata tcgttcgacc tcgcccgtag cgagcgcaca  22500
gaacaggacg gcgactactt attggaagcc gaaatcctgc ttaaacactt tgccagacag  22560
agcactatcg tcaaggaagc tctgcaagac cgcagcgaag tgcccctgga cgtgtgcgag  22620
ctgtcgcgag cctacgaggc aaacctcttt tcgccccgag tgcctccaaa gaagcagccc  22680
aacggtacct gcgagcccaa cccccgcctc aacttttacc cggtgttcgc ggtacccgag  22740
gcgctggcta cctatcacat ttttttaag aaccaaggca ttcccctgtc gtgtcgtgcc  22800
aacagaacca aagccgatag aaagctgaga ttgagagcgg gggctcgcat acctgagata  22860
gcttccttag aagaagtgcc caagattttc gaggggttag gacgagacga gaatcgggcc  22920
gcaaacgctc tgcaaaaaga acagaaagag gctcagagtg ttttaataga actggaggga  22980
gacaacgcac gcttagccgt tcttaaacgc accgtggagg tttcccactt tgcctatccg  23040
gccctgaacc ttcccccgaa agtcatgcgc tccgtgatgg atcatcttct cattaaacgg  23100
gccgaacccc tcaaccctga aaatcctgac ccggaaaact ccgaggacgg caaacccgtg  23160
gtttcagacg aggagctgga acggtggttg ggcacaaaag atcccgagcg cttgcaagag  23220
aagcgcaaga tgatgatggc ggccatcctg gtgaccgccg agctggagtg tttgcaacgc  23280
ttttttgcgg acgtagagac tatacgcaag gtggaagaat ctttacacta cacctttcgc  23340
cacggctacg tccgacaagc ctgcaagatc tccaacgtag aactcagcaa cctcgtgtcc  23400
tatatgggcg tcctccacga aaaccgctta ggtcaaagcg tgctccactg cactttgcaa  23460
ggggaagcgc ggcgagatta cgtccgcgac tgtgtttacc tttttctgct gctcacatgg  23520
cagacggcca tgggagtgtg gcagcagtgc ttggaagaaa ggaatctgaa ggagctagac  23580
aagctcttaa caaagcagag aaaagcgctg tggaccggtt ttagtgagcg agcggcagct  23640
agccagctgg cagatataat tttcccagag cggctaatga aaacgctaca gaacggcctg  23700
ccggatttca ttagccagag catcctccag aacttccgct cgttcgtgct ggaacgctcc  23760
ggaattttgc ccgccatgag ctgcgcgctg ccttccgact ttgttccact cacctaccgc  23820
gagtgccctc ccccctgtg gagccactgc tacctgctac aactggctaa ctacttggcc  23880
tatcactgtg atcttatgga aaacgtgagc ggagaagggc tgctggagtg tcactgccgc  23940
tgcaacctct gcaccccca ccggtccctg gtttgcaaca ccgagctgct tagcgaaacc  24000
caggtcatag gtacctttga gatccaaggt cccgaacagc acgagggggc ttccggttta  24060
aaactgactc cggcgctgtg gacctcggct tacttacgca aatttgtagc cgaggactac  24120
cacgcctcca aaattcaatt ttacgaagac caatctcagc cccccaaggc ccctctcacc  24180
gcctgcgtca ttacccaaag caacatttta gcccaattgc aaaccatcaa tcaggcgcga  24240
cgagagtttc tcttaaaaaa aggtcacggg gtgtatctgg acccccagac cggcgaagaa  24300
ctaaacccat ccacactctc cgccgaagca gcccccaagc agcatgccgc ccaaaggagt  24360
caaacagctg atagctcagc agagagcgaa gaagcagcaa gagctcctgc ggcacatgga  24420
agaggaggag gaagccagcg atgcgtggga cagtcaggca gaggaggctt cggaggacga  24480
ggagatggaa ggctgggaca gcctagacga ggtggaggag gaggaagagg tagaggacga  24540
accgatcggc gaaaaaccac cggcttccag cgcactttct ccgagccgtc tggcgaaaac  24600
ccgcgtccca accccgggag gctcacgcaa agccagccgt agatgggaca caaccggatc  24660
tccagtagca tcggcggcgg gtaagccagg gcggccgcgg cggggttatt gctcctggcg  24720
```

-continued

```
ggttcataaa agcagcattg tgaactgctt gcaacactgc ggggggaaca tctcctttgc  24780
ccggcggtat ctcctttatc atcacggggt ggctgtgcct cggaatgtgc tctattatta  24840
ccgtcatctc tacagcccct acgaaacgct cggagaaaaa atctaaagcc tcgtcgcgct  24900
cagccaccgc cttctccgcc gccaaagact cgccagccgc cagagaactg cgaaaccgca  24960
tttttcctac tctgtacgct atttttcagc agagccgcgg gcagcagcaa gaactaaaaa  25020
taaaaaaccg ctccctacgg tcactcaccc gcagctgtct gtaccacagg agggaagacc  25080
aactacagcg cactctggac gacgccgagg ctctgttcaa caagtattgc tcagtgtctc  25140
ttaaagacta aaaaacccgc gttttttacc caaaaaagcg ccaagcacac gtcatctcaa  25200
gcatgagtaa agaaattccc acgccttaca tgtggagcta ccagccgcag atgggcttag  25260
ccgcgggcgc cgcccaggat tactccagca aaatgaactg gctaagcgcc ggcccccata  25320
tgatttcaca agtaaacggc atccgagccc gccgaaacca aatcctccta gaacaggcgg  25380
caattacctc cacacccagg cggctcctaa accctcccag ctggcccgct gcccgggtgt  25440
atcaggaaac ccccgccccg accacagtcc ttctgccacg cgacgcagag gccgaagttc  25500
agatgactaa cgctggggcg caattagcgg gcgggtccag gtacgtcagg tacagaggtc  25560
gctccgcacc ttatcctccc gggggtataa agagagtgtt tattcgcggt cgaggtatcc  25620
agctcaacga cgaggttgtg agctcctcag cgggcctcag acctgacgga gttttccagc  25680
tcggcggagc cggccggtcc tccttcacca cccgtcaagc ctacctgacc cttcagagct  25740
cttcctccca gcctcgctcg ggcggaatcg gcactctcca gtttgtggaa gagttcgttc  25800
cttcggttta cttcaacccg ttttccggct cacctggacg ttaccccgac tccttcattc  25860
ccaactacga cgcagtgagt gaatctgtgg acggctacga ctgatgacag atggtgcggc  25920
cgtaactgcg cggctgcgac acctgcatca ttgccgacgg tttcgctgct ttgcccggga  25980
gcctttggtg tttagctact ttgagctacc tgaacatcat cttcaagggc cggctcacgg  26040
aataaaactc gaagttgaaa aggaacttga gtctcgcctc attcgtgact ttactcctca  26100
ccctcttttg gtggaaaaag aacacggaac cactattata actgtgtttt gcatctgccc  26160
aactcctgga ctgcatgaag gcctttgttg tcgtctttgc gctgagttta atttatagcc  26220
gcggaactgc tgacgacctt gtgttcgaag gtactattga aactgtttta ttttctgact  26280
ctacttcttc cattacacta aattgtagct gcactaacga actaattcag tggaacgcca  26340
acagaacctt ctgtaaagct ttctaccgca actttactta ctacagtaac aactctctct  26400
gcgcggtttg tacgcgacag gctttgcatt tataccctcc ctttgtcgct ggcagttatc  26460
tgtgtattgg ctctggagcc cagccttgct ttcaccgctg gtacctatac gaagacaaca  26520
cttcattcac aacttccacc ccaaaacaag tttcctactt acacgtctct ttaaaacctc  26580
tattcgccct tgcggctttt atacttgtta tattagccaa ttttatttta attaacaatc  26640
tgccatgatg ctcactgtct taacaactct tctcttgcca gctgttattt gcattagacc  26700
tcctgaacct cctcccgccc acggtattaa tactaaatcc ctgcctaata gtttacaaaa  26760
tccatcccgc gtttatgcta aagttgggca aaaccttacc ctcgaatcca ggtactcgtc  26820
acattctaat agcatgccac atgtggtttg gtacttagaa gtttttaacg atgatactat  26880
ttttcctagc agtgtagttc ctccaatttt ttcaggcatc aaactgtgtg aaattactga  26940
acaaaactac caaactttta accacgcacc aaaagaattt aactgcatta acaagagctt  27000
aaatttattt aacctgaaac caagcgactc tggcctttac aacgtcaagg tttataaaga  27060
```

-continued

```
tgacattgaa cataacacct actttcgctt gtctgtaatt cgctttgctc agccccagtg  27120
cactattaat tcctcctact taactgaaag ttactgttta ataagcattg attgttttca  27180
tttagaatac cctgccatag ttgagtttaa tggctctcgc agtaattttc actactatgt  27240
actttccaaa ggcggtaaaa acttagccga ttactatacc gttacctatg attatcatgg  27300
ccttaaacaa acctttaaag tagaataccc ttttaacgat atttgcaatg acattatttc  27360
cttggaaaca cttgcagact ttacaccagt ttttattgtt accattgtaa tgagcgtcat  27420
tacaattgta gttagccttt tattttgctg cttttataaa ccaaaatcta aatcaaactt  27480
ccaacaagtt aaactaaaaa caattcaact agtgtaattt atttttcagc atggtagctg  27540
tcttcttctt ccttctctgt ttgcccatca tcttcgtgtc ttcgactttc gccgccgttt  27600
ctcacgtgga agcagagtgc ctaccacctt ttgctgtgta cctaatattt acattcgtct  27660
gctgcactgc catagctagc atagcctgtt tttttgtaac aatttttcaa gccgctgatt  27720
acttgtacgt gcgttttgtt tatttcagac accaccctga atacagaaat caaaacgtag  27780
cttctttatt atgtttagca tgattcctct actagtaata ctctgtgatc tccttccgtt  27840
tacttactgc cactgccccc taaacaaacc ttggtcactg tatacttgct atgccgagtt  27900
gccggacatt cctgtaatct ggttgtacgt agctactgca gccctagtgt ttgtagctac  27960
ttgtgttggt gtaaaaattt acttttgttt aaaaatcggc tggcttcatc ctccagaaga  28020
cttaccaaga tttcctctcg ttaatgcctt tcaaatgcag cctccccctc ctgatcttat  28080
tcgagcacct tctgttgtca gctacttcca actagccggt ggagatgact gattcgcacg  28140
acattaacat taccatggag cggggaatcg ctcagcgaca gcgtgaagct cgcgcaatgg  28200
attaccttag actacaagaa cttaaagaaa cacattggtg cgatagagga tcgctttgcc  28260
ttgttaaatt ggcttcactc tcctatgata tctctaccca agggcatgaa ttgtcttaca  28320
ctgtagccgg gcaaaaacaa accttttcaa ctataatggg cggcacatct cttaaaatta  28380
ctcatcaatc taaacctgtc gaaggggcta ttctctgcca ctgtcataag cctgattgca  28440
tggaaaaatt aattaccacc ctctgcgccg tggcggaaat ttttaagtaa aaaaaaataa  28500
aactcaccta agttgtctca gtagcttttt gtcaaatttt ttcagcagca ccaccttgcc  28560
ctcttcccag ctttcatagg ggatgtggta gtgggcggca aacttcctcc aaaccctaaa  28620
agctatgatc gtgtccactt ctctccccta acccacaatc ttcatctttt catagatgaa  28680
aagaacccga attgacgaag acttcaatcc cgtctaccca tatgactcca ctactacccc  28740
caccgtccct tttattgctc caccatttgt ttcatccaat ggtttgcaag aaagtccccc  28800
cggaatgctg tctttaaact atgctgaccc cattacaacc aataacggta aactaaccgt  28860
taaattaggg aataacttaa gccttagtag tgacggagcc atcacctctg caacagctgt  28920
gacggatcct cttacaaaca atggtggaac cataggatta gctctctctg ccccccttaac  28980
cactacttcc actgggctgg gtatttcaat ttctccaccc attactctat ccaacaacgc  29040
tttaaatatt tcacttggaa atgggctaac atcctcttca aactcgctag ccattaaaac  29100
ctctggcgct attgggtttg acaaccaggg caacttacgc cttaacaccg gaggaggtat  29160
gagattggcg ggcgacagat taattctaga tgttaattat ccttttaatg gcgatcccaa  29220
attgtcccta agaattggta agggtttata tcttcaaaac aatcaggatt tagctgtgct  29280
actaggttct agaagtggtc ttgactttag tggaaacaac ttagttgtaa aattaggatc  29340
cggacttgca tttgacaaca acggagcaat taccacctca acttcccggt ctcgtttcgc  29400
tgactatttg ccatacgttt ctacatggcc cccccctaaac gagcctaact gttccatcta  29460
```

```
cgaatcacta gatgctatgc taggtctaca cttcagcaaa cacggactac acgtaattgg  29520
tacaatctcc ttaaaggcca taaaaggaga actgtgcaac atgcagcgtg atacagttac  29580
tcttaagcta ctttttaaca gcagcggacg ccttttaaat tgtccgctgc tcccatcatt  29640
ttggaaccct gaaacgccct tacagtttat gccaagcagt actttttatc cccgtaatgt  29700
atccccaagc acactcaccc aaactctgcc agactctagg tgcacattta ctgttgcata  29760
caacacggaa ggtgcagatt actcatttac cttcacttgg tccgtctgtt ccggagaaaa  29820
gtttaatgcc cccgctgcga tgttctgttt tgttgctgaa caataaagct tgcaaagcca  29880
cctttgtttt ctttcagatg aaacgcgcca gaattgacga cgacttcaat cccgtgtacc  29940
cctatgacca acctaacgcc ccgcttttgc catttattac cccacctttt acctcctctg  30000
acggcttgca agaaaaaccg ccgggagtgt taagcttaaa ttacaaaaac cccattacca  30060
cccaaaatgg agccctcact cttaaaattg gagaggggat tgaggtgaac gacaaagggg  30120
aactgacatc taacgcagtg tcagtttcgc cccctctctc taaaatcgac aacactctga  30180
gcctagtgta cagcgaccca ctcacagttc gtgaaaactc cctacactta aaaactgctc  30240
ttcctatttc tctcaacgct accagggaac tcactttggt ggccaatgct ccgcttgcta  30300
ctaccaacgg agcgcttcaa ttacaaagcg cggctccttt aggagttgcc gaacgaactc  30360
tgaaactgtt gttttccaac ccactgtact tacaaaacaa ctttctatcc gttgctgtgg  30420
acaaacctct agccatggct tccacgggtg ccattgctct gcagtgggca ccccctttgc  30480
aagtaggaac aggaggctta acagtagcca ctgtcgagcc ccttaccgtc accaacggaa  30540
atttaaacat taacacaaag cggcctctca tcattgaaga cagtagtttg tatttagctt  30600
ttagaccccc tttaagatta tttaacagcg accctgaact tggtgtaaac ttcatccctc  30660
ctattacaat ccgcgatgac ggtttagctc taaacacagg agagggtctc actcttgtgc  30720
gtgacagact aagtgtaaac ctcggcaaag atttgcagtt tgtggacaac accgtctcac  30780
tggcattaag cacagcttta ccgcttcaat acactgatca actgcggcta aacattggcc  30840
agggcctacg ctacaaccca accagtaaga agctagacgt ggatcttaat cagaacaaag  30900
ggttaaactg ggaagacaac aaagtcatta ctaaattagg ggacggtttg cagtttgatt  30960
cagcggggaa cattagtgtt atcccacctt ccgtaacacc acatacgttg tggactacgg  31020
ctgacccctc tcctaattgc tcagtatata cagacctgga tgccaagctg tggctgtctc  31080
tggtaaaatg caatggcata gtccaaggca ctatcgcctt gaaagctcta aagggagtgc  31140
ttttaaaacc cacggccagc tctatctcta ttgtcattta tttctatagt aatggcgtga  31200
ggcgaacaaa ttaccctacc tttgacaacg aaggcacgct agctaacacc gccacctggg  31260
gctacagaca aggccagtca gctaacacca atgtaactaa cgccgtagag tttatgccta  31320
gctccgccag gtaccccatt aacaggggcg atgacgtgca aaaccaaatg atgggctata  31380
cttgcttgca aggggcgtta aacatggctg tagggtacaa ggtcacattt aaccacgctc  31440
ttgaaggata ttccctaaaa ttcacatggc ctgtgtacaa caaccaagcc tttgacgttc  31500
cctgttgctc tttctcttac ataaccgaag aataaacaat ggttttcaaa tttttatttt  31560
acattatgcg tacagttaaa cttcccccac ccttccactt tacactgtat accatccttt  31620
ctcccttggt agcggtaaac aactgaaact gggtgttcaa acaaggattt ttaggtgtca  31680
gagtccacac ggtttcttta cgtgcaaatc tctcatccgt cacggacacg aagccctcgc  31740
cgacgtcttc caacagtggc gtgtcgtcca aacaatccta caacacacaa agttttaagt  31800
```

-continued tctccacggg ttttcacctc tgccgtactc agccagtgtg aacgggcggt gacgctccat 31860
cagtcctctt aacaagcttt gcctagcagc ttctagacga gctctccgag gctggtaaga 31920
agtcaggcgg tctaatagcc tcacagcgcg gataagaaat ctgcgagtcc gtttagcgca 31980
gcagcgcatc tgaatctcac tcaagtcctt acagtaggta cagaccatta taattaaatt 32040
gttcaaaatc ccatagctaa acgcgctcca cccaaagctg ctgttttcta acacggctac 32100
cgcatgcccg tctagaaaaa tcctaacata gatcaggtgt ctcccgcgaa tgaacacact 32160
gcccacatac agcacttcct tgggtaagtg gtaatttacc acttgtctgt accaggggaa 32220
cctaacattt actaaagacc catatatcgc cattctgaac caattagcta aaaccactcc 32280
acccgcttta cactgaaggg atccgggaga attacagtgg cagtgaagca cccacctttc 32340
atagcctctt atgatctgat tatattctac atctatcgta gcacaacata tacaaatctg 32400
catgtatgtt ttcatcacat gtttttccca ggcagttaat acagagtccc aatacacagg 32460
ccattcctgt aaaacagtaa agctaacaca agacggtacg cccctcacct cgctcacatt 32520
gtgcatgtta agattttcac attccagata cggggggattt tcaatggtgg cacagggcgt 32580
ctcgtcacac ggcggtagct ggtgtctgtt gtaaggaccc agtctgcagc gataccgtct 32640
gtcgcgttgc atcgtaagtc aagttctttc gcaagtcctc gtacttccga tagcaaaacc 32700
aggttcgccg ccaacaaatc tccacgcgac ggccgtccct acgccgctgc cgctcggtgt 32760
ttaccgcaaa atggagccac tgctgcaatg cgcacaactc cctctcggcc tctggagtaa 32820
taaaaacttc gtacctgatg atatccctga atagttccaa gctagaagtg agggccaact 32880
ccaaccaagc gatacatgca gacttgtccc gacacactgg gggtggagga agacacggaa 32940
gaggcatgtt attccaggcg atcgcgtaag gtcacaaaat gcagatcgcg aagatgacaa 33000
cggtcgcctc cggtacgctg gtggtaaaga acggccaaat caaaatgaat tctgttctcc 33060
aggtgatcta ctaccgcttc caacagcgcc tgaacccgca catccaaaaa caccaacaga 33120
gcaaacgcgt cgtgttcaaa atcttcaatg atcacactgc aattctgcac catgcccaaa 33180
taattttcag ccctccactc gcggactata tcgcaacaca gttcttgtaa atttactcct 33240
cgcatttgaa aaagctgaac gagggcgccc tctattgaca tgcgcagaca caccatcatg 33300
cttgcaaaat atcaagctcc tgcgacacct gcagtaaatt caacatatca gggtcaggat 33360
gaaccccacg atcgcgaatc tccacgcgca atgttaactg caaaaagttt agcagatccg 33420
cacacactaa agcggtcagc tccccgtcag gtgtcatttc tggcgtggcc acgcagcaca 33480
aaagttggat agagggcgcc aggctcaaca gcaccgcgcc gttatagcaa aactgaaacg 33540
gcggagtcaa gcagtgtaac aaatggagcc aaaagtcact gagctgtctt ttcaaaaagt 33600
ctaaaacctc aatgtccaaa tcgtgcaagt actgccgtag agcagccggt acaataacgc 33660
aaacaaaaac aggctgcctc tgatacatag cgaacctata aattaaacaa gagaagcacg 33720
atgaagacag gggtaaatca cccgctccag cagcaggcag gccaccggct gtcctctaaa 33780
cccgtagaaa aattcatccg agtgattaaa aagcaccaca gacatttccc accacgtact 33840
gggctgtatg tcttgagcgc caacaaaaac ccccccttaca ttcatatccg ataacgagaa 33900
taagcggccc aagtacccct gaggaatgtc catagacaac tgcagagaaa ctaaaagcac 33960
gcctctcgga gaaatcacaa agttttccgg tgaaaaaagc acatacagat tagaaaagcc 34020
ttgctgctgt ggcataatag cccgcgagcc cagcaaatgc acgtaaattg cctcgtcagc 34080
catcgcccag tcttaccgcg taaaaacacc gcgcaaaata acgcctagct caacgcgtcc 34140
ttcagtgaat atatatatgc gtagtcccct cccagttacg ttattaccca ccgccgccca 34200
agcgcaaagg tcgcccacac ccaaaaagcc cgcgaaaaat ccaccgtcgt cagcacttcc 34260
gcaaaaatgt cgttcccaca gcgtcacatc cggtccctcg tccccttccg ctcccgcgcc 34320
gcccaccccg tcaccccgca cgtcacttct tcccaccccc tgccaccccc actcctcctc 34380
tctcattatc a 34391

<210> SEQ ID NO 2
<211> LENGTH: 34391
<212> TYPE: DNA
<213> ORGANISM: Adenovirus

<400> SEQUENCE: 2
tgataatgag agaggaggag tgggggtggc agggggtggg aagaagtgac gtgcggggtg 60
acggggtggg cggcgcggga gcggaagttg gtttgtgcta atgaggcgca tcggaactga 120
cgtgtaaaag gcgactttgg accggaaatg aggcgtgttt tggcatttct gcaagttttc 180
tgcggatttt ggcgcgaaaa ctgggcaatg aggaagttgt ggttaatgtg tactttttat 240
gactgggagg gaaaactgct gatgtgcagt gaactttggg cgctgacggg taggtttcgc 300
tacgtggcag tgccacgaga aggctcaaag gtcccattta ttgtactgct cagcgttttc 360
cgtgcctatt taaacgcctt cagatcgtca agaggccact cttgagtgct ggcgagtaga 420
gttttctcct ccgcgctgtg aagatgaggc tggttcctga gatgtacgga gtgtcctggg 480
atgagacggc cgaagagctg ctgaatgctg aaatttacga cgtgccgaat ttgcctccag 540
gaacaccctc gcttcacgat ttgtttgatg tggaaaatga tggcggacag gacgagaacg 600
aagacgcggt aaatagtatg tttcctgact caatgctgtc ggcgggcgag ggttacgctg 660
gggatgtaga tccgagtggg agcgacatgg acttaaagtg ctacgaagat ggtttgccga 720
gcagcagttc agaaggatca gatgaggatg agcaaaagcc tttgaaacat gaactggtct 780
tagactgtcc taagaaccct ggccatgatt gtcgcgcctg tgctttccat agagctacca 840
gcggaaatac tgaagcaata tgctgtttgt gttatatgcg ccttaccagc gattttgtat 900
acagtaagta taggcgatta tgagggacgg gtggtatgtc tgtgtgtatg ccagtgtgct 960
taatgttgtg tgtgatttca ggcgatgtgt ccgacgtgga aggagacgga gacaagtcaa 1020
aagtatctga gtctcctggc tctttgggga ctgtggttcc agatggtgtt cttaagccca 1080
ccgcggtgag agtatcggca aggcgacgcc aagcggtaga gaagttggaa gatttgctcc 1140
aggaaccaga gcaaactgaa cctttggact tgtccttaaa gcaacccagg atgacctaat 1200
cgtttatggt attttatgac gcgcaataaa gagtgttaaa ccttaacttg tgtttattta 1260
ttgggcggtc tgcgggtata taagcaggtg gctgacactg aggcgttact tttttccgaa 1320
tggatctcct aaggttgctc agtgattacg aggtgctgcg caagttgctg gagacagcct 1380
gtgagaaaac ttccagctgt tggaggtttt tctttggctc tactcttagc aacgtggtgc 1440
acagagtcaa gcgagagcac agtgaggaat tttctagact agtggcagat gttcccgggc 1500
tttttgtttc tttagactta ggacatcact cttactttca ggagaaaatt gtaaagggtc 1560
tagtgtttga gtcaactggc cgcacggttg tgtccgtggc ttttatctgt tttcttttgg 1620
ataaatggag cagcgacagc cacctgtcgt gggattacat gctggattac atgaccatgg 1680
cgctgtggcg ggcgctcctg aggaggagga gggcttgcat ttacttgccg gtgcagcctc 1740
agcgaggtct ggagcgagtg gaggaagagg aggaggagaa cgagaacccg agggccggcg 1800
tggaccctcc tctggaatag aagctgtggg cgagccagaa gagggtacta gtgatggggt 1860

-continued

```
tagaaagagg cggaggacag aaatggaaga ggtgaacgct cgagattacc ttactgattt   1920
gactgtgcgg ttgatgagtc gtaggcgacc tgaaacggtt gcatggagtg aactggagac   1980
tgaatttaaa aatggcaata tgaatttgct gtacaagtat agctttgaac agatacaaac   2040
tcattggttg gaaccgtggg aggattggga gacggccttt gccaattttg caaaaatcgc   2100
cctgcggcca gataaaatct acaccataag gcgcatggtt aacattagga agtgtgtgta   2160
tgtcctgggg aatggggcta tggttcagat tcagacgtgt gaccgcgtgg cttttaattg   2220
ctgcatgcag agcatgggcc ccggggtaat aggcatgagc ggcgtgactt ttgccaacgt   2280
gcgattcacc ggggaaaact tctttggcgc tgtgattatg aacaacacta gccttactct   2340
tcacggggtc tattttctaa atctcagtaa cacctgtgta gagtgctggg gtcgcgcgtg   2400
tctgaggggc tgtacgttct atggctgttg gaaagcagtg gtgggcagaa caaaaagtca   2460
tgtgtctgta aagaagtgta tgtttgaacg ctgtgtgatt gctataatgg tggaggggca   2520
ggggcgtata agaaacaatg ttggggcaga gaacgggtgt tttcttttgt tgaagggctc   2580
ggccagtgtt aagcacaaca tgatctgtgg tactggcact tgtaacatat cacacttgtt   2640
aacgtgttca gatggaaatt gccaggcttt acgcaccttg catattgtgt ctcatcgacg   2700
cctcccctgg ccggttcttg aacacaatat gctgacgcgc tgttctgttc acgtaggcgc   2760
tagacgaggt atgctggtgc cttaccaatg taacttcagc tatactaaag ttttactgga   2820
aacagatgcg tttcctaggg tgtgttttaa tggagtgttt gacatgactg tggaggtttt   2880
taaagttgta aggtatgacg agtcaaagtc tcgttgtcgc ccatgtgagt gcggagccaa   2940
tcacctgaga ttgtatcctg tgaccctgaa tgtgacggag gagttaagag cggaccactt   3000
gacactatcg tgtttgcgaa cggactacga gtctagtgac gaggagtaag gtaatatggg   3060
cggagttaca aaaggtataa aacggacgtg gtggtggggt ggtttcattg ccaaaatgag   3120
cgggtctacg gatagcaact ctgtgaactt cgagggaggg gtgtttagcc catatttgac   3180
aactcgtctt ccttcttggg caggggtgcg tcagaatgtg gtgggctcta gcatggacgg   3240
tcgcccggtt gcccccgcga actctgctac tctcacctac gctacggtgg gatcgtcgtt   3300
ggacgctgct gccgctgctg ctgcttctgc tgccgcttct acagctcgtg ttatggcggt   3360
tgattttgga ctgtacaacc aactggctac cgcggctgct gcatctcgct ctgtggttca   3420
gcaagatgcc ctgaacgtca tactggctcg cctggaaatg ttgtctcaac gtttggatca   3480
gctcgctgcc cagattgccc tttccccagc ccccgattcc acttcagatt cttaaataaa   3540
gtaaataaag taaaaaaaca tttgatttaa aataaacgtt ttatttgttt tttttggcgc   3600
ggtaggctct agaccatctg tcgcggtcgt taaggacttt gtgtatggtt tccaaaacac   3660
ggtacaagtg ggactgaatg tttaagtaca taggcatgag gccgtctttg gggtgcaggt   3720
aagaccactg aagggcgtcg tgctctgggg tagtgttata aatcacccag tcgtagcaag   3780
gtttttgggc atggaattgg aagatgtctt ttagaagcaa gctaatagct aagggaaggc   3840
ctttggtgta ggtgttgaca aagcgattaa gctgtgaggg atgcatgcga ggggagatga   3900
tgtgcatttt agcctggatc ttaaggttag caatattgcc ccccaggtct ctgcgaggat   3960
tcatgttatg caacaccacc aacacggtgt acccggtgca tttggggaac ttgtcatgta   4020
gctttgaagg aaaggcgtga aagaatttgg aaacccccttt gtgccctcct aggttttcca   4080
tgcattcgtc cataataatg gcaatgggtc ccctggcggc cgctttggca aacacgttgt   4140
ctgggttgga cacgtcatag ttttgttcca gagtaaggtc gtcgtaggcc atctttacaa   4200
agcgcgggag tagggtgcca gattggggga tgatagtgcc ctcgggacct ggagcgtagt   4260
```

-continued ttccctcgca gatttgcatc tcccaagcct taatttctga ggggggtatc atgtccactt 4320
gaggggcgat aaaaaacaca gtttccggag ggggattaat gagctgggtg gagagcaagt 4380
tgcgtaaaag ctgggactta ccacagcctg tggggccgta gatgacccca atgacaggct 4440
gcagctggta gttaagagac ttgcagctgc cgtcattgcg caacaatggg gccacttcat 4500
tcatcatact tcttacatgg cggttttccc tcaccaagtt ttggagaagt cgctccccgc 4560
ctagggagag tagctcttcc aagctgttaa agtgtttcag cggtttgaga ccatctgcca 4620
tgggcatttt ttcaagcgat tggcgcagta gatacaagcg atcccacagt tcggtaacgt 4680
gttctatggc atctcgatcc agcagacttc ttggttgcga gggttgggac gactttcgct 4740
gtagggcacc agccggtggg cgtccagggc tgcgagagtc atgtccttcc agggtctgag 4800
ggtccgcgtc agggtggtct cggtgacggt aaaagggtgg gcccctggtt gggcgcttgc 4860
cagtgtgcgt ttgaggctca tcctgctggt gctgaagtgg acgttttcgc cctgggaatc 4920
ggccaagtag cacttaagca tgaggtcgta gctgagagat tcagccgcgt gtcctttggc 4980
gcgcagcttc cccttagaaa catgcagaca cttgctacag tgcagagact tgagcgcata 5040
gagcttaggg gctaaaaaaa ctgattcagg ggaaaaggca tctgcgccac actgagcgca 5100
tacagtctca cactctacca gccaggtgag ctcgggttgg tttgggtcaa aaaccaactt 5160
gcctccattt tttttaatcc gcttcttacc tcgggtttcc atgagtctgt gtcctgcttc 5220
ggtcacaaaa agactgtcgg tgtccccgta gaccgatttg agctgtctct gttccagagg 5280
ggtgccgcgg tcctcgtcgt acaaaaactg agaccactct gagacgaaag ctctggtcca 5340
cgctaataca aatgaagcta tctgcgaggg gtatctgtca ttttcaatga gagggtcaac 5400
cttttgtaag gtgtggagac agaggtcgtc ctcttccgcg tccataaaag tgattggctt 5460
ataggtgtaa gtcacgtgac catcggggtg gcgtggtggg ctataaaagg gggcgttacc 5520
cgcttcgtcg tcactttctt ccgcatcgct gtggatcaga gccagttgtt ctggtaagta 5580
agccctttcg aaggcgggca tgacctcggc gctcaaggtg tcagtttcta caaacgaggt 5640
ggatttgata ttcacgcggc cggaggcaat gtccttgacg gtggaggttt ccatttggtc 5700
agaaaagaca atctttttat tgtcaagttt ggtggcaaac gacccgtaga gggcgttaga 5760
tagcaatttg gcaatggaac gtaaagtttg attttttca cggtcggccc gctccttggc 5820
cgcgatgtta agttgtacgt actcccgggc cacgcagcgc cactccggga aaacagtagt 5880
gcgctcgtcg ggcactatac ggacgctcca gcccctgttg tgcagggtaa taaggtccac 5940
actggtagct acctcacccc tgagcggttc gttggtccag cacaacctac cgccttttcg 6000
ggagcaaaac gggggaagta cgtctagcaa gttggaagcc ggtgggtcgg cgtcgatggt 6060
gaagatgccg gggaggagag acttgttaaa ataattaatt tctacgcggt gttgcaaggc 6120
caagtcccac tttttgacgg ccagagccct ctcgtacgga ttaaggggag gaccccaagg 6180
catggggtgg gtaagggcgg aagcgtacat gccacaaatg tcataaacat aaagaggctg 6240
gcgtaaaacg ccaatgtatg taggatagca acgtccgccg cgaatgctgg ccctgacgta 6300
atcgtacatt tcatgggagg gtgccaaaag gccgctcccc aggtgggttt tttggggttt 6360
tacggcgcgg taggcgatct gtcgaaagat ggcgtgggag ttggaagaga tggtaggcct 6420
ctgaaacaca ttgaagctgg cctgcgaaag gcccacggcg tcctgtagga actgcgcgta 6480
cgactccctg agtttgtcca ccagcgcagc ggtgacgagg acgtccaagg cgcagtagtc 6540
cagggtttcg cgtacgaggt cgtaggtttt ttcttgcttt ttttcccaga gttcgcggtt 6600

-continued

```
gaggaggtac tcttcgcggt ctttccagta gtctgcggca ggaaatcctc ggtcgtctgc   6660
tcggtaagcg cccaacatgt aaaactcgtt aaccgctttg taaggacaac agcctttttc   6720
tatgggcagg gcgtaggcct gagccgcctt gcgaagagag gtgtgggtga gctggaaggt   6780
gtctcttacc atgaccttta agtactgatg tttgaagtcg gtgtcgtcgc aacagccctg   6840
ctcccacaag gtgaaatccg tgcgcttttt ctgccgagga tttggcaggg caaaggtgac   6900
atcgttaaac aggattttac cggcgcgagg cataaaattt ctggagatgc ggaaaggccc   6960
gggaacgtcc gagcgattgt tgataacctg cgcggccaga acaatctcgt caaatccgtt   7020
gatgttatgc ccgacgatgt aaagttcgag aaagcgcgga acgcctttga gggcgggagc   7080
tttctttagt tcttcaaacg ttaggcattc tggagaaaag agccctagct ccgctcggga   7140
ccattcttct aagtgggaat tggctgcaag aaacgagcgc cacagttcgc gggctagcag   7200
agtttggagg cgatctctaa agtctctgaa ctttctgcct accgccattt tttccggcgt   7260
gacaacgtaa aaggtagcag ggcggttgtt ccaggtgtcc catttcaact caacggctag   7320
ggcacaggct ttaagaacga gagcgtcgtc gccggagatg tgcataacca gcatgaaggg   7380
caccaactgt tttccgaagg aacccatcca cgtataggtt tctacgtcgt aggtaacaaa   7440
cagcctctcg gtgcgaggat gggaaccgat cggaaagaag ctgatctcct gccaccagct   7500
ggaggagtgc gcgttaatgt gatggaagta gaagtttcgc cggcgcacag agcattcgtg   7560
ctgatgtttg taaaagcgac cgcagtagtc gcagcgctgc acgctctgta tctcttcaat   7620
gagatgtacc ttgcgaccgc ggaccaaaaa tcgcaagggg aaagtcagtg ggaggaggc   7680
ctgtggttcg ttttcccctt cgcggtgttc gtcggggtat gcgccggcgc cctgatcttg   7740
ggggtggatg acaacagggg tcacgacgcc ccttgtgccg caagaccaga tttccgccac   7800
cgtagggcgc aggcggcgca caagggcttc cagttgactg cagtccagag aatccaaaga   7860
gccgttcgcc aagtcggagg gaagagactg caggttgact tgcaagagag cggtaagggc   7920
gcgggtgaga tgcaaatggt acttgatctc tagcgggcag ttagaagaag agtctacggc   7980
atacaggaga gcgtgaccgc gtggggcgac gacggttccc ctggggagtt ttatctcatc   8040
cggcggggtc gcgcacccgg aggtagtgga ggctcgacgc ctggagggag cggaggaaga   8100
ggcacgtttt cgtgaagatt tggcagcggc aggtgacgcg ctcggagatc gctggcatgg   8160
gcgacgacgc ggcggttgag atcttgaatg tgctgcctct gcgtaaagac taccggtccc   8220
ctggttctga acctgaaaga gagttccaca gaatcaatat cggtgtcgtt aacggccgcc   8280
tgccgcagaa tctcctgtac gtcgccagag ttgtcctggt aggcgatctc ggccataaac   8340
tgctcgatct cctcttcttg gaggtcgccg tggccggccc tctccacggt ggcggccagg   8400
tcgttagaga tgcgacgcat gagttgagaa aaggcgttta ggccgtttc gttccacacg   8460
cggctgtaca ccaccccccc ggcggagtca cgggcccgca tgacgacctg agcgacgttc   8520
aattctacgt gacgggcgaa gacagcgtag tttctaagac gctgaaagag gtagttgagg   8580
gtggtggcga tgtgctcgca cacgaaaaag tacatgatcc agcggcgcag tgtggactcg   8640
ttgatgtctc cgatggcctc gaggcgctcc atggcctcgt agaaatccac ggcaaaattg   8700
aaaaactggg aatttcgggc cgacaccgtg agttcctctt gcagcagacg gattaggtcc   8760
gctatggtgt cgcggacttc tcgctcgaaa gccccggggg gcgcctcttc ttcttccagt   8820
tcctcctcct ccccctcttc cagcagcata ggctcttctg gaacttccgc tgcgggagcc   8880
ggacggcggc ggcgtcgtct caccggcagt cggtccacga agcgttcgat catttcaccg   8940
cgacggcggc gcatggtttc cgtgacggcg cggccgtgtt cgcgaggacg cagttcgaaa   9000
```

acgccgcctc gtagtccgcc gccctgtagg gagggtaagt gatgggggcc gtcgggtaga 9060
gagaccgcac taacgatgca ttttattaat tgctgcgtag gcactccgtg caaggatctg 9120
agagcatcca agtcaacggg atctgagaac ttctctaaga aggcgtttaa ccaatcgcaa 9180
tcgcaaggta agctaagaac gctgggccgc tgggtgcttt cggggggcag gcgggaggtg 9240
atgctgctga tgatgtaatt aaagtaggcg gttttcaaac ggcggatggt ggcgaggaga 9300
accacgtctt ttggtccagc ctgttggatg cgaaggcggt cggccattcc ccacgcttcg 9360
ttttgacagc gacgcaggtc cttgtagtag tcttgcatca gtctctccac cgggatttct 9420
gcttctcctc tgtctgccat tctggtcgat ccgtagcctc gtagtggttg cagcaaggcc 9480
aagtccgcta ccactctttc ggccaaaact gcctgctgaa cctgcgtgag ggtggtttga 9540
aaatcatcta gatctacgaa gcggtggtat gcgccggtgt tgatggtgta cgtacagtta 9600
gccatcacgg accaatttac cacttgcatt cctggttggg tgatttctgt gtactttaga 9660
cgagagtaag cgcgggattc aaagacgtag tcgttgcaag tgcgcacgag gtactggtat 9720
cctactagga agtgaggcgg aggctcgcgg tagaggggcc aacccacggt ggccggcgcc 9780
ccaggggcga gatcgtccag catgagccgg tgataatgat agacgtatcg ggagagccac 9840
gtgatgccgg cggaggtggt ggccgctctg gtgaactctc gtacgcggtt ccagatgttg 9900
cgcagtgggc ggaaacgttc catggtgggc acgctctgtc ccgtgaggcg ggcgcagtcc 9960
tgtacgctct agacagaaaa aacagagagc catcatcgac tcctctccgt agtctggagg 10020
ttaggtcgca agggtgcggc ggcggggaac cctggttcga gaccagctgg atccgccgtc 10080
ccgatgcgct tggctccgca tccacgacgg ccgcgggcgt cgagacccag ccgcgatgcg 10140
cacaccccaa atacggaggg gagtcttttt gttgtttgtt ttgtagatgc atcccgtgct 10200
gcggcagatg cgacctcaga ccgccgcatt tcagcctacc accaccgcca cggcggccgt 10260
gtgtggcgcc ggccgcgggg aggaggaact ggccttagac ttggaggagg gggaaggctt 10320
agctcgcttg ggagcgccct ctcccgaacg ccatccccgg gtgcagctgg ccagggacgc 10380
ccggcaggcc tacgttccgc ggcagaacct ctttagagac ggcagcggac aggaggccga 10440
ggagatgcgc gactgtcggt ttcgggcagg gaaggagctg cgagcggggt ttgaccgaga 10500
aaagctgttg cgcgccgagg actttgaacc ggacgagggt tcgggcatca gtccggcccg 10560
cgcccacgtg acggctgcca atctagttac cgcgtacgag cagacggtga acgaggagcg 10620
aaacttccaa aaaagcttta acaatcacgt taggaccctg attgcgcgag aggaggtggc 10680
cacgggactg atgcatctgt gggatttcat agaggcgtac gtacagaatc ctactagcaa 10740
gccgttgacg gcgcagctgt tcttgatagt tcagcacagt cgcgacaacg aaacgtttcg 10800
cgaggccatg ttaaacatcg cggagcccga gggtcggtgg ttgctggatc tggtgaacat 10860
cttgcaaagc atagtagttc aggagaggag cctgagcttg gccgataagg tagcggctat 10920
taactactca atgcagagtc tgggtaaatt ttacgcccgc aaaatctaca agagtccata 10980
cgttcccatc gacaaagagg taaagatcga cagcttttac atgcgcatgg ctctaaaggt 11040
gctgaccctc agcgacgacc tcggggtgta ccgcaacgat cggatacaca aagctgtgag 11100
cgccagccgg cggagggaac tgagcgacag ggagctgatg cacagcttgc gaagggctct 11160
ggcgggcgcg ggcgacccgg accgcgaaac gtactttgac atgggggccg acctgcagtg 11220
gaggcccagc gcccgggcgt tagaggcggc cggttatcgc ggcgagcgag aggagataga 11280
tgatgaagac gaagagtacg aggacgaccc ctgaccgggc agctgttttt ttagatgcag 11340

-continued

```
cagcagtcgt cggcggacgg gaccagcgtg aatcccgcac ttttggcgtc catgcaaagt  11400
caaccatcgg gcgtgaacgc ctccgatgac tggtcggcgg ccatggatcg cataatggcg  11460
ctgacgaccc gtaatcccga agcttttaga cagcagcctc aggctaaccg tttttcggcc  11520
attctggagg ccgtggttcc ttcccgcact aaccctacgc atgaaaaggt tctgacgatc  11580
gtaaacgccc tggtggacag caaagccatc cgccgcgacg aggcgggctt gatttacaac  11640
gctctactgg aacgcgtggc gcgctacaac agcactaacg tgcaggctaa cctcgaccgt  11700
ctgaatacag acgttagaga ggcgctggcg caaaaggagc gctttctgcg agacagcaat  11760
ctggggtcct tggtggcgtt gaacgctttt ttgagcactc agcctgctaa cgtccctcgc  11820
ggtcaggagg attacgtgag cttcatcagc gccctgcgtc tcctggtgtc cgaggtcccc  11880
cagagcgagg tgtaccagtc aggcccggat tacttctttc aaacctcccg ccagggcttg  11940
cagacggtaa atctcagcca ggcctttaag aacttgcagg gcatgtgggg tgttaaagct  12000
ccgctggggg atcgcgccac catctccagc cttctgaccc ctaacacgcg cctgttgttg  12060
ctgctcatcg ccccgtttac taacagcagc agcatcagcc gtgactctta cctagggcat  12120
ttaatcactc tttatcggga ggccatagga caggcgcagg tggacgaaca cacctaccag  12180
gagattacta acgttagtcg ggcgctgggg caggaggaca ccggcagcct ggaggccacg  12240
ctgaacttcc tgctcaccaa ccgcagacag aaaatcccct cacagtttac gctgagcgcc  12300
gaggaggaaa gaatcctccg ctacgtgcag cagtcggtta gcctgtactt gatgcgagag  12360
ggcgccaccg cttctacggc gctggacatg acggctcgta acatggagcc ctctttttac  12420
gcgtccaacc gtcccttcat aaaccgcttg atggactact tgcatcgtgc cgccgccatg  12480
aacggggaat actttacgaa cgccattcta aatccgcact ggatgccccc gtctggcttt  12540
tatacgggcg agtttgacct gcccgaggcg gatgacggct ttctctggga tgacgtgtcc  12600
gacagcattt tttctccgtc gagtcagcgg atgcaaaaaa aagagggagg agatgagctg  12660
cctttgtcta gcattgaagc ggctagtcgc ggcgagagtc ctttccctag tctgtcttcc  12720
gtgagtagcg gacgggtgtc gcgtccgagg ctccccgccg agagcgaata cctaagcgat  12780
ccgattctgc agcccagtcg caagaaaaac tttcccaata acggggtgga gagcttggta  12840
gataagatga aacgttggaa aacctacgcc caggaacaaa aggagtggga agaaacgcag  12900
gtgcggccgg ttcccccgcc gacgcaacgg cgctggcgtc gcccgcgcga agaccctgac  12960
gactccgccg acgacagtag cgtgttggat ctgggaggga gcggagctaa cccctttgcc  13020
cacttgcgac cccaagggcg cctgggacgc ttgtactaat aataaaaaac ccaaccttac  13080
cagagccatg gccacagcgt ccttcctttt tgtttcttcc tcgctagcgg tacaatgaga  13140
agagccgtga gagtgccgcc ggtgtatccc gagggtccgc ctccgtctta cgaaagcgta  13200
atggaagctc tcaatacgcc ggccacgctg gaggcccctt acgttcctcc cagatacctg  13260
ggacctacag aggggagaaa cagcattcgt tactccgagc tggcacccct gtacgacacc  13320
accaaggtgt acctggtgga caacaagtcg gccgacatag cttccctgaa ttaccagaac  13380
gatcacagta actttttaac caccgtagtt caaaataacg acttcacccc ggtagaggct  13440
ggcacgcaaa ctattaattt tgacgagcgc tctcgctggg gcggtcagct aaagactatt  13500
ctgcacacca acatgcccaa cattaacgag tttatgtata cgaacaagtt tagggctaga  13560
ctgatggtgg agaaaccgca gacgggctct cctcggtacg agtggtttga atttaccatt  13620
cccgagggca actactcgga aacgatgacc attgatctca tgaacaatgc cattgtggac  13680
aattacctgc aagtaggacg acagaacggc gtccttgaga gcgatatagg cgtgaaattc  13740
```

gatacccgaa acttccgact ggggtgggat ccggtgacca ggctggtgat gcccggggtg 13800
tacaccaacg aagcttttca cccggacatc gtgctgctgc cgggctgcgg ggtggacttt 13860
acgcagagcc ggctgagtaa cctgctagga attagaaagc gccgtccctt tcaagaaggc 13920
tttcaaatca tgtatgaaga tttggaggga ggaaacatcc ccgccctgct ggacgtgccc 13980
gcctacgagg ccagcctgtc tctggccgaa gcggaagggc gcgtaactcg cggagacacc 14040
ttcgctaccg ctcctcagga gctgaccatc cagcctctta ccaaagacag taaaaatcgc 14100
agttacaacc tactgcccaa caacaccgac acggcgtacc gcagctggtt tttggcttac 14160
aactacggag atcccgagaa gggagtgcgc tcgtggacgt tgctgacgac tacggacgtg 14220
acgtgcggct cgcagcaagt ctattggtct ctgcccgata tgatgcagga ccctgtgacg 14280
tttcggtcct ccacccaagt gaacaatttt ccggtggtgg gcaccgagct gcttcccgtc 14340
tacgcgaaaa gcttttacaa cgagcaggcc gtctactcgc aactcattcg ccagtccacc 14400
gccctcaccc acgtgtttaa ccgatttccc gagaaccaga ttttggtgcg tcctcccgct 14460
cctaccatta ccaccgtgag tgaaaacgtt cccgccctca cagatcacgg aaccctgccg 14520
ctgcgcagca gtatcagtgg agttcagcgc gtgaccatca ccgacgccag acgtcgaacg 14580
tgtccctacg tttacaaagc tttgggcgta gtggcaccta aagtcctttc tagtcgcact 14640
ttctaaacat gtccatcttg atctctcccg ataacaacac cggctggggt ctcggctcca 14700
ccaagatgta cggcggcgcc aagaggcgtt ctagtcagca tccggtgcgc gtccgaggtc 14760
actaccgcgc tccctggggg gcctataagc gcggactgtc cgcccgcacg gccgtggatg 14820
acactatcga cgccgtcatc gccgacgccc gacagtacaa acctgccgtg tccacagtgg 14880
attccgtaat agacagcgtg gtggccggag cccgagccta tgctcgtcgc aagaggaggc 14940
tgcacaggcg aaggcgtccc acggcggcga tgctggcagc cagggccgtg ctgcgtcgtg 15000
cgcgcagggt aggcagaagg gcgatgcgcc gggcagccgc cgccaacgcc gggagagtga 15060
gacggcaagc agctcgtcag gccgccgccg ccatcgccaa catggccaga ccccgaagag 15120
ggaacgtgta ctgggttcga gattctgtca cgggagtccg ggttccggtg cggactcgcc 15180
ctcctcgaag ttagaagacg catgtgcgaa gacggcggtt ctcagtttcc catgttgtta 15240
ccagccagcc atgagcaagc gcaagtttaa agaagagctg ctgcagaccc tggcgccaga 15300
aatctatggg ccaccggaag tgaagcgtga cattaagcct cgcgacatta agcgagttaa 15360
aaagcgggaa aaaaaggagg aggagctggc gatggcggcg gctgcagagg acgcggtgga 15420
gtttgttagg tctttcgcac cgcggcgcag ggtgcggtgg aaagggcggc gtgtccagcg 15480
cgtgctgaga cccggcacca cggtggtgtt taccccggga cagcgttcgg ctgtgcgggg 15540
tttcaagcgg cagtacgatg aggtgtacgg cgacgaagac attttggagc aagccgcgca 15600
gcaaattgga gagtttgcgt acggaaagcg ctctcgtggc gaaaacgtcg ccgtggctct 15660
ggacgagggc aatcccacgc ctagcttgaa acccgtgacg ctacaacagg tgttgcccgt 15720
tagcgccagc actgaaagca agaggggaat caagagagag ttggacctac agcccactct 15780
gcagcttatg gttccaaagc gccaaaaatt agaggaggtg ctggaaaaca tgaaagtgga 15840
tccaaccgtc gagccggatg ttaaagtcag gcccatcaag gaggtggctc ccggtctggg 15900
ggtacagacg gtggacattc aaatccccgt tagttcctct gcggccgctg tggaggccat 15960
ggaaacccaa accgaaacgc cgacggccgc cgccaccaga gaagtggcgc tgcagaccga 16020
gccgtggtat gaatatgcaa cgtccgcgcg tccaaggcga tccaggcgct acgccgtaac 16080
tagcgccctt atgccggagt acgctttgca cccctctatc acgcccacgc cgggctaccg 16140
cggagttacc ttccgcccct cgggcactcg ccgacgatct cgccgcagaa catcgcgtcg 16200
tcgctctcgt cgcgttttag ctcccgtgtc cgtgcgtcgc gtgacccgcc ggggaagaac 16260
ggtgacaatt cctaacccgc gctaccatcc tagcattctt taataactct gccgttttgc 16320
agatggctct gacatgtcgc gtgcgcatcc cagttccgca ctatcgagga agaactcgcc 16380
gtaggagagg catggcgggc agcggccgcc ggcgcgctct tcgccggcgc atgaaagggg 16440
gcattttgcc cgcgctgatc cccattatcg ccgccgctat tggggcgatt cccggcatcg 16500
cctctgtggc cgtgcaagca tctcgcaaat aataaataaa aaccatcgct tttcacttat 16560
gtcatggtcc tgactatttt atgcagaaag atcatggaag acatcaattt ttcgtcgctg 16620
gctccgcggc acggctcgcg gccgttcatg ggcacctgga acgacatcgg caccagccag 16680
ctcaacgggg gcgctttcag ttggagcagc ctttggagcg gccttaaaaa ctttggctcc 16740
acgattaaaa cctatggcaa caaagcctgg aacagtagta ctggtcagat gctccgagat 16800
aaactgaaag accagaactt ccagcagaaa gtagtggacg ggctggcctc gggcatcaac 16860
ggggtggtgg acctagctaa ccaagcggtg cagaatcaga ttaaccagcg tttggagaac 16920
tctcgagtac cgccgcaaaa aggggcggag gttgaggaag tagaagtgga ggaaaagctg 16980
cctcctttgg aagttgttcc cggagcccct cctaagggag aaaagcgacc taggccagac 17040
ttagaagaaa ccttagtcac cggcaccttg gaacctcctt cctacgagca ggctttgaag 17100
gaaggcgctt ccccttaccc catgaccaag cctatcgctc ccatggcccg ccccgtgtac 17160
gggaaggacc acaaacccgt gacgctagag ttacctccgc cgccgaccgt ccctccgctg 17220
cccgctcctt cggtgggaac cgtggccagc gctcccgccg tggttccggc gccgcagccg 17280
gccgttcgtc ccgtggccgt ggcaaccgcc agaaacccca gaggagccaa ctggcaaagc 17340
acgctgaaca gcattgtggg cctgggagtg aaaaccctga aacgccgccg ttgttattat 17400
taaagtgcag ctaaaaattt cccgttgtat gcgcctccta tgttaccgcc agagacgcgt 17460
gactggtcgc cgctaccgcc gctttcaaga tggccacccc atcgatgatg ccgcagtggt 17520
cttacatgca catcgccggg caggacgcct cggagtacct gagccccggc ctcgtgcagt 17580
ttgcccgcgc caccgacacc tacttcagct tgggaaacaa gtttagaaac cccaccgtgg 17640
cccccacgca cgatgtgacc acggaccgct cgcagagact gaccctgcgc tttgtgcccg 17700
tagaccgcga ggacaccgcg tactcgtaca aagtgcgcta cacgctagcc gtaggggaca 17760
acagggtgct ggacatggcc agcacgtact tcgatatccg gggcgtttta gatcggggtc 17820
ccagctttaa accctactcc gggaccgcgt acaactcgtt ggcgcccaaa ggggctccca 17880
atccaagtca atggacaaca acaaatggag gaaacaaaac taattctttc ggtcaagcgc 17940
cttttattgg agaaagcctc acaaaggacg gaattcaagt aggggtagat accggaaatc 18000
caggcactgc cgtatacgct gacaaattat accagccaga gccccaagta gggctctcaa 18060
aatggaatca gaatccatcg gaaaacgctg cgggcagaat cctaaaacca tcaactccca 18120
tgcagccgtg ctacggttct tatgcgtatc ctaccaacac aaacggtggg caggtgaaaa 18180
ccagcgcgac cgatgctact ggggcaaata acgttaccct aaattttttt aacaacgcgg 18240
cagataacgg taacaataat cccaaagtgg tgctgtacag tgaagatgtg aatcttgaag 18300
cgcccgatac gcatctcgtt tttaaacctg atgctaacaa cgcaacaagt gcagaaacgc 18360
tactaggtca gcaagcggct cccaatcggc ctaactacat tggcttcaga gacaacttta 18420
ttggcttaat gtactacaat tctactggaa acatgggcgt tttggccggt caggcgtctc 18480

```
aactgaatgc tgtggtggat ctccaagaca ggaacaccga actgtcgtat cagcttatgc  18540
ttgatgcctt gggggatcgc agccgctatt tttctatgtg gaaccaggcc gtagatagtt  18600
atgatccgga cgtaaggatt attgagaacc acggtgtaga agacgagcta ccaaactact  18660
gctttccgct aaacgggcaa ggaatatcga atacatacaa aggagtaaaa accaacaacg  18720
gtggagcggc ttggactcaa gatacagacg ttgtcactac taacgaaatc tccataggaa  18780
atgttttcgc tatggaaatc aacctggctg caaatctgtg gcgcagcttt ctatactcaa  18840
atgtagcgct ctatctgcca gattcttaca aatacactcc agataacatt gagctcccac  18900
aaaacaaaaa cagttacggt tacataaacg gtagggtcac tgctccaaat gccatagaca  18960
cctacgttaa catcggcgct cgctggtcgc cagatcccat ggacaacgtc aacccgttta  19020
atcaccaccg aaacgccggg ctccgttacc gctctatgct tttgggtaac ggacggtacg  19080
tgcccttcca cattcaagtg ccccagaaat tcttcgccat taaaaacctt ttgctgctac  19140
caggttcgta cacgtatgaa tggaacttca ggaaggacgt gaacatgatt ttgcagagca  19200
cgcttggtaa cgacttacgg gtggacggtg ccagcatacg atttgacagc attaacttat  19260
acgccaattt ctttccgatg gcgcataaca ctgcttctac tctggaggcc atgctgcgca  19320
acgatactaa cgaccagtcg ttcaacgact acctgtgcgc tgctaacatg ctgtacccca  19380
ttcccagcaa tgccaccagc gtgcctattt ctatcccatc aagaaactgg gccgccttta  19440
gaggatggag ctttacccga ctaaaaacga aggaaacgcc ttccctgggc tcaggctttg  19500
atccctactt tgtgtactct ggctccattc cttacctgga tggtacattt tacctaaatc  19560
acaccttcaa aaaagtgtct attatgtttg actcgtccgt gagctggcca ggtaatgacc  19620
gccttctcac ccctaacgag tttgaaatta agcgctcagt ggacggagaa ggctacaacg  19680
tagctcaaag caatatgact aaggactggt ttttaattca aatgttaagt cactacaaca  19740
tcggctacca aggcttctac gtgccggagt catacaaaga cagaatgtac tccttcttca  19800
gaaacttcca gccgatgagt cgtcaagtgg tagacaccgt taactatgct aactacaaag  19860
aggtcaaaat gccattccag cacaacaact ctggcttcgt gggttacatg ggtcccacca  19920
tgagggaggg acaggcgtac cccgccaatt atccctatcc acttattgga gaaacggcag  19980
tgcctagtgt cacccagaaa aagtttctgt gcgacagggt gatgtggaga attccctttt  20040
ctagcaactt tatgtctatg gggggcttaa ccgatctggg gcagaacatg ctgtatgcca  20100
actccgctca tgccttggac atgactttg aggtggatcc catggatgag cccacgcttc  20160
tttatgtttt gtttgaagtc ttcgacgtgg tgcgcatcca tcagccgcac cgcggcgtca  20220
tcgaggctgt ctacctgcgc acgcctttct ctgccggcaa cgccaccacc taagaagcca  20280
atgggctcca gcgaacagga gctgcggagc attgtgcgcg atctgggctg cggaccttat  20340
tttttaggca ctttcgacaa acgctttccg ggctttatgt ccccccaaaa gccggcctgt  20400
gccattgtca acacggcagg acgggaaacc ggcggagtgc actggttagc ttttgcctgg  20460
aatccgcaaa accgaacgtg ctacctgttt gacccttttg gtttttcaga tgaaagactg  20520
aaacagatct accagtttca gtacgaaggc ctgctgaaac gcagcgccct ggcttccacg  20580
ccggaccact gcgtcaccct ggaaaagtct acccagtctg ttcagggacc actttcggcg  20640
gcctgcgggc ttttttgttg tatgtttctg cacgcctttg ttcactggcc tcactcccct  20700
atggacaaaa atcccaccat ggacctcctg accggggttc ctaacagtat gcttcaaagc  20760
ccccaggttg ttcccaccct gcgtcgcaac caagaacagt tgtatcattt tcttagtaaa  20820
```

-continued aattcagcct attttcgccg tcatcggcaa cgtatagaga aagccactga ttttgaaagc 20880
atgaaacaca cagtgtaact tgcaataaaa ggttgatttt atttatacaa gtgcgcatct 20940
ttcgttatta aaactcaaag ggctcggggc agtcgtcgcc gtggctgctg gggagggcca 21000
cgtttcggta ctgaaaacgg ggatgccagc gaaattcggg aatgatcatc tttgggagcg 21060
gtttgtcttc catgttctcc ttccaaaact gccgaacgag ctgcagggct ccgatgatgt 21120
cgggtcccga aattttgaaa tcgcaattgg gcgccgcgcc gccgcgggaa ttgcggtaca 21180
ccgggttggc acactggaac accagaacgc tgggatactt gatactggct agggccgtag 21240
cgtcgttcac ttctgccaca tccaagtcgt ctgcgttgct cagaccgtaa ggggtgacct 21300
tgcacatttg tcgacccatg cgagggatga catcgggctt atggagacaa tcgcagcgca 21360
ggggaatgag tatgcgcccc tgaccacgct gcatctcggg gtagctggcg cgcagaaacg 21420
cttccaactg cctgaaggcc atttgggctt tcaaaccttc cgtataaaac aggccacagg 21480
atttaccaga aaacacatta gggccacagc tcacgtcttc cgggcagcag cgcgcgtcat 21540
cgtttctaat ttgcaccacg ttgcgtcccc agcgattctg gactacctta gctttgccgg 21600
ggttctcctt caaggccttc tgaccgtttt cgctggtcac gtccatctcc gtgacgtgct 21660
ccttgcgaat catctcggtt ccatggaagc agcacaggac tccgtcttcc ttggcgctgc 21720
gatgctgcca caccgcacag ccggtagctt cccaattttt ctgaacaacc cccgcatagg 21780
attgcatgta ggccatcaag aatcttccca tcatctcggt aaaggttttg ttgctagtga 21840
aggtgagcgc caagccccga tgttcctcgt ttagccatgt ttgacagatt tttctataca 21900
ccgggccctg ctccggcaga aacttgaacg tggctctgtc ttcgtgggga acgtggaact 21960
tttccatcag tatcatcata gcttccatgc cctttcccca cgccgttacc aacggagagc 22020
tgtgcggatt taccactagc acagacgaac gctcctctct ctcagggttt gcttcttcta 22080
ctgttactct ttgaaacaca cggccgccgt cggcttgctt cacaatgcgc accggagggt 22140
agctgaaacc caccccgatt accgtgcctt cgccttcgct gtcggagatg atttccggcg 22200
agggcgggcg agcctgcgag cttttgcgtg cctttttctt gggaggtagg ggaacagcta 22260
cgtccctctc cgggcttctt tcccgcagat acggggtgat agaacgctcg cccgggttct 22320
gattgccggc catgatttac tcctaggcga aaaaacatgg atcttatgcg caaagaatcc 22380
ttaaccaccc cgcccctcag cgacgaagac gtgccaatcg agcaggaccc gggttttgtt 22440
acgccgcccg aagagccaga gttgcccata tcgttcgacc tcgcccgtag cgagcgcaca 22500
gaacaggacg gcgactactt attggaagcc gaaatcctgc ttaaacactt tgccagacag 22560
agcactatcg tcaaggaagc tctgcaagac cgcagcgaag tgcccctgga cgtgtgcgag 22620
ctgtcgcgag cctacgaggc aaacctcttt tcgccccgag tgcctccaaa gaagcagccc 22680
aacggtacct gcgagcccaa cccccgcctc aacttttacc cggtgttcgc ggtacccgag 22740
gcgctggcta cctatcacat ttttttaag aaccaaggca ttcccctgtc gtgtcgtgcc 22800
aacagaacca aagccgatag aaagctgaga ttgagagcgg gggctcgcat acctgagata 22860
gcttccttag aagaagtgcc caagattttc gaggggttag gacgagacga gaatcgggcc 22920
gcaaacgctc tgcaaaaaga acagaaagag gctcagagtg ttttaataga actggaggga 22980
gacaacgcac gcttagccgt tcttaaacgc accgtggagg tttcccactt tgcctatccg 23040
gccctgaacc ttcccccgaa agtcatgcgc tccgtgatgg atcatcttct cattaaacgg 23100
gccgaacccc tcaaccctga aaatcctgac ccggaaaact ccgaggacgg caaacccgtg 23160
gtttcagacg aggagctgga acggtggttg ggcacaaaag atcccgagcg cttgcaagag 23220
aagcgcaaga tgatgatggc ggccatcctg gtgaccgccg agctggagtg tttgcaacgc 23280
ttttttgcgg acgtagagac tatacgcaag gtggaagaat ctttacacta cacctttcgc 23340
cacggctacg tccgacaagc ctgcaagatc tccaacgtag aactcagcaa cctcgtgtcc 23400
tatatgggcg tcctccacga aaaccgctta ggtcaaagcg tgctccactg cactttgcaa 23460
ggggaagcgc ggcgagatta cgtccgcgac tgtgtttacc tttttctgct gctcacatgg 23520
cagacggcca tgggagtgtg gcagcagtgc ttggaagaaa ggaatctgaa ggagctagac 23580
aagctcttaa caaagcagag aaaagcgctg tggaccggtt ttagtgagcg agcggcagct 23640
agccagctgg cagatataat tttcccagag cggctaatga aaacgctaca gaacggcctg 23700
ccggatttca ttagccagag catcctccag aacttccgct cgttcgtgct ggaacgctcc 23760
ggaattttgc ccgccatgag ctgcgcgctg ccttccgact ttgttccact cacctaccgc 23820
gagtgccctc ccccctgtg gagccactgc tacctgctac aactggctaa ctacttggcc 23880
tatcactgtg atcttatgga aaacgtgagc ggagaagggc tgctggagtg tcactgccgc 23940
tgcaacctct gcacccccca ccggtccctg gtttgcaaca ccgagctgct tagcgaaacc 24000
caggtcatag gtacctttga gatccaaggt cccgaacagc acgagggggc ttccggttta 24060
aaactgactc cggcgctgtg gacctcggct tacttacgca aatttgtagc cgaggactac 24120
cacgcctcca aaattcaatt ttacgaagac caatctcagc cccccaaggc ccctctcacc 24180
gcctgcgtca ttacccaaag caacatttta gcccaattgc aaaccatcaa tcaggcgcga 24240
cgagagtttc tcttaaaaaa aggtcacggg gtgtatctgg acccccagac cggcgaagaa 24300
ctaaacccat ccacactctc cgccgaagca gcccccaagc agcatgccgc ccaaaggagt 24360
caaacagctg atagctcagc agagagcgaa gaagcagcaa gagctcctgc ggcacatgga 24420
agaggaggag gaagccagcg atgcgtggga cagtcaggca gaggaggctt cggaggacga 24480
ggagatggaa ggctgggaca gcctagacga ggtggaggag gaggaagagg tagaggacga 24540
accgatcggc gaaaaaccac cggcttccag cgcactttct ccgagccgtc tggcgaaaac 24600
ccgcgtccca accccgggag gctcacgcaa agccagccgt agatgggaca caaccggatc 24660
tccagtagca tcggcggcgg gtaagccagg gcggccgcgg cggggttatt gctcctggcg 24720
ggttcataaa agcagcattg tgaactgctt gcaacactgc ggggggaaca tctcctttgc 24780
ccggcggtat ctcctttatc atcacggggt ggctgtgcct cggaatgtgc tctattatta 24840
ccgtcatctc tacagcccct acgaaacgct cggagaaaaa atctaaagcc tcgtcgcgct 24900
cagccaccgc cttctccgcc gccaaagact cgccagccgc cagagaactg cgaaaccgca 24960
tttttcctac tctgtacgct atttttcagc agagccgcgg gcagcagcaa gaactaaaaa 25020
taaaaaaccg ctccctacgg tcactcaccc gcagctgtct gtaccacagg agggaagacc 25080
aactacagcg cactctggac gacgccgagg ctctgttcaa caagtattgc tcagtgtctc 25140
ttaaagacta aaaaacccgc gtttttttacc caaaaaagcg ccaagcacac gtcatctcaa 25200
gcatgagtaa agaaattccc acgccttaca tgtggagcta ccagccgcag atgggcttag 25260
ccgcgggcgc cgcccaggat tactccagca aaatgaactg gctaagcgcc ggcccccata 25320
tgatttcaca agtaaacggc atccgagccc gccgaaacca aatcctccta gaacaggcgg 25380
caattacctc cacacccagg cggctcctaa accctcccag ctggcccgct gcccgggtgt 25440
atcaggaaac cccgccccg accacagtcc ttctgccacg cgacgcagag gccgaagttc 25500
agatgactaa cgctggggcg caattagcgg gcgggtccag gtacgtcagg tacagaggtc 25560

```
gctccgcacc ttatcctccc gggggtataa agagagtgtt tattcgcggt cgaggtatcc  25620
agctcaacga cgaggttgtg agctcctcag cgggcctcag acctgacgga gttttccagc  25680
tcggcggagc cggccggtcc tccttcacca cccgtcaagc ctacctgacc cttcagagct  25740
cttcctccca gcctcgctcg ggcggaatcg gcactctcca gtttgtggaa gagttcgttc  25800
cttcggttta cttcaacccg ttttccggct cacctggacg ttaccccgac tccttcattc  25860
ccaactacga cgcagtgagt gaatctgtgg acggctacga ctgatgacag atggtgcggc  25920
cgtaactgcg cggctgcgac acctgcatca ttgccgacgg tttcgctgct ttgcccggga  25980
gcctttggtg tttagctact ttgagctacc tgaacatcat cttcaagggc cggctcacgg  26040
aataaaactc gaagttgaaa aggaacttga gtctcgcctc attcgtgact ttactcctca  26100
ccctcttttg gtggaaaaag aacacggaac cactattata actgtgtttt gcatctgccc  26160
aactcctgga ctgcatgaag gcctttgttg tcgtctttgc gctgagttta atttatagcc  26220
gcggaactgc tgacgacctt gtgttcgaag gtactattga aactgtttta ttttctgact  26280
ctacttcttc cattacacta aattgtagct gcactaacga actaattcag tggaacgcca  26340
acagaacctt ctgtaaagct ttctaccgca actttactta ctacagtaac aactctctct  26400
gcgcggtttg tacgcgacag gctttgcatt tataccctcc ctttgtcgct ggcagttatc  26460
tgtgtattgg ctctggagcc cagccttgct ttcaccgctg gtacctatac gaagacaaca  26520
cttcattcac aacttccacc ccaaaacaag tttcctactt acacgtctct ttaaaacctc  26580
tattcgccct tgcggctttt atacttgtta tattagccaa ttttatttta attaacaatc  26640
tgccatgatg ctcactgtct taacaactct tctcttgcca gctgttattt gcattagacc  26700
tcctgaacct cctcccgccc acggtattaa tactaaatcc ctgcctaata gtttacaaaa  26760
tccatcccgc gtttatgcta aagttgggca aaaccttacc ctcgaatcca ggtactcgtc  26820
acattctaat agcatgccac atgtggtttg gtacttagaa gtttttaacg atgatactat  26880
ttttcctagc agtgtagttc ctccaatttt ttcaggcatc aaactgtgtg aaattactga  26940
acaaaactac caaactttta accacgcacc aaaagaattt aactgcatta acaagagctt  27000
aaatttattt aacctgaaac caagcgactc tggcctttac aacgtcaagg tttataaaga  27060
tgacattgaa cataacacct actttcgctt gtctgtaatt cgctttgctc agccccagtg  27120
cactattaat tcctcctact taactgaaag ttactgttta ataagcattg attgttttca  27180
tttagaatac cctgccatag ttgagtttaa tggctctcgc agtaattttc actactatgt  27240
actttccaaa ggcggtaaaa acttagccga ttactatacc gttacctatg attatcatgg  27300
ccttaaacaa acctttaaag tagaataccc ttttaacgat atttgcaatg acattatttc  27360
cttggaaaca cttgcagact ttacaccagt ttttattgtt accattgtaa tgagcgtcat  27420
tacaattgta gttagccttt tattttgctg cttttataaa ccaaaatcta aatcaaactt  27480
ccaacaagtt aaactaaaaa caattcaact agtgtaattt atttttcagc atggtagctg  27540
tcttcttctt ccttctctgt ttgcccatca tcttcgtgtc ttcgactttc gccgccgttt  27600
ctcacgtgga agcagagtgc ctaccacctt ttgctgtgta cctaatattt acattcgtct  27660
gctgcactgc catagctagc atagcctgtt tttttgtaac aatttttcaa gccgctgatt  27720
acttgtacgt gcgttttgtt tatttcagac accaccctga atacagaaat caaaacgtag  27780
cttctttatt atgtttagca tgattcctct actagtaata ctctgtgatc tccttccgtt  27840
tacttactgc cactgccccc taaacaaacc ttggtcactg tatacttgct atgccgagtt  27900
gccggacatt cctgtaatct ggttgtacgt agctactgca gccctagtgt ttgtagctac  27960
```

```
ttgtgttggt gtaaaaattt acttttgttt aaaaatcggc tggcttcatc ctccagaaga  28020
cttaccaaga tttcctctcg ttaatgcctt tcaaatgcag cctccccctc ctgatcttat  28080
tcgagcacct tctgttgtca gctacttcca actagccggt ggagatgact gattcgcacg  28140
acattaacat taccatggag cggggaatcg ctcagcgaca gcgtgaagct cgcgcaatgg  28200
attaccttag actacaagaa cttaaagaaa cacattggtg cgatagagga tcgctttgcc  28260
ttgttaaatt ggcttcactc tcctatgata tctctaccca agggcatgaa ttgtcttaca  28320
ctgtagccgg gcaaaaacaa accttttcaa ctataatggg cggcacatct cttaaaatta  28380
ctcatcaatc taaacctgtc gaaggggcta ttctctgcca ctgtcataag cctgattgca  28440
tggaaaaatt aattaccacc ctctgcgccg tggcggaaat ttttaagtaa aaaaaaataa  28500
aactcaccta agttgtctca gtagcttttt gtcaaatttt ttcagcagca ccaccttgcc  28560
ctcttcccag ctttcatagg ggatgtggta gtgggcggca aacttcctcc aaaccctaaa  28620
agctatgatc gtgtccactt ctctcccctc acccacaatc ttcatctttt catagatgaa  28680
aagaacccga attgacgaag acttcaatcc cgtctaccca tatgactcca ctactacccc  28740
caccgtccct tttattgctc caccatttgt ttcatccaat ggtttgcaag aaagtccccc  28800
cggaatgctg tctttaaact atgctgaccc cattacaacc aataacggta aactaaccgt  28860
taaattaggg aataacttaa gccttagtag tgacggagcc atcacctctg caacagctgt  28920
gacggatcct cttacaaaca atggtggaac cataggatta gctctctctg ccccccttaac  28980
cactacttcc actgggctgg gtatttcaat ttctccaccc attactctat ccaacaacgc  29040
tttaaatatt tcacttggaa atgggctaac atcctcttca aactcgctag ccattaaaac  29100
ctctggcgct attgggtttg acaaccaggg caacttacgc cttaacaccg gaggaggtat  29160
gagattggcg ggcgacagat taattctaga tgttaattat ccttttaatg gcgatcccaa  29220
attgtcccta agaattggta agggtttata tcttcaaaac aatcaggatt tagctgtgct  29280
actaggttct agaagtggtc ttgactttag tggaaacaac ttagttgtaa aattaggatc  29340
cggacttgca tttgacaaca acggagcaat taccacctca acttcccggt ctcgtttcgc  29400
tgactatttg ccatacgttt ctacatggcc ccccctaaac gagcctaact gttccatcta  29460
cgaatcacta gatgctatgc taggtctaca cttcagcaaa cacggactac acgtaattgg  29520
tacaatctcc ttaaaggcca taaaaggaga actgtgcaac atgcagcgtg atacagttac  29580
tcttaagcta ctttttaaca gcagcggacg ccttttaaat tgtccgctgc tcccatcatt  29640
ttggaaccct gaaacgccct tacagtttat gccaagcagt actttttatc cccgtaatgt  29700
atccccaagc acactcaccc aaactctgcc agactctagg tgcacattta ctgttgcata  29760
caacacggaa ggtgcagatt actcatttac cttcacttgg tccgtctgtt ccggagaaaa  29820
gtttaatgcc cccgctgcga tgttctgttt tgttgctgaa caataaagct tgcaaagcca  29880
cctttgtttt ctttcagatg aaacgcgcca gaattgacga cgacttcaat cccgtgtacc  29940
cctatgacca acctaacgcc ccgcttttgc catttattac cccacctttt acctcctctg  30000
acggcttgca agaaaaaccg ccgggagtgt taagcttaaa ttacaaaaac cccattacca  30060
cccaaaatgg agccctcact cttaaaattg gagaggggat tgaggtgaac gacaaagggg  30120
aactgacatc taacgcagtg tcagtttcgc cccctctctc taaaatcgac aacactctga  30180
gcctagtgta cagcgaccca ctcacagttc gtgaaaactc cctacactta aaaactgctc  30240
ttcctatttc tctcaacgct accagggaac tcactttggt ggccaatgct ccgcttgcta  30300
```

ctaccaacgg agcgcttcaa ttacaaagcg cggctccttt aggagttgcc gaacgaactc 30360
tgaaactgtt gttttccaac ccactgtact tacaaaacaa ctttctatcc gttgctgtgg 30420
acaaacctct agccatggct tccacgggtg ccattgctct gcagtgggca cccccctttgc 30480
aagtaggaac aggaggctta acagtagcca ctgtcgagcc ccttaccgtc accaacggaa 30540
atttaaacat taacacaaag cggcctctca tcattgaaga cagtagtttg tatttagctt 30600
ttagaccccc tttaagatta tttaacagcg accctgaact tggtgtaaac ttcatccctc 30660
ctattacaat ccgcgatgac ggtttagctc taaacacagg agagggtctc actcttgtgc 30720
gtgacagact aagtgtaaac ctcggcaaag atttgcagtt tgtggacaac accgtctcac 30780
tggcattaag cacagcttta ccgcttcaat acactgatca actgcggcta aacattggcc 30840
agggcctacg ctacaaccca accagtaaga agctagacgt ggatcttaat cagaacaaag 30900
ggttaaactg ggaagacaac aaagtcatta ctaaattagg ggacggtttg cagtttgatt 30960
cagcggggaa cattagtgtt atcccacctt ccgtaacacc acatacgttg tggactacgg 31020
ctgacccctc tcctaattgc tcagtatata cagacctgga tgccaagctg tggctgtctc 31080
tggtaaaatg caatggcata gtccaaggca ctatcgcctt gaaagctcta aagggagtgc 31140
ttttaaaacc cacggccagc tctatctcta ttgtcattta tttctatagt aatggcgtga 31200
ggcgaacaaa ttaccctacc tttgacaacg aaggcacgct agctaacacc gccacctggg 31260
gctacagaca aggccagtca gctaacacca atgtaactaa cgccgtagag tttatgccta 31320
gctccgccag gtaccccatt aacaggggcg atgacgtgca aaaccaaatg atgggctata 31380
cttgcttgca aggggcgtta aacatggctg tagggtacaa ggtcacattt aaccacgctc 31440
ttgaaggata ttccctaaaa ttcacatggc ctgtgtacaa caaccaagcc tttgacgttc 31500
cctgttgctc tttctcttac ataaccgaag aataaacaat ggttttcaaa tttttatttt 31560
acattatgcg tacagttaaa cttcccccac ccttccactt tacactgtat accatccttt 31620
ctcccttggt agcggtaaac aactgaaact gggtgttcaa acaaggattt ttaggtgtca 31680
gagtccacac ggtttcttta cgtgcaaatc tctcatccgt cacggacacg aagccctcgc 31740
cgacgtcttc caacagtggc gtgtcgtcca aacaatccta caacacacaa agttttaagt 31800
tctccacggg ttttcacctc tgccgtactc agccagtgtg aacgggcggt gacgctccat 31860
cagtcctctt aacaagcttt gcctagcagc ttctagacga gctctccgag gctggtaaga 31920
agtcaggcgg tctaatagcc tcacagcgcg gataagaaat ctgcgagtcc gtttagcgca 31980
gcagcgcatc tgaatctcac tcaagtcctt acagtaggta cagaccatta taattaaatt 32040
gttcaaaatc ccatagctaa acgcgctcca cccaaagctg ctgttttcta acacggctac 32100
cgcatgcccg tctagaaaaa tcctaacata gatcaggtgt ctcccgcgaa tgaacacact 32160
gcccacatac agcacttcct tgggtaagtg gtaatttacc acttgtctgt accaggggaa 32220
cctaacattt actaaagacc catatatcgc cattctgaac caattagcta aaaccactcc 32280
acccgcttta cactgaaggg atccgggaga attacagtgg cagtgaagca cccacctttc 32340
atagcctctt atgatctgat tatattctac atctatcgta gcacaacata tacaaatctg 32400
catgtatgtt ttcatcacat gtttttccca ggcagttaat acagagtccc aatacacagg 32460
ccattcctgt aaaacagtaa agctaacaca agacggtacg cccctcacct cgctcacatt 32520
gtgcatgtta agattttcac attccagata cgggggattt tcaatggtgg cacagggcgt 32580
ctcgtcacac ggcggtagct ggtgtctgtt gtaaggaccc agtctgcagc gataccgtct 32640
gtcgcgttgc atcgtaagtc aagttctttc gcaagtcctc gtacttccga tagcaaaacc 32700

```
aggttcgccg ccaacaaatc tccacgcgac ggccgtccct acgccgctgc cgctcggtgt  32760
ttaccgcaaa atggagccac tgctgcaatg cgcacaactc cctctcggcc tctggagtaa  32820
taaaaacttc gtacctgatg atatccctga atagttccaa gctagaagtg agggccaact  32880
ccaaccaagc gatacatgca gacttgtccc gacacactgg gggtggagga agacacggaa  32940
gaggcatgtt attccaggcg atcgcgtaag gtcacaaaat gcagatcgcg aagatgacaa  33000
cggtcgcctc cggtacgctg gtggtaaaga acggccaaat caaaatgaat tctgttctcc  33060
aggtgatcta ctaccgcttc caacagcgcc tgaacccgca catccaaaaa caccaacaga  33120
gcaaacgcgt cgtgttcaaa atcttcaatg atcacactgc aattctgcac catgcccaaa  33180
taattttcag ccctccactc gcggactata tcgcaacaca gttcttgtaa atttactcct  33240
cgcatttgaa aaagctgaac gagggcgccc tctattgaca tgcgcagaca caccatcatg  33300
cttgcaaaat atcaagctcc tgcgacacct gcagtaaatt caacatatca gggtcaggat  33360
gaaccccacg atcgcgaatc tccacgcgca atgttaactg caaaaagttt agcagatccg  33420
cacacactaa agcggtcagc tccccgtcag gtgtcatttc tggcgtggcc acgcagcaca  33480
aaagttggat agagggcgcc aggctcaaca gcaccgcgcc gttatagcaa aactgaaacg  33540
gcggagtcaa gcagtgtaac aaatggagcc aaaagtcact gagctgtctt ttcaaaaagt  33600
ctaaaacctc aatgtccaaa tcgtgcaagt actgccgtag agcagccggt acaataacgc  33660
aaacaaaaac aggctgcctc tgatacatag cgaacctata aattaaacaa gagaagcacg  33720
atgaagacag gggtaaatca cccgctccag cagcaggcag gccaccggct gtcctctaaa  33780
cccgtagaaa aattcatccg agtgattaaa aagcaccaca gacatttccc accacgtact  33840
gggctgtatg tcttgagcgc caacaaaaac ccccccttaca ttcatatccg ataacgagaa  33900
taagcggccc aagtacccct gaggaatgtc catagacaac tgcagagaaa ctaaaagcac  33960
gcctctcgga gaaatcacaa agttttccgg tgaaaaaagc acatacagat tagaaaagcc  34020
ttgctgctgt ggcataatag cccgcgagcc cagcaaatgc acgtaaattg cctcgtcagc  34080
catcgcccag tcttaccgcg taaaaacacc gcgcaaaata acgcctagct caacgcgtcc  34140
ttcagtgaat atatatatgc gtagtcccct cccagttacg ttattaccca ccgccgccca  34200
agcgcaaagg tcgcccacac ccaaaaagcc cgcgaaaaat ccaccgtcgt cagcacttcc  34260
gcaaaaatgt cgttcccaca gcgtcacatc cggtccctcg tccccttccg ctcccgcgcc  34320
gcccaccccg tcaccccgca cgtcacttct tcccaccccc tgccaccccc actcctcctc  34380
tctcattatc a                                                      34391
```

<210> SEQ ID NO 3
<211> LENGTH: 34402
<212> TYPE: DNA
<213> ORGANISM: Adenovirus

<400> SEQUENCE: 3

```
catcatcaat aatatacctt attctggaaa cgtgccaata tgataatgag agaggagggc     60
ggaggcggcg cgaggggcgg gccggtgtga cgtgtggggc ggcgggcgtg ggcgggagcg    120
gaagggggag gaggggtgtg ttaggcagac gcagcggaac tgacgtgtga aatgtgactt    180
tggaccggaa atgaggcgtg ttttgccatt tttgcaagtt ttttgcggat tttggcgcga    240
aaactgggca atgaggaagt tgtggttaat gtgtactttt tatgactggg agggaaaact    300
gctgatgtgc agtgaacttt gggcgctgac ggggaggttt cgctacgtgg cagtgccacg    360
```

-continued

```
agaaggctca aaggtcccat ttattgtact tctcagcgtt ttccgtgcct atttaaacgc    420
cttcagaccg tcaagaggcc actcttgagt gctggcgagt agagttttct cctccgcgct    480
gtgaagatga gactggttcc tgagatgtac ggggtgtcct gggatgagac ggccgaagag    540
ctactgaatg ctgaaattta cgacgtgccg aattcgcctc caggaacacc ctcgcttcat    600
gatttgtttg atgtgaacgc agaaagtgct gacgggccgg acgagaacga agacgcggta    660
aatagtatgt ttcctgactc aatgctgtcg gcaggcgagg gttatgctgg ggatgtagag    720
ccgagtggga gcgacatgga cttaaagtgc tacgaagatt tgccgagtag cagttcagaa    780
ggatcagatg aggatgaaca aaagccttta aaacatgaac tggtgttaga ctgtcctaag    840
aaccctggcc atgattgtcg cgcctgtgct tttcatagag ctaccagcgg aaatactgaa    900
gcaatatgct gtttgtgtta tatgcgcctt accagcgatt ttgtatacag taagtatggg    960
ttgtttaatg cggcgggtgg catgagcgtt tgtgttagca tgcttaatgg tgtgtgattt   1020
caggcgatgt gtccgacgtg gaaggagacg gagacaagtc aaaagtatgt gagtctcctg   1080
gctctttggg gactgtggct ccagatggtg ttcttaagcc caccgcggtg agagtatcgt   1140
cgaggcgacg cccagcggta gagaagttgg aagacttgct ccaggaacca gagcaaactg   1200
aacctttgga cttgtcctta aagcacccca ggatgaccta attgtttatg gtattttatg   1260
gcgcgcaata aagagtgtta aaccttaact tgtgtttatt taatgggcgg tttgctgggt   1320
atataagcag gtggctgaca ctgaggcgtt actttttttc cgaatggatc tcctaaggct   1380
gctcagcgat tacgaggtgc tgcgcaagtt gctggagaca gcctgtgaga aaaatcgcag   1440
ctgttggagg tttttctttg gctctactct tagcaacgtg gtgcacagag tcaagcgaga   1500
gcacagtgaa gaattttcta gactagtggc agatgttccc gggcttttttg tttctttaga   1560
tttaggacat cactcttact ttcaggagaa gattgtcaag ggtctagtgt ttgagtcaac   1620
tggccgcacg gttgtgtctg tggcttttat ctgttttctt ttggataaat ggagcagcga   1680
cagccacctg tcgtgggatt acatgctgga ttacatgacc atggcgttgt ggcgggcgct   1740
cctgaggagg aggagggctt gcatttactt gccggtgcag cctcagcaag gtctggagcg   1800
agtggaggaa gaggaggagg agaacccgag ggcaggcgtg gaccctcctc tggaatagaa   1860
gctgtgggcg agccagaaga gggcactagc gatggggtta gaaagaggcg gagaacagaa   1920
acggaagagg tgaacgctcg agattaccta actgatttga ctgtgcggtt gatgagtcgt   1980
aggcgacctg aaacggttgc atggagtgaa ctggagactg aatttaaaaa tggcaatatg   2040
aatttgctgt acaagtatag ctttgaacag atacaaacgc attggttgga accgtgggag   2100
gattgggaga cagcctttgc caattttgca aaaatcgcct tgcggccaga taaaatctac   2160
accataagcc gcatggttaa cattaggaag tgtgtgtatg tgctggggaa tggggctacg   2220
gttcagattc aaacgtgtga ccgcgtggct tttaattgct gcatgcagag catgggcccc   2280
ggggtaatag gcatgagcgg tgtgaccttt gccaacgtgc gattcaccgg ggaaaacttc   2340
tttggcgctg tgtttatgaa caacactagc cttactcttc acggggtgta ttttctgaat   2400
ctcagtaaca cctgtgtaga gtgctggggt cgcgcgtgtc tgaggggctg tacgttctat   2460
ggctgttgga aagcagtggt aggcagaaca aaaagtcatg tgtctgtaaa aaagtgtatg   2520
tttgaacgtt gtgtgatcgc tattatggtg gaggggcagg ggcgtgtaag gaacaatgtt   2580
ggggcggaga acgggtgttt tcttctgtta aagggctcgg ccagcgttaa gcacaacatg   2640
atctgtggta ctggcacttg taacatatca cacttgttaa cgtgttcaga tggaaattgc   2700
caggctttac gcaccttgca tattgtgtct catcgtcgcc tcccctggcc ggttcttgaa   2760
```

cacaatatgc tgacgcgctg ttctgttcac gtaggcgcta gacgaggtat gctggtgcct 2820
taccaatgta acttcagcta tactaaagtt ttactggaaa cagatgcgtt tcctagggtg 2880
tgttttaatg gagtgtttga catgactgtg gaggttttta aagttgtaag gtatgacgag 2940
tcaaagtctc gttgtcgccc atgtgagtgt ggagccaatc acctgagatt gtatcctgtg 3000
accctgaacg tgacggagga gttaagagcg gaccacttga cactatcgtg tctgcgcacg 3060
gactacgagt ccagcgacga ggagtaaggt aatgggcgga gttacaaaag gtataaaacg 3120
gacggggcgg tggggtggtt tcattgccaa aatgagcggg tctacggata gcaactccgt 3180
gaactttgat ggaggggtgt ttagcccata tttgacaact cgtcttcctt cttgggcagg 3240
ggtgcgtcag aatgtggtgg gctctagcat ggacggccgc ccggttgccc ccgcgaactc 3300
tgctactctc acctacgcta cggtgggatc gtcgttggac gccgctgccg ctgctgctgc 3360
ttctgctgcc gcttctacag ctcgcgttat ggcggttgat tttggactgt acaaccaact 3420
ggctaccgcg gctgctgcat ctcgctctgt ggttcagcaa gatgccctga acgtcatact 3480
ggctcgcctg gaaatgctgt ctcaacgttt ggatcagctc gctgcccaga ttgcccttcc 3540
cccagccccc gattccactt cagattctta aataaagtaa aagaaacatt tgattttaat 3600
aaacgtttta tttgtttttt ttggcgcggt aggctctaga ccatctgtcg cggtcgttaa 3660
ggactttgtg tatggtttcc aaaacacggt acaagtggga ctggatgttt aagtacatag 3720
gcatgaggcc gtctttgggg tgcaggtaag accactgaag ggcatcgtgc tctggagtgg 3780
tgttataaat cagatagtcg tagcagggtt tttgggcatg gaattggaag atgtctttta 3840
gaagcaaact aatagctaag ggaaggcctt tggtgtaggt gttaacaaag cgattaagct 3900
gtgagggatg catgcgaggg gagatgatgt gcatcttagc ttggatctta aggttagcaa 3960
tattgccccc caggtctctg cggggattca tgttatgcaa caccaccaac acggtgtacc 4020
cggtgcattt ggggaacttg tcatgcagct ttgaaggaaa ggcgtgaaag aatttggaaa 4080 ccccttttgtg ccctcctagg ttttccatgc attcgtccat aataatggca atgggtcccc 4140
tggcggccgc tttggcaaac acgttgtttg ggttggacac gtcatagttt tgttccagag 4200
taaggtcgtc gtaggccatc tttacaaagc gcgggagtag ggtgccagat tgggggatga 4260
tagtgccctc tggacctgga gcgtagtttc cctcgcagat ctgcatctcc caagccttaa 4320
tttctgaggg gggaatcatg tccacttgag gggcaataaa aaaaacagtt tccggagggg 4380
gatttatgag ctgggtggag agcaagttgc gtaaaagctg ggacttacca cagcctgtgg 4440
ggccgtagat aaccccaatg acaggctgca gctggtagtt aagagacttg cagctgccat 4500
cattgcgcaa caatggggcg acttcattca tcatacttct tacatggcgg ttttccctca 4560
ccaagttctg gagaagtcgt tccccgccta gggagaggag ctcttccaag ctgttaaagt 4620
gtttcagcgg tttgagacca tctgccattg gcatttttc aagcgtttgg cgcagtagat 4680
acaagcgatc ccacagttcg gtaacgtgtt ctatggcatc tcgatccagc agacttcttg 4740
gttgcgaggg ttggggcgac tttcgctgta gggaaccagt cggtgggcgt ccagggctgc 4800
gagagtcatg tccttccagg gtctgagggt tcgcgtcagg gtggtctcgg tgacggtaaa 4860
agggtgggcc cctggttggg cgcttgccag tgtgcgtttc aggctcatcc tgctggtgct 4920
gaagtggacg ttttcgccct gggaatcggc caagtagcac ttaagcatga ggtcgtagct 4980
gagagattca gccgcgtgtc ctttggcgcg cagcttcccc ttagaaacat gcagacactt 5040
gctacaatgc agagacttga gcgcatagag cttaggggct aaaaaaactg attcagggga 5100

-continued

```
aaaggcatct gcgccacact gagcgcatac agtctcacac tctaccagcc aggtgagctc   5160
gggctggttt gggtcaaaaa ccaacttgcc tccatttttt ttaatccgct tcttacctcg   5220
ggtttccatg agtctgtgtc ctgcttcggt cacaaaaaga ctgtcggtgt ccccgtagac   5280
cgatttgagc tctctgtgtt ccagcggagt gccgcggtcc tcgtcgtaca aaaactgaga   5340
ccactctgag acgaaagctc tggtccacgc tagtacaaat gaagctatct gcgaggggta   5400
tctgtcattt tctatgagag ggtcaacctt ttgtaaagtg tggaggcaga ggtcgtcttc   5460
ttctgcatcc ataaacgtga ttggcttgta ggtgtaagtc acgtgaccat cggggtggca   5520
tggtgggcta taaaaggggg cgttacccac ttcgtcgtca ctttcttccg catcgctgtg   5580
gatcagagcc agttgttctg gtaagtaagc cctttcgaag gcgggcatga cctcggcgct   5640
caaggtgtca gtttctacaa acgaggtgga tttgatattc acgcggccgg aggcaatgtc   5700
cttgacggtg gaggtttcca tttggtcaga aaacacaatc tttttattgt caagtttggt   5760
ggcaaacgac ccgtagaggg cgttagatag caatttggca atggaacgta aagtttgatt   5820
tttttcgcgg tcggcccgct ccttggccgc gatgttaagt tgtacgtact cccgggccac   5880
gcagcgccac tccgggaaaa cagtagtgcg ctcgtcgggc actatgcgga cgcaccagcc   5940
cctgttgtgc agggtaatga ggtccacgct ggtggctacc tcacccctga gcggttcgtt   6000
ggtccagcac aacctaccgc cttttcggga gcaaaacggg ggaagtacgt ctagcaagtt   6060
ggaagcaggg gggtcggcgt cgatggtaaa gatgccgggg aggagagact tgttaaaata   6120
attaatttcc acgcggtgtt gcaaggccaa gtcccacttt ttcaccgcca aagccctctc   6180
gtacggatta aggggaggac cccagggcat ggggtgcgta agggcggaag cgtacatgcc   6240
acaaatgtca taaacataaa gaggctggcg caaaacgccg atgtatgtag gatagcaacg   6300
tccgccgcga atgctggccc tgacgtaatc gtacatttct tgggaggggg ccaaaaggcc   6360
gctccccagg tgggtttttt gaggttttac ggcgcggtag gcgatctgtc gaaagatggc   6420
gtgggagttg gaagagatgg taggcctttg aaacacattg aagctggcct gcgaaaggcc   6480
cacggcgtcc tgcagaaact gcgcgtacga ctctctgagt ttgtccacca gcgcagcggt   6540
gacgagaacg tccaacgcgc agtagtccag cgtttcgcgt acgaggtcgt aggtttttttc   6600
ttgctttttt tcccagagtt cgcggttgag gaggtactct tcgcggtctt tccagtagtc   6660
ttcggcagga aatcctcggt cgtctgctcg gtaagcgccc aacatgtaaa actcattaac   6720
cgctttgtaa ggacaacagc ctttttctat gggtagagcg taggcctgag ccgccttgcg   6780
aagagaggtg tgggtgagct ggaaggtgtc tcttaccatg acctttaagt actgatgttt   6840
gaagtcggtg tcgtcgcaac agccttgctc ccacaaggtg aaatccgtgc gctttttctg   6900
ccgaggattt ggcagggcaa aggtgatatc gttaaacagg attttaccgg cgcgaggcat   6960
gaaatttctg gagatgcgga aaggtccggg aacgtccgag cgattgttaa taacctgcgc   7020
ggccagaacg atctcgtcaa agccgttgat gttatgcccg acgatgtaaa gttcgagaaa   7080
gcgcggaacg cctttgaggg cgggagcttt ctttagttct tcgaacgtca ggcattcggg   7140
agaaaagagc cctaactccg cgcgggacca ttcttctaag tgggaattgg ccgcaagaaa   7200
cgagcaccac agttcgcggg ctagcagagt ttggaggcgg tccctaaagt ctctgaactt   7260
tttgcctacc gccatttttt ccggcgtaac aacgtaaaag gtggtagggc ggttgttcca   7320
ggtgtcccat ttcaactcaa cggccagcgc acaggcttta agaacgagat cgtcgttgcc   7380
ggagatatgc ataaccagca tgaagggcac caactgtttt ccaaaggaac ccatccacgt   7440
ataggtttct acgtcgtagg taacaaacag cctctcggtg cgaggatggg aaccgatcgg   7500
```

-continued

```
aaagaagctg atctcctgcc accagctgga ggagtgcgcg ttaatgtgat ggaagtaaaa   7560
gtttcgccgg cgcacagagc attcgtgctg atgtttgtaa aagcgaccgc agtagtcgca   7620
gcgctgcacg ctctgtatct gttcaatgag atgtaccttg cgaccgcgga ccaaaaatcg   7680
caaggggaaa gtcagtgggg aggaggcctg tggttcgttt tccccttcgc ggtgttcgtc   7740
ggggtatgcg ccggcgccct gattttgggg gtggaccaaa acaggggtca cgacgccccg   7800
tgtgccgcaa gaccagattt ccgccaccgt agggcgcagg cggcgcacaa gggcttccag   7860
ttgaccgcag tccagagaat ccaaagagcc gttcgccaag tcggagggaa gagactgcag   7920
gttgacttgc aagagagcgg taagggcgcg ggtgagatgc aaatggtact tgatctctag   7980
tgggcagtta gaagaagagt ctacggcata caggagagcg tgaccgcgtg gggcaacgac   8040
ggttccccctg gggagtttta tctcatccgt cggggtcgcg cacccggagg taggggaggc   8100
tcgacgcctg gaggcagcgg aggaagaggc acgttttcgt gaagatttgg cagcggcagg   8160
tgacgcgctc ggagatcgct ggcatgggcg acgacgcgtc ggttgagatc ttggatgtgc   8220
cgcctctgcg taaagaccac cggtcccctg gttctgaacc tgaaagagag ttccacagaa   8280
tcaatatcgg tgtcgttaac ggccgcctgc cgcagaatct cctgtacgtc gccagagttg   8340
tcctggtagg cgatctcggc cataaactgc tcgatctctt cttcttggag gtcgccgtga   8400
ccggctctct ccacggtggc ggccaggtcg ttagagatgc gccgcatgag ttgagaaaac   8460
gcgtttaggc cgttttcgtt ccacacgcgg ctgtacacca cccccctgc ggagtcacgg   8520
gctcgcatga cgacctgagc gacgttcaat tctacgtgtc gggagaagac agcgtagttt   8580
ctgagacgct gaaataggta gttgagggtg gtggcgatgt gctcgcacac gaaaaagtac   8640
atgatccagc ggcgcagagt ggactcgttg atgtctccga tggcctcgag acgctccatg   8700
gcctcgtaga aatccacggc aaaattgaaa aactgggagt ttcgagcgga caccgtgagt   8760
tcctcttgca gcaggcggat caggtccgct atggtgtcgc ggacttctcg ctcgaaagcc   8820
ccgggggca cctcttcttc ttccagttcc tcctcctctt ccagcagcat aggctcttct   8880
ggaacttccg ctgcgggagc cggacggcgg cggcgtcgtc tcaccggcag tcggtccacg   8940
aagcgttcga tcatttcacc gcgacggcgg cgcatggttt ccgtgacggc gcggccgtgt   9000
tcgcgaggac gcagttcgaa aacgccgcct cgtagtccgc cgccctgtag ggagggtaag   9060
tgatggggc cgtcgggtag ggagaccgca ctaacgatgc attttattaa ttgctgcgta   9120
ggcactccgt gcaaggatct gagagcatcc aagtcaacgg gatccgagaa cttctctaaa   9180
aaggcgttta accaatcgca atcgcaaggt aagctgagaa cgctgggccg ctgggtgctt   9240
gcggggggca ggcgggaggt gatgctgctg atgatgtaat taaagtaggc ggttttcaaa   9300
cggcggatgg tggcgaggag aaccacgtct tttggtccag cctgttgaat gcgaaggcgg   9360
tcggccattc cccacgcttc gttttgacag cgacgcaggt ccttgtagta gtcttgcatc   9420
agtctctcca ccgggatttc tgcttctcct ctgtctgcca ttctggttga tccatagcct   9480
cgtagtggct gtagcaaggc caagtcggct accactcttt cggccaaaac tgcctgctga   9540
acctgcgtga gggtggtttg aaaatcatct agatccacga agcggtggta tgcgccggtg   9600
ttgatggtgt acgtacagtt agccatcacg gaccaattta ccacttgcat tcctggttgg   9660
gtgatttctg tgtacttaag gcgcgagtaa gcgcgggatt caaagacgta gtcgttgcaa   9720
gtgcgcacga ggtactggta tcctactaga aagtgtggcg gaggctcgcg gtagaggggc   9780
caacctacgg tggccggcgc cccaggggcg agatcgtcca gcatcagtcg gtgatagtga   9840
```

-continued

```
tagacgtatc gggagagcca cgtgatgccg gcggaggtgg tggccgctct ggtaaactct   9900
cgtacgcggt tccagatgtt gcgcagtggg cggaaacgtt ccatggtggg cacgctctgt   9960
cccgtgaggc gggcgcagtc ctgtacgctc tagacagaaa aaacagagag cgatcatcga  10020
ctcctctccg tagtctggag gttaggtcgc aagggtgcgg cggcggggaa ccctggttcg  10080
aaaccagctg gatccgccgt cccgatgcgc ttggctccgc atccacgacg gccgcgggcg  10140
tcgagaccca gccgcgatgc gcacacccca aatacggagg ggagtctttt tgttgtttgt  10200
tttgtagatg catcccgtgc tgcggcagat gcgacctcag accgccgcat ttcagcctac  10260
caccaccgcc acggcggccg tgtgtggcgc cggccgcggg gaggaggaac tggccttaga  10320
cttggaggag ggggaaggct tagctcgctt gggagcgccc tctcccgaac gccatccccg  10380
ggtgcagctg gccagggacg cccgacaggc ctacgttccg cggcagaacc tctttagaga  10440
cggcagcgga caggaggccg aggagatgcg cgactgtcgg tttcgggcag ggaaggagct  10500
gcgagcgggg tttgaccgag aaaagctgtt gcgcgccgag gactttgaac cggacgaggg  10560
ttcgggcatc agtccggccc gcgcccacgt gacggctgcc aatctagtta ccgcgtacga  10620
gcagacggtg aacgaggagc gaaacttcca aaaaagcttt aacaatcacg tcaggaccct  10680
aattgcgcga gaggaggtgg ccacgggact gatgcatctg tgggatttca tagaggcgta  10740
cgtacagaat cctactagca agccgttgac ggcgcagctg ttcttgatag ttcagcacag  10800
tcgcgacaac gaaacgtttc gcgaggccat gttaaacatc gcggagcccg agggtcgttg  10860
gttgctggat ctggtgaaca tcttgcaaag catagtagtt caggagagga gcttgagctt  10920
ggccgataag gtagcggcta ttaactactc gatgcagagt ctgggcaaat tttacgcccg  10980
caaaatctac aagagtccat acgtgcccat cgacaaggag gtaaagattg acagctttta  11040
catgcgcatg gctctaaagg tgctgacgct cagcgacgac ctcggggtgt accgcaacga  11100
tcggatacac aaagctgtga gcgccagccg gcggagggaa ttgagcgaca gagagctgat  11160
gcacagcttg cgaagggctc tggcgggtgc gggcgacccg gaccgcgaaa cgtactttga  11220
catgggggcc gacctgcagt ggaggcccag cgcccgggcg ttagaggcgg ccggttaccg  11280
cggcgagcga gacgagatag gtgatgaaga cgaagagtac gaggacgacc cctgaccggg  11340
caggtgtttt tttagatgca gcagcagtcg tcggcggacg ggaccagcgt gaatcccgca  11400
cttttggcgt ccatgcaaag tcaaccatcg ggcgtgaacg ccaccgatga ctggtcggcg  11460
gccatggatc gcataatggc gctgacgacc cgtaatcccg aagcttttag acagcagccg  11520
caggctaacc gtttttcggc cattctggag gccgtggttc cttcccgcac taaccctacg  11580
catgaaaagg ttctgactat tgtaaacgcc ctggtagaca gcaaagccat tcgccgcgac  11640
gaggcgggcc tgatctacaa cgctctactg gaacgcgtag cgcgctacaa cagcactaac  11700
gtgcaggcta acctcgaccg tctgaataca gacgttagag aggcgctggc gcaaaaggag  11760
cgatttctgc gagatagcaa tttgggctcc ttggtggcgt tgaacgcttt tttaagcact  11820
cagcctgcta acgtccctcg cggtcaggag gattacgtga gcttcattag cgccctgcgt  11880
ctgctggtgt ccgaggttcc ccagagtgag gtgtaccagt caggcccgga ttactttttt  11940
caaacctccc gccagggctt gcagacggta aatctcagtc aggcctttaa gaacttgcag  12000
ggtatgtggg gcgttaaagc tccgctgggg gatcgcgcca ccatctccag ccttctgacc  12060
cctaacacgc gcttgttgtt gctgctcatc gccccgttta ctaacagcag cagcatcagc  12120
cgtgactctt acctagggca tttaatcacc ctttatcggg aggccatcgg acaggcgcag  12180
gtggacgaac acacctacca ggagattact aacgttagtc gggcgctggg gcaggaggac  12240
```

-continued

```
accggcagcc tggaggccac gctgaacttc ctgcttacca accgcagaca gaaaatcccc  12300
tcgcagttta cgctcagcgc cgaggaggaa agaatcctcc gctacgtgca gcagtcggtt  12360
agcctgtact taatgcgaga gggcgccacc gcttctacgg cgctggacat gacggctcgt  12420
aacatggagc cctcttttta cgcgtccaac cgtcccttta tcaaccgctt gatggactac  12480
ttgcaccgcg ccgccgccat gaacggggaa tacttcacga acgccattct aaatccgcac  12540
tggatgcccc cgtctggctt ttacacgggc gagtttgact tgcccgaggc ggatgacggc  12600
tttctctggg atgacgtgtc cgacagcatt ttttctccgt cgagtcagcg gatgcagaaa  12660
aaagagggag gagatgagct gcctttatct agcatcgaag cggctagccg cggcgagagt  12720
cctttcccta gtctgtcttc cgtgagtagc ggacgggtgt cgcgtccgag gctccccgcc  12780
gagagcgaat acctaagcga cccgattctg cagcccagtc gcaagaaaaa ctttcccaat  12840
aacggggtgg agagtttggt agataaaatg aaacgctgga aaacctacgc ccaggaacaa  12900
aaggagtggg aagaaacgca ggtgcggccg gttcccccgc caacgcaacg gcgctggcgt  12960
cgcccgcgcg aagaccctga cgactccgcc gacgacagta gcgtgttgga tctgggaggg  13020
agcggagcta acccctttgc ccacttgcaa ccccaggggc gcctgggacg cttgtactaa  13080
taaaaaaaaa aaacccaacc ttaccagagc catggccaca gcgtccttcc tttttgtttc  13140
ttcctcgcta gcggtacaat gagaagagcc gtgagagtgc caccggtgta tcccgagggt  13200
ccacctccgt cttacgaaag cgtaatggaa gctctcaata cgccggccac gctggaggcc  13260
ccttacgttc ctcccagata cctgggacct accgagggga gaaacagcat tcgttactcc  13320
gagctggcac ccctgtacga caccaccaag gtgtacctgg tggacaacaa gtcggccgac  13380
atagcttccc tgaattacca gaacgatcac agtaactttt taaccaccgt tgttcaaaac  13440
aacgacttca ccccagtaga ggctggcacg caaactatta attttgacga gcgctctcgc  13500
tggggcggtc agctaaagac tattctgcac accaacatgc ccaacattaa tgaatttatg  13560
tacacgaaca agttcagggc taagctgatg gtagagaaac aaaacgcgga aacgcaggcg  13620
ccccgctacg agtggtttga gtttaccatt ccggagggaa actactcgga gacgatgacc  13680
attgatctca tgaacaatgc catcgtggac aactacctgc aagttggaag acagaacggg  13740
gtgcttgaga gcgatatcgg tgtaaaattt gacaccagaa atttccgttt aggatgggac  13800
cctgaaacta aactagtaat gcccggtgtg tataccaatg aggccttcca tccagacatt  13860
attttactgc ctggctgcgg tgtggacttt actcaaagtc gtttaaacaa cctcctcggg  13920
atcaggaagc gccggccgtt tgaggttggc tttcaaatta tgtatgaaga tttggaagga  13980
ggaaatattc ccgcattgct ggacgtacaa aagtacgaag atagtaaaaa ccaatccaat  14040
accacggaga gggcgattcg cggtgataac tttgcaccga ccgcccaaac cgttgttgtg  14100
gaacctctta ccaaagacag caaggaccgc agttacaatg taatagaggg cactacagac  14160
acgcagtatc gcagttggtt tttggcctac aattacggcg accccgaaaa gggagttaga  14220
tcgtggaccc tacttaccac caccgacgtg acgtgcggct cccagcaagt gtactggtca  14280
ctgccagaca tgatgcaaga tccagttacc ttccgagctt ctactcaagt aagcaacttc  14340
ccggtggtgg gcacggaact gctgcccgta tacgccaaga gtttttacaa cgaacaagcc  14400
gtttactcgc aactcattcg tcagtctact gcgctcaccc acgtgtttaa ccgttttccc  14460
gagaaccaaa ttttggtgcg tcctcccgct cctaccatta ccaccgtgag tgaaaacgtt  14520
cccgccctca cagatcacgg aaccctgccg ctgcgcagca gtatcagtgg agttcagcgc  14580
```

gtgaccatca ccgacgccag acgtcgaacg tgtccctacg tttacaaagc tttgggcgta 14640
gtggcaccta aagttctttc tagtcgcact ttctaaacat gtccatcttg atctctcccg 14700
ataacaacac cggctggggt ctcggttcca ccaagatgta cggcggcgcc aagaggcgtt 14760
ccagtcagca tccggtgcgc gtccgaggtc actaccgcgc tccctgggga gcctataagc 14820
gcggactgtc cgcccgcacg gccgtggatg acactatcga cgccgtcatc gccgacgccc 14880
gacagtacca acctgccgcg gccgccgtgt ccacagtgga ttccgtaata gacagcgtgg 14940
tggccggagc ccgagcctat gctcgtcgca agaggaggct gcacaggcga aggcgtccca 15000
cggcggcgat gttggcagcc agggccgtgc tgcgtcgtgc gcgcagggta gggagaaggg 15060
caatgcgccg ggcagccgcc aacgccggga gagtgagacg gcaagcagct cgtcaggccg 15120
ccgccgccat cgccaacatg gccagacccc gaagagggaa cgtgtactgg gttcgagatt 15180
ctgtcacggg agtccgggtt ccagtgcgga ctcgccctcc tcgaagttag aagacgcatg 15240
tgcgaagacg gcggttctct gtttccccat gttgttacca gccagccatg agcaagcgca 15300
agtttaaaga agagctgctg cagaccctgg cgccagaaat ctatgggtca ccggaagtga 15360
agcgtgacat taagcgccgc gacattaagc gagttaaaaa gcgggaaaaa aaggaggagg 15420
agctggcgat ggcggcggct gcagaggacg cggtggagtt tgttaggtct ttcgcgccgc 15480
ggcgcagggt gcagtggaaa gggcggcgcg tccagcgcgt gctgaggccc ggcaccacgg 15540
tggtgtttac cccaggacag cgttcggctg tgcgggggtt caagcggcag tacgatgagg 15600
tgtacggcga cgaagacatt ttggagcaag ccgcgcagca aattggagag tttgcgtacg 15660
gaaagcgctc tcgcggcgaa aacgtcgccg tggctctgga cgagggcaat cccacgccta 15720
gcttaaaacc cgtgacgcta caacaggtgt tgcccgttag cgccagcact gaaagcaaga 15780
gaggaatcaa gagagagttg gacttgcagc ccactctgca gcttatggtc ccaaagcgcc 15840
aaaaactaga ggaggtgttg gaaaacatga aagtggatcc aaccgtcgaa ccggatgtta 15900
aagtcaggcc catcaaggag gtggctcccg gtctgggagt acagacggtg gacattcaaa 15960
tccccgttag ttcctctgtg gaggccatgg aaacccaaac cgagacgccg acggccgcca 16020
ccagagaagt ggcgctgcag accgagccgt ggtatgaata tgcgacgtct gcgcgtccaa 16080
ggcgaaccag gcgctatgcc gcaactagcg cccttatgcc ggagtacgca ttgcacccct 16140
ctatcacgcc cacgccgggc taccgcgggg ttaccttccg cccctcgggc actcgccgac 16200
gatctcgccg cagaacatcg cgtcgtcgct ctcgtcgcgt tttagctccc gtgtccgtgc 16260
gtcgcgtgac ccgccgggga agaacggtga caattcctaa cccgcgctac catcctagca 16320
ttctttaata actctgccgt tttgcagatg gctctgacat gtcgcctgcg catcccagtt 16380
ccgcactatc gaggaagaac tcgccgtagg agaggcatgg cgggcagcgg ccgccggcgc 16440
gctcttcgca ggcgcatgaa agggggcatt ttgcccgcgc tgatccccat tatcgctgcc 16500
gctattgggg cgattcccgg catcgcctct gtggccgtac aagcatctcg caaataaaca 16560
accatcgctt ttcacttatg tcatggtcct gactatttta tgcagaaaga tcatggaaga 16620
catcaatttt tcgtcgctgg ctccgcggca cggctcgcgg ccgttcatgg gcacctggaa 16680
cgacatcggc accagccagc tcaacggggg cgctttcagt tggagcagcc tttggagcgg 16740
ccttaaaaac tttggctcca cgattaaaac ctatggcaac aaagcctgga acagtagtac 16800
tggtcagatg ctccgagata aactaaaaga ccagaacttc cagcagaaag tagtggacgg 16860
gctggcctcg ggcatcaacg gggtggtgga cctagctaac caagcggtgc agaatcagat 16920
taaccagcgt ttggagaact ctcgagtacc gccgcaaaaa ggggcggagg ttgaggaagt 16980
agaagtggag gaaaagctgc ctcctttgga agttgttccc ggagcccctc ctaagggaga 17040
aaaacgacct aggccagact tagaagaaac cttagtcacc ggcaccttgg aacccccttc 17100
ctacgagcag gctttaaagg aaggcgcttc accttacccc atgaccaagc cgatcgctcc 17160
catggcccgc cccgtgtacg ggaaggacca caaacccgtc acgctagagt tacctccgcc 17220
gccgaccgtc cctccgctgc ccgctccttc cgtgggaacc gtggccagcg ctccctccgt 17280
ggttccggcg ccgcagccgg ccgttcgtcc cgtggccgtg gcaaccgcca gaaaccccag 17340
aggagccaac tggcaaagca cgctgaacag cattgtgggc ctgggagtga aaaccctgaa 17400
acgccgccgt tgttattatt aaagtgcagc taaaaatttc ccgttgtatg cgcctcctat 17460
gttaccgcca gagacgcgtg actggtcgcc gctaccgccg ctttcaagat ggccacccca 17520
tcgatgatgc cgcagtggtc ttacatgcac atcgccgggc aggacgcctc ggagtacctg 17580
agccccggcc tcgtgcagtt tgcccgcgcc accgacacct acttcagctt gggaaacaag 17640
tttagaaatc ccaccgtggc ccccacgcat gatgtaacca cggaccgctc gcagagactg 17700
actctgcgtt tcgtacccgt agatcgggag gacactgcgt actcgtacaa agtgcgcttc 17760
accttagccg tgggggacaa ccgggtgttg gacatggcca gcacgtactt tgacatccgg 17820
ggaatgcttg atcgcggtcc cagttttaag ccctactccg gcaccgccta taactccctg 17880
gctcctaaag gcgcgcctaa tcctagtcag tggataacaa atggaggaaa caaaaccaac 17940
tcgttcggtc aggcgccatt cattggacta ggtcaaaatg taacaaaaga cggcatacaa 18000
gtgggaacgg attcagacaa aggggatgcc gcgatatatg ccgacaaaac ttatcagcca 18060
gagccccaag taggagtaaa ccagtggaac caaaacccta cggaaaacgc ggcaggaaga 18120
atactaaaga gcactactcc catgcaacca tgctacggat cttacgcgca acccaccaac 18180
gtccatggcg ggcaggtgaa aattaccagc gaggctgacc caacgggagc tgctaacgtg 18240
acgatgaact ttttcaacgt cgcttccgac aacgggagca atgatcccaa ggtggtatta 18300
tatgctgaag atgtgaacct agaagctccc gacacgcact tggtttttaa accaagtgtt 18360
gtgaatgacg caagaagcgc tgaaactctt ttgggacagc aagctgcgcc aaacaggccc 18420
aattacattg gcttccgaga taactttatt ggtcttatgt actacaactc caccggaaat 18480
atgggtgtgc tggccggtca ggcctcccaa ctaaacgcgg tagtagattt acaggacaga 18540
aacactgagt tatcctacca gctgatgctg gacgctttag gcgaccgcag tcgctatttt 18600
tcaatgtgga atcaggcagt ggacagttac gacccagacg tcagaataat tgaaaaccat 18660
ggagttgaag acgagcttcc gaattactgc tttccgctaa acggccaggg aatttcaaac 18720
acgtacaagg gcgtaaagcg taacactgga gataccggat gggaaaaaga cactaatgtg 18780
gaagaaacaa atgaaatatc aattggaaac atttttgcca tggaaattaa tttagctgca 18840
aacctatgga gaaacttttt attttctaac gtggccctgt atttacccga ctcgtacaaa 18900
tacactccgg caaacgtaga gctgccggcc aacaaaaaca gttacgacta catgaatggc 18960
agagtaacgt cccctagcgc gctggatacc tacgtaaaca ttggcgcgcg atggtctccc 19020
gatcctatgg ataatgttaa ccccttcaac caccaccgca atgcagggct gcgataccgc 19080
tctatgttgc ttggcaatgg tcgctatgta ccttttcaca tccaagtacc ccagaagttt 19140
ttcgcgatta aaaacttgct tctgctaccc ggttcttaca cttacgagtg gaacttccga 19200
aaagacgtga acatgatttt gcaaagtact ctaggaaacg acctgcgagt ggatggtgcc 19260
agcgtccggt tcgacagcat taacctgtat gcgagctttt ttcctatggc acacaatact 19320

-continued

```
gcctctacgt tggaagccat gctgcgcaat gacaccaacg accagtcgtt taacgactac  19380
ctgtgcgccg cgaacatgct ttacccaatt ccagccaacg ccaccagcgt accaatttcc  19440
attccttctc gcaattgggc agctttccgg ggctggagct tcacgcgact taaaactcgg  19500
gaaacgcctt ccctgggctc cggctttgat ccttattttg tatactccgg ctccattcct  19560
tacctggatg gcacatttta cctgaaccac actttcaaaa aagtgtctat tatgttcgac  19620
tcttccgtca gctggccggg aaacgaccgt ctactgacgc caaatgagtt tgaaattaag  19680
cggtcagtgg acggagaagg ctacaatgta gcccaaagca acatgacaaa agattggttc  19740
ctcattcaaa tgttaagtca ctacaacatt ggatatcaag gattctatgt gcctgagtcg  19800
tacaaagaca gaatgtactc ttttttcaga aacttccaac ctatgagccg acaggtggtg  19860
gaccctgtaa attatacaaa gtacaaggaa gttaccttgc cgtatcagca taataattca  19920
ggtttcgtgg ggtacatggg tcccaccatg agagaggggc aggcctaccc ggctaactac  19980
ccttacccct taataggcaa aactgcagtg acaagcctca cccagaaaaa gttcttgtgc  20040
gacagggtaa tgtggagaat tcccttttct agcaacttca tgtctatggg ggctctgacc  20100
gacctagggc agaacatgct gtatgccaac tccgctcacg ccttggacat gacttttgag  20160
gtggatccca tggatgagcc cacgcttctt tatgttttgt ttgaagtctt cgacgtggtg  20220
cgtatccatc agccgcaccg gggcgtcatc gaggccgtct acctgcgcac gcctttctct  20280
gccggcaacg ccaccaccta agaagccaat gggctccagc gaacaggagc tgcggagcat  20340
tgtgcgcgat ctgggctgcg gaccttattt tttgggcact ttcgacaaac gctttccggg  20400
ctttatgtcc ccccaaaagc cggcctgcgc cattgtcaac acggcaggac gggaaaccgg  20460
gggggtgcac tggctagctt ttgcctggaa tccgcagaac cgaacgtgct acctgtttga  20520
ccccttttggt ttttcagatg aaagactgaa acagatctac caatttcagt acgaaggcct  20580
gcttaaacgc agcgccctgg cctccacgcc ggaccactgc gtcaccctgg aaaagtctac  20640
ccagtctgtt cagggaccat tttcggcggc ctgcgggctt ttttgttgta tgtttctgca  20700
tgcttttgtt cactggcctc actcccctat gaacaaaaat cccaccatgg acctgctgac  20760
cggggtccct aacagtatgc ttcaaagccc ccaggttgtt cccaccctgc gttgcaacca  20820
agaacagctg tatcattttc ttggtaaaaa ttcagcctat tttcgccgtc atcggcaacg  20880
tatagaaaaa gccaccgatt ttgaaagcat gaaacacaca gtgtaacttg caataaaagg  20940
ttgattttat ttttacaagt gcgcatcttt cgttattaaa actcaaaggg ctcggggcag  21000
tcgtcgccgt ggctgctggg gagggccacg tttcggtact ggaaacgggg atgccagcga  21060
aactcgggaa tgatcatctt cggaagcggt ttgtcttcca tgttctcctt ccaaaactgc  21120
cgaacgagct gcagggctcc gatgatgtcg gggcccgaga ttttgaaatc gcaattgggc  21180
gccgcgccgc cgcgggaatt acgatacacc gggttggcac actggaacac cagaacgctg  21240
ggatacttga tactggctag ggccgtagca tcgttcactt ctgccacatc caagtcgtct  21300
gcgttactca gaccgtaagg ggtgaccttg cacatttgac gacccatgcg agggatgaca  21360
tcgggcttgt ggagacaatc gcagcgcagg ggaatgagta tgcgcccctg accacgctgc  21420
atctcggggt agctggcgcg cagaaacgct tccaactgcc tgaaggccat ttgggctttc  21480
aaaccttccg tataaaacag gccgcaggat ttaccagaaa acacattagg gccacagctc  21540
acgtcttccg ggcagcagcg cgcgtcatcg tttctaatct gcaccacgtt gcgtccccag  21600
cgattctgga ccaccttagc tttgccgggg ttctccttca aggccttctg accgttttcg  21660
ctggtcacgt ccatctccgt gacgtgctcc ttgtgaatca tctcggttcc atggaagcaa  21720
```

cacaggactc cgtcttcctt ggcgctgcga tgttgccaca ccgcacagcc ggtagcttcc 21780
caatttttct gaacaacccc cgcatatgat tgcatgtagg ccgtcaagaa tcttcccatc 21840
atctcggtaa aggttttgtt gctagtgaag gtgagcgcca agccccgatg ttcctcgttc 21900
agccatgtct gacagatttt tctatacacc ggaccctgct ccggaagaaa cttgaaagtg 21960
gctttgtctt cgttggaaac gtggaacttt tccatcagga tcatcatggc ttccatgccc 22020
ttttcccacg ccgttaccaa cggagagctg tgtggattta ccactagcac agacgaacgc 22080
tcctctctct cagcgtttgc ttcttctact gttactcttt gaaacacacg gccgccgtcg 22140
gcttgcttca caatgcgcac cggagggtag ctgaaaccca ccccgattac cgtgccttcg 22200
ccttcgctgt cggagacaat ttccggcgag ggcgggcgag cctgcgagct tttgcgtgcc 22260
tttttcttgg gaggcagggg aacagctacg tccctctccg ggcttctttc ccgcagatac 22320
ggggtgatag aacgctcgcc cgggttctga ttgccggcca tgatttactc ctaggcgaaa 22380
aaacatggat cttatgcgca aagaatcctt aaccaccccg cccctcagcg acgaagacgt 22440
gccaatcgag caggacccgg gttatgttac gccgtccgaa gagctgccca tatcgttcga 22500
cctcgcccgt agcgagcgca cagaacagga cggcgactac ttattggaag ccgaaatcct 22560
gcttaaacac tttgccagac agagcactat tgtcaaggaa gctctgcaag accgcagcga 22620
agtgcccctg gacgtgtgcg agctgtcgcg agcctacgag gcaaacctct tttcgccccg 22680
agtgcctcca aagaagcagc ccaacggtac ctgcgagccc aacccccgcc tcaactttta 22740
cccggtgttt gcggtacccg aggcgctggc tacctatcac attttttta agaaccaagg 22800
cattcccctg tcgtgtcgtg ccaacagaac caaagccgat agaaagctga gattgagagc 22860
gggggctcgc atacctgaga tagcttcctt agaagaagtg cccaagattt tcgaggggtt 22920
aggacgagac gagaatcggg ccgcaaacgc tctgcaaaaa gaacagaaag aggctcagag 22980
tgttttaata gaactggagg gagacaacgc acgcttagcc gttcttaaac gcaccgtgga 23040
ggtttcccac tttgcctatc cggccctgaa ccttcccccg aaagtcatgc gctccgtaat 23100
ggatcatctc ctcatcaaac gagccgaacc cctcaaccct gaaaatcccg acccggaaaa 23160
ctccgaggac ggcaaacccg tggtttcaga cgaggagctg gaacggtggt tgggcacaaa 23220
agatcccgaa cgcttgcaag acaagcgcaa aatgatgatg gcggccatcc tggtgaccgc 23280
cgagctggag tgtttgcaac gctttttgc ggacgtagaa actatacgca aggtggaaga 23340
atctttacac tacacctttc gccacggcta cgtccgacaa gcctgcaaga tctccaacgt 23400
agaactcagc aaccttgtgt cctatatggg cgtcctccac gaaaaccgct taggtcaaag 23460
cgtgctccac tgcaccttgc aaggcgaagc gcggcgagat tacgtccgcg actgcgttta 23520
cctttttctg ctgctcacct ggcagacggc catgggagtg tggcagcagt gcttggaaga 23580
aaggaacgta aaagagctag acaagctctt aacaaagcag agaaaagcgc tgtggaccag 23640
tttcagcgaa cgagcggcgg ccagccacct agcagatatt attttccccc agcggctgat 23700
gaaaacgctg caaaacggtc tgccggattt catcagccag agcatcctcc agaacttccg 23760
ctcgtttgtg ctggaacgtt ccggaattct gcccgccatg agctgcgcgc tgccttccga 23820
ctttgttcca ctcacctacc gcgagtgtcc ccctcccctg tggagccact gctacctgct 23880
acaactggct aactacttgg cctaccactg tgatcttatg gaaaacgtga gcggagaagg 23940
gctgctggag tgtcactgcc gctgcaacct ctgcaccccc caccggtccc tggtttgcaa 24000
caccgagctg cttagcgaaa cccaggtcat aggtaccttt gagatccaag gtcccgaaca 24060
gcacgagggg gcttccggtt taaaactgac tccggcgctg tggacctcgg cttacttacg 24120
caaatttgta gccgaggact accacgcctc caaaattcaa ttttacgaag accaatctca 24180
gcccccccaag gcccctctca ccgcctgcgt cattacccaa agcaacattt tagcccaatt 24240
gcaaaccatc aatcaggcgc gacgagagtt tctcttaaaa aaaggtcacg gggtgtatct 24300
ggaccccccag accggcgaag aactaaaccc atccacactc tccgccgaag cagcccccaa 24360
gcagcatgcc gcccaaagga gtcaaacagc tgatagctca gcagagagcg aagaagcagc 24420
aagagctcct gcagcacatg gaagaggagg aggaagccag cgatgcgtgg gacagtcagg 24480
cagaggaggc ttcggaggac gaggagatgg aaggctggga cagcccagac gaggcggagg 24540
aggaagaggt agaggacgaa gcgatcggcg aaaaaccacc ggcttccagc gcactttctc 24600
cgagccgtct gccgaaaacc cgcgtcccaa ccccgggagg ctcacgcaaa gccagccgta 24660
gatgggacac taccggatct ccagtagcat cggcggcggg taagccaggg cggccgcggc 24720
ggggttattg ctcctggcgg gttcataaaa gcagcattgt gaactgcttg caacactgcg 24780
gggggaacat ctcctttgcc cggcggtatc tcctttacca tcacggggtg gctgtgcctc 24840
ggaatgtgct ctattattac cgtcatctct acagccccta cgaaacgctc ggagaaaaaa 24900
tctaaagcct cgtcgcgctc ggccaccgcc ttctccgccg ccaaagactc gccagccgcc 24960
agagaactgc gaaaccgcat ttttcctact ctgtacgcta tctttcagca gagccgcggg 25020
cagcagcaag aactaaaaat aaaaaaccgc tccctacggt cactcacccg cagctgtctg 25080
taccacagga gggaagacca actacagcgc actctggacg acgccgaggc tctgttcaac 25140
aagtattgct cagtgtctct taaagactaa aaaacccgcg ttttttttacc caaaaagcgc 25200
caaacacacg tcatctccag catgagtaaa gaaattccca cgccttacat gtggagctac 25260
cagccgcaga tgggcttagc tgcaggcgcc gcccaggatt actccagcaa aatgaactgg 25320
ctaagcgccg gcccccatat gatttcacaa gtcaacgaca tccgagcccg ccgaaaccaa 25380
atcctcttag aacaggcggc aattacctcc acacccaggc ggctcctaaa ccctcccagc 25440
tggcccgctg cccaggtgta tcaggaaact cccgccccga ccacagtcct cctgccacgc 25500
gacgcagagg ccgaagttca gatgactaac gctggggcgc aattagcggg cgggtccagg 25560
tacgtcaggt acagaggtcg ctccgcacct tatcctcccg gaggtataaa gagagtgttc 25620
attcgcggtc gaggtatcca gctcaacgac gaggttgtga gctcctcagc gggcctcaga 25680
cctgacggag ttttccagct cggcggagcc ggccggtcct ccttcaccac ccgtcaagcc 25740
tacctgaccc ttcagagctc ttcctcccag cctcgctcgg gcggaatcgg cactctccag 25800
tttgtggaag agttcgttcc ttcggtttac ttcaacccgt tttccggctc acctggacgt 25860
taccccgact ccttcattcc caactacgac gcagtgagtg aatctgtgga cggctacgac 25920
tgatgacaga tggtgcggct gtaactgcgc ggctgcgaca cctgcatcat tgccgacggt 25980
ttcgctgctt tgctcgggaa ccatttgtgt tcggatactt ccagcttttt gacgaccacc 26040
cccacggtcc agctcacggg gtagaactcc gggttgaaaa ggaactagat tcctacctgc 26100
ttcgcctccc tcgccccatc ttggttgaaa aagaacacgg aactactatt gtaaaactgt 26160
attgtatttg ctcatcgcct ggattacatg aagatttatg ctgtcttctt tgcgctgaat 26220
ttaataaata acatctggac ttccaaatct gctcacatcg ttcgttcatc taccgagtcg 26280
tccatcaaag gtatcagaca gactctgttc ttttatccct ctaccccact tattactctg 26340
aactgcaact gcactaacga aatcatccag tggttggtaa acgggaaact gtgtaaagtt 26400
ttttttttccg acggttcgca gtttaataga aataacagtt tttgcaataa ctgcagcaaa 26460
cattacctta ccctctatcc gcctttccct tctgctcgtt tttcttgcgt aggcactggt 26520
cacggaacta gctgctacta caactggttt ttgaaagaag ctaagcgcga gccttattct 26580
gttcttcctc acggctttac taaagcatca acgccttcaa ctccgttttc ctttacacac 26640
cctttgttca gcgtcttagc tattatttta ctagtttcct ttaacttggt gttgcttacc 26700
agttgtcccg tttctttaac atgatgcttc tgctgtttgt atcgctaatc tcttacgtca 26760
ttcttgccga cgcctctaca atttttactc aggtcggttc caatgtaact ttccaatcat 26820
atttttcacc ctatcctgat gaaatccctt acattacatg gtataaacaa gtcagttatg 26880
attcctcttt ttacgaagca aacaaacttt gcgaggctgg taatacaact cacacttatc 26940
ctcatccttt tttaaagttt gactgcgtta acaaaagttt aaacctttat aatttacaac 27000
ttcaagattc aggcttgtac cacgccacag tactggtgaa tgatattgaa caacacaatg 27060
acatagtaca gctacacgta attgatttgt ctgcacctca atgtgatgtt tcctcttact 27120
acaccaacca aacccaactg gaattttgtt tgattttaat taactgctct aaagttgcac 27180
atcgcacgac aatttatttt aatggcaaat acagctcaac aagttttata actgagtacg 27240
gtggaactca cctgcctaac ttttataatg ttactgtaga attttttaca gccacagaca 27300
aactacaaaa aacacacaac attccctatg actttaatga tctctgtcaa attattgtct 27360
ctcccgaatc acttaattct tttaatgatt ttataccaat tttgatagca gccgttattg 27420
caactatctt taccatttct gtaagcctcg gcttctactg cctgtacaag ccaaaaaaag 27480
taaagtttga acagcttaag ctgaaacaac ggccgaaaat tgaaaccgta taattttttt 27540
tccagcatgg tagctgcctt cgtactgctt ctctgtttac ccatcatttt cgtctctaca 27600
tctttcgccg ctgtttccca tctggatcca gactgccttc cagccttcga tgtttactta 27660
atattcactt ttctttgcat tattgccatt tgtagtatag ccagcttttt tgttgtaata 27720
tttcaagctg ctgactacgc atacgtaaga attgtgtact ttagacatca ccctcagtat 27780
agaaatagag acgtagctac tttactgtgt ttagcatgat tgctttatta ctgtttaatt 27840
tttttaccct aattgactgt aagtgcccct ttactaaacc ttggaaactt cacacctgct 27900
acaatgaaat tcccgacact cctattgctt ggctttacgt actaaccgcg gccttggtat 27960
ttatttccac ctgtctggga gttaagttgt actttacttt taactttggc tggcttcatc 28020
caaatgaaga tttaccaaga taccctaatg ctcttccact acagccactt cctcctcaac 28080
ctgttcccct tgttcgcgct ccttctgtga ttagctactt ccaacttatc ggtggagatg 28140
actgaatcgc aagacattaa cattaacatg gagcggggaa tcgctcagcg tcaacgagaa 28200
gctcgcgcga tggattacct tagattgcaa gaacttaaag aaacacactg gtgcgataga 28260
gggtcgcttt gccttgttaa attggcttca ctctcctatg atgtttccac ccaagggcat 28320
gagttgtctt acactttagc cgggcaaaaa caaacctttt caactataat gggctctaca 28380
tctcttaaaa ttactcatca ttctaaacct gtcgaagggg ctattctttg tcactgtcat 28440
aagcctgatt gcatggaaaa actaatcacc accctctgcg ccgtggcaga aatttttaaa 28500
taaacttacc tgagattgct taatagcttt ttgtcaaatt cttttatcac gaccaccttg 28560
ccctcttccc aactttcata gggaacgtgg tagtgagcag caaattttct ccaagtttta 28620
aaggatatgt ttatgtccac ctctcgttcc tcatccacaa ttttcatctt ttcatagatg 28680
aaaagaacac gaattgacga agacttcaat cccgtgtacc cctatgactc caccgttacc 28740
cctaccatcc cttttattgc tccaccattt gtatcagcca atggcttaca agaaaacccc 28800

```
cccggaatat tgtctctaaa ctacgcagat cctctcacaa ccaataacgg caaactgagt  28860
atgaaattag gaagcaacct aagccttaac agcaacggag cgcttacctg tagcacgcct  28920
gttactgagc ctcttaccaa taatggcacc ttaggattag ctttctcccc acccttaaat  28980
accacgtctg cgaggttagg tatctcactt ttgcccccaa taaccgtaac aagcaacgca  29040
ctaagcctct ctcttggaaa cggtttaacc acttcaaatt catcccttac cgttaaaact  29100
accggtgcta ttaattttaa cagtcaaggg tacttacagc tgagaaccgc ggggggtatg  29160
agaatcgaca acagtaacac cctaatttta gacgttgatt acccatttga cgcagcaaat  29220
cagctgcgac taagactagg aaaaggaatg tatcttgaaa acggaagaga cttatctgtt  29280
aaacttggaa atggactttc atttgatagc agcgggcgca tagcggcgtc tgcaactgca  29340
cgctcacgca caatggacca tccgtcttca atctcaacat ggccccaacc gttacaggct  29400
aactgtacag tgtttgaacc cttagacgcc acactggggt tagagctaat taaaataggt  29460
tcccatgtat taggagcggt tactttaaaa ggagttaaag ggcaactttg caacatgcaa  29520
accaacacag taactattaa acttactttt aatgccaacg gtcacttgct aaaatgcccc  29580
ttagtgtcgt cctattggca aagtgaaact gtggagttta tgcccaacag aatcatttat  29640
cccccgcaat ctgccgccgc tgaactgtca cctaattccc aaccccatgc cttcagtgtt  29700
gcctataaca ccgaaccctc aggattttcg tttctttttta attggtctgc tgttgttggg  29760
cagccgttta acgctcctgc tgcaatgttt tgctatgttg ctgaacaata aagctcgcaa  29820
agccaccttt gttttctttc agatgaaacg cgccagaatt gacgacgact tcaatcccgt  29880
gtaccccctat gaccaaccta acgccccgct tttgccattt attacccctc cttttacctc  29940
ctctgacggc ttgcaagaaa aaccgccggg agtgttaagc ttaaattaca aaaaccccat  30000
taccacccaa aatggagccc tcactcttaa aattggagag gggattgaca taaacgacaa  30060
aggggaactg acatctaacg cagtgtcagt ttcgcccccct ctctctaaaa tcaacaacac  30120
tctaagccta gtgtacagcg acccactcac agttcgtgaa aacgccctac acttaaaaac  30180
tgctcttcct atttctctca acgctgccag ggaactcact ttggtcgcca atgctccgct  30240
tgctactacc aacggagcgc ttcaattaca aagcgcggct cctttaggag ttgccgaacg  30300
aactcttaaa ttgttgtttt ccaacccact gtacttacaa aacaactttc tatccgttgc  30360
tgtggacaaa cctctagcca tggcttccac gggtgccatt gctctgcagt gggcaccccc  30420
tttgcaagta gggacaggag gcttaacagt ggccactgtc gagcccctta ccgtcaccaa  30480
cggaaattta aacattaaca caaagcggcc tctcgtcatt gaagacagta gtttgtattt  30540
agctttcaga cccccctttac gattatttaa cagcgaccct gaacttggtg taaacttcat  30600
ccctcctatt acaatccgcg atgacggttt agctctaaac acaggagagg gtctcactct  30660
tgtgcgtgac agactaagtg tgaaccttgg caaagacttg cagtttgtgg acaacactgt  30720
ctcactggca ttaagcacag ctttaccgct tcaatacact gatcaactac ggctaaacat  30780
cggtcagggc ctacgctaca acccaaccag taagaagcta gacgtggatc ttaatcagaa  30840
caaagggtta aactgggaag acaacaaagt cattactaaa ttagggtacg gtttgcagtt  30900
tgattcggcg gggaacatta gtgttatccc accttccgtg acaccacata cgttgtggac  30960
tacggctgac ccctctccta attgctcagt gtatacagac ctggatgcca agctgtggtt  31020
gtcgttggta aaatgcaatg gcatggtcca aggcactatc gccttgaaag ctctaaaggg  31080
agtgctttta aaccccacgg ccagctctat ctctattgtc atttattttt atagtaatgg  31140
cgtgaggcgc acaaactacc ctacctttga caacgaaggc actttagcta acaccgccac  31200
```

ctggggatac agacagggcg aatcggccaa caccaatgta actaacgccg tagagtttat 31260
gcctagctcc gccaggtacc ccatcaacag gggcaatgac gtgcagaacc aaatgatggg 31320
ctatacttgc ttgcaagggg cgttaaacat ggctgtaggg tacaaggtca catttaacca 31380
cgctcttgaa ggatattcac taaaattcac atggcctgtg tacaacaacc aagcctttga 31440
cgttccctgt tgctctttct cttacataac cgaagaataa acaatggttt tcaaattttt 31500
attttacatt atgcgtacag ttaaacttcc cccacccttc cactttacac tgtataccat 31560
cctttctccc ttggtagcgg taaacaactg aaactgggtg ttcaaacaag gatttttagg 31620
tgtcagagtc cagacggttt ctttacgcgc aaatctctcg tccgtcacgg acacgaatcc 31680
ctcgccgacg tcttccaaca gtggcgtgtc gtccaagcaa tcctacaaca cacaaagttt 31740
taagttctcc acgggttttc acctctgccg tactcagcca gcgtgaacgg gcgatggcgc 31800
tccattagtc ctcttaacaa gatggcgctc cattagtcct cttaacaagc tttgcctagg 31860
cgtctccagt cgagatctcc gaggctggta agacgtcagg cggtctaata gtctcacagc 31920
gcggataaga aatctgcgag tccgtttagc gcagcagcgc atttgaatct cactcaagtc 31980
cttacagtgg gtacacacca tgataattaa attgtttaaa atcccataac taaacgcgct 32040
ccacccaaag ctgctgtttt ctaacacggc taccgcatgc ccgtctagaa aaaccctaac 32100
ataaataaga tgtctcccgc gaataaacac actgcccaca tacagcactt ccttgggtaa 32160
gtggtaattt accacttgtc tgtaccaggg gaacctaaca tttactaaag acccatatat 32220
cgccattcta aaccaattag ccaaaaccac tccacccgcc ttacactgaa gggatccggg 32280
agaactacag tgacagtgaa gcacccacct ttcatagccc cttataatct gattatattc 32340
tacatctatt gtagcacaac agatacaaat ctgcatgtat gttttcatga catgtttttc 32400
ccaagcagtt aatacagagt cccaatacac aggccattcc tgtaaaacag taaagctaac 32460
acaagacggt acgcccctca cctcgctcac attgtgcatg ttaagatttt cacattccag 32520
atacggggga ttctcaatgg tggcgcaggg catttcatca cacggcggta gctggtgtct 32580
gttgtaagga cccagtctgc agcgataccg tctgtcgcgt tgcatcgtaa atcaagttct 32640
ttcgcaagtc ctcgtacttc cgatagcaaa accaagttcg acgccaacag atatccacgc 32700
gacggccgtc cctccgccgc tgccgctcgg tcgttaccgc aaagtgaagc cactgctgca 32760
atccacacag ctccctctcg gcctctggag taataaaaac ttcgtacctg atgatatccc 32820
tgaatagttc caaactagaa gtgagggcca actccaacca agcaatacat gcagatttgt 32880
cccggcacac tggaggtgga ggaagacacg gaagaggcat gttattccag gcgatcgcgt 32940
aaggtcacaa aatgcaaatc gcgaagatgg caccgctcgc ctccggtacg ctggtgataa 33000
agaacggcca aatcaaaatg aattctgttt tccaagtgat ccgtgaccgc ttccaacaac 33060
gcctgaaccc gcacatccaa aaacaccaac agagcaaacg cgtcgtgttc aaactcttca 33120
ataatcacac tgcaattctg caccatgccc aaataatttt cagccctcca ctcgcggatt 33180
atattgcaac acagatcttg taaatttact cctcgcattc caaaaagctg agtgagggcg 33240
ccctctattg ccatgcgcag acacaccatc atgatgacaa aatatcaagc tcctgtgaca 33300
cctgcagtaa attcaacata tcagggtcag gatgcacccc gcgatcgcga atctccacgc 33360
gcaaggttaa ctgcaagaag tttagcagat ccgcacacac taaagcggtc agctccccgt 33420
caggtgtcat ttcaggcgta gccacgcagc acaaaagttg aatagagggc gccaggctta 33480
acagcaccgc gccattatag caaaactgaa atggcggagt caagcagtgt aataaatgga 33540
gccaaaagtc actgagctgt ctttttaaaa agtctaaaac ctcaatgtcc aaatcgtgca 33600
agtactgccg tagagcagcc ggtacggtaa cgcacacaaa aacaggctgc ctctgataca 33660
tagcgaccta taaattaaac aagagaagca cgatgaagac aggggtaaat cacccgctcc 33720
aacagcaggc aggccaccgg ctgtcctcta aacccgtaaa aaaattcatc tgagtgatta 33780
aaaagcacca cagacatttc ccaccacgta ctgggctgta tgtcttgagc gccaacaaaa 33840
acccccctta cattcatatc agataacgag aacaggcggc ccaagtatcc ccgaggaatg 33900
tccatagaca actgcagaga aactaaaagc acgcctctcg gagaaatcac aaagttttcc 33960
ggtgaaaaaa gcacatagag attagaaaaa ccttgctgct gtggcataat agcccgcgag 34020
cccagcaaat gcacgtaaat tgcctcgtca gccattgccc cgtcttaccg cgtaaaaagg 34080
ccgcgcaaaa taacgcctag ctcaacccgt ccttcagtga atatatatac gtagtcccct 34140
cccaattacg ctattccccg caccgccgcc caagcgcaaa ggtcgcccac acccaaaaag 34200
cccgcgaaaa atccaccgtc gtcagcactt ccgcaacaat gtcgttccca cggcgtcaca 34260
tcccgttcaa cctcccaact tccgctcccg cccacgcccg ccgcccccaca cgtcacaccg 34320 gcccgcccct cgcgccgcct ccgccctcct ctctcattat catattggca cgtttccaga 34380
ataaggtata ttattgatga tg 34402

<210> SEQ ID NO 4
<211> LENGTH: 35537
<212> TYPE: DNA
<213> ORGANISM: Adenovirus

<400> SEQUENCE: 4
catcatcaat aatatacctt attttggctg cacgccaata tgataatgag gtaggcggag 60
ccagtgacgt cagcggaaaa ggaagtgacg cagtgggcgg agcgaggggt ggagttttga 120
cgtcagcgcg gtgggcggag cgggcgtggg aagggaagtg acgtgggtgg gcgtgtcggg 180
gggtggggct ctggccgccg gcgcgcagga agtgacgttt taggcgggat ttttaaccgg 240
aaattgggat ttttgaatgt ttgggcggtg ttaatttgca tgtttagcgc gaaaaactga 300
ataatgcgga agtcgggtta atcgttaatt tttacggtag ggtggaatat ttgccgaggg 360
ccggtggact ttgagcgctg acgcggtggt ttcgctacgt ggcgctatta cgcgaaagag 420
ctcaaagtcc tttttattgt tctactgggt atttaaaccg gccggccacg tcaagaggcc 480
actcttgagt gctggcgaga agagttttct cctgtcgcgc tgccgccatg aagacttggg 540
gtttggattg cggactgcac ccgcaggagg tggacgagtg gctgcgttcc gaatactgcc 600
ccactcctgg ctattacggt gagaacctgt cgctgcacga tctgtacgat atagacgtgg 660
acgagccagc ggagggggac gagaatgagg ttccggtaaa tgactttttc cccgattcgc 720
tgctgttggc ggtggatgag gggattgagg tggactaccc gccgccgctc gacactcccg 780
gtgagccgtc cgggagtcac tttatgccga acctgtctct ggaggaggtt gatctgtact 840
gccacgaaga cggctttccg ccgagcgact ccgaaggtga gcagagcgaa gcgaaagacg 900
agcggctgat ggcggaggcg gcggcgacag gtgcggctgc ggctgcgcgc agggcctggg 960
aggaggagga gtttcgttta gactgccccg tgttacctgg ccacggctgt gcttcctgcg 1020
actatcaccg caaaactagt ggctttccag aaattatgtg ttcgctgtgc tatttgcgag 1080
ctcacggcat gtttgtgtac agtaagtgtt atttttgtgt ggtggttaac acggctggct 1140
tggctgcgcg ctcgctcact cgcgggacag gtgtgttttt gctgagactt atgtaacttt 1200
ttatgcttgc aggtccggtc tctgacgccg agggtgaacc ggacagcact accgaccact 1260

```
cgggtggtcc tggcagcccg cccaagcttc acaatactcc gcccagaaat gtcccccgcc   1320
ccgttcccct gcgagtttcc ggggtgagac gggcagcagt ggaaagtctc catgacctca   1380
ttggggggga ggaggaacag gtggtacctt tggacttgtc cgcgaaacgc cccccgtcat   1440
ttaaagttta acgagcctcc gcccttaagt tatgtgccaa taaagttaat gattaacgat   1500
gtgaactttg tctgtttatt caaaggggat tacctgggag gtataaaggg agcggtggtg   1560
aggttggggc atttcaccat ggatctgcga gtggagttgc agacttttga gagtacccgg   1620
tgcttgctgg agctgtgctc caacagagat ccttggtgga agaggctttt gtttggtact   1680
tctctctgcc ggttagtgag gcaggtgaag gaagagtacc agagcgagtt tgagcatatt   1740
ctttccactt gccaggggct tttcgagtct ctggagttgg gtcaccacac ggtgtttcag   1800
gagaaaattg tgaaggcttt ggatttttcc tctccgggca gggcagtcgc ggccattgct   1860
tttgccgcct ttattttgga tagatggaac acccagaccc agctgtcccc ggggtacacc   1920
ctggattaca tcagcctgca gctgtggagg ttctggctgc gccggcgggt ttacaactac   1980
tcgcgggggc tgcctccgct cgggcgggca tcgtcgccgg aggagcagtc gccggaggtg   2040
aagccggagg tggcggggca gggggaggag caggagcagg agccagcgct gcggtccggc   2100
ctggaccctc cggaggagaa ttaagtgctg agccacaggt ggccgagggt caagtggggc   2160
caaagcgctc gccgaagcgc gccaagaatg aagaggagca gtcggaggag gctttaactc   2220
gcttgaccct gagtttgatt aaccgccagc gaccagagac ggtgttttac tatgagctgg   2280
agcatgaatt ccagcacggg gacatgcact tacagtgcaa gtttggattt gaacagatta   2340
agacccactg gctggagccg tgggaggaca tggccacggt gctgaatcag tttgtaaaag   2400
tggccctgcg gccggaccgg gtgtataagg tgtcgagcac cgtgcacttg cgcaaatgcg   2460
tttacgtaat cgggaacggg gcgacggtgg aggtggaggg gagcgaccgg gtggcgttta   2520
attgtcttat gcagcgaatg ggtcccgggg tgatggggct gagtggggtg acttttgaga   2580
acgtgcggtt ggtgtgtcgg gactttcacg gggtgatgtt tgcctgcacc actgagctga   2640
acctgcacgg ggtgtatttt tttaacgtga atcacgcctg cgtggagtgc tggggccagc   2700
tgcgcgctcg cggctgcacc tttcaccagt gtttcaaggg ggtggtgggg cgccccaaga   2760
gccgcgtgtc cattaaaaag tgtgtgtttg agcgttgcct gctgggcgtg agcgtggagg   2820
gccacggtcg cctgcgcaac aatgcggcct cggaaaacat ctgctttgcg ctcatcaaag   2880
gtacggccgt gttaaagagt aacatgatct gcggcacggg ggacgaccgc ggaggcaagc   2940
atctgatcac ctgcgcgaac ggctggtgcc actgcctgcg gagcgtgcac gtggtgagcc   3000
acccgcgccg ctcctggccg ctgtttgaga gcaacatgct gatgcgctgc acggtgcacc   3060
tgggcgcgcg ccgcggcatg ttcctgcccc accagtgtaa ctttagccac acgagcgtgt   3120
tgctggagcc cgaggccttc acccgggtgt gctttaacgc ggtgtttgac gtgtccctgg   3180
aggtgtttaa gattgttagg tacgacgaga gccgggcccg cagccgcctg tgcgagtgcg   3240
gcgccaacca cctgcgcagc gtgcccctga cggtgaacgt gacggaggag ctgcgggcgg   3300
accacgtgat gctaccttgc aaccgcacgg actacgcgac cagcgacgag gagagcggct   3360
gaggtgagga gcgagccggt gggtataaaa gggggcggct gggtgttttt ccctcagtta   3420
ccgcagagat gagcgggatc gcgggcgacg cgagcgtgaa ctttcagggc ggggtgttca   3480
gcccctatct gacatctcgc cttcctccct gggcaggagt gcgtcagaat gtggtgggct   3540
ctaacctgga cggccgtccc gtggctccgg ctaactcgac gaccctcacc tacgcaaccg   3600
```

-continued

```
tgggcgcctc tccgttggac accgccgccg ccgccgccgc ttccgccgcc gcttctacgg   3660
ctcgcgttct ggcggctgat ctgggccttt acaaccatct ggcgaccaca gcggccgttt   3720
cccggtccct ggtgagagaa gacgcgatgc agctggtgtt ggcgcgcctg gagacgctgg   3780
cgcaggatcg ggacgagctg tcagcgaaag tggccgactt gtcctcagcc gccctcgtgg   3840
cggccgcccc ccttcccgcc tcccctcccg tgatttaaga aaataaacaa cactcgagtg   3900
aaagcgaagc tgtgtttatt gcttgttttt gcgggcgtgg taggctcggg accatctgtc   3960
gcggtcgttg aggacgcggt ggatgtcttc caggacgcgg tagaggcgcg cctggatgtg   4020
caagtacatg ggcatgaggc cctctcgcgg gtgcaggtag caccactgca tggcctcgtg   4080
ctcgggggtg gtgttgtaga tgatccagtc gtaggcgggc ttctgggcgt ggtggtggaa   4140
gatgtctttg agcaggagac tgatggcgag gggcagccct ttggtgtatg tgttgacgaa   4200
gcggttgagc tgggagggat gcatgcgggg ggagatgatg tgcatcttgg cctggatctt   4260
gaggttggcg atgttgccgc ccaggtcccg gcgggggttc atgttgtgca ggaccaccag   4320
cacggtgtag ccggtgcagc gagggaactt gtcgtgcagc ttggaggggga aagcgtgaaa   4380
gaacttggag acgcccttgt ggccgcccag gttttccatg cactcgtcca taatgatggc   4440
gatgggcccc cgggcggcgg cttgggcaaa aatgttgcgg gggtcggaga cgtcatagtt   4500
gtgctccagg gtgaggtcgt cgtaggagag cttgacgaag cgggggcgca gggtccccga   4560
ctggggtacg atggtcccct cgggcccggg ggcgtaattg ccctcgcaga tttgcatctc   4620
ccaggctttg atctcggagg ggggaatcat gtccacctgg ggcgcgatga aaaaaacggt   4680
ctccggggcc ggcgagacca gctgcgcgga aagcaagttg cgcaagagct gagacttgcc   4740
gcagccggtg ggaccgtaga tgaccccgat gacgggctgc agctggtagt tgagcgagga   4800
gcagctgccg tccgggcgga ggagggggc gacctcatcc atcatgcaac ggacctggcg   4860
gttttcgcgc gccaagtgcg tcagcaggcg ctggccgccc agggagagga gctcggcgag   4920
ggtgtcgaag cccttgagcg gcttcaggcc gtcggccatg ggcatgttct gcagggactg   4980
gcggagcagc tgcaggcgct cccagagctc gctgacgtcc tcgactaggg catctcgatc   5040
cagcagatct cctggttgcg gggttgggg cggctttcgc tgtagggcac caggcggtgg   5100
gcgtcgaggg gggtcagggt ccggtcgcgc cagggtctca gggtccgcgt gagggtggtc   5160
tcggtgacgg tgaagggatg ggccccgggt tgggcgctgg ccagcgtgcg cttgaggctg   5220
aggcggctgg tgctgaagcg ggcgttttct tccccctgga agtcggccag gaagcagcgc   5280
agcatgagct cgtagctgag cgactcggcc gcgtggcctt tggcgcgcag cttgcctttg   5340
gagacgtgtc cgcaggcggg acagacgagg cacttgaggg cgtagagctt gggggcgagg   5400
aagacggact cgggggagta ggcgtcggcg ccgcaggccg cgcagacggt ctcgcactcg   5460
acgagccagg tgagttcggg ctgctggggg tcaaaaacga ggcggccgcc gttttttttg   5520
atgcgtttct tacctcggct ctccatgagg cggtgtccgg cttcggtgac gaagaggctg   5580
tctgtgtcgc cgtagacgga cttgaggggg cgtcgctcga gcggcgtgcc gcggtcctcc   5640
gcgtagagaa actcggacca ctctgagacg aaggcccgcg tccaggcgag gacgaaggag   5700
gccacgtggg aggggtagcg gtcgttgtcc accagggggt ccgtcttttc gacggtgtgc   5760
aggcagaggt ccccctcctc cgcgtccagg aaggtgattg gcttgtaggt gtaggccacg   5820
tgaccctcgg cggcgggcgg ggggctataa aagggggcgg cgccgttgtc gtcgtcactg   5880
tcctctgcgt cgctgtggac gatcgccagc tgctccggtg agtagaggcg ctcgaaggcg   5940
ggcatgacgt cggcgctaag ggtgtcagtt tccacgaacg aggaggattt gatgttgacc   6000
```

-continued

```
tgcccggcgg cgatgccttt gaggagggcg gggtccatct ggtcggcaaa gacgatcttt   6060
ttgttgtcga gcttggtggc gaaggacccg tagagggcgt tggagagcag cttggcgatg   6120
gagcgcaggg tctggttctt gtcgcggtcg gcgcgctcct tggcggcgat gttgagctgc   6180
acgtactcgc gcgccaggca gcgccatcga ggaaagacgg tggtgcgctc gtcgggcagg   6240
aggcgcacgc gccagccgcg gttgtgcagg gtgaccaggt cgacgctggt ggcgacctcg   6300
ccgcgcaggc gctcgttggt ccagcagagg cggccgccct tgcgcgagca gaaagggggc   6360
agcacgtcga gctggtcctc gggcggcggg tcggcgtcca cggtgaagat gccgggcagc   6420
aggcgggggg caaagtagtc gatgggcgcc tggaggttgt ccagcgcgcg ctgccagtcc   6480
cgggcggcca gcgcccgctc gtaggggttc agcgggggcc cccagggcat ggggtgagtg   6540
agggccgagg cgtacatgcc gcagatgtcg tagacgtaga ggggctcctt gaggacgccg   6600
atgtaggtgg ggtagcagcg gccgccgcgg atgctggcgc gcacgtagtc gtacatctcg   6660
tgggaggggg ccaggaggtc gggccccagg tgggtgcggg cggggcgctc ggcgcggtag   6720
aggatctggc gaaagatggc gtgggagttg gaggagatgg tgggccgctg gaagacgttg   6780
aaggcggcgc gcggcaggcc cacggcgtcg ctgacgaagg cggcgtagga ctcttgcagc   6840
ttcttgacga gctcggcggt gaccagcacg tcgagggcgc agtagtcgag ggtctcgcgg   6900
atgaggtcgt aagaagcttc ttgctttttt tcccagagct cgcgattcaa gaggtattct   6960
tggcggtctt gccagtactc gggaagcgga aacccctgcg cgtcggcccg gtaagcgccc   7020
agcatgtaaa actcgttgac ggcccggtag gggcagcagc ccttctccac ggggagcgcg   7080
taggcctgcg cggccttgcg cagggaggtg tgcgtgaggg cgaaggtgtc gcgcaccatg   7140
accttgagga actggtggcg gaagtcggtg tcgtcgcagg cgccctgctc ccagagcgta   7200
aagtcgaggc gcttctgcga gcgcgggttg ggcagggcga aggtgatgtc gttgaagagg   7260
atcttgccgg cgcgcggcat aaagttgcgc gtgacgcgaa aggggcccgg cacctcggag   7320
cggtggtcga tgacctgcgc ggccaggacg atctcgtcga agccgttgat gttgtggccg   7380
acgatgtaga gttcgagaaa gcgcgggggc ccgtgcagct tgggcgcctt cttgagttcg   7440
tcgtaggtga ggtcctcggg acgggcgagg cccagttcct ggcgcgccca ctcggctagg   7500
tgcgggttgg ccagcaggaa ggagtcccag aggtcgcggg ccaggaggag ctggaggcgg   7560
tcgcggaact ggcgaaagcg gcgccccacg gccaggcgct cgggggtgag acagtagtag   7620
gtggcgggtt gggcctccca gacgtcccag cggagctcgc gggccaggtc gcaggcctcg   7680
cgcaccaggc gctcgtcgcc gtggagatgc atgacgagca tgaagggcac gagttgcttg   7740
ccgaaggcgc ccatccaagt gtaggtttcc acgtcgtagg tgacaaagag ccgctcggtg   7800
cgcggatggg agccgatggg gaagaaggag atctcctgcc accagcccga ggactgggcg   7860
tggacgtggt gaaagtaaaa gtcgcgccgc cgcgccgagc actcgtgctg gtacttgtaa   7920
aagcgggcgc agtactcgca gcgctgcacg cgctccactt cctgcacgag atgcgcgcga   7980
ccgtcgtgca ccaggaagca gaggggcagc cccagctccg gggtggctg gcggccgtcg   8040
tggccctcct gggcctgggg ctcctctggg acgtgcgccg acgcggctcg ggggtcgggc   8100
caaaccctct ggcaggagac gaggccgcgg ctgccgcagg tccagacctc ggcggaggcg   8160
ggacgcaggc ggcggaggag cggccccagc tgcgccggcg tgagacggtc gagctcggag   8220
gggggcggca gtcccgccgg cgcgggcttg cggttgacct ccagcaggcg ggtaagcgcg   8280
tcggcgagac gcaggtgata cttgatggta acgggctgcc ccgtgtcggc gtcgacggcg   8340
```

-continued

```
tggcaaaggc cgtgggcgag gggagcgacg agggtgccgc ggtagcgccg ccgacgcggg   8400
ggcgggggga gcggcgggtc tagaagcggc ggcggggccg ggctcccggg gggagagggg   8460
gttcgggccc cgggggggaga tcggggagcg gcacgtcttc gtggagctcg ggcagcagct   8520
gatgtcgcgc gcggagctcg ctggcgaagg cgaccacgcg gcggttgagg tcctggatct   8580
gcctcctctg cgtcaagacc acgggtcccg tgagcttgaa cctgaaagag agttcgacag   8640
agtcaacctc ggcgtcgttc atggcggcct gccgcaggat ctcctggacg tcgcccgagt   8700
tgtcctggta ggcgatctcg gccatgaact gctcgacctc ctcttcctgg agctcgccgc   8760
ggccggcgcg ctcgacggtg gcggccaggt cgttggagat gcggttcatg agctgagaga   8820
aggcgttcag cccggtctcg ttccagacgc ggctgtaaac cacgtccccg tcggcgtcgc   8880
gcgcgcgcat gacgacctgc gccaggttaa gctcgacgtg ccgcgcgaag acggcgtaat   8940
tgcgcaggcg ctggaagagg tagttgagcg tggtggccac gtgctcggag acaaaaaagt   9000
acatgatcca gcggcggagc gtgagctcgt tgacgtcgcc cagcgcttcc aggcgttcca   9060
tggcctcgta aaagtctacc gcaaagttaa aaaactgcga gttgcgcgcc gacaccgtga   9120
gctcctcctc cagcagccgg atgacgtcgg ccaccgtgtc ccggacctcg cgctcgaagg   9180
cctcgggggc ggcttcttcc agctcctctt cctccggctc gagcgcttct tccaggggag   9240
gcagcggcgg cgacgggggg gctggcggcc ccggcgggac cggtacgggg cggcggcgct   9300
gacggcggcg cacggggagg cggtcgacga agcgctcgat gagctccccg cggcgacggc   9360
gcatggtttc ggtgacggcg cgtccgtcct cgcgcgggcg cagttcgaag acgccgccgc   9420
gcaggggcgc caggcccgct ccgcggagca ggctgcaggg gttgtggggg gagcggttgg   9480
gcagcgagac ggcgctgacg atgcatttga tcaactgctg cgtaggcacc tgacgccagg   9540
acctgaaggc ggaaaaatcc accggatcgg agaacttgtc gaggaaggcg tgtagccaat   9600
cgcagtcaca aggtaagctg aggacggtct ccgggggcgg cgggcggcgg tcgggcgaga   9660
cggcggaggt gaggctgctg aggaggtaat tgaagtaggc ggtcttgagg cggcggatgg   9720
tggcgaggag caccacgtcc ttgggcccgg cctgctggat gcgcaggcgg tcggccatgc   9780
cccaggcctc gtgctggcag cggcgcaggt ccttgtagta gtcctgcatg agccgctcga   9840
cgggcacctc gtcgcggccg tgggcgcggt cggccatgcg cgtggagccg tagccgcgca   9900
ggggctgcag gagggcgagg tcggcgacaa cgcgttcggc gaggatggcc tgctggacct   9960
gggtgagggt ggcctggaag ttgtcgaggt ccacgaagcg gtggtaggcg cccgtgttga  10020
tggtgtaggt gcagttggcc aggacggacc agttgaggag ctgcacgccg ttctgcgtga  10080
gctcggtgta gcgcaggcgc gagtatgcgc gcgtgtcgaa gatgtagtcg ttgcaggtgc  10140
gcaccaggta ctggtagccg acgaggaggt ggggcggcgg ctcgccgtag aggggccagc  10200
gggcggtggc gggcgcgccg ggggccaggt cctcgagcat gaggcggtgg tagccgtaga  10260
tgtagcgcga catccaggtg aggccggcgg cggtggtggc ggcgcgggcg aactcgcgca  10320
cgcggttcca gaggttgcgc aggggcgcga accgctgcac ggtggcgacg ctctggccgg  10380
tgaggcgggc gcagtcctgc acgctctaga cggaacaaaa gcggggaggt gagcgactcc  10440
gctccgtagc tcggcggaca gatcgccagg gtgcggcggc ggggaacccc ggttcgaagc  10500
cggccggatc cgccgtcccc gatgcgccgg ccccgcatcc acggcccctc gaggtcgaga  10560
cccagccgcg accccggata cggaggggag tcttttgctg ttttcgcagc catgcatccg  10620
gtcctgcgcc agatgcgccc ccagccggcg tcggcggcgg ggtctcgcgg cggggcggcg  10680
gcggtcgagc cggaggcgga ggaggcggag cggacgctgg acctggaaga gggggagggc  10740
```

ctggcccgcc tgggcgcgca cgtgccggag cggcacccgc gggtgcagct ggcccgcgac 10800
agccgcgcgg cgtacgtgcc gcggcagaac ctgtttcggg acgcgagcgg agaggagggg 10860
gaggagctgc gcgactgccg cttccgggcg gggcgcgagc tgcgcgcggg gctggaccgc 10920
gagcggctgc tgcgggccga ggactttgag gcggaggagg gccgcggggt gagcccggcg 10980
cgcgcgcacc tggcggcggc caacctggtg acggcgtacg agcagacggt gaaggaggag 11040
cgcagcttcc agcagagttt caacaaccac gtgcgcacgc tggtggcgcg cgaggaggtg 11100
gccatcgggc tgatgcacct gtgggacttt gtggaggcgt tcgtgcacaa cccgggcagc 11160
aaggcgctga cggcgcagct gttcctgatc gtgcagcaca gccgcgacaa cgagctgttt 11220
cgcgacgcgc tgctgaacat cgccgagccc gagggccggt ggctgctgga cctgattaac 11280
atcctgcaga gcatcgtggt gcaggagcgc tcgctcagcc tggccgacaa agtggcggcc 11340
atcaactact caatgctgag cctgggcaag ttttacgcgc gcaaaatcta ccgcagcccg 11400
tacgtgccca tcgacaagga ggtgaagatc gatagctttt acatgcggat ggccctgaag 11460
gtgctgacgc tgagcgacga cctgggcgtg taccgcaacg accgcatcca caaggcggtc 11520
agcgccagcc ggcggcgcga gctgagcgac cgcgagctgc tgcacagcct gcgtcgggcg 11580
ctggcggggg cgggggaccc ggagcgcgag gcttactttg aggcgggcgc ggacctggcg 11640
tggcagccga gcgcgcgggc cctggaggcg gcgggcgcgg cggcggaaga ggacgaggag 11700
gcggaggagg acttggaaga ggacgaggcg tactgaggcg gcggctcttt gtagatgcag 11760
gcggcagcgg cggcggcggg gacggcggcg gggcccgctc ccgtggaccc cgcggcgctg 11820
gcggcgcggc agagtcaggc gacgggcgtg acggcctcgg acgactgggg cgcggccatg 11880
gaacgcatca tggcgctgac ggcccggcac cccgaggcct tccggcagca gccgcaggcg 11940
aaccggtttt cggccatcct ggaggcggtg gtgccgtcgc gcaccaaccc cacgcacgag 12000
aaggtgctga cgatcgtgaa cgcgctggtg gacaacaagg ccatccgcaa ggacgaggcg 12060
gggctgattt acaacgcgct gctggagcgc gtggcccgct acaacagcac gaacgtgcag 12120
gccaacctgg atcggctgag cacggacgtg cgcgaggcgg tggcgcagcg cgagcggttc 12180
ttccgcgagg gcaacctggg ctcgctggtg gcgctgaacg cgttcctgag ctcgcagccg 12240
gccaacgtgc cgcgcgggca ggaggactac gtgaacttta tcagcgcgct gcggctgatg 12300
gtgagcgagg tgccgcagag cgaggtgtac cagtcgggcc cgaactactt tttccagacc 12360
tcgcggcagg gcctgcagac ggtgaacctg acgcaggcct tcaagaacct gcaggggctg 12420
tggggcgtga aggcgccgct gggcgaccgg gccacggtct cgagcctgct gacgcccaac 12480
agccgcttgc tgctgctgct gatcgcgccg ttcaccgaca gccagagcgt gagccgcgac 12540
tcgtacctgg ggcacctgct gacgctgtac cgcgaggcca tcggccaggc gcgggtggac 12600
gagcagacct tccaggagat cacgagcgtg agccgcgcgc tggggcagga ggacacgggc 12660
agcctggagg cgaccctgaa ctttctgctg accaaccggc ggcagaaaat cccgccccag 12720
tacacgctga gcgcggagga ggagcgcatc ctccgctacg tgcagcagtc cgtcagcctg 12780
tacctgatgc gggagggggc cacggccacc tcggcgctgg acatgacggc gcgcaacatg 12840
gagccgtcct tttacgccag ccaccggccg ttcatcaacc gcctgatgga ctacctgcac 12900
cgggcggcgg cgctgaacgc ggagtacttt accaacgcca tcttgaaccc gcactggctg 12960
ccgccgcccg gcttctacac gggcgagttt gacctgcccg aggccgacga cggcttcctg 13020
tgggacgact cgggcgacag cctgctgacg cccacgcggc tgctgaagaa agaggcgggc 13080
gacgagctgc cgctggccag cgtggaggcg gccacgcgcg gggagagccc ggcgccgagc 13140
ctgccgctgt cgctgcgcag ccagagcgga cgcaccgcgc ggccgcgcct gccgggcgag 13200
agcgagtacc tgaacgaccc gctgctgctg cccgagcggg aaaagaaccg ccgccagagc 13260
ctgcccaaca acgcgctgga gagcctggta gacaagatga accgttggaa gacgtacgcg 13320
caggagcagc gggagtggga ggcttcgcag ccgcggccgc tgctgccgcc cccgcagcgg 13380
tgggagacgc gccgccagcg ccggcgtcgc ctggaagagg ggccccgcgc ggacgaggag 13440
gactcggccg acgacagcag cgtgctggac ctgggcggca cgggccgggg cggggcgagc 13500
aacccgttcg cgcacctgcg tccccagggg cgcctggggc gactgtacta gcgagagaat 13560
aaaggtggcg actcaccaga gccatggcgt cgacgagcgc gcgtgcgtcc tgtcttgtgt 13620
ctccttagcg gcgaaatgag gcgggcggtc ccggcggcgg cgatcccggc gagggtggcg 13680
tacgcggacc ctcctccctc ttacgagagc gtgatggcgg gggtgccggc cacgctggag 13740
gcgccttacg tgcccccgcg ttacctggga cctacggagg gcagaaacag catccgttac 13800
tcggagctgg cgccgctgta cgacaccacc cgggtgtacc tggtggacaa caagtcggcg 13860
gacatcgcct cgctcaacta ccagaacgac cacagcaact tcctgaccac ggtggtgcag 13920
aacaacgact tcaccccggt ggaggcgggc acgcagacca tcaactttga cgagcggtcg 13980
cgctggggcg ggcagctcaa gaccatcctg cacaccaaca tgcccaacgt gaacgagttc 14040
atgttcacca actcgttccg ggccaaggtg atggtgtcgc ggaagcagaa cgaggagggg 14100
cagacggagc tcgagtacga gtgggtggag tttgtactgc ccgagggcaa ctactcggag 14160
accatgaccc tggatctcat gaacaacgcc atcgtggacc actacctgct ggtggggcgg 14220
cagaacgggg tgctggagag cgacatcggg gtgaagttcg acacgcgcaa cttccggctg 14280
ggctgggacc ccgtgaccaa gctggtcatg ccgggcgtgt acaccaacga ggccttccac 14340
ccggacgtgg tgctgctgcc gggctgcggg gtggacttta cgcagagccg cctgagcaac 14400
ctgctgggca tccgcaagcg gcagcccttc caggagggct tccgcatcat gtacgaggac 14460
ctggagggcg gcaacatccc cgcgctcctg gacgtgaagg cctacgagga cagcatcgcg 14520
gcggccatgc ggaagcacaa cctgccgctg cgcggggacg tctttgccgt gcagcctcag 14580
gagattgtca ttaagcccgt ggccaaagac ggcaaggacc gcagttacaa cctgctgccc 14640
gacgaccaaa acaacacggc ctaccgcagc tggtacctgg cctacaacta cggcgacccc 14700
ctcaagggcg tgcgctcctg gacgctgctg accacgcccg acgtgacctg cggctccgag 14760
caggtgtact ggtcgctgcc cgacctcatg caggaccccg tgaccttccg cccctccagc 14820
caggtcagca actacccggt ggtgggcgcc gagctcctgc cgctgcaggc caagagcttc 14880
tacaacgagc aggccgtcta ctcgcagctc atccgccagt ccaccgcgct cacgcacgtc 14940
tttaatcgct ttcccgagaa ccagatcctc gtgcggccgc ccgccgccac catcaccacc 15000
gtcagcgaga acgtgcccgc cctcacggac cacggcaccc tgccgctgcg cagcagcatt 15060
agcggagtcc agcgcgtgac catcaccgac gcccgccgcc gcacctgccc ctacgtctac 15120
aaggcgctgg gcatcgtcgc gccgcgcgtc ctctccagcc gcacctttta gccggcctgc 15180
ccgcctgcct gcctttctca tgtccgtcct catctcgcct agcaacaaca ccggctgggg 15240
cctgggcgtc agcaagatgt acgggggcgc caaacgccgc tccagcgagc acccggtgcg 15300
cgtgcgcggc cactaccgcg cgccctgggg ggcccacaag cgcggccgcg cggggcgcac 15360
cacggtcgac gaggtcattg acagcgtggt ggccgacacc gccaactaca cgccggccgc 15420
cggcccctcc acggtcgact cggtgatcga cagcgtggtg gcagacgccc gcgcctacgc 15480

```
ccgccgcaaa caacgccggc gccgcgccgc cgccgctcgc cgcctgacgc ccgccatgcg  15540
cgccgcccgg gccgtgctcc gtcgcgcgcg tcgcgtgggg cgtcaggtcc tgcgccaggc  15600
ggcttctaac gcacgggtgc gccgacgagc ggcccgtcgc gccgcggccg ccatcagccg  15660
catgtcccgg gggcgccgcg gcaacgtgta ctgggtgcgc gactcggtca cgggcctgcg  15720
cgtgccggtg cgcttccgcc cccctcgcca gtaaaaaaaa tccagtctga gctctgcgtg  15780
ttgttcgttc agcggcgccg gcatgagcaa acgcaagttt aaagaagaac tgctgcaggc  15840
ggtggcgccc gagatctacg ggccgccaga cgtcaagccc ctccgcgacc ttaagcgcgc  15900
gataaaaaag cgcgaaaaaa aggaagagaa aaaagaggag gcggcggcgg aggcctgggg  15960
cgacgcggtc gagtttgtgc gcgccacggc ccccgcggcgg cgggtgcagt ggaagggtcg  16020
gcgggtgcgg cgcgtgctgc ggcccggcac agcggtggtg ttctcgcccg gcgagcggtc  16080
ggcgctgcga gcgctgaagc gcgactacga cgaagtgtac gcggacgaag acctgctgga  16140
gcaggcggag cggcacgagg gcgagttcgc ctacgggaag cgagggcgct acggcgacgt  16200
ggccctggcc ctggacgagt ccaaccccac gcccagcctg aaggcggtga ccctgcagca  16260
ggtcctgccg gtggccgaaa gcaagaaggg gattaagcgc gaggcggccg agctgcagcc  16320
caccatgcag ctgatggtgc ccaaacggca gcggctggaa gaggtgctcg agcagatgaa  16380
ggtggacccc acggtccagc ccgacgtgaa gatccgcccc atcaagcagg tggcgccggg  16440
cctcggggtg cagaccgtgg acattcagat tcccgtgcgc acggcggcgg tggaggccat  16500
ggaaacgcag acggagcccg ccgtggtggg tccctcggcc acggccgccg ccctgggcgc  16560
cgcgctggga cgggccgcca cggcggaggt gggcatccag acggatcccc gttacgagta  16620
cgtcgccgtg gccgccagca ctccgcgggt gaggcgtcgc cgcgccacgg cagcggccgc  16680
ttccgcgttg ctgcccgact acgtcttgca tcccttcatc gcgcccacgc cgggctatcc  16740
cgggcgcccg taccgtcccc gccgccgtcg ccacgccacc accaccaccc gccgccgccg  16800
acgcctgccg acgctggccc ccgtccgcgt gcgccgcgtg acgcgccgag gtcgcacgct  16860
ggtgctgccg accgcgcgct accaccccag cattctcgtt taacgccccg gccgcctttt  16920
gcagatggcg ctgacgtgcc gcgtgcgcat ccccgtcccg ggctaccgag gaagaagcca  16980
ccgccgccac cgacgcgggc tggcgggacg cggactgcgg cggcgacggg ccgtgcggcg  17040
tcgcatgcgg ggcggggtgc tgcccctgtt gattcccctg atcgcggcgg ccatcggggc  17100
cgtgcccggc atcgcctcgg tggcgctgca ggcctcccgc aagaactaaa taaaaaatgc  17160
gttggactga cgcgctggtc ctgcctcctg ttttgtcaga gcgatggaag acatcaattt  17220
tgcgtcgttg gccccgcgac acggctcccg gccctatatg gcgacctgga acgacatcgg  17280
cacgagccag ctgaacgggg gcgcctttag ctggggcagc ctgtggagcg gccttaaaaa  17340
ctttgggacc accataaaaa actacggcag caaggcctgg aacagcagca cgggccagat  17400
gctgagggac aagctgaaag accataactt tcagcagaag gtggtagacg gcctggcgtc  17460
gggcatcaac ggggtggtag acctggcctc gcaggccgtg cagaagcaga tcagcagccg  17520
cctggacccg ccccctcccg cggcggtgga gccctcggcc ccgccgctgg aagaggtgga  17580
ggtggaggag aagctgccgc ccctggaggt ggcgctgccg cccaaagggg agaagcgtcc  17640
gcgtcccgac aaagaggaga cgctggtgac cgagacggtg gagcccccgt cgtacgagga  17700
ggcgctgaag gacggcgccg ccccaccccc ttacacgcgg cccacggcgg ccctggcgcg  17760
gccggtgctg tcgagcagcg cgcataagaa ggccgtgacc acgctggacc tgccgccgcc  17820
```

tcccgccccg gtggtgaccg ccgccccgcc ggccgcttcg ctgcccgtcc gcccggtggc 17880
cgtggccacg ccggcacgcg tgccccgcgg ttcgcgccag ggcaactggc agagcacgct 17940
gaacagcatc gtgggcctgg gcgtgcgttc gctgaagcgc cggcggtgct actattaaat 18000
ttgcctttcg gtccgctgtc gtcgccaggg agcgaagtcg ccgtcgccgg tgcgtcgttg 18060
agccagcaag atggccaccc cctccatgat gccccagtgg tcgtacatgc acatcgccgg 18120
tcaggacgcc tcggagtacc tgagccccgg cctggtgcag ttcgcgcggg ccacggacac 18180
gtactttagc ctgggtaaca agttccgcaa ccccacggtg gcgccgaccc acgacgtaac 18240
cacggaccgt tcgcagcggc tgacgctgcg cttcgtgccg gtggaccgcg aggacacggc 18300
gtactcgtac aaggcgcgtt tcacgctggc cgtgggcgac aaccgcgtgc tggacatggc 18360
gagcacgtac tttgacatcc gcggcgtgct ggaccgcggc cccagcttca agccctactc 18420
cggcaccgcc tacaactgcc tggcccccaa gggcgccccc aacccgtcgg agtgggaaga 18480
cacaactgac aacaaaacca aagtgagagg gcaggctcca tacgtgagcg atgaaattac 18540
caaagatggt ataaaagtgg gcacagatac cgctacacct acacaggcaa tatatgctga 18600
caagctgtac cagcctgaac cgcaaatagg agaaacacag tggaacagtg aagttcccaa 18660
caacggtaaa gtgggaggca gagtgttgaa aaaaaccact ccaatgtatc cttgttatgg 18720
ctcttttgca agaccaacaa atcaacaggg agggcaagta aaagatcaag tggatttaca 18780
attcttttct tcgaccagta gtgacaataa tccaaaagcg gttctttatg ctgaggacgt 18840
gaacttagaa gcaccagaca cccacttggt gtttaaacct attgtaacag aaggaactac 18900
cagtgcagaa gcgttactag cccaacaagc tgctccaaat cgtccaaact atattggctt 18960
tagagataac tttattggat taatgtacta caacagtact ggtaatatgg gcgtgctggc 19020
gggtcaggct tcccagctta atgcggtggt ggatcttcag gaccgaaaca ctgaattgtc 19080
ttatcagctt atgctggact ccccttggtga tcgcagtcgg tacttttcta tgtggaacca 19140
ggctgtggac agttatgacc ctgatgtaag aatagtggaa aatcatggtg tagaggatga 19200
gcttcccaac tattgttttc cacttggggg catggccgtt acagacactt attctgcttt 19260
aaaagttcaa aacggaaacg gcacatttac ctcagatgac agctttgcaa ctaggggcat 19320
tgaaattggc tctggaaaca tgtttgccat ggaaattaac ctgcaggcta atctctggcg 19380
cagctttctt tactccaaca ttggtcttta cctgccagat actttaaaat acactccaga 19440
caacgttacg ttgccagaca acaaaaacac ctacgggtac atgaatggcc gcgtaacgcc 19500
ccccggtttg attgacacat atgttaacat tggagcgcgg tggtcacccg acgttatgga 19560
taacattaat ccctttaacc accaccgcaa cgctggcctg cgctatcgct ccatgttgtt 19620
gggcaacggc cgttacgtac cttttcacat ccaggtgccc caaaagtttt ttgccattaa 19680
aaaccttttg cttctccccg ggtcctatac ctacgagtgg aactttcgca aggacgttaa 19740
catgattctt caaagctctt taggcaacga cctgcgagta gatggggcca ccattcgatt 19800
cgacagcatt aacctctacg ccaacttttt ccccatggcg cacaacaccg cttctacttt 19860
ggaagccatg ctgcgcaacg acaccaacga ccagtccttt aacgactacc tctgtgcggc 19920
caacatgctg taccccattc ccgccaatgc cactagcgtg cccatttcca ttccctctcg 19980
caactgggcg gcttttcgag ggtggagctt tacccgtctt aaaactaaag aaaccccctc 20040
cctgggctcc ggttttgatc cctactttgt gtactctggc agcattccct acctagatgg 20100
tactttttac cttaaccaca cctttaaaaa ggtgtcaatc atgtttgatt cctccgtgag 20160
ctggccgggc aacgatcgcc tgctcacgcc caacgagttt gaaatcaaac gttcggtgga 20220
cggggagggt tataacgtgg cccaaagcaa catgacaaag gactggtttt tgattcaaat 20280
gctgagtcac tacaacattg gctaccaggg cttttacgtg cctgaagggt acaaggacag 20340
gatgtactcc ttctttagaa acttccaacc catgagccgg caggtggtgg acactgttac 20400
ttacaaagac acttaccagg aagtaaaact gccttaccaa cacaacaact cgggcttcgt 20460
ggggtacatg ggacccacca tgcgcgaggg ccaggcctac ccggccaact tcccctaccc 20520
cctcatcggg cccaccgccg tgcccagcct cacgcagaaa aagttcctct gcgaccgcgt 20580
catgtggcgc atcccgttct ccagcaactt catgtccatg gggggcgctca cggacctggg 20640
ccagaacatg ctctacgcca actcggcgca cgcgctcgac atgaccttcg aggtggaccc 20700
catggatgag cccacccttc tctatgttct gttcgaagtt ttcgacgtcg tgcgcatcca 20760
ccagccgcac cgcggcgtca tcgaggccgt ctacctgcgc acgcccttct cggccggcaa 20820
cgccaccacc taaatgggct cctgcgaagg ggaactgcgg gccatcgcgc gcgatctcgg 20880
ctgcgggccg tactttttgg gcaccttcga caagcgcttt cccggcttcg tttcccctcg 20940
caagatggcc tgtgccatcg tcaacacggc cgcccgcgag accggcggcg tgcactggct 21000
ggcgctgggc tggaacccac gctcccagat ctgctacctt tttgaccctt ttggcttttc 21060
ggaccagcgg ctcaagcaga tctactcctt cgagtacgaa ggcctgctgc gccgtagcgc 21120
cctggcctcc actcccgacc gctgcgtcac cctggaaaag tctacccaga ccgtgcaggg 21180
gccccactcg gccgcctgcg ggctcttttg ctgcatgttc ctgcacgctt tcgtgcactg 21240
gcccgactca cccatggacc ggaaccccac catgaacttg ctgacgggag tgcccaacgc 21300
catgcttcag agcccctcag tgcagggcac cctgaagcgc aaccaggaaa acctctacgc 21360
ttttctggaa cagcactcgg cttattttcg ccagcacgcc gctcagatta aacgcgatac 21420
cgcttttgac aaagtgacac agcactcgtg aataaaccat gcaactttat tgaaccgcac 21480
cgtctcggct tggttttttt aaaactcaaa ggggttcagc tggtaatcga ggtgggcggt 21540
gggcagcgtg agattcttgt actggtagcg cggctgccac ttgaactcgg gaagcaccat 21600
cttgggcaga cccgcctcca caaagtggtc gtgccacaag ttgcgcacca gctgcagcgc 21660
cagcagcacg tcggtggccg agatcttgaa atcgcagttg acttggttgg tcgcgcgcgt 21720
gttgcggtag gcggggttgg cacactggaa caccagcagg ctggggtgat tcaggctggc 21780
cagggccacg ggatccgtca cctcgtcgtg cttcatgtct tcggcgcccg gcagcgcgaa 21840
gggggtgatc ttgcacacct ggcggccggc acgggggacg gcgtcgccca ggtagttgca 21900
gtcgcagcgc aggggcatca gcaggtgctt ctgaccgcgt tgcatgtgcg gataggccgc 21960
ctgcatgtaa gcctcgatct ggcggaaggc ctgctgcgcc ttgccgccct cggagtagaa 22020
catgccgcag gacttgccgg aaaacacgtt ggtgccgcac tgcgcgtcga acatgcagca 22080
gcgggcgttg tcgtgacgta gctgcaccac gttgcgcccc cagcggttct gcaccacctt 22140
ggccaactga ggcgtttcct tcagggcgcg ctgcccggcc tcgctgctca catccatctc 22200
caccacgtga tccttggcga tcatcggcag gccgtgcagg cacatcagct gaccttcctg 22260
ctccgtgcag cggtgctccc acaccacaca gccggtgggc tcccacgact tgtacagggg 22320
gttttcgatg ccggcgtgca gcagaacgta cttgttaaga aagcggccca tcatggcgct 22380
gaaggtcttc tgggtgctga acgtcagcgg gcagtacttg aggtcttcct ggagccacgt 22440
gtggcagatt ttgcggtaca cctcgaagga ctgcggcata aagtcgaagg ccgcgcggtc 22500
ttcgatcttg tacttatcca tcagcacgtg catcaccgcc atgcccttct cccaggcgct 22560

-continued

```
gaccaccggc ttgctcaggg ggttgcgcac caccacggcg gcccgggagg tgctgggctg  22620
ctcctcgtcc ttttcggcgt ccgcgggtag cgggggcgga ggcagctttt tgaaggcgcg  22680
actgccgtcc gggttgcggg taatctgtac cggcgggtag ctgaagccca ccatggttac  22740
cacgccggct tggctttcct cggcgatggc gagattttct tcgtcgtcgc tgtccaacac  22800
gatctcgggg gacggaggca tctccgccag gggcgccagc agactcttgc gggccttttt  22860
ttgaggaggc gccggtgtcg gggcgcgctc ggggctcgcc tgcaggtacc gccggataga  22920
cggggtggcg gggcggggcc gctcgggcgt acgctctctc tggtcttgac gatcggccat  22980
ggcggttgtc tgcttctagg cgcacaaaga caacggcatg gaagttagca agagcggcgg  23040
cgagacgcgg cccccgaccc ccgcaccctt ttctcggcgg gaagcggaag agcaggacga  23100
gcgagacaac tttgaggagg tgatcataga gcaggacccc ggctacgtga caccacccga  23160
gcagctgtcg gaggccgaag acgaacccgc agcgacgcag cccctccggg acggtcagac  23220
ccaaacagaa ggcgacgagc ccgactacct cacccccgag gtgctcctga agcacctccg  23280
gcggcagagc gccatcgtca gcgacgcctt gcgcgagctc gaaacggcgc cacccagcgt  23340
tcgcgagctt agcgcgctct acgaaagcca tctcttttca ccccgcgtgc cgcccaaacg  23400
ccagcccaac ggcacctgcg agcccaatcc tcggctcaac ttttaccccg tttttgccgt  23460
gcccgaggcc ctggccacct accacctgtt tttcaagaac caacgcatcc ccctctcctg  23520
ccgcgctaac cgcagtctgg cggacgagcg gctggccctg aagcaaggcg accgcttacc  23580
tggggtggtg tccttggaag aggtgccgaa gattttcgaa ggcctgggct ccgaggaaaa  23640
gcgggcggcg aacgctctgc cggaaaacac agaaaaccgc agcgtgttag tggagctggc  23700
cggcgacaac gcgcgcctgg cggtgctcaa acgcagcgtg gaagtctccc actttgccta  23760
cccggccctc aacctgcctc ccaaagtcat gagctgcgtc atggaccagt tgctgattaa  23820
acgcgcccag cccctgagcg acgccgccga agccgactcg gacgacggtc agccggtggt  23880
ggacgacgcg gaactcggcc ggtggctggg gaccgccgac cccgactccc tgcaggagcg  23940
acgtaagcta gttatggcgg cggtgctagt cagctgcgaa ctgcagtgtc tgcggcgctt  24000
tttcgccgat ccacgcaccc tgcagaagct ggaggagagc cttcactaca ctttccgcca  24060
cggctacgtc cgccaagcct ccctcatttc caacgtggag ctcagcaacc tggtctccta  24120
cctgggcatc ctccacgaaa accgcctggg gcagagcgtg ctgcattcca ccctgaaagg  24180
agaagcccgc cgcgactacg tgcgcgactg cgtctacctg tttctggtct tgacctggca  24240
gagtgccatg gggtatggc aacagtgtct ggaggaacaa aacctccggg agctggaaaa  24300
gctgctgcga cgtcacaaaa aggccctgtg gacgggcttc gacgagacca ccgtggccac  24360
cgccctggcc gacattgtgt ttcccgaacg cctgcggcag acccttcaga acggcctacc  24420
ggactttatc agtcagagca tgctgcacaa ctttcgctct ttcgttttgg agcgctccgc  24480
cattctcccg gccacgagct gcgccctccc ctccgacttc gtgcccctaa cgtaccgaga  24540
gtgtcccccct cccctctgga gccactgcta cctgctgcag ctggccaact acctggccta  24600
tcactgcgac ctcatggaag acgtcagcgg cgagggtctg ctggcctgcc actgccgctg  24660
caacctctgc accccccacc gctccctggc ctgcaacccc gaactcctta gcgaaagtca  24720
gcttatcggc acctttgagc tgcaggggcc ggaagggggc gcgcaaggaa cgcctctaaa  24780
gctcacccca gccgcctgga cctccgctta cctgcgcaag ttccaccccg aggactacca  24840
cccccacgaa attcggtttt acgaggagca ggctcagccg ccgcgagccc ccctctcggc  24900
ctgcgtcatt acccagagca cgattttggc ccaattgcaa gccattaacc aagccaggcg  24960
```

```
ggaatttctg ctaaaaaagg gtcgcggagt gtacctcgac ccccagacgg gcgaggagct  25020
gaacgccgct tcgccggact gcccgccctc ctctaatttc tcccaccagc atggccccca  25080
agcgccagac gcaactcctg cgagaaaagc gctccaaaaa gcaggagcag aggctgcccc  25140
cgaccccaga gacctgggac gaggagagcc aggactcctg ggagagccaa gccgcgacca  25200
ccgaagagga ggactgggag gagaccagca gtttaggcga ggcggaggaa caaccagacg  25260
aggaacaggc cgaggaagaa acccccagcg ccgccgcacc gttacgctcg gtcgccggtc  25320
ccaaaacgcc gcgacctccg gcccccactc ctccgctgcc gccgaaaaaa gccaatcgta  25380
gatgggacgc caaaaccccg gcgccggccg ctcccgtcgg taagatgctg gccggtcaac  25440
gccggcagcg aggtgcttac tgttcgtggc gtgcttacaa aagcgacatc cttgcctgct  25500
tgctgcactg tgggggggaac gtgtccttca cccgccgcta cctgctcttt caccgcgggg  25560
tggccgtgcc tcgcaacgtc ctgcattact accgtcatct ttacagcccc ttccaccagc  25620
agcagcagtt ccccgaaacg gcccgtcaga ggggggaacc ggacctccgc gccccgggac  25680
acgccgcaga cgcaggagct gagaacgcgg atctttccca cgctgtacgc catttttcag  25740
cagagtcgcg ggcagcgaca cgaactgaaa attaaaaacc gcaccttgcg ctcactcacc  25800
cgaagctgcc tgtaccaccg acgcgaggat cagctacagc gcaccttgga ggacgccgaa  25860
gctctgttca ataaatactg ctcggcgacc ctccaggact aaaattggcg cgcacctttt  25920
cccgcgctcc caccctccgc tgacgtcatg agtaaagaaa ttcccacgcc ttacatgtgg  25980
agctaccagc cgcagatggg cttggcggcc ggggcggcgc aagactactc tagcaagatg  26040
aactggctca gcgccgggcc ccacatgatc tcgcgggtga acggcattcg cgctcacaga  26100
aaccaaattc tcctggagca ggccgccatc accgccacgc cccgttccca gctcaacccc  26160
ccgagttggc ccgctgccct ggtgtaccag gaaaccccccg ccccgaccac ggttttattg  26220
ccccgcgacg cccaggccga agtccgcatg actaactcgg gagcgcaatt agcgggcgga  26280
gcccggggcg gcaggtacat aggtcgctcc tcgccctact cctctcagag tataaaacgt  26340
ctgctcattc gaggccgagg tgtgcagctc aacgacgagg cggtgagctc ctcttgggga  26400
ttacgacctg acggcgtttt ccagctcgga ggagccggtc gctcttcgtt cacctctcgt  26460
caggcctacc tgacgctcca gagctcgtct tcccgtcctc gctcgggcgg catcggcacc  26520
gtgcagtttg tggaggagtt tactccctcg gtttacttca acccgttctc gggctcgccc  26580
ggacgctacc cggacgcctt cattcccaac ttcgacgcca tcagcgagtc ggtggacggc  26640
tacgattgat gacggatggt gaggccgacc gagcgcggct gagacatctg catcactgcc  26700
gccagttcca ctgcttcgcc cgggaggcgc acagcttcat ctactttgtg attcccgagg  26760
accacccgca gggtcccgct cacggagtta agctcgagat cgaggaggag ctctcttccc  26820
acctcattta cctgttcacc gcccgcccgc tgcttgccga gaaggcccag ggaactacta  26880
ccctcaccct cttctgcatc tgccgcgaac ctgccctaca tgaagatctt tgttgtcatc  26940
tgtgctctga gtacaataag catcgcagcg gctaattaca ccaccgttgc ctcaaagaaa  27000
cttcccgcct acagaggtat tactttgcat tatactaact ttactgatta cattcaactg  27060
gtttgcactt gctctaacga actaattttg tggcttgcta acggcagcgt ttgccaagtt  27120
tttcttgagc acgtcctttt tgaaaaaaga aacccccttgt gtgaaaacag cagctctcaa  27180
taccttattt tacatcctcc ctttgtgtca ggaccttacc tttgcattgg gtcaggaaaa  27240
ggggacgcgt gtgtaaaaag gtgggtttta ttgccaaaac ctcaacctac cgctgcccct  27300
```

-continued

```
aaacctcaac ccacttctcc gccttcttta gcctttatac gcgccgctgc ttctcgcacc  27360
cacctgtggt tgccattaat ttttattgta gtgtttggct gtcacacctt ttctttgacc  27420
atgcgtatgt tacttttatt agccattatt gcttcaacct ccgctcaaag tttgcacaaa  27480
cctctgcaga tatatgctaa gattggtgac aaccttactt tacaaagcca tgagtttcac  27540
aatcctagtt taatgaaaga agtgtcgtgg tacgtagaat tgtgggacaa tgttaaaccc  27600
acctctacgg ctttatttat gggatctaaa ttgtgtcagt ttaaggaaga tgggtctaac  27660
aacacctgga actacccttc tttgcacttt aactgtgcta acaaaagcct tcacttgttt  27720
aaccttaatt ctttgaactc aggcctttac aatgtaaaag ttaccaacaa taccttggag  27780
cataatacct attttaacct ccaagtaatt tctattccta agcctcagtg catggtgact  27840
tccttttaca ttgctgtgga ttattgctat attgaaatta attgtactaa ctcaaagtac  27900
cccaacaaag tgctgtataa tggcattact aaagcttact acaacagcgc tcgcggcgga  27960
aaacacacct taccagagca tttttatact ttaattaatt accatggcgt gcgggcaaat  28020
ttcagctact actacccatt taacagtttg tgcaaaaact caggccgcgc accccacagc  28080
gcccctcgtt tcgtgcctcg ttacgggccg caaccggcgc gcttgctggg agttcgcctt  28140
ctttcccctc ctccttacga ggaaaacccc gatgctaaca gcgacgacgc ctacgaaaag  28200
gccatggccg tggtggttat tgccgccgtc gtttgctccc tcgtcatcct ggccgccctg  28260
ctttttctct gctactggcg ccgccgtctc aggcagcgcc gtcgacgcgg tccccagctc  28320
atgatgacca accagctgta acttttctct tacagcatgc ccaccctcct tttaatcctc  28380
ctcggcctgc ccgtcatttt tctctccacc gcctacgcag ccgccagcca cctcgaagcc  28440
gagtgcctct cccctttgt ggtttacctc atttttactt ttctcggctg catctccatc  28500
tgcagcatcg tcgcttttct catcaccacc tttcaatgcg tcgactacgt ctacgtcagg  28560
tgggtgtacc gccgccacca cccccagtac caaaaccggg aagtggccgc gttgctctgt  28620
ctctcgtaat tttctcgcc ctctggcctt ccgccgcggc cgcggaaacc gcagtcgccc  28680
gacactgtcg ctttcagcgg ctctggggct ttcccgactg ctaccacaaa aaacccgagt  28740
ttcccgccgc ctggctctac gtggccactt tttttctcgt cttcatctcc accgtgctgg  28800
gccttttcat ttttggccgt ctgcgctacg gctggattca cgccaccaac gagctgcctg  28860
cctcgccctc tccccttctt ccccctccgc cgccacctcc gccgccccct ccccccgtgg  28920
ccgccgtgat tcagttgatt catctcaact cccctcccag gcgcccttca gtcatcagct  28980
actttgaact gagctagcca tggccgactg ccgcgacgac agcgctcagc tggacattga  29040
cggcgtccgc accgagcagc tgctagcggc ccgtcagcgc cagcgccagg agcagcgtca  29100
gcgcgagctg caggatctta aaaacctgca ccagtgcaag cagggagtct tctgcctcgt  29160
taaacaagcc cagctctcct accacctcac ctccatgggc caccagctct cctacgtgct  29220
ccccgtgcgt cgtcagaacc tgctaaccat ggtgggcacc gtgcccgtca aaatcagcca  29280
gcaggccggc cagagcgagg gctccattct ctgtcagtgc gccaaccccg aatgtctgta  29340
cactttgatt aaaaccctgt gtggattgaa agaaatcgta ccttttaact aatcatgcct  29400
aataaaactt actttaagcg cagcttcagt ctcgggtcaa atttctccag cagcctcacc  29460
acctgcccct cctcccagct ctcgtagcgc aggcgctcgc gggcggcaaa cttgcgccac  29520
agccgaaagg aaatcggggt ggcccactcg cgcccctcac acaccatctt cattttctct  29580
tctagatgaa gagagcgcgc gttgccgaag actttaaccc cgtctacccc tatggctccg  29640
agagctcgcc caacgtcccc tttatctccc cgccctttgt ctcctccgaa gggctgcagg  29700
```

aaaaccccccc cggagtgctg gccttaaagt accaggaccc catcaccacc accgccgagg 29760
gcaagctcac cctcaagctg ggcagcgggg tctccctcaa cgacggagcc ctcaccgcca 29820
ccgctccccc cgtctcggcc cctttaacca gcacccaggg caccatcggg ctcagcagct 29880
ccccgcccct caccgtctcc gcgggcagcc tcaccctcgc ccaaaccgaa ccgctcaccg 29940
tcacctccga cgccctggcc ctctcctact cctccccgct caccgtggcc tctggagccc 30000
ttacccttac ctccccctcc gaacccctca ccctctcttc cggatccctc gccctcactc 30060
aaaccccccc tctcaccgtt acctcgggcg ctttgggatt gtcttacagc tccccccctca 30120 ccctcaccga cagttctctg ggcctgagtt accagggacc cctgactgtg accgacaacg 30180
ccctggggct gagcgccacg gcacccttgc aagtgagcaa cagctcccta gctctcacca 30240
cctccccccc gctgaccgtc agcaacaact ctctgggtct caacctaggc aacggactta 30300
ctactaccaa ctcccaactg accgttaaaa ccggcggagg cattgccttc gacagttccg 30360
gtaacctgcg cattaatgcc gccgggggca tgcgggtaga caacaacaac actctaattt 30420
tacacgtagc ctatcctttt gaagccgcta accaactaac tattagaatt ggtccgggcc 30480
ttaatattaa caccaacaac cagctgcagg ttaatactgg cccaggactg gtttttctca 30540
acaacgtgct gcaagtgagc gtagacacca gcaaagggct gcagtacgcc accacggggt 30600
cctccatctc cgttaaggtg ggctccggcc tccgctttga cagcaacggg gccatcaccc 30660
tcaactccac caccgcccga gccttccacg gcctggcttc ccaatccctc tggtcgcatc 30720
ccgtcagggc caactgcacc gtttacgagc ccctggacgc ccagctggcc ctctgtctca 30780
ccaagtgcgg ctcacacgtg ctcggaaccg tctccctgca gccgctctcg ggacagctgg 30840
ccacggccat gcccgccgag tctctaaccc tgcaactact ttttgacgaa caggggggcgc 30900 ttctcaccac gggacccctg gaacccaccg cctgggggta tcgagaggac aacgccctct 30960
cccccgaccc cgtcgcccac gccctggaat tcatgcccag cgccctggcc tacccccgag 31020
aagccgaccc gccccacttt agcgcccagt tttaccctc ctccccgccc gtgactttca 31080
gtgtagctta caacaccgcc ccctccggtt ttgccctcgc cttcacctgg tccgccaccc 31140
ccgggcagcc cttcgtcgcc cctctcgcca ccttctgtta cgtcactgaa caataaacgc 31200
gtggttttta tttgcagatg aaacgaagtc gtcccgctga ttttaacccc gtctacccct 31260 ttccctttc gccgccgccc ttctttatta ccccaccctt tgtggaagcc cggggtttgc 31320
aagaatcccc acgaggggtg ctctcccttc gcctgggggga agggctctct gtggacgaac 31380
agggggccat tgccgcggct taccgtcagg ccgctgcccc tttgattttg caaaacggca 31440
ccctggccct tacctactcc tccccccctca tgctgactcc acaaaacact ctgggactgc 31500
aggtgcagca tcccctccgc gtgcaaaact ccacgggtct ctcgctcctc accgcgccac 31560
cgctggccct cggagctacc gggcttaccc tgcaaaccgg ccccggactg caggtgcaag 31620
actcttccct cgcccccgc ctgggtgacg ggctggagct taacaccgac ggcgccattc 31680
aagtggctac cgcggccgcc ctgaccctc aaaatcacaa ggtagggctg gcggtcgact 31740
ggcccctcac cgccaccgac aagctccgcc tccttacgtc tcacggcctc acggttgacc 31800
ccaatctgca ccagctcaag gtagacgtaa acatttttaa aggcctcacc tttgacaaca 31860
accaactcgt ggttaaagcc ggccacggcc tgcgctttga cgagggaggc tttctcactc 31920
tgacccaacc ccccgatacc ctttggacca cctccgaccc ctcccccaac tgcaccgtta 31980
aggaagagct ggacagcaaa ctctccctcg ccctcaccaa aaacggagga caggtgcacg 32040
gccttgttag cctgctgggc ctcaagggtc cccttgcttc cattcccgcc tctaacatgg 32100
ggtgggttac catcaccctg gcctttgacg agcaagggcg cctacagttt ggggaaaaca 32160
ccaacttggc ttccagcgcc acctggggct accgccaagg gcaatccgtt aaccccaccc 32220
ctcccgaaaa cgccctggga ttcatgccca actccctcgc ctacacccgg ggacagggac 32280
agcacacccg caaccacacc tttgtaccca cctacatgaa agccgaccac cagaagcccc 32340
tgtccctcca agttaccttt aatgagctca gcgttggcta ctccctgcgc ttcacctgga 32400
tgggggtttt tcactaccct ggggaacaat tttggcccc accctgtgcc ttttcctacc 32460
tggctgaaga ataaaaacac caacaaaaat acgtttataa actttattaa attactctca 32520
ccgtcagact ccccccgccc tgccacttta cgcgataaac caccctctcc ccgggcgcca 32580
tggtgtacgt ctgcagccga gcgctagcca gcccggaccg ctcgggggtt aaaatccaca 32640
cttgctccgt ggtggccagg cggggatccg taatggacac gaaaccctcc gaacagtctc 32700
gcagatccgg ctcgccctcc agcagctgcc agggggggctg ctaaaaaaca aacatcagtc 32760
aacaccggtc gagcgccagg ggttctcgca gccgtcataa gcccttaagg tgaaaggctg 32820
agcgcgcagc atcaggtttc gcagcagctg ctgtcggcgc ggttccaagc aactgcggta 32880
cagggggctg cgcgtatgct caccgatcag tcgcacggcc cttagcatca gcgcgcgtgt 32940
gcggcgggcg cagcagcgca tctgaatctc agacaggtct ttacagtacg tgcagcccaa 33000
aatcaccaag ttgtttaaaa tgccatagct caacacgctc caaccgaagc tcatattggc 33060
caacaccacg cccacgtggc cgtcgtaccg gatccgcacg taaatcaggt ggcggccccg 33120
cacgtacgtg ctgcccacgt agcacacctc cttgggcagg ttaaagttca ccacctctcg 33180
gtaccacagg cagcgctggt taatgagggc cccgtagacc agcatcttaa accagcgcgt 33240
cagcaccacc gcacccgcct tgcactgcag agaccccggg cgccgacagt ggcagtgcaa 33300
gatccagcgc tcgtggccgt gcaccagctg acggctctcc acgtccaggg tggcgcaaca 33360
cacgcacacg cgcaggtacg tgcgcaacac gtacagctcc caccgggtca gcaccatgtc 33420
ccacagcacc ggccactctt gcagcacgat aaatcccgca cagcagggca gccccctcac 33480
ctccgccacg ttgtgcatgc ggaagttgtc gcagtccatc gataactggc tgtcgtccat 33540
caccgccgcc gaacacggct gctcacaagg cggtagacgg tgacgggcat acgggcccag 33600
cctgtagcga aaccgtcttt cgcgttgcat cgtacgccag cacgcggctc acccacagcc 33660
acttctggta gcaaaaccac gtgcggcccc aacacgcctc cttgcgccgc cgaaacgccg 33720
cgcggcgctg acgctcgcta ttcaaagcaa agtacagcca ttctcggtaa ccgctgagga 33780
ttcgcgccgc cgccggggtc agggtgatgc cgtgcaggcg gatgttgcgc aacacgtcca 33840
ggtagatggc gtaggccagc tccagccacg ccaagcaggc aggcggctcg cggcacactg 33900
gaggcggagg aagagacggg agagacattt ttttattcca agcggtctcg cagcacctca 33960
aagtgcaagt cgcgcaggtg gcaccggtcc ccgccgctgt tctgatgata aatgacagcc 34020
aggtcaaatc ccatgcgatt atccaggtgg tccaccaccg cctccaccag cgcctccacg 34080
cgaacttcca caaacaaaag cacagcaaag ctaccgtcct caaactcctc caccatcagg 34140
ctgcacgact gcaccatgcc caagtaattt tcgtttttcc attctctaat gatatcagtg 34200
caacacgtca ccaagttcat ccccccgcatg ttaaacagct ctctcagggc cgactccacc 34260
tgaagccgca ggcacaactt catgttggcg gctctaaaaa aagttcacct cttgggacac 34320
ctgcagcaga ttcaacagct cggggttagg gacgtgaccg tgctcgcgaa tctcatacat 34380
tagcgccaag cgcagcacct cgtacaggtc aaaagccgtg gcggaagcca gctcgccgtt 34440

```
aggcgtgagt tcgggggcca ttacgcagca gagcacttga aaagagggcg acaggctcag  34500

caacgtagcc cccgccgaag cggattcaaa aggaggggtt aaatacagca gcatctgccg  34560

ccaaaactca ggcagaacgc gcagcatcag ctcgtaaacc tccacgctgc aagcgtgcag  34620

gtggtccacc agcggctgag gtaggcacac ggaaaaaaac accggacgtc gctcgtacat  34680

gtcggcggca cctaaaaggc aacgttacac ctgtgacgcc tgtcgaagag gagggaaaaa  34740

cacccgctcc aaaatcaaac aggccaccgg ctggccgcgc gccccaaagt aaaactcatc  34800

cgaatgatta aaaagcacca ccgaggactc ccaccagctg tctggacaca gctcctgggc  34860

ggcaacgtac acgccgcgcg tagccatgtc ggccagcgaa aaaaaccgcc ccaaatagcc  34920

agtgggaatt tgcacagaaa gctgcagagc tagcaggtta atgccccgag gagaaatcat  34980

aaaattttca ggagcaaaaa acacataaac attactataa ccctgctgcg cgggcataag  35040

cgcgcgggga ctcagcaaat gcacataaac agcctgcgat tcagccatgg tagcgtctcc  35100

ttaccgcctt ggcgcacaca gcactcggca ctcaacagct cactcgcacc acacactcgg  35160

cacctgccct atatactctc taaatgacgt caacgcacac gccacccggc caaaggtcac  35220

cccgcccaga aactcccgcc aaaaagccca gaaaaaagcc cgcgaaaaaa acccgcgaaa  35280

ttccgcagca cttccgcaaa gtagaccacg cctactctta catcacttcc tgcgcgccgg  35340

cggccagagc cccacccccc gacacgccca cccacgtcac ttcccttccc acgcccgctc  35400

cgcccaccgc gctgacgtca aaactccacc cctcgctccg cccactgcgt cacttccttt  35460

tccgctgacg tcactggctc cgcctacctc attatcatat tggcgtgcag ccaaaataag  35520

gtatattatt gatgatg                                                 35537
```

```
<210> SEQ ID NO 5
<211> LENGTH: 761
<212> TYPE: PRT
<213> ORGANISM: Adenovirus

<400> SEQUENCE: 5

Met Asp Leu Met Arg Lys Glu Ser Leu Thr Thr Pro Pro Leu Ser Asp
1               5                   10                  15

Glu Asp Val Pro Ile Glu Gln Asp Pro Gly Phe Val Thr Pro Pro Glu
            20                  25                  30

Glu Pro Glu Leu Pro Ile Ser Phe Asp Leu Ala Arg Ser Glu Arg Thr
        35                  40                  45

Glu Gln Asp Gly Asp Tyr Leu Leu Glu Ala Glu Ile Leu Leu Lys His
    50                  55                  60

Phe Ala Arg Gln Ser Thr Ile Val Lys Glu Ala Leu Gln Asp Arg Ser
65                  70                  75                  80

Glu Val Pro Leu Asp Val Cys Glu Leu Ser Arg Ala Tyr Glu Ala Asn
                85                  90                  95

Leu Phe Ser Pro Arg Val Pro Pro Lys Lys Gln Pro Asn Gly Thr Cys
            100                 105                 110

Glu Pro Asn Pro Arg Leu Asn Phe Tyr Pro Val Phe Ala Val Pro Glu
        115                 120                 125

Ala Leu Ala Thr Tyr His Ile Phe Phe Lys Asn Gln Gly Ile Pro Leu
    130                 135                 140

Ser Cys Arg Ala Asn Arg Thr Lys Ala Asp Arg Lys Leu Arg Leu Arg
145                 150                 155                 160

Ala Gly Ala Arg Ile Pro Glu Ile Ala Ser Leu Glu Glu Val Pro Lys
                165                 170                 175
```

-continued

```
Ile Phe Glu Gly Leu Gly Arg Asp Glu Asn Arg Ala Ala Asn Ala Leu
            180                 185                 190

Gln Lys Glu Gln Lys Glu Ala Gln Ser Val Leu Ile Glu Leu Glu Gly
        195                 200                 205

Asp Asn Ala Arg Leu Ala Val Leu Lys Arg Thr Val Glu Val Ser His
    210                 215                 220

Phe Ala Tyr Pro Ala Leu Asn Leu Pro Pro Lys Val Met Arg Ser Val
225                 230                 235                 240

Met Asp His Leu Leu Ile Lys Arg Ala Glu Pro Leu Asn Pro Glu Asn
                245                 250                 255

Pro Asp Pro Glu Asn Ser Glu Asp Gly Lys Pro Val Val Ser Asp Glu
            260                 265                 270

Glu Leu Glu Arg Trp Leu Gly Thr Lys Asp Pro Glu Arg Leu Gln Glu
        275                 280                 285

Lys Arg Lys Met Met Met Ala Ala Ile Leu Val Thr Ala Glu Leu Glu
    290                 295                 300

Cys Leu Gln Arg Phe Phe Ala Asp Val Glu Thr Ile Arg Lys Val Glu
305                 310                 315                 320

Glu Ser Leu His Tyr Thr Phe Arg His Gly Tyr Val Arg Gln Ala Cys
                325                 330                 335

Lys Ile Ser Asn Val Glu Leu Ser Asn Leu Val Ser Tyr Met Gly Val
            340                 345                 350

Leu His Glu Asn Arg Leu Gly Gln Ser Val Leu His Cys Thr Leu Gln
        355                 360                 365

Gly Glu Ala Arg Arg Asp Tyr Val Arg Asp Cys Val Tyr Leu Phe Leu
    370                 375                 380

Leu Leu Thr Trp Gln Thr Ala Met Gly Val Trp Gln Gln Cys Leu Glu
385                 390                 395                 400

Glu Arg Asn Leu Lys Glu Leu Asp Lys Leu Leu Thr Lys Gln Arg Lys
                405                 410                 415

Ala Leu Trp Thr Gly Phe Ser Glu Arg Ala Ala Ala Ser Gln Leu Ala
            420                 425                 430

Asp Ile Ile Phe Pro Glu Arg Leu Met Lys Thr Leu Gln Asn Gly Leu
        435                 440                 445

Pro Asp Phe Ile Ser Gln Ser Ile Leu Gln Asn Phe Arg Ser Phe Val
    450                 455                 460

Leu Glu Arg Ser Gly Ile Leu Pro Ala Met Ser Cys Ala Leu Pro Ser
465                 470                 475                 480

Asp Phe Val Pro Leu Thr Tyr Arg Glu Cys Pro Pro Pro Leu Trp Ser
                485                 490                 495

His Cys Tyr Leu Leu Gln Leu Ala Asn Tyr Leu Ala Tyr His Cys Asp
            500                 505                 510

Leu Met Glu Asn Val Ser Gly Glu Gly Leu Leu Glu Cys His Cys Arg
        515                 520                 525

Cys Asn Leu Cys Thr Pro His Arg Ser Leu Val Cys Asn Thr Glu Leu
    530                 535                 540

Leu Ser Glu Thr Gln Val Ile Gly Thr Phe Glu Ile Gln Gly Pro Glu
545                 550                 555                 560

Gln His Glu Gly Ala Ser Gly Leu Lys Leu Thr Pro Ala Leu Trp Thr
                565                 570                 575

Ser Ala Tyr Leu Arg Lys Phe Val Ala Glu Asp Tyr His Ala Ser Lys
            580                 585                 590
```

```
Ile Gln Phe Tyr Glu Asp Gln Ser Gln Pro Pro Lys Ala Pro Leu Thr
        595                 600                 605

Ala Cys Val Ile Thr Gln Ser Asn Ile Leu Ala Gln Leu Gln Thr Ile
    610                 615                 620

Asn Gln Ala Arg Arg Glu Phe Leu Leu Lys Lys Gly His Gly Val Tyr
625                 630                 635                 640

Leu Asp Pro Gln Thr Gly Glu Glu Leu Asn Pro Ser Thr Leu Ser Ala
                645                 650                 655

Glu Ala Ala Pro Lys Gln His Ala Ala Gln Arg Ser Gln Thr Ala Asp
            660                 665                 670

Ser Ser Ala Glu Ser Glu Glu Ala Ala Arg Ala Pro Ala Ala His Gly
        675                 680                 685

Arg Gly Gly Gly Ser Gln Arg Cys Val Gly Gln Ser Gly Arg Gly Gly
    690                 695                 700

Phe Gly Gly Arg Gly Asp Gly Arg Leu Gly Gln Pro Arg Arg Gly Gly
705                 710                 715                 720

Gly Gly Gly Arg Gly Arg Gly Arg Thr Asp Arg Arg Lys Thr Thr Gly
                725                 730                 735

Phe Gln Arg Thr Phe Ser Glu Pro Ser Gly Glu Asn Pro Arg Pro Asn
            740                 745                 750

Pro Gly Arg Leu Thr Gln Ser Gln Pro
        755                 760


<210> SEQ ID NO 6
<211> LENGTH: 180
<212> TYPE: PRT
<213> ORGANISM: Adenovirus

<400> SEQUENCE: 6

Met Pro Pro Lys Gly Val Lys Gln Leu Ile Ala Gln Gln Arg Ala Lys
1               5                   10                  15

Lys Gln Gln Glu Leu Leu Arg His Met Glu Glu Glu Glu Glu Ala Ser
            20                  25                  30

Asp Ala Trp Asp Ser Gln Ala Glu Glu Ala Ser Glu Asp Glu Glu Met
        35                  40                  45

Glu Gly Trp Asp Ser Leu Asp Glu Val Glu Glu Glu Glu Glu Val Glu
    50                  55                  60

Asp Glu Pro Ile Gly Glu Lys Pro Pro Ala Ser Ser Ala Leu Ser Pro
65                  70                  75                  80

Ser Arg Leu Ala Lys Thr Arg Val Pro Thr Pro Gly Gly Ser Arg Lys
                85                  90                  95

Ala Ser Arg Arg Trp Asp Thr Thr Gly Ser Pro Val Ala Ser Ala Ala
            100                 105                 110

Gly Lys Pro Gly Arg Pro Arg Arg Gly Tyr Cys Ser Trp Arg Val His
        115                 120                 125

Lys Ser Ser Ile Val Asn Cys Leu Gln His Cys Gly Gly Asn Ile Ser
    130                 135                 140

Phe Ala Arg Arg Tyr Leu Leu Tyr His His Gly Val Ala Val Pro Arg
145                 150                 155                 160

Asn Val Leu Tyr Tyr Tyr Arg His Leu Tyr Ser Pro Tyr Glu Thr Leu
                165                 170                 175

Gly Glu Lys Ile
            180


<210> SEQ ID NO 7
```

<211> LENGTH: 173
<212> TYPE: PRT
<213> ORGANISM: Adenovirus

<400> SEQUENCE: 7

Met Pro Pro Lys Gly Val Lys Gln Leu Ile Ala Gln Gln Arg Ala Lys
1               5                   10                  15

Lys Gln Gln Glu Leu Leu Arg His Met Glu Glu Glu Glu Glu Ala Ser
            20                  25                  30

Asp Ala Trp Asp Ser Gln Ala Glu Glu Ala Ser Glu Asp Glu Glu Met
        35                  40                  45

Glu Gly Trp Asp Ser Leu Asp Glu Val Glu Glu Glu Glu Glu Val Glu
    50                  55                  60

Asp Glu Pro Ile Gly Glu Lys Pro Pro Ala Ser Ser Ala Leu Ser Pro
65                  70                  75                  80

Ser Arg Leu Ala Lys Thr Arg Val Pro Thr Pro Gly Gly Ser Arg Lys
                85                  90                  95

Ala Ser Arg Arg Trp Asp Thr Thr Gly Ser Pro Arg Thr Ala Lys Pro
            100                 105                 110

His Phe Ser Tyr Ser Val Arg Tyr Phe Ser Ala Glu Pro Arg Ala Ala
        115                 120                 125

Ala Arg Thr Lys Asn Lys Lys Pro Leu Pro Thr Val Thr His Pro Gln
    130                 135                 140

Leu Ser Val Pro Gln Glu Gly Arg Pro Thr Thr Ala His Ser Gly Arg
145                 150                 155                 160

Arg Arg Gly Ser Val Gln Gln Val Leu Leu Ser Val Ser
                165                 170

<210> SEQ ID NO 8
<211> LENGTH: 375
<212> TYPE: PRT
<213> ORGANISM: Adenovirus

<400> SEQUENCE: 8

Met His Pro Val Leu Arg Gln Met Arg Pro Gln Thr Ala Ala Phe Gln
1               5                   10                  15

Pro Thr Thr Thr Ala Thr Ala Ala Val Cys Gly Ala Gly Arg Gly Glu
            20                  25                  30

Glu Glu Leu Ala Leu Asp Leu Glu Glu Gly Glu Gly Leu Ala Arg Leu
        35                  40                  45

Gly Ala Pro Ser Pro Glu Arg His Pro Arg Val Gln Leu Ala Arg Asp
    50                  55                  60

Ala Arg Gln Ala Tyr Val Pro Arg Gln Asn Leu Phe Arg Asp Gly Ser
65                  70                  75                  80

Gly Gln Glu Ala Glu Glu Met Arg Asp Cys Arg Phe Arg Ala Gly Lys
                85                  90                  95

Glu Leu Arg Ala Gly Phe Asp Arg Glu Lys Leu Leu Arg Ala Glu Asp
            100                 105                 110

Phe Glu Pro Asp Glu Gly Ser Gly Ile Ser Pro Ala Arg Ala His Val
        115                 120                 125

Thr Ala Ala Asn Leu Val Thr Ala Tyr Glu Gln Thr Val Asn Glu Glu
    130                 135                 140

Arg Asn Phe Gln Lys Ser Phe Asn Asn His Val Arg Thr Leu Ile Ala
145                 150                 155                 160

Arg Glu Glu Val Ala Thr Gly Leu Met His Leu Trp Asp Phe Ile Glu
                165                 170                 175

```
Ala Tyr Val Gln Asn Pro Thr Ser Lys Pro Leu Thr Ala Gln Leu Phe
            180                 185                 190

Leu Ile Val Gln His Ser Arg Asp Asn Glu Thr Phe Arg Glu Ala Met
        195                 200                 205

Leu Asn Ile Ala Glu Pro Glu Gly Arg Trp Leu Leu Asp Leu Val Asn
    210                 215                 220

Ile Leu Gln Ser Ile Val Val Gln Glu Arg Ser Leu Ser Leu Ala Asp
225                 230                 235                 240

Lys Val Ala Ala Ile Asn Tyr Ser Met Gln Ser Leu Gly Lys Phe Tyr
                245                 250                 255

Ala Arg Lys Ile Tyr Lys Ser Pro Tyr Val Pro Ile Asp Lys Glu Val
            260                 265                 270

Lys Ile Asp Ser Phe Tyr Met Arg Met Ala Leu Lys Val Leu Thr Leu
        275                 280                 285

Ser Asp Asp Leu Gly Val Tyr Arg Asn Asp Arg Ile His Lys Ala Val
    290                 295                 300

Ser Ala Ser Arg Arg Arg Glu Leu Ser Asp Arg Glu Leu Met His Ser
305                 310                 315                 320

Leu Arg Arg Ala Leu Ala Gly Ala Gly Asp Pro Asp Arg Glu Thr Tyr
                325                 330                 335

Phe Asp Met Gly Ala Asp Leu Gln Trp Arg Pro Ser Ala Arg Ala Leu
            340                 345                 350

Glu Ala Ala Gly Tyr Arg Gly Glu Arg Glu Glu Ile Asp Asp Glu Asp
        355                 360                 365

Glu Glu Tyr Glu Asp Asp Pro
    370                 375


<210> SEQ ID NO 9
<211> LENGTH: 461
<212> TYPE: PRT
<213> ORGANISM: Adenovirus

<400> SEQUENCE: 9

Met Ala Gly Asn Gln Asn Pro Gly Glu Arg Ser Ile Thr Pro Tyr Leu
1               5                   10                  15

Arg Glu Arg Ser Pro Glu Arg Asp Val Ala Val Pro Leu Pro Pro Lys
            20                  25                  30

Lys Lys Ala Arg Lys Ser Ser Gln Ala Arg Pro Pro Ser Pro Glu Ile
        35                  40                  45

Ile Ser Asp Ser Glu Gly Glu Gly Thr Val Ile Gly Val Gly Phe Ser
    50                  55                  60

Tyr Pro Pro Val Arg Ile Val Lys Gln Ala Asp Gly Gly Arg Val Phe
65                  70                  75                  80

Gln Arg Val Thr Val Glu Glu Ala Asn Pro Glu Arg Glu Glu Arg Ser
                85                  90                  95

Ser Val Leu Val Val Asn Pro His Ser Ser Pro Leu Val Thr Ala Trp
            100                 105                 110

Glu Lys Gly Met Glu Ala Met Met Ile Leu Met Glu Lys Phe His Val
        115                 120                 125

Pro His Glu Asp Arg Ala Thr Phe Lys Phe Leu Pro Glu Gln Gly Pro
    130                 135                 140

Val Tyr Arg Lys Ile Cys Gln Thr Trp Leu Asn Glu Glu His Arg Gly
145                 150                 155                 160

Leu Ala Leu Thr Phe Thr Ser Asn Lys Thr Phe Thr Glu Met Met Gly
```

```
                165                 170                 175

Arg Phe Leu Met Ala Tyr Met Gln Ser Tyr Ala Gly Val Val Gln Lys
            180                 185                 190

Asn Trp Glu Ala Thr Gly Cys Ala Val Trp Gln His Arg Ser Ala Lys
        195                 200                 205

Glu Asp Gly Val Leu Cys Cys Phe His Gly Thr Glu Met Ile Arg Lys
    210                 215                 220

Glu His Val Thr Glu Met Asp Val Thr Ser Glu Asn Gly Gln Lys Ala
225                 230                 235                 240

Leu Lys Glu Asn Pro Gly Lys Ala Lys Val Val Gln Asn Arg Trp Gly
                245                 250                 255

Arg Asn Val Val Gln Ile Arg Asn Asp Asp Ala Arg Cys Cys Pro Glu
            260                 265                 270

Asp Val Ser Cys Gly Pro Asn Val Phe Ser Gly Lys Ser Cys Gly Leu
        275                 280                 285

Phe Tyr Thr Glu Gly Leu Lys Ala Gln Met Ala Phe Arg Gln Leu Glu
    290                 295                 300

Ala Phe Leu Arg Ala Ser Tyr Pro Glu Met Gln Arg Gly Gln Gly Arg
305                 310                 315                 320

Ile Leu Ile Pro Leu Arg Cys Asp Cys Leu His Lys Pro Asp Val Ile
                325                 330                 335

Pro Arg Met Gly Arg Gln Met Cys Lys Val Thr Pro Tyr Gly Leu Ser
            340                 345                 350

Asn Ala Asp Asp Leu Asp Val Ala Glu Val Asn Asp Ala Thr Ala Leu
        355                 360                 365

Ala Ser Ile Lys Tyr Pro Ser Val Leu Val Phe Gln Cys Ala Asn Pro
    370                 375                 380

Val Tyr Arg Asn Ser Arg Gly Gly Ala Ala Pro Asn Cys Asp Phe Lys
385                 390                 395                 400

Ile Ser Gly Pro Asp Ile Ile Gly Ala Leu Gln Leu Val Arg Gln Phe
                405                 410                 415

Trp Lys Glu Asn Met Glu Asp Lys Pro Leu Pro Lys Met Ile Ile Pro
            420                 425                 430

Glu Phe Arg Trp His Pro Arg Phe Gln Tyr Arg Asn Val Ala Leu Pro
        435                 440                 445

Ser Ser His Gly Asp Asp Cys Pro Glu Pro Phe Glu Phe
    450                 455                 460


<210> SEQ ID NO 10
<211> LENGTH: 225
<212> TYPE: PRT
<213> ORGANISM: Adenovirus

<400> SEQUENCE: 10

Met Arg Leu Val Pro Glu Met Tyr Gly Val Ser Trp Asp Glu Thr Ala
1               5                   10                  15

Glu Glu Leu Leu Asn Ala Glu Ile Tyr Asp Val Pro Asn Leu Pro Pro
            20                  25                  30

Gly Thr Pro Ser Leu His Asp Leu Phe Asp Val Glu Asn Asp Gly Gly
        35                  40                  45

Gln Asp Glu Asn Glu Asp Ala Val Asn Ser Met Phe Pro Asp Ser Met
    50                  55                  60

Leu Ser Ala Gly Glu Gly Tyr Ala Gly Asp Val Asp Pro Ser Gly Ser
65                  70                  75                  80
```

```
Asp Met Asp Leu Lys Cys Tyr Glu Asp Gly Leu Pro Ser Ser Ser Ser
                85                  90                  95

Glu Gly Ser Asp Glu Asp Glu Gln Lys Pro Leu Lys His Glu Leu Val
            100                 105                 110

Leu Asp Cys Pro Lys Asn Pro Gly His Asp Cys Arg Ala Cys Ala Phe
        115                 120                 125

His Arg Ala Thr Ser Gly Asn Thr Glu Ala Ile Cys Cys Leu Cys Tyr
    130                 135                 140

Met Arg Leu Thr Ser Asp Phe Val Tyr Ser Asp Val Ser Asp Val Glu
145                 150                 155                 160

Gly Asp Gly Asp Lys Ser Lys Val Ser Glu Ser Pro Gly Ser Leu Gly
                165                 170                 175

Thr Val Val Pro Asp Gly Val Leu Lys Pro Thr Ala Val Arg Val Ser
            180                 185                 190

Ala Arg Arg Arg Gln Ala Val Glu Lys Leu Glu Asp Leu Leu Gln Glu
        195                 200                 205

Pro Glu Gln Thr Glu Pro Leu Asp Leu Ser Leu Lys Gln Pro Arg Met
    210                 215                 220

Thr
225


<210> SEQ ID NO 11
<211> LENGTH: 474
<212> TYPE: PRT
<213> ORGANISM: Adenovirus

<400> SEQUENCE: 11

Met Glu Gln Arg Gln Pro Pro Val Val Gly Leu His Ala Gly Leu His
1               5                   10                  15

Asp His Gly Ala Val Ala Gly Ala Pro Glu Glu Glu Glu Gly Leu His
            20                  25                  30

Leu Leu Ala Gly Ala Ala Ser Ala Arg Ser Gly Ala Ser Gly Gly Arg
        35                  40                  45

Gly Gly Gly Glu Arg Glu Pro Glu Gly Arg Arg Gly Pro Ser Ser Gly
    50                  55                  60

Ile Glu Ala Val Gly Glu Pro Glu Glu Gly Thr Ser Asp Gly Val Arg
65                  70                  75                  80

Lys Arg Arg Arg Thr Glu Met Glu Glu Val Asn Ala Arg Asp Tyr Leu
                85                  90                  95

Thr Asp Leu Thr Val Arg Leu Met Ser Arg Arg Arg Pro Glu Thr Val
            100                 105                 110

Ala Trp Ser Glu Leu Glu Thr Glu Phe Lys Asn Gly Asn Met Asn Leu
        115                 120                 125

Leu Tyr Lys Tyr Ser Phe Glu Gln Ile Gln Thr His Trp Leu Glu Pro
    130                 135                 140

Trp Glu Asp Trp Glu Thr Ala Phe Ala Asn Phe Ala Lys Ile Ala Leu
145                 150                 155                 160

Arg Pro Asp Lys Ile Tyr Thr Ile Arg Arg Met Val Asn Ile Arg Lys
                165                 170                 175

Cys Val Tyr Val Leu Gly Asn Gly Ala Met Val Gln Ile Gln Thr Cys
            180                 185                 190

Asp Arg Val Ala Phe Asn Cys Cys Met Gln Ser Met Gly Pro Gly Val
        195                 200                 205

Ile Gly Met Ser Gly Val Thr Phe Ala Asn Val Arg Phe Thr Gly Glu
    210                 215                 220
```

```
Asn Phe Phe Gly Ala Val Ile Met Asn Asn Thr Ser Leu Thr Leu His
225                 230                 235                 240

Gly Val Tyr Phe Leu Asn Leu Ser Asn Thr Cys Val Glu Cys Trp Gly
                245                 250                 255

Arg Ala Cys Leu Arg Gly Cys Thr Phe Tyr Gly Cys Trp Lys Ala Val
            260                 265                 270

Val Gly Arg Thr Lys Ser His Val Ser Val Lys Lys Cys Met Phe Glu
        275                 280                 285

Arg Cys Val Ile Ala Ile Met Val Glu Gly Gln Gly Arg Ile Arg Asn
    290                 295                 300

Asn Val Gly Ala Glu Asn Gly Cys Phe Leu Leu Leu Lys Gly Ser Ala
305                 310                 315                 320

Ser Val Lys His Asn Met Ile Cys Gly Thr Gly Thr Cys Asn Ile Ser
                325                 330                 335

His Leu Leu Thr Cys Ser Asp Gly Asn Cys Gln Ala Leu Arg Thr Leu
            340                 345                 350

His Ile Val Ser His Arg Arg Leu Pro Trp Pro Val Leu Glu His Asn
        355                 360                 365

Met Leu Thr Arg Cys Ser Val His Val Gly Ala Arg Arg Gly Met Leu
    370                 375                 380

Val Pro Tyr Gln Cys Asn Phe Ser Tyr Thr Lys Val Leu Leu Glu Thr
385                 390                 395                 400

Asp Ala Phe Pro Arg Val Cys Phe Asn Gly Val Phe Asp Met Thr Val
                405                 410                 415

Glu Val Phe Lys Val Val Arg Tyr Asp Glu Ser Lys Ser Arg Cys Arg
            420                 425                 430

Pro Cys Glu Cys Gly Ala Asn His Leu Arg Leu Tyr Pro Val Thr Leu
        435                 440                 445

Asn Val Thr Glu Glu Leu Arg Ala Asp His Leu Thr Leu Ser Cys Leu
    450                 455                 460

Arg Thr Asp Tyr Glu Ser Ser Asp Glu Glu
465                 470
```

<210> SEQ ID NO 12
<211> LENGTH: 104
<212> TYPE: PRT
<213> ORGANISM: Adenovirus

<400> SEQUENCE: 12

```
Met Thr Asp Gly Ala Ala Val Thr Ala Arg Leu Arg His Leu His His
1               5                   10                  15

Cys Arg Arg Phe Arg Cys Phe Ala Arg Glu Pro Leu Val Phe Ser Tyr
            20                  25                  30

Phe Glu Leu Pro Glu His His Leu Gln Gly Pro Ala His Gly Ile Lys
        35                  40                  45

Leu Glu Val Glu Lys Glu Leu Glu Ser Arg Leu Ile Arg Asp Phe Thr
    50                  55                  60

Pro His Pro Leu Leu Val Glu Lys Glu His Gly Thr Thr Ile Ile Thr
65                  70                  75                  80

Val Phe Cys Ile Cys Pro Thr Pro Gly Leu His Glu Gly Leu Cys Cys
                85                  90                  95

Arg Leu Cys Ala Glu Phe Asn Leu
            100
```

```
<210> SEQ ID NO 13
<211> LENGTH: 121
<212> TYPE: PRT
<213> ORGANISM: Adenovirus

<400> SEQUENCE: 13

Met Thr Asp Ser His Asp Ile Asn Ile Thr Met Glu Arg Gly Ile Ala
1               5                   10                  15

Gln Arg Gln Arg Glu Ala Arg Ala Met Asp Tyr Leu Arg Leu Gln Glu
            20                  25                  30

Leu Lys Glu Thr His Trp Cys Asp Arg Gly Ser Leu Cys Leu Val Lys
        35                  40                  45

Leu Ala Ser Leu Ser Tyr Asp Ile Ser Thr Gln Gly His Glu Leu Ser
    50                  55                  60

Tyr Thr Val Ala Gly Gln Lys Gln Thr Phe Ser Thr Ile Met Gly Gly
65                  70                  75                  80

Thr Ser Leu Lys Ile Thr His Gln Ser Lys Pro Val Glu Gly Ala Ile
                85                  90                  95

Leu Cys His Cys His Lys Pro Asp Cys Met Glu Lys Leu Ile Thr Thr
            100                 105                 110

Leu Cys Ala Val Ala Glu Ile Phe Lys
        115                 120


<210> SEQ ID NO 14
<211> LENGTH: 157
<212> TYPE: PRT
<213> ORGANISM: Adenovirus

<400> SEQUENCE: 14

Met Lys Ala Phe Val Val Val Phe Ala Leu Ser Leu Ile Tyr Ser Arg
1               5                   10                  15

Gly Thr Ala Asp Asp Leu Val Phe Glu Gly Thr Ile Glu Thr Val Leu
            20                  25                  30

Phe Ser Asp Ser Thr Ser Ser Ile Thr Leu Asn Cys Ser Cys Thr Asn
        35                  40                  45

Glu Leu Ile Gln Trp Asn Ala Asn Arg Thr Phe Cys Lys Ala Phe Tyr
    50                  55                  60

Arg Asn Phe Thr Tyr Tyr Ser Asn Asn Ser Leu Cys Ala Val Cys Thr
65                  70                  75                  80

Arg Gln Ala Leu His Leu Tyr Pro Pro Phe Val Ala Gly Ser Tyr Leu
                85                  90                  95

Cys Ile Gly Ser Gly Ala Gln Pro Cys Phe His Arg Trp Tyr Leu Tyr
            100                 105                 110

Glu Asp Asn Thr Ser Phe Thr Thr Ser Thr Pro Lys Gln Val Ser Tyr
        115                 120                 125

Leu His Val Ser Leu Lys Pro Leu Phe Ala Leu Ala Ala Phe Ile Leu
    130                 135                 140

Val Ile Leu Ala Asn Phe Ile Leu Ile Asn Asn Leu Pro
145                 150                 155


<210> SEQ ID NO 15
<211> LENGTH: 290
<212> TYPE: PRT
<213> ORGANISM: Adenovirus

<400> SEQUENCE: 15

Met Met Leu Thr Val Leu Thr Thr Leu Leu Leu Pro Ala Val Ile Cys
1               5                   10                  15
```

-continued

```
Ile Arg Pro Pro Glu Pro Pro Pro Ala His Gly Ile Asn Thr Lys Ser
            20                  25                  30

Leu Pro Asn Ser Leu Gln Asn Pro Ser Arg Val Tyr Ala Lys Val Gly
        35                  40                  45

Gln Asn Leu Thr Leu Glu Ser Arg Tyr Ser Ser His Ser Asn Ser Met
    50                  55                  60

Pro His Val Val Trp Tyr Leu Glu Val Phe Asn Asp Asp Thr Ile Phe
65                  70                  75                  80

Pro Ser Ser Val Val Pro Pro Ile Phe Ser Gly Ile Lys Leu Cys Glu
                85                  90                  95

Ile Thr Glu Gln Asn Tyr Gln Thr Phe Asn His Ala Pro Lys Glu Phe
            100                 105                 110

Asn Cys Ile Asn Lys Ser Leu Asn Leu Phe Asn Leu Lys Pro Ser Asp
        115                 120                 125

Ser Gly Leu Tyr Asn Val Lys Val Tyr Lys Asp Asp Ile Glu His Asn
    130                 135                 140

Thr Tyr Phe Arg Leu Ser Val Ile Arg Phe Ala Gln Pro Gln Cys Thr
145                 150                 155                 160

Ile Asn Ser Ser Tyr Leu Thr Glu Ser Tyr Cys Leu Ile Ser Ile Asp
                165                 170                 175

Cys Phe His Leu Glu Tyr Pro Ala Ile Val Glu Phe Asn Gly Ser Arg
            180                 185                 190

Ser Asn Phe His Tyr Tyr Val Leu Ser Lys Gly Gly Lys Asn Leu Ala
        195                 200                 205

Asp Tyr Tyr Thr Val Thr Tyr Asp Tyr His Gly Leu Lys Gln Thr Phe
    210                 215                 220

Lys Val Glu Tyr Pro Phe Asn Asp Ile Cys Asn Asp Ile Ile Ser Leu
225                 230                 235                 240

Glu Thr Leu Ala Asp Phe Thr Pro Val Phe Ile Val Thr Ile Val Met
                245                 250                 255

Ser Val Ile Thr Ile Val Val Ser Leu Leu Phe Cys Cys Phe Tyr Lys
            260                 265                 270

Pro Lys Ser Lys Ser Asn Phe Gln Gln Val Lys Leu Lys Thr Ile Gln
        275                 280                 285

Leu Val
    290


<210> SEQ ID NO 16
<211> LENGTH: 90
<212> TYPE: PRT
<213> ORGANISM: Adenovirus

<400> SEQUENCE: 16

Met Val Ala Val Phe Phe Phe Leu Leu Cys Leu Pro Ile Ile Phe Val
1               5                   10                  15

Ser Ser Thr Phe Ala Ala Val Ser His Val Glu Ala Glu Cys Leu Pro
            20                  25                  30

Pro Phe Ala Val Tyr Leu Ile Phe Thr Phe Val Cys Cys Thr Ala Ile
        35                  40                  45

Ala Ser Ile Ala Cys Phe Phe Val Thr Ile Phe Gln Ala Ala Asp Tyr
    50                  55                  60

Leu Tyr Val Arg Phe Val Tyr Phe Arg His His Pro Glu Tyr Arg Asn
65                  70                  75                  80

Gln Asn Val Ala Ser Leu Leu Cys Leu Ala
```

85 90

<210> SEQ ID NO 17
<211> LENGTH: 113
<212> TYPE: PRT
<213> ORGANISM: Adenovirus

<400> SEQUENCE: 17

Met Phe Ser Met Ile Pro Leu Leu Val Ile Leu Cys Asp Leu Leu Pro
1 5 10 15

Phe Thr Tyr Cys His Cys Pro Leu Asn Lys Pro Trp Ser Leu Tyr Thr
20 25 30

Cys Tyr Ala Glu Leu Pro Asp Ile Pro Val Ile Trp Leu Tyr Val Ala
35 40 45

Thr Ala Ala Leu Val Phe Val Ala Thr Cys Val Gly Val Lys Ile Tyr
50 55 60

Phe Cys Leu Lys Ile Gly Trp Leu His Pro Pro Glu Asp Leu Pro Arg
65 70 75 80

Phe Pro Leu Val Asn Ala Phe Gln Met Gln Pro Pro Pro Pro Asp Leu
85 90 95

Ile Arg Ala Pro Ser Val Val Ser Tyr Phe Gln Leu Ala Gly Gly Asp
100 105 110

Asp

<210> SEQ ID NO 18
<211> LENGTH: 285
<212> TYPE: PRT
<213> ORGANISM: Adenovirus

<400> SEQUENCE: 18

Met Gln Arg Asp Arg Arg Tyr Arg Cys Arg Leu Gly Pro Tyr Asn Arg
1 5 10 15

His Gln Leu Pro Pro Cys Asp Glu Thr Pro Cys Ala Thr Ile Glu Asn
20 25 30

Pro Pro Tyr Leu Glu Cys Glu Asn Leu Asn Met His Asn Val Ser Glu
35 40 45

Val Arg Gly Val Pro Ser Cys Val Ser Phe Thr Val Leu Gln Glu Trp
50 55 60

Pro Val Tyr Trp Asp Ser Val Leu Thr Ala Trp Glu Lys His Val Met
65 70 75 80

Lys Thr Tyr Met Gln Ile Cys Ile Cys Cys Ala Thr Ile Asp Val Glu
85 90 95

Tyr Asn Gln Ile Ile Arg Gly Tyr Glu Arg Trp Val Leu His Cys His
100 105 110

Cys Asn Ser Pro Gly Ser Leu Gln Cys Lys Ala Gly Gly Val Val Leu
115 120 125

Ala Asn Trp Phe Arg Met Ala Ile Tyr Gly Ser Leu Val Asn Val Arg
130 135 140

Phe Pro Trp Tyr Arg Gln Val Val Asn Tyr His Leu Pro Lys Glu Val
145 150 155 160

Leu Tyr Val Gly Ser Val Phe Ile Arg Gly Arg His Leu Ile Tyr Val
165 170 175

Arg Ile Phe Leu Asp Gly His Ala Val Ala Val Leu Glu Asn Ser Ser
180 185 190

Phe Gly Trp Ser Ala Phe Ser Tyr Gly Ile Leu Asn Asn Leu Ile Ile
195 200 205

```
Met Val Cys Thr Tyr Cys Lys Asp Leu Ser Glu Ile Gln Met Arg Cys
    210                 215                 220

Cys Ala Lys Arg Thr Arg Arg Phe Leu Ile Arg Ala Val Arg Leu Leu
225                 230                 235                 240

Asp Arg Leu Thr Ser Tyr Gln Pro Arg Arg Ala Arg Leu Glu Ala Ala
                245                 250                 255

Arg Gln Ser Leu Leu Arg Gly Leu Met Glu Arg His Arg Pro Phe Thr
            260                 265                 270

Leu Ala Glu Tyr Gly Arg Gly Glu Asn Pro Trp Arg Thr
        275                 280                 285


<210> SEQ ID NO 19
<211> LENGTH: 120
<212> TYPE: PRT
<213> ORGANISM: Adenovirus

<400> SEQUENCE: 19

Met Gln Arg Asp Arg Arg Tyr Arg Cys Arg Leu Gly Pro Tyr Asn Arg
1               5                   10                  15

His Gln Leu Pro Pro Cys Asp Glu Thr Pro Cys Ala Thr Ile Glu Asn
            20                  25                  30

Pro Pro Tyr Leu Glu Cys Glu Asn Leu Asn Met His Asn Val Ser Glu
        35                  40                  45

Asp Cys Leu Asp Asp Thr Pro Leu Leu Glu Asp Val Gly Glu Gly Phe
    50                  55                  60

Val Ser Val Thr Asp Glu Arg Phe Ala Arg Lys Glu Thr Val Trp Thr
65                  70                  75                  80

Leu Thr Pro Lys Asn Pro Cys Leu Asn Thr Gln Phe Gln Leu Phe Thr
                85                  90                  95

Ala Thr Lys Gly Glu Arg Met Val Tyr Ser Val Lys Trp Lys Gly Gly
            100                 105                 110

Gly Ser Leu Thr Val Arg Ile Met
        115                 120


<210> SEQ ID NO 20
<211> LENGTH: 126
<212> TYPE: PRT
<213> ORGANISM: Adenovirus

<400> SEQUENCE: 20

Met Ala Asp Glu Ala Ile Tyr Val His Leu Leu Gly Ser Arg Ala Ile
1               5                   10                  15

Met Pro Gln Gln Gln Gly Phe Ser Asn Leu Tyr Val Leu Phe Ser Pro
            20                  25                  30

Glu Asn Phe Val Ile Ser Pro Arg Gly Val Leu Leu Val Ser Leu Gln
        35                  40                  45

Leu Ser Met Asp Ile Pro Gln Gly Tyr Leu Gly Arg Leu Phe Ser Leu
    50                  55                  60

Ser Asp Met Asn Val Arg Gly Val Phe Val Gly Ala Gln Asp Ile Gln
65                  70                  75                  80

Pro Ser Thr Trp Trp Glu Met Ser Val Val Leu Phe Asn His Ser Asp
                85                  90                  95

Glu Phe Phe Tyr Gly Phe Arg Gly Gln Pro Val Ala Cys Leu Leu Leu
            100                 105                 110

Glu Arg Val Ile Tyr Pro Cys Leu His Arg Ala Ser Leu Val
        115                 120                 125
```

<210> SEQ ID NO 21
<211> LENGTH: 130
<212> TYPE: PRT
<213> ORGANISM: Adenovirus

<400> SEQUENCE: 21

```
Met Tyr Gln Arg Gln Pro Val Phe Val Cys Val Ile Val Pro Ala Ala
1               5                   10                  15

Leu Arg Gln Tyr Leu His Asp Leu Asp Ile Glu Val Leu Asp Phe Leu
            20                  25                  30

Lys Arg Gln Leu Ser Asp Phe Trp Leu His Leu Leu His Cys Leu Thr
        35                  40                  45

Pro Pro Phe Gln Phe Cys Tyr Asn Gly Ala Val Leu Leu Ser Leu Ala
    50                  55                  60

Pro Ser Ile Gln Leu Leu Cys Cys Val Ala Thr Pro Glu Met Thr Pro
65                  70                  75                  80

Asp Gly Glu Leu Thr Ala Leu Val Cys Ala Asp Leu Leu Asn Phe Leu
                85                  90                  95

Gln Leu Thr Leu Arg Val Glu Ile Arg Asp Arg Gly Val His Pro Asp
            100                 105                 110

Pro Asp Met Leu Asn Leu Leu Gln Val Ser Gln Glu Leu Asp Ile Leu
        115                 120                 125

Gln Ala
    130
```

<210> SEQ ID NO 22
<211> LENGTH: 116
<212> TYPE: PRT
<213> ORGANISM: Adenovirus

<400> SEQUENCE: 22

```
Met Met Val Cys Leu Arg Met Ser Ile Glu Gly Ala Leu Val Gln Leu
1               5                   10                  15

Phe Gln Met Arg Gly Val Asn Leu Gln Glu Leu Cys Cys Asp Ile Val
            20                  25                  30

Arg Glu Trp Arg Ala Glu Asn Tyr Leu Gly Met Val Gln Asn Cys Ser
        35                  40                  45

Val Ile Ile Glu Asp Phe Glu His Asp Ala Phe Ala Leu Leu Val Phe
    50                  55                  60

Leu Asp Val Arg Val Gln Ala Leu Leu Glu Ala Val Val Asp His Leu
65                  70                  75                  80

Glu Asn Arg Ile His Phe Asp Leu Ala Val Leu Tyr His Gln Arg Thr
                85                  90                  95

Gly Gly Asp Arg Cys His Leu Arg Asp Leu His Phe Val Thr Leu Arg
            100                 105                 110

Asp Arg Leu Glu
        115
```

<210> SEQ ID NO 23
<211> LENGTH: 120
<212> TYPE: PRT
<213> ORGANISM: Adenovirus

<400> SEQUENCE: 23

```
Met Pro Leu Pro Cys Leu Pro Pro Pro Pro Val Cys Arg Asp Lys Ser
1               5                   10                  15
```

Ala Cys Ile Ala Trp Leu Glu Leu Ala Leu Thr Ser Ser Leu Glu Leu
20 25 30

Phe Arg Asp Ile Ile Arg Tyr Glu Val Phe Ile Thr Pro Glu Ala Glu
35 40 45

Arg Glu Leu Cys Ala Leu Gln Gln Trp Leu His Phe Ala Val Asn Thr
50 55 60

Glu Arg Gln Arg Arg Arg Asp Gly Arg Arg Val Glu Ile Cys Trp Arg
65 70 75 80

Arg Thr Trp Phe Cys Tyr Arg Lys Tyr Glu Asp Leu Arg Lys Asn Leu
85 90 95

Thr Tyr Asp Ala Thr Arg Gln Thr Val Ser Leu Gln Thr Gly Ser Leu
100 105 110

Gln Gln Thr Pro Ala Thr Ala Val
115 120

<210> SEQ ID NO 24
<211> LENGTH: 927
<212> TYPE: PRT
<213> ORGANISM: Adenovirus

<400> SEQUENCE: 24

Met Ala Thr Pro Ser Met Met Pro Gln Trp Ser Tyr Met His Ile Ala
1 5 10 15

Gly Gln Asp Ala Ser Glu Tyr Leu Ser Pro Gly Leu Val Gln Phe Ala
20 25 30

Arg Ala Thr Asp Thr Tyr Phe Ser Leu Gly Asn Lys Phe Arg Asn Pro
35 40 45

Thr Val Ala Pro Thr His Asp Val Thr Thr Asp Arg Ser Gln Arg Leu
50 55 60

Thr Leu Arg Phe Val Pro Val Asp Arg Glu Asp Thr Ala Tyr Ser Tyr
65 70 75 80

Lys Val Arg Tyr Thr Leu Ala Val Gly Asp Asn Arg Val Leu Asp Met
85 90 95

Ala Ser Thr Tyr Phe Asp Ile Arg Gly Val Leu Asp Arg Gly Pro Ser
100 105 110

Phe Lys Pro Tyr Ser Gly Thr Ala Tyr Asn Ser Leu Ala Pro Lys Gly
115 120 125

Ala Pro Asn Pro Ser Gln Trp Thr Thr Thr Asn Gly Gly Asn Lys Thr
130 135 140

Asn Ser Phe Gly Gln Ala Pro Phe Ile Gly Glu Ser Leu Thr Lys Asp
145 150 155 160

Gly Ile Gln Val Gly Val Asp Thr Gly Asn Pro Gly Thr Ala Val Tyr
165 170 175

Ala Asp Lys Leu Tyr Gln Pro Glu Pro Gln Val Gly Leu Ser Lys Trp
180 185 190

Asn Gln Asn Pro Ser Glu Asn Ala Ala Gly Arg Ile Leu Lys Pro Ser
195 200 205

Thr Pro Met Gln Pro Cys Tyr Gly Ser Tyr Ala Tyr Pro Thr Asn Thr
210 215 220

Asn Gly Gly Gln Val Lys Thr Ser Ala Thr Asp Ala Thr Gly Ala Asn
225 230 235 240

Asn Val Thr Leu Asn Phe Phe Asn Asn Ala Ala Asp Asn Gly Asn Asn
245 250 255

Asn Pro Lys Val Val Leu Tyr Ser Glu Asp Val Asn Leu Glu Ala Pro
260 265 270

```
Asp Thr His Leu Val Phe Lys Pro Asp Ala Asn Asn Ala Thr Ser Ala
        275                 280                 285

Glu Thr Leu Leu Gly Gln Gln Ala Ala Pro Asn Arg Pro Asn Tyr Ile
    290                 295                 300

Gly Phe Arg Asp Asn Phe Ile Gly Leu Met Tyr Tyr Asn Ser Thr Gly
305                 310                 315                 320

Asn Met Gly Val Leu Ala Gly Gln Ala Ser Gln Leu Asn Ala Val Val
                325                 330                 335

Asp Leu Gln Asp Arg Asn Thr Glu Leu Ser Tyr Gln Leu Met Leu Asp
            340                 345                 350

Ala Leu Gly Asp Arg Ser Arg Tyr Phe Ser Met Trp Asn Gln Ala Val
        355                 360                 365

Asp Ser Tyr Asp Pro Asp Val Arg Ile Ile Glu Asn His Gly Val Glu
    370                 375                 380

Asp Glu Leu Pro Asn Tyr Cys Phe Pro Leu Asn Gly Gln Gly Ile Ser
385                 390                 395                 400

Asn Thr Tyr Lys Gly Val Lys Thr Asn Asn Gly Gly Ala Ala Trp Thr
                405                 410                 415

Gln Asp Thr Asp Val Val Thr Thr Asn Glu Ile Ser Ile Gly Asn Val
            420                 425                 430

Phe Ala Met Glu Ile Asn Leu Ala Ala Asn Leu Trp Arg Ser Phe Leu
        435                 440                 445

Tyr Ser Asn Val Ala Leu Tyr Leu Pro Asp Ser Tyr Lys Tyr Thr Pro
    450                 455                 460

Asp Asn Ile Glu Leu Pro Gln Asn Lys Asn Ser Tyr Gly Tyr Ile Asn
465                 470                 475                 480

Gly Arg Val Thr Ala Pro Asn Ala Ile Asp Thr Tyr Val Asn Ile Gly
                485                 490                 495

Ala Arg Trp Ser Pro Asp Pro Met Asp Asn Val Asn Pro Phe Asn His
            500                 505                 510

His Arg Asn Ala Gly Leu Arg Tyr Arg Ser Met Leu Leu Gly Asn Gly
        515                 520                 525

Arg Tyr Val Pro Phe His Ile Gln Val Pro Gln Lys Phe Phe Ala Ile
    530                 535                 540

Lys Asn Leu Leu Leu Leu Pro Gly Ser Tyr Thr Tyr Glu Trp Asn Phe
545                 550                 555                 560

Arg Lys Asp Val Asn Met Ile Leu Gln Ser Thr Leu Gly Asn Asp Leu
                565                 570                 575

Arg Val Asp Gly Ala Ser Ile Arg Phe Asp Ser Ile Asn Leu Tyr Ala
            580                 585                 590

Asn Phe Phe Pro Met Ala His Asn Thr Ala Ser Thr Leu Glu Ala Met
        595                 600                 605

Leu Arg Asn Asp Thr Asn Asp Gln Ser Phe Asn Asp Tyr Leu Cys Ala
    610                 615                 620

Ala Asn Met Leu Tyr Pro Ile Pro Ser Asn Ala Thr Ser Val Pro Ile
625                 630                 635                 640

Ser Ile Pro Ser Arg Asn Trp Ala Ala Phe Arg Gly Trp Ser Phe Thr
                645                 650                 655

Arg Leu Lys Thr Lys Glu Thr Pro Ser Leu Gly Ser Gly Phe Asp Pro
            660                 665                 670

Tyr Phe Val Tyr Ser Gly Ser Ile Pro Tyr Leu Asp Gly Thr Phe Tyr
        675                 680                 685
```

```
Leu Asn His Thr Phe Lys Lys Val Ser Ile Met Phe Asp Ser Ser Val
    690                 695                 700

Ser Trp Pro Gly Asn Asp Arg Leu Leu Thr Pro Asn Glu Phe Glu Ile
705                 710                 715                 720

Lys Arg Ser Val Asp Gly Glu Gly Tyr Asn Val Ala Gln Ser Asn Met
                725                 730                 735

Thr Lys Asp Trp Phe Leu Ile Gln Met Leu Ser His Tyr Asn Ile Gly
            740                 745                 750

Tyr Gln Gly Phe Tyr Val Pro Glu Ser Tyr Lys Asp Arg Met Tyr Ser
        755                 760                 765

Phe Phe Arg Asn Phe Gln Pro Met Ser Arg Gln Val Val Asp Thr Val
    770                 775                 780

Asn Tyr Ala Asn Tyr Lys Glu Val Lys Met Pro Phe Gln His Asn Asn
785                 790                 795                 800

Ser Gly Phe Val Gly Tyr Met Gly Pro Thr Met Arg Glu Gly Gln Ala
                805                 810                 815

Tyr Pro Ala Asn Tyr Pro Tyr Pro Leu Ile Gly Glu Thr Ala Val Pro
            820                 825                 830

Ser Val Thr Gln Lys Lys Phe Leu Cys Asp Arg Val Met Trp Arg Ile
        835                 840                 845

Pro Phe Ser Ser Asn Phe Met Ser Met Gly Ala Leu Thr Asp Leu Gly
    850                 855                 860

Gln Asn Met Leu Tyr Ala Asn Ser Ala His Ala Leu Asp Met Thr Phe
865                 870                 875                 880

Glu Val Asp Pro Met Asp Glu Pro Thr Leu Leu Tyr Val Leu Phe Glu
                885                 890                 895

Val Phe Asp Val Val Arg Ile His Gln Pro His Arg Gly Val Ile Glu
            900                 905                 910

Ala Val Tyr Leu Arg Thr Pro Phe Ser Ala Gly Asn Ala Thr Thr
        915                 920                 925


<210> SEQ ID NO 25
<211> LENGTH: 503
<212> TYPE: PRT
<213> ORGANISM: Adenovirus

<400> SEQUENCE: 25

Met Arg Arg Ala Val Arg Val Pro Pro Val Tyr Pro Glu Gly Pro Pro
1               5                   10                  15

Pro Ser Tyr Glu Ser Val Met Glu Ala Leu Asn Thr Pro Ala Thr Leu
            20                  25                  30

Glu Ala Pro Tyr Val Pro Pro Arg Tyr Leu Gly Pro Thr Glu Gly Arg
        35                  40                  45

Asn Ser Ile Arg Tyr Ser Glu Leu Ala Pro Leu Tyr Asp Thr Thr Lys
    50                  55                  60

Val Tyr Leu Val Asp Asn Lys Ser Ala Asp Ile Ala Ser Leu Asn Tyr
65                  70                  75                  80

Gln Asn Asp His Ser Asn Phe Leu Thr Thr Val Val Gln Asn Asn Asp
                85                  90                  95

Phe Thr Pro Val Glu Ala Gly Thr Gln Thr Ile Asn Phe Asp Glu Arg
            100                 105                 110

Ser Arg Trp Gly Gly Gln Leu Lys Thr Ile Leu His Thr Asn Met Pro
        115                 120                 125

Asn Ile Asn Glu Phe Met Tyr Thr Asn Lys Phe Arg Ala Arg Leu Met
    130                 135                 140
```

Val Glu Lys Pro Gln Thr Gly Ser Pro Arg Tyr Glu Trp Phe Glu Phe
145 150 155 160

Thr Ile Pro Glu Gly Asn Tyr Ser Glu Thr Met Thr Ile Asp Leu Met
165 170 175

Asn Asn Ala Ile Val Asp Asn Tyr Leu Gln Val Gly Arg Gln Asn Gly
180 185 190

Val Leu Glu Ser Asp Ile Gly Val Lys Phe Asp Thr Arg Asn Phe Arg
195 200 205

Leu Gly Trp Asp Pro Val Thr Arg Leu Val Met Pro Gly Val Tyr Thr
210 215 220

Asn Glu Ala Phe His Pro Asp Ile Val Leu Leu Pro Gly Cys Gly Val
225 230 235 240

Asp Phe Thr Gln Ser Arg Leu Ser Asn Leu Leu Gly Ile Arg Lys Arg
245 250 255

Arg Pro Phe Gln Glu Gly Phe Gln Ile Met Tyr Glu Asp Leu Glu Gly
260 265 270

Gly Asn Ile Pro Ala Leu Leu Asp Val Pro Ala Tyr Glu Ala Ser Leu
275 280 285

Ser Leu Ala Glu Ala Glu Gly Arg Val Thr Arg Gly Asp Thr Phe Ala
290 295 300

Thr Ala Pro Gln Glu Leu Thr Ile Gln Pro Leu Thr Lys Asp Ser Lys
305 310 315 320

Asn Arg Ser Tyr Asn Leu Leu Pro Asn Asn Thr Asp Thr Ala Tyr Arg
325 330 335

Ser Trp Phe Leu Ala Tyr Asn Tyr Gly Asp Pro Glu Lys Gly Val Arg
340 345 350

Ser Trp Thr Leu Leu Thr Thr Thr Asp Val Thr Cys Gly Ser Gln Gln
355 360 365

Val Tyr Trp Ser Leu Pro Asp Met Met Gln Asp Pro Val Thr Phe Arg
370 375 380

Ser Ser Thr Gln Val Asn Asn Phe Pro Val Val Gly Thr Glu Leu Leu
385 390 395 400

Pro Val Tyr Ala Lys Ser Phe Tyr Asn Glu Gln Ala Val Tyr Ser Gln
405 410 415

Leu Ile Arg Gln Ser Thr Ala Leu Thr His Val Phe Asn Arg Phe Pro
420 425 430

Glu Asn Gln Ile Leu Val Arg Pro Pro Ala Pro Thr Ile Thr Thr Val
435 440 445

Ser Glu Asn Val Pro Ala Leu Thr Asp His Gly Thr Leu Pro Leu Arg
450 455 460

Ser Ser Ile Ser Gly Val Gln Arg Val Thr Ile Thr Asp Ala Arg Arg
465 470 475 480

Arg Thr Cys Pro Tyr Val Tyr Lys Ala Leu Gly Val Val Ala Pro Lys
485 490 495

Val Leu Ser Ser Arg Thr Phe
500

<210> SEQ ID NO 26
<211> LENGTH: 396
<212> TYPE: PRT
<213> ORGANISM: Adenovirus

<400> SEQUENCE: 26

Met Lys Arg Thr Arg Ile Asp Glu Asp Phe Asn Pro Val Tyr Pro Tyr

-continued

```
1               5                   10                  15

Asp Ser Thr Thr Thr Pro Thr Val Pro Phe Ile Ala Pro Pro Phe Val
            20                  25                  30

Ser Ser Asn Gly Leu Gln Glu Ser Pro Pro Gly Met Leu Ser Leu Asn
        35                  40                  45

Tyr Ala Asp Pro Ile Thr Thr Asn Asn Gly Lys Leu Thr Val Lys Leu
    50                  55                  60

Gly Asn Asn Leu Ser Leu Ser Ser Asp Gly Ala Ile Thr Ser Ala Thr
65                  70                  75                  80

Ala Val Thr Asp Pro Leu Thr Asn Asn Gly Gly Thr Ile Gly Leu Ala
                85                  90                  95

Leu Ser Ala Pro Leu Thr Thr Thr Ser Thr Gly Leu Gly Ile Ser Ile
            100                 105                 110

Ser Pro Pro Ile Thr Leu Ser Asn Asn Ala Leu Asn Ile Ser Leu Gly
        115                 120                 125

Asn Gly Leu Thr Ser Ser Ser Asn Ser Leu Ala Ile Lys Thr Ser Gly
    130                 135                 140

Ala Ile Gly Phe Asp Asn Gln Gly Asn Leu Arg Leu Asn Thr Gly Gly
145                 150                 155                 160

Gly Met Arg Leu Ala Gly Asp Arg Leu Ile Leu Asp Val Asn Tyr Pro
                165                 170                 175

Phe Asn Gly Asp Pro Lys Leu Ser Leu Arg Ile Gly Lys Gly Leu Tyr
            180                 185                 190

Leu Gln Asn Asn Gln Asp Leu Ala Val Leu Leu Gly Ser Arg Ser Gly
        195                 200                 205

Leu Asp Phe Ser Gly Asn Asn Leu Val Val Lys Leu Gly Ser Gly Leu
    210                 215                 220

Ala Phe Asp Asn Asn Gly Ala Ile Thr Thr Ser Thr Ser Arg Ser Arg
225                 230                 235                 240

Phe Ala Asp Tyr Leu Pro Tyr Val Ser Thr Trp Pro Pro Leu Asn Glu
                245                 250                 255

Pro Asn Cys Ser Ile Tyr Glu Ser Leu Asp Ala Met Leu Gly Leu His
            260                 265                 270

Phe Ser Lys His Gly Leu His Val Ile Gly Thr Ile Ser Leu Lys Ala
        275                 280                 285

Ile Lys Gly Glu Leu Cys Asn Met Gln Arg Asp Thr Val Thr Leu Lys
    290                 295                 300

Leu Leu Phe Asn Ser Ser Gly Arg Leu Leu Asn Cys Pro Leu Leu Pro
305                 310                 315                 320

Ser Phe Trp Asn Pro Glu Thr Pro Leu Gln Phe Met Pro Ser Ser Thr
                325                 330                 335

Phe Tyr Pro Arg Asn Val Ser Pro Ser Thr Leu Thr Gln Thr Leu Pro
            340                 345                 350

Asp Ser Arg Cys Thr Phe Thr Val Ala Tyr Asn Thr Glu Gly Ala Asp
        355                 360                 365

Tyr Ser Phe Thr Phe Thr Trp Ser Val Cys Ser Gly Glu Lys Phe Asn
    370                 375                 380

Ala Pro Ala Ala Met Phe Cys Phe Val Ala Glu Gln
385                 390                 395
```

<210> SEQ ID NO 27
<211> LENGTH: 612
<212> TYPE: PRT
<213> ORGANISM: Adenovirus

<400> SEQUENCE: 27

Met Tyr Pro Gln Ala His Ser Pro Lys Leu Cys Gln Thr Leu Gly Ala
1               5                   10                  15

His Leu Leu Leu His Thr Thr Arg Lys Val Gln Ile Thr His Leu Pro
            20                  25                  30

Ser Leu Gly Pro Ser Val Pro Glu Lys Ser Leu Met Pro Pro Leu Arg
        35                  40                  45

Cys Ser Val Leu Leu Leu Asn Asn Lys Ala Cys Lys Ala Thr Phe Val
    50                  55                  60

Phe Phe Gln Met Lys Arg Ala Arg Ile Asp Asp Asp Phe Asn Pro Val
65                  70                  75                  80

Tyr Pro Tyr Asp Gln Pro Asn Ala Pro Leu Leu Pro Phe Ile Thr Pro
                85                  90                  95

Pro Phe Thr Ser Ser Asp Gly Leu Gln Glu Lys Pro Pro Gly Val Leu
            100                 105                 110

Ser Leu Asn Tyr Lys Asn Pro Ile Thr Thr Gln Asn Gly Ala Leu Thr
        115                 120                 125

Leu Lys Ile Gly Glu Gly Ile Glu Val Asn Asp Lys Gly Glu Leu Thr
    130                 135                 140

Ser Asn Ala Val Ser Val Ser Pro Pro Leu Ser Lys Ile Asp Asn Thr
145                 150                 155                 160

Leu Ser Leu Val Tyr Ser Asp Pro Leu Thr Val Arg Glu Asn Ser Leu
                165                 170                 175

His Leu Lys Thr Ala Leu Pro Ile Ser Leu Asn Ala Thr Arg Glu Leu
            180                 185                 190

Thr Leu Val Ala Asn Ala Pro Leu Ala Thr Thr Asn Gly Ala Leu Gln
        195                 200                 205

Leu Gln Ser Ala Ala Pro Leu Gly Val Ala Glu Arg Thr Leu Lys Leu
    210                 215                 220

Leu Phe Ser Asn Pro Leu Tyr Leu Gln Asn Asn Phe Leu Ser Val Ala
225                 230                 235                 240

Val Asp Lys Pro Leu Ala Met Ala Ser Thr Gly Ala Ile Ala Leu Gln
                245                 250                 255

Trp Ala Pro Pro Leu Gln Val Gly Thr Gly Gly Leu Thr Val Ala Thr
            260                 265                 270

Val Glu Pro Leu Thr Val Thr Asn Gly Asn Leu Asn Ile Asn Thr Lys
        275                 280                 285

Arg Pro Leu Ile Ile Glu Asp Ser Ser Leu Tyr Leu Ala Phe Arg Pro
    290                 295                 300

Pro Leu Arg Leu Phe Asn Ser Asp Pro Glu Leu Gly Val Asn Phe Ile
305                 310                 315                 320

Pro Pro Ile Thr Ile Arg Asp Asp Gly Leu Ala Leu Asn Thr Gly Glu
                325                 330                 335

Gly Leu Thr Leu Val Arg Asp Arg Leu Ser Val Asn Leu Gly Lys Asp
            340                 345                 350

Leu Gln Phe Val Asp Asn Thr Val Ser Leu Ala Leu Ser Thr Ala Leu
        355                 360                 365

Pro Leu Gln Tyr Thr Asp Gln Leu Arg Leu Asn Ile Gly Gln Gly Leu
    370                 375                 380

Arg Tyr Asn Pro Thr Ser Lys Lys Leu Asp Val Asp Leu Asn Gln Asn
385                 390                 395                 400

Lys Gly Leu Asn Trp Glu Asp Asn Lys Val Ile Thr Lys Leu Gly Asp

```
                405                 410                 415

Gly Leu Gln Phe Asp Ser Ala Gly Asn Ile Ser Val Ile Pro Pro Ser
            420                 425                 430

Val Thr Pro His Thr Leu Trp Thr Thr Ala Asp Pro Ser Pro Asn Cys
        435                 440                 445

Ser Val Tyr Thr Asp Leu Asp Ala Lys Leu Trp Leu Ser Leu Val Lys
    450                 455                 460

Cys Asn Gly Ile Val Gln Gly Thr Ile Ala Leu Lys Ala Leu Lys Gly
465                 470                 475                 480

Val Leu Leu Lys Pro Thr Ala Ser Ser Ile Ser Ile Val Ile Tyr Phe
                485                 490                 495

Tyr Ser Asn Gly Val Arg Arg Thr Asn Tyr Pro Thr Phe Asp Asn Glu
            500                 505                 510

Gly Thr Leu Ala Asn Thr Ala Thr Trp Gly Tyr Arg Gln Gly Gln Ser
        515                 520                 525

Ala Asn Thr Asn Val Thr Asn Ala Val Glu Phe Met Pro Ser Ser Ala
    530                 535                 540

Arg Tyr Pro Ile Asn Arg Gly Asp Asp Val Gln Asn Gln Met Met Gly
545                 550                 555                 560

Tyr Thr Cys Leu Gln Gly Ala Leu Asn Met Ala Val Gly Tyr Lys Val
                565                 570                 575

Thr Phe Asn His Ala Leu Glu Gly Tyr Ser Leu Lys Phe Thr Trp Pro
            580                 585                 590

Val Tyr Asn Asn Gln Ala Phe Asp Val Pro Cys Cys Ser Phe Ser Tyr
        595                 600                 605

Ile Thr Glu Glu
    610


<210> SEQ ID NO 28
<211> LENGTH: 447
<212> TYPE: PRT
<213> ORGANISM: Adenovirus

<400> SEQUENCE: 28

Met Glu Thr Arg Gly Arg Lys Arg Pro Leu Gln His Gln Gln Asp Glu
1               5                   10                  15

Pro Gln Thr His Thr Gly Lys Arg Pro Thr Arg Gly Pro Pro Phe Tyr
            20                  25                  30

Arg His Arg Asp His Pro Asp Ala Asp Pro Gln Thr Leu Glu Gly His
        35                  40                  45

Asp Ser Arg Ser Pro Gly Arg Pro Pro Ala Gly Ala Leu Gln Arg Lys
    50                  55                  60

Ser Ser Gln Pro Ser Gln Pro Arg Ser Leu Leu Asp Arg Asp Ala Ile
65                  70                  75                  80

Glu His Val Thr Glu Leu Trp Asp Arg Leu Tyr Leu Leu Arg Gln Ser
                85                  90                  95

Leu Glu Lys Met Pro Met Ala Asp Gly Leu Lys Pro Leu Lys His Phe
            100                 105                 110

Asn Ser Leu Glu Glu Leu Leu Ser Leu Gly Gly Glu Arg Leu Leu Gln
        115                 120                 125

Asn Leu Val Arg Glu Asn Arg His Val Arg Ser Met Met Asn Glu Val
    130                 135                 140

Ala Pro Leu Leu Arg Asn Asp Gly Ser Cys Lys Ser Leu Asn Tyr Gln
145                 150                 155                 160
```

Leu Gln Pro Val Ile Gly Val Ile Tyr Gly Pro Thr Gly Cys Gly Lys
165 170 175

Ser Gln Leu Leu Arg Asn Leu Leu Ser Thr Gln Leu Ile Asn Pro Pro
180 185 190

Pro Glu Thr Val Phe Phe Ile Ala Pro Gln Val Asp Met Ile Pro Pro
195 200 205

Ser Glu Ile Lys Ala Trp Glu Met Gln Ile Cys Glu Gly Asn Tyr Ala
210 215 220

Pro Gly Pro Glu Gly Thr Ile Ile Pro Gln Ser Gly Thr Leu Leu Pro
225 230 235 240

Arg Phe Val Lys Met Ala Tyr Asp Asp Leu Thr Leu Glu Gln Asn Tyr
245 250 255

Asp Val Ser Asn Pro Asp Asn Val Phe Ala Lys Ala Ala Ala Arg Gly
260 265 270

Pro Ile Ala Ile Ile Met Asp Glu Cys Met Glu Asn Leu Gly Gly His
275 280 285

Lys Gly Val Ser Lys Phe Phe His Ala Phe Pro Ser Lys Leu His Asp
290 295 300

Lys Phe Pro Lys Cys Thr Gly Tyr Thr Val Leu Val Val Leu His Asn
305 310 315 320

Met Asn Pro Arg Arg Asp Leu Gly Gly Asn Ile Ala Asn Leu Lys Ile
325 330 335

Gln Ala Lys Met His Ile Ile Ser Pro Arg Met His Pro Ser Gln Leu
340 345 350

Asn Arg Phe Val Asn Thr Tyr Thr Lys Gly Leu Pro Leu Ala Ile Ser
355 360 365

Leu Leu Leu Lys Asp Ile Phe Gln Phe His Ala Gln Lys Pro Cys Tyr
370 375 380

Asp Trp Val Ile Tyr Asn Thr Thr Pro Glu His Asp Ala Leu Gln Trp
385 390 395 400

Ser Tyr Leu His Pro Lys Asp Gly Leu Met Pro Met Tyr Leu Asn Ile
405 410 415

Gln Ser His Leu Tyr Arg Val Leu Glu Thr Ile His Lys Val Leu Asn
420 425 430

Asp Arg Asp Arg Trp Ser Arg Ala Tyr Arg Ala Lys Lys Asn Lys
435 440 445

<210> SEQ ID NO 29
<211> LENGTH: 159
<212> TYPE: PRT
<213> ORGANISM: Adenovirus

<400> SEQUENCE: 29

Met Gly Gly Val Thr Lys Gly Ile Lys Arg Thr Trp Trp Trp Gly Gly
1 5 10 15

Phe Ile Ala Lys Met Ser Gly Ser Thr Asp Ser Asn Ser Val Asn Phe
20 25 30

Glu Gly Gly Val Phe Ser Pro Tyr Leu Thr Thr Arg Leu Pro Ser Trp
35 40 45

Ala Gly Val Arg Gln Asn Val Val Gly Ser Ser Met Asp Gly Arg Pro
50 55 60

Val Ala Pro Ala Asn Ser Ala Thr Leu Thr Tyr Ala Thr Val Gly Ser
65 70 75 80

Ser Leu Asp Ala Ala Ala Ala Ala Ala Ala Ser Ala Ala Ala Ser Thr
85 90 95

Ala Arg Val Met Ala Val Asp Phe Gly Leu Tyr Asn Gln Leu Ala Thr
100 105 110

Ala Ala Ala Ala Ser Arg Ser Val Val Gln Gln Asp Ala Leu Asn Val
115 120 125

Ile Leu Ala Arg Leu Glu Met Leu Ser Gln Arg Leu Asp Gln Leu Ala
130 135 140

Ala Gln Ile Ala Leu Ser Pro Ala Pro Asp Ser Thr Ser Asp Ser
145 150 155

<210> SEQ ID NO 30
<211> LENGTH: 574
<212> TYPE: PRT
<213> ORGANISM: Adenovirus

<400> SEQUENCE: 30

Met Gln Gln Gln Ser Ser Ala Asp Gly Thr Ser Val Asn Pro Ala Leu
1 5 10 15

Leu Ala Ser Met Gln Ser Gln Pro Ser Gly Val Asn Ala Ser Asp Asp
20 25 30

Trp Ser Ala Ala Met Asp Arg Ile Met Ala Leu Thr Thr Arg Asn Pro
35 40 45

Glu Ala Phe Arg Gln Gln Pro Gln Ala Asn Arg Phe Ser Ala Ile Leu
50 55 60

Glu Ala Val Val Pro Ser Arg Thr Asn Pro Thr His Glu Lys Val Leu
65 70 75 80

Thr Ile Val Asn Ala Leu Val Asp Ser Lys Ala Ile Arg Arg Asp Glu
85 90 95

Ala Gly Leu Ile Tyr Asn Ala Leu Leu Glu Arg Val Ala Arg Tyr Asn
100 105 110

Ser Thr Asn Val Gln Ala Asn Leu Asp Arg Leu Asn Thr Asp Val Arg
115 120 125

Glu Ala Leu Ala Gln Lys Glu Arg Phe Leu Arg Asp Ser Asn Leu Gly
130 135 140

Ser Leu Val Ala Leu Asn Ala Phe Leu Ser Thr Gln Pro Ala Asn Val
145 150 155 160

Pro Arg Gly Gln Glu Asp Tyr Val Ser Phe Ile Ser Ala Leu Arg Leu
165 170 175

Leu Val Ser Glu Val Pro Gln Ser Glu Val Tyr Gln Ser Gly Pro Asp
180 185 190

Tyr Phe Phe Gln Thr Ser Arg Gln Gly Leu Gln Thr Val Asn Leu Ser
195 200 205

Gln Ala Phe Lys Asn Leu Gln Gly Met Trp Gly Val Lys Ala Pro Leu
210 215 220

Gly Asp Arg Ala Thr Ile Ser Ser Leu Leu Thr Pro Asn Thr Arg Leu
225 230 235 240

Leu Leu Leu Leu Ile Ala Pro Phe Thr Asn Ser Ser Ser Ile Ser Arg
245 250 255

Asp Ser Tyr Leu Gly His Leu Ile Thr Leu Tyr Arg Glu Ala Ile Gly
260 265 270

Gln Ala Gln Val Asp Glu His Thr Tyr Gln Glu Ile Thr Asn Val Ser
275 280 285

Arg Ala Leu Gly Gln Glu Asp Thr Gly Ser Leu Glu Ala Thr Leu Asn
290 295 300

Phe Leu Leu Thr Asn Arg Arg Gln Lys Ile Pro Ser Gln Phe Thr Leu

-continued

```
305                 310                 315                 320

Ser Ala Glu Glu Glu Arg Ile Leu Arg Tyr Val Gln Gln Ser Val Ser
                325                 330                 335

Leu Tyr Leu Met Arg Glu Gly Ala Thr Ala Ser Thr Ala Leu Asp Met
            340                 345                 350

Thr Ala Arg Asn Met Glu Pro Ser Phe Tyr Ala Ser Asn Arg Pro Phe
        355                 360                 365

Ile Asn Arg Leu Met Asp Tyr Leu His Arg Ala Ala Met Asn Gly
    370                 375                 380

Glu Tyr Phe Thr Asn Ala Ile Leu Asn Pro His Trp Met Pro Pro Ser
385                 390                 395                 400

Gly Phe Tyr Thr Gly Glu Phe Asp Leu Pro Glu Ala Asp Asp Gly Phe
                405                 410                 415

Leu Trp Asp Asp Val Ser Asp Ser Ile Phe Ser Pro Ser Ser Gln Arg
            420                 425                 430

Met Gln Lys Lys Glu Gly Gly Asp Glu Leu Pro Leu Ser Ser Ile Glu
        435                 440                 445

Ala Ala Ser Arg Gly Glu Ser Pro Phe Pro Ser Leu Ser Ser Val Ser
    450                 455                 460

Ser Gly Arg Val Ser Arg Pro Arg Leu Pro Ala Glu Ser Glu Tyr Leu
465                 470                 475                 480

Ser Asp Pro Ile Leu Gln Pro Ser Arg Lys Lys Asn Phe Pro Asn Asn
                485                 490                 495

Gly Val Glu Ser Leu Val Asp Lys Met Lys Arg Trp Lys Thr Tyr Ala
            500                 505                 510

Gln Glu Gln Lys Glu Trp Glu Glu Thr Gln Val Arg Pro Val Pro Pro
        515                 520                 525

Pro Thr Gln Arg Arg Trp Arg Arg Pro Arg Glu Asp Pro Asp Asp Ser
    530                 535                 540

Ala Asp Asp Ser Ser Val Leu Asp Leu Gly Gly Ser Gly Ala Asn Pro
545                 550                 555                 560

Phe Ala His Leu Arg Pro Gln Gly Arg Leu Gly Arg Leu Tyr
                565                 570


<210> SEQ ID NO 31
<211> LENGTH: 1185
<212> TYPE: PRT
<213> ORGANISM: Adenovirus

<400> SEQUENCE: 31

Met Ala Leu Val Gln Asn Gln Gly Thr Gly Ser Leu Tyr Ala Glu Ala
1               5                   10                  15

Ala His Ser Arg Ser Gln Pro Pro Arg Arg Arg Pro Cys Gln Arg Ser
            20                  25                  30

Pro Ser Ala Ser Pro Ala Ala Ala Lys Ser Ser Arg Lys Arg Ala Ser
        35                  40                  45

Ser Ser Ala Pro Ser Arg Arg Arg Ala Ser Thr Thr Ser Gly Cys Ala
    50                  55                  60

Thr Pro Pro Asp Glu Ile Lys Leu Pro Arg Gly Thr Val Val Ala Pro
65                  70                  75                  80

Arg Gly His Ala Leu Leu Tyr Ala Val Asp Ser Ser Ser Asn Cys Pro
                85                  90                  95

Leu Glu Ile Lys Tyr His Leu His Leu Thr Arg Ala Leu Thr Ala Leu
            100                 105                 110
```

-continued

```
Leu Gln Val Asn Leu Gln Ser Leu Pro Ser Asp Leu Ala Asn Gly Ser
        115                 120                 125

Leu Asp Ser Leu Asp Cys Ser Gln Leu Glu Ala Leu Val Arg Arg Leu
    130                 135                 140

Arg Pro Thr Val Ala Glu Ile Trp Ser Cys Gly Thr Arg Gly Val Val
145                 150                 155                 160

Thr Pro Val Val Ile His Pro Gln Asp Gln Gly Ala Gly Ala Tyr Pro
                165                 170                 175

Asp Glu His Arg Glu Gly Glu Asn Glu Pro Gln Ala Ser Ser Pro Leu
            180                 185                 190

Thr Phe Pro Leu Arg Phe Leu Val Arg Gly Arg Lys Val His Leu Ile
        195                 200                 205

Glu Glu Ile Gln Ser Val Gln Arg Cys Asp Tyr Cys Gly Arg Phe Tyr
    210                 215                 220

Lys His Gln His Glu Cys Ser Val Arg Arg Arg Asn Phe Tyr Phe His
225                 230                 235                 240

His Ile Asn Ala His Ser Ser Ser Trp Trp Gln Glu Ile Ser Phe Phe
                245                 250                 255

Pro Ile Gly Ser His Pro Arg Thr Glu Arg Leu Phe Val Thr Tyr Asp
            260                 265                 270

Val Glu Thr Tyr Thr Trp Met Gly Ser Phe Gly Lys Gln Leu Val Pro
        275                 280                 285

Phe Met Leu Val Met His Ile Ser Gly Asp Asp Ala Leu Val Leu Lys
    290                 295                 300

Ala Cys Ala Leu Ala Val Glu Leu Lys Trp Asp Thr Trp Asn Asn Arg
305                 310                 315                 320

Pro Ala Thr Phe Tyr Val Val Thr Pro Glu Lys Met Ala Val Gly Arg
                325                 330                 335

Lys Phe Arg Asp Phe Arg Asp Arg Leu Gln Thr Leu Leu Ala Arg Glu
            340                 345                 350

Leu Trp Arg Ser Phe Leu Ala Ala Asn Ser His Leu Glu Glu Trp Ser
        355                 360                 365

Arg Ala Glu Leu Gly Leu Phe Ser Pro Glu Cys Leu Thr Phe Glu Glu
    370                 375                 380

Leu Lys Lys Ala Pro Ala Leu Lys Gly Val Pro Arg Phe Leu Glu Leu
385                 390                 395                 400

Tyr Ile Val Gly His Asn Ile Asn Gly Phe Asp Glu Ile Val Leu Ala
                405                 410                 415

Ala Gln Val Ile Asn Asn Arg Ser Asp Val Pro Gly Pro Phe Arg Ile
            420                 425                 430

Ser Arg Asn Phe Met Pro Arg Ala Gly Lys Ile Leu Phe Asn Asp Val
        435                 440                 445

Thr Phe Ala Leu Pro Asn Pro Arg Gln Lys Lys Arg Thr Asp Phe Thr
    450                 455                 460

Leu Trp Glu Gln Gly Cys Cys Asp Asp Thr Asp Phe Lys His Gln Tyr
465                 470                 475                 480

Leu Lys Val Met Val Arg Asp Thr Phe Gln Leu Thr His Thr Ser Leu
                485                 490                 495

Arg Lys Ala Ala Gln Ala Tyr Ala Leu Pro Ile Glu Lys Gly Cys Cys
            500                 505                 510

Pro Tyr Lys Ala Val Asn Glu Phe Tyr Met Leu Gly Ala Tyr Arg Ala
        515                 520                 525

Asp Asp Arg Gly Phe Pro Ala Ala Asp Tyr Trp Lys Asp Arg Glu Glu
```

```
    530                 535                 540

Tyr Leu Leu Asn Arg Glu Leu Trp Glu Lys Lys Gln Glu Lys Thr Tyr
545                 550                 555                 560

Asp Leu Val Arg Glu Thr Leu Asp Tyr Cys Ala Leu Asp Val Leu Val
                565                 570                 575

Thr Ala Ala Leu Val Asp Lys Leu Arg Glu Ser Tyr Ala Gln Phe Leu
            580                 585                 590

Gln Asp Ala Val Gly Leu Ser Gln Ala Ser Phe Asn Val Phe Gln Arg
        595                 600                 605

Pro Thr Ile Ser Ser Asn Ser His Ala Ile Phe Arg Gln Ile Ala Tyr
    610                 615                 620

Arg Ala Val Lys Pro Gln Lys Thr His Leu Gly Ser Gly Leu Leu Ala
625                 630                 635                 640

Pro Ser His Glu Met Tyr Asp Tyr Val Arg Ala Ser Ile Arg Gly Gly
                645                 650                 655

Arg Cys Tyr Pro Thr Tyr Ile Gly Val Leu Arg Gln Pro Leu Tyr Val
            660                 665                 670

Tyr Asp Ile Cys Gly Met Tyr Ala Ser Ala Leu Thr His Pro Met Pro
        675                 680                 685

Trp Gly Pro Pro Leu Asn Pro Tyr Glu Arg Ala Leu Ala Val Lys Lys
    690                 695                 700

Trp Asp Leu Ala Leu Gln His Arg Val Glu Ile Asn Tyr Phe Asn Lys
705                 710                 715                 720

Ser Leu Leu Pro Gly Ile Phe Thr Ile Asp Ala Asp Pro Pro Ala Ser
                725                 730                 735

Asn Leu Leu Asp Val Leu Pro Pro Phe Cys Ser Arg Lys Gly Gly Arg
            740                 745                 750

Leu Cys Trp Thr Asn Glu Pro Leu Arg Gly Glu Val Ala Thr Ser Val
        755                 760                 765

Asp Leu Ile Thr Leu His Asn Arg Gly Trp Ser Val Arg Ile Val Pro
    770                 775                 780

Asp Glu Arg Thr Thr Val Phe Pro Glu Trp Arg Cys Val Ala Arg Glu
785                 790                 795                 800

Tyr Val Gln Leu Asn Ile Ala Ala Lys Glu Arg Ala Asp Arg Glu Lys
                805                 810                 815

Asn Gln Thr Leu Arg Ser Ile Ala Lys Leu Leu Ser Asn Ala Leu Tyr
            820                 825                 830

Gly Ser Phe Ala Thr Lys Leu Asp Asn Lys Lys Ile Val Phe Ser Asp
        835                 840                 845

Gln Met Glu Thr Ser Thr Val Lys Asp Ile Ala Ser Gly Arg Val Asn
    850                 855                 860

Ile Lys Ser Thr Ser Phe Val Glu Thr Asp Thr Leu Ser Ala Glu Val
865                 870                 875                 880

Met Pro Ala Phe Glu Arg Ala Tyr Leu Pro Glu Gln Leu Ala Leu Ile
                885                 890                 895

His Ser Asp Ala Glu Glu Ser Asp Asp Glu Ala Gly Asn Ala Pro Phe
            900                 905                 910

Tyr Ser Pro Pro Arg His Pro Asp Gly His Val Thr Tyr Thr Tyr Lys
        915                 920                 925

Pro Ile Thr Phe Met Asp Ala Glu Glu Asp Asp Leu Cys Leu His Thr
    930                 935                 940

Leu Gln Lys Val Asp Pro Leu Ile Glu Asn Asp Arg Tyr Pro Ser Gln
945                 950                 955                 960
```

```
Ile Ala Ser Phe Val Leu Ala Trp Thr Arg Ala Phe Val Ser Glu Trp
                965                 970                 975

Ser Gln Phe Leu Tyr Asp Glu Asp Arg Gly Thr Pro Leu Glu Gln Arg
            980                 985                 990

Gln Leu Lys Ser Val Tyr Gly Asp  Thr Asp Ser Leu Phe  Val Thr Glu
        995                 1000                 1005

Ala Gly  His Arg Leu Met Glu  Thr Arg Gly Lys Lys  Arg Ile Lys
    1010                 1015                 1020

Lys Asn  Gly Gly Lys Leu Val  Phe Asp Pro Asn Gln  Pro Glu Leu
    1025                 1030                 1035

Thr Trp  Leu Val Glu Cys Glu  Thr Val Cys Ala Gln  Cys Gly Ala
    1040                 1045                 1050

Asp Ala  Phe Ser Pro Glu Ser  Val Phe Leu Ala Pro  Lys Leu Tyr
    1055                 1060                 1065

Ala Leu  Lys Ser Leu His Cys  Ser Lys Cys Leu His  Val Ser Lys
    1070                 1075                 1080

Gly Lys  Leu Arg Ala Lys Gly  His Ala Ala Glu Ser  Leu Ser Tyr
    1085                 1090                 1095

Asp Leu  Met Leu Lys Cys Tyr  Leu Ala Asp Ser Gln  Gly Glu Asn
    1100                 1105                 1110

Val His  Phe Ser Thr Ser Arg  Met Ser Leu Lys Arg  Thr Leu Ala
    1115                 1120                 1125

Ser Ala  Gln Pro Gly Ala His  Pro Phe Thr Val Thr  Glu Thr Thr
    1130                 1135                 1140

Leu Thr  Arg Thr Leu Arg Pro  Trp Lys Asp Met Thr  Leu Ala Ala
    1145                 1150                 1155

Leu Asp  Ala His Arg Leu Val  Pro Tyr Ser Glu Ser  Arg Pro Asn
    1160                 1165                 1170

Pro Arg  Asn Gln Glu Val Cys  Trp Ile Glu Met Pro
    1175                 1180                 1185


<210> SEQ ID NO 32
<211> LENGTH: 250
<212> TYPE: PRT
<213> ORGANISM: Adenovirus

<400> SEQUENCE: 32

Met Ser Pro Arg Phe Phe Met Phe Cys Leu Lys Ser Ser Thr Trp Cys
1               5                   10                  15

Ala Ser Ile Ser Arg Thr Ala Ala Ser Ser Arg Leu Ser Thr Cys Ala
            20                  25                  30

Arg Leu Ser Leu Pro Ala Thr Pro Pro Pro Lys Lys Pro Met Gly Ser
        35                  40                  45

Ser Glu Gln Glu Leu Arg Ser Ile Val Arg Asp Leu Gly Cys Gly Pro
    50                  55                  60

Tyr Phe Leu Gly Thr Phe Asp Lys Arg Phe Pro Gly Phe Met Ser Pro
65                  70                  75                  80

Gln Lys Pro Ala Cys Ala Ile Val Asn Thr Ala Gly Arg Glu Thr Gly
                85                  90                  95

Gly Val His Trp Leu Ala Phe Ala Trp Asn Pro Gln Asn Arg Thr Cys
            100                 105                 110

Tyr Leu Phe Asp Pro Phe Gly Phe Ser Asp Glu Arg Leu Lys Gln Ile
        115                 120                 125

Tyr Gln Phe Gln Tyr Glu Gly Leu Leu Lys Arg Ser Ala Leu Ala Ser
```

```
    130                 135                 140

Thr Pro Asp His Cys Val Thr Leu Glu Lys Ser Thr Gln Ser Val Gln
145                 150                 155                 160

Gly Pro Leu Ser Ala Ala Cys Gly Leu Phe Cys Cys Met Phe Leu His
                165                 170                 175

Ala Phe Val His Trp Pro His Ser Pro Met Asp Lys Asn Pro Thr Met
            180                 185                 190

Asp Leu Leu Thr Gly Val Pro Asn Ser Met Leu Gln Ser Pro Gln Val
        195                 200                 205

Val Pro Thr Leu Arg Arg Asn Gln Glu Gln Leu Tyr His Phe Leu Ser
    210                 215                 220

Lys Asn Ser Ala Tyr Phe Arg Arg His Arg Gln Arg Ile Glu Lys Ala
225                 230                 235                 240

Thr Asp Phe Glu Ser Met Lys His Thr Val
                245                 250


<210> SEQ ID NO 33
<211> LENGTH: 648
<212> TYPE: PRT
<213> ORGANISM: Adenovirus

<400> SEQUENCE: 33

Met Ala Leu Ser Val Gln Asp Cys Ala Arg Leu Thr Gly Gln Ser Val
1               5                   10                  15

Pro Thr Met Glu Arg Phe Arg Pro Leu Arg Asn Ile Trp Asn Arg Val
            20                  25                  30

Arg Glu Phe Thr Arg Ala Ala Thr Thr Ser Ala Gly Ile Thr Trp Leu
        35                  40                  45

Ser Arg Tyr Val Tyr His Tyr His Arg Leu Met Leu Asp Asp Leu Ala
    50                  55                  60

Pro Gly Ala Pro Ala Thr Val Gly Trp Pro Leu Tyr Arg Glu Pro Pro
65                  70                  75                  80

Pro His Phe Leu Val Gly Tyr Gln Tyr Leu Val Arg Thr Cys Asn Asp
                85                  90                  95

Tyr Val Phe Glu Ser Arg Ala Tyr Ser Arg Leu Lys Tyr Thr Glu Ile
            100                 105                 110

Thr Gln Pro Gly Met Gln Val Val Asn Trp Ser Val Met Ala Asn Cys
        115                 120                 125

Thr Tyr Thr Ile Asn Thr Gly Ala Tyr His Arg Phe Val Asp Leu Asp
    130                 135                 140

Asp Phe Gln Thr Thr Leu Thr Gln Val Gln Gln Ala Val Leu Ala Glu
145                 150                 155                 160

Arg Val Val Ala Asp Leu Ala Leu Leu Gln Pro Leu Arg Gly Tyr Gly
                165                 170                 175

Ser Thr Arg Met Ala Asp Arg Gly Glu Ala Glu Ile Pro Val Glu Arg
            180                 185                 190

Leu Met Gln Asp Tyr Tyr Lys Asp Leu Arg Arg Cys Gln Asn Glu Ala
        195                 200                 205

Trp Gly Met Ala Asp Arg Leu Arg Ile Gln Gln Ala Gly Pro Lys Asp
    210                 215                 220

Val Val Leu Leu Ala Thr Ile Arg Arg Leu Lys Thr Ala Tyr Phe Asn
225                 230                 235                 240

Tyr Ile Ile Ser Ser Ile Thr Ser Arg Leu Pro Pro Glu Ser Thr Gln
                245                 250                 255
```

```
Arg Pro Ser Val Leu Ser Leu Pro Cys Asp Cys Asp Trp Leu Asn Ala
            260                 265                 270

Phe Leu Glu Lys Phe Ser Asp Pro Val Asp Leu Asp Ala Leu Arg Ser
        275                 280                 285

Leu His Gly Val Pro Thr Gln Gln Leu Ile Lys Cys Ile Val Ser Ala
    290                 295                 300

Val Ser Leu Pro Asp Gly Pro His His Leu Pro Ser Leu Gln Gly Gly
305                 310                 315                 320

Gly Leu Arg Gly Gly Val Phe Glu Leu Arg Pro Arg Glu His Gly Arg
                325                 330                 335

Ala Val Thr Glu Thr Met Arg Arg Arg Arg Gly Glu Met Ile Glu Arg
            340                 345                 350

Phe Val Asp Arg Leu Pro Val Arg Arg Arg Arg Arg Arg Pro Ala Pro
        355                 360                 365

Ala Ala Glu Val Pro Glu Glu Pro Met Leu Leu Glu Glu Gly Glu Glu
    370                 375                 380

Glu Glu Leu Glu Glu Glu Glu Ala Pro Pro Gly Ala Phe Glu Arg Glu
385                 390                 395                 400

Val Arg Asp Thr Ile Ala Asp Leu Ile Arg Leu Leu Gln Glu Glu Leu
                405                 410                 415

Thr Val Ser Ala Arg Asn Ser Gln Phe Phe Asn Phe Ala Val Asp Phe
            420                 425                 430

Tyr Glu Ala Met Glu Arg Leu Glu Ala Ile Gly Asp Ile Asn Glu Ser
        435                 440                 445

Thr Leu Arg Arg Trp Ile Met Tyr Phe Phe Val Cys Glu His Ile Ala
    450                 455                 460

Thr Thr Leu Asn Tyr Leu Phe Gln Arg Leu Arg Asn Tyr Ala Val Phe
465                 470                 475                 480

Ala Arg His Val Glu Leu Asn Val Ala Gln Val Val Met Arg Ala Arg
                485                 490                 495

Asp Ser Ala Gly Gly Val Val Tyr Ser Arg Val Trp Asn Glu Asn Gly
            500                 505                 510

Leu Asn Ala Phe Ser Gln Leu Met Arg Arg Ile Ser Asn Asp Leu Ala
        515                 520                 525

Ala Thr Val Glu Arg Ala Gly His Gly Asp Leu Gln Glu Glu Glu Ile
    530                 535                 540

Glu Gln Phe Met Ala Glu Ile Ala Tyr Gln Asp Asn Ser Gly Asp Val
545                 550                 555                 560

Gln Glu Ile Leu Arg Gln Ala Ala Val Asn Asp Thr Asp Ile Asp Ser
                565                 570                 575

Val Glu Leu Ser Phe Arg Phe Arg Thr Arg Gly Pro Val Val Phe Thr
            580                 585                 590

Gln Arg Gln His Ile Gln Asp Leu Asn Arg Arg Val Val Ala His Ala
        595                 600                 605

Ser Asp Leu Arg Ala Arg His Leu Pro Leu Pro Asn Leu His Glu Asn
    610                 615                 620

Val Pro Leu Pro Pro Leu Pro Pro Gly Val Glu Pro Pro Leu Pro Pro
625                 630                 635                 640

Gly Ala Arg Pro Arg Arg Met Arg
                645
```

<210> SEQ ID NO 34
<211> LENGTH: 350
<212> TYPE: PRT

<213> ORGANISM: Adenovirus

<400> SEQUENCE: 34

Met Ser Lys Arg Lys Phe Lys Glu Glu Leu Leu Gln Thr Leu Ala Pro
1 5 10 15

Glu Ile Tyr Gly Pro Pro Glu Val Lys Arg Asp Ile Lys Pro Arg Asp
20 25 30

Ile Lys Arg Val Lys Lys Arg Glu Lys Lys Glu Glu Glu Leu Ala Met
35 40 45

Ala Ala Ala Ala Glu Asp Ala Val Glu Phe Val Arg Ser Phe Ala Pro
50 55 60

Arg Arg Arg Val Arg Trp Lys Gly Arg Arg Val Gln Arg Val Leu Arg
65 70 75 80

Pro Gly Thr Thr Val Val Phe Thr Pro Gly Gln Arg Ser Ala Val Arg
85 90 95

Gly Phe Lys Arg Gln Tyr Asp Glu Val Tyr Gly Asp Glu Asp Ile Leu
100 105 110

Glu Gln Ala Ala Gln Gln Ile Gly Glu Phe Ala Tyr Gly Lys Arg Ser
115 120 125

Arg Gly Glu Asn Val Ala Val Ala Leu Asp Glu Gly Asn Pro Thr Pro
130 135 140

Ser Leu Lys Pro Val Thr Leu Gln Gln Val Leu Pro Val Ser Ala Ser
145 150 155 160

Thr Glu Ser Lys Arg Gly Ile Lys Arg Glu Leu Asp Leu Gln Pro Thr
165 170 175

Leu Gln Leu Met Val Pro Lys Arg Gln Lys Leu Glu Glu Val Leu Glu
180 185 190

Asn Met Lys Val Asp Pro Thr Val Glu Pro Asp Val Lys Val Arg Pro
195 200 205

Ile Lys Glu Val Ala Pro Gly Leu Gly Val Gln Thr Val Asp Ile Gln
210 215 220

Ile Pro Val Ser Ser Ser Ala Ala Ala Val Glu Ala Met Glu Thr Gln
225 230 235 240

Thr Glu Thr Pro Thr Ala Ala Ala Thr Arg Glu Val Ala Leu Gln Thr
245 250 255

Glu Pro Trp Tyr Glu Tyr Ala Thr Ser Ala Arg Pro Arg Arg Ser Arg
260 265 270

Arg Tyr Ala Val Thr Ser Ala Leu Met Pro Glu Tyr Ala Leu His Pro
275 280 285

Ser Ile Thr Pro Thr Pro Gly Tyr Arg Gly Val Thr Phe Arg Pro Ser
290 295 300

Gly Thr Arg Arg Arg Ser Arg Arg Arg Thr Ser Arg Arg Arg Ser Arg
305 310 315 320

Arg Val Leu Ala Pro Val Ser Val Arg Arg Val Thr Arg Arg Gly Arg
325 330 335

Thr Val Thr Ile Pro Asn Pro Arg Tyr His Pro Ser Ile Leu
340 345 350

<210> SEQ ID NO 35
<211> LENGTH: 279
<212> TYPE: PRT
<213> ORGANISM: Adenovirus

<400> SEQUENCE: 35

Met Val Leu Thr Ile Leu Cys Arg Lys Ile Met Glu Asp Ile Asn Phe

-continued

```
1               5                   10                  15

Ser Ser Leu Ala Pro Arg His Gly Ser Arg Pro Phe Met Gly Thr Trp
            20                  25                  30

Asn Asp Ile Gly Thr Ser Gln Leu Asn Gly Gly Ala Phe Ser Trp Ser
        35                  40                  45

Ser Leu Trp Ser Gly Leu Lys Asn Phe Gly Ser Thr Ile Lys Thr Tyr
    50                  55                  60

Gly Asn Lys Ala Trp Asn Ser Ser Thr Gly Gln Met Leu Arg Asp Lys
65                  70                  75                  80

Leu Lys Asp Gln Asn Phe Gln Gln Lys Val Val Asp Gly Leu Ala Ser
                85                  90                  95

Gly Ile Asn Gly Val Val Asp Leu Ala Asn Gln Ala Val Gln Asn Gln
            100                 105                 110

Ile Asn Gln Arg Leu Glu Asn Ser Arg Val Pro Pro Gln Lys Gly Ala
        115                 120                 125

Glu Val Glu Glu Val Glu Val Glu Glu Lys Leu Pro Pro Leu Glu Val
    130                 135                 140

Val Pro Gly Ala Pro Pro Lys Gly Glu Lys Arg Pro Arg Pro Asp Leu
145                 150                 155                 160

Glu Glu Thr Leu Val Thr Gly Thr Leu Glu Pro Pro Ser Tyr Glu Gln
                165                 170                 175

Ala Leu Lys Glu Gly Ala Ser Pro Tyr Pro Met Thr Lys Pro Ile Ala
            180                 185                 190

Pro Met Ala Arg Pro Val Tyr Gly Lys Asp His Lys Pro Val Thr Leu
        195                 200                 205

Glu Leu Pro Pro Pro Pro Thr Val Pro Pro Leu Pro Ala Pro Ser Val
    210                 215                 220

Gly Thr Val Ala Ser Ala Pro Ala Val Val Pro Ala Pro Gln Pro Ala
225                 230                 235                 240

Val Arg Pro Val Ala Val Ala Thr Ala Arg Asn Pro Arg Gly Ala Asn
                245                 250                 255

Trp Gln Ser Thr Leu Asn Ser Ile Val Gly Leu Gly Val Lys Thr Leu
            260                 265                 270

Lys Arg Arg Arg Cys Tyr Tyr
        275


<210> SEQ ID NO 36
<211> LENGTH: 181
<212> TYPE: PRT
<213> ORGANISM: Adenovirus

<400> SEQUENCE: 36

Met Ser Ile Leu Ile Ser Pro Asp Asn Asn Thr Gly Trp Gly Leu Gly
1               5                   10                  15

Ser Thr Lys Met Tyr Gly Gly Ala Lys Arg Arg Ser Ser Gln His Pro
            20                  25                  30

Val Arg Val Arg Gly His Tyr Arg Ala Pro Trp Gly Ala Tyr Lys Arg
        35                  40                  45

Gly Leu Ser Ala Arg Thr Ala Val Asp Asp Thr Ile Asp Ala Val Ile
    50                  55                  60

Ala Asp Ala Arg Gln Tyr Lys Pro Ala Val Ser Thr Val Asp Ser Val
65                  70                  75                  80

Ile Asp Ser Val Val Ala Gly Ala Arg Ala Tyr Ala Arg Arg Lys Arg
                85                  90                  95
```

```
Arg Leu His Arg Arg Arg Arg Pro Thr Ala Ala Met Leu Ala Ala Arg
            100                 105                 110

Ala Val Leu Arg Arg Ala Arg Arg Val Gly Arg Arg Ala Met Arg Arg
        115                 120                 125

Ala Ala Ala Ala Asn Ala Gly Arg Val Arg Arg Gln Ala Ala Arg Gln
    130                 135                 140

Ala Ala Ala Ala Ile Ala Asn Met Ala Arg Pro Arg Arg Gly Asn Val
145                 150                 155                 160

Tyr Trp Val Arg Asp Ser Val Thr Gly Val Arg Val Pro Val Arg Thr
                165                 170                 175

Arg Pro Pro Arg Ser
            180


<210> SEQ ID NO 37
<211> LENGTH: 233
<212> TYPE: PRT
<213> ORGANISM: Adenovirus

<400> SEQUENCE: 37

Met Ser Lys Glu Ile Pro Thr Pro Tyr Met Trp Ser Tyr Gln Pro Gln
1               5                   10                  15

Met Gly Leu Ala Ala Gly Ala Ala Gln Asp Tyr Ser Ser Lys Met Asn
            20                  25                  30

Trp Leu Ser Ala Gly Pro His Met Ile Ser Gln Val Asn Gly Ile Arg
        35                  40                  45

Ala Arg Arg Asn Gln Ile Leu Leu Glu Gln Ala Ala Ile Thr Ser Thr
    50                  55                  60

Pro Arg Arg Leu Leu Asn Pro Pro Ser Trp Pro Ala Ala Arg Val Tyr
65                  70                  75                  80

Gln Glu Thr Pro Ala Pro Thr Thr Val Leu Leu Pro Arg Asp Ala Glu
                85                  90                  95

Ala Glu Val Gln Met Thr Asn Ala Gly Ala Gln Leu Ala Gly Gly Ser
            100                 105                 110

Arg Tyr Val Arg Tyr Arg Gly Arg Ser Ala Pro Tyr Pro Pro Gly Gly
        115                 120                 125

Ile Lys Arg Val Phe Ile Arg Gly Arg Gly Ile Gln Leu Asn Asp Glu
    130                 135                 140

Val Val Ser Ser Ser Ala Gly Leu Arg Pro Asp Gly Val Phe Gln Leu
145                 150                 155                 160

Gly Gly Ala Gly Arg Ser Ser Phe Thr Thr Arg Gln Ala Tyr Leu Thr
                165                 170                 175

Leu Gln Ser Ser Ser Ser Gln Pro Arg Ser Gly Gly Ile Gly Thr Leu
            180                 185                 190

Gln Phe Val Glu Glu Phe Val Pro Ser Val Tyr Phe Asn Pro Phe Ser
        195                 200                 205

Gly Ser Pro Gly Arg Tyr Pro Asp Ser Phe Ile Pro Asn Tyr Asp Ala
    210                 215                 220

Val Ser Glu Ser Val Asp Gly Tyr Asp
225                 230


<210> SEQ ID NO 38
<211> LENGTH: 69
<212> TYPE: PRT
<213> ORGANISM: Adenovirus

<400> SEQUENCE: 38
```

```
Met Ala Leu Thr Cys Arg Val Arg Ile Pro Val Pro His Tyr Arg Gly
1               5                   10                  15

Arg Thr Arg Arg Arg Arg Gly Met Ala Gly Ser Gly Arg Arg Arg Ala
            20                  25                  30

Leu Arg Arg Arg Met Lys Gly Gly Ile Leu Pro Ala Leu Ile Pro Ile
        35                  40                  45

Ile Ala Ala Ala Ile Gly Ala Ile Pro Gly Ile Ala Ser Val Ala Val
    50                  55                  60

Gln Ala Ser Arg Lys
65


<210> SEQ ID NO 39
<211> LENGTH: 53
<212> TYPE: PRT
<213> ORGANISM: Adenovirus

<400> SEQUENCE: 39

Met Lys Ile Val Gly Glu Gly Arg Glu Val Asp Thr Ile Ile Ala Phe
1               5                   10                  15

Arg Val Trp Arg Lys Phe Ala Ala His Tyr His Ile Pro Tyr Glu Ser
            20                  25                  30

Trp Glu Glu Gly Lys Val Val Leu Leu Lys Lys Phe Asp Lys Lys Leu
        35                  40                  45

Leu Arg Gln Leu Arg
    50


<210> SEQ ID NO 40
<211> LENGTH: 53
<212> TYPE: PRT
<213> ORGANISM: Adenovirus

<400> SEQUENCE: 40

Met Lys Ile Val Gly Glu Gly Arg Glu Val Asp Thr Ile Ile Ala Phe
1               5                   10                  15

Arg Val Trp Arg Lys Phe Ala Ala His Tyr His Ile Pro Tyr Glu Ser
            20                  25                  30

Trp Glu Glu Gly Lys Val Val Leu Leu Lys Lys Phe Asp Lys Lys Leu
        35                  40                  45

Leu Arg Gln Leu Arg
    50


<210> SEQ ID NO 41
<211> LENGTH: 69
<212> TYPE: PRT
<213> ORGANISM: Adenovirus

<400> SEQUENCE: 41

Met Ala Leu Thr Cys Arg Val Arg Ile Pro Val Pro His Tyr Arg Gly
1               5                   10                  15

Arg Thr Arg Arg Arg Arg Gly Met Ala Gly Ser Gly Arg Arg Arg Ala
            20                  25                  30

Leu Arg Arg Arg Met Lys Gly Gly Ile Leu Pro Ala Leu Ile Pro Ile
        35                  40                  45

Ile Ala Ala Ala Ile Gly Ala Ile Pro Gly Ile Ala Ser Val Ala Val
    50                  55                  60

Gln Ala Ser Arg Lys
65
```

-continued

<210> SEQ ID NO 42
<211> LENGTH: 233
<212> TYPE: PRT
<213> ORGANISM: Adenovirus

<400> SEQUENCE: 42

```
Met Ser Lys Glu Ile Pro Thr Pro Tyr Met Trp Ser Tyr Gln Pro Gln
1               5                   10                  15

Met Gly Leu Ala Ala Gly Ala Ala Gln Asp Tyr Ser Ser Lys Met Asn
            20                  25                  30

Trp Leu Ser Ala Gly Pro His Met Ile Ser Gln Val Asn Gly Ile Arg
        35                  40                  45

Ala Arg Arg Asn Gln Ile Leu Leu Glu Gln Ala Ala Ile Thr Ser Thr
    50                  55                  60

Pro Arg Arg Leu Leu Asn Pro Pro Ser Trp Pro Ala Ala Arg Val Tyr
65                  70                  75                  80

Gln Glu Thr Pro Ala Pro Thr Thr Val Leu Leu Pro Arg Asp Ala Glu
                85                  90                  95

Ala Glu Val Gln Met Thr Asn Ala Gly Ala Gln Leu Ala Gly Gly Ser
            100                 105                 110

Arg Tyr Val Arg Tyr Arg Gly Arg Ser Ala Pro Tyr Pro Pro Gly Gly
        115                 120                 125

Ile Lys Arg Val Phe Ile Arg Gly Arg Gly Ile Gln Leu Asn Asp Glu
    130                 135                 140

Val Val Ser Ser Ser Ala Gly Leu Arg Pro Asp Gly Val Phe Gln Leu
145                 150                 155                 160

Gly Gly Ala Gly Arg Ser Ser Phe Thr Thr Arg Gln Ala Tyr Leu Thr
                165                 170                 175

Leu Gln Ser Ser Ser Ser Gln Pro Arg Ser Gly Gly Ile Gly Thr Leu
            180                 185                 190

Gln Phe Val Glu Glu Phe Val Pro Ser Val Tyr Phe Asn Pro Phe Ser
        195                 200                 205

Gly Ser Pro Gly Arg Tyr Pro Asp Ser Phe Ile Pro Asn Tyr Asp Ala
    210                 215                 220

Val Ser Glu Ser Val Asp Gly Tyr Asp
225                 230
```

<210> SEQ ID NO 43
<211> LENGTH: 181
<212> TYPE: PRT
<213> ORGANISM: Adenovirus

<400> SEQUENCE: 43

```
Met Ser Ile Leu Ile Ser Pro Asp Asn Asn Thr Gly Trp Gly Leu Gly
1               5                   10                  15

Ser Thr Lys Met Tyr Gly Gly Ala Lys Arg Arg Ser Ser Gln His Pro
            20                  25                  30

Val Arg Val Arg Gly His Tyr Arg Ala Pro Trp Gly Ala Tyr Lys Arg
        35                  40                  45

Gly Leu Ser Ala Arg Thr Ala Val Asp Asp Thr Ile Asp Ala Val Ile
    50                  55                  60

Ala Asp Ala Arg Gln Tyr Lys Pro Ala Val Ser Thr Val Asp Ser Val
65                  70                  75                  80

Ile Asp Ser Val Val Ala Gly Ala Arg Ala Tyr Ala Arg Arg Lys Arg
                85                  90                  95

Arg Leu His Arg Arg Arg Arg Pro Thr Ala Ala Met Leu Ala Ala Arg
```

100 105 110

Ala Val Leu Arg Arg Ala Arg Arg Val Gly Arg Arg Ala Met Arg Arg
115 120 125

Ala Ala Ala Ala Asn Ala Gly Arg Val Arg Arg Gln Ala Ala Arg Gln
130 135 140

Ala Ala Ala Ala Ile Ala Asn Met Ala Arg Pro Arg Arg Gly Asn Val
145 150 155 160

Tyr Trp Val Arg Asp Ser Val Thr Gly Val Arg Val Pro Val Arg Thr
165 170 175

Arg Pro Pro Arg Ser
180

<210> SEQ ID NO 44
<211> LENGTH: 279
<212> TYPE: PRT
<213> ORGANISM: Adenovirus

<400> SEQUENCE: 44

Met Val Leu Thr Ile Leu Cys Arg Lys Ile Met Glu Asp Ile Asn Phe
1 5 10 15

Ser Ser Leu Ala Pro Arg His Gly Ser Arg Pro Phe Met Gly Thr Trp
20 25 30

Asn Asp Ile Gly Thr Ser Gln Leu Asn Gly Gly Ala Phe Ser Trp Ser
35 40 45

Ser Leu Trp Ser Gly Leu Lys Asn Phe Gly Ser Thr Ile Lys Thr Tyr
50 55 60

Gly Asn Lys Ala Trp Asn Ser Ser Thr Gly Gln Met Leu Arg Asp Lys
65 70 75 80

Leu Lys Asp Gln Asn Phe Gln Gln Lys Val Val Asp Gly Leu Ala Ser
85 90 95

Gly Ile Asn Gly Val Val Asp Leu Ala Asn Gln Ala Val Gln Asn Gln
100 105 110

Ile Asn Gln Arg Leu Glu Asn Ser Arg Val Pro Pro Gln Lys Gly Ala
115 120 125

Glu Val Glu Glu Val Glu Val Glu Glu Lys Leu Pro Pro Leu Glu Val
130 135 140

Val Pro Gly Ala Pro Pro Lys Gly Glu Lys Arg Pro Arg Pro Asp Leu
145 150 155 160

Glu Glu Thr Leu Val Thr Gly Thr Leu Glu Pro Pro Ser Tyr Glu Gln
165 170 175

Ala Leu Lys Glu Gly Ala Ser Pro Tyr Pro Met Thr Lys Pro Ile Ala
180 185 190

Pro Met Ala Arg Pro Val Tyr Gly Lys Asp His Lys Pro Val Thr Leu
195 200 205

Glu Leu Pro Pro Pro Pro Thr Val Pro Pro Leu Pro Ala Pro Ser Val
210 215 220

Gly Thr Val Ala Ser Ala Pro Ala Val Val Pro Ala Pro Gln Pro Ala
225 230 235 240

Val Arg Pro Val Ala Val Ala Thr Ala Arg Asn Pro Arg Gly Ala Asn
245 250 255

Trp Gln Ser Thr Leu Asn Ser Ile Val Gly Leu Gly Val Lys Thr Leu
260 265 270

Lys Arg Arg Arg Cys Tyr Tyr
275

<210> SEQ ID NO 45
<211> LENGTH: 350
<212> TYPE: PRT
<213> ORGANISM: Adenovirus

<400> SEQUENCE: 45

Met Ser Lys Arg Lys Phe Lys Glu Glu Leu Leu Gln Thr Leu Ala Pro
1 5 10 15

Glu Ile Tyr Gly Pro Pro Glu Val Lys Arg Asp Ile Lys Pro Arg Asp
20 25 30

Ile Lys Arg Val Lys Lys Arg Glu Lys Lys Glu Glu Glu Leu Ala Met
35 40 45

Ala Ala Ala Ala Glu Asp Ala Val Glu Phe Val Arg Ser Phe Ala Pro
50 55 60

Arg Arg Arg Val Arg Trp Lys Gly Arg Arg Val Gln Arg Val Leu Arg
65 70 75 80

Pro Gly Thr Thr Val Val Phe Thr Pro Gly Gln Arg Ser Ala Val Arg
85 90 95

Gly Phe Lys Arg Gln Tyr Asp Glu Val Tyr Gly Asp Glu Asp Ile Leu
100 105 110

Glu Gln Ala Ala Gln Gln Ile Gly Glu Phe Ala Tyr Gly Lys Arg Ser
115 120 125

Arg Gly Glu Asn Val Ala Val Ala Leu Asp Glu Gly Asn Pro Thr Pro
130 135 140

Ser Leu Lys Pro Val Thr Leu Gln Gln Val Leu Pro Val Ser Ala Ser
145 150 155 160

Thr Glu Ser Lys Arg Gly Ile Lys Arg Glu Leu Asp Leu Gln Pro Thr
165 170 175

Leu Gln Leu Met Val Pro Lys Arg Gln Lys Leu Glu Glu Val Leu Glu
180 185 190

Asn Met Lys Val Asp Pro Thr Val Glu Pro Asp Val Lys Val Arg Pro
195 200 205

Ile Lys Glu Val Ala Pro Gly Leu Gly Val Gln Thr Val Asp Ile Gln
210 215 220

Ile Pro Val Ser Ser Ser Ala Ala Ala Val Glu Ala Met Glu Thr Gln
225 230 235 240

Thr Glu Thr Pro Thr Ala Ala Ala Thr Arg Glu Val Ala Leu Gln Thr
245 250 255

Glu Pro Trp Tyr Glu Tyr Ala Thr Ser Ala Arg Pro Arg Arg Ser Arg
260 265 270

Arg Tyr Ala Val Thr Ser Ala Leu Met Pro Glu Tyr Ala Leu His Pro
275 280 285

Ser Ile Thr Pro Thr Pro Gly Tyr Arg Gly Val Thr Phe Arg Pro Ser
290 295 300

Gly Thr Arg Arg Arg Ser Arg Arg Arg Thr Ser Arg Arg Arg Ser Arg
305 310 315 320

Arg Val Leu Ala Pro Val Ser Val Arg Arg Val Thr Arg Arg Gly Arg
325 330 335

Thr Val Thr Ile Pro Asn Pro Arg Tyr His Pro Ser Ile Leu
340 345 350

<210> SEQ ID NO 46
<211> LENGTH: 648
<212> TYPE: PRT
<213> ORGANISM: Adenovirus

<400> SEQUENCE: 46

Met Ala Leu Ser Val Gln Asp Cys Ala Arg Leu Thr Gly Gln Ser Val
1               5                   10                  15

Pro Thr Met Glu Arg Phe Arg Pro Leu Arg Asn Ile Trp Asn Arg Val
            20                  25                  30

Arg Glu Phe Thr Arg Ala Ala Thr Thr Ser Ala Gly Ile Thr Trp Leu
        35                  40                  45

Ser Arg Tyr Val Tyr His Tyr His Arg Leu Met Leu Asp Asp Leu Ala
    50                  55                  60

Pro Gly Ala Pro Ala Thr Val Gly Trp Pro Leu Tyr Arg Glu Pro Pro
65                  70                  75                  80

Pro His Phe Leu Val Gly Tyr Gln Tyr Leu Val Arg Thr Cys Asn Asp
                85                  90                  95

Tyr Val Phe Glu Ser Arg Ala Tyr Ser Arg Leu Lys Tyr Thr Glu Ile
            100                 105                 110

Thr Gln Pro Gly Met Gln Val Val Asn Trp Ser Val Met Ala Asn Cys
        115                 120                 125

Thr Tyr Thr Ile Asn Thr Gly Ala Tyr His Arg Phe Val Asp Leu Asp
    130                 135                 140

Asp Phe Gln Thr Thr Leu Thr Gln Val Gln Gln Ala Val Leu Ala Glu
145                 150                 155                 160

Arg Val Val Ala Asp Leu Ala Leu Leu Gln Pro Leu Arg Gly Tyr Gly
                165                 170                 175

Ser Thr Arg Met Ala Asp Arg Gly Glu Ala Glu Ile Pro Val Glu Arg
            180                 185                 190

Leu Met Gln Asp Tyr Tyr Lys Asp Leu Arg Arg Cys Gln Asn Glu Ala
        195                 200                 205

Trp Gly Met Ala Asp Arg Leu Arg Ile Gln Gln Ala Gly Pro Lys Asp
    210                 215                 220

Val Val Leu Leu Ala Thr Ile Arg Arg Leu Lys Thr Ala Tyr Phe Asn
225                 230                 235                 240

Tyr Ile Ile Ser Ser Ile Thr Ser Arg Leu Pro Pro Glu Ser Thr Gln
                245                 250                 255

Arg Pro Ser Val Leu Ser Leu Pro Cys Asp Cys Asp Trp Leu Asn Ala
            260                 265                 270

Phe Leu Glu Lys Phe Ser Asp Pro Val Asp Leu Asp Ala Leu Arg Ser
        275                 280                 285

Leu His Gly Val Pro Thr Gln Gln Leu Ile Lys Cys Ile Val Ser Ala
    290                 295                 300

Val Ser Leu Pro Asp Gly Pro His His Leu Pro Ser Leu Gln Gly Gly
305                 310                 315                 320

Gly Leu Arg Gly Gly Val Phe Glu Leu Arg Pro Arg Glu His Gly Arg
                325                 330                 335

Ala Val Thr Glu Thr Met Arg Arg Arg Arg Gly Glu Met Ile Glu Arg
            340                 345                 350

Phe Val Asp Arg Leu Pro Val Arg Arg Arg Arg Arg Arg Pro Ala Pro
        355                 360                 365

Ala Ala Glu Val Pro Glu Glu Pro Met Leu Leu Glu Glu Gly Glu Glu
    370                 375                 380

Glu Glu Leu Glu Glu Glu Glu Ala Pro Pro Gly Ala Phe Glu Arg Glu
385                 390                 395                 400

Val Arg Asp Thr Ile Ala Asp Leu Ile Arg Leu Leu Gln Glu Glu Leu 405 410 415

Thr Val Ser Ala Arg Asn Ser Gln Phe Phe Asn Phe Ala Val Asp Phe
420 425 430

Tyr Glu Ala Met Glu Arg Leu Glu Ala Ile Gly Asp Ile Asn Glu Ser
435 440 445

Thr Leu Arg Arg Trp Ile Met Tyr Phe Phe Val Cys Glu His Ile Ala
450 455 460

Thr Thr Leu Asn Tyr Leu Phe Gln Arg Leu Arg Asn Tyr Ala Val Phe
465 470 475 480

Ala Arg His Val Glu Leu Asn Val Ala Gln Val Val Met Arg Ala Arg
485 490 495

Asp Ser Ala Gly Gly Val Val Tyr Ser Arg Val Trp Asn Glu Asn Gly
500 505 510

Leu Asn Ala Phe Ser Gln Leu Met Arg Arg Ile Ser Asn Asp Leu Ala
515 520 525

Ala Thr Val Glu Arg Ala Gly His Gly Asp Leu Gln Glu Glu Glu Ile
530 535 540

Glu Gln Phe Met Ala Glu Ile Ala Tyr Gln Asp Asn Ser Gly Asp Val
545 550 555 560

Gln Glu Ile Leu Arg Gln Ala Ala Val Asn Asp Thr Asp Ile Asp Ser
565 570 575

Val Glu Leu Ser Phe Arg Phe Arg Thr Arg Gly Pro Val Val Phe Thr
580 585 590

Gln Arg Gln His Ile Gln Asp Leu Asn Arg Arg Val Val Ala His Ala
595 600 605

Ser Asp Leu Arg Ala Arg His Leu Pro Leu Pro Asn Leu His Glu Asn
610 615 620

Val Pro Leu Pro Pro Leu Pro Pro Gly Val Glu Pro Pro Leu Pro Pro
625 630 635 640

Gly Ala Arg Pro Arg Arg Met Arg
645

<210> SEQ ID NO 47
<211> LENGTH: 205
<212> TYPE: PRT
<213> ORGANISM: Adenovirus

<400> SEQUENCE: 47

Met Gly Ser Ser Glu Gln Glu Leu Arg Ser Ile Val Arg Asp Leu Gly
1 5 10 15

Cys Gly Pro Tyr Phe Leu Gly Thr Phe Asp Lys Arg Phe Pro Gly Phe
20 25 30

Met Ser Pro Gln Lys Pro Ala Cys Ala Ile Val Asn Thr Ala Gly Arg
35 40 45

Glu Thr Gly Gly Val His Trp Leu Ala Phe Ala Trp Asn Pro Gln Asn
50 55 60

Arg Thr Cys Tyr Leu Phe Asp Pro Phe Gly Phe Ser Asp Glu Arg Leu
65 70 75 80

Lys Gln Ile Tyr Gln Phe Gln Tyr Glu Gly Leu Leu Lys Arg Ser Ala
85 90 95

Leu Ala Ser Thr Pro Asp His Cys Val Thr Leu Glu Lys Ser Thr Gln
100 105 110

Ser Val Gln Gly Pro Leu Ser Ala Ala Cys Gly Leu Phe Cys Cys Met
115 120 125

```
Phe Leu His Ala Phe Val His Trp Pro His Ser Pro Met Asp Lys Asn
    130                 135                 140

Pro Thr Met Asp Leu Leu Thr Gly Val Pro Asn Ser Met Leu Gln Ser
145                 150                 155                 160

Pro Gln Val Val Pro Thr Leu Arg Arg Asn Gln Glu Gln Leu Tyr His
                165                 170                 175

Phe Leu Ser Lys Asn Ser Ala Tyr Phe Arg Arg His Arg Gln Arg Ile
            180                 185                 190

Glu Lys Ala Thr Asp Phe Glu Ser Met Lys His Thr Val
        195                 200                 205


<210> SEQ ID NO 48
<211> LENGTH: 1185
<212> TYPE: PRT
<213> ORGANISM: Adenovirus

<400> SEQUENCE: 48

Met Ala Leu Val Gln Asn Gln Gly Thr Gly Ser Leu Tyr Ala Glu Ala
1               5                   10                  15

Ala His Ser Arg Ser Gln Pro Pro Arg Arg Arg Pro Cys Gln Arg Ser
            20                  25                  30

Pro Ser Ala Ser Pro Ala Ala Ala Lys Ser Ser Arg Lys Arg Ala Ser
        35                  40                  45

Ser Ser Ala Pro Ser Arg Arg Arg Ala Ser Thr Thr Ser Gly Cys Ala
    50                  55                  60

Thr Pro Pro Asp Glu Ile Lys Leu Pro Arg Gly Thr Val Val Ala Pro
65                  70                  75                  80

Arg Gly His Ala Leu Leu Tyr Ala Val Asp Ser Ser Ser Asn Cys Pro
                85                  90                  95

Leu Glu Ile Lys Tyr His Leu His Leu Thr Arg Ala Leu Thr Ala Leu
            100                 105                 110

Leu Gln Val Asn Leu Gln Ser Leu Pro Ser Asp Leu Ala Asn Gly Ser
        115                 120                 125

Leu Asp Ser Leu Asp Cys Ser Gln Leu Glu Ala Leu Val Arg Arg Leu
    130                 135                 140

Arg Pro Thr Val Ala Glu Ile Trp Ser Cys Gly Thr Arg Gly Val Val
145                 150                 155                 160

Thr Pro Val Val Ile His Pro Gln Asp Gln Gly Ala Gly Ala Tyr Pro
                165                 170                 175

Asp Glu His Arg Glu Gly Glu Asn Glu Pro Gln Ala Ser Ser Pro Leu
            180                 185                 190

Thr Phe Pro Leu Arg Phe Leu Val Arg Gly Arg Lys Val His Leu Ile
        195                 200                 205

Glu Glu Ile Gln Ser Val Gln Arg Cys Asp Tyr Cys Gly Arg Phe Tyr
    210                 215                 220

Lys His Gln His Glu Cys Ser Val Arg Arg Arg Asn Phe Tyr Phe His
225                 230                 235                 240

His Ile Asn Ala His Ser Ser Ser Trp Trp Gln Glu Ile Ser Phe Phe
                245                 250                 255

Pro Ile Gly Ser His Pro Arg Thr Glu Arg Leu Phe Val Thr Tyr Asp
            260                 265                 270

Val Glu Thr Tyr Thr Trp Met Gly Ser Phe Gly Lys Gln Leu Val Pro
        275                 280                 285

Phe Met Leu Val Met His Ile Ser Gly Asp Asp Ala Leu Val Leu Lys
    290                 295                 300
```

-continued

Ala Cys Ala Leu Ala Val Glu Leu Lys Trp Asp Thr Trp Asn Asn Arg
305 310 315 320

Pro Ala Thr Phe Tyr Val Val Thr Pro Glu Lys Met Ala Val Gly Arg
325 330 335

Lys Phe Arg Asp Phe Arg Asp Arg Leu Gln Thr Leu Leu Ala Arg Glu
340 345 350

Leu Trp Arg Ser Phe Leu Ala Ala Asn Ser His Leu Glu Glu Trp Ser
355 360 365

Arg Ala Glu Leu Gly Leu Phe Ser Pro Glu Cys Leu Thr Phe Glu Glu
370 375 380

Leu Lys Lys Ala Pro Ala Leu Lys Gly Val Pro Arg Phe Leu Glu Leu
385 390 395 400

Tyr Ile Val Gly His Asn Ile Asn Gly Phe Asp Glu Ile Val Leu Ala
405 410 415

Ala Gln Val Ile Asn Asn Arg Ser Asp Val Pro Gly Pro Phe Arg Ile
420 425 430

Ser Arg Asn Phe Met Pro Arg Ala Gly Lys Ile Leu Phe Asn Asp Val
435 440 445

Thr Phe Ala Leu Pro Asn Pro Arg Gln Lys Lys Arg Thr Asp Phe Thr
450 455 460

Leu Trp Glu Gln Gly Cys Cys Asp Asp Thr Asp Phe Lys His Gln Tyr
465 470 475 480

Leu Lys Val Met Val Arg Asp Thr Phe Gln Leu Thr His Thr Ser Leu
485 490 495

Arg Lys Ala Ala Gln Ala Tyr Ala Leu Pro Ile Glu Lys Gly Cys Cys
500 505 510

Pro Tyr Lys Ala Val Asn Glu Phe Tyr Met Leu Gly Ala Tyr Arg Ala
515 520 525

Asp Asp Arg Gly Phe Pro Ala Ala Asp Tyr Trp Lys Asp Arg Glu Glu
530 535 540

Tyr Leu Leu Asn Arg Glu Leu Trp Glu Lys Lys Gln Glu Lys Thr Tyr
545 550 555 560

Asp Leu Val Arg Glu Thr Leu Asp Tyr Cys Ala Leu Asp Val Leu Val
565 570 575

Thr Ala Ala Leu Val Asp Lys Leu Arg Glu Ser Tyr Ala Gln Phe Leu
580 585 590

Gln Asp Ala Val Gly Leu Ser Gln Ala Ser Phe Asn Val Phe Gln Arg
595 600 605

Pro Thr Ile Ser Ser Asn Ser His Ala Ile Phe Arg Gln Ile Ala Tyr
610 615 620

Arg Ala Val Lys Pro Gln Lys Thr His Leu Gly Ser Gly Leu Leu Ala
625 630 635 640

Pro Ser His Glu Met Tyr Asp Tyr Val Arg Ala Ser Ile Arg Gly Gly
645 650 655

Arg Cys Tyr Pro Thr Tyr Ile Gly Val Leu Arg Gln Pro Leu Tyr Val
660 665 670

Tyr Asp Ile Cys Gly Met Tyr Ala Ser Ala Leu Thr His Pro Met Pro
675 680 685

Trp Gly Pro Pro Leu Asn Pro Tyr Glu Arg Ala Leu Ala Val Lys Lys
690 695 700

Trp Asp Leu Ala Leu Gln His Arg Val Glu Ile Asn Tyr Phe Asn Lys
705 710 715 720

```
Ser Leu Leu Pro Gly Ile Phe Thr Ile Asp Ala Asp Pro Pro Ala Ser
                725                 730                 735

Asn Leu Leu Asp Val Leu Pro Pro Phe Cys Ser Arg Lys Gly Gly Arg
            740                 745                 750

Leu Cys Trp Thr Asn Glu Pro Leu Arg Gly Glu Val Ala Thr Ser Val
        755                 760                 765

Asp Leu Ile Thr Leu His Asn Arg Gly Trp Ser Val Arg Ile Val Pro
    770                 775                 780

Asp Glu Arg Thr Thr Val Phe Pro Glu Trp Arg Cys Val Ala Arg Glu
785                 790                 795                 800

Tyr Val Gln Leu Asn Ile Ala Ala Lys Glu Arg Ala Asp Arg Glu Lys
                805                 810                 815

Asn Gln Thr Leu Arg Ser Ile Ala Lys Leu Leu Ser Asn Ala Leu Tyr
            820                 825                 830

Gly Ser Phe Ala Thr Lys Leu Asp Asn Lys Lys Ile Val Phe Ser Asp
        835                 840                 845

Gln Met Glu Thr Ser Thr Val Lys Asp Ile Ala Ser Gly Arg Val Asn
    850                 855                 860

Ile Lys Ser Thr Ser Phe Val Glu Thr Asp Thr Leu Ser Ala Glu Val
865                 870                 875                 880

Met Pro Ala Phe Glu Arg Ala Tyr Leu Pro Glu Gln Leu Ala Leu Ile
                885                 890                 895

His Ser Asp Ala Glu Glu Ser Asp Asp Glu Ala Gly Asn Ala Pro Phe
            900                 905                 910

Tyr Ser Pro Pro Arg His Pro Asp Gly His Val Thr Tyr Thr Tyr Lys
        915                 920                 925

Pro Ile Thr Phe Met Asp Ala Glu Glu Asp Asp Leu Cys Leu His Thr
    930                 935                 940

Leu Gln Lys Val Asp Pro Leu Ile Glu Asn Asp Arg Tyr Pro Ser Gln
945                 950                 955                 960

Ile Ala Ser Phe Val Leu Ala Trp Thr Arg Ala Phe Val Ser Glu Trp
                965                 970                 975

Ser Gln Phe Leu Tyr Asp Glu Asp Arg Gly Thr Pro Leu Glu Gln Arg
            980                 985                 990

Gln Leu Lys Ser Val Tyr Gly Asp  Thr Asp Ser Leu Phe  Val Thr Glu
        995                 1000                1005

Ala Gly  His Arg Leu Met Glu  Thr Arg Gly Lys Lys  Arg Ile Lys
    1010                1015                1020

Lys Asn  Gly Gly Lys Leu Val  Phe Asp Pro Asn Gln  Pro Glu Leu
    1025                1030                1035

Thr Trp  Leu Val Glu Cys Glu  Thr Val Cys Ala Gln  Cys Gly Ala
    1040                1045                1050

Asp Ala  Phe Ser Pro Glu Ser  Val Phe Leu Ala Pro  Lys Leu Tyr
    1055                1060                1065

Ala Leu  Lys Ser Leu His Cys  Ser Lys Cys Leu His  Val Ser Lys
    1070                1075                1080

Gly Lys  Leu Arg Ala Lys Gly  His Ala Ala Glu Ser  Leu Ser Tyr
    1085                1090                1095

Asp Leu  Met Leu Lys Cys Tyr  Leu Ala Asp Ser Gln  Gly Glu Asn
    1100                1105                1110

Val His  Phe Ser Thr Ser Arg  Met Ser Leu Lys Arg  Thr Leu Ala
    1115                1120                1125

Ser Ala  Gln Pro Gly Ala His  Pro Phe Thr Val Thr  Glu Thr Thr
```

```
    1130                1135                1140

Leu Thr  Arg Thr Leu Arg Pro  Trp Lys Asp Met Thr  Leu Ala Ala
    1145                1150                1155

Leu Asp  Ala His Arg Leu Val  Pro Tyr Ser Glu Ser  Arg Pro Asn
    1160                1165                1170

Pro Arg  Asn Gln Glu Val Cys  Trp Ile Glu Met Pro
    1175                1180                1185


<210> SEQ ID NO 49
<211> LENGTH: 574
<212> TYPE: PRT
<213> ORGANISM: Adenovirus

<400> SEQUENCE: 49

Met Gln Gln Gln Ser Ser Ala Asp Gly Thr Ser Val Asn Pro Ala Leu
1               5                   10                  15

Leu Ala Ser Met Gln Ser Gln Pro Ser Gly Val Asn Ala Ser Asp Asp
            20                  25                  30

Trp Ser Ala Ala Met Asp Arg Ile Met Ala Leu Thr Thr Arg Asn Pro
        35                  40                  45

Glu Ala Phe Arg Gln Gln Pro Gln Ala Asn Arg Phe Ser Ala Ile Leu
    50                  55                  60

Glu Ala Val Val Pro Ser Arg Thr Asn Pro Thr His Glu Lys Val Leu
65                  70                  75                  80

Thr Ile Val Asn Ala Leu Val Asp Ser Lys Ala Ile Arg Arg Asp Glu
                85                  90                  95

Ala Gly Leu Ile Tyr Asn Ala Leu Leu Glu Arg Val Ala Arg Tyr Asn
            100                 105                 110

Ser Thr Asn Val Gln Ala Asn Leu Asp Arg Leu Asn Thr Asp Val Arg
        115                 120                 125

Glu Ala Leu Ala Gln Lys Glu Arg Phe Leu Arg Asp Ser Asn Leu Gly
    130                 135                 140

Ser Leu Val Ala Leu Asn Ala Phe Leu Ser Thr Gln Pro Ala Asn Val
145                 150                 155                 160

Pro Arg Gly Gln Glu Asp Tyr Val Ser Phe Ile Ser Ala Leu Arg Leu
                165                 170                 175

Leu Val Ser Glu Val Pro Gln Ser Glu Val Tyr Gln Ser Gly Pro Asp
            180                 185                 190

Tyr Phe Phe Gln Thr Ser Arg Gln Gly Leu Gln Thr Val Asn Leu Ser
        195                 200                 205

Gln Ala Phe Lys Asn Leu Gln Gly Met Trp Gly Val Lys Ala Pro Leu
    210                 215                 220

Gly Asp Arg Ala Thr Ile Ser Ser Leu Leu Thr Pro Asn Thr Arg Leu
225                 230                 235                 240

Leu Leu Leu Leu Ile Ala Pro Phe Thr Asn Ser Ser Ser Ile Ser Arg
                245                 250                 255

Asp Ser Tyr Leu Gly His Leu Ile Thr Leu Tyr Arg Glu Ala Ile Gly
            260                 265                 270

Gln Ala Gln Val Asp Glu His Thr Tyr Gln Glu Ile Thr Asn Val Ser
        275                 280                 285

Arg Ala Leu Gly Gln Glu Asp Thr Gly Ser Leu Glu Ala Thr Leu Asn
    290                 295                 300

Phe Leu Leu Thr Asn Arg Arg Gln Lys Ile Pro Ser Gln Phe Thr Leu
305                 310                 315                 320
```

```
Ser Ala Glu Glu Glu Arg Ile Leu Arg Tyr Val Gln Gln Ser Val Ser
                325                 330                 335

Leu Tyr Leu Met Arg Glu Gly Ala Thr Ala Ser Thr Ala Leu Asp Met
            340                 345                 350

Thr Ala Arg Asn Met Glu Pro Ser Phe Tyr Ala Ser Asn Arg Pro Phe
        355                 360                 365

Ile Asn Arg Leu Met Asp Tyr Leu His Arg Ala Ala Ala Met Asn Gly
    370                 375                 380

Glu Tyr Phe Thr Asn Ala Ile Leu Asn Pro His Trp Met Pro Pro Ser
385                 390                 395                 400

Gly Phe Tyr Thr Gly Glu Phe Asp Leu Pro Glu Ala Asp Asp Gly Phe
                405                 410                 415

Leu Trp Asp Asp Val Ser Asp Ser Ile Phe Ser Pro Ser Ser Gln Arg
            420                 425                 430

Met Gln Lys Lys Glu Gly Gly Asp Glu Leu Pro Leu Ser Ser Ile Glu
        435                 440                 445

Ala Ala Ser Arg Gly Glu Ser Pro Phe Pro Ser Leu Ser Ser Val Ser
    450                 455                 460

Ser Gly Arg Val Ser Arg Pro Arg Leu Pro Ala Glu Ser Glu Tyr Leu
465                 470                 475                 480

Ser Asp Pro Ile Leu Gln Pro Ser Arg Lys Lys Asn Phe Pro Asn Asn
                485                 490                 495

Gly Val Glu Ser Leu Val Asp Lys Met Lys Arg Trp Lys Thr Tyr Ala
            500                 505                 510

Gln Glu Gln Lys Glu Trp Glu Glu Thr Gln Val Arg Pro Val Pro Pro
        515                 520                 525

Pro Thr Gln Arg Arg Trp Arg Arg Pro Arg Glu Asp Pro Asp Asp Ser
    530                 535                 540

Ala Asp Asp Ser Ser Val Leu Asp Leu Gly Gly Ser Gly Ala Asn Pro
545                 550                 555                 560

Phe Ala His Leu Arg Pro Gln Gly Arg Leu Gly Arg Leu Tyr
                565                 570


<210> SEQ ID NO 50
<211> LENGTH: 159
<212> TYPE: PRT
<213> ORGANISM: Adenovirus

<400> SEQUENCE: 50

Met Gly Gly Val Thr Lys Gly Ile Lys Arg Thr Trp Trp Trp Gly Gly
1               5                   10                  15

Phe Ile Ala Lys Met Ser Gly Ser Thr Asp Ser Asn Ser Val Asn Phe
            20                  25                  30

Glu Gly Gly Val Phe Ser Pro Tyr Leu Thr Thr Arg Leu Pro Ser Trp
        35                  40                  45

Ala Gly Val Arg Gln Asn Val Val Gly Ser Ser Met Asp Gly Arg Pro
    50                  55                  60

Val Ala Pro Ala Asn Ser Ala Thr Leu Thr Tyr Ala Thr Val Gly Ser
65                  70                  75                  80

Ser Leu Asp Ala Ala Ala Ala Ala Ala Ala Ser Ala Ala Ala Ser Thr
                85                  90                  95

Ala Arg Val Met Ala Val Asp Phe Gly Leu Tyr Asn Gln Leu Ala Thr
            100                 105                 110

Ala Ala Ala Ala Ser Arg Ser Val Val Gln Gln Asp Ala Leu Asn Val
        115                 120                 125
```

Ile Leu Ala Arg Leu Glu Met Leu Ser Gln Arg Leu Asp Gln Leu Ala
    130                 135                 140

Ala Gln Ile Ala Leu Ser Pro Ala Pro Asp Ser Thr Ser Asp Ser
145                 150                 155

<210> SEQ ID NO 51
<211> LENGTH: 447
<212> TYPE: PRT
<213> ORGANISM: Adenovirus

<400> SEQUENCE: 51

Met Glu Thr Arg Gly Arg Lys Arg Pro Leu Gln His Gln Gln Asp Glu
1               5                   10                  15

Pro Gln Thr His Thr Gly Lys Arg Pro Thr Arg Gly Pro Pro Phe Tyr
            20                  25                  30

Arg His Arg Asp His Pro Asp Ala Asp Pro Gln Thr Leu Glu Gly His
        35                  40                  45

Asp Ser Arg Ser Pro Gly Arg Pro Pro Ala Gly Ala Leu Gln Arg Lys
    50                  55                  60

Ser Ser Gln Pro Ser Gln Pro Arg Ser Leu Leu Asp Arg Asp Ala Ile
65                  70                  75                  80

Glu His Val Thr Glu Leu Trp Asp Arg Leu Tyr Leu Leu Arg Gln Ser
                85                  90                  95

Leu Glu Lys Met Pro Met Ala Asp Gly Leu Lys Pro Leu Lys His Phe
            100                 105                 110

Asn Ser Leu Glu Glu Leu Leu Ser Leu Gly Gly Glu Arg Leu Leu Gln
        115                 120                 125

Asn Leu Val Arg Glu Asn Arg His Val Arg Ser Met Met Asn Glu Val
    130                 135                 140

Ala Pro Leu Leu Arg Asn Asp Gly Ser Cys Lys Ser Leu Asn Tyr Gln
145                 150                 155                 160

Leu Gln Pro Val Ile Gly Val Ile Tyr Gly Pro Thr Gly Cys Gly Lys
                165                 170                 175

Ser Gln Leu Leu Arg Asn Leu Leu Ser Thr Gln Leu Ile Asn Pro Pro
            180                 185                 190

Pro Glu Thr Val Phe Phe Ile Ala Pro Gln Val Asp Met Ile Pro Pro
        195                 200                 205

Ser Glu Ile Lys Ala Trp Glu Met Gln Ile Cys Glu Gly Asn Tyr Ala
    210                 215                 220

Pro Gly Pro Glu Gly Thr Ile Ile Pro Gln Ser Gly Thr Leu Leu Pro
225                 230                 235                 240

Arg Phe Val Lys Met Ala Tyr Asp Asp Leu Thr Leu Glu Gln Asn Tyr
                245                 250                 255

Asp Val Ser Asn Pro Asp Asn Val Phe Ala Lys Ala Ala Ala Arg Gly
            260                 265                 270

Pro Ile Ala Ile Ile Met Asp Glu Cys Met Glu Asn Leu Gly Gly His
        275                 280                 285

Lys Gly Val Ser Lys Phe Phe His Ala Phe Pro Ser Lys Leu His Asp
    290                 295                 300

Lys Phe Pro Lys Cys Thr Gly Tyr Thr Val Leu Val Val Leu His Asn
305                 310                 315                 320

Met Asn Pro Arg Arg Asp Leu Gly Gly Asn Ile Ala Asn Leu Lys Ile
                325                 330                 335

Gln Ala Lys Met His Ile Ile Ser Pro Arg Met His Pro Ser Gln Leu

```
            340                 345                 350

Asn Arg Phe Val Asn Thr Tyr Thr Lys Gly Leu Pro Leu Ala Ile Ser
        355                 360                 365

Leu Leu Leu Lys Asp Ile Phe Gln Phe His Ala Gln Lys Pro Cys Tyr
    370                 375                 380

Asp Trp Val Ile Tyr Asn Thr Thr Pro Glu His Asp Ala Leu Gln Trp
385                 390                 395                 400

Ser Tyr Leu His Pro Lys Asp Gly Leu Met Pro Met Tyr Leu Asn Ile
                405                 410                 415

Gln Ser His Leu Tyr Arg Val Leu Glu Thr Ile His Lys Val Leu Asn
            420                 425                 430

Asp Arg Asp Arg Trp Ser Arg Ala Tyr Arg Ala Lys Lys Asn Lys
        435                 440                 445


<210> SEQ ID NO 52
<211> LENGTH: 396
<212> TYPE: PRT
<213> ORGANISM: Adenovirus

<400> SEQUENCE: 52

Met Lys Arg Thr Arg Ile Asp Glu Asp Phe Asn Pro Val Tyr Pro Tyr
1               5                   10                  15

Asp Ser Thr Thr Thr Pro Thr Val Pro Phe Ile Ala Pro Pro Phe Val
            20                  25                  30

Ser Ser Asn Gly Leu Gln Glu Ser Pro Pro Gly Met Leu Ser Leu Asn
        35                  40                  45

Tyr Ala Asp Pro Ile Thr Thr Asn Asn Gly Lys Leu Thr Val Lys Leu
    50                  55                  60

Gly Asn Asn Leu Ser Leu Ser Ser Asp Gly Ala Ile Thr Ser Ala Thr
65                  70                  75                  80

Ala Val Thr Asp Pro Leu Thr Asn Asn Gly Gly Thr Ile Gly Leu Ala
                85                  90                  95

Leu Ser Ala Pro Leu Thr Thr Thr Ser Thr Gly Leu Gly Ile Ser Ile
            100                 105                 110

Ser Pro Pro Ile Thr Leu Ser Asn Asn Ala Leu Asn Ile Ser Leu Gly
        115                 120                 125

Asn Gly Leu Thr Ser Ser Ser Asn Ser Leu Ala Ile Lys Thr Ser Gly
    130                 135                 140

Ala Ile Gly Phe Asp Asn Gln Gly Asn Leu Arg Leu Asn Thr Gly Gly
145                 150                 155                 160

Gly Met Arg Leu Ala Gly Asp Arg Leu Ile Leu Asp Val Asn Tyr Pro
                165                 170                 175

Phe Asn Gly Asp Pro Lys Leu Ser Leu Arg Ile Gly Lys Gly Leu Tyr
            180                 185                 190

Leu Gln Asn Asn Gln Asp Leu Ala Val Leu Leu Gly Ser Arg Ser Gly
        195                 200                 205

Leu Asp Phe Ser Gly Asn Asn Leu Val Val Lys Leu Gly Ser Gly Leu
    210                 215                 220

Ala Phe Asp Asn Asn Gly Ala Ile Thr Thr Ser Thr Ser Arg Ser Arg
225                 230                 235                 240

Phe Ala Asp Tyr Leu Pro Tyr Val Ser Thr Trp Pro Pro Leu Asn Glu
                245                 250                 255

Pro Asn Cys Ser Ile Tyr Glu Ser Leu Asp Ala Met Leu Gly Leu His
            260                 265                 270
```

```
Phe Ser Lys His Gly Leu His Val Ile Gly Thr Ile Ser Leu Lys Ala
        275                 280                 285

Ile Lys Gly Glu Leu Cys Asn Met Gln Arg Asp Thr Val Thr Leu Lys
    290                 295                 300

Leu Leu Phe Asn Ser Ser Gly Arg Leu Leu Asn Cys Pro Leu Leu Pro
305                 310                 315                 320

Ser Phe Trp Asn Pro Glu Thr Pro Leu Gln Phe Met Pro Ser Ser Thr
                325                 330                 335

Phe Tyr Pro Arg Asn Val Ser Pro Ser Thr Leu Thr Gln Thr Leu Pro
            340                 345                 350

Asp Ser Arg Cys Thr Phe Thr Val Ala Tyr Asn Thr Glu Gly Ala Asp
        355                 360                 365

Tyr Ser Phe Thr Phe Thr Trp Ser Val Cys Ser Gly Glu Lys Phe Asn
    370                 375                 380

Ala Pro Ala Ala Met Phe Cys Phe Val Ala Glu Gln
385                 390                 395


<210> SEQ ID NO 53
<211> LENGTH: 612
<212> TYPE: PRT
<213> ORGANISM: Adenovirus

<400> SEQUENCE: 53

Met Tyr Pro Gln Ala His Ser Pro Lys Leu Cys Gln Thr Leu Gly Ala
1               5                   10                  15

His Leu Leu Leu His Thr Thr Arg Lys Val Gln Ile Thr His Leu Pro
            20                  25                  30

Ser Leu Gly Pro Ser Val Pro Glu Lys Ser Leu Met Pro Pro Leu Arg
        35                  40                  45

Cys Ser Val Leu Leu Leu Asn Asn Lys Ala Cys Lys Ala Thr Phe Val
    50                  55                  60

Phe Phe Gln Met Lys Arg Ala Arg Ile Asp Asp Asp Phe Asn Pro Val
65                  70                  75                  80

Tyr Pro Tyr Asp Gln Pro Asn Ala Pro Leu Leu Pro Phe Ile Thr Pro
                85                  90                  95

Pro Phe Thr Ser Ser Asp Gly Leu Gln Glu Lys Pro Pro Gly Val Leu
            100                 105                 110

Ser Leu Asn Tyr Lys Asn Pro Ile Thr Thr Gln Asn Gly Ala Leu Thr
        115                 120                 125

Leu Lys Ile Gly Glu Gly Ile Glu Val Asn Asp Lys Gly Glu Leu Thr
    130                 135                 140

Ser Asn Ala Val Ser Val Ser Pro Pro Leu Ser Lys Ile Asp Asn Thr
145                 150                 155                 160

Leu Ser Leu Val Tyr Ser Asp Pro Leu Thr Val Arg Glu Asn Ser Leu
                165                 170                 175

His Leu Lys Thr Ala Leu Pro Ile Ser Leu Asn Ala Thr Arg Glu Leu
            180                 185                 190

Thr Leu Val Ala Asn Ala Pro Leu Ala Thr Thr Asn Gly Ala Leu Gln
        195                 200                 205

Leu Gln Ser Ala Ala Pro Leu Gly Val Ala Glu Arg Thr Leu Lys Leu
    210                 215                 220

Leu Phe Ser Asn Pro Leu Tyr Leu Gln Asn Asn Phe Leu Ser Val Ala
225                 230                 235                 240

Val Asp Lys Pro Leu Ala Met Ala Ser Thr Gly Ala Ile Ala Leu Gln
                245                 250                 255
```

```
Trp Ala Pro Pro Leu Gln Val Gly Thr Gly Gly Leu Thr Val Ala Thr
            260                 265                 270

Val Glu Pro Leu Thr Val Thr Asn Gly Asn Leu Asn Ile Asn Thr Lys
        275                 280                 285

Arg Pro Leu Ile Ile Glu Asp Ser Ser Leu Tyr Leu Ala Phe Arg Pro
    290                 295                 300

Pro Leu Arg Leu Phe Asn Ser Asp Pro Glu Leu Gly Val Asn Phe Ile
305                 310                 315                 320

Pro Pro Ile Thr Ile Arg Asp Asp Gly Leu Ala Leu Asn Thr Gly Glu
                325                 330                 335

Gly Leu Thr Leu Val Arg Asp Arg Leu Ser Val Asn Leu Gly Lys Asp
            340                 345                 350

Leu Gln Phe Val Asp Asn Thr Val Ser Leu Ala Leu Ser Thr Ala Leu
        355                 360                 365

Pro Leu Gln Tyr Thr Asp Gln Leu Arg Leu Asn Ile Gly Gln Gly Leu
    370                 375                 380

Arg Tyr Asn Pro Thr Ser Lys Lys Leu Asp Val Asp Leu Asn Gln Asn
385                 390                 395                 400

Lys Gly Leu Asn Trp Glu Asp Asn Lys Val Ile Thr Lys Leu Gly Asp
                405                 410                 415

Gly Leu Gln Phe Asp Ser Ala Gly Asn Ile Ser Val Ile Pro Pro Ser
            420                 425                 430

Val Thr Pro His Thr Leu Trp Thr Thr Ala Asp Pro Ser Pro Asn Cys
        435                 440                 445

Ser Val Tyr Thr Asp Leu Asp Ala Lys Leu Trp Leu Ser Leu Val Lys
    450                 455                 460

Cys Asn Gly Ile Val Gln Gly Thr Ile Ala Leu Lys Ala Leu Lys Gly
465                 470                 475                 480

Val Leu Leu Lys Pro Thr Ala Ser Ser Ile Ser Ile Val Ile Tyr Phe
                485                 490                 495

Tyr Ser Asn Gly Val Arg Arg Thr Asn Tyr Pro Thr Phe Asp Asn Glu
            500                 505                 510

Gly Thr Leu Ala Asn Thr Ala Thr Trp Gly Tyr Arg Gln Gly Gln Ser
        515                 520                 525

Ala Asn Thr Asn Val Thr Asn Ala Val Glu Phe Met Pro Ser Ser Ala
    530                 535                 540

Arg Tyr Pro Ile Asn Arg Gly Asp Asp Val Gln Asn Gln Met Met Gly
545                 550                 555                 560

Tyr Thr Cys Leu Gln Gly Ala Leu Asn Met Ala Val Gly Tyr Lys Val
                565                 570                 575

Thr Phe Asn His Ala Leu Glu Gly Tyr Ser Leu Lys Phe Thr Trp Pro
            580                 585                 590

Val Tyr Asn Asn Gln Ala Phe Asp Val Pro Cys Cys Ser Phe Ser Tyr
        595                 600                 605

Ile Thr Glu Glu
    610


<210> SEQ ID NO 54
<211> LENGTH: 503
<212> TYPE: PRT
<213> ORGANISM: Adenovirus

<400> SEQUENCE: 54

Met Arg Arg Ala Val Arg Val Pro Pro Val Tyr Pro Glu Gly Pro Pro
```

-continued

```
1               5                   10                  15

Pro Ser Tyr Glu Ser Val Met Glu Ala Leu Asn Thr Pro Ala Thr Leu
            20                  25                  30

Glu Ala Pro Tyr Val Pro Pro Arg Tyr Leu Gly Pro Thr Glu Gly Arg
        35                  40                  45

Asn Ser Ile Arg Tyr Ser Glu Leu Ala Pro Leu Tyr Asp Thr Thr Lys
    50                  55                  60

Val Tyr Leu Val Asp Asn Lys Ser Ala Asp Ile Ala Ser Leu Asn Tyr
65                  70                  75                  80

Gln Asn Asp His Ser Asn Phe Leu Thr Thr Val Val Gln Asn Asn Asp
                85                  90                  95

Phe Thr Pro Val Glu Ala Gly Thr Gln Thr Ile Asn Phe Asp Glu Arg
            100                 105                 110

Ser Arg Trp Gly Gly Gln Leu Lys Thr Ile Leu His Thr Asn Met Pro
        115                 120                 125

Asn Ile Asn Glu Phe Met Tyr Thr Asn Lys Phe Arg Ala Arg Leu Met
    130                 135                 140

Val Glu Lys Pro Gln Thr Gly Ser Pro Arg Tyr Glu Trp Phe Glu Phe
145                 150                 155                 160

Thr Ile Pro Glu Gly Asn Tyr Ser Glu Thr Met Thr Ile Asp Leu Met
                165                 170                 175

Asn Asn Ala Ile Val Asp Asn Tyr Leu Gln Val Gly Arg Gln Asn Gly
            180                 185                 190

Val Leu Glu Ser Asp Ile Gly Val Lys Phe Asp Thr Arg Asn Phe Arg
        195                 200                 205

Leu Gly Trp Asp Pro Val Thr Arg Leu Val Met Pro Gly Val Tyr Thr
    210                 215                 220

Asn Glu Ala Phe His Pro Asp Ile Val Leu Leu Pro Gly Cys Gly Val
225                 230                 235                 240

Asp Phe Thr Gln Ser Arg Leu Ser Asn Leu Leu Gly Ile Arg Lys Arg
                245                 250                 255

Arg Pro Phe Gln Glu Gly Phe Gln Ile Met Tyr Glu Asp Leu Glu Gly
            260                 265                 270

Gly Asn Ile Pro Ala Leu Leu Asp Val Pro Ala Tyr Glu Ala Ser Leu
        275                 280                 285

Ser Leu Ala Glu Ala Glu Gly Arg Val Thr Arg Gly Asp Thr Phe Ala
    290                 295                 300

Thr Ala Pro Gln Glu Leu Thr Ile Gln Pro Leu Thr Lys Asp Ser Lys
305                 310                 315                 320

Asn Arg Ser Tyr Asn Leu Leu Pro Asn Asn Thr Asp Thr Ala Tyr Arg
                325                 330                 335

Ser Trp Phe Leu Ala Tyr Asn Tyr Gly Asp Pro Glu Lys Gly Val Arg
            340                 345                 350

Ser Trp Thr Leu Leu Thr Thr Thr Asp Val Thr Cys Gly Ser Gln Gln
        355                 360                 365

Val Tyr Trp Ser Leu Pro Asp Met Met Gln Asp Pro Val Thr Phe Arg
    370                 375                 380

Ser Ser Thr Gln Val Asn Asn Phe Pro Val Val Gly Thr Glu Leu Leu
385                 390                 395                 400

Pro Val Tyr Ala Lys Ser Phe Tyr Asn Glu Gln Ala Val Tyr Ser Gln
                405                 410                 415

Leu Ile Arg Gln Ser Thr Ala Leu Thr His Val Phe Asn Arg Phe Pro
            420                 425                 430
```

Glu Asn Gln Ile Leu Val Arg Pro Pro Ala Pro Thr Ile Thr Thr Val
435 440 445

Ser Glu Asn Val Pro Ala Leu Thr Asp His Gly Thr Leu Pro Leu Arg
450 455 460

Ser Ser Ile Ser Gly Val Gln Arg Val Thr Ile Thr Asp Ala Arg Arg
465 470 475 480

Arg Thr Cys Pro Tyr Val Tyr Lys Ala Leu Gly Val Val Ala Pro Lys
485 490 495

Val Leu Ser Ser Arg Thr Phe
500

<210> SEQ ID NO 55
<211> LENGTH: 927
<212> TYPE: PRT
<213> ORGANISM: Adenovirus

<400> SEQUENCE: 55

Met Ala Thr Pro Ser Met Met Pro Gln Trp Ser Tyr Met His Ile Ala
1 5 10 15

Gly Gln Asp Ala Ser Glu Tyr Leu Ser Pro Gly Leu Val Gln Phe Ala
20 25 30

Arg Ala Thr Asp Thr Tyr Phe Ser Leu Gly Asn Lys Phe Arg Asn Pro
35 40 45

Thr Val Ala Pro Thr His Asp Val Thr Thr Asp Arg Ser Gln Arg Leu
50 55 60

Thr Leu Arg Phe Val Pro Val Asp Arg Glu Asp Thr Ala Tyr Ser Tyr
65 70 75 80

Lys Val Arg Tyr Thr Leu Ala Val Gly Asp Asn Arg Val Leu Asp Met
85 90 95

Ala Ser Thr Tyr Phe Asp Ile Arg Gly Val Leu Asp Arg Gly Pro Ser
100 105 110

Phe Lys Pro Tyr Ser Gly Thr Ala Tyr Asn Ser Leu Ala Pro Lys Gly
115 120 125

Ala Pro Asn Pro Ser Gln Trp Thr Thr Thr Asn Gly Gly Asn Lys Thr
130 135 140

Asn Ser Phe Gly Gln Ala Pro Phe Ile Gly Glu Ser Leu Thr Lys Asp
145 150 155 160

Gly Ile Gln Val Gly Val Asp Thr Gly Asn Pro Gly Thr Ala Val Tyr
165 170 175

Ala Asp Lys Leu Tyr Gln Pro Glu Pro Gln Val Gly Leu Ser Lys Trp
180 185 190

Asn Gln Asn Pro Ser Glu Asn Ala Ala Gly Arg Ile Leu Lys Pro Ser
195 200 205

Thr Pro Met Gln Pro Cys Tyr Gly Ser Tyr Ala Tyr Pro Thr Asn Thr
210 215 220

Asn Gly Gly Gln Val Lys Thr Ser Ala Thr Asp Ala Thr Gly Ala Asn
225 230 235 240

Asn Val Thr Leu Asn Phe Phe Asn Asn Ala Ala Asp Asn Gly Asn Asn
245 250 255

Asn Pro Lys Val Val Leu Tyr Ser Glu Asp Val Asn Leu Glu Ala Pro
260 265 270

Asp Thr His Leu Val Phe Lys Pro Asp Ala Asn Asn Ala Thr Ser Ala
275 280 285

Glu Thr Leu Leu Gly Gln Gln Ala Ala Pro Asn Arg Pro Asn Tyr Ile

```
    290                 295                 300

Gly Phe Arg Asp Asn Phe Ile Gly Leu Met Tyr Tyr Asn Ser Thr Gly
305                 310                 315                 320

Asn Met Gly Val Leu Ala Gly Gln Ala Ser Gln Leu Asn Ala Val Val
                325                 330                 335

Asp Leu Gln Asp Arg Asn Thr Glu Leu Ser Tyr Gln Leu Met Leu Asp
            340                 345                 350

Ala Leu Gly Asp Arg Ser Arg Tyr Phe Ser Met Trp Asn Gln Ala Val
        355                 360                 365

Asp Ser Tyr Asp Pro Asp Val Arg Ile Ile Glu Asn His Gly Val Glu
    370                 375                 380

Asp Glu Leu Pro Asn Tyr Cys Phe Pro Leu Asn Gly Gln Gly Ile Ser
385                 390                 395                 400

Asn Thr Tyr Lys Gly Val Lys Thr Asn Asn Gly Gly Ala Ala Trp Thr
                405                 410                 415

Gln Asp Thr Asp Val Val Thr Thr Asn Glu Ile Ser Ile Gly Asn Val
            420                 425                 430

Phe Ala Met Glu Ile Asn Leu Ala Ala Asn Leu Trp Arg Ser Phe Leu
        435                 440                 445

Tyr Ser Asn Val Ala Leu Tyr Leu Pro Asp Ser Tyr Lys Tyr Thr Pro
    450                 455                 460

Asp Asn Ile Glu Leu Pro Gln Asn Lys Asn Ser Tyr Gly Tyr Ile Asn
465                 470                 475                 480

Gly Arg Val Thr Ala Pro Asn Ala Ile Asp Thr Tyr Val Asn Ile Gly
                485                 490                 495

Ala Arg Trp Ser Pro Asp Pro Met Asp Asn Val Asn Pro Phe Asn His
            500                 505                 510

His Arg Asn Ala Gly Leu Arg Tyr Arg Ser Met Leu Leu Gly Asn Gly
        515                 520                 525

Arg Tyr Val Pro Phe His Ile Gln Val Pro Gln Lys Phe Phe Ala Ile
    530                 535                 540

Lys Asn Leu Leu Leu Leu Pro Gly Ser Tyr Thr Tyr Glu Trp Asn Phe
545                 550                 555                 560

Arg Lys Asp Val Asn Met Ile Leu Gln Ser Thr Leu Gly Asn Asp Leu
                565                 570                 575

Arg Val Asp Gly Ala Ser Ile Arg Phe Asp Ser Ile Asn Leu Tyr Ala
            580                 585                 590

Asn Phe Phe Pro Met Ala His Asn Thr Ala Ser Thr Leu Glu Ala Met
        595                 600                 605

Leu Arg Asn Asp Thr Asn Asp Gln Ser Phe Asn Asp Tyr Leu Cys Ala
    610                 615                 620

Ala Asn Met Leu Tyr Pro Ile Pro Ser Asn Ala Thr Ser Val Pro Ile
625                 630                 635                 640

Ser Ile Pro Ser Arg Asn Trp Ala Ala Phe Arg Gly Trp Ser Phe Thr
                645                 650                 655

Arg Leu Lys Thr Lys Glu Thr Pro Ser Leu Gly Ser Gly Phe Asp Pro
            660                 665                 670

Tyr Phe Val Tyr Ser Gly Ser Ile Pro Tyr Leu Asp Gly Thr Phe Tyr
        675                 680                 685

Leu Asn His Thr Phe Lys Lys Val Ser Ile Met Phe Asp Ser Ser Val
    690                 695                 700

Ser Trp Pro Gly Asn Asp Arg Leu Leu Thr Pro Asn Glu Phe Glu Ile
705                 710                 715                 720
```

```
Lys Arg Ser Val Asp Gly Glu Gly Tyr Asn Val Ala Gln Ser Asn Met
                725                 730                 735

Thr Lys Asp Trp Phe Leu Ile Gln Met Leu Ser His Tyr Asn Ile Gly
            740                 745                 750

Tyr Gln Gly Phe Tyr Val Pro Glu Ser Tyr Lys Asp Arg Met Tyr Ser
        755                 760                 765

Phe Phe Arg Asn Phe Gln Pro Met Ser Arg Gln Val Val Asp Thr Val
    770                 775                 780

Asn Tyr Ala Asn Tyr Lys Glu Val Lys Met Pro Phe Gln His Asn Asn
785                 790                 795                 800

Ser Gly Phe Val Gly Tyr Met Gly Pro Thr Met Arg Glu Gly Gln Ala
                805                 810                 815

Tyr Pro Ala Asn Tyr Pro Tyr Pro Leu Ile Gly Glu Thr Ala Val Pro
            820                 825                 830

Ser Val Thr Gln Lys Lys Phe Leu Cys Asp Arg Val Met Trp Arg Ile
        835                 840                 845

Pro Phe Ser Ser Asn Phe Met Ser Met Gly Ala Leu Thr Asp Leu Gly
    850                 855                 860

Gln Asn Met Leu Tyr Ala Asn Ser Ala His Ala Leu Asp Met Thr Phe
865                 870                 875                 880

Glu Val Asp Pro Met Asp Glu Pro Thr Leu Leu Tyr Val Leu Phe Glu
                885                 890                 895

Val Phe Asp Val Val Arg Ile His Gln Pro His Arg Gly Val Ile Glu
            900                 905                 910

Ala Val Tyr Leu Arg Thr Pro Phe Ser Ala Gly Asn Ala Thr Thr
        915                 920                 925


<210> SEQ ID NO 56
<211> LENGTH: 120
<212> TYPE: PRT
<213> ORGANISM: Adenovirus

<400> SEQUENCE: 56

Met Pro Leu Pro Cys Leu Pro Pro Pro Pro Val Cys Arg Asp Lys Ser
1               5                   10                  15

Ala Cys Ile Ala Trp Leu Glu Leu Ala Leu Thr Ser Ser Leu Glu Leu
            20                  25                  30

Phe Arg Asp Ile Ile Arg Tyr Glu Val Phe Ile Thr Pro Glu Ala Glu
        35                  40                  45

Arg Glu Leu Cys Ala Leu Gln Gln Trp Leu His Phe Ala Val Asn Thr
    50                  55                  60

Glu Arg Gln Arg Arg Arg Asp Gly Arg Arg Val Glu Ile Cys Trp Arg
65                  70                  75                  80

Arg Thr Trp Phe Cys Tyr Arg Lys Tyr Glu Asp Leu Arg Lys Asn Leu
                85                  90                  95

Thr Tyr Asp Ala Thr Arg Gln Thr Val Ser Leu Gln Thr Gly Ser Leu
            100                 105                 110

Gln Gln Thr Pro Ala Thr Ala Val
        115                 120


<210> SEQ ID NO 57
<211> LENGTH: 116
<212> TYPE: PRT
<213> ORGANISM: Adenovirus

<400> SEQUENCE: 57
```

```
Met Met Val Cys Leu Arg Met Ser Ile Glu Gly Ala Leu Val Gln Leu
1               5                   10                  15

Phe Gln Met Arg Gly Val Asn Leu Gln Glu Leu Cys Cys Asp Ile Val
            20                  25                  30

Arg Glu Trp Arg Ala Glu Asn Tyr Leu Gly Met Val Gln Asn Cys Ser
        35                  40                  45

Val Ile Ile Glu Asp Phe Glu His Asp Ala Phe Ala Leu Leu Val Phe
    50                  55                  60

Leu Asp Val Arg Val Gln Ala Leu Leu Glu Ala Val Val Asp His Leu
65                  70                  75                  80

Glu Asn Arg Ile His Phe Asp Leu Ala Val Leu Tyr His Gln Arg Thr
                85                  90                  95

Gly Gly Asp Arg Cys His Leu Arg Asp Leu His Phe Val Thr Leu Arg
            100                 105                 110

Asp Arg Leu Glu
        115
```

<210> SEQ ID NO 58
<211> LENGTH: 130
<212> TYPE: PRT
<213> ORGANISM: Adenovirus

<400> SEQUENCE: 58

```
Met Tyr Gln Arg Gln Pro Val Phe Val Cys Val Ile Val Pro Ala Ala
1               5                   10                  15

Leu Arg Gln Tyr Leu His Asp Leu Asp Ile Glu Val Leu Asp Phe Leu
            20                  25                  30

Lys Arg Gln Leu Ser Asp Phe Trp Leu His Leu Leu His Cys Leu Thr
        35                  40                  45

Pro Pro Phe Gln Phe Cys Tyr Asn Gly Ala Val Leu Leu Ser Leu Ala
    50                  55                  60

Pro Ser Ile Gln Leu Leu Cys Cys Val Ala Thr Pro Glu Met Thr Pro
65                  70                  75                  80

Asp Gly Glu Leu Thr Ala Leu Val Cys Ala Asp Leu Leu Asn Phe Leu
                85                  90                  95

Gln Leu Thr Leu Arg Val Glu Ile Arg Asp Arg Gly Val His Pro Asp
            100                 105                 110

Pro Asp Met Leu Asn Leu Leu Gln Val Ser Gln Glu Leu Asp Ile Leu
        115                 120                 125

Gln Ala
    130
```

<210> SEQ ID NO 59
<211> LENGTH: 126
<212> TYPE: PRT
<213> ORGANISM: Adenovirus

<400> SEQUENCE: 59

```
Met Ala Asp Glu Ala Ile Tyr Val His Leu Leu Gly Ser Arg Ala Ile
1               5                   10                  15

Met Pro Gln Gln Gln Gly Phe Ser Asn Leu Tyr Val Leu Phe Ser Pro
            20                  25                  30

Glu Asn Phe Val Ile Ser Pro Arg Gly Val Leu Leu Val Ser Leu Gln
        35                  40                  45

Leu Ser Met Asp Ile Pro Gln Gly Tyr Leu Gly Arg Leu Phe Ser Leu
    50                  55                  60
```

Ser Asp Met Asn Val Arg Gly Val Phe Val Gly Ala Gln Asp Ile Gln
65 70 75 80

Pro Ser Thr Trp Trp Glu Met Ser Val Val Leu Phe Asn His Ser Asp
85 90 95

Glu Phe Phe Tyr Gly Phe Arg Gly Gln Pro Val Ala Cys Leu Leu Leu
100 105 110

Glu Arg Val Ile Tyr Pro Cys Leu His Arg Ala Ser Leu Val
115 120 125

<210> SEQ ID NO 60
<211> LENGTH: 106
<212> TYPE: PRT
<213> ORGANISM: Adenovirus

<400> SEQUENCE: 60

Met Gln Arg Asp Arg Arg Tyr Arg Cys Arg Leu Gly Pro Tyr Asn Arg
1 5 10 15

His Gln Leu Pro Pro Cys Asp Glu Thr Pro Cys Ala Thr Ile Glu Asn
20 25 30

Pro Pro Tyr Leu Glu Cys Glu Asn Leu Asn Met His Asn Val Ser Glu
35 40 45

Gly Phe Val Ser Val Thr Asp Glu Arg Phe Ala Arg Lys Glu Thr Val
50 55 60

Trp Thr Leu Thr Pro Lys Asn Pro Cys Leu Asn Thr Gln Phe Gln Leu
65 70 75 80

Phe Thr Ala Thr Lys Gly Glu Arg Met Val Tyr Ser Val Lys Trp Lys
85 90 95

Gly Gly Gly Ser Leu Thr Val Arg Ile Met
100 105

<210> SEQ ID NO 61
<211> LENGTH: 285
<212> TYPE: PRT
<213> ORGANISM: Adenovirus

<400> SEQUENCE: 61

Met Gln Arg Asp Arg Arg Tyr Arg Cys Arg Leu Gly Pro Tyr Asn Arg
1 5 10 15

His Gln Leu Pro Pro Cys Asp Glu Thr Pro Cys Ala Thr Ile Glu Asn
20 25 30

Pro Pro Tyr Leu Glu Cys Glu Asn Leu Asn Met His Asn Val Ser Glu
35 40 45

Val Arg Gly Val Pro Ser Cys Val Ser Phe Thr Val Leu Gln Glu Trp
50 55 60

Pro Val Tyr Trp Asp Ser Val Leu Thr Ala Trp Glu Lys His Val Met
65 70 75 80

Lys Thr Tyr Met Gln Ile Cys Ile Cys Cys Ala Thr Ile Asp Val Glu
85 90 95

Tyr Asn Gln Ile Ile Arg Gly Tyr Glu Arg Trp Val Leu His Cys His
100 105 110

Cys Asn Ser Pro Gly Ser Leu Gln Cys Lys Ala Gly Gly Val Val Leu
115 120 125

Ala Asn Trp Phe Arg Met Ala Ile Tyr Gly Ser Leu Val Asn Val Arg
130 135 140

Phe Pro Trp Tyr Arg Gln Val Val Asn Tyr His Leu Pro Lys Glu Val
145 150 155 160

```
Leu Tyr Val Gly Ser Val Phe Ile Arg Gly Arg His Leu Ile Tyr Val
                165                 170                 175

Arg Ile Phe Leu Asp Gly His Ala Val Ala Val Leu Glu Asn Ser Ser
            180                 185                 190

Phe Gly Trp Ser Ala Phe Ser Tyr Gly Ile Leu Asn Asn Leu Ile Ile
        195                 200                 205

Met Val Cys Thr Tyr Cys Lys Asp Leu Ser Glu Ile Gln Met Arg Cys
    210                 215                 220

Cys Ala Lys Arg Thr Arg Arg Phe Leu Ile Arg Ala Val Arg Leu Leu
225                 230                 235                 240

Asp Arg Leu Thr Ser Tyr Gln Pro Arg Arg Ala Arg Leu Glu Ala Ala
                245                 250                 255

Arg Gln Ser Leu Leu Arg Gly Leu Met Glu Arg His Arg Pro Phe Thr
            260                 265                 270

Leu Ala Glu Tyr Gly Arg Gly Glu Asn Pro Trp Arg Thr
        275                 280                 285


<210> SEQ ID NO 62
<211> LENGTH: 113
<212> TYPE: PRT
<213> ORGANISM: Adenovirus

<400> SEQUENCE: 62

Met Phe Ser Met Ile Pro Leu Leu Val Ile Leu Cys Asp Leu Leu Pro
1               5                   10                  15

Phe Thr Tyr Cys His Cys Pro Leu Asn Lys Pro Trp Ser Leu Tyr Thr
            20                  25                  30

Cys Tyr Ala Glu Leu Pro Asp Ile Pro Val Ile Trp Leu Tyr Val Ala
        35                  40                  45

Thr Ala Ala Leu Val Phe Val Ala Thr Cys Val Gly Val Lys Ile Tyr
    50                  55                  60

Phe Cys Leu Lys Ile Gly Trp Leu His Pro Pro Glu Asp Leu Pro Arg
65                  70                  75                  80

Phe Pro Leu Val Asn Ala Phe Gln Met Gln Pro Pro Pro Pro Asp Leu
                85                  90                  95

Ile Arg Ala Pro Ser Val Val Ser Tyr Phe Gln Leu Ala Gly Gly Asp
            100                 105                 110

Asp


<210> SEQ ID NO 63
<211> LENGTH: 90
<212> TYPE: PRT
<213> ORGANISM: Adenovirus

<400> SEQUENCE: 63

Met Val Ala Val Phe Phe Phe Leu Leu Cys Leu Pro Ile Ile Phe Val
1               5                   10                  15

Ser Ser Thr Phe Ala Ala Val Ser His Val Glu Ala Glu Cys Leu Pro
            20                  25                  30

Pro Phe Ala Val Tyr Leu Ile Phe Thr Phe Val Cys Cys Thr Ala Ile
        35                  40                  45

Ala Ser Ile Ala Cys Phe Phe Val Thr Ile Phe Gln Ala Ala Asp Tyr
    50                  55                  60

Leu Tyr Val Arg Phe Val Tyr Phe Arg His His Pro Glu Tyr Arg Asn
65                  70                  75                  80
```

```
Gln Asn Val Ala Ser Leu Leu Cys Leu Ala
                85                  90


<210> SEQ ID NO 64
<211> LENGTH: 290
<212> TYPE: PRT
<213> ORGANISM: Adenovirus

<400> SEQUENCE: 64

Met Met Leu Thr Val Leu Thr Thr Leu Leu Leu Pro Ala Val Ile Cys
1               5                   10                  15

Ile Arg Pro Pro Glu Pro Pro Pro Ala His Gly Ile Asn Thr Lys Ser
            20                  25                  30

Leu Pro Asn Ser Leu Gln Asn Pro Ser Arg Val Tyr Ala Lys Val Gly
        35                  40                  45

Gln Asn Leu Thr Leu Glu Ser Arg Tyr Ser Ser His Ser Asn Ser Met
    50                  55                  60

Pro His Val Val Trp Tyr Leu Glu Val Phe Asn Asp Asp Thr Ile Phe
65                  70                  75                  80

Pro Ser Ser Val Val Pro Pro Ile Phe Ser Gly Ile Lys Leu Cys Glu
                85                  90                  95

Ile Thr Glu Gln Asn Tyr Gln Thr Phe Asn His Ala Pro Lys Glu Phe
            100                 105                 110

Asn Cys Ile Asn Lys Ser Leu Asn Leu Phe Asn Leu Lys Pro Ser Asp
        115                 120                 125

Ser Gly Leu Tyr Asn Val Lys Val Tyr Lys Asp Asp Ile Glu His Asn
    130                 135                 140

Thr Tyr Phe Arg Leu Ser Val Ile Arg Phe Ala Gln Pro Gln Cys Thr
145                 150                 155                 160

Ile Asn Ser Ser Tyr Leu Thr Glu Ser Tyr Cys Leu Ile Ser Ile Asp
                165                 170                 175

Cys Phe His Leu Glu Tyr Pro Ala Ile Val Glu Phe Asn Gly Ser Arg
            180                 185                 190

Ser Asn Phe His Tyr Tyr Val Leu Ser Lys Gly Gly Lys Asn Leu Ala
        195                 200                 205

Asp Tyr Tyr Thr Val Thr Tyr Asp Tyr His Gly Leu Lys Gln Thr Phe
    210                 215                 220

Lys Val Glu Tyr Pro Phe Asn Asp Ile Cys Asn Asp Ile Ile Ser Leu
225                 230                 235                 240

Glu Thr Leu Ala Asp Phe Thr Pro Val Phe Ile Val Thr Ile Val Met
                245                 250                 255

Ser Val Ile Thr Ile Val Val Ser Leu Leu Phe Cys Cys Phe Tyr Lys
            260                 265                 270

Pro Lys Ser Lys Ser Asn Phe Gln Gln Val Lys Leu Lys Thr Ile Gln
        275                 280                 285

Leu Val
    290


<210> SEQ ID NO 65
<211> LENGTH: 157
<212> TYPE: PRT
<213> ORGANISM: Adenovirus

<400> SEQUENCE: 65

Met Lys Ala Phe Val Val Val Phe Ala Leu Ser Leu Ile Tyr Ser Arg
1               5                   10                  15
```

```
Gly Thr Ala Asp Asp Leu Val Phe Glu Gly Thr Ile Glu Thr Val Leu
            20                  25                  30

Phe Ser Asp Ser Thr Ser Ser Ile Thr Leu Asn Cys Ser Cys Thr Asn
        35                  40                  45

Glu Leu Ile Gln Trp Asn Ala Asn Arg Thr Phe Cys Lys Ala Phe Tyr
    50                  55                  60

Arg Asn Phe Thr Tyr Tyr Ser Asn Asn Ser Leu Cys Ala Val Cys Thr
65                  70                  75                  80

Arg Gln Ala Leu His Leu Tyr Pro Pro Phe Val Ala Gly Ser Tyr Leu
                85                  90                  95

Cys Ile Gly Ser Gly Ala Gln Pro Cys Phe His Arg Trp Tyr Leu Tyr
            100                 105                 110

Glu Asp Asn Thr Ser Phe Thr Thr Ser Thr Pro Lys Gln Val Ser Tyr
        115                 120                 125

Leu His Val Ser Leu Lys Pro Leu Phe Ala Leu Ala Ala Phe Ile Leu
    130                 135                 140

Val Ile Leu Ala Asn Phe Ile Leu Ile Asn Asn Leu Pro
145                 150                 155


<210> SEQ ID NO 66
<211> LENGTH: 121
<212> TYPE: PRT
<213> ORGANISM: Adenovirus

<400> SEQUENCE: 66

Met Thr Asp Ser His Asp Ile Asn Ile Thr Met Glu Arg Gly Ile Ala
1               5                   10                  15

Gln Arg Gln Arg Glu Ala Arg Ala Met Asp Tyr Leu Arg Leu Gln Glu
            20                  25                  30

Leu Lys Glu Thr His Trp Cys Asp Arg Gly Ser Leu Cys Leu Val Lys
        35                  40                  45

Leu Ala Ser Leu Ser Tyr Asp Ile Ser Thr Gln Gly His Glu Leu Ser
    50                  55                  60

Tyr Thr Val Ala Gly Gln Lys Gln Thr Phe Ser Thr Ile Met Gly Gly
65                  70                  75                  80

Thr Ser Leu Lys Ile Thr His Gln Ser Lys Pro Val Glu Gly Ala Ile
                85                  90                  95

Leu Cys His Cys His Lys Pro Asp Cys Met Glu Lys Leu Ile Thr Thr
            100                 105                 110

Leu Cys Ala Val Ala Glu Ile Phe Lys
        115                 120


<210> SEQ ID NO 67
<211> LENGTH: 91
<212> TYPE: PRT
<213> ORGANISM: Adenovirus

<400> SEQUENCE: 67

Met Thr Asp Gly Ala Ala Val Thr Ala Arg Leu Arg His Leu His His
1               5                   10                  15

Cys Arg Arg Phe Arg Cys Phe Ala Arg Glu Pro Leu Val Phe Ser Tyr
            20                  25                  30

Phe Glu Leu Pro Glu His His Leu Gln Gly Pro Ala His Gly Ile Lys
        35                  40                  45

Leu Glu Val Glu Lys Glu Leu Glu Ser Arg Leu Ile Arg Asp Phe Thr
    50                  55                  60
```

Pro His Pro Leu Leu Val Glu Lys Glu His Gly Thr Thr Ile Ile Thr
65 70 75 80

Val Phe Cys Ile Cys Pro Thr Pro Gly Leu His
85 90

<210> SEQ ID NO 68
<211> LENGTH: 474
<212> TYPE: PRT
<213> ORGANISM: Adenovirus

<400> SEQUENCE: 68

Met Glu Gln Arg Gln Pro Pro Val Val Gly Leu His Ala Gly Leu His
1 5 10 15

Asp His Gly Ala Val Ala Gly Ala Pro Glu Glu Glu Glu Gly Leu His
20 25 30

Leu Leu Ala Gly Ala Ala Ser Ala Arg Ser Gly Ala Ser Gly Gly Arg
35 40 45

Gly Gly Gly Glu Arg Glu Pro Glu Gly Arg Arg Gly Pro Ser Ser Gly
50 55 60

Ile Glu Ala Val Gly Glu Pro Glu Glu Gly Thr Ser Asp Gly Val Arg
65 70 75 80

Lys Arg Arg Arg Thr Glu Met Glu Glu Val Asn Ala Arg Asp Tyr Leu
85 90 95

Thr Asp Leu Thr Val Arg Leu Met Ser Arg Arg Arg Pro Glu Thr Val
100 105 110

Ala Trp Ser Glu Leu Glu Thr Glu Phe Lys Asn Gly Asn Met Asn Leu
115 120 125

Leu Tyr Lys Tyr Ser Phe Glu Gln Ile Gln Thr His Trp Leu Glu Pro
130 135 140

Trp Glu Asp Trp Glu Thr Ala Phe Ala Asn Phe Ala Lys Ile Ala Leu
145 150 155 160

Arg Pro Asp Lys Ile Tyr Thr Ile Arg Arg Met Val Asn Ile Arg Lys
165 170 175

Cys Val Tyr Val Leu Gly Asn Gly Ala Met Val Gln Ile Gln Thr Cys
180 185 190

Asp Arg Val Ala Phe Asn Cys Cys Met Gln Ser Met Gly Pro Gly Val
195 200 205

Ile Gly Met Ser Gly Val Thr Phe Ala Asn Val Arg Phe Thr Gly Glu
210 215 220

Asn Phe Phe Gly Ala Val Ile Met Asn Asn Thr Ser Leu Thr Leu His
225 230 235 240

Gly Val Tyr Phe Leu Asn Leu Ser Asn Thr Cys Val Glu Cys Trp Gly
245 250 255

Arg Ala Cys Leu Arg Gly Cys Thr Phe Tyr Gly Cys Trp Lys Ala Val
260 265 270

Val Gly Arg Thr Lys Ser His Val Ser Val Lys Lys Cys Met Phe Glu
275 280 285

Arg Cys Val Ile Ala Ile Met Val Glu Gly Gln Gly Arg Ile Arg Asn
290 295 300

Asn Val Gly Ala Glu Asn Gly Cys Phe Leu Leu Leu Lys Gly Ser Ala
305 310 315 320

Ser Val Lys His Asn Met Ile Cys Gly Thr Gly Thr Cys Asn Ile Ser
325 330 335

His Leu Leu Thr Cys Ser Asp Gly Asn Cys Gln Ala Leu Arg Thr Leu
340 345 350

His Ile Val Ser His Arg Arg Leu Pro Trp Pro Val Leu Glu His Asn
355 360 365

Met Leu Thr Arg Cys Ser Val His Val Gly Ala Arg Arg Gly Met Leu
370 375 380

Val Pro Tyr Gln Cys Asn Phe Ser Tyr Thr Lys Val Leu Leu Glu Thr
385 390 395 400

Asp Ala Phe Pro Arg Val Cys Phe Asn Gly Val Phe Asp Met Thr Val
405 410 415

Glu Val Phe Lys Val Val Arg Tyr Asp Glu Ser Lys Ser Arg Cys Arg
420 425 430

Pro Cys Glu Cys Gly Ala Asn His Leu Arg Leu Tyr Pro Val Thr Leu
435 440 445

Asn Val Thr Glu Glu Leu Arg Ala Asp His Leu Thr Leu Ser Cys Leu
450 455 460

Arg Thr Asp Tyr Glu Ser Ser Asp Glu Glu
465 470

<210> SEQ ID NO 69
<211> LENGTH: 225
<212> TYPE: PRT
<213> ORGANISM: Adenovirus

<400> SEQUENCE: 69

Met Arg Leu Val Pro Glu Met Tyr Gly Val Ser Trp Asp Glu Thr Ala
1 5 10 15

Glu Glu Leu Leu Asn Ala Glu Ile Tyr Asp Val Pro Asn Leu Pro Pro
20 25 30

Gly Thr Pro Ser Leu His Asp Leu Phe Asp Val Glu Asn Asp Gly Gly
35 40 45

Gln Asp Glu Asn Glu Asp Ala Val Asn Ser Met Phe Pro Asp Ser Met
50 55 60

Leu Ser Ala Gly Glu Gly Tyr Ala Gly Asp Val Asp Pro Ser Gly Ser
65 70 75 80

Asp Met Asp Leu Lys Cys Tyr Glu Asp Gly Leu Pro Ser Ser Ser Ser
85 90 95

Glu Gly Ser Asp Glu Asp Glu Gln Lys Pro Leu Lys His Glu Leu Val
100 105 110

Leu Asp Cys Pro Lys Asn Pro Gly His Asp Cys Arg Ala Cys Ala Phe
115 120 125

His Arg Ala Thr Ser Gly Asn Thr Glu Ala Ile Cys Cys Leu Cys Tyr
130 135 140

Met Arg Leu Thr Ser Asp Phe Val Tyr Ser Asp Val Ser Asp Val Glu
145 150 155 160

Gly Asp Gly Asp Lys Ser Lys Val Ser Glu Ser Pro Gly Ser Leu Gly
165 170 175

Thr Val Val Pro Asp Gly Val Leu Lys Pro Thr Ala Val Arg Val Ser
180 185 190

Ala Arg Arg Arg Gln Ala Val Glu Lys Leu Glu Asp Leu Leu Gln Glu
195 200 205

Pro Glu Gln Thr Glu Pro Leu Asp Leu Ser Leu Lys Gln Pro Arg Met
210 215 220

Thr
225

<210> SEQ ID NO 70
<211> LENGTH: 461
<212> TYPE: PRT
<213> ORGANISM: Adenovirus

<400> SEQUENCE: 70

```
Met Ala Gly Asn Gln Asn Pro Gly Glu Arg Ser Ile Thr Pro Tyr Leu
1               5                   10                  15

Arg Glu Arg Ser Pro Glu Arg Asp Val Ala Val Pro Leu Pro Pro Lys
            20                  25                  30

Lys Lys Ala Arg Lys Ser Ser Gln Ala Arg Pro Pro Ser Pro Glu Ile
        35                  40                  45

Ile Ser Asp Ser Glu Gly Glu Gly Thr Val Ile Gly Val Gly Phe Ser
    50                  55                  60

Tyr Pro Pro Val Arg Ile Val Lys Gln Ala Asp Gly Gly Arg Val Phe
65                  70                  75                  80

Gln Arg Val Thr Val Glu Glu Ala Asn Pro Glu Arg Glu Glu Arg Ser
                85                  90                  95

Ser Val Leu Val Val Asn Pro His Ser Ser Pro Leu Val Thr Ala Trp
            100                 105                 110

Glu Lys Gly Met Glu Ala Met Met Ile Leu Met Glu Lys Phe His Val
        115                 120                 125

Pro His Glu Asp Arg Ala Thr Phe Lys Phe Leu Pro Glu Gln Gly Pro
    130                 135                 140

Val Tyr Arg Lys Ile Cys Gln Thr Trp Leu Asn Glu Glu His Arg Gly
145                 150                 155                 160

Leu Ala Leu Thr Phe Thr Ser Asn Lys Thr Phe Thr Glu Met Met Gly
                165                 170                 175

Arg Phe Leu Met Ala Tyr Met Gln Ser Tyr Ala Gly Val Val Gln Lys
            180                 185                 190

Asn Trp Glu Ala Thr Gly Cys Ala Val Trp Gln His Arg Ser Ala Lys
        195                 200                 205

Glu Asp Gly Val Leu Cys Cys Phe His Gly Thr Glu Met Ile Arg Lys
    210                 215                 220

Glu His Val Thr Glu Met Asp Val Thr Ser Glu Asn Gly Gln Lys Ala
225                 230                 235                 240

Leu Lys Glu Asn Pro Gly Lys Ala Lys Val Val Gln Asn Arg Trp Gly
                245                 250                 255

Arg Asn Val Val Gln Ile Arg Asn Asp Asp Ala Arg Cys Cys Pro Glu
            260                 265                 270

Asp Val Ser Cys Gly Pro Asn Val Phe Ser Gly Lys Ser Cys Gly Leu
        275                 280                 285

Phe Tyr Thr Glu Gly Leu Lys Ala Gln Met Ala Phe Arg Gln Leu Glu
    290                 295                 300

Ala Phe Leu Arg Ala Ser Tyr Pro Glu Met Gln Arg Gly Gln Gly Arg
305                 310                 315                 320

Ile Leu Ile Pro Leu Arg Cys Asp Cys Leu His Lys Pro Asp Val Ile
                325                 330                 335

Pro Arg Met Gly Arg Gln Met Cys Lys Val Thr Pro Tyr Gly Leu Ser
            340                 345                 350

Asn Ala Asp Asp Leu Asp Val Ala Glu Val Asn Asp Ala Thr Ala Leu
        355                 360                 365

Ala Ser Ile Lys Tyr Pro Ser Val Leu Val Phe Gln Cys Ala Asn Pro
    370                 375                 380
```

```
Val Tyr Arg Asn Ser Arg Gly Gly Ala Ala Pro Asn Cys Asp Phe Lys
385                 390                 395                 400

Ile Ser Gly Pro Asp Ile Ile Gly Ala Leu Gln Leu Val Arg Gln Phe
                405                 410                 415

Trp Lys Glu Asn Met Glu Asp Lys Pro Leu Pro Lys Met Ile Ile Pro
            420                 425                 430

Glu Phe Arg Trp His Pro Arg Phe Gln Tyr Arg Asn Val Ala Leu Pro
        435                 440                 445

Ser Ser His Gly Asp Asp Cys Pro Glu Pro Phe Glu Phe
    450                 455                 460


<210> SEQ ID NO 71
<211> LENGTH: 375
<212> TYPE: PRT
<213> ORGANISM: Adenovirus

<400> SEQUENCE: 71

Met His Pro Val Leu Arg Gln Met Arg Pro Gln Thr Ala Ala Phe Gln
1               5                   10                  15

Pro Thr Thr Thr Ala Thr Ala Ala Val Cys Gly Ala Gly Arg Gly Glu
            20                  25                  30

Glu Glu Leu Ala Leu Asp Leu Glu Glu Gly Glu Gly Leu Ala Arg Leu
        35                  40                  45

Gly Ala Pro Ser Pro Glu Arg His Pro Arg Val Gln Leu Ala Arg Asp
    50                  55                  60

Ala Arg Gln Ala Tyr Val Pro Arg Gln Asn Leu Phe Arg Asp Gly Ser
65                  70                  75                  80

Gly Gln Glu Ala Glu Glu Met Arg Asp Cys Arg Phe Arg Ala Gly Lys
                85                  90                  95

Glu Leu Arg Ala Gly Phe Asp Arg Glu Lys Leu Leu Arg Ala Glu Asp
            100                 105                 110

Phe Glu Pro Asp Glu Gly Ser Gly Ile Ser Pro Ala Arg Ala His Val
        115                 120                 125

Thr Ala Ala Asn Leu Val Thr Ala Tyr Glu Gln Thr Val Asn Glu Glu
    130                 135                 140

Arg Asn Phe Gln Lys Ser Phe Asn Asn His Val Arg Thr Leu Ile Ala
145                 150                 155                 160

Arg Glu Glu Val Ala Thr Gly Leu Met His Leu Trp Asp Phe Ile Glu
                165                 170                 175

Ala Tyr Val Gln Asn Pro Thr Ser Lys Pro Leu Thr Ala Gln Leu Phe
            180                 185                 190

Leu Ile Val Gln His Ser Arg Asp Asn Glu Thr Phe Arg Glu Ala Met
        195                 200                 205

Leu Asn Ile Ala Glu Pro Glu Gly Arg Trp Leu Leu Asp Leu Val Asn
    210                 215                 220

Ile Leu Gln Ser Ile Val Val Gln Glu Arg Ser Leu Ser Leu Ala Asp
225                 230                 235                 240

Lys Val Ala Ala Ile Asn Tyr Ser Met Gln Ser Leu Gly Lys Phe Tyr
                245                 250                 255

Ala Arg Lys Ile Tyr Lys Ser Pro Tyr Val Pro Ile Asp Lys Glu Val
            260                 265                 270

Lys Ile Asp Ser Phe Tyr Met Arg Met Ala Leu Lys Val Leu Thr Leu
        275                 280                 285

Ser Asp Asp Leu Gly Val Tyr Arg Asn Asp Arg Ile His Lys Ala Val
    290                 295                 300
```

```
Ser Ala Ser Arg Arg Arg Glu Leu Ser Asp Arg Glu Leu Met His Ser
305                 310                 315                 320

Leu Arg Arg Ala Leu Ala Gly Ala Gly Asp Pro Asp Arg Glu Thr Tyr
                325                 330                 335

Phe Asp Met Gly Ala Asp Leu Gln Trp Arg Pro Ser Ala Arg Ala Leu
            340                 345                 350

Glu Ala Ala Gly Tyr Arg Gly Glu Arg Glu Glu Ile Asp Asp Glu Asp
        355                 360                 365

Glu Glu Tyr Glu Asp Asp Pro
    370                 375


<210> SEQ ID NO 72
<211> LENGTH: 198
<212> TYPE: PRT
<213> ORGANISM: Adenovirus

<400> SEQUENCE: 72

Met Pro Pro Lys Gly Val Lys Gln Leu Ile Ala Gln Gln Arg Ala Lys
1               5                   10                  15

Lys Gln Gln Glu Leu Leu Arg His Met Glu Glu Glu Glu Glu Ala Ser
            20                  25                  30

Asp Ala Trp Asp Ser Gln Ala Glu Glu Ala Ser Glu Asp Glu Glu Met
        35                  40                  45

Glu Gly Trp Asp Ser Leu Asp Glu Val Glu Glu Glu Glu Glu Val Glu
    50                  55                  60

Asp Glu Pro Ile Gly Glu Lys Pro Pro Ala Ser Ser Ala Leu Ser Pro
65                  70                  75                  80

Ser Arg Leu Ala Lys Thr Arg Val Pro Thr Pro Gly Gly Ser Arg Lys
                85                  90                  95

Ala Ser Arg Arg Trp Asp Thr Thr Gly Ser Pro Lys Lys Ser Lys Ala
            100                 105                 110

Ser Ser Arg Ser Ala Thr Ala Phe Ser Ala Ala Lys Asp Ser Pro Ala
        115                 120                 125

Ala Arg Glu Leu Arg Asn Arg Ile Phe Pro Thr Leu Tyr Ala Ile Phe
    130                 135                 140

Gln Gln Ser Arg Gly Gln Gln Gln Glu Leu Lys Ile Lys Asn Arg Ser
145                 150                 155                 160

Leu Arg Ser Leu Thr Arg Ser Cys Leu Tyr His Arg Arg Glu Asp Gln
                165                 170                 175

Leu Gln Arg Thr Leu Asp Asp Ala Glu Ala Leu Phe Asn Lys Tyr Cys
            180                 185                 190

Ser Val Ser Leu Lys Asp
        195


<210> SEQ ID NO 73
<211> LENGTH: 180
<212> TYPE: PRT
<213> ORGANISM: Adenovirus

<400> SEQUENCE: 73

Met Pro Pro Lys Gly Val Lys Gln Leu Ile Ala Gln Gln Arg Ala Lys
1               5                   10                  15

Lys Gln Gln Glu Leu Leu Arg His Met Glu Glu Glu Glu Glu Ala Ser
            20                  25                  30

Asp Ala Trp Asp Ser Gln Ala Glu Glu Ala Ser Glu Asp Glu Glu Met
        35                  40                  45
```

```
Glu Gly Trp Asp Ser Leu Asp Glu Val Glu Glu Glu Glu Glu Val Glu
    50                  55                  60

Asp Glu Pro Ile Gly Glu Lys Pro Pro Ala Ser Ser Ala Leu Ser Pro
65                  70                  75                  80

Ser Arg Leu Ala Lys Thr Arg Val Pro Thr Pro Gly Gly Ser Arg Lys
                85                  90                  95

Ala Ser Arg Arg Trp Asp Thr Thr Gly Ser Pro Val Ala Ser Ala Ala
            100                 105                 110

Gly Lys Pro Gly Arg Pro Arg Arg Gly Tyr Cys Ser Trp Arg Val His
        115                 120                 125

Lys Ser Ser Ile Val Asn Cys Leu Gln His Cys Gly Gly Asn Ile Ser
    130                 135                 140

Phe Ala Arg Arg Tyr Leu Leu Tyr His His Gly Val Ala Val Pro Arg
145                 150                 155                 160

Asn Val Leu Tyr Tyr Tyr Arg His Leu Tyr Ser Pro Tyr Glu Thr Leu
                165                 170                 175

Gly Glu Lys Ile
            180


<210> SEQ ID NO 74
<211> LENGTH: 761
<212> TYPE: PRT
<213> ORGANISM: Adenovirus

<400> SEQUENCE: 74

Met Asp Leu Met Arg Lys Glu Ser Leu Thr Thr Pro Pro Leu Ser Asp
1               5                   10                  15

Glu Asp Val Pro Ile Glu Gln Asp Pro Gly Phe Val Thr Pro Pro Glu
            20                  25                  30

Glu Pro Glu Leu Pro Ile Ser Phe Asp Leu Ala Arg Ser Glu Arg Thr
        35                  40                  45

Glu Gln Asp Gly Asp Tyr Leu Leu Glu Ala Glu Ile Leu Leu Lys His
    50                  55                  60

Phe Ala Arg Gln Ser Thr Ile Val Lys Glu Ala Leu Gln Asp Arg Ser
65                  70                  75                  80

Glu Val Pro Leu Asp Val Cys Glu Leu Ser Arg Ala Tyr Glu Ala Asn
                85                  90                  95

Leu Phe Ser Pro Arg Val Pro Pro Lys Lys Gln Pro Asn Gly Thr Cys
            100                 105                 110

Glu Pro Asn Pro Arg Leu Asn Phe Tyr Pro Val Phe Ala Val Pro Glu
        115                 120                 125

Ala Leu Ala Thr Tyr His Ile Phe Phe Lys Asn Gln Gly Ile Pro Leu
    130                 135                 140

Ser Cys Arg Ala Asn Arg Thr Lys Ala Asp Arg Lys Leu Arg Leu Arg
145                 150                 155                 160

Ala Gly Ala Arg Ile Pro Glu Ile Ala Ser Leu Glu Glu Val Pro Lys
                165                 170                 175

Ile Phe Glu Gly Leu Gly Arg Asp Glu Asn Arg Ala Ala Asn Ala Leu
            180                 185                 190

Gln Lys Glu Gln Lys Glu Ala Gln Ser Val Leu Ile Glu Leu Glu Gly
        195                 200                 205

Asp Asn Ala Arg Leu Ala Val Leu Lys Arg Thr Val Glu Val Ser His
    210                 215                 220

Phe Ala Tyr Pro Ala Leu Asn Leu Pro Pro Lys Val Met Arg Ser Val
```

```
225                 230                 235                 240

Met Asp His Leu Leu Ile Lys Arg Ala Glu Pro Leu Asn Pro Glu Asn
                245                 250                 255

Pro Asp Pro Glu Asn Ser Glu Asp Gly Lys Pro Val Val Ser Asp Glu
            260                 265                 270

Glu Leu Glu Arg Trp Leu Gly Thr Lys Asp Pro Glu Arg Leu Gln Glu
        275                 280                 285

Lys Arg Lys Met Met Met Ala Ala Ile Leu Val Thr Ala Glu Leu Glu
    290                 295                 300

Cys Leu Gln Arg Phe Phe Ala Asp Val Glu Thr Ile Arg Lys Val Glu
305                 310                 315                 320

Glu Ser Leu His Tyr Thr Phe Arg His Gly Tyr Val Arg Gln Ala Cys
                325                 330                 335

Lys Ile Ser Asn Val Glu Leu Ser Asn Leu Val Ser Tyr Met Gly Val
            340                 345                 350

Leu His Glu Asn Arg Leu Gly Gln Ser Val Leu His Cys Thr Leu Gln
        355                 360                 365

Gly Glu Ala Arg Arg Asp Tyr Val Arg Asp Cys Val Tyr Leu Phe Leu
    370                 375                 380

Leu Leu Thr Trp Gln Thr Ala Met Gly Val Trp Gln Gln Cys Leu Glu
385                 390                 395                 400

Glu Arg Asn Leu Lys Glu Leu Asp Lys Leu Leu Thr Lys Gln Arg Lys
                405                 410                 415

Ala Leu Trp Thr Gly Phe Ser Glu Arg Ala Ala Ala Ser Gln Leu Ala
            420                 425                 430

Asp Ile Ile Phe Pro Glu Arg Leu Met Lys Thr Leu Gln Asn Gly Leu
        435                 440                 445

Pro Asp Phe Ile Ser Gln Ser Ile Leu Gln Asn Phe Arg Ser Phe Val
    450                 455                 460

Leu Glu Arg Ser Gly Ile Leu Pro Ala Met Ser Cys Ala Leu Pro Ser
465                 470                 475                 480

Asp Phe Val Pro Leu Thr Tyr Arg Glu Cys Pro Pro Pro Leu Trp Ser
                485                 490                 495

His Cys Tyr Leu Leu Gln Leu Ala Asn Tyr Leu Ala Tyr His Cys Asp
            500                 505                 510

Leu Met Glu Asn Val Ser Gly Glu Gly Leu Leu Glu Cys His Cys Arg
        515                 520                 525

Cys Asn Leu Cys Thr Pro His Arg Ser Leu Val Cys Asn Thr Glu Leu
    530                 535                 540

Leu Ser Glu Thr Gln Val Ile Gly Thr Phe Glu Ile Gln Gly Pro Glu
545                 550                 555                 560

Gln His Glu Gly Ala Ser Gly Leu Lys Leu Thr Pro Ala Leu Trp Thr
                565                 570                 575

Ser Ala Tyr Leu Arg Lys Phe Val Ala Glu Asp Tyr His Ala Ser Lys
            580                 585                 590

Ile Gln Phe Tyr Glu Asp Gln Ser Gln Pro Pro Lys Ala Pro Leu Thr
        595                 600                 605

Ala Cys Val Ile Thr Gln Ser Asn Ile Leu Ala Gln Leu Gln Thr Ile
    610                 615                 620

Asn Gln Ala Arg Arg Glu Phe Leu Leu Lys Lys Gly His Gly Val Tyr
625                 630                 635                 640

Leu Asp Pro Gln Thr Gly Glu Glu Leu Asn Pro Ser Thr Leu Ser Ala
                645                 650                 655
```

```
Glu Ala Ala Pro Lys Gln His Ala Ala Gln Arg Ser Gln Thr Ala Asp
            660                 665                 670

Ser Ser Ala Glu Ser Glu Glu Ala Ala Arg Ala Pro Ala Ala His Gly
        675                 680                 685

Arg Gly Gly Gly Ser Gln Arg Cys Val Gly Gln Ser Gly Arg Gly Gly
    690                 695                 700

Phe Gly Gly Arg Gly Asp Gly Arg Leu Gly Gln Pro Arg Arg Gly Gly
705                 710                 715                 720

Gly Gly Gly Arg Gly Arg Gly Arg Thr Asp Arg Arg Lys Thr Thr Gly
                725                 730                 735

Phe Gln Arg Thr Phe Ser Glu Pro Ser Gly Glu Asn Pro Arg Pro Asn
            740                 745                 750

Pro Gly Arg Leu Thr Gln Ser Gln Pro
        755                 760


<210> SEQ ID NO 75
<211> LENGTH: 758
<212> TYPE: PRT
<213> ORGANISM: Adenovirus

<400> SEQUENCE: 75

Met Asp Leu Met Arg Lys Glu Ser Leu Thr Thr Pro Pro Leu Ser Asp
1               5                   10                  15

Glu Asp Val Pro Ile Glu Gln Asp Pro Gly Tyr Val Thr Pro Ser Glu
            20                  25                  30

Glu Leu Pro Ile Ser Phe Asp Leu Ala Arg Ser Glu Arg Thr Glu Gln
        35                  40                  45

Asp Gly Asp Tyr Leu Leu Glu Ala Glu Ile Leu Leu Lys His Phe Ala
    50                  55                  60

Arg Gln Ser Thr Ile Val Lys Glu Ala Leu Gln Asp Arg Ser Glu Val
65                  70                  75                  80

Pro Leu Asp Val Cys Glu Leu Ser Arg Ala Tyr Glu Ala Asn Leu Phe
                85                  90                  95

Ser Pro Arg Val Pro Pro Lys Lys Gln Pro Asn Gly Thr Cys Glu Pro
            100                 105                 110

Asn Pro Arg Leu Asn Phe Tyr Pro Val Phe Ala Val Pro Glu Ala Leu
        115                 120                 125

Ala Thr Tyr His Ile Phe Phe Lys Asn Gln Gly Ile Pro Leu Ser Cys
    130                 135                 140

Arg Ala Asn Arg Thr Lys Ala Asp Arg Lys Leu Arg Leu Arg Ala Gly
145                 150                 155                 160

Ala Arg Ile Pro Glu Ile Ala Ser Leu Glu Glu Val Pro Lys Ile Phe
                165                 170                 175

Glu Gly Leu Gly Arg Asp Glu Asn Arg Ala Ala Asn Ala Leu Gln Lys
            180                 185                 190

Glu Gln Lys Glu Ala Gln Ser Val Leu Ile Glu Leu Glu Gly Asp Asn
        195                 200                 205

Ala Arg Leu Ala Val Leu Lys Arg Thr Val Glu Val Ser His Phe Ala
    210                 215                 220

Tyr Pro Ala Leu Asn Leu Pro Pro Lys Val Met Arg Ser Val Met Asp
225                 230                 235                 240

His Leu Leu Ile Lys Arg Ala Glu Pro Leu Asn Pro Glu Asn Pro Asp
                245                 250                 255

Pro Glu Asn Ser Glu Asp Gly Lys Pro Val Val Ser Asp Glu Glu Leu
```

-continued

```
            260                 265                 270

Glu Arg Trp Leu Gly Thr Lys Asp Pro Glu Arg Leu Gln Asp Lys Arg
        275                 280                 285

Lys Met Met Met Ala Ala Ile Leu Val Thr Ala Glu Leu Glu Cys Leu
    290                 295                 300

Gln Arg Phe Phe Ala Asp Val Glu Thr Ile Arg Lys Val Glu Glu Ser
305                 310                 315                 320

Leu His Tyr Thr Phe Arg His Gly Tyr Val Arg Gln Ala Cys Lys Ile
                325                 330                 335

Ser Asn Val Glu Leu Ser Asn Leu Val Ser Tyr Met Gly Val Leu His
            340                 345                 350

Glu Asn Arg Leu Gly Gln Ser Val Leu His Cys Thr Leu Gln Gly Glu
        355                 360                 365

Ala Arg Arg Asp Tyr Val Arg Asp Cys Val Tyr Leu Phe Leu Leu Leu
    370                 375                 380

Thr Trp Gln Thr Ala Met Gly Val Trp Gln Gln Cys Leu Glu Glu Arg
385                 390                 395                 400

Asn Val Lys Glu Leu Asp Lys Leu Leu Thr Lys Gln Arg Lys Ala Leu
                405                 410                 415

Trp Thr Ser Phe Ser Glu Arg Ala Ala Ala Ser His Leu Ala Asp Ile
            420                 425                 430

Ile Phe Pro Gln Arg Leu Met Lys Thr Leu Gln Asn Gly Leu Pro Asp
        435                 440                 445

Phe Ile Ser Gln Ser Ile Leu Gln Asn Phe Arg Ser Phe Val Leu Glu
    450                 455                 460

Arg Ser Gly Ile Leu Pro Ala Met Ser Cys Ala Leu Pro Ser Asp Phe
465                 470                 475                 480

Val Pro Leu Thr Tyr Arg Glu Cys Pro Pro Pro Leu Trp Ser His Cys
                485                 490                 495

Tyr Leu Leu Gln Leu Ala Asn Tyr Leu Ala Tyr His Cys Asp Leu Met
            500                 505                 510

Glu Asn Val Ser Gly Glu Gly Leu Leu Glu Cys His Cys Arg Cys Asn
        515                 520                 525

Leu Cys Thr Pro His Arg Ser Leu Val Cys Asn Thr Glu Leu Leu Ser
    530                 535                 540

Glu Thr Gln Val Ile Gly Thr Phe Glu Ile Gln Gly Pro Glu Gln His
545                 550                 555                 560

Glu Gly Ala Ser Gly Leu Lys Leu Thr Pro Ala Leu Trp Thr Ser Ala
                565                 570                 575

Tyr Leu Arg Lys Phe Val Ala Glu Asp Tyr His Ala Ser Lys Ile Gln
            580                 585                 590

Phe Tyr Glu Asp Gln Ser Gln Pro Pro Lys Ala Pro Leu Thr Ala Cys
        595                 600                 605

Val Ile Thr Gln Ser Asn Ile Leu Ala Gln Leu Gln Thr Ile Asn Gln
    610                 615                 620

Ala Arg Arg Glu Phe Leu Leu Lys Lys Gly His Gly Val Tyr Leu Asp
625                 630                 635                 640

Pro Gln Thr Gly Glu Glu Leu Asn Pro Ser Thr Leu Ser Ala Glu Ala
                645                 650                 655

Ala Pro Lys Gln His Ala Ala Gln Arg Ser Gln Thr Ala Asp Ser Ser
            660                 665                 670

Ala Glu Ser Glu Glu Ala Ala Arg Ala Pro Ala Ala His Gly Arg Gly
        675                 680                 685
```

Gly Gly Ser Gln Arg Cys Val Gly Gln Ser Gly Arg Gly Gly Phe Gly
    690                 695                 700

Gly Arg Gly Asp Gly Arg Leu Gly Gln Pro Arg Arg Gly Gly Gly Gly
705                 710                 715                 720

Arg Gly Arg Gly Arg Ser Asp Arg Arg Lys Thr Thr Gly Phe Gln Arg
                725                 730                 735

Thr Phe Ser Glu Pro Ser Ala Glu Asn Pro Arg Pro Asn Pro Gly Arg
            740                 745                 750

Leu Thr Gln Ser Gln Pro
        755

<210> SEQ ID NO 76
<211> LENGTH: 179
<212> TYPE: PRT
<213> ORGANISM: Adenovirus

<400> SEQUENCE: 76

Met Pro Pro Lys Gly Val Lys Gln Leu Ile Ala Gln Gln Arg Ala Lys
1               5                   10                  15

Lys Gln Gln Glu Leu Leu Gln His Met Glu Glu Glu Glu Glu Ala Ser
            20                  25                  30

Asp Ala Trp Asp Ser Gln Ala Glu Glu Ala Ser Glu Asp Glu Glu Met
        35                  40                  45

Glu Gly Trp Asp Ser Pro Asp Glu Ala Glu Glu Glu Glu Val Glu Asp
    50                  55                  60

Glu Ala Ile Gly Glu Lys Pro Pro Ala Ser Ser Ala Leu Ser Pro Ser
65                  70                  75                  80

Arg Leu Pro Lys Thr Arg Val Pro Thr Pro Gly Gly Ser Arg Lys Ala
                85                  90                  95

Ser Arg Arg Trp Asp Thr Thr Gly Ser Pro Val Ala Ser Ala Ala Gly
            100                 105                 110

Lys Pro Gly Arg Pro Arg Arg Gly Tyr Cys Ser Trp Arg Val His Lys
        115                 120                 125

Ser Ser Ile Val Asn Cys Leu Gln His Cys Gly Gly Asn Ile Ser Phe
    130                 135                 140

Ala Arg Arg Tyr Leu Leu Tyr His His Gly Val Ala Val Pro Arg Asn
145                 150                 155                 160

Val Leu Tyr Tyr Tyr Arg His Leu Tyr Ser Pro Tyr Glu Thr Leu Gly
                165                 170                 175

Glu Lys Ile

<210> SEQ ID NO 77
<211> LENGTH: 195
<212> TYPE: PRT
<213> ORGANISM: Adenovirus

<400> SEQUENCE: 77

Met Pro Pro Lys Gly Val Lys Gln Leu Ile Ala Gln Gln Arg Ala Lys
1               5                   10                  15

Lys Gln Gln Glu Leu Leu Gln His Met Glu Glu Glu Glu Glu Ala Ser
            20                  25                  30

Asp Ala Trp Asp Ser Gln Ala Glu Glu Ala Ser Glu Asp Glu Glu Met
        35                  40                  45

Glu Gly Trp Asp Ser Pro Asp Glu Ala Glu Glu Glu Glu Val Glu Asp
    50                  55                  60

```
Glu Ala Ile Gly Glu Lys Pro Pro Ala Ser Ser Ala Leu Ser Pro Ser
65                  70                  75                  80

Arg Leu Pro Lys Thr Arg Val Pro Thr Pro Gly Gly Ser Arg Lys Ala
                85                  90                  95

Ser Arg Arg Trp Asp Thr Thr Gly Ser Pro Lys Lys Ser Lys Ala Ser
            100                 105                 110

Ser Arg Ser Ala Thr Ala Phe Ser Ala Ala Lys Asp Ser Pro Ala Ala
        115                 120                 125

Arg Glu Leu Arg Asn Arg Ile Phe Pro Thr Leu Tyr Ala Ile Phe Gln
    130                 135                 140

Gln Ser Arg Gly Gln Gln Gln Glu Leu Lys Ile Lys Asn Arg Ser Leu
145                 150                 155                 160

Arg Ser Leu Thr Arg Ser Cys Leu Tyr His Arg Arg Glu Asp Gln Leu
                165                 170                 175

Gln Arg Thr Leu Asp Asp Ala Glu Ala Leu Phe Asn Lys Tyr Cys Ser
            180                 185                 190

Val Ser Leu
        195


<210> SEQ ID NO 78
<211> LENGTH: 375
<212> TYPE: PRT
<213> ORGANISM: Adenovirus

<400> SEQUENCE: 78

Met His Pro Val Leu Arg Gln Met Arg Pro Gln Thr Ala Ala Phe Gln
1               5                   10                  15

Pro Thr Thr Thr Ala Thr Ala Ala Val Cys Gly Ala Gly Arg Gly Glu
            20                  25                  30

Glu Glu Leu Ala Leu Asp Leu Glu Glu Gly Glu Gly Leu Ala Arg Leu
        35                  40                  45

Gly Ala Pro Ser Pro Glu Arg His Pro Arg Val Gln Leu Ala Arg Asp
    50                  55                  60

Ala Arg Gln Ala Tyr Val Pro Arg Gln Asn Leu Phe Arg Asp Gly Ser
65                  70                  75                  80

Gly Gln Glu Ala Glu Glu Met Arg Asp Cys Arg Phe Arg Ala Gly Lys
                85                  90                  95

Glu Leu Arg Ala Gly Phe Asp Arg Glu Lys Leu Leu Arg Ala Glu Asp
            100                 105                 110

Phe Glu Pro Asp Glu Gly Ser Gly Ile Ser Pro Ala Arg Ala His Val
        115                 120                 125

Thr Ala Ala Asn Leu Val Thr Ala Tyr Glu Gln Thr Val Asn Glu Glu
    130                 135                 140

Arg Asn Phe Gln Lys Ser Phe Asn Asn His Val Arg Thr Leu Ile Ala
145                 150                 155                 160

Arg Glu Glu Val Ala Thr Gly Leu Met His Leu Trp Asp Phe Ile Glu
                165                 170                 175

Ala Tyr Val Gln Asn Pro Thr Ser Lys Pro Leu Thr Ala Gln Leu Phe
            180                 185                 190

Leu Ile Val Gln His Ser Arg Asp Asn Glu Thr Phe Arg Glu Ala Met
        195                 200                 205

Leu Asn Ile Ala Glu Pro Glu Gly Arg Trp Leu Leu Asp Leu Val Asn
    210                 215                 220

Ile Leu Gln Ser Ile Val Val Gln Glu Arg Ser Leu Ser Leu Ala Asp
225                 230                 235                 240
```

```
Lys Val Ala Ala Ile Asn Tyr Ser Met Gln Ser Leu Gly Lys Phe Tyr
                245                 250                 255

Ala Arg Lys Ile Tyr Lys Ser Pro Tyr Val Pro Ile Asp Lys Glu Val
            260                 265                 270

Lys Ile Asp Ser Phe Tyr Met Arg Met Ala Leu Lys Val Leu Thr Leu
        275                 280                 285

Ser Asp Asp Leu Gly Val Tyr Arg Asn Asp Arg Ile His Lys Ala Val
    290                 295                 300

Ser Ala Ser Arg Arg Arg Glu Leu Ser Asp Arg Glu Leu Met His Ser
305                 310                 315                 320

Leu Arg Arg Ala Leu Ala Gly Ala Gly Asp Pro Asp Arg Glu Thr Tyr
                325                 330                 335

Phe Asp Met Gly Ala Asp Leu Gln Trp Arg Pro Ser Ala Arg Ala Leu
            340                 345                 350

Glu Ala Ala Gly Tyr Arg Gly Glu Arg Asp Glu Ile Gly Asp Glu Asp
        355                 360                 365

Glu Glu Tyr Glu Asp Asp Pro
    370                 375


<210> SEQ ID NO 79
<211> LENGTH: 461
<212> TYPE: PRT
<213> ORGANISM: Adenovirus

<400> SEQUENCE: 79

Met Ala Gly Asn Gln Asn Pro Gly Glu Arg Ser Ile Thr Pro Tyr Leu
1               5                   10                  15

Arg Glu Arg Ser Pro Glu Arg Asp Val Ala Val Pro Leu Pro Pro Lys
            20                  25                  30

Lys Lys Ala Arg Lys Ser Ser Gln Ala Arg Pro Pro Ser Pro Glu Ile
        35                  40                  45

Val Ser Asp Ser Glu Gly Glu Gly Thr Val Ile Gly Val Gly Phe Ser
    50                  55                  60

Tyr Pro Pro Val Arg Ile Val Lys Gln Ala Asp Gly Gly Arg Val Phe
65                  70                  75                  80

Gln Arg Val Thr Val Glu Glu Ala Asn Ala Glu Arg Glu Glu Arg Ser
                85                  90                  95

Ser Val Leu Val Val Asn Pro His Ser Ser Pro Leu Val Thr Ala Trp
            100                 105                 110

Glu Lys Gly Met Glu Ala Met Met Ile Leu Met Glu Lys Phe His Val
        115                 120                 125

Ser Asn Glu Asp Lys Ala Thr Phe Lys Phe Leu Pro Glu Gln Gly Pro
    130                 135                 140

Val Tyr Arg Lys Ile Cys Gln Thr Trp Leu Asn Glu Glu His Arg Gly
145                 150                 155                 160

Leu Ala Leu Thr Phe Thr Ser Asn Lys Thr Phe Thr Glu Met Met Gly
                165                 170                 175

Arg Phe Leu Thr Ala Tyr Met Gln Ser Tyr Ala Gly Val Val Gln Lys
            180                 185                 190

Asn Trp Glu Ala Thr Gly Cys Ala Val Trp Gln His Arg Ser Ala Lys
        195                 200                 205

Glu Asp Gly Val Leu Cys Cys Phe His Gly Thr Glu Met Ile His Lys
    210                 215                 220

Glu His Val Thr Glu Met Asp Val Thr Ser Glu Asn Gly Gln Lys Ala
```

```
225                 230                 235                 240

Leu Lys Glu Asn Pro Gly Lys Ala Lys Val Val Gln Asn Arg Trp Gly
                245                 250                 255

Arg Asn Val Val Gln Ile Arg Asn Asp Asp Ala Arg Cys Cys Pro Glu
            260                 265                 270

Asp Val Ser Cys Gly Pro Asn Val Phe Ser Gly Lys Ser Cys Gly Leu
        275                 280                 285

Phe Tyr Thr Glu Gly Leu Lys Ala Gln Met Ala Phe Arg Gln Leu Glu
    290                 295                 300

Ala Phe Leu Arg Ala Ser Tyr Pro Glu Met Gln Arg Gly Gln Gly Arg
305                 310                 315                 320

Ile Leu Ile Pro Leu Arg Cys Asp Cys Leu His Lys Pro Asp Val Ile
                325                 330                 335

Pro Arg Met Gly Arg Gln Met Cys Lys Val Thr Pro Tyr Gly Leu Ser
            340                 345                 350

Asn Ala Asp Asp Leu Asp Val Ala Glu Val Asn Asp Ala Thr Ala Leu
        355                 360                 365

Ala Ser Ile Lys Tyr Pro Ser Val Leu Val Phe Gln Cys Ala Asn Pro
    370                 375                 380

Val Tyr Arg Asn Ser Arg Gly Gly Ala Ala Pro Asn Cys Asp Phe Lys
385                 390                 395                 400

Ile Ser Gly Pro Asp Ile Ile Gly Ala Leu Gln Leu Val Arg Gln Phe
                405                 410                 415

Trp Lys Glu Asn Met Glu Asp Lys Pro Leu Pro Lys Met Ile Ile Pro
            420                 425                 430

Glu Phe Arg Trp His Pro Arg Phe Gln Tyr Arg Asn Val Ala Leu Pro
        435                 440                 445

Ser Ser His Gly Asp Asp Cys Pro Glu Pro Phe Glu Phe
    450                 455                 460


<210> SEQ ID NO 80
<211> LENGTH: 226
<212> TYPE: PRT
<213> ORGANISM: Adenovirus

<400> SEQUENCE: 80

Met Arg Leu Val Pro Glu Met Tyr Gly Val Ser Trp Asp Glu Thr Ala
1               5                   10                  15

Glu Glu Leu Leu Asn Ala Glu Ile Tyr Asp Val Pro Asn Ser Pro Pro
            20                  25                  30

Gly Thr Pro Ser Leu His Asp Leu Phe Asp Val Asn Ala Glu Ser Ala
        35                  40                  45

Asp Gly Pro Asp Glu Asn Glu Asp Ala Val Asn Ser Met Phe Pro Asp
    50                  55                  60

Ser Met Leu Ser Ala Gly Glu Gly Tyr Ala Gly Asp Val Glu Pro Ser
65                  70                  75                  80

Gly Ser Asp Met Asp Leu Lys Cys Tyr Glu Asp Leu Pro Ser Ser Ser
                85                  90                  95

Ser Glu Gly Ser Asp Glu Asp Glu Gln Lys Pro Leu Lys His Glu Leu
            100                 105                 110

Val Leu Asp Cys Pro Lys Asn Pro Gly His Asp Cys Arg Ala Cys Ala
        115                 120                 125

Phe His Arg Ala Thr Ser Gly Asn Thr Glu Ala Ile Cys Cys Leu Cys
    130                 135                 140
```

Tyr Met Arg Leu Thr Ser Asp Phe Val Tyr Ser Asp Val Ser Asp Val
145 150 155 160

Glu Gly Asp Gly Asp Lys Ser Lys Val Cys Glu Ser Pro Gly Ser Leu
165 170 175

Gly Thr Val Ala Pro Asp Gly Val Leu Lys Pro Thr Ala Val Arg Val
180 185 190

Ser Ser Arg Arg Arg Pro Ala Val Glu Lys Leu Glu Asp Leu Leu Gln
195 200 205

Glu Pro Glu Gln Thr Glu Pro Leu Asp Leu Ser Leu Lys His Pro Arg
210 215 220

Met Thr
225

<210> SEQ ID NO 81
<211> LENGTH: 472
<212> TYPE: PRT
<213> ORGANISM: Adenovirus

<400> SEQUENCE: 81

Met Glu Gln Arg Gln Pro Pro Val Val Gly Leu His Ala Gly Leu His
1 5 10 15

Asp His Gly Val Val Ala Gly Ala Pro Glu Glu Glu Glu Gly Leu His
20 25 30

Leu Leu Ala Gly Ala Ala Ser Ala Arg Ser Gly Ala Ser Gly Gly Arg
35 40 45

Gly Gly Gly Glu Pro Glu Gly Arg Arg Gly Pro Ser Ser Gly Ile Glu
50 55 60

Ala Val Gly Glu Pro Glu Glu Gly Thr Ser Asp Gly Val Arg Lys Arg
65 70 75 80

Arg Arg Thr Glu Thr Glu Glu Val Asn Ala Arg Asp Tyr Leu Thr Asp
85 90 95

Leu Thr Val Arg Leu Met Ser Arg Arg Arg Pro Glu Thr Val Ala Trp
100 105 110

Ser Glu Leu Glu Thr Glu Phe Lys Asn Gly Asn Met Asn Leu Leu Tyr
115 120 125

Lys Tyr Ser Phe Glu Gln Ile Gln Thr His Trp Leu Glu Pro Trp Glu
130 135 140

Asp Trp Glu Thr Ala Phe Ala Asn Phe Ala Lys Ile Ala Leu Arg Pro
145 150 155 160

Asp Lys Ile Tyr Thr Ile Ser Arg Met Val Asn Ile Arg Lys Cys Val
165 170 175

Tyr Val Leu Gly Asn Gly Ala Thr Val Gln Ile Gln Thr Cys Asp Arg
180 185 190

Val Ala Phe Asn Cys Cys Met Gln Ser Met Gly Pro Gly Val Ile Gly
195 200 205

Met Ser Gly Val Thr Phe Ala Asn Val Arg Phe Thr Gly Glu Asn Phe
210 215 220

Phe Gly Ala Val Phe Met Asn Asn Thr Ser Leu Thr Leu His Gly Val
225 230 235 240

Tyr Phe Leu Asn Leu Ser Asn Thr Cys Val Glu Cys Trp Gly Arg Ala
245 250 255

Cys Leu Arg Gly Cys Thr Phe Tyr Gly Cys Trp Lys Ala Val Val Gly
260 265 270

Arg Thr Lys Ser His Val Ser Val Lys Lys Cys Met Phe Glu Arg Cys
275 280 285

-continued

```
Val Ile Ala Ile Met Val Glu Gly Gln Gly Arg Val Arg Asn Asn Val
    290                 295                 300

Gly Ala Glu Asn Gly Cys Phe Leu Leu Leu Lys Gly Ser Ala Ser Val
305                 310                 315                 320

Lys His Asn Met Ile Cys Gly Thr Gly Thr Cys Asn Ile Ser His Leu
                325                 330                 335

Leu Thr Cys Ser Asp Gly Asn Cys Gln Ala Leu Arg Thr Leu His Ile
            340                 345                 350

Val Ser His Arg Arg Leu Pro Trp Pro Val Leu Glu His Asn Met Leu
        355                 360                 365

Thr Arg Cys Ser Val His Val Gly Ala Arg Arg Gly Met Leu Val Pro
    370                 375                 380

Tyr Gln Cys Asn Phe Ser Tyr Thr Lys Val Leu Leu Glu Thr Asp Ala
385                 390                 395                 400

Phe Pro Arg Val Cys Phe Asn Gly Val Phe Asp Met Thr Val Glu Val
                405                 410                 415

Phe Lys Val Val Arg Tyr Asp Glu Ser Lys Ser Arg Cys Arg Pro Cys
            420                 425                 430

Glu Cys Gly Ala Asn His Leu Arg Leu Tyr Pro Val Thr Leu Asn Val
        435                 440                 445

Thr Glu Glu Leu Arg Ala Asp His Leu Thr Leu Ser Cys Leu Arg Thr
    450                 455                 460

Asp Tyr Glu Ser Ser Asp Glu Glu
465                 470


<210> SEQ ID NO 82
<211> LENGTH: 103
<212> TYPE: PRT
<213> ORGANISM: Adenovirus

<400> SEQUENCE: 82

Met Met Thr Asp Gly Ala Ala Val Thr Ala Arg Leu Arg His Leu His
1               5                   10                  15

His Cys Arg Arg Phe Arg Cys Phe Ala Arg Glu Pro Phe Val Phe Gly
            20                  25                  30

Tyr Phe Gln Leu Phe Asp Asp His Pro His Gly Pro Ala His Gly Val
        35                  40                  45

Glu Leu Arg Val Glu Lys Glu Leu Asp Ser Tyr Leu Leu Arg Leu Pro
    50                  55                  60

Arg Pro Ile Leu Val Glu Lys Glu His Gly Thr Thr Ile Val Lys Leu
65                  70                  75                  80

Tyr Cys Ile Cys Ser Ser Pro Gly Leu His Glu Asp Leu Cys Cys Leu
                85                  90                  95

Leu Cys Ala Glu Phe Asn Lys
            100


<210> SEQ ID NO 83
<211> LENGTH: 121
<212> TYPE: PRT
<213> ORGANISM: Adenovirus

<400> SEQUENCE: 83

Met Thr Glu Ser Gln Asp Ile Asn Ile Asn Met Glu Arg Gly Ile Ala
1               5                   10                  15

Gln Arg Gln Arg Glu Ala Arg Ala Met Asp Tyr Leu Arg Leu Gln Glu
            20                  25                  30
```

```
Leu Lys Glu Thr His Trp Cys Asp Arg Gly Ser Leu Cys Leu Val Lys
        35                  40                  45

Leu Ala Ser Leu Ser Tyr Asp Val Ser Thr Gln Gly His Glu Leu Ser
    50                  55                  60

Tyr Thr Leu Ala Gly Gln Lys Gln Thr Phe Ser Thr Ile Met Gly Ser
65                  70                  75                  80

Thr Ser Leu Lys Ile Thr His His Ser Lys Pro Val Glu Gly Ala Ile
                85                  90                  95

Leu Cys His Cys His Lys Pro Asp Cys Met Glu Lys Leu Ile Thr Thr
            100                 105                 110

Leu Cys Ala Val Ala Glu Ile Phe Lys
        115                 120


<210> SEQ ID NO 84
<211> LENGTH: 270
<212> TYPE: PRT
<213> ORGANISM: Adenovirus

<400> SEQUENCE: 84

Met Met Leu Leu Leu Phe Val Ser Leu Ile Ser Tyr Val Ile Leu Ala
1               5                   10                  15

Asp Ala Ser Thr Ile Phe Thr Gln Val Gly Ser Asn Val Thr Phe Gln
            20                  25                  30

Ser Tyr Phe Ser Pro Tyr Pro Asp Glu Ile Pro Tyr Ile Thr Trp Tyr
        35                  40                  45

Lys Gln Val Ser Tyr Asp Ser Ser Phe Tyr Glu Ala Asn Lys Leu Cys
    50                  55                  60

Glu Ala Gly Asn Thr Thr His Thr Tyr Pro His Pro Phe Leu Lys Phe
65                  70                  75                  80

Asp Cys Val Asn Lys Ser Leu Asn Leu Tyr Asn Leu Gln Leu Gln Asp
                85                  90                  95

Ser Gly Leu Tyr His Ala Thr Val Leu Val Asn Asp Ile Glu Gln His
            100                 105                 110

Asn Asp Ile Val Gln Leu His Val Ile Asp Leu Ser Ala Pro Gln Cys
        115                 120                 125

Asp Val Ser Ser Tyr Tyr Thr Asn Gln Thr Gln Leu Glu Phe Cys Leu
    130                 135                 140

Ile Leu Ile Asn Cys Ser Lys Val Ala His Arg Thr Thr Ile Tyr Phe
145                 150                 155                 160

Asn Gly Lys Tyr Ser Ser Thr Ser Phe Ile Thr Glu Tyr Gly Gly Thr
                165                 170                 175

His Leu Pro Asn Phe Tyr Asn Val Thr Val Glu Phe Phe Thr Ala Thr
            180                 185                 190

Asp Lys Leu Gln Lys Thr His Asn Ile Pro Tyr Asp Phe Asn Asp Leu
        195                 200                 205

Cys Gln Ile Ile Val Ser Pro Glu Ser Leu Asn Ser Phe Asn Asp Phe
    210                 215                 220

Ile Pro Ile Leu Ile Ala Ala Val Ile Ala Thr Ile Phe Thr Ile Ser
225                 230                 235                 240

Val Ser Leu Gly Phe Tyr Cys Leu Tyr Lys Pro Lys Lys Val Lys Phe
                245                 250                 255

Glu Gln Leu Lys Leu Lys Gln Arg Pro Lys Ile Glu Thr Val
            260                 265                 270
```

<210> SEQ ID NO 85
<211> LENGTH: 90
<212> TYPE: PRT
<213> ORGANISM: Adenovirus

<400> SEQUENCE: 85

```
Met Val Ala Ala Phe Val Leu Leu Leu Cys Leu Pro Ile Ile Phe Val
1               5                   10                  15

Ser Thr Ser Phe Ala Ala Val Ser His Leu Asp Pro Asp Cys Leu Pro
            20                  25                  30

Ala Phe Asp Val Tyr Leu Ile Phe Thr Phe Leu Cys Ile Ile Ala Ile
        35                  40                  45

Cys Ser Ile Ala Ser Phe Phe Val Val Ile Phe Gln Ala Ala Asp Tyr
    50                  55                  60

Ala Tyr Val Arg Ile Val Tyr Phe Arg His His Pro Gln Tyr Arg Asn
65                  70                  75                  80

Arg Asp Val Ala Thr Leu Leu Cys Leu Ala
                85                  90
```

<210> SEQ ID NO 86
<211> LENGTH: 109
<212> TYPE: PRT
<213> ORGANISM: Adenovirus

<400> SEQUENCE: 86

```
Met Ile Ala Leu Leu Leu Phe Asn Phe Phe Thr Leu Ile Asp Cys Lys
1               5                   10                  15

Cys Pro Phe Thr Lys Pro Trp Lys Leu His Thr Cys Tyr Asn Glu Ile
            20                  25                  30

Pro Asp Thr Pro Ile Ala Trp Leu Tyr Val Leu Thr Ala Ala Leu Val
        35                  40                  45

Phe Ile Ser Thr Cys Leu Gly Val Lys Leu Tyr Phe Thr Phe Asn Phe
    50                  55                  60

Gly Trp Leu His Pro Asn Glu Asp Leu Pro Arg Tyr Pro Asn Ala Leu
65                  70                  75                  80

Pro Leu Gln Pro Leu Pro Pro Gln Pro Val Pro Leu Val Arg Ala Pro
                85                  90                  95

Ser Val Ile Ser Tyr Phe Gln Leu Ile Gly Gly Asp Asp
            100                 105
```

<210> SEQ ID NO 87
<211> LENGTH: 181
<212> TYPE: PRT
<213> ORGANISM: Adenovirus

<400> SEQUENCE: 87

```
Met Asp Tyr Met Lys Ile Tyr Ala Val Phe Phe Ala Leu Asn Leu Ile
1               5                   10                  15

Asn Asn Ile Trp Thr Ser Lys Ser Ala His Ile Val Arg Ser Ser Thr
            20                  25                  30

Glu Ser Ser Ile Lys Gly Ile Arg Gln Thr Leu Phe Phe Tyr Pro Ser
        35                  40                  45

Thr Pro Leu Ile Thr Leu Asn Cys Asn Cys Thr Asn Glu Ile Ile Gln
    50                  55                  60

Trp Leu Val Asn Gly Lys Leu Cys Lys Val Phe Phe Ser Asp Gly Ser
65                  70                  75                  80

Gln Phe Asn Arg Asn Asn Ser Phe Cys Asn Asn Cys Ser Lys His Tyr
                85                  90                  95
```

```
Leu Thr Leu Tyr Pro Pro Phe Pro Ser Ala Arg Phe Ser Cys Val Gly
            100                 105                 110

Thr Gly His Gly Thr Ser Cys Tyr Tyr Asn Trp Phe Leu Lys Glu Ala
        115                 120                 125

Lys Arg Glu Pro Tyr Ser Val Leu Pro His Gly Phe Thr Lys Ala Ser
    130                 135                 140

Thr Pro Ser Thr Pro Phe Ser Phe Thr His Pro Leu Phe Ser Val Leu
145                 150                 155                 160

Ala Ile Ile Leu Leu Val Ser Phe Asn Leu Val Leu Leu Thr Ser Cys
                165                 170                 175

Pro Val Ser Leu Thr
            180


<210> SEQ ID NO 88
<211> LENGTH: 283
<212> TYPE: PRT
<213> ORGANISM: Adenovirus

<400> SEQUENCE: 88

Met Gln Arg Asp Arg Arg Tyr Arg Cys Arg Leu Gly Pro Tyr Asn Arg
1               5                   10                  15

His Gln Leu Pro Pro Cys Asp Glu Met Pro Cys Ala Thr Ile Glu Asn
            20                  25                  30

Pro Pro Tyr Leu Glu Cys Glu Asn Leu Asn Met His Asn Val Ser Glu
        35                  40                  45

Val Arg Gly Val Pro Ser Cys Val Ser Phe Thr Val Leu Gln Glu Trp
    50                  55                  60

Pro Val Tyr Trp Asp Ser Val Leu Thr Ala Trp Glu Lys His Val Met
65                  70                  75                  80

Lys Thr Tyr Met Gln Ile Cys Ile Cys Cys Ala Thr Ile Asp Val Glu
                85                  90                  95

Tyr Asn Gln Ile Ile Arg Gly Tyr Glu Arg Trp Val Leu His Cys His
            100                 105                 110

Cys Ser Ser Pro Gly Ser Leu Gln Cys Lys Ala Gly Gly Val Val Leu
        115                 120                 125

Ala Asn Trp Phe Arg Met Ala Ile Tyr Gly Ser Leu Val Asn Val Arg
    130                 135                 140

Phe Pro Trp Tyr Arg Gln Val Val Asn Tyr His Leu Pro Lys Glu Val
145                 150                 155                 160

Leu Tyr Val Gly Ser Val Phe Ile Arg Gly Arg His Leu Ile Tyr Val
                165                 170                 175

Arg Val Phe Leu Asp Gly His Ala Val Ala Val Leu Glu Asn Ser Ser
            180                 185                 190

Phe Gly Trp Ser Ala Phe Ser Tyr Gly Ile Leu Asn Asn Leu Ile Ile
        195                 200                 205

Met Val Cys Thr His Cys Lys Asp Leu Ser Glu Ile Gln Met Arg Cys
    210                 215                 220

Cys Ala Lys Arg Thr Arg Arg Phe Leu Ile Arg Ala Val Arg Leu Leu
225                 230                 235                 240

Asp Arg Leu Thr Ser Tyr Gln Pro Arg Arg Ser Arg Leu Glu Thr Pro
                245                 250                 255

Arg Gln Ser Leu Leu Arg Gly Leu Met Glu Arg His Leu Val Lys Arg
            260                 265                 270

Thr Asn Gly Ala Pro Ser Pro Val His Ala Gly
```

```
        275                 280


<210> SEQ ID NO 89
<211> LENGTH: 106
<212> TYPE: PRT
<213> ORGANISM: Adenovirus

<400> SEQUENCE: 89

Met Gln Arg Asp Arg Arg Tyr Arg Cys Arg Leu Gly Pro Tyr Asn Arg
1               5                   10                  15

His Gln Leu Pro Pro Cys Asp Glu Met Pro Cys Ala Thr Ile Glu Asn
            20                  25                  30

Pro Pro Tyr Leu Glu Cys Glu Asn Leu Asn Met His Asn Val Ser Glu
        35                  40                  45

Gly Phe Val Ser Val Thr Asp Glu Arg Phe Ala Arg Lys Glu Thr Val
    50                  55                  60

Trp Thr Leu Thr Pro Lys Asn Pro Cys Leu Asn Thr Gln Phe Gln Leu
65                  70                  75                  80

Phe Thr Ala Thr Lys Gly Glu Arg Met Val Tyr Ser Val Lys Trp Lys
                85                  90                  95

Gly Gly Gly Ser Leu Thr Val Arg Ile Met
            100                 105


<210> SEQ ID NO 90
<211> LENGTH: 126
<212> TYPE: PRT
<213> ORGANISM: Adenovirus

<400> SEQUENCE: 90

Met Ala Asp Glu Ala Ile Tyr Val His Leu Leu Gly Ser Arg Ala Ile
1               5                   10                  15

Met Pro Gln Gln Gln Gly Phe Ser Asn Leu Tyr Val Leu Phe Ser Pro
            20                  25                  30

Glu Asn Phe Val Ile Ser Pro Arg Gly Val Leu Leu Val Ser Leu Gln
        35                  40                  45

Leu Ser Met Asp Ile Pro Arg Gly Tyr Leu Gly Arg Leu Phe Ser Leu
    50                  55                  60

Ser Asp Met Asn Val Arg Gly Val Phe Val Gly Ala Gln Asp Ile Gln
65                  70                  75                  80

Pro Ser Thr Trp Trp Glu Met Ser Val Val Leu Phe Asn His Ser Asp
                85                  90                  95

Glu Phe Phe Tyr Gly Phe Arg Gly Gln Pro Val Ala Cys Leu Leu Leu
            100                 105                 110

Glu Arg Val Ile Tyr Pro Cys Leu His Arg Ala Ser Leu Val
        115                 120                 125


<210> SEQ ID NO 91
<211> LENGTH: 130
<212> TYPE: PRT
<213> ORGANISM: Adenovirus

<400> SEQUENCE: 91

Met Tyr Gln Arg Gln Pro Val Phe Val Cys Val Thr Val Pro Ala Ala
1               5                   10                  15

Leu Arg Gln Tyr Leu His Asp Leu Asp Ile Glu Val Leu Asp Phe Leu
            20                  25                  30

Lys Arg Gln Leu Ser Asp Phe Trp Leu His Leu Leu His Cys Leu Thr
        35                  40                  45
```

-continued

```
Pro Pro Phe Gln Phe Cys Tyr Asn Gly Ala Val Leu Leu Ser Leu Ala
    50                  55                  60

Pro Ser Ile Gln Leu Leu Cys Cys Val Ala Thr Pro Glu Met Thr Pro
65                  70                  75                  80

Asp Gly Glu Leu Thr Ala Leu Val Cys Ala Asp Leu Leu Asn Phe Leu
                85                  90                  95

Gln Leu Thr Leu Arg Val Glu Ile Arg Asp Arg Gly Val His Pro Asp
            100                 105                 110

Pro Asp Met Leu Asn Leu Leu Gln Val Ser Gln Glu Leu Asp Ile Leu
        115                 120                 125

Ser Ser
    130


<210> SEQ ID NO 92
<211> LENGTH: 116
<212> TYPE: PRT
<213> ORGANISM: Adenovirus

<400> SEQUENCE: 92

Met Met Val Cys Leu Arg Met Ala Ile Glu Gly Ala Leu Thr Gln Leu
1               5                   10                  15

Phe Gly Met Arg Gly Val Asn Leu Gln Asp Leu Cys Cys Asn Ile Ile
            20                  25                  30

Arg Glu Trp Arg Ala Glu Asn Tyr Leu Gly Met Val Gln Asn Cys Ser
        35                  40                  45

Val Ile Ile Glu Glu Phe Glu His Asp Ala Phe Ala Leu Leu Val Phe
    50                  55                  60

Leu Asp Val Arg Val Gln Ala Leu Leu Glu Ala Val Thr Asp His Leu
65                  70                  75                  80

Glu Asn Arg Ile His Phe Asp Leu Ala Val Leu Tyr His Gln Arg Thr
                85                  90                  95

Gly Gly Glu Arg Cys His Leu Arg Asp Leu His Phe Val Thr Leu Arg
            100                 105                 110

Asp Arg Leu Glu
        115


<210> SEQ ID NO 93
<211> LENGTH: 120
<212> TYPE: PRT
<213> ORGANISM: Adenovirus

<400> SEQUENCE: 93

Met Pro Leu Pro Cys Leu Pro Pro Pro Pro Val Cys Arg Asp Lys Ser
1               5                   10                  15

Ala Cys Ile Ala Trp Leu Glu Leu Ala Leu Thr Ser Ser Leu Glu Leu
            20                  25                  30

Phe Arg Asp Ile Ile Arg Tyr Glu Val Phe Ile Thr Pro Glu Ala Glu
        35                  40                  45

Arg Glu Leu Cys Gly Leu Gln Gln Trp Leu His Phe Ala Val Thr Thr
    50                  55                  60

Glu Arg Gln Arg Arg Arg Asp Gly Arg Arg Val Asp Ile Cys Trp Arg
65                  70                  75                  80

Arg Thr Trp Phe Cys Tyr Arg Lys Tyr Glu Asp Leu Arg Lys Asn Leu
                85                  90                  95

Ile Tyr Asp Ala Thr Arg Gln Thr Val Ser Leu Gln Thr Gly Ser Leu
            100                 105                 110
```

Gln Gln Thr Pro Ala Thr Ala Val
        115                 120

<210> SEQ ID NO 94
<211> LENGTH: 930
<212> TYPE: PRT
<213> ORGANISM: Adenovirus

<400> SEQUENCE: 94

Met Ala Thr Pro Ser Met Met Pro Gln Trp Ser Tyr Met His Ile Ala
1               5                   10                  15

Gly Gln Asp Ala Ser Glu Tyr Leu Ser Pro Gly Leu Val Gln Phe Ala
            20                  25                  30

Arg Ala Thr Asp Thr Tyr Phe Ser Leu Gly Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Val Pro Val Asp Arg Glu Asp Thr Ala Tyr Ser Tyr
65                  70                  75                  80

Lys Val Arg Phe Thr Leu Ala Val Gly Asp Asn Arg Val Leu Asp Met
                85                  90                  95

Ala Ser Thr Tyr Phe Asp Ile Arg Gly Met Leu Asp Arg Gly Pro Ser
            100                 105                 110

Phe Lys Pro Tyr Ser Gly Thr Ala Tyr Asn Ser Leu Ala Pro Lys Gly
        115                 120                 125

Ala Pro Asn Pro Ser Gln Trp Ile Thr Asn Gly Gly Asn Lys Thr Asn
    130                 135                 140

Ser Phe Gly Gln Ala Pro Phe Ile Gly Leu Gly Gln Asn Val Thr Lys
145                 150                 155                 160

Asp Gly Ile Gln Val Gly Thr Asp Ser Asp Lys Gly Asp Ala Ala Ile
                165                 170                 175

Tyr Ala Asp Lys Thr Tyr Gln Pro Glu Pro Gln Val Gly Val Asn Gln
            180                 185                 190

Trp Asn Gln Asn Pro Thr Glu Asn Ala Ala Gly Arg Ile Leu Lys Ser
        195                 200                 205

Thr Thr Pro Met Gln Pro Cys Tyr Gly Ser Tyr Ala Gln Pro Thr Asn
    210                 215                 220

Val His Gly Gly Gln Val Lys Ile Thr Ser Glu Ala Asp Pro Thr Gly
225                 230                 235                 240

Ala Ala Asn Val Thr Met Asn Phe Phe Asn Val Ala Ser Asp Asn Gly
                245                 250                 255

Ser Asn Asp Pro Lys Val Val Leu Tyr Ala Glu Asp Val Asn Leu Glu
            260                 265                 270

Ala Pro Asp Thr His Leu Val Phe Lys Pro Ser Val Val Asn Asp Ala
        275                 280                 285

Arg Ser Ala Glu Thr Leu Leu Gly Gln Gln Ala Ala Pro Asn Arg Pro
    290                 295                 300

Asn Tyr Ile Gly Phe Arg Asp Asn Phe Ile Gly Leu Met Tyr Tyr Asn
305                 310                 315                 320

Ser Thr Gly Asn Met Gly Val Leu Ala Gly Gln Ala Ser Gln Leu Asn
                325                 330                 335

Ala Val Val Asp Leu Gln Asp Arg Asn Thr Glu Leu Ser Tyr Gln Leu
            340                 345                 350

Met Leu Asp Ala Leu Gly Asp Arg Ser Arg Tyr Phe Ser Met Trp Asn

-continued

```
        355                 360                 365

Gln Ala Val Asp Ser Tyr Asp Pro Asp Val Arg Ile Ile Glu Asn His
    370                 375                 380

Gly Val Glu Asp Glu Leu Pro Asn Tyr Cys Phe Pro Leu Asn Gly Gln
385                 390                 395                 400

Gly Ile Ser Asn Thr Tyr Lys Gly Val Lys Arg Asn Thr Gly Asp Thr
                405                 410                 415

Gly Trp Glu Lys Asp Thr Asn Val Glu Glu Thr Asn Glu Ile Ser Ile
            420                 425                 430

Gly Asn Ile Phe Ala Met Glu Ile Asn Leu Ala Ala Asn Leu Trp Arg
        435                 440                 445

Asn Phe Leu Phe Ser Asn Val Ala Leu Tyr Leu Pro Asp Ser Tyr Lys
    450                 455                 460

Tyr Thr Pro Ala Asn Val Glu Leu Pro Ala Asn Lys Asn Ser Tyr Asp
465                 470                 475                 480

Tyr Met Asn Gly Arg Val Thr Ser Pro Ser Ala Leu Asp Thr Tyr Val
                485                 490                 495

Asn Ile Gly Ala Arg Trp Ser Pro Asp Pro Met Asp Asn Val Asn Pro
            500                 505                 510

Phe Asn His His Arg Asn Ala Gly Leu Arg Tyr Arg Ser Met Leu Leu
        515                 520                 525

Gly Asn Gly Arg Tyr Val Pro Phe His Ile Gln Val Pro Gln Lys Phe
    530                 535                 540

Phe Ala Ile Lys Asn Leu Leu Leu Leu Pro Gly Ser Tyr Thr Tyr Glu
545                 550                 555                 560

Trp Asn Phe Arg Lys Asp Val Asn Met Ile Leu Gln Ser Thr Leu Gly
                565                 570                 575

Asn Asp Leu Arg Val Asp Gly Ala Ser Val Arg Phe Asp Ser Ile Asn
            580                 585                 590

Leu Tyr Ala Ser Phe Phe Pro Met Ala His Asn Thr Ala Ser Thr Leu
        595                 600                 605

Glu Ala Met Leu Arg Asn Asp Thr Asn Asp Gln Ser Phe Asn Asp Tyr
    610                 615                 620

Leu Cys Ala Ala Asn Met Leu Tyr Pro Ile Pro Ala Asn Ala Thr Ser
625                 630                 635                 640

Val Pro Ile Ser Ile Pro Ser Arg Asn Trp Ala Ala Phe Arg Gly Trp
                645                 650                 655

Ser Phe Thr Arg Leu Lys Thr Arg Glu Thr Pro Ser Leu Gly Ser Gly
            660                 665                 670

Phe Asp Pro Tyr Phe Val Tyr Ser Gly Ser Ile Pro Tyr Leu Asp Gly
        675                 680                 685

Thr Phe Tyr Leu Asn His Thr Phe Lys Lys Val Ser Ile Met Phe Asp
    690                 695                 700

Ser Ser Val Ser Trp Pro Gly Asn Asp Arg Leu Leu Thr Pro Asn Glu
705                 710                 715                 720

Phe Glu Ile Lys Arg Ser Val Asp Gly Glu Gly Tyr Asn Val Ala Gln
                725                 730                 735

Ser Asn Met Thr Lys Asp Trp Phe Leu Ile Gln Met Leu Ser His Tyr
            740                 745                 750

Asn Ile Gly Tyr Gln Gly Phe Tyr Val Pro Glu Ser Tyr Lys Asp Arg
        755                 760                 765

Met Tyr Ser Phe Phe Arg Asn Phe Gln Pro Met Ser Arg Gln Val Val
    770                 775                 780
```

```
Asp Pro Val Asn Tyr Thr Lys Tyr Lys Glu Val Thr Leu Pro Tyr Gln
785                 790                 795                 800

His Asn Asn Ser Gly Phe Val Gly Tyr Met Gly Pro Thr Met Arg Glu
                805                 810                 815

Gly Gln Ala Tyr Pro Ala Asn Tyr Pro Tyr Pro Leu Ile Gly Lys Thr
            820                 825                 830

Ala Val Thr Ser Leu Thr Gln Lys Lys Phe Leu Cys Asp Arg Val Met
        835                 840                 845

Trp Arg Ile Pro Phe Ser Ser Asn Phe Met Ser Met Gly Ala Leu Thr
    850                 855                 860

Asp Leu Gly Gln Asn Met Leu Tyr Ala Asn Ser Ala His Ala Leu Asp
865                 870                 875                 880

Met Thr Phe Glu Val Asp Pro Met Asp Glu Pro Thr Leu Leu Tyr Val
                885                 890                 895

Leu Phe Glu Val Phe Asp Val Val Arg Ile His Gln Pro His Arg Gly
            900                 905                 910

Val Ile Glu Ala Val Tyr Leu Arg Thr Pro Phe Ser Ala Gly Asn Ala
        915                 920                 925

Thr Thr
    930


<210> SEQ ID NO 95
<211> LENGTH: 505
<212> TYPE: PRT
<213> ORGANISM: Adenovirus

<400> SEQUENCE: 95

Met Arg Arg Ala Val Arg Val Pro Pro Val Tyr Pro Glu Gly Pro Pro
1               5                   10                  15

Pro Ser Tyr Glu Ser Val Met Glu Ala Leu Asn Thr Pro Ala Thr Leu
            20                  25                  30

Glu Ala Pro Tyr Val Pro Pro Arg Tyr Leu Gly Pro Thr Glu Gly Arg
        35                  40                  45

Asn Ser Ile Arg Tyr Ser Glu Leu Ala Pro Leu Tyr Asp Thr Thr Lys
    50                  55                  60

Val Tyr Leu Val Asp Asn Lys Ser Ala Asp Ile Ala Ser Leu Asn Tyr
65                  70                  75                  80

Gln Asn Asp His Ser Asn Phe Leu Thr Thr Val Val Gln Asn Asn Asp
                85                  90                  95

Phe Thr Pro Val Glu Ala Gly Thr Gln Thr Ile Asn Phe Asp Glu Arg
            100                 105                 110

Ser Arg Trp Gly Gly Gln Leu Lys Thr Ile Leu His Thr Asn Met Pro
        115                 120                 125

Asn Ile Asn Glu Phe Met Tyr Thr Asn Lys Phe Arg Ala Lys Leu Met
    130                 135                 140

Val Glu Lys Gln Asn Ala Glu Thr Gln Ala Pro Arg Tyr Glu Trp Phe
145                 150                 155                 160

Glu Phe Thr Ile Pro Glu Gly Asn Tyr Ser Glu Thr Met Thr Ile Asp
                165                 170                 175

Leu Met Asn Asn Ala Ile Val Asp Asn Tyr Leu Gln Val Gly Arg Gln
            180                 185                 190

Asn Gly Val Leu Glu Ser Asp Ile Gly Val Lys Phe Asp Thr Arg Asn
        195                 200                 205

Phe Arg Leu Gly Trp Asp Pro Glu Thr Lys Leu Val Met Pro Gly Val
```

```
    210                 215                 220

Tyr Thr Asn Glu Ala Phe His Pro Asp Ile Ile Leu Leu Pro Gly Cys
225                 230                 235                 240

Gly Val Asp Phe Thr Gln Ser Arg Leu Asn Asn Leu Leu Gly Ile Arg
                245                 250                 255

Lys Arg Arg Pro Phe Glu Val Gly Phe Gln Ile Met Tyr Glu Asp Leu
            260                 265                 270

Glu Gly Gly Asn Ile Pro Ala Leu Leu Asp Val Gln Lys Tyr Glu Asp
        275                 280                 285

Ser Lys Asn Gln Ser Asn Thr Thr Glu Arg Ala Ile Arg Gly Asp Asn
    290                 295                 300

Phe Ala Pro Thr Ala Gln Thr Val Val Val Glu Pro Leu Thr Lys Asp
305                 310                 315                 320

Ser Lys Asp Arg Ser Tyr Asn Val Ile Glu Gly Thr Thr Asp Thr Gln
                325                 330                 335

Tyr Arg Ser Trp Phe Leu Ala Tyr Asn Tyr Gly Asp Pro Glu Lys Gly
            340                 345                 350

Val Arg Ser Trp Thr Leu Leu Thr Thr Thr Asp Val Thr Cys Gly Ser
        355                 360                 365

Gln Gln Val Tyr Trp Ser Leu Pro Asp Met Met Gln Asp Pro Val Thr
    370                 375                 380

Phe Arg Ala Ser Thr Gln Val Ser Asn Phe Pro Val Val Gly Thr Glu
385                 390                 395                 400

Leu Leu Pro Val Tyr Ala Lys Ser Phe Tyr Asn Glu Gln Ala Val Tyr
                405                 410                 415

Ser Gln Leu Ile Arg Gln Ser Thr Ala Leu Thr His Val Phe Asn Arg
            420                 425                 430

Phe Pro Glu Asn Gln Ile Leu Val Arg Pro Pro Ala Pro Thr Ile Thr
        435                 440                 445

Thr Val Ser Glu Asn Val Pro Ala Leu Thr Asp His Gly Thr Leu Pro
    450                 455                 460

Leu Arg Ser Ser Ile Ser Gly Val Gln Arg Val Thr Ile Thr Asp Ala
465                 470                 475                 480

Arg Arg Arg Thr Cys Pro Tyr Val Tyr Lys Ala Leu Gly Val Val Ala
                485                 490                 495

Pro Lys Val Leu Ser Ser Arg Thr Phe
            500                 505


<210> SEQ ID NO 96
<211> LENGTH: 597
<212> TYPE: PRT
<213> ORGANISM: Adenovirus

<400> SEQUENCE: 96

Met Pro Ser Val Leu Pro Ile Thr Pro Asn Pro Gln Asp Phe Arg Phe
1               5                   10                  15

Phe Leu Ile Gly Leu Leu Leu Leu Gly Ser Arg Leu Thr Leu Leu Leu
            20                  25                  30

Gln Cys Phe Ala Met Leu Leu Asn Asn Lys Ala Arg Lys Ala Thr Phe
        35                  40                  45

Val Phe Phe Gln Met Lys Arg Ala Arg Ile Asp Asp Asp Phe Asn Pro
    50                  55                  60

Val Tyr Pro Tyr Asp Gln Pro Asn Ala Pro Leu Leu Pro Phe Ile Thr
65                  70                  75                  80
```

```
Pro Pro Phe Thr Ser Ser Asp Gly Leu Gln Glu Lys Pro Pro Gly Val
                85                  90                  95

Leu Ser Leu Asn Tyr Lys Asn Pro Ile Thr Thr Gln Asn Gly Ala Leu
            100                 105                 110

Thr Leu Lys Ile Gly Glu Gly Ile Asp Ile Asn Asp Lys Gly Glu Leu
        115                 120                 125

Thr Ser Asn Ala Val Ser Val Ser Pro Pro Leu Ser Lys Ile Asn Asn
    130                 135                 140

Thr Leu Ser Leu Val Tyr Ser Asp Pro Leu Thr Val Arg Glu Asn Ala
145                 150                 155                 160

Leu His Leu Lys Thr Ala Leu Pro Ile Ser Leu Asn Ala Ala Arg Glu
                165                 170                 175

Leu Thr Leu Val Ala Asn Ala Pro Leu Ala Thr Thr Asn Gly Ala Leu
            180                 185                 190

Gln Leu Gln Ser Ala Ala Pro Leu Gly Val Ala Glu Arg Thr Leu Lys
        195                 200                 205

Leu Leu Phe Ser Asn Pro Leu Tyr Leu Gln Asn Asn Phe Leu Ser Val
    210                 215                 220

Ala Val Asp Lys Pro Leu Ala Met Ala Ser Thr Gly Ala Ile Ala Leu
225                 230                 235                 240

Gln Trp Ala Pro Pro Leu Gln Val Gly Thr Gly Gly Leu Thr Val Ala
                245                 250                 255

Thr Val Glu Pro Leu Thr Val Thr Asn Gly Asn Leu Asn Ile Asn Thr
            260                 265                 270

Lys Arg Pro Leu Val Ile Glu Asp Ser Ser Leu Tyr Leu Ala Phe Arg
        275                 280                 285

Pro Pro Leu Arg Leu Phe Asn Ser Asp Pro Glu Leu Gly Val Asn Phe
    290                 295                 300

Ile Pro Pro Ile Thr Ile Arg Asp Asp Gly Leu Ala Leu Asn Thr Gly
305                 310                 315                 320

Glu Gly Leu Thr Leu Val Arg Asp Arg Leu Ser Val Asn Leu Gly Lys
                325                 330                 335

Asp Leu Gln Phe Val Asp Asn Thr Val Ser Leu Ala Leu Ser Thr Ala
            340                 345                 350

Leu Pro Leu Gln Tyr Thr Asp Gln Leu Arg Leu Asn Ile Gly Gln Gly
        355                 360                 365

Leu Arg Tyr Asn Pro Thr Ser Lys Lys Leu Asp Val Asp Leu Asn Gln
    370                 375                 380

Asn Lys Gly Leu Asn Trp Glu Asp Asn Lys Val Ile Thr Lys Leu Gly
385                 390                 395                 400

Tyr Gly Leu Gln Phe Asp Ser Ala Gly Asn Ile Ser Val Ile Pro Pro
                405                 410                 415

Ser Val Thr Pro His Thr Leu Trp Thr Thr Ala Asp Pro Ser Pro Asn
            420                 425                 430

Cys Ser Val Tyr Thr Asp Leu Asp Ala Lys Leu Trp Leu Ser Leu Val
        435                 440                 445

Lys Cys Asn Gly Met Val Gln Gly Thr Ile Ala Leu Lys Ala Leu Lys
    450                 455                 460

Gly Val Leu Leu Asn Pro Thr Ala Ser Ser Ile Ser Ile Val Ile Tyr
465                 470                 475                 480

Phe Tyr Ser Asn Gly Val Arg Arg Thr Asn Tyr Pro Thr Phe Asp Asn
                485                 490                 495

Glu Gly Thr Leu Ala Asn Thr Ala Thr Trp Gly Tyr Arg Gln Gly Glu
```

```
            500                 505                 510

Ser Ala Asn Thr Asn Val Thr Asn Ala Val Glu Phe Met Pro Ser Ser
        515                 520                 525

Ala Arg Tyr Pro Ile Asn Arg Gly Asn Asp Val Gln Asn Gln Met Met
    530                 535                 540

Gly Tyr Thr Cys Leu Gln Gly Ala Leu Asn Met Ala Val Gly Tyr Lys
545                 550                 555                 560

Val Thr Phe Asn His Ala Leu Glu Gly Tyr Ser Leu Lys Phe Thr Trp
                565                 570                 575

Pro Val Tyr Asn Asn Gln Ala Phe Asp Val Pro Cys Cys Ser Phe Ser
            580                 585                 590

Tyr Ile Thr Glu Glu
        595


<210> SEQ ID NO 97
<211> LENGTH: 377
<212> TYPE: PRT
<213> ORGANISM: Adenovirus

<400> SEQUENCE: 97

Met Lys Arg Thr Arg Ile Asp Glu Asp Phe Asn Pro Val Tyr Pro Tyr
1               5                   10                  15

Asp Ser Thr Val Thr Pro Thr Ile Pro Phe Ile Ala Pro Pro Phe Val
            20                  25                  30

Ser Ala Asn Gly Leu Gln Glu Asn Pro Pro Gly Ile Leu Ser Leu Asn
        35                  40                  45

Tyr Ala Asp Pro Leu Thr Thr Asn Asn Gly Lys Leu Ser Met Lys Leu
    50                  55                  60

Gly Ser Asn Leu Ser Leu Asn Ser Asn Gly Ala Leu Thr Cys Ser Thr
65                  70                  75                  80

Pro Val Thr Glu Pro Leu Thr Asn Asn Gly Thr Leu Gly Leu Ala Phe
                85                  90                  95

Ser Pro Pro Leu Asn Thr Thr Ser Ala Arg Leu Gly Ile Ser Leu Leu
            100                 105                 110

Pro Pro Ile Thr Val Thr Ser Asn Ala Leu Ser Leu Ser Leu Gly Asn
        115                 120                 125

Gly Leu Thr Thr Ser Asn Ser Ser Leu Thr Val Lys Thr Thr Gly Ala
    130                 135                 140

Ile Asn Phe Asn Ser Gln Gly Tyr Leu Gln Leu Arg Thr Ala Gly Gly
145                 150                 155                 160

Met Arg Ile Asp Asn Ser Asn Thr Leu Ile Leu Asp Val Asp Tyr Pro
                165                 170                 175

Phe Asp Ala Ala Asn Gln Leu Arg Leu Arg Leu Gly Lys Gly Met Tyr
            180                 185                 190

Leu Glu Asn Gly Arg Asp Leu Ser Val Lys Leu Gly Asn Gly Leu Ser
        195                 200                 205

Phe Asp Ser Ser Gly Arg Ile Ala Ala Ser Ala Thr Ala Arg Ser Arg
    210                 215                 220

Thr Met Asp His Pro Ser Ser Ile Ser Thr Trp Pro Gln Pro Leu Gln
225                 230                 235                 240

Ala Asn Cys Thr Val Phe Glu Pro Leu Asp Ala Thr Leu Gly Leu Glu
                245                 250                 255

Leu Ile Lys Ile Gly Ser His Val Leu Gly Ala Val Thr Leu Lys Gly
            260                 265                 270
```

```
Val Lys Gly Gln Leu Cys Asn Met Gln Thr Asn Thr Val Thr Ile Lys
        275                 280                 285

Leu Thr Phe Asn Ala Asn Gly His Leu Leu Lys Cys Pro Leu Val Ser
    290                 295                 300

Ser Tyr Trp Gln Ser Glu Thr Val Glu Phe Met Pro Asn Arg Ile Ile
305                 310                 315                 320

Tyr Pro Pro Gln Ser Ala Ala Ala Glu Leu Ser Pro Asn Ser Gln Pro
                325                 330                 335

His Ala Phe Ser Val Ala Tyr Asn Thr Glu Pro Ser Gly Phe Ser Phe
            340                 345                 350

Leu Phe Asn Trp Ser Ala Val Val Gly Gln Pro Phe Asn Ala Pro Ala
        355                 360                 365

Ala Met Phe Cys Tyr Val Ala Glu Gln
    370                 375


<210> SEQ ID NO 98
<211> LENGTH: 447
<212> TYPE: PRT
<213> ORGANISM: Adenovirus

<400> SEQUENCE: 98

Met Glu Thr Arg Gly Arg Lys Arg Pro Leu Gln His Gln Gln Asp Glu
1               5                   10                  15

Pro Glu Thr His Thr Gly Lys Arg Pro Thr Arg Gly Pro Pro Phe Tyr
            20                  25                  30

Arg His Arg Asp His Pro Asp Ala Asn Pro Gln Thr Leu Glu Gly His
        35                  40                  45

Asp Ser Arg Ser Pro Gly Arg Pro Pro Thr Gly Ser Leu Gln Arg Lys
    50                  55                  60

Ser Pro Gln Pro Ser Gln Pro Arg Ser Leu Leu Asp Arg Asp Ala Ile
65                  70                  75                  80

Glu His Val Thr Glu Leu Trp Asp Arg Leu Tyr Leu Leu Arg Gln Thr
                85                  90                  95

Leu Glu Lys Met Pro Met Ala Asp Gly Leu Lys Pro Leu Lys His Phe
            100                 105                 110

Asn Ser Leu Glu Glu Leu Leu Ser Leu Gly Gly Glu Arg Leu Leu Gln
        115                 120                 125

Asn Leu Val Arg Glu Asn Arg His Val Arg Ser Met Met Asn Glu Val
    130                 135                 140

Ala Pro Leu Leu Arg Asn Asp Gly Ser Cys Lys Ser Leu Asn Tyr Gln
145                 150                 155                 160

Leu Gln Pro Val Ile Gly Val Ile Tyr Gly Pro Thr Gly Cys Gly Lys
                165                 170                 175

Ser Gln Leu Leu Arg Asn Leu Leu Ser Thr Gln Leu Ile Asn Pro Pro
            180                 185                 190

Pro Glu Thr Val Phe Phe Ile Ala Pro Gln Val Asp Met Ile Pro Pro
        195                 200                 205

Ser Glu Ile Lys Ala Trp Glu Met Gln Ile Cys Glu Gly Asn Tyr Ala
    210                 215                 220

Pro Gly Pro Glu Gly Thr Ile Ile Pro Gln Ser Gly Thr Leu Leu Pro
225                 230                 235                 240

Arg Phe Val Lys Met Ala Tyr Asp Asp Leu Thr Leu Glu Gln Asn Tyr
                245                 250                 255

Asp Val Ser Asn Pro Asn Asn Val Phe Ala Lys Ala Ala Ala Arg Gly
            260                 265                 270
```

```
Pro Ile Ala Ile Ile Met Asp Glu Cys Met Glu Asn Leu Gly Gly His
        275                 280                 285

Lys Gly Val Ser Lys Phe Phe His Ala Phe Pro Ser Lys Leu His Asp
    290                 295                 300

Lys Phe Pro Lys Cys Thr Gly Tyr Thr Val Leu Val Val Leu His Asn
305                 310                 315                 320

Met Asn Pro Arg Arg Asp Leu Gly Gly Asn Ile Ala Asn Leu Lys Ile
                325                 330                 335

Gln Ala Lys Met His Ile Ile Ser Pro Arg Met His Pro Ser Gln Leu
            340                 345                 350

Asn Arg Phe Val Asn Thr Tyr Thr Lys Gly Leu Pro Leu Ala Ile Ser
        355                 360                 365

Leu Leu Leu Lys Asp Ile Phe Gln Phe His Ala Gln Lys Pro Cys Tyr
    370                 375                 380

Asp Tyr Leu Ile Tyr Asn Thr Thr Pro Glu His Asp Ala Leu Gln Trp
385                 390                 395                 400

Ser Tyr Leu His Pro Lys Asp Gly Leu Met Pro Met Tyr Leu Asn Ile
                405                 410                 415

Gln Ser His Leu Tyr Arg Val Leu Glu Thr Ile His Lys Val Leu Asn
            420                 425                 430

Asp Arg Asp Arg Trp Ser Arg Ala Tyr Arg Ala Lys Lys Asn Lys
        435                 440                 445


<210> SEQ ID NO 99
<211> LENGTH: 574
<212> TYPE: PRT
<213> ORGANISM: Adenovirus

<400> SEQUENCE: 99

Met Gln Gln Gln Ser Ser Ala Asp Gly Thr Ser Val Asn Pro Ala Leu
1               5                   10                  15

Leu Ala Ser Met Gln Ser Gln Pro Ser Gly Val Asn Ala Thr Asp Asp
            20                  25                  30

Trp Ser Ala Ala Met Asp Arg Ile Met Ala Leu Thr Thr Arg Asn Pro
        35                  40                  45

Glu Ala Phe Arg Gln Gln Pro Gln Ala Asn Arg Phe Ser Ala Ile Leu
    50                  55                  60

Glu Ala Val Val Pro Ser Arg Thr Asn Pro Thr His Glu Lys Val Leu
65                  70                  75                  80

Thr Ile Val Asn Ala Leu Val Asp Ser Lys Ala Ile Arg Arg Asp Glu
                85                  90                  95

Ala Gly Leu Ile Tyr Asn Ala Leu Leu Glu Arg Val Ala Arg Tyr Asn
            100                 105                 110

Ser Thr Asn Val Gln Ala Asn Leu Asp Arg Leu Asn Thr Asp Val Arg
        115                 120                 125

Glu Ala Leu Ala Gln Lys Glu Arg Phe Leu Arg Asp Ser Asn Leu Gly
    130                 135                 140

Ser Leu Val Ala Leu Asn Ala Phe Leu Ser Thr Gln Pro Ala Asn Val
145                 150                 155                 160

Pro Arg Gly Gln Glu Asp Tyr Val Ser Phe Ile Ser Ala Leu Arg Leu
                165                 170                 175

Leu Val Ser Glu Val Pro Gln Ser Glu Val Tyr Gln Ser Gly Pro Asp
            180                 185                 190

Tyr Phe Phe Gln Thr Ser Arg Gln Gly Leu Gln Thr Val Asn Leu Ser
```

```
        195                 200                 205

Gln Ala Phe Lys Asn Leu Gln Gly Met Trp Gly Val Lys Ala Pro Leu
    210                 215                 220

Gly Asp Arg Ala Thr Ile Ser Ser Leu Leu Thr Pro Asn Thr Arg Leu
225                 230                 235                 240

Leu Leu Leu Leu Ile Ala Pro Phe Thr Asn Ser Ser Ser Ile Ser Arg
                245                 250                 255

Asp Ser Tyr Leu Gly His Leu Ile Thr Leu Tyr Arg Glu Ala Ile Gly
            260                 265                 270

Gln Ala Gln Val Asp Glu His Thr Tyr Gln Glu Ile Thr Asn Val Ser
        275                 280                 285

Arg Ala Leu Gly Gln Glu Asp Thr Gly Ser Leu Glu Ala Thr Leu Asn
    290                 295                 300

Phe Leu Leu Thr Asn Arg Arg Gln Lys Ile Pro Ser Gln Phe Thr Leu
305                 310                 315                 320

Ser Ala Glu Glu Glu Arg Ile Leu Arg Tyr Val Gln Gln Ser Val Ser
                325                 330                 335

Leu Tyr Leu Met Arg Glu Gly Ala Thr Ala Ser Thr Ala Leu Asp Met
            340                 345                 350

Thr Ala Arg Asn Met Glu Pro Ser Phe Tyr Ala Ser Asn Arg Pro Phe
        355                 360                 365

Ile Asn Arg Leu Met Asp Tyr Leu His Arg Ala Ala Ala Met Asn Gly
    370                 375                 380

Glu Tyr Phe Thr Asn Ala Ile Leu Asn Pro His Trp Met Pro Pro Ser
385                 390                 395                 400

Gly Phe Tyr Thr Gly Glu Phe Asp Leu Pro Glu Ala Asp Asp Gly Phe
                405                 410                 415

Leu Trp Asp Asp Val Ser Asp Ser Ile Phe Ser Pro Ser Ser Gln Arg
            420                 425                 430

Met Gln Lys Lys Glu Gly Gly Asp Glu Leu Pro Leu Ser Ser Ile Glu
        435                 440                 445

Ala Ala Ser Arg Gly Glu Ser Pro Phe Pro Ser Leu Ser Ser Val Ser
    450                 455                 460

Ser Gly Arg Val Ser Arg Pro Arg Leu Pro Ala Glu Ser Glu Tyr Leu
465                 470                 475                 480

Ser Asp Pro Ile Leu Gln Pro Ser Arg Lys Lys Asn Phe Pro Asn Asn
                485                 490                 495

Gly Val Glu Ser Leu Val Asp Lys Met Lys Arg Trp Lys Thr Tyr Ala
            500                 505                 510

Gln Glu Gln Lys Glu Trp Glu Glu Thr Gln Val Arg Pro Val Pro Pro
        515                 520                 525

Pro Thr Gln Arg Arg Trp Arg Arg Pro Arg Glu Asp Pro Asp Asp Ser
    530                 535                 540

Ala Asp Asp Ser Ser Val Leu Asp Leu Gly Gly Ser Gly Ala Asn Pro
545                 550                 555                 560

Phe Ala His Leu Gln Pro Gln Gly Arg Leu Gly Arg Leu Tyr
                565                 570


<210> SEQ ID NO 100
<211> LENGTH: 159
<212> TYPE: PRT
<213> ORGANISM: Adenovirus

<400> SEQUENCE: 100
```

-continued

```
Met Gly Gly Val Thr Lys Gly Ile Lys Arg Thr Gly Arg Trp Gly Gly
1               5                   10                  15

Phe Ile Ala Lys Met Ser Gly Ser Thr Asp Ser Asn Ser Val Asn Phe
            20                  25                  30

Asp Gly Gly Val Phe Ser Pro Tyr Leu Thr Thr Arg Leu Pro Ser Trp
        35                  40                  45

Ala Gly Val Arg Gln Asn Val Val Gly Ser Ser Met Asp Gly Arg Pro
    50                  55                  60

Val Ala Pro Ala Asn Ser Ala Thr Leu Thr Tyr Ala Thr Val Gly Ser
65                  70                  75                  80

Ser Leu Asp Ala Ala Ala Ala Ala Ala Ala Ser Ala Ala Ala Ser Thr
                85                  90                  95

Ala Arg Val Met Ala Val Asp Phe Gly Leu Tyr Asn Gln Leu Ala Thr
            100                 105                 110

Ala Ala Ala Ala Ser Arg Ser Val Val Gln Gln Asp Ala Leu Asn Val
        115                 120                 125

Ile Leu Ala Arg Leu Glu Met Leu Ser Gln Arg Leu Asp Gln Leu Ala
    130                 135                 140

Ala Gln Ile Ala Leu Pro Pro Ala Pro Asp Ser Thr Ser Asp Ser
145                 150                 155


<210> SEQ ID NO 101
<211> LENGTH: 1185
<212> TYPE: PRT
<213> ORGANISM: Adenovirus

<400> SEQUENCE: 101

Met Ala Leu Val Gln Asn Gln Gly Thr Gly Gly Leu Tyr Ala Glu Ala
1               5                   10                  15

Ala His Pro Arg Ser Gln Pro Thr Arg Arg Arg Pro Cys Gln Arg Ser
            20                  25                  30

Pro Ser Ala Ser Pro Ala Ala Ala Lys Ser Ser Arg Lys Arg Ala Ser
        35                  40                  45

Ser Ser Ala Ala Ser Arg Arg Arg Ala Ser Pro Thr Ser Gly Cys Ala
    50                  55                  60

Thr Pro Thr Asp Glu Ile Lys Leu Pro Arg Gly Thr Val Val Ala Pro
65                  70                  75                  80

Arg Gly His Ala Leu Leu Tyr Ala Val Asp Ser Ser Ser Asn Cys Pro
                85                  90                  95

Leu Glu Ile Lys Tyr His Leu His Leu Thr Arg Ala Leu Thr Ala Leu
            100                 105                 110

Leu Gln Val Asn Leu Gln Ser Leu Pro Ser Asp Leu Ala Asn Gly Ser
        115                 120                 125

Leu Asp Ser Leu Asp Cys Gly Gln Leu Glu Ala Leu Val Arg Arg Leu
    130                 135                 140

Arg Pro Thr Val Ala Glu Ile Trp Ser Cys Gly Thr Arg Gly Val Val
145                 150                 155                 160

Thr Pro Val Leu Val His Pro Gln Asn Gln Gly Ala Gly Ala Tyr Pro
                165                 170                 175

Asp Glu His Arg Glu Gly Glu Asn Glu Pro Gln Ala Ser Ser Pro Leu
            180                 185                 190

Thr Phe Pro Leu Arg Phe Leu Val Arg Gly Arg Lys Val His Leu Ile
        195                 200                 205

Glu Gln Ile Gln Ser Val Gln Arg Cys Asp Tyr Cys Gly Arg Phe Tyr
    210                 215                 220
```

```
Lys His Gln His Glu Cys Ser Val Arg Arg Arg Asn Phe Tyr Phe His
225                 230                 235                 240

His Ile Asn Ala His Ser Ser Ser Trp Trp Gln Glu Ile Ser Phe Phe
                245                 250                 255

Pro Ile Gly Ser His Pro Arg Thr Glu Arg Leu Phe Val Thr Tyr Asp
            260                 265                 270

Val Glu Thr Tyr Thr Trp Met Gly Ser Phe Gly Lys Gln Leu Val Pro
        275                 280                 285

Phe Met Leu Val Met His Ile Ser Gly Asn Asp Asp Leu Val Leu Lys
    290                 295                 300

Ala Cys Ala Leu Ala Val Glu Leu Lys Trp Asp Thr Trp Asn Asn Arg
305                 310                 315                 320

Pro Thr Thr Phe Tyr Val Val Thr Pro Glu Lys Met Ala Val Gly Lys
                325                 330                 335

Lys Phe Arg Asp Phe Arg Asp Arg Leu Gln Thr Leu Leu Ala Arg Glu
            340                 345                 350

Leu Trp Cys Ser Phe Leu Ala Ala Asn Ser His Leu Glu Glu Trp Ser
        355                 360                 365

Arg Ala Glu Leu Gly Leu Phe Ser Pro Glu Cys Leu Thr Phe Glu Glu
    370                 375                 380

Leu Lys Lys Ala Pro Ala Leu Lys Gly Val Pro Arg Phe Leu Glu Leu
385                 390                 395                 400

Tyr Ile Val Gly His Asn Ile Asn Gly Phe Asp Glu Ile Val Leu Ala
                405                 410                 415

Ala Gln Val Ile Asn Asn Arg Ser Asp Val Pro Gly Pro Phe Arg Ile
            420                 425                 430

Ser Arg Asn Phe Met Pro Arg Ala Gly Lys Ile Leu Phe Asn Asp Ile
        435                 440                 445

Thr Phe Ala Leu Pro Asn Pro Arg Gln Lys Lys Arg Thr Asp Phe Thr
    450                 455                 460

Leu Trp Glu Gln Gly Cys Cys Asp Asp Thr Asp Phe Lys His Gln Tyr
465                 470                 475                 480

Leu Lys Val Met Val Arg Asp Thr Phe Gln Leu Thr His Thr Ser Leu
                485                 490                 495

Arg Lys Ala Ala Gln Ala Tyr Ala Leu Pro Ile Glu Lys Gly Cys Cys
            500                 505                 510

Pro Tyr Lys Ala Val Asn Glu Phe Tyr Met Leu Gly Ala Tyr Arg Ala
        515                 520                 525

Asp Asp Arg Gly Phe Pro Ala Glu Asp Tyr Trp Lys Asp Arg Glu Glu
    530                 535                 540

Tyr Leu Leu Asn Arg Glu Leu Trp Glu Lys Lys Gln Glu Lys Thr Tyr
545                 550                 555                 560

Asp Leu Val Arg Glu Thr Leu Asp Tyr Cys Ala Leu Asp Val Leu Val
                565                 570                 575

Thr Ala Ala Leu Val Asp Lys Leu Arg Glu Ser Tyr Ala Gln Phe Leu
            580                 585                 590

Gln Asp Ala Val Gly Leu Ser Gln Ala Ser Phe Asn Val Phe Gln Arg
        595                 600                 605

Pro Thr Ile Ser Ser Asn Ser His Ala Ile Phe Arg Gln Ile Ala Tyr
    610                 615                 620

Arg Ala Val Lys Pro Gln Lys Thr His Leu Gly Ser Gly Leu Leu Ala
625                 630                 635                 640
```

```
Pro Ser Gln Glu Met Tyr Asp Tyr Val Arg Ala Ser Ile Arg Gly Gly
                645                 650                 655

Arg Cys Tyr Pro Thr Tyr Ile Gly Val Leu Arg Gln Pro Leu Tyr Val
            660                 665                 670

Tyr Asp Ile Cys Gly Met Tyr Ala Ser Ala Leu Thr His Pro Met Pro
        675                 680                 685

Trp Gly Pro Pro Leu Asn Pro Tyr Glu Arg Ala Leu Ala Val Lys Lys
    690                 695                 700

Trp Asp Leu Ala Leu Gln His Arg Val Glu Ile Asn Tyr Phe Asn Lys
705                 710                 715                 720

Ser Leu Leu Pro Gly Ile Phe Thr Ile Asp Ala Asp Pro Pro Ala Ser
                725                 730                 735

Asn Leu Leu Asp Val Leu Pro Pro Phe Cys Ser Arg Lys Gly Gly Arg
            740                 745                 750

Leu Cys Trp Thr Asn Glu Pro Leu Arg Gly Glu Val Ala Thr Ser Val
        755                 760                 765

Asp Leu Ile Thr Leu His Asn Arg Gly Trp Cys Val Arg Ile Val Pro
    770                 775                 780

Asp Glu Arg Thr Thr Val Phe Pro Glu Trp Arg Cys Val Ala Arg Glu
785                 790                 795                 800

Tyr Val Gln Leu Asn Ile Ala Ala Lys Glu Arg Ala Asp Arg Glu Lys
                805                 810                 815

Asn Gln Thr Leu Arg Ser Ile Ala Lys Leu Leu Ser Asn Ala Leu Tyr
            820                 825                 830

Gly Ser Phe Ala Thr Lys Leu Asp Asn Lys Lys Ile Val Phe Ser Asp
        835                 840                 845

Gln Met Glu Thr Ser Thr Val Lys Asp Ile Ala Ser Gly Arg Val Asn
    850                 855                 860

Ile Lys Ser Thr Ser Phe Val Glu Thr Asp Thr Leu Ser Ala Glu Val
865                 870                 875                 880

Met Pro Ala Phe Glu Arg Ala Tyr Leu Pro Glu Gln Leu Ala Leu Ile
                885                 890                 895

His Ser Asp Ala Glu Glu Ser Asp Asp Glu Val Gly Asn Ala Pro Phe
            900                 905                 910

Tyr Ser Pro Pro Cys His Pro Asp Gly His Val Thr Tyr Thr Tyr Lys
        915                 920                 925

Pro Ile Thr Phe Met Asp Ala Glu Glu Asp Asp Leu Cys Leu His Thr
    930                 935                 940

Leu Gln Lys Val Asp Pro Leu Ile Glu Asn Asp Arg Tyr Pro Ser Gln
945                 950                 955                 960

Ile Ala Ser Phe Val Leu Ala Trp Thr Arg Ala Phe Val Ser Glu Trp
                965                 970                 975

Ser Gln Phe Leu Tyr Asp Glu Asp Arg Gly Thr Pro Leu Glu His Arg
            980                 985                 990

Glu Leu Lys Ser Val Tyr Gly Asp  Thr Asp Ser Leu Phe  Val Thr Glu
        995                 1000                1005

Ala Gly  His Arg Leu Met Glu  Thr Arg Gly Lys Lys  Arg Ile Lys
    1010                1015                1020

Lys Asn  Gly Gly Lys Leu Val  Phe Asp Pro Asn Gln  Pro Glu Leu
    1025                1030                1035

Thr Trp  Leu Val Glu Cys Glu  Thr Val Cys Ala Gln  Cys Gly Ala
    1040                1045                1050

Asp Ala  Phe Ser Pro Glu Ser  Val Phe Leu Ala Pro  Lys Leu Tyr
```

```
    1055                1060                1065

Ala Leu  Lys Ser Leu His Cys  Ser Lys Cys Leu His  Val Ser Lys
    1070                1075                1080

Gly Lys  Leu Arg Ala Lys Gly  His Ala Ala Glu Ser  Leu Ser Tyr
    1085                1090                1095

Asp Leu  Met Leu Lys Cys Tyr  Leu Ala Asp Ser Gln  Gly Glu Asn
    1100                1105                1110

Val His  Phe Ser Thr Ser Arg  Met Ser Leu Lys Arg  Thr Leu Ala
    1115                1120                1125

Ser Ala  Gln Pro Gly Ala His  Pro Phe Thr Val Thr  Glu Thr Thr
    1130                1135                1140

Leu Thr  Arg Thr Leu Arg Pro  Trp Lys Asp Met Thr  Leu Ala Ala
    1145                1150                1155

Leu Asp  Ala His Arg Leu Val  Pro Tyr Ser Glu Ser  Arg Pro Asn
    1160                1165                1170

Pro Arg  Asn Gln Glu Val Cys  Trp Ile Glu Met Pro
    1175                1180                1185


<210> SEQ ID NO 102
<211> LENGTH: 256
<212> TYPE: PRT
<213> ORGANISM: Adenovirus

<400> SEQUENCE: 102

Met Arg Trp Ile Pro Trp Met Ser Pro Arg Phe Phe Met Phe Cys Leu
1               5                   10                  15

Lys Ser Ser Thr Trp Cys Val Ser Ile Ser Arg Thr Gly Ala Ser Ser
            20                  25                  30

Arg Pro Ser Thr Cys Ala Arg Leu Ser Leu Pro Ala Thr Pro Pro Pro
        35                  40                  45

Lys Lys Pro Met Gly Ser Ser Glu Gln Glu Leu Arg Ser Ile Val Arg
    50                  55                  60

Asp Leu Gly Cys Gly Pro Tyr Phe Leu Gly Thr Phe Asp Lys Arg Phe
65                  70                  75                  80

Pro Gly Phe Met Ser Pro Gln Lys Pro Ala Cys Ala Ile Val Asn Thr
                85                  90                  95

Ala Gly Arg Glu Thr Gly Gly Val His Trp Leu Ala Phe Ala Trp Asn
            100                 105                 110

Pro Gln Asn Arg Thr Cys Tyr Leu Phe Asp Pro Phe Gly Phe Ser Asp
        115                 120                 125

Glu Arg Leu Lys Gln Ile Tyr Gln Phe Gln Tyr Glu Gly Leu Leu Lys
    130                 135                 140

Arg Ser Ala Leu Ala Ser Thr Pro Asp His Cys Val Thr Leu Glu Lys
145                 150                 155                 160

Ser Thr Gln Ser Val Gln Gly Pro Phe Ser Ala Ala Cys Gly Leu Phe
                165                 170                 175

Cys Cys Met Phe Leu His Ala Phe Val His Trp Pro His Ser Pro Met
            180                 185                 190

Asn Lys Asn Pro Thr Met Asp Leu Leu Thr Gly Val Pro Asn Ser Met
        195                 200                 205

Leu Gln Ser Pro Gln Val Val Pro Thr Leu Arg Cys Asn Gln Glu Gln
    210                 215                 220

Leu Tyr His Phe Leu Gly Lys Asn Ser Ala Tyr Phe Arg Arg His Arg
225                 230                 235                 240
```

```
Gln Arg Ile Glu Lys Ala Thr Asp Phe Glu Ser Met Lys His Thr Val
                245                 250                 255


<210> SEQ ID NO 103
<211> LENGTH: 646
<212> TYPE: PRT
<213> ORGANISM: Adenovirus

<400> SEQUENCE: 103

Met Ala Leu Ser Val Gln Asp Cys Ala Arg Leu Thr Gly Gln Ser Val
1               5                   10                  15

Pro Thr Met Glu Arg Phe Arg Pro Leu Arg Asn Ile Trp Asn Arg Val
            20                  25                  30

Arg Glu Phe Thr Arg Ala Ala Thr Thr Ser Ala Gly Ile Thr Trp Leu
        35                  40                  45

Ser Arg Tyr Val Tyr His Tyr His Arg Leu Met Leu Asp Asp Leu Ala
    50                  55                  60

Pro Gly Ala Pro Ala Thr Val Gly Trp Pro Leu Tyr Arg Glu Pro Pro
65                  70                  75                  80

Pro His Phe Leu Val Gly Tyr Gln Tyr Leu Val Arg Thr Cys Asn Asp
                85                  90                  95

Tyr Val Phe Glu Ser Arg Ala Tyr Ser Arg Leu Lys Tyr Thr Glu Ile
            100                 105                 110

Thr Gln Pro Gly Met Gln Val Val Asn Trp Ser Val Met Ala Asn Cys
        115                 120                 125

Thr Tyr Thr Ile Asn Thr Gly Ala Tyr His Arg Phe Val Asp Leu Asp
    130                 135                 140

Asp Phe Gln Thr Thr Leu Thr Gln Val Gln Gln Ala Val Leu Ala Glu
145                 150                 155                 160

Arg Val Val Ala Asp Leu Ala Leu Leu Gln Pro Leu Arg Gly Tyr Gly
                165                 170                 175

Ser Thr Arg Met Ala Asp Arg Gly Glu Ala Glu Ile Pro Val Glu Arg
            180                 185                 190

Leu Met Gln Asp Tyr Tyr Lys Asp Leu Arg Arg Cys Gln Asn Glu Ala
        195                 200                 205

Trp Gly Met Ala Asp Arg Leu Arg Ile Gln Gln Ala Gly Pro Lys Asp
    210                 215                 220

Val Val Leu Leu Ala Thr Ile Arg Arg Leu Lys Thr Ala Tyr Phe Asn
225                 230                 235                 240

Tyr Ile Ile Ser Ser Ile Thr Ser Arg Leu Pro Pro Ala Ser Thr Gln
                245                 250                 255

Arg Pro Ser Val Leu Ser Leu Pro Cys Asp Cys Asp Trp Leu Asn Ala
            260                 265                 270

Phe Leu Glu Lys Phe Ser Asp Pro Val Asp Leu Asp Ala Leu Arg Ser
        275                 280                 285

Leu His Gly Val Pro Thr Gln Gln Leu Ile Lys Cys Ile Val Ser Ala
    290                 295                 300

Val Ser Leu Pro Asp Gly Pro His His Leu Pro Ser Leu Gln Gly Gly
305                 310                 315                 320

Gly Leu Arg Gly Gly Val Phe Glu Leu Arg Pro Arg Glu His Gly Arg
                325                 330                 335

Ala Val Thr Glu Thr Met Arg Arg Arg Arg Gly Glu Met Ile Glu Arg
            340                 345                 350

Phe Val Asp Arg Leu Pro Val Arg Arg Arg Arg Arg Arg Pro Ala Pro
        355                 360                 365
```

```
Ala Ala Glu Val Pro Glu Glu Pro Met Leu Leu Glu Glu Glu Glu Glu
    370                 375                 380

Leu Glu Glu Glu Glu Val Pro Pro Gly Ala Phe Glu Arg Glu Val Arg
385                 390                 395                 400

Asp Thr Ile Ala Asp Leu Ile Arg Leu Leu Gln Glu Glu Leu Thr Val
                405                 410                 415

Ser Ala Arg Asn Ser Gln Phe Phe Asn Phe Ala Val Asp Phe Tyr Glu
            420                 425                 430

Ala Met Glu Arg Leu Glu Ala Ile Gly Asp Ile Asn Glu Ser Thr Leu
        435                 440                 445

Arg Arg Trp Ile Met Tyr Phe Phe Val Cys Glu His Ile Ala Thr Thr
    450                 455                 460

Leu Asn Tyr Leu Phe Gln Arg Leu Arg Asn Tyr Ala Val Phe Ser Arg
465                 470                 475                 480

His Val Glu Leu Asn Val Ala Gln Val Val Met Arg Ala Arg Asp Ser
                485                 490                 495

Ala Gly Gly Val Val Tyr Ser Arg Val Trp Asn Glu Asn Gly Leu Asn
            500                 505                 510

Ala Phe Ser Gln Leu Met Arg Arg Ile Ser Asn Asp Leu Ala Ala Thr
        515                 520                 525

Val Glu Arg Ala Gly His Gly Asp Leu Gln Glu Glu Glu Ile Glu Gln
    530                 535                 540

Phe Met Ala Glu Ile Ala Tyr Gln Asp Asn Ser Gly Asp Val Gln Glu
545                 550                 555                 560

Ile Leu Arg Gln Ala Ala Val Asn Asp Thr Asp Ile Asp Ser Val Glu
                565                 570                 575

Leu Ser Phe Arg Phe Arg Thr Arg Gly Pro Val Val Phe Thr Gln Arg
            580                 585                 590

Arg His Ile Gln Asp Leu Asn Arg Arg Val Val Ala His Ala Ser Asp
        595                 600                 605

Leu Arg Ala Arg His Leu Pro Leu Pro Asn Leu His Glu Asn Val Pro
    610                 615                 620

Leu Pro Pro Leu Pro Pro Gly Val Glu Pro Pro Leu Pro Pro Gly Ala
625                 630                 635                 640

Arg Pro Arg Arg Met Arg
                645


<210> SEQ ID NO 104
<211> LENGTH: 346
<212> TYPE: PRT
<213> ORGANISM: Adenovirus

<400> SEQUENCE: 104

Met Ser Lys Arg Lys Phe Lys Glu Glu Leu Leu Gln Thr Leu Ala Pro
1               5                   10                  15

Glu Ile Tyr Gly Ser Pro Glu Val Lys Arg Asp Ile Lys Arg Arg Asp
            20                  25                  30

Ile Lys Arg Val Lys Lys Arg Glu Lys Lys Glu Glu Glu Leu Ala Met
        35                  40                  45

Ala Ala Ala Ala Glu Asp Ala Val Glu Phe Val Arg Ser Phe Ala Pro
    50                  55                  60

Arg Arg Arg Val Gln Trp Lys Gly Arg Arg Val Gln Arg Val Leu Arg
65                  70                  75                  80

Pro Gly Thr Thr Val Val Phe Thr Pro Gly Gln Arg Ser Ala Val Arg
```

-continued

```
                85                  90                  95

Gly Phe Lys Arg Gln Tyr Asp Glu Val Tyr Gly Asp Glu Asp Ile Leu
            100                 105                 110

Glu Gln Ala Ala Gln Gln Ile Gly Glu Phe Ala Tyr Gly Lys Arg Ser
        115                 120                 125

Arg Gly Glu Asn Val Ala Val Ala Leu Asp Glu Gly Asn Pro Thr Pro
    130                 135                 140

Ser Leu Lys Pro Val Thr Leu Gln Gln Val Leu Pro Val Ser Ala Ser
145                 150                 155                 160

Thr Glu Ser Lys Arg Gly Ile Lys Arg Glu Leu Asp Leu Gln Pro Thr
                165                 170                 175

Leu Gln Leu Met Val Pro Lys Arg Gln Lys Leu Glu Glu Val Leu Glu
            180                 185                 190

Asn Met Lys Val Asp Pro Thr Val Glu Pro Asp Val Lys Val Arg Pro
        195                 200                 205

Ile Lys Glu Val Ala Pro Gly Leu Gly Val Gln Thr Val Asp Ile Gln
    210                 215                 220

Ile Pro Val Ser Ser Ser Val Glu Ala Met Glu Thr Gln Thr Glu Thr
225                 230                 235                 240

Pro Thr Ala Ala Thr Arg Glu Val Ala Leu Gln Thr Glu Pro Trp Tyr
                245                 250                 255

Glu Tyr Ala Thr Ser Ala Arg Pro Arg Arg Thr Arg Arg Tyr Ala Ala
            260                 265                 270

Thr Ser Ala Leu Met Pro Glu Tyr Ala Leu His Pro Ser Ile Thr Pro
        275                 280                 285

Thr Pro Gly Tyr Arg Gly Val Thr Phe Arg Pro Ser Gly Thr Arg Arg
    290                 295                 300

Arg Ser Arg Arg Arg Thr Ser Arg Arg Arg Ser Arg Arg Val Leu Ala
305                 310                 315                 320

Pro Val Ser Val Arg Arg Val Thr Arg Arg Gly Arg Thr Val Thr Ile
                325                 330                 335

Pro Asn Pro Arg Tyr His Pro Ser Ile Leu
            340                 345


<210> SEQ ID NO 105
<211> LENGTH: 308
<212> TYPE: PRT
<213> ORGANISM: Adenovirus

<400> SEQUENCE: 105

Met Pro Leu Leu Gly Arg Phe Pro Ala Ser Pro Leu Trp Pro Tyr Lys
1               5                   10                  15

His Leu Ala Asn Lys Gln Pro Ser Leu Phe Thr Tyr Val Met Val Leu
            20                  25                  30

Thr Ile Leu Cys Arg Lys Ile Met Glu Asp Ile Asn Phe Ser Ser Leu
        35                  40                  45

Ala Pro Arg His Gly Ser Arg Pro Phe Met Gly Thr Trp Asn Asp Ile
    50                  55                  60

Gly Thr Ser Gln Leu Asn Gly Gly Ala Phe Ser Trp Ser Ser Leu Trp
65                  70                  75                  80

Ser Gly Leu Lys Asn Phe Gly Ser Thr Ile Lys Thr Tyr Gly Asn Lys
                85                  90                  95

Ala Trp Asn Ser Ser Thr Gly Gln Met Leu Arg Asp Lys Leu Lys Asp
            100                 105                 110
```

```
Gln Asn Phe Gln Gln Lys Val Val Asp Gly Leu Ala Ser Gly Ile Asn
        115                 120                 125

Gly Val Val Asp Leu Ala Asn Gln Ala Val Gln Asn Gln Ile Asn Gln
    130                 135                 140

Arg Leu Glu Asn Ser Arg Val Pro Pro Gln Lys Gly Ala Glu Val Glu
145                 150                 155                 160

Glu Val Glu Val Glu Glu Lys Leu Pro Pro Leu Glu Val Val Pro Gly
                165                 170                 175

Ala Pro Pro Lys Gly Glu Lys Arg Pro Arg Pro Asp Leu Glu Glu Thr
            180                 185                 190

Leu Val Thr Gly Thr Leu Glu Pro Pro Ser Tyr Glu Gln Ala Leu Lys
        195                 200                 205

Glu Gly Ala Ser Pro Tyr Pro Met Thr Lys Pro Ile Ala Pro Met Ala
    210                 215                 220

Arg Pro Val Tyr Gly Lys Asp His Lys Pro Val Thr Leu Glu Leu Pro
225                 230                 235                 240

Pro Pro Pro Thr Val Pro Pro Leu Pro Ala Pro Ser Val Gly Thr Val
                245                 250                 255

Ala Ser Ala Pro Ser Val Val Pro Ala Pro Gln Pro Ala Val Arg Pro
            260                 265                 270

Val Ala Val Ala Thr Ala Arg Asn Pro Arg Gly Ala Asn Trp Gln Ser
        275                 280                 285

Thr Leu Asn Ser Ile Val Gly Leu Gly Val Lys Thr Leu Lys Arg Arg
    290                 295                 300

Arg Cys Tyr Tyr
305


<210> SEQ ID NO 106
<211> LENGTH: 183
<212> TYPE: PRT
<213> ORGANISM: Adenovirus

<400> SEQUENCE: 106

Met Ser Ile Leu Ile Ser Pro Asp Asn Asn Thr Gly Trp Gly Leu Gly
1               5                   10                  15

Ser Thr Lys Met Tyr Gly Gly Ala Lys Arg Arg Ser Ser Gln His Pro
            20                  25                  30

Val Arg Val Arg Gly His Tyr Arg Ala Pro Trp Gly Ala Tyr Lys Arg
        35                  40                  45

Gly Leu Ser Ala Arg Thr Ala Val Asp Asp Thr Ile Asp Ala Val Ile
    50                  55                  60

Ala Asp Ala Arg Gln Tyr Gln Pro Ala Ala Ala Ala Val Ser Thr Val
65                  70                  75                  80

Asp Ser Val Ile Asp Ser Val Val Ala Gly Ala Arg Ala Tyr Ala Arg
                85                  90                  95

Arg Lys Arg Arg Leu His Arg Arg Arg Arg Pro Thr Ala Ala Met Leu
            100                 105                 110

Ala Ala Arg Ala Val Leu Arg Arg Ala Arg Arg Val Gly Arg Arg Ala
        115                 120                 125

Met Arg Arg Ala Ala Ala Asn Ala Gly Arg Val Arg Arg Gln Ala Ala
    130                 135                 140

Arg Gln Ala Ala Ala Ala Ile Ala Asn Met Ala Arg Pro Arg Arg Gly
145                 150                 155                 160

Asn Val Tyr Trp Val Arg Asp Ser Val Thr Gly Val Arg Val Pro Val
                165                 170                 175
```

Arg Thr Arg Pro Pro Arg Ser
180

<210> SEQ ID NO 107
<211> LENGTH: 233
<212> TYPE: PRT
<213> ORGANISM: Adenovirus

<400> SEQUENCE: 107

Met Ser Lys Glu Ile Pro Thr Pro Tyr Met Trp Ser Tyr Gln Pro Gln
1 5 10 15

Met Gly Leu Ala Ala Gly Ala Ala Gln Asp Tyr Ser Ser Lys Met Asn
20 25 30

Trp Leu Ser Ala Gly Pro His Met Ile Ser Gln Val Asn Asp Ile Arg
35 40 45

Ala Arg Arg Asn Gln Ile Leu Leu Glu Gln Ala Ala Ile Thr Ser Thr
50 55 60

Pro Arg Arg Leu Leu Asn Pro Pro Ser Trp Pro Ala Ala Gln Val Tyr
65 70 75 80

Gln Glu Thr Pro Ala Pro Thr Thr Val Leu Leu Pro Arg Asp Ala Glu
85 90 95

Ala Glu Val Gln Met Thr Asn Ala Gly Ala Gln Leu Ala Gly Gly Ser
100 105 110

Arg Tyr Val Arg Tyr Arg Gly Arg Ser Ala Pro Tyr Pro Pro Gly Gly
115 120 125

Ile Lys Arg Val Phe Ile Arg Gly Arg Gly Ile Gln Leu Asn Asp Glu
130 135 140

Val Val Ser Ser Ser Ala Gly Leu Arg Pro Asp Gly Val Phe Gln Leu
145 150 155 160

Gly Gly Ala Gly Arg Ser Ser Phe Thr Thr Arg Gln Ala Tyr Leu Thr
165 170 175

Leu Gln Ser Ser Ser Ser Gln Pro Arg Ser Gly Gly Ile Gly Thr Leu
180 185 190

Gln Phe Val Glu Glu Phe Val Pro Ser Val Tyr Phe Asn Pro Phe Ser
195 200 205

Gly Ser Pro Gly Arg Tyr Pro Asp Ser Phe Ile Pro Asn Tyr Asp Ala
210 215 220

Val Ser Glu Ser Val Asp Gly Tyr Asp
225 230

<210> SEQ ID NO 108
<211> LENGTH: 71
<212> TYPE: PRT
<213> ORGANISM: Adenovirus

<400> SEQUENCE: 108

Met Gln Met Ala Leu Thr Cys Arg Leu Arg Ile Pro Val Pro His Tyr
1 5 10 15

Arg Gly Arg Thr Arg Arg Arg Arg Gly Met Ala Gly Ser Gly Arg Arg
20 25 30

Arg Ala Leu Arg Arg Arg Met Lys Gly Gly Ile Leu Pro Ala Leu Ile
35 40 45

Pro Ile Ile Ala Ala Ala Ile Gly Ala Ile Pro Gly Ile Ala Ser Val
50 55 60

Ala Val Gln Ala Ser Arg Lys
65 70

<210> SEQ ID NO 109
<211> LENGTH: 53
<212> TYPE: PRT
<213> ORGANISM: Adenovirus

<400> SEQUENCE: 109

Met Lys Ile Val Asp Glu Glu Arg Glu Val Asp Ile Asn Ile Ser Phe
1 5 10 15

Lys Thr Trp Arg Lys Phe Ala Ala His Tyr His Val Pro Tyr Glu Ser
20 25 30

Trp Glu Glu Gly Lys Val Val Val Ile Lys Glu Phe Asp Lys Lys Leu
35 40 45

Leu Ser Asn Leu Arg
50

<210> SEQ ID NO 110
<211> LENGTH: 787
<212> TYPE: PRT
<213> ORGANISM: Adenovirus

<400> SEQUENCE: 110

Met Glu Val Ser Lys Ser Gly Gly Glu Thr Arg Pro Pro Thr Pro Ala
1 5 10 15

Pro Phe Ser Arg Arg Glu Ala Glu Glu Gln Asp Glu Arg Asp Asn Phe
20 25 30

Glu Glu Val Ile Ile Glu Gln Asp Pro Gly Tyr Val Thr Pro Pro Glu
35 40 45

Gln Leu Ser Glu Ala Glu Asp Glu Pro Ala Ala Thr Gln Pro Leu Arg
50 55 60

Asp Gly Gln Thr Gln Thr Glu Gly Asp Glu Pro Asp Tyr Leu Thr Pro
65 70 75 80

Glu Val Leu Leu Lys His Leu Arg Arg Gln Ser Ala Ile Val Ser Asp
85 90 95

Ala Leu Arg Glu Leu Glu Thr Ala Pro Pro Ser Val Arg Glu Leu Ser
100 105 110

Ala Leu Tyr Glu Ser His Leu Phe Ser Pro Arg Val Pro Pro Lys Arg
115 120 125

Gln Pro Asn Gly Thr Cys Glu Pro Asn Pro Arg Leu Asn Phe Tyr Pro
130 135 140

Val Phe Ala Val Pro Glu Ala Leu Ala Thr Tyr His Leu Phe Phe Lys
145 150 155 160

Asn Gln Arg Ile Pro Leu Ser Cys Arg Ala Asn Arg Ser Leu Ala Asp
165 170 175

Glu Arg Leu Ala Leu Lys Gln Gly Asp Arg Leu Pro Gly Val Val Ser
180 185 190

Leu Glu Glu Val Pro Lys Ile Phe Glu Gly Leu Gly Ser Glu Glu Lys
195 200 205

Arg Ala Ala Asn Ala Leu Pro Glu Asn Thr Glu Asn Arg Ser Val Leu
210 215 220

Val Glu Leu Ala Gly Asp Asn Ala Arg Leu Ala Val Leu Lys Arg Ser
225 230 235 240

Val Glu Val Ser His Phe Ala Tyr Pro Ala Leu Asn Leu Pro Pro Lys
245 250 255

Val Met Ser Cys Val Met Asp Gln Leu Leu Ile Lys Arg Ala Gln Pro
260 265 270

```
Leu Ser Asp Ala Ala Glu Ala Asp Ser Asp Asp Gly Gln Pro Val Val
        275                 280                 285

Asp Asp Ala Glu Leu Gly Arg Trp Leu Gly Thr Ala Asp Pro Asp Ser
    290                 295                 300

Leu Gln Glu Arg Arg Lys Leu Val Met Ala Ala Val Leu Val Ser Cys
305                 310                 315                 320

Glu Leu Gln Cys Leu Arg Arg Phe Phe Ala Asp Pro Arg Thr Leu Gln
                325                 330                 335

Lys Leu Glu Glu Ser Leu His Tyr Thr Phe Arg His Gly Tyr Val Arg
            340                 345                 350

Gln Ala Ser Leu Ile Ser Asn Val Glu Leu Ser Asn Leu Val Ser Tyr
        355                 360                 365

Leu Gly Ile Leu His Glu Asn Arg Leu Gly Gln Ser Val Leu His Ser
    370                 375                 380

Thr Leu Lys Gly Glu Ala Arg Arg Asp Tyr Val Arg Asp Cys Val Tyr
385                 390                 395                 400

Leu Phe Leu Val Leu Thr Trp Gln Ser Ala Met Gly Val Trp Gln Gln
                405                 410                 415

Cys Leu Glu Glu Gln Asn Leu Arg Glu Leu Glu Lys Leu Leu Arg Arg
            420                 425                 430

His Lys Lys Ala Leu Trp Thr Gly Phe Asp Glu Thr Thr Val Ala Thr
        435                 440                 445

Ala Leu Ala Asp Ile Val Phe Pro Glu Arg Leu Arg Gln Thr Leu Gln
    450                 455                 460

Asn Gly Leu Pro Asp Phe Ile Ser Gln Ser Met Leu His Asn Phe Arg
465                 470                 475                 480

Ser Phe Val Leu Glu Arg Ser Ala Ile Leu Pro Ala Thr Ser Cys Ala
                485                 490                 495

Leu Pro Ser Asp Phe Val Pro Leu Thr Tyr Arg Glu Cys Pro Pro Pro
            500                 505                 510

Leu Trp Ser His Cys Tyr Leu Leu Gln Leu Ala Asn Tyr Leu Ala Tyr
        515                 520                 525

His Cys Asp Leu Met Glu Asp Val Ser Gly Glu Gly Leu Leu Ala Cys
    530                 535                 540

His Cys Arg Cys Asn Leu Cys Thr Pro His Arg Ser Leu Ala Cys Asn
545                 550                 555                 560

Pro Glu Leu Leu Ser Glu Ser Gln Leu Ile Gly Thr Phe Glu Leu Gln
                565                 570                 575

Gly Pro Glu Gly Gly Ala Gln Gly Thr Pro Leu Lys Leu Thr Pro Ala
            580                 585                 590

Ala Trp Thr Ser Ala Tyr Leu Arg Lys Phe His Pro Glu Asp Tyr His
        595                 600                 605

Pro His Glu Ile Arg Phe Tyr Glu Glu Gln Ala Gln Pro Pro Arg Ala
    610                 615                 620

Pro Leu Ser Ala Cys Val Ile Thr Gln Ser Thr Ile Leu Ala Gln Leu
625                 630                 635                 640

Gln Ala Ile Asn Gln Ala Arg Arg Glu Phe Leu Leu Lys Lys Gly Arg
                645                 650                 655

Gly Val Tyr Leu Asp Pro Gln Thr Gly Glu Glu Leu Asn Ala Ala Ser
            660                 665                 670

Pro Asp Cys Pro Pro Ser Ser Asn Phe Ser His Gln His Gly Pro Gln
        675                 680                 685
```

```
Ala Pro Asp Ala Thr Pro Ala Arg Lys Ala Leu Gln Lys Ala Gly Ala
    690                 695                 700

Glu Ala Ala Pro Asp Pro Arg Asp Leu Gly Arg Gly Glu Pro Gly Leu
705                 710                 715                 720

Leu Gly Glu Pro Ser Arg Asp His Arg Arg Gly Gly Leu Gly Gly Asp
                725                 730                 735

Gln Gln Phe Arg Arg Gly Gly Gly Thr Thr Arg Arg Gly Thr Gly Arg
            740                 745                 750

Gly Arg Asn Pro Gln Arg Arg Arg Thr Val Thr Leu Gly Arg Arg Ser
        755                 760                 765

Gln Asn Ala Ala Thr Ser Gly Pro His Ser Ser Ala Ala Ala Glu Lys
    770                 775                 780

Ser Gln Ser
785


<210> SEQ ID NO 111
<211> LENGTH: 234
<212> TYPE: PRT
<213> ORGANISM: Adenovirus

<400> SEQUENCE: 111

Met Ala Pro Lys Arg Gln Thr Gln Leu Leu Arg Glu Lys Arg Ser Lys
1               5                   10                  15

Lys Gln Glu Gln Arg Leu Pro Pro Thr Pro Glu Thr Trp Asp Glu Glu
            20                  25                  30

Ser Gln Asp Ser Trp Glu Ser Gln Ala Ala Thr Thr Glu Glu Glu Asp
        35                  40                  45

Trp Glu Glu Thr Ser Ser Leu Gly Glu Ala Glu Glu Gln Pro Asp Glu
    50                  55                  60

Glu Gln Ala Glu Glu Glu Thr Pro Ser Ala Ala Ala Pro Leu Arg Ser
65                  70                  75                  80

Val Ala Gly Pro Lys Thr Pro Arg Pro Pro Ala Pro Thr Pro Pro Leu
                85                  90                  95

Pro Pro Lys Lys Ala Asn Arg Arg Trp Asp Ala Lys Thr Pro Ala Pro
            100                 105                 110

Ala Ala Pro Val Gly Lys Met Leu Ala Gly Gln Arg Arg Gln Arg Gly
        115                 120                 125

Ala Tyr Cys Ser Trp Arg Ala Tyr Lys Ser Asp Ile Leu Ala Cys Leu
    130                 135                 140

Leu His Cys Gly Gly Asn Val Ser Phe Thr Arg Arg Tyr Leu Leu Phe
145                 150                 155                 160

His Arg Gly Val Ala Val Pro Arg Asn Val Leu His Tyr Tyr Arg His
                165                 170                 175

Leu Tyr Ser Pro Phe His Gln Gln Gln Gln Phe Pro Glu Thr Ala Arg
            180                 185                 190

Gln Arg Gly Glu Pro Asp Leu Arg Ala Pro Gly His Ala Ala Asp Ala
        195                 200                 205

Gly Ala Glu Asn Ala Asp Leu Ser His Ala Val Arg His Phe Ser Ala
    210                 215                 220

Glu Ser Arg Ala Ala Thr Arg Thr Glu Asn
225                 230


<210> SEQ ID NO 112
<211> LENGTH: 217
<212> TYPE: PRT
<213> ORGANISM: Adenovirus
```

<400> SEQUENCE: 112

```
Met Ala Pro Lys Arg Gln Thr Gln Leu Leu Arg Glu Lys Arg Ser Lys
1               5                   10                  15

Lys Gln Glu Gln Arg Leu Pro Pro Thr Pro Glu Thr Trp Asp Glu Glu
            20                  25                  30

Ser Gln Asp Ser Trp Glu Ser Gln Ala Ala Thr Thr Glu Glu Glu Asp
        35                  40                  45

Trp Glu Glu Thr Ser Ser Leu Gly Glu Ala Glu Glu Gln Pro Asp Glu
    50                  55                  60

Glu Gln Ala Glu Glu Glu Thr Pro Ser Ala Ala Ala Pro Leu Arg Ser
65                  70                  75                  80

Val Ala Gly Pro Lys Thr Pro Arg Pro Pro Ala Pro Thr Pro Pro Leu
                85                  90                  95

Pro Pro Lys Lys Ala Asn Arg Arg Trp Asp Ala Lys Thr Pro Ala Pro
            100                 105                 110

Ala Ala Pro Val Gly Lys Met Leu Ala Gly Gln Arg Arg Gln Arg Gly
        115                 120                 125

Ala Tyr Cys Ser Trp Arg Ala Tyr Lys Ser Asp Ile Leu Ala Cys Leu
    130                 135                 140

Leu His Cys Gly Gly Asn Val Ser Phe Thr Arg Arg Tyr Leu Leu Phe
145                 150                 155                 160

His Arg Gly Val Ala Val Pro Arg Asn Val Leu His Tyr Tyr Arg His
                165                 170                 175

Leu Tyr Ser Pro Phe His Gln Gln Gln His Cys Leu Tyr His Arg Arg
            180                 185                 190

Glu Asp Gln Leu Gln Arg Thr Leu Glu Asp Ala Glu Ala Leu Phe Asn
        195                 200                 205

Lys Tyr Cys Ser Ala Thr Leu Gln Asp
    210                 215
```

<210> SEQ ID NO 113
<211> LENGTH: 404
<212> TYPE: PRT
<213> ORGANISM: Adenovirus

<400> SEQUENCE: 113

```
Met Arg Arg Pro Arg Ile His Gly Pro Ser Arg Ser Arg Pro Ser Arg
1               5                   10                  15

Asp Pro Gly Tyr Gly Gly Glu Ser Phe Ala Val Phe Ala Ala Met His
            20                  25                  30

Pro Val Leu Arg Gln Met Arg Pro Gln Pro Ala Ser Ala Ala Gly Ser
        35                  40                  45

Arg Gly Gly Ala Ala Ala Val Glu Pro Glu Ala Glu Glu Ala Glu Arg
    50                  55                  60

Thr Leu Asp Leu Glu Glu Gly Glu Gly Leu Ala Arg Leu Gly Ala His
65                  70                  75                  80

Val Pro Glu Arg His Pro Arg Val Gln Leu Ala Arg Asp Ser Arg Ala
                85                  90                  95

Ala Tyr Val Pro Arg Gln Asn Leu Phe Arg Asp Ala Ser Gly Glu Glu
            100                 105                 110

Gly Glu Glu Leu Arg Asp Cys Arg Phe Arg Ala Gly Arg Glu Leu Arg
        115                 120                 125

Ala Gly Leu Asp Arg Glu Arg Leu Leu Arg Ala Glu Asp Phe Glu Ala
    130                 135                 140
```

Glu Glu Gly Arg Gly Val Ser Pro Ala Arg Ala His Leu Ala Ala Ala
145 150 155 160

Asn Leu Val Thr Ala Tyr Glu Gln Thr Val Lys Glu Glu Arg Ser Phe
165 170 175

Gln Gln Ser Phe Asn Asn His Val Arg Thr Leu Val Ala Arg Glu Glu
180 185 190

Val Ala Ile Gly Leu Met His Leu Trp Asp Phe Val Glu Ala Phe Val
195 200 205

His Asn Pro Gly Ser Lys Ala Leu Thr Ala Gln Leu Phe Leu Ile Val
210 215 220

Gln His Ser Arg Asp Asn Glu Leu Phe Arg Asp Ala Leu Leu Asn Ile
225 230 235 240

Ala Glu Pro Glu Gly Arg Trp Leu Leu Asp Leu Ile Asn Ile Leu Gln
245 250 255

Ser Ile Val Val Gln Glu Arg Ser Leu Ser Leu Ala Asp Lys Val Ala
260 265 270

Ala Ile Asn Tyr Ser Met Leu Ser Leu Gly Lys Phe Tyr Ala Arg Lys
275 280 285

Ile Tyr Arg Ser Pro Tyr Val Pro Ile Asp Lys Glu Val Lys Ile Asp
290 295 300

Ser Phe Tyr Met Arg Met Ala Leu Lys Val Leu Thr Leu Ser Asp Asp
305 310 315 320

Leu Gly Val Tyr Arg Asn Asp Arg Ile His Lys Ala Val Ser Ala Ser
325 330 335

Arg Arg Arg Glu Leu Ser Asp Arg Glu Leu Leu His Ser Leu Arg Arg
340 345 350

Ala Leu Ala Gly Ala Gly Asp Pro Glu Arg Glu Ala Tyr Phe Glu Ala
355 360 365

Gly Ala Asp Leu Ala Trp Gln Pro Ser Ala Arg Ala Leu Glu Ala Ala
370 375 380

Gly Ala Ala Ala Glu Glu Asp Glu Glu Ala Glu Glu Asp Leu Glu Glu
385 390 395 400

Asp Glu Ala Tyr

<210> SEQ ID NO 114
<211> LENGTH: 493
<212> TYPE: PRT
<213> ORGANISM: Adenovirus

<400> SEQUENCE: 114

Met Ala Asp Arg Gln Asp Gln Arg Glu Arg Thr Pro Glu Arg Pro Arg
1 5 10 15

Pro Ala Thr Pro Ser Ile Arg Arg Tyr Leu Gln Ala Ser Pro Glu Arg
20 25 30

Ala Pro Thr Pro Ala Pro Pro Gln Lys Lys Ala Arg Lys Ser Leu Leu
35 40 45

Ala Pro Leu Ala Glu Met Pro Pro Ser Pro Glu Ile Val Leu Asp Ser
50 55 60

Asp Asp Glu Glu Asn Leu Ala Ile Ala Glu Glu Ser Gln Ala Gly Val
65 70 75 80

Val Thr Met Val Gly Phe Ser Tyr Pro Pro Val Gln Ile Thr Arg Asn
85 90 95

Pro Asp Gly Ser Arg Ala Phe Lys Lys Leu Pro Pro Pro Pro Leu Pro
100 105 110

```
Ala Asp Ala Glu Lys Asp Glu Glu Gln Pro Ser Thr Ser Arg Ala Ala
        115                 120                 125

Val Val Val Arg Asn Pro Leu Ser Lys Pro Val Val Ser Ala Trp Glu
    130                 135                 140

Lys Gly Met Ala Val Met His Val Leu Met Asp Lys Tyr Lys Ile Glu
145                 150                 155                 160

Asp Arg Ala Ala Phe Asp Phe Met Pro Gln Ser Phe Glu Val Tyr Arg
                165                 170                 175

Lys Ile Cys His Thr Trp Leu Gln Glu Asp Leu Lys Tyr Cys Pro Leu
            180                 185                 190

Thr Phe Ser Thr Gln Lys Thr Phe Ser Ala Met Met Gly Arg Phe Leu
        195                 200                 205

Asn Lys Tyr Val Leu Leu His Ala Gly Ile Glu Asn Pro Leu Tyr Lys
    210                 215                 220

Ser Trp Glu Pro Thr Gly Cys Val Val Trp Glu His Arg Cys Thr Glu
225                 230                 235                 240

Gln Glu Gly Gln Leu Met Cys Leu His Gly Leu Pro Met Ile Ala Lys
                245                 250                 255

Asp His Val Val Glu Met Asp Val Ser Ser Glu Ala Gly Gln Arg Ala
            260                 265                 270

Leu Lys Glu Thr Pro Gln Leu Ala Lys Val Val Gln Asn Arg Trp Gly
        275                 280                 285

Arg Asn Val Val Gln Leu Arg His Asp Asn Ala Arg Cys Cys Met Phe
    290                 295                 300

Asp Ala Gln Cys Gly Thr Asn Val Phe Ser Gly Lys Ser Cys Gly Met
305                 310                 315                 320

Phe Tyr Ser Glu Gly Gly Lys Ala Gln Gln Ala Phe Arg Gln Ile Glu
                325                 330                 335

Ala Tyr Met Gln Ala Ala Tyr Pro His Met Gln Arg Gly Gln Lys His
            340                 345                 350

Leu Leu Met Pro Leu Arg Cys Asp Cys Asn Tyr Leu Gly Asp Ala Val
        355                 360                 365

Pro Arg Ala Gly Arg Gln Val Cys Lys Ile Thr Pro Phe Ala Leu Pro
    370                 375                 380

Gly Ala Glu Asp Met Lys His Asp Glu Val Thr Asp Pro Val Ala Leu
385                 390                 395                 400

Ala Ser Leu Asn His Pro Ser Leu Leu Val Phe Gln Cys Ala Asn Pro
                405                 410                 415

Ala Tyr Arg Asn Thr Arg Ala Thr Asn Gln Val Asn Cys Asp Phe Lys
            420                 425                 430

Ile Ser Ala Thr Asp Val Leu Leu Ala Leu Gln Leu Val Arg Asn Leu
        435                 440                 445

Trp His Asp His Phe Val Glu Ala Gly Leu Pro Lys Met Val Leu Pro
    450                 455                 460

Glu Phe Lys Trp Gln Pro Arg Tyr Gln Tyr Lys Asn Leu Thr Leu Pro
465                 470                 475                 480

Thr Ala His Leu Asp Tyr Gln Leu Asn Pro Phe Glu Phe
                485                 490
```

<210> SEQ ID NO 115
<211> LENGTH: 270
<212> TYPE: PRT
<213> ORGANISM: Adenovirus

<400> SEQUENCE: 115

Met Lys Thr Trp Gly Leu Asp Cys Gly Leu His Pro Gln Glu Val Asp
1               5                   10                  15

Glu Trp Leu Arg Ser Glu Tyr Cys Pro Thr Pro Gly Tyr Tyr Gly Glu
            20                  25                  30

Asn Leu Ser Leu His Asp Leu Tyr Asp Ile Asp Val Asp Glu Pro Ala
        35                  40                  45

Glu Gly Asp Glu Asn Glu Val Pro Val Asn Asp Phe Phe Pro Asp Ser
    50                  55                  60

Leu Leu Leu Ala Val Asp Glu Gly Ile Glu Val Asp Tyr Pro Pro Pro
65                  70                  75                  80

Leu Asp Thr Pro Gly Glu Pro Ser Gly Ser His Phe Met Pro Asn Leu
                85                  90                  95

Ser Leu Glu Glu Val Asp Leu Tyr Cys His Glu Asp Gly Phe Pro Pro
            100                 105                 110

Ser Asp Ser Glu Gly Glu Gln Ser Glu Ala Lys Asp Glu Arg Leu Met
        115                 120                 125

Ala Glu Ala Ala Ala Thr Gly Ala Ala Ala Ala Ala Arg Arg Ala Trp
    130                 135                 140

Glu Glu Glu Glu Phe Arg Leu Asp Cys Pro Val Leu Pro Gly His Gly
145                 150                 155                 160

Cys Ala Ser Cys Asp Tyr His Arg Lys Thr Ser Gly Phe Pro Glu Ile
                165                 170                 175

Met Cys Ser Leu Cys Tyr Leu Arg Ala His Gly Met Phe Val Tyr Ser
            180                 185                 190

Pro Val Ser Asp Ala Glu Gly Glu Pro Asp Ser Thr Thr Asp His Ser
        195                 200                 205

Gly Gly Pro Gly Ser Pro Pro Lys Leu His Asn Thr Pro Pro Arg Asn
    210                 215                 220

Val Pro Arg Pro Val Pro Leu Arg Val Ser Gly Val Arg Arg Ala Ala
225                 230                 235                 240

Val Glu Ser Leu His Asp Leu Ile Gly Gly Glu Glu Glu Gln Val Val
                245                 250                 255

Pro Leu Asp Leu Ser Ala Lys Arg Pro Pro Ser Phe Lys Val
            260                 265                 270

<210> SEQ ID NO 116
<211> LENGTH: 492
<212> TYPE: PRT
<213> ORGANISM: Adenovirus

<400> SEQUENCE: 116

Met Glu His Pro Asp Pro Ala Val Pro Gly Val His Pro Gly Leu His
1               5                   10                  15

Gln Pro Ala Ala Val Glu Val Leu Ala Ala Pro Ala Gly Leu Gln Leu
            20                  25                  30

Leu Ala Gly Ala Ala Ser Ala Arg Ala Gly Ile Val Ala Gly Gly Ala
        35                  40                  45

Val Ala Gly Gly Glu Ala Gly Gly Gly Gly Ala Gly Gly Gly Ala Gly
    50                  55                  60

Ala Gly Ala Ser Ala Ala Val Arg Pro Gly Pro Ser Gly Gly Glu Leu
65                  70                  75                  80

Ser Ala Glu Pro Gln Val Ala Glu Gly Gln Val Gly Pro Lys Arg Ser
                85                  90                  95

```
Pro Lys Arg Ala Lys Asn Glu Glu Glu Gln Ser Glu Glu Ala Leu Thr
            100                 105                 110

Arg Leu Thr Leu Ser Leu Ile Asn Arg Gln Arg Pro Glu Thr Val Phe
        115                 120                 125

Tyr Tyr Glu Leu Glu His Glu Phe Gln His Gly Asp Met His Leu Gln
    130                 135                 140

Cys Lys Phe Gly Phe Glu Gln Ile Lys Thr His Trp Leu Glu Pro Trp
145                 150                 155                 160

Glu Asp Met Ala Thr Val Leu Asn Gln Phe Val Lys Val Ala Leu Arg
                165                 170                 175

Pro Asp Arg Val Tyr Lys Val Ser Ser Thr Val His Leu Arg Lys Cys
            180                 185                 190

Val Tyr Val Ile Gly Asn Gly Ala Thr Val Glu Val Glu Gly Ser Asp
        195                 200                 205

Arg Val Ala Phe Asn Cys Leu Met Gln Arg Met Gly Pro Gly Val Met
    210                 215                 220

Gly Leu Ser Gly Val Thr Phe Glu Asn Val Arg Leu Val Cys Arg Asp
225                 230                 235                 240

Phe His Gly Val Met Phe Ala Cys Thr Thr Glu Leu Asn Leu His Gly
                245                 250                 255

Val Tyr Phe Phe Asn Val Asn His Ala Cys Val Glu Cys Trp Gly Gln
            260                 265                 270

Leu Arg Ala Arg Gly Cys Thr Phe His Gln Cys Phe Lys Gly Val Val
        275                 280                 285

Gly Arg Pro Lys Ser Arg Val Ser Ile Lys Lys Cys Val Phe Glu Arg
    290                 295                 300

Cys Leu Leu Gly Val Ser Val Glu Gly His Gly Arg Leu Arg Asn Asn
305                 310                 315                 320

Ala Ala Ser Glu Asn Ile Cys Phe Ala Leu Ile Lys Gly Thr Ala Val
                325                 330                 335

Leu Lys Ser Asn Met Ile Cys Gly Thr Gly Asp Asp Arg Gly Gly Lys
            340                 345                 350

His Leu Ile Thr Cys Ala Asn Gly Trp Cys His Cys Leu Arg Ser Val
        355                 360                 365

His Val Val Ser His Pro Arg Arg Ser Trp Pro Leu Phe Glu Ser Asn
    370                 375                 380

Met Leu Met Arg Cys Thr Val His Leu Gly Ala Arg Arg Gly Met Phe
385                 390                 395                 400

Leu Pro His Gln Cys Asn Phe Ser His Thr Ser Val Leu Leu Glu Pro
                405                 410                 415

Glu Ala Phe Thr Arg Val Cys Phe Asn Ala Val Phe Asp Val Ser Leu
            420                 425                 430

Glu Val Phe Lys Ile Val Arg Tyr Asp Glu Ser Arg Ala Arg Ser Arg
        435                 440                 445

Leu Cys Glu Cys Gly Ala Asn His Leu Arg Ser Val Pro Leu Thr Val
    450                 455                 460

Asn Val Thr Glu Glu Leu Arg Ala Asp His Val Met Leu Pro Cys Asn
465                 470                 475                 480

Arg Thr Asp Tyr Ala Thr Ser Asp Glu Glu Ser Gly
                485                 490
```

<210> SEQ ID NO 117
<211> LENGTH: 108
<212> TYPE: PRT

<213> ORGANISM: Adenovirus

<400> SEQUENCE: 117

Met Thr Asp Gly Glu Ala Asp Arg Ala Arg Leu Arg His Leu His His
1 5 10 15

Cys Arg Gln Phe His Cys Phe Ala Arg Glu Ala His Ser Phe Ile Tyr
20 25 30

Phe Val Ile Pro Glu Asp His Pro Gln Gly Pro Ala His Gly Val Lys
35 40 45

Leu Glu Ile Glu Glu Glu Leu Ser Ser His Leu Ile Tyr Leu Phe Thr
50 55 60

Ala Arg Pro Leu Leu Ala Glu Lys Ala Gln Gly Thr Thr Thr Leu Thr
65 70 75 80

Leu Phe Cys Ile Cys Arg Glu Pro Ala Leu His Glu Asp Leu Cys Cys
85 90 95

His Leu Cys Ser Glu Tyr Asn Lys His Arg Ser Gly
100 105

<210> SEQ ID NO 118
<211> LENGTH: 130
<212> TYPE: PRT
<213> ORGANISM: Adenovirus

<400> SEQUENCE: 118

Met Ala Asp Cys Arg Asp Asp Ser Ala Gln Leu Asp Ile Asp Gly Val
1 5 10 15

Arg Thr Glu Gln Leu Leu Ala Ala Arg Gln Arg Gln Arg Gln Glu Gln
20 25 30

Arg Gln Arg Glu Leu Gln Asp Leu Lys Asn Leu His Gln Cys Lys Gln
35 40 45

Gly Val Phe Cys Leu Val Lys Gln Ala Gln Leu Ser Tyr His Leu Thr
50 55 60

Ser Met Gly His Gln Leu Ser Tyr Val Leu Pro Val Arg Arg Gln Asn
65 70 75 80

Leu Leu Thr Met Val Gly Thr Val Pro Val Lys Ile Ser Gln Gln Ala
85 90 95

Gly Gln Ser Glu Gly Ser Ile Leu Cys Gln Cys Ala Asn Pro Glu Cys
100 105 110

Leu Tyr Thr Leu Ile Lys Thr Leu Cys Gly Leu Lys Glu Ile Val Pro
115 120 125

Phe Asn
130

<210> SEQ ID NO 119
<211> LENGTH: 473
<212> TYPE: PRT
<213> ORGANISM: Adenovirus

<400> SEQUENCE: 119

Met Lys Ile Phe Val Val Ile Cys Ala Leu Ser Thr Ile Ser Ile Ala
1 5 10 15

Ala Ala Asn Tyr Thr Thr Val Ala Ser Lys Lys Leu Pro Ala Tyr Arg
20 25 30

Gly Ile Thr Leu His Tyr Thr Asn Phe Thr Asp Tyr Ile Gln Leu Val
35 40 45

Cys Thr Cys Ser Asn Glu Leu Ile Leu Trp Leu Ala Asn Gly Ser Val
50 55 60

```
Cys Gln Val Phe Leu Glu His Val Leu Phe Glu Lys Arg Asn Pro Leu
65                  70                  75                  80

Cys Glu Asn Ser Ser Ser Gln Tyr Leu Ile Leu His Pro Pro Phe Val
                85                  90                  95

Ser Gly Pro Tyr Leu Cys Ile Gly Ser Gly Lys Gly Asp Ala Cys Val
            100                 105                 110

Lys Arg Trp Val Leu Leu Pro Lys Pro Gln Pro Thr Ala Ala Pro Lys
        115                 120                 125

Pro Gln Pro Thr Ser Pro Pro Ser Leu Ala Phe Ile Arg Ala Ala Ala
    130                 135                 140

Ser Arg Thr His Leu Trp Leu Pro Leu Ile Phe Ile Val Val Phe Gly
145                 150                 155                 160

Cys His Thr Phe Ser Leu Thr Met Arg Met Leu Leu Leu Leu Ala Ile
                165                 170                 175

Ile Ala Ser Thr Ser Ala Gln Ser Leu His Lys Pro Leu Gln Ile Tyr
            180                 185                 190

Ala Lys Ile Gly Asp Asn Leu Thr Leu Gln Ser His Glu Phe His Asn
        195                 200                 205

Pro Ser Leu Met Lys Glu Val Ser Trp Tyr Val Glu Leu Trp Asp Asn
    210                 215                 220

Val Lys Pro Thr Ser Thr Ala Leu Phe Met Gly Ser Lys Leu Cys Gln
225                 230                 235                 240

Phe Lys Glu Asp Gly Ser Asn Asn Thr Trp Asn Tyr Pro Ser Leu His
                245                 250                 255

Phe Asn Cys Ala Asn Lys Ser Leu His Leu Phe Asn Leu Asn Ser Leu
            260                 265                 270

Asn Ser Gly Leu Tyr Asn Val Lys Val Thr Asn Asn Thr Leu Glu His
        275                 280                 285

Asn Thr Tyr Phe Asn Leu Gln Val Ile Ser Ile Pro Lys Pro Gln Cys
    290                 295                 300

Met Val Thr Ser Phe Tyr Ile Ala Val Asp Tyr Cys Tyr Ile Glu Ile
305                 310                 315                 320

Asn Cys Thr Asn Ser Lys Tyr Pro Asn Lys Val Leu Tyr Asn Gly Ile
                325                 330                 335

Thr Lys Ala Tyr Tyr Asn Ser Ala Arg Gly Gly Lys His Thr Leu Pro
            340                 345                 350

Glu His Phe Tyr Thr Leu Ile Asn Tyr His Gly Val Arg Ala Asn Phe
        355                 360                 365

Ser Tyr Tyr Tyr Pro Phe Asn Ser Leu Cys Lys Asn Ser Gly Arg Ala
    370                 375                 380

Pro His Ser Ala Pro Arg Phe Val Pro Arg Tyr Gly Pro Gln Pro Ala
385                 390                 395                 400

Arg Leu Leu Gly Val Arg Leu Leu Ser Pro Pro Pro Tyr Glu Glu Asn
                405                 410                 415

Pro Asp Ala Asn Ser Asp Asp Ala Tyr Glu Lys Ala Met Ala Val Val
            420                 425                 430

Val Ile Ala Ala Val Val Cys Ser Leu Val Ile Leu Ala Ala Leu Leu
        435                 440                 445

Phe Leu Cys Tyr Trp Arg Arg Arg Leu Arg Gln Arg Arg Arg Arg Gly
    450                 455                 460

Pro Gln Leu Met Met Thr Asn Gln Leu
465                 470
```

<210> SEQ ID NO 120
<211> LENGTH: 90
<212> TYPE: PRT
<213> ORGANISM: Adenovirus

<400> SEQUENCE: 120

```
Met Pro Thr Leu Leu Leu Ile Leu Leu Gly Leu Pro Val Ile Phe Leu
1               5                   10                  15

Ser Thr Ala Tyr Ala Ala Ala Ser His Leu Glu Ala Glu Cys Leu Ser
            20                  25                  30

Pro Phe Val Val Tyr Leu Ile Phe Thr Phe Leu Gly Cys Ile Ser Ile
        35                  40                  45

Cys Ser Ile Val Ala Phe Leu Ile Thr Thr Phe Gln Cys Val Asp Tyr
    50                  55                  60

Val Tyr Val Arg Trp Val Tyr Arg Arg His His Pro Gln Tyr Gln Asn
65                  70                  75                  80

Arg Glu Val Ala Ala Leu Leu Cys Leu Ser
                85                  90
```

<210> SEQ ID NO 121
<211> LENGTH: 153
<212> TYPE: PRT
<213> ORGANISM: Adenovirus

<400> SEQUENCE: 121

```
Met Arg Arg Leu Arg Leu Arg Gln Val Gly Val Pro Pro Pro Pro Pro
1               5                   10                  15

Pro Val Pro Lys Pro Gly Ser Gly Arg Val Ala Leu Ser Leu Val Ile
            20                  25                  30

Phe Leu Ala Leu Trp Pro Ser Ala Ala Ala Ala Glu Thr Ala Val Ala
        35                  40                  45

Arg His Cys Arg Phe Gln Arg Leu Trp Gly Phe Pro Asp Cys Tyr His
    50                  55                  60

Lys Lys Pro Glu Phe Pro Ala Ala Trp Leu Tyr Val Ala Thr Phe Phe
65                  70                  75                  80

Leu Val Phe Ile Ser Thr Val Leu Gly Leu Phe Ile Phe Gly Arg Leu
                85                  90                  95

Arg Tyr Gly Trp Ile His Ala Thr Asn Glu Leu Pro Ala Ser Pro Ser
            100                 105                 110

Pro Leu Leu Pro Pro Pro Pro Pro Pro Pro Pro Pro Pro Pro Pro Val
        115                 120                 125

Ala Ala Val Ile Gln Leu Ile His Leu Asn Ser Pro Pro Arg Arg Pro
    130                 135                 140

Ser Val Ile Ser Tyr Phe Glu Leu Ser
145                 150
```

<210> SEQ ID NO 122
<211> LENGTH: 291
<212> TYPE: PRT
<213> ORGANISM: Adenovirus

<400> SEQUENCE: 122

```
Met Gln Arg Glu Arg Arg Phe Arg Tyr Arg Leu Gly Pro Tyr Ala Arg
1               5                   10                  15

His Arg Leu Pro Pro Cys Glu Gln Pro Cys Ser Ala Ala Val Met Asp
            20                  25                  30

Asp Ser Gln Leu Ser Met Asp Cys Asp Asn Phe Arg Met His Asn Val
```

```
        35                  40                  45

Ala Glu Val Arg Gly Leu Pro Cys Cys Ala Gly Phe Ile Val Leu Gln
    50                  55                  60

Glu Trp Pro Val Leu Trp Asp Met Val Leu Thr Arg Trp Glu Leu Tyr
65                  70                  75                  80

Val Leu Arg Thr Tyr Leu Arg Val Cys Val Cys Cys Ala Thr Leu Asp
                85                  90                  95

Val Glu Ser Arg Gln Leu Val His Gly His Glu Arg Trp Ile Leu His
            100                 105                 110

Cys His Cys Arg Arg Pro Gly Ser Leu Gln Cys Lys Ala Gly Ala Val
        115                 120                 125

Val Leu Thr Arg Trp Phe Lys Met Leu Val Tyr Gly Ala Leu Ile Asn
    130                 135                 140

Gln Arg Cys Leu Trp Tyr Arg Glu Val Val Asn Phe Asn Leu Pro Lys
145                 150                 155                 160

Glu Val Cys Tyr Val Gly Ser Thr Tyr Val Arg Gly Arg His Leu Ile
                165                 170                 175

Tyr Val Arg Ile Arg Tyr Asp Gly His Val Gly Val Val Leu Ala Asn
            180                 185                 190

Met Ser Phe Gly Trp Ser Val Leu Ser Tyr Gly Ile Leu Asn Asn Leu
        195                 200                 205

Val Ile Leu Gly Cys Thr Tyr Cys Lys Asp Leu Ser Glu Ile Gln Met
    210                 215                 220

Arg Cys Cys Ala Arg Arg Thr Arg Ala Leu Met Leu Arg Ala Val Arg
225                 230                 235                 240

Leu Ile Gly Glu His Thr Arg Ser Pro Leu Tyr Arg Ser Cys Leu Glu
                245                 250                 255

Pro Arg Arg Gln Gln Leu Leu Arg Asn Leu Met Leu Arg Ala Gln Pro
            260                 265                 270

Phe Thr Leu Arg Ala Tyr Asp Gly Cys Glu Asn Pro Trp Arg Ser Thr
        275                 280                 285

Gly Val Asp
    290


<210> SEQ ID NO 123
<211> LENGTH: 119
<212> TYPE: PRT
<213> ORGANISM: Adenovirus

<400> SEQUENCE: 123

Met Gln Arg Glu Arg Arg Phe Arg Tyr Arg Leu Gly Pro Tyr Ala Arg
1               5                   10                  15

His Arg Leu Pro Pro Cys Glu Gln Pro Cys Ser Ala Ala Val Met Asp
            20                  25                  30

Asp Ser Gln Leu Ser Met Asp Cys Asp Asn Phe Arg Met His Asn Val
        35                  40                  45

Ala Glu Gly Glu Pro Asp Leu Arg Asp Cys Ser Glu Gly Phe Val Ser
    50                  55                  60

Ile Thr Asp Pro Arg Leu Ala Thr Thr Glu Gln Val Trp Ile Leu Thr
65                  70                  75                  80

Pro Glu Arg Ser Gly Leu Ala Ser Ala Arg Leu Gln Thr Tyr Thr Met
                85                  90                  95

Ala Pro Gly Glu Arg Val Val Tyr Arg Val Lys Trp Gln Gly Gly Gly
            100                 105                 110
```

```
Ser Leu Thr Val Arg Val Ile
        115


<210> SEQ ID NO 124
<211> LENGTH: 127
<212> TYPE: PRT
<213> ORGANISM: Adenovirus

<400> SEQUENCE: 124

Met Ala Glu Ser Gln Ala Val Tyr Val His Leu Leu Ser Pro Arg Ala
1               5                   10                  15

Leu Met Pro Ala Gln Gln Gly Tyr Ser Asn Val Tyr Val Phe Phe Ala
            20                  25                  30

Pro Glu Asn Phe Met Ile Ser Pro Arg Gly Ile Asn Leu Leu Ala Leu
        35                  40                  45

Gln Leu Ser Val Gln Ile Pro Thr Gly Tyr Leu Gly Arg Phe Phe Ser
    50                  55                  60

Leu Ala Asp Met Ala Thr Arg Gly Val Tyr Val Ala Ala Gln Glu Leu
65                  70                  75                  80

Cys Pro Asp Ser Trp Trp Glu Ser Ser Val Val Leu Phe Asn His Ser
                85                  90                  95

Asp Glu Phe Tyr Phe Gly Ala Arg Gly Gln Pro Val Ala Cys Leu Ile
            100                 105                 110

Leu Glu Arg Val Phe Phe Pro Pro Leu Arg Gln Ala Ser Gln Val
        115                 120                 125


<210> SEQ ID NO 125
<211> LENGTH: 128
<212> TYPE: PRT
<213> ORGANISM: Adenovirus

<400> SEQUENCE: 125

Met Tyr Glu Arg Arg Pro Val Phe Phe Ser Val Cys Leu Pro Gln Pro
1               5                   10                  15

Leu Val Asp His Leu His Ala Cys Ser Val Glu Val Tyr Glu Leu Met
            20                  25                  30

Leu Arg Val Leu Pro Glu Phe Trp Arg Gln Met Leu Leu Tyr Leu Thr
        35                  40                  45

Pro Pro Phe Glu Ser Ala Ser Ala Gly Ala Thr Leu Leu Ser Leu Ser
    50                  55                  60

Pro Ser Phe Gln Val Leu Cys Cys Val Met Ala Pro Glu Leu Thr Pro
65                  70                  75                  80

Asn Gly Glu Leu Ala Ser Ala Thr Ala Phe Asp Leu Tyr Glu Val Leu
                85                  90                  95

Arg Leu Ala Leu Met Tyr Glu Ile Arg Glu His Gly His Val Pro Asn
            100                 105                 110

Pro Glu Leu Leu Asn Leu Leu Gln Val Ser Gln Glu Val Asn Phe Phe
        115                 120                 125


<210> SEQ ID NO 126
<211> LENGTH: 116
<212> TYPE: PRT
<213> ORGANISM: Adenovirus

<400> SEQUENCE: 126

Met Lys Leu Cys Leu Arg Leu Gln Val Glu Ser Ala Leu Arg Glu Leu
1               5                   10                  15

Phe Asn Met Arg Gly Met Asn Leu Val Thr Cys Cys Thr Asp Ile Ile
```

20 25 30

Arg Glu Trp Lys Asn Glu Asn Tyr Leu Gly Met Val Gln Ser Cys Ser
35 40 45

Leu Met Val Glu Glu Phe Glu Asp Gly Ser Phe Ala Val Leu Leu Phe
50 55 60

Val Glu Val Arg Val Glu Ala Leu Val Glu Ala Val Val Asp His Leu
65 70 75 80

Asp Asn Arg Met Gly Phe Asp Leu Ala Val Ile Tyr His Gln Asn Ser
85 90 95

Gly Gly Asp Arg Cys His Leu Arg Asp Leu His Phe Glu Val Leu Arg
100 105 110

Asp Arg Leu Glu
115

<210> SEQ ID NO 127
<211> LENGTH: 121
<212> TYPE: PRT
<213> ORGANISM: Adenovirus

<400> SEQUENCE: 127

Met Ser Leu Pro Ser Leu Pro Pro Pro Pro Val Cys Arg Glu Pro Pro
1 5 10 15

Ala Cys Leu Ala Trp Leu Glu Leu Ala Tyr Ala Ile Tyr Leu Asp Val
20 25 30

Leu Arg Asn Ile Arg Leu His Gly Ile Thr Leu Thr Pro Ala Ala Ala
35 40 45

Arg Ile Leu Ser Gly Tyr Arg Glu Trp Leu Tyr Phe Ala Leu Asn Ser
50 55 60

Glu Arg Gln Arg Arg Ala Ala Phe Arg Arg Arg Lys Glu Ala Cys Trp
65 70 75 80

Gly Arg Thr Trp Phe Cys Tyr Gln Lys Trp Leu Trp Val Ser Arg Val
85 90 95

Leu Ala Tyr Asp Ala Thr Arg Lys Thr Val Ser Leu Gln Ala Gly Pro
100 105 110

Val Cys Pro Ser Pro Ser Thr Ala Leu
115 120

<210> SEQ ID NO 128
<211> LENGTH: 920
<212> TYPE: PRT
<213> ORGANISM: Adenovirus

<400> SEQUENCE: 128

Met Ala Thr Pro Ser Met Met Pro Gln Trp Ser Tyr Met His Ile Ala
1 5 10 15

Gly Gln Asp Ala Ser Glu Tyr Leu Ser Pro Gly Leu Val Gln Phe Ala
20 25 30

Arg Ala Thr Asp Thr Tyr Phe Ser Leu Gly Asn Lys Phe Arg Asn Pro
35 40 45

Thr Val Ala Pro Thr His Asp Val Thr Thr Asp Arg Ser Gln Arg Leu
50 55 60

Thr Leu Arg Phe Val Pro Val Asp Arg Glu Asp Thr Ala Tyr Ser Tyr
65 70 75 80

Lys Ala Arg Phe Thr Leu Ala Val Gly Asp Asn Arg Val Leu Asp Met
85 90 95

Ala Ser Thr Tyr Phe Asp Ile Arg Gly Val Leu Asp Arg Gly Pro Ser

```
            100                 105                 110

Phe Lys Pro Tyr Ser Gly Thr Ala Tyr Asn Cys Leu Ala Pro Lys Gly
        115                 120                 125

Ala Pro Asn Pro Ser Glu Trp Glu Asp Thr Thr Asp Asn Lys Thr Lys
    130                 135                 140

Val Arg Gly Gln Ala Pro Tyr Val Ser Asp Glu Ile Thr Lys Asp Gly
145                 150                 155                 160

Ile Lys Val Gly Thr Asp Thr Ala Thr Pro Thr Gln Ala Ile Tyr Ala
                165                 170                 175

Asp Lys Leu Tyr Gln Pro Glu Pro Gln Ile Gly Glu Thr Gln Trp Asn
            180                 185                 190

Ser Glu Val Pro Asn Asn Gly Lys Val Gly Gly Arg Val Leu Lys Lys
        195                 200                 205

Thr Thr Pro Met Tyr Pro Cys Tyr Gly Ser Phe Ala Arg Pro Thr Asn
    210                 215                 220

Gln Gln Gly Gly Gln Val Lys Asp Gln Val Asp Leu Gln Phe Phe Ser
225                 230                 235                 240

Ser Thr Ser Ser Asp Asn Asn Pro Lys Ala Val Leu Tyr Ala Glu Asp
                245                 250                 255

Val Asn Leu Glu Ala Pro Asp Thr His Leu Val Phe Lys Pro Ile Val
            260                 265                 270

Thr Glu Gly Thr Thr Ser Ala Glu Ala Leu Leu Ala Gln Gln Ala Ala
        275                 280                 285

Pro Asn Arg Pro Asn Tyr Ile Gly Phe Arg Asp Asn Phe Ile Gly Leu
    290                 295                 300

Met Tyr Tyr Asn Ser Thr Gly Asn Met Gly Val Leu Ala Gly Gln Ala
305                 310                 315                 320

Ser Gln Leu Asn Ala Val Val Asp Leu Gln Asp Arg Asn Thr Glu Leu
                325                 330                 335

Ser Tyr Gln Leu Met Leu Asp Ser Leu Gly Asp Arg Ser Arg Tyr Phe
            340                 345                 350

Ser Met Trp Asn Gln Ala Val Asp Ser Tyr Asp Pro Asp Val Arg Ile
        355                 360                 365

Val Glu Asn His Gly Val Glu Asp Glu Leu Pro Asn Tyr Cys Phe Pro
    370                 375                 380

Leu Gly Gly Met Ala Val Thr Asp Thr Tyr Ser Ala Leu Lys Val Gln
385                 390                 395                 400

Asn Gly Asn Gly Thr Phe Thr Ser Asp Asp Ser Phe Ala Thr Arg Gly
                405                 410                 415

Ile Glu Ile Gly Ser Gly Asn Met Phe Ala Met Glu Ile Asn Leu Gln
            420                 425                 430

Ala Asn Leu Trp Arg Ser Phe Leu Tyr Ser Asn Ile Gly Leu Tyr Leu
        435                 440                 445

Pro Asp Thr Leu Lys Tyr Thr Pro Asp Asn Val Thr Leu Pro Asp Asn
    450                 455                 460

Lys Asn Thr Tyr Gly Tyr Met Asn Gly Arg Val Thr Pro Pro Gly Leu
465                 470                 475                 480

Ile Asp Thr Tyr Val Asn Ile Gly Ala Arg Trp Ser Pro Asp Val Met
                485                 490                 495

Asp Asn Ile Asn Pro Phe Asn His His Arg Asn Ala Gly Leu Arg Tyr
            500                 505                 510

Arg Ser Met Leu Leu Gly Asn Gly Arg Tyr Val Pro Phe His Ile Gln
        515                 520                 525
```

```
Val Pro Gln Lys Phe Phe Ala Ile Lys Asn Leu Leu Leu Leu Pro Gly
    530                 535                 540

Ser Tyr Thr Tyr Glu Trp Asn Phe Arg Lys Asp Val Asn Met Ile Leu
545                 550                 555                 560

Gln Ser Ser Leu Gly Asn Asp Leu Arg Val Asp Gly Ala Thr Ile Arg
                565                 570                 575

Phe Asp Ser Ile Asn Leu Tyr Ala Asn Phe Phe Pro Met Ala His Asn
            580                 585                 590

Thr Ala Ser Thr Leu Glu Ala Met Leu Arg Asn Asp Thr Asn Asp Gln
        595                 600                 605

Ser Phe Asn Asp Tyr Leu Cys Ala Ala Asn Met Leu Tyr Pro Ile Pro
    610                 615                 620

Ala Asn Ala Thr Ser Val Pro Ile Ser Ile Pro Ser Arg Asn Trp Ala
625                 630                 635                 640

Ala Phe Arg Gly Trp Ser Phe Thr Arg Leu Lys Thr Lys Glu Thr Pro
                645                 650                 655

Ser Leu Gly Ser Gly Phe Asp Pro Tyr Phe Val Tyr Ser Gly Ser Ile
            660                 665                 670

Pro Tyr Leu Asp Gly Thr Phe Tyr Leu Asn His Thr Phe Lys Lys Val
        675                 680                 685

Ser Ile Met Phe Asp Ser Ser Val Ser Trp Pro Gly Asn Asp Arg Leu
    690                 695                 700

Leu Thr Pro Asn Glu Phe Glu Ile Lys Arg Ser Val Asp Gly Glu Gly
705                 710                 715                 720

Tyr Asn Val Ala Gln Ser Asn Met Thr Lys Asp Trp Phe Leu Ile Gln
                725                 730                 735

Met Leu Ser His Tyr Asn Ile Gly Tyr Gln Gly Phe Tyr Val Pro Glu
            740                 745                 750

Gly Tyr Lys Asp Arg Met Tyr Ser Phe Phe Arg Asn Phe Gln Pro Met
        755                 760                 765

Ser Arg Gln Val Val Asp Thr Val Thr Tyr Lys Asp Thr Tyr Gln Glu
    770                 775                 780

Val Lys Leu Pro Tyr Gln His Asn Asn Ser Gly Phe Val Gly Tyr Met
785                 790                 795                 800

Gly Pro Thr Met Arg Glu Gly Gln Ala Tyr Pro Ala Asn Phe Pro Tyr
                805                 810                 815

Pro Leu Ile Gly Pro Thr Ala Val Pro Ser Leu Thr Gln Lys Lys Phe
            820                 825                 830

Leu Cys Asp Arg Val Met Trp Arg Ile Pro Phe Ser Ser Asn Phe Met
        835                 840                 845

Ser Met Gly Ala Leu Thr Asp Leu Gly Gln Asn Met Leu Tyr Ala Asn
    850                 855                 860

Ser Ala His Ala Leu Asp Met Thr Phe Glu Val Asp Pro Met Asp Glu
865                 870                 875                 880

Pro Thr Leu Leu Tyr Val Leu Phe Glu Val Phe Asp Val Val Arg Ile
                885                 890                 895

His Gln Pro His Arg Gly Val Ile Glu Ala Val Tyr Leu Arg Thr Pro
            900                 905                 910

Phe Ser Ala Gly Asn Ala Thr Thr
        915                 920
```

<210> SEQ ID NO 129
<211> LENGTH: 511

<212> TYPE: PRT
<213> ORGANISM: Adenovirus

<400> SEQUENCE: 129

```
Met Arg Arg Ala Val Pro Ala Ala Ala Ile Pro Ala Arg Val Ala Tyr
1               5                   10                  15

Ala Asp Pro Pro Pro Ser Tyr Glu Ser Val Met Ala Gly Val Pro Ala
            20                  25                  30

Thr Leu Glu Ala Pro Tyr Val Pro Pro Arg Tyr Leu Gly Pro Thr Glu
        35                  40                  45

Gly Arg Asn Ser Ile Arg Tyr Ser Glu Leu Ala Pro Leu Tyr Asp Thr
    50                  55                  60

Thr Arg Val Tyr Leu Val Asp Asn Lys Ser Ala Asp Ile Ala Ser Leu
65                  70                  75                  80

Asn Tyr Gln Asn Asp His Ser Asn Phe Leu Thr Thr Val Val Gln Asn
                85                  90                  95

Asn Asp Phe Thr Pro Val Glu Ala Gly Thr Gln Thr Ile Asn Phe Asp
            100                 105                 110

Glu Arg Ser Arg Trp Gly Gly Gln Leu Lys Thr Ile Leu His Thr Asn
        115                 120                 125

Met Pro Asn Val Asn Glu Phe Met Phe Thr Asn Ser Phe Arg Ala Lys
    130                 135                 140

Val Met Val Ser Arg Lys Gln Asn Glu Glu Gly Gln Thr Glu Leu Glu
145                 150                 155                 160

Tyr Glu Trp Val Glu Phe Val Leu Pro Glu Gly Asn Tyr Ser Glu Thr
                165                 170                 175

Met Thr Leu Asp Leu Met Asn Asn Ala Ile Val Asp His Tyr Leu Leu
            180                 185                 190

Val Gly Arg Gln Asn Gly Val Leu Glu Ser Asp Ile Gly Val Lys Phe
        195                 200                 205

Asp Thr Arg Asn Phe Arg Leu Gly Trp Asp Pro Val Thr Lys Leu Val
    210                 215                 220

Met Pro Gly Val Tyr Thr Asn Glu Ala Phe His Pro Asp Val Val Leu
225                 230                 235                 240

Leu Pro Gly Cys Gly Val Asp Phe Thr Gln Ser Arg Leu Ser Asn Leu
                245                 250                 255

Leu Gly Ile Arg Lys Arg Gln Pro Phe Gln Glu Gly Phe Arg Ile Met
            260                 265                 270

Tyr Glu Asp Leu Glu Gly Gly Asn Ile Pro Ala Leu Leu Asp Val Lys
        275                 280                 285

Ala Tyr Glu Asp Ser Ile Ala Ala Ala Met Arg Lys His Asn Leu Pro
    290                 295                 300

Leu Arg Gly Asp Val Phe Ala Val Gln Pro Gln Glu Ile Val Ile Lys
305                 310                 315                 320

Pro Val Ala Lys Asp Gly Lys Asp Arg Ser Tyr Asn Leu Leu Pro Asp
                325                 330                 335

Asp Gln Asn Asn Thr Ala Tyr Arg Ser Trp Tyr Leu Ala Tyr Asn Tyr
            340                 345                 350

Gly Asp Pro Leu Lys Gly Val Arg Ser Trp Thr Leu Leu Thr Thr Pro
        355                 360                 365

Asp Val Thr Cys Gly Ser Glu Gln Val Tyr Trp Ser Leu Pro Asp Leu
    370                 375                 380

Met Gln Asp Pro Val Thr Phe Arg Pro Ser Ser Gln Val Ser Asn Tyr
385                 390                 395                 400
```

```
Pro Val Val Gly Ala Glu Leu Leu Pro Leu Gln Ala Lys Ser Phe Tyr
                405                 410                 415

Asn Glu Gln Ala Val Tyr Ser Gln Leu Ile Arg Gln Ser Thr Ala Leu
            420                 425                 430

Thr His Val Phe Asn Arg Phe Pro Glu Asn Gln Ile Leu Val Arg Pro
        435                 440                 445

Pro Ala Ala Thr Ile Thr Thr Val Ser Glu Asn Val Pro Ala Leu Thr
    450                 455                 460

Asp His Gly Thr Leu Pro Leu Arg Ser Ser Ile Ser Gly Val Gln Arg
465                 470                 475                 480

Val Thr Ile Thr Asp Ala Arg Arg Arg Thr Cys Pro Tyr Val Tyr Lys
                485                 490                 495

Ala Leu Gly Ile Val Ala Pro Arg Val Leu Ser Ser Arg Thr Phe
            500                 505                 510


<210> SEQ ID NO 130
<211> LENGTH: 536
<212> TYPE: PRT
<213> ORGANISM: Adenovirus

<400> SEQUENCE: 130

Met Lys Arg Ala Arg Val Ala Glu Asp Phe Asn Pro Val Tyr Pro Tyr
1               5                   10                  15

Gly Ser Glu Ser Ser Pro Asn Val Pro Phe Ile Ser Pro Pro Phe Val
            20                  25                  30

Ser Ser Glu Gly Leu Gln Glu Asn Pro Pro Gly Val Leu Ala Leu Lys
        35                  40                  45

Tyr Gln Asp Pro Ile Thr Thr Thr Ala Glu Gly Lys Leu Thr Leu Lys
    50                  55                  60

Leu Gly Ser Gly Val Ser Leu Asn Asp Gly Ala Leu Thr Ala Thr Ala
65                  70                  75                  80

Pro Pro Val Ser Ala Pro Leu Thr Ser Thr Gln Gly Thr Ile Gly Leu
                85                  90                  95

Ser Ser Ser Pro Pro Leu Thr Val Ser Ala Gly Ser Leu Thr Leu Ala
            100                 105                 110

Gln Thr Glu Pro Leu Thr Val Thr Ser Asp Ala Leu Ala Leu Ser Tyr
        115                 120                 125

Ser Ser Pro Leu Thr Val Ala Ser Gly Ala Leu Thr Leu Thr Ser Pro
    130                 135                 140

Ser Glu Pro Leu Thr Leu Ser Ser Gly Ser Leu Ala Leu Thr Gln Thr
145                 150                 155                 160

Pro Pro Leu Thr Val Thr Ser Gly Ala Leu Gly Leu Ser Tyr Ser Ser
                165                 170                 175

Pro Leu Thr Leu Thr Asp Ser Ser Leu Gly Leu Ser Tyr Gln Gly Pro
            180                 185                 190

Leu Thr Val Thr Asp Asn Ala Leu Gly Leu Ser Ala Thr Ala Pro Leu
        195                 200                 205

Gln Val Ser Asn Ser Ser Leu Ala Leu Thr Thr Ser Pro Pro Leu Thr
    210                 215                 220

Val Ser Asn Asn Ser Leu Gly Leu Asn Leu Gly Asn Gly Leu Thr Thr
225                 230                 235                 240

Thr Asn Ser Gln Leu Thr Val Lys Thr Gly Gly Gly Ile Ala Phe Asp
                245                 250                 255

Ser Ser Gly Asn Leu Arg Ile Asn Ala Ala Gly Gly Met Arg Val Asp
```

```
            260                 265                 270

Asn Asn Asn Thr Leu Ile Leu His Val Ala Tyr Pro Phe Glu Ala Ala
        275                 280                 285

Asn Gln Leu Thr Ile Arg Ile Gly Pro Gly Leu Asn Ile Asn Thr Asn
    290                 295                 300

Asn Gln Leu Gln Val Asn Thr Gly Pro Gly Leu Val Phe Ser Asn Asn
305                 310                 315                 320

Val Leu Gln Val Ser Val Asp Thr Ser Lys Gly Leu Gln Tyr Ala Thr
                325                 330                 335

Thr Gly Ser Ser Ile Ser Val Lys Val Gly Ser Gly Leu Arg Phe Asp
            340                 345                 350

Ser Asn Gly Ala Ile Thr Leu Asn Ser Thr Thr Ala Arg Ala Phe His
        355                 360                 365

Gly Leu Ala Ser Gln Ser Leu Trp Ser His Pro Val Arg Ala Asn Cys
    370                 375                 380

Thr Val Tyr Glu Pro Leu Asp Ala Gln Leu Ala Leu Cys Leu Thr Lys
385                 390                 395                 400

Cys Gly Ser His Val Leu Gly Thr Val Ser Leu Gln Pro Leu Ser Gly
                405                 410                 415

Gln Leu Ala Thr Ala Met Pro Ala Glu Ser Leu Thr Leu Gln Leu Leu
            420                 425                 430

Phe Asp Glu Gln Gly Ala Leu Leu Thr Thr Gly Pro Leu Glu Pro Thr
        435                 440                 445

Ala Trp Gly Tyr Arg Glu Asp Asn Ala Leu Ser Pro Asp Pro Val Ala
    450                 455                 460

His Ala Leu Glu Phe Met Pro Ser Ala Leu Ala Tyr Pro Arg Glu Ala
465                 470                 475                 480

Asp Pro Pro His Phe Ser Ala Gln Phe Leu Pro Ser Ser Pro Pro Val
                485                 490                 495

Thr Phe Ser Val Ala Tyr Asn Thr Ala Pro Ser Gly Phe Ala Leu Ala
            500                 505                 510

Phe Thr Trp Ser Ala Thr Pro Gly Gln Pro Phe Val Ala Pro Leu Ala
        515                 520                 525

Thr Phe Cys Tyr Val Thr Glu Gln
    530                 535


<210> SEQ ID NO 131
<211> LENGTH: 418
<212> TYPE: PRT
<213> ORGANISM: Adenovirus

<400> SEQUENCE: 131

Met Lys Arg Ser Arg Pro Ala Asp Phe Asn Pro Val Tyr Pro Phe Pro
1               5                   10                  15

Phe Ser Pro Pro Pro Phe Phe Ile Thr Pro Pro Phe Val Glu Ala Arg
            20                  25                  30

Gly Leu Gln Glu Ser Pro Arg Gly Val Leu Ser Leu Arg Leu Gly Glu
        35                  40                  45

Gly Leu Ser Val Asp Glu Gln Gly Ala Ile Ala Ala Ala Tyr Arg Gln
    50                  55                  60

Ala Ala Ala Pro Leu Ile Leu Gln Asn Gly Thr Leu Ala Leu Thr Tyr
65                  70                  75                  80

Ser Ser Pro Leu Met Leu Thr Pro Gln Asn Thr Leu Gly Leu Gln Val
                85                  90                  95
```

```
Gln His Pro Leu Arg Val Gln Asn Ser Thr Gly Leu Ser Leu Leu Thr
            100                 105                 110

Ala Pro Pro Leu Ala Leu Gly Ala Thr Gly Leu Thr Leu Gln Thr Gly
        115                 120                 125

Pro Gly Leu Gln Val Gln Asp Ser Ser Leu Ala Pro Arg Leu Gly Asp
    130                 135                 140

Gly Leu Glu Leu Asn Thr Asp Gly Ala Ile Gln Val Ala Thr Ala Ala
145                 150                 155                 160

Ala Leu Thr Leu Gln Asn His Lys Val Gly Leu Ala Val Asp Trp Pro
                165                 170                 175

Leu Thr Ala Thr Asp Lys Leu Arg Leu Leu Thr Ser His Gly Leu Thr
            180                 185                 190

Val Asp Pro Asn Leu His Gln Leu Lys Val Asp Val Asn Ile Phe Lys
        195                 200                 205

Gly Leu Thr Phe Asp Asn Asn Gln Leu Val Val Lys Ala Gly His Gly
    210                 215                 220

Leu Arg Phe Asp Glu Gly Gly Phe Leu Thr Leu Thr Gln Pro Pro Asp
225                 230                 235                 240

Thr Leu Trp Thr Thr Ser Asp Pro Ser Pro Asn Cys Thr Val Lys Glu
                245                 250                 255

Glu Leu Asp Ser Lys Leu Ser Leu Ala Leu Thr Lys Asn Gly Gly Gln
            260                 265                 270

Val His Gly Leu Val Ser Leu Leu Gly Leu Lys Gly Pro Leu Ala Ser
        275                 280                 285

Ile Pro Ala Ser Asn Met Gly Trp Val Thr Ile Thr Leu Ala Phe Asp
    290                 295                 300

Glu Gln Gly Arg Leu Gln Phe Gly Glu Asn Thr Asn Leu Ala Ser Ser
305                 310                 315                 320

Ala Thr Trp Gly Tyr Arg Gln Gly Gln Ser Val Asn Pro Thr Pro Pro
                325                 330                 335

Glu Asn Ala Leu Gly Phe Met Pro Asn Ser Leu Ala Tyr Thr Arg Gly
            340                 345                 350

Gln Gly Gln His Thr Arg Asn His Thr Phe Val Pro Thr Tyr Met Lys
        355                 360                 365

Ala Asp His Gln Lys Pro Leu Ser Leu Gln Val Thr Phe Asn Glu Leu
    370                 375                 380

Ser Val Gly Tyr Ser Leu Arg Phe Thr Trp Met Gly Val Phe His Tyr
385                 390                 395                 400

Pro Gly Glu Gln Phe Leu Ala Pro Pro Cys Ala Phe Ser Tyr Leu Ala
                405                 410                 415

Glu Glu


<210> SEQ ID NO 132
<211> LENGTH: 450
<212> TYPE: PRT
<213> ORGANISM: Adenovirus

<400> SEQUENCE: 132

Met Glu Ser Arg Gly Gly Arg Lys Arg Pro Leu Gln His Gln Pro Pro
1               5                   10                  15

Gln Pro Gln Ala His Ala Gly Gln Arg Pro Thr Arg Gly Pro Ser Leu
            20                  25                  30

His Arg His Arg Asp His Pro His Ala Asp Pro Glu Thr Leu Ala Arg
        35                  40                  45
```

```
Pro Asp Pro Asp Pro Pro Arg Arg Pro Pro Pro Gly Ala Leu Gln Arg
    50                  55                  60

Lys Pro Pro Gln Pro Pro Gln Pro Gly Asp Leu Leu Asp Arg Asp Ala
65                  70                  75                  80

Leu Val Glu Asp Val Ser Glu Leu Trp Glu Arg Leu Gln Leu Leu Arg
                85                  90                  95

Gln Ser Leu Gln Asn Met Pro Met Ala Asp Gly Leu Lys Pro Leu Lys
            100                 105                 110

Gly Phe Asp Thr Leu Ala Glu Leu Leu Ser Leu Gly Gly Gln Arg Leu
        115                 120                 125

Leu Thr His Leu Ala Arg Glu Asn Arg Gln Val Arg Cys Met Met Asp
    130                 135                 140

Glu Val Ala Pro Leu Leu Arg Pro Asp Gly Ser Cys Ser Ser Leu Asn
145                 150                 155                 160

Tyr Gln Leu Gln Pro Val Ile Gly Val Ile Tyr Gly Pro Thr Gly Cys
                165                 170                 175

Gly Lys Ser Gln Leu Leu Arg Asn Leu Leu Ser Ala Gln Leu Val Ser
            180                 185                 190

Pro Ala Pro Glu Thr Val Phe Phe Ile Ala Pro Gln Val Asp Met Ile
        195                 200                 205

Pro Pro Ser Glu Ile Lys Ala Trp Glu Met Gln Ile Cys Glu Gly Asn
    210                 215                 220

Tyr Ala Pro Gly Pro Glu Gly Thr Ile Val Pro Gln Ser Gly Thr Leu
225                 230                 235                 240

Arg Pro Arg Phe Val Lys Leu Ser Tyr Asp Asp Leu Thr Leu Glu His
                245                 250                 255

Asn Tyr Asp Val Ser Asp Pro Arg Asn Ile Phe Ala Gln Ala Ala Ala
            260                 265                 270

Arg Gly Pro Ile Ala Ile Ile Met Asp Glu Cys Met Glu Asn Leu Gly
        275                 280                 285

Gly His Lys Gly Val Ser Lys Phe Phe His Ala Phe Pro Ser Lys Leu
    290                 295                 300

His Asp Lys Phe Pro Arg Cys Thr Gly Tyr Thr Val Leu Val Val Leu
305                 310                 315                 320

His Asn Met Asn Pro Arg Arg Asp Leu Gly Gly Asn Ile Ala Asn Leu
                325                 330                 335

Lys Ile Gln Ala Lys Met His Ile Ile Ser Pro Arg Met His Pro Ser
            340                 345                 350

Gln Leu Asn Arg Phe Val Asn Thr Tyr Thr Lys Gly Leu Pro Leu Ala
        355                 360                 365

Ile Ser Leu Leu Leu Lys Asp Ile Phe His His His Ala Gln Lys Pro
    370                 375                 380

Ala Tyr Asp Trp Ile Ile Tyr Asn Thr Thr Pro Glu His Glu Ala Met
385                 390                 395                 400

Gln Trp Cys Tyr Leu His Pro Arg Glu Gly Leu Met Pro Met Tyr Leu
                405                 410                 415

His Ile Gln Ala Arg Leu Tyr Arg Val Leu Glu Asp Ile His Arg Val
            420                 425                 430

Leu Asn Asp Arg Asp Arg Trp Ser Arg Ala Tyr His Ala Arg Lys Asn
        435                 440                 445

Lys Gln
    450
```

<210> SEQ ID NO 133
<211> LENGTH: 598
<212> TYPE: PRT
<213> ORGANISM: Adenovirus

<400> SEQUENCE: 133

```
Met Gln Ala Ala Ala Ala Ala Ala Gly Thr Ala Ala Gly Pro Ala Pro
1               5                   10                  15

Val Asp Pro Ala Ala Leu Ala Ala Arg Gln Ser Gln Ala Thr Gly Val
            20                  25                  30

Thr Ala Ser Asp Asp Trp Gly Ala Ala Met Glu Arg Ile Met Ala Leu
        35                  40                  45

Thr Ala Arg His Pro Glu Ala Phe Arg Gln Gln Pro Gln Ala Asn Arg
    50                  55                  60

Phe Ser Ala Ile Leu Glu Ala Val Val Pro Ser Arg Thr Asn Pro Thr
65                  70                  75                  80

His Glu Lys Val Leu Thr Ile Val Asn Ala Leu Val Asp Asn Lys Ala
                85                  90                  95

Ile Arg Lys Asp Glu Ala Gly Leu Ile Tyr Asn Ala Leu Leu Glu Arg
            100                 105                 110

Val Ala Arg Tyr Asn Ser Thr Asn Val Gln Ala Asn Leu Asp Arg Leu
        115                 120                 125

Ser Thr Asp Val Arg Glu Ala Val Ala Gln Arg Glu Arg Phe Phe Arg
    130                 135                 140

Glu Gly Asn Leu Gly Ser Leu Val Ala Leu Asn Ala Phe Leu Ser Ser
145                 150                 155                 160

Gln Pro Ala Asn Val Pro Arg Gly Gln Glu Asp Tyr Val Asn Phe Ile
                165                 170                 175

Ser Ala Leu Arg Leu Met Val Ser Glu Val Pro Gln Ser Glu Val Tyr
            180                 185                 190

Gln Ser Gly Pro Asn Tyr Phe Phe Gln Thr Ser Arg Gln Gly Leu Gln
        195                 200                 205

Thr Val Asn Leu Thr Gln Ala Phe Lys Asn Leu Gln Gly Leu Trp Gly
    210                 215                 220

Val Lys Ala Pro Leu Gly Asp Arg Ala Thr Val Ser Ser Leu Leu Thr
225                 230                 235                 240

Pro Asn Ser Arg Leu Leu Leu Leu Leu Ile Ala Pro Phe Thr Asp Ser
                245                 250                 255

Gln Ser Val Ser Arg Asp Ser Tyr Leu Gly His Leu Leu Thr Leu Tyr
            260                 265                 270

Arg Glu Ala Ile Gly Gln Ala Arg Val Asp Glu Gln Thr Phe Gln Glu
        275                 280                 285

Ile Thr Ser Val Ser Arg Ala Leu Gly Gln Glu Asp Thr Gly Ser Leu
    290                 295                 300

Glu Ala Thr Leu Asn Phe Leu Leu Thr Asn Arg Arg Gln Lys Ile Pro
305                 310                 315                 320

Pro Gln Tyr Thr Leu Ser Ala Glu Glu Glu Arg Ile Leu Arg Tyr Val
                325                 330                 335

Gln Gln Ser Val Ser Leu Tyr Leu Met Arg Glu Gly Ala Thr Ala Thr
            340                 345                 350

Ser Ala Leu Asp Met Thr Ala Arg Asn Met Glu Pro Ser Phe Tyr Ala
        355                 360                 365

Ser His Arg Pro Phe Ile Asn Arg Leu Met Asp Tyr Leu His Arg Ala
    370                 375                 380
```

```
Ala Ala Leu Asn Ala Glu Tyr Phe Thr Asn Ala Ile Leu Asn Pro His
385                 390                 395                 400

Trp Leu Pro Pro Pro Gly Phe Tyr Thr Gly Glu Phe Asp Leu Pro Glu
                405                 410                 415

Ala Asp Asp Gly Phe Leu Trp Asp Asp Ser Gly Asp Ser Leu Leu Thr
            420                 425                 430

Pro Thr Arg Leu Leu Lys Lys Glu Ala Gly Asp Glu Leu Pro Leu Ala
        435                 440                 445

Ser Val Glu Ala Ala Thr Arg Gly Glu Ser Pro Ala Pro Ser Leu Pro
    450                 455                 460

Leu Ser Leu Arg Ser Gln Ser Gly Arg Thr Ala Arg Pro Arg Leu Pro
465                 470                 475                 480

Gly Glu Ser Glu Tyr Leu Asn Asp Pro Leu Leu Leu Pro Glu Arg Glu
                485                 490                 495

Lys Asn Arg Arg Gln Ser Leu Pro Asn Asn Ala Leu Glu Ser Leu Val
            500                 505                 510

Asp Lys Met Asn Arg Trp Lys Thr Tyr Ala Gln Glu Gln Arg Glu Trp
        515                 520                 525

Glu Ala Ser Gln Pro Arg Pro Leu Leu Pro Pro Pro Gln Arg Trp Glu
    530                 535                 540

Thr Arg Arg Gln Arg Arg Arg Arg Leu Glu Glu Gly Pro Arg Ala Asp
545                 550                 555                 560

Glu Glu Asp Ser Ala Asp Asp Ser Ser Val Leu Asp Leu Gly Gly Thr
                565                 570                 575

Gly Arg Gly Gly Ala Ser Asn Pro Phe Ala His Leu Arg Pro Gln Gly
            580                 585                 590

Arg Leu Gly Arg Leu Tyr
        595


<210> SEQ ID NO 134
<211> LENGTH: 149
<212> TYPE: PRT
<213> ORGANISM: Adenovirus

<400> SEQUENCE: 134

Met Ser Gly Ile Ala Gly Asp Ala Ser Val Asn Phe Gln Gly Gly Val
1               5                   10                  15

Phe Ser Pro Tyr Leu Thr Ser Arg Leu Pro Pro Trp Ala Gly Val Arg
            20                  25                  30

Gln Asn Val Val Gly Ser Asn Leu Asp Gly Arg Pro Val Ala Pro Ala
        35                  40                  45

Asn Ser Thr Thr Leu Thr Tyr Ala Thr Val Gly Ala Ser Pro Leu Asp
    50                  55                  60

Thr Ala Ala Ala Ala Ala Ala Ser Ala Ala Ala Ser Thr Ala Arg Val
65                  70                  75                  80

Leu Ala Ala Asp Leu Gly Leu Tyr Asn His Leu Ala Thr Thr Ala Ala
                85                  90                  95

Val Ser Arg Ser Leu Val Arg Glu Asp Ala Met Gln Leu Val Leu Ala
            100                 105                 110

Arg Leu Glu Thr Leu Ala Gln Asp Arg Asp Glu Leu Ser Ala Lys Val
        115                 120                 125

Ala Asp Leu Ser Ser Ala Ala Leu Val Ala Ala Ala Pro Leu Pro Ala
    130                 135                 140

Ser Pro Pro Val Ile
145
```

<210> SEQ ID NO 135
<211> LENGTH: 1201
<212> TYPE: PRT
<213> ORGANISM: Adenovirus

<400> SEQUENCE: 135

Met Ala Leu Val Gln Ala His Gly Thr Arg Gly Leu Asp Ala Glu Glu
1 5 10 15

Ala Asp Pro Gly Pro Gln Pro Pro Arg Gly Arg Leu Arg Gln Arg Ala
20 25 30

Pro Arg Ala Thr Ser Ala Ala Ala Arg Ala Pro Arg Arg Arg Ala Ala
35 40 45

Pro Arg Ser Pro Pro Gly Ala Arg Thr Pro Ser Pro Pro Gly Ser Pro
50 55 60

Ala Pro Pro Pro Leu Leu Asp Pro Pro Leu Pro Pro Pro Pro Arg Arg
65 70 75 80

Arg Arg Tyr Arg Gly Thr Leu Val Ala Pro Leu Ala His Gly Leu Cys
85 90 95

His Ala Val Asp Ala Asp Thr Gly Gln Pro Val Thr Ile Lys Tyr His
100 105 110

Leu Arg Leu Ala Asp Ala Leu Thr Arg Leu Leu Glu Val Asn Arg Lys
115 120 125

Pro Ala Pro Ala Gly Leu Pro Pro Pro Ser Glu Leu Asp Arg Leu Thr
130 135 140

Pro Ala Gln Leu Gly Pro Leu Leu Arg Arg Leu Arg Pro Ala Ser Ala
145 150 155 160

Glu Val Trp Thr Cys Gly Ser Arg Gly Leu Val Ser Cys Gln Arg Val
165 170 175

Trp Pro Asp Pro Arg Ala Ala Ser Ala His Val Pro Glu Glu Pro Gln
180 185 190

Ala Gln Glu Gly His Asp Gly Arg Gln Pro Pro Pro Glu Leu Gly Leu
195 200 205

Pro Leu Cys Phe Leu Val His Asp Gly Arg Ala His Leu Val Gln Glu
210 215 220

Val Glu Arg Val Gln Arg Cys Glu Tyr Cys Ala Arg Phe Tyr Lys Tyr
225 230 235 240

Gln His Glu Cys Ser Ala Arg Arg Arg Asp Phe Tyr Phe His His Val
245 250 255

His Ala Gln Ser Ser Gly Trp Trp Gln Glu Ile Ser Phe Phe Pro Ile
260 265 270

Gly Ser His Pro Arg Thr Glu Arg Leu Phe Val Thr Tyr Asp Val Glu
275 280 285

Thr Tyr Thr Trp Met Gly Ala Phe Gly Lys Gln Leu Val Pro Phe Met
290 295 300

Leu Val Met His Leu His Gly Asp Glu Arg Leu Val Arg Glu Ala Cys
305 310 315 320

Asp Leu Ala Arg Glu Leu Arg Trp Asp Val Trp Glu Ala Gln Pro Ala
325 330 335

Thr Tyr Tyr Cys Leu Thr Pro Glu Arg Leu Ala Val Gly Arg Arg Phe
340 345 350

Arg Gln Phe Arg Asp Arg Leu Gln Leu Leu Leu Ala Arg Asp Leu Trp
355 360 365

Asp Ser Phe Leu Leu Ala Asn Pro His Leu Ala Glu Trp Ala Arg Gln

```
    370                 375                 380

Glu Leu Gly Leu Ala Arg Pro Glu Asp Leu Thr Tyr Asp Glu Leu Lys
385                 390                 395                 400

Lys Ala Pro Lys Leu His Gly Pro Pro Arg Phe Leu Glu Leu Tyr Ile
                405                 410                 415

Val Gly His Asn Ile Asn Gly Phe Asp Glu Ile Val Leu Ala Ala Gln
            420                 425                 430

Val Ile Asp His Arg Ser Glu Val Pro Gly Pro Phe Arg Val Thr Arg
        435                 440                 445

Asn Phe Met Pro Arg Ala Gly Lys Ile Leu Phe Asn Asp Ile Thr Phe
    450                 455                 460

Ala Leu Pro Asn Pro Arg Ser Gln Lys Arg Leu Asp Phe Thr Leu Trp
465                 470                 475                 480

Glu Gln Gly Ala Cys Asp Asp Thr Asp Phe Arg His Gln Phe Leu Lys
                485                 490                 495

Val Met Val Arg Asp Thr Phe Ala Leu Thr His Thr Ser Leu Arg Lys
            500                 505                 510

Ala Ala Gln Ala Tyr Ala Leu Pro Val Glu Lys Gly Cys Cys Pro Tyr
        515                 520                 525

Arg Ala Val Asn Glu Phe Tyr Met Leu Gly Ala Tyr Arg Ala Asp Ala
    530                 535                 540

Gln Gly Phe Pro Leu Pro Glu Tyr Trp Gln Asp Arg Gln Glu Tyr Leu
545                 550                 555                 560

Leu Asn Arg Glu Leu Trp Glu Lys Lys Gln Glu Ala Ser Tyr Asp Leu
                565                 570                 575

Ile Arg Glu Thr Leu Asp Tyr Cys Ala Leu Asp Val Leu Val Thr Ala
            580                 585                 590

Glu Leu Val Lys Lys Leu Gln Glu Ser Tyr Ala Ala Phe Val Ser Asp
        595                 600                 605

Ala Val Gly Leu Pro Arg Ala Ala Phe Asn Val Phe Gln Arg Pro Thr
    610                 615                 620

Ile Ser Ser Asn Ser His Ala Ile Phe Arg Gln Ile Leu Tyr Arg Ala
625                 630                 635                 640

Glu Arg Pro Ala Arg Thr His Leu Gly Pro Asp Leu Leu Ala Pro Ser
                645                 650                 655

His Glu Met Tyr Asp Tyr Val Arg Ala Ser Ile Arg Gly Gly Arg Cys
            660                 665                 670

Tyr Pro Thr Tyr Ile Gly Val Leu Lys Glu Pro Leu Tyr Val Tyr Asp
        675                 680                 685

Ile Cys Gly Met Tyr Ala Ser Ala Leu Thr His Pro Met Pro Trp Gly
    690                 695                 700

Pro Pro Leu Asn Pro Tyr Glu Arg Ala Leu Ala Ala Arg Asp Trp Gln
705                 710                 715                 720

Arg Ala Leu Asp Asn Leu Gln Ala Pro Ile Asp Tyr Phe Ala Pro Arg
                725                 730                 735

Leu Leu Pro Gly Ile Phe Thr Val Asp Ala Asp Pro Pro Pro Glu Asp
            740                 745                 750

Gln Leu Asp Val Leu Pro Pro Phe Cys Ser Arg Lys Gly Gly Arg Leu
        755                 760                 765

Cys Trp Thr Asn Glu Arg Leu Arg Gly Glu Val Ala Thr Ser Val Asp
    770                 775                 780

Leu Val Thr Leu His Asn Arg Gly Trp Arg Val Arg Leu Leu Pro Asp
785                 790                 795                 800
```

```
Glu Arg Thr Thr Val Phe Pro Arg Trp Arg Cys Leu Ala Arg Glu Tyr
                805                 810                 815

Val Gln Leu Asn Ile Ala Ala Lys Glu Arg Ala Asp Arg Asp Lys Asn
            820                 825                 830

Gln Thr Leu Arg Ser Ile Ala Lys Leu Leu Ser Asn Ala Leu Tyr Gly
        835                 840                 845

Ser Phe Ala Thr Lys Leu Asp Asn Lys Lys Ile Val Phe Ala Asp Gln
    850                 855                 860

Met Asp Pro Ala Leu Leu Lys Gly Ile Ala Ala Gly Gln Val Asn Ile
865                 870                 875                 880

Lys Ser Ser Ser Phe Val Glu Thr Asp Thr Leu Ser Ala Asp Val Met
                885                 890                 895

Pro Ala Phe Glu Arg Leu Tyr Ser Pro Glu Gln Leu Ala Ile Val His
            900                 905                 910

Ser Asp Ala Glu Asp Ser Asp Asp Asp Asn Gly Ala Ala Pro Phe Tyr
        915                 920                 925

Ser Pro Pro Pro Ala Ala Glu Gly His Val Ala Tyr Thr Tyr Lys Pro
    930                 935                 940

Ile Thr Phe Leu Asp Ala Glu Glu Gly Asp Leu Cys Leu His Thr Val
945                 950                 955                 960

Glu Lys Thr Asp Pro Leu Val Asp Asn Asp Arg Tyr Pro Ser His Val
                965                 970                 975

Ala Ser Phe Val Leu Ala Trp Thr Arg Ala Phe Val Ser Glu Trp Ser
            980                 985                 990

Glu Phe Leu Tyr Ala Glu Asp Arg  Gly Thr Pro Leu Glu  Arg Arg Pro
        995                 1000                1005

Leu Lys  Ser Val Tyr Gly Asp  Thr Asp Ser Leu Phe  Val Thr Glu
    1010                1015                1020

Ala Gly  His Arg Leu Met Glu  Ser Arg Gly Lys Lys  Arg Ile Lys
    1025                1030                1035

Lys Asn  Gly Gly Arg Leu Val  Phe Asp Pro Gln Gln  Pro Glu Leu
    1040                1045                1050

Thr Trp  Leu Val Glu Cys Glu  Thr Val Cys Ala Ala  Cys Gly Ala
    1055                1060                1065

Asp Ala  Tyr Ser Pro Glu Ser  Val Phe Leu Ala Pro  Lys Leu Tyr
    1070                1075                1080

Ala Leu  Lys Cys Leu Val Cys  Pro Ala Cys Gly His  Val Ser Lys
    1085                1090                1095

Gly Lys  Leu Arg Ala Lys Gly  His Ala Ala Glu Ser  Leu Ser Tyr
    1100                1105                1110

Glu Leu  Met Leu Arg Cys Phe  Leu Ala Asp Phe Gln  Gly Glu Glu
    1115                1120                1125

Asn Ala  Arg Phe Ser Thr Ser  Arg Leu Ser Leu Lys  Arg Thr Leu
    1130                1135                1140

Ala Ser  Ala Gln Pro Gly Ala  His Pro Phe Thr Val  Thr Glu Thr
    1145                1150                1155

Thr Leu  Thr Arg Thr Leu Arg  Pro Trp Arg Asp Arg  Thr Leu Thr
    1160                1165                1170

Pro Leu  Asp Ala His Arg Leu  Val Pro Tyr Ser Glu  Ser Arg Pro
    1175                1180                1185

Asn Pro  Arg Asn Gln Glu Ile  Cys Trp Ile Glu Met  Pro
    1190                1195                1200
```

<210> SEQ ID NO 136
<211> LENGTH: 205
<212> TYPE: PRT
<213> ORGANISM: Adenovirus

<400> SEQUENCE: 136

```
Met Gly Ser Cys Glu Gly Glu Leu Arg Ala Ile Ala Arg Asp Leu Gly
1               5                   10                  15

Cys Gly Pro Tyr Phe Leu Gly Thr Phe Asp Lys Arg Phe Pro Gly Phe
            20                  25                  30

Val Ser Pro Arg Lys Met Ala Cys Ala Ile Val Asn Thr Ala Ala Arg
        35                  40                  45

Glu Thr Gly Gly Val His Trp Leu Ala Leu Gly Trp Asn Pro Arg Ser
    50                  55                  60

Gln Ile Cys Tyr Leu Phe Asp Pro Phe Gly Phe Ser Asp Gln Arg Leu
65                  70                  75                  80

Lys Gln Ile Tyr Ser Phe Glu Tyr Glu Gly Leu Leu Arg Arg Ser Ala
                85                  90                  95

Leu Ala Ser Thr Pro Asp Arg Cys Val Thr Leu Glu Lys Ser Thr Gln
            100                 105                 110

Thr Val Gln Gly Pro His Ser Ala Ala Cys Gly Leu Phe Cys Cys Met
        115                 120                 125

Phe Leu His Ala Phe Val His Trp Pro Asp Ser Pro Met Asp Arg Asn
    130                 135                 140

Pro Thr Met Asn Leu Leu Thr Gly Val Pro Asn Ala Met Leu Gln Ser
145                 150                 155                 160

Pro Ser Val Gln Gly Thr Leu Lys Arg Asn Gln Glu Asn Leu Tyr Ala
                165                 170                 175

Phe Leu Glu Gln His Ser Ala Tyr Phe Arg Gln His Ala Ala Gln Ile
            180                 185                 190

Lys Arg Asp Thr Ala Phe Asp Lys Val Thr Gln His Ser
        195                 200                 205
```

<210> SEQ ID NO 137
<211> LENGTH: 664
<212> TYPE: PRT
<213> ORGANISM: Adenovirus

<400> SEQUENCE: 137

```
Met Ala Leu Ser Val Gln Asp Cys Ala Arg Leu Thr Gly Gln Ser Val
1               5                   10                  15

Ala Thr Val Gln Arg Phe Ala Pro Leu Arg Asn Leu Trp Asn Arg Val
            20                  25                  30

Arg Glu Phe Ala Arg Ala Ala Thr Thr Ala Ala Gly Leu Thr Trp Met
        35                  40                  45

Ser Arg Tyr Ile Tyr Gly Tyr His Arg Leu Met Leu Glu Asp Leu Ala
    50                  55                  60

Pro Gly Ala Pro Ala Thr Ala Arg Trp Pro Leu Tyr Gly Glu Pro Pro
65                  70                  75                  80

Pro His Leu Leu Val Gly Tyr Gln Tyr Leu Val Arg Thr Cys Asn Asp
                85                  90                  95

Tyr Ile Phe Asp Thr Arg Ala Tyr Ser Arg Leu Arg Tyr Thr Glu Leu
            100                 105                 110

Thr Gln Asn Gly Val Gln Leu Leu Asn Trp Ser Val Leu Ala Asn Cys
        115                 120                 125
```

-continued

```
Thr Tyr Thr Ile Asn Thr Gly Ala Tyr His Arg Phe Val Asp Leu Asp
    130                 135                 140

Asn Phe Gln Ala Thr Leu Thr Gln Val Gln Gln Ala Ile Leu Ala Glu
145                 150                 155                 160

Arg Val Val Ala Asp Leu Ala Leu Leu Gln Pro Leu Arg Gly Tyr Gly
                165                 170                 175

Ser Thr Arg Met Ala Asp Arg Ala His Gly Arg Asp Glu Val Pro Val
            180                 185                 190

Glu Arg Leu Met Gln Asp Tyr Tyr Lys Asp Leu Arg Arg Cys Gln His
        195                 200                 205

Glu Ala Trp Gly Met Ala Asp Arg Leu Arg Ile Gln Gln Ala Gly Pro
    210                 215                 220

Lys Asp Val Val Leu Leu Ala Thr Ile Arg Arg Leu Lys Thr Ala Tyr
225                 230                 235                 240

Phe Asn Tyr Leu Leu Ser Ser Leu Thr Ser Ala Val Ser Pro Asp Arg
                245                 250                 255

Arg Pro Pro Pro Pro Glu Thr Val Leu Ser Leu Pro Cys Asp Cys Asp
            260                 265                 270

Trp Leu His Ala Phe Leu Asp Lys Phe Ser Asp Pro Val Asp Phe Ser
        275                 280                 285

Ala Phe Arg Ser Trp Arg Gln Val Pro Thr Gln Gln Leu Ile Lys Cys
    290                 295                 300

Ile Val Ser Ala Val Ser Leu Pro Asn Arg Ser Pro His Asn Pro Cys
305                 310                 315                 320

Ser Leu Leu Arg Gly Ala Gly Leu Ala Pro Leu Arg Gly Gly Val Phe
                325                 330                 335

Glu Leu Arg Pro Arg Glu Asp Gly Arg Ala Val Thr Glu Thr Met Arg
            340                 345                 350

Arg Arg Arg Gly Glu Leu Ile Glu Arg Phe Val Asp Arg Leu Pro Val
        355                 360                 365

Arg Arg Arg Gln Arg Arg Arg Pro Val Pro Val Pro Pro Gly Pro Pro
    370                 375                 380

Ala Pro Pro Ser Pro Pro Leu Pro Pro Leu Glu Glu Ala Leu Glu Pro
385                 390                 395                 400

Glu Glu Glu Glu Leu Glu Glu Ala Ala Pro Glu Ala Phe Glu Arg Glu
                405                 410                 415

Val Arg Asp Thr Val Ala Asp Val Ile Arg Leu Leu Glu Glu Glu Leu
            420                 425                 430

Thr Val Ser Ala Arg Asn Ser Gln Phe Phe Asn Phe Ala Val Asp Phe
        435                 440                 445

Tyr Glu Ala Met Glu Arg Leu Glu Ala Leu Gly Asp Val Asn Glu Leu
    450                 455                 460

Thr Leu Arg Arg Trp Ile Met Tyr Phe Phe Val Ser Glu His Val Ala
465                 470                 475                 480

Thr Thr Leu Asn Tyr Leu Phe Gln Arg Leu Arg Asn Tyr Ala Val Phe
                485                 490                 495

Ala Arg His Val Glu Leu Asn Leu Ala Gln Val Val Met Arg Ala Arg
            500                 505                 510

Asp Ala Asp Gly Asp Val Val Tyr Ser Arg Val Trp Asn Glu Thr Gly
        515                 520                 525

Leu Asn Ala Phe Ser Gln Leu Met Asn Arg Ile Ser Asn Asp Leu Ala
    530                 535                 540

Ala Thr Val Glu Arg Ala Gly Arg Gly Glu Leu Gln Glu Glu Glu Val
```

```
545                 550                 555                 560

Glu Gln Phe Met Ala Glu Ile Ala Tyr Gln Asp Asn Ser Gly Asp Val
                565                 570                 575

Gln Glu Ile Leu Arg Gln Ala Ala Met Asn Asp Ala Glu Val Asp Ser
            580                 585                 590

Val Glu Leu Ser Phe Arg Phe Lys Leu Thr Gly Pro Val Val Leu Thr
        595                 600                 605

Gln Arg Arg Gln Ile Gln Asp Leu Asn Arg Arg Val Val Ala Phe Ala
    610                 615                 620

Ser Glu Leu Arg Ala Arg His Gln Leu Leu Pro Glu Leu His Glu Asp
625                 630                 635                 640

Val Pro Leu Pro Asp Leu Pro Pro Gly Pro Glu Pro Pro Leu Pro Pro
                645                 650                 655

Gly Ala Arg Pro Arg Arg Arg Phe
            660


<210> SEQ ID NO 138
<211> LENGTH: 366
<212> TYPE: PRT
<213> ORGANISM: Adenovirus

<400> SEQUENCE: 138

Met Ser Lys Arg Lys Phe Lys Glu Glu Leu Leu Gln Ala Val Ala Pro
1               5                   10                  15

Glu Ile Tyr Gly Pro Pro Asp Val Lys Pro Leu Arg Asp Leu Lys Arg
            20                  25                  30

Ala Ile Lys Lys Arg Glu Lys Lys Glu Glu Lys Lys Glu Glu Ala Ala
        35                  40                  45

Ala Glu Ala Trp Gly Asp Ala Val Glu Phe Val Arg Ala Thr Ala Pro
    50                  55                  60

Arg Arg Arg Val Gln Trp Lys Gly Arg Arg Val Arg Arg Val Leu Arg
65                  70                  75                  80

Pro Gly Thr Ala Val Val Phe Ser Pro Gly Glu Arg Ser Ala Leu Arg
                85                  90                  95

Ala Leu Lys Arg Asp Tyr Asp Glu Val Tyr Ala Asp Glu Asp Leu Leu
            100                 105                 110

Glu Gln Ala Glu Arg His Glu Gly Glu Phe Ala Tyr Gly Lys Arg Gly
        115                 120                 125

Arg Tyr Gly Asp Val Ala Leu Ala Leu Asp Glu Ser Asn Pro Thr Pro
    130                 135                 140

Ser Leu Lys Ala Val Thr Leu Gln Gln Val Leu Pro Val Ala Glu Ser
145                 150                 155                 160

Lys Lys Gly Ile Lys Arg Glu Ala Ala Glu Leu Gln Pro Thr Met Gln
                165                 170                 175

Leu Met Val Pro Lys Arg Gln Arg Leu Glu Glu Val Leu Glu Gln Met
            180                 185                 190

Lys Val Asp Pro Thr Val Gln Pro Asp Val Lys Ile Arg Pro Ile Lys
        195                 200                 205

Gln Val Ala Pro Gly Leu Gly Val Gln Thr Val Asp Ile Gln Ile Pro
    210                 215                 220

Val Arg Thr Ala Ala Val Glu Ala Met Glu Thr Gln Thr Glu Pro Ala
225                 230                 235                 240

Val Val Gly Pro Ser Ala Thr Ala Ala Ala Leu Gly Ala Ala Leu Gly
                245                 250                 255
```

```
Arg Ala Ala Thr Ala Glu Val Gly Ile Gln Thr Asp Pro Arg Tyr Glu
            260                 265                 270

Tyr Val Ala Val Ala Ala Ser Thr Pro Arg Val Arg Arg Arg Arg Ala
        275                 280                 285

Thr Ala Ala Ala Ala Ser Ala Leu Leu Pro Asp Tyr Val Leu His Pro
    290                 295                 300

Phe Ile Ala Pro Thr Pro Gly Tyr Pro Gly Arg Pro Tyr Arg Pro Arg
305                 310                 315                 320

Arg Arg Arg His Ala Thr Thr Thr Thr Arg Arg Arg Arg Arg Leu Pro
                325                 330                 335

Thr Leu Ala Pro Val Arg Val Arg Arg Val Thr Arg Arg Gly Arg Thr
            340                 345                 350

Leu Val Leu Pro Thr Ala Arg Tyr His Pro Ser Ile Leu Val
        355                 360                 365
```

<210> SEQ ID NO 139
<211> LENGTH: 264
<212> TYPE: PRT
<213> ORGANISM: Adenovirus

<400> SEQUENCE: 139

```
Met Glu Asp Ile Asn Phe Ala Ser Leu Ala Pro Arg His Gly Ser Arg
1               5                   10                  15

Pro Tyr Met Ala Thr Trp Asn Asp Ile Gly Thr Ser Gln Leu Asn Gly
            20                  25                  30

Gly Ala Phe Ser Trp Gly Ser Leu Trp Ser Gly Leu Lys Asn Phe Gly
        35                  40                  45

Thr Thr Ile Lys Asn Tyr Gly Ser Lys Ala Trp Asn Ser Ser Thr Gly
    50                  55                  60

Gln Met Leu Arg Asp Lys Leu Lys Asp His Asn Phe Gln Gln Lys Val
65                  70                  75                  80

Val Asp Gly Leu Ala Ser Gly Ile Asn Gly Val Val Asp Leu Ala Ser
                85                  90                  95

Gln Ala Val Gln Lys Gln Ile Ser Ser Arg Leu Asp Pro Pro Pro Pro
            100                 105                 110

Ala Ala Val Glu Pro Ser Ala Pro Pro Leu Glu Glu Val Glu Val Glu
        115                 120                 125

Glu Lys Leu Pro Pro Leu Glu Val Ala Leu Pro Pro Lys Gly Glu Lys
    130                 135                 140

Arg Pro Arg Pro Asp Lys Glu Glu Thr Leu Val Thr Glu Thr Val Glu
145                 150                 155                 160

Pro Pro Ser Tyr Glu Glu Ala Leu Lys Asp Gly Ala Ala Pro Pro Pro
                165                 170                 175

Tyr Thr Arg Pro Thr Ala Ala Leu Ala Arg Pro Val Leu Ser Ser Ser
            180                 185                 190

Ala His Lys Lys Ala Val Thr Thr Leu Asp Leu Pro Pro Pro Pro Ala
        195                 200                 205

Pro Val Val Thr Ala Ala Pro Pro Ala Ala Ser Leu Pro Val Arg Pro
    210                 215                 220

Val Ala Val Ala Thr Pro Ala Arg Val Pro Arg Gly Ser Arg Gln Gly
225                 230                 235                 240

Asn Trp Gln Ser Thr Leu Asn Ser Ile Val Gly Leu Gly Val Arg Ser
                245                 250                 255

Leu Lys Arg Arg Arg Cys Tyr Tyr
            260
```

<210> SEQ ID NO 140
<211> LENGTH: 184
<212> TYPE: PRT
<213> ORGANISM: Adenovirus

<400> SEQUENCE: 140

Met Ser Val Leu Ile Ser Pro Ser Asn Asn Thr Gly Trp Gly Leu Gly
1               5                   10                  15

Val Ser Lys Met Tyr Gly Gly Ala Lys Arg Arg Ser Ser Glu His Pro
            20                  25                  30

Val Arg Val Arg Gly His Tyr Arg Ala Pro Trp Gly Ala His Lys Arg
        35                  40                  45

Gly Arg Ala Gly Arg Thr Thr Val Asp Glu Val Ile Asp Ser Val Val
    50                  55                  60

Ala Asp Thr Ala Asn Tyr Thr Pro Ala Ala Gly Pro Ser Thr Val Asp
65                  70                  75                  80

Ser Val Ile Asp Ser Val Val Ala Asp Ala Arg Ala Tyr Ala Arg Arg
                85                  90                  95

Lys Gln Arg Arg Arg Arg Ala Ala Ala Ala Arg Arg Leu Thr Pro Ala
            100                 105                 110

Met Arg Ala Ala Arg Ala Val Leu Arg Arg Ala Arg Arg Val Gly Arg
        115                 120                 125

Gln Val Leu Arg Gln Ala Ala Ser Asn Ala Arg Val Arg Arg Arg Ala
    130                 135                 140

Ala Arg Arg Ala Ala Ala Ala Ile Ser Arg Met Ser Arg Gly Arg Arg
145                 150                 155                 160

Gly Asn Val Tyr Trp Val Arg Asp Ser Val Thr Gly Leu Arg Val Pro
                165                 170                 175

Val Arg Phe Arg Pro Pro Arg Gln
            180

<210> SEQ ID NO 141
<211> LENGTH: 233
<212> TYPE: PRT
<213> ORGANISM: Adenovirus

<400> SEQUENCE: 141

Met Ser Lys Glu Ile Pro Thr Pro Tyr Met Trp Ser Tyr Gln Pro Gln
1               5                   10                  15

Met Gly Leu Ala Ala Gly Ala Ala Gln Asp Tyr Ser Ser Lys Met Asn
            20                  25                  30

Trp Leu Ser Ala Gly Pro His Met Ile Ser Arg Val Asn Gly Ile Arg
        35                  40                  45

Ala His Arg Asn Gln Ile Leu Leu Glu Gln Ala Ala Ile Thr Ala Thr
    50                  55                  60

Pro Arg Ser Gln Leu Asn Pro Pro Ser Trp Pro Ala Ala Leu Val Tyr
65                  70                  75                  80

Gln Glu Thr Pro Ala Pro Thr Thr Val Leu Leu Pro Arg Asp Ala Gln
                85                  90                  95

Ala Glu Val Arg Met Thr Asn Ser Gly Ala Gln Leu Ala Gly Gly Ala
            100                 105                 110

Arg Gly Gly Arg Tyr Ile Gly Arg Ser Ser Pro Tyr Ser Ser Gln Ser
        115                 120                 125

Ile Lys Arg Leu Leu Ile Arg Gly Arg Gly Val Gln Leu Asn Asp Glu
    130                 135                 140

-continued

```
Ala Val Ser Ser Ser Trp Gly Leu Arg Pro Asp Gly Val Phe Gln Leu
145                 150                 155                 160

Gly Gly Ala Gly Arg Ser Ser Phe Thr Ser Arg Gln Ala Tyr Leu Thr
                165                 170                 175

Leu Gln Ser Ser Ser Ser Arg Pro Arg Ser Gly Gly Ile Gly Thr Val
            180                 185                 190

Gln Phe Val Glu Glu Phe Thr Pro Ser Val Tyr Phe Asn Pro Phe Ser
        195                 200                 205

Gly Ser Pro Gly Arg Tyr Pro Asp Ala Phe Ile Pro Asn Phe Asp Ala
    210                 215                 220

Ile Ser Glu Ser Val Asp Gly Tyr Asp
225                 230


<210> SEQ ID NO 142
<211> LENGTH: 74
<212> TYPE: PRT
<213> ORGANISM: Adenovirus

<400> SEQUENCE: 142

Met Ala Leu Thr Cys Arg Val Arg Ile Pro Val Pro Gly Tyr Arg Gly
1               5                   10                  15

Arg Ser His Arg Arg His Arg Arg Gly Leu Ala Gly Arg Gly Leu Arg
            20                  25                  30

Arg Arg Arg Ala Val Arg Arg Arg Met Arg Gly Gly Val Leu Pro Leu
        35                  40                  45

Leu Ile Pro Leu Ile Ala Ala Ala Ile Gly Ala Val Pro Gly Ile Ala
    50                  55                  60

Ser Val Ala Leu Gln Ala Ser Arg Lys Asn
65                  70


<210> SEQ ID NO 143
<211> LENGTH: 52
<212> TYPE: PRT
<213> ORGANISM: Adenovirus

<400> SEQUENCE: 143

Met Val Cys Glu Gly Arg Glu Trp Ala Thr Pro Ile Ser Phe Arg Leu
1               5                   10                  15

Trp Arg Lys Phe Ala Ala Arg Glu Arg Leu Arg Tyr Glu Ser Trp Glu
            20                  25                  30

Glu Gly Gln Val Val Arg Leu Leu Glu Lys Phe Asp Pro Arg Leu Lys
        35                  40                  45

Leu Arg Leu Lys
    50
```